United States Patent
Ward et al.

(10) Patent No.: US 12,365,908 B2
(45) Date of Patent: Jul. 22, 2025

(54) POLYPLOID HYBRID MAIZE BREEDING

(71) Applicant: Ohalo Genetics, Inc., Aptos, CA (US)

(72) Inventors: Judson Arthur Ward, Watsonville, CA (US); Jason A. Peiffer, Hendersonville, NC (US); Lien Diana Bertier, Santa Cruz, CA (US); Morgan Edward McCaw, Aptos, CA (US); Xingang Wang, Aptos, CA (US); Benjamin Thomas Berube, Scotts Valley, CA (US)

(73) Assignee: Ohalo Genetics, Inc., Aptos, CA (US)

( * ) Notice: Subject to any disclaimer, the term of this patent is extended or adjusted under 35 U.S.C. 154(b) by 0 days.

(21) Appl. No.: 18/504,917

(22) Filed: Nov. 8, 2023

(65) Prior Publication Data
US 2024/0150778 A1 May 9, 2024

Related U.S. Application Data

(60) Provisional application No. 63/461,174, filed on Apr. 21, 2023, provisional application No. 63/461,170, (Continued)

(51) Int. Cl.
*C12N 15/82* (2006.01)

(52) U.S. Cl.
CPC ..... *C12N 15/8242* (2013.01); *C12N 15/8213* (2013.01)

(58) Field of Classification Search
None
See application file for complete search history.

(56) References Cited

U.S. PATENT DOCUMENTS 10,883,112 B2   1/2021  Mercier et al.
2005/0064474 A1  3/2005  Urniv et al.
(Continued)

FOREIGN PATENT DOCUMENTS

EP           4477069 A1    12/2024
WO    WO-2012075195 A1     6/2012
(Continued)

OTHER PUBLICATIONS

D'Erfurth et al. "Turning Meiosis into Mitosis" 2009 PLoS Biology 7(6):e1000124 (10 total pages). (Year: 2009).*
(Continued)

*Primary Examiner* — Matthew R Keogh
*Assistant Examiner* — Rebecca Stephens
(74) *Attorney, Agent, or Firm* — Morrison & Foerster LLP

(57) ABSTRACT

The present inventions relate to a breeding system for the production of polyploid maize seeds, maize plants, or maize plant parts where cycles of meiosis, syngamy, and selection are used for interpopulation improvement of progenitor lines, and sexual polyploidization occurs during hybrid production by inducing clonal gamete formation in the parents that are to be crossed. Reciprocal recurrent selection can be used to inform selection of candidate maize lines that are either advanced to a gene editing or genetic modification system or crossed and selected to induce clonal gamete formation by arresting meiotic recombination and chromosome reduction. Crosses of parent maize plants bearing clonal gametes are planned and executed based upon predicted heterotic performance at the polyploid level. The final product is a homogeneous population of hybrid polyploid maize seed, or derivative thereof, bearing both parents' complete nuclear genomes.

6 Claims, 57 Drawing Sheets

Specification includes a Sequence Listing.

Related U.S. Application Data filed on Apr. 21, 2023, provisional application No. 63/497,670, filed on Apr. 21, 2023, provisional application No. 63/423,768, filed on Nov. 8, 2022, provisional application No. 63/423,765, filed on Nov. 8, 2022.

(56) References Cited

U.S. PATENT DOCUMENTS

| | | |
|---|---|---|
| 2009/0075829 A1 | 3/2009 | Bush et al. |
| 2009/0117617 A1 | 5/2009 | Holmes et al. |
| 2012/0042408 A1 | 2/2012 | Mercier et al. |
| 2012/0142062 A1 | 6/2012 | Doyon et al. |
| 2019/0098858 A1 | 4/2019 | Albertsen et al. |
| 2019/0300900 A1 | 10/2019 | Sirizzotti et al. |
| 2020/0362366 A1 | 11/2020 | Davey et al. |
| 2021/0002657 A1 | 1/2021 | Bass et al. |
| 2021/0054390 A1 | 2/2021 | Chen et al. |
| 2021/0363537 A1 | 11/2021 | Wang et al. |
| 2024/0147926 A1 | 5/2024 | Ward et al. |
| 2024/0409950 A1 | 12/2024 | Ward et al. |

FOREIGN PATENT DOCUMENTS

| | | | | |
|---|---|---|---|---|
| WO | WO-2017161264 A1 | * | 9/2017 | ............... A01H 1/08 |
| WO | WO-2024256682 A1 | | 12/2024 | |

OTHER PUBLICATIONS

Washburn et al. "Progressive heterosis in genetically defined tetraploid maize" 2019 J. Genetics and Genomics 46:389-396. (Year: 2019).*
Brownfield and Kohler "Unreduced Gamete Formation in Plants: Mechanisms and Prospects" 2011 J. Exp. Botany 62(5):1659-1668. (Year: 2011).*
Mieulet et al. "Turning Rice Meiosis Into Mitosis" 2016 Cell Research 26:1242-1254 (Year: 2016).*
Beurdeley et al., (2013). "Compact designer TALENs for efficient genome engineering," Nature Communications, 4:1762, 8 pages.
Brownfield et al., (2011). "Unreduced gamete formation in plants: mechanisms and prospects," Journal of Experimental Botany, 62(5):1659-1668.
Cao et al., (2014). "PEG-mediated transient gene expression and silencing system in maize mesophyll protoplasts: a valuable tool for signal transduction study in maize," Acta Physiologiae Plantarum, 36(5):1271-1281.
Cermak et al., (2011). "Efficient design and assembly of custom TALEN and other TAL effector-based constructs for DNA targeting," Nucleic Acids Research, 39(12):e82, 11 pages.
Clasen et al., (2016). "Improving cold storage and processing traits in potato through targeted gene knockout," Plant Biotechnology Journal, 14(1):169-176.
Colle et al., (2019). "Haplotype-phased genome and evolution of phytonutrient pathways of tetraploid blueberry," GigaScience, 8(3):giz012, 15 pages.
d'Erfurth et al., (2009). "Turning Meiosis into Mitosis," PLoS Biology, 7(6):e1000124, 10 pages.
Dhed'a et al., (1991). "Plant regeneration in cell suspension cultures of the cooking banana cv. Bluggoes'(*musa* spp. ABB group)," Fruits, 46(2):125-135.
Doyle et al., (2012). "TAL Effector-Nucleotide Targeter (TALE-NT) 2.0: tools for TAL effector design and target prediction," Nucleic Acids Research, 40:W117-122.
Fossi et al., (2019). "Regeneration of Solanum tuberosum plants from protoplasts induces widespread genome instability," Plant Physiology, 180(1):78-86.
Gabsalilow et al., (2013). "Site- and strand-specific nicking of DNA by fusion proteins derived from MutH and I-SceI or TALE repeats," Nucleic Acids Research, 41:e83, 11 pages.

Gallais, (1984). "An Analysis of Heterosis Vs. Inbreeding Effects With An Autotetraploid Cross-Fertilized Plant: *Medicago sativa* L.," Genetics, 106(1):123-137.
Groose et al., (1989). "Progressive Heterosis in Autotetraploid Alfalfa: Studies Using Two Types of Inbreds," Crop Sci., 29:1173-1177.
Guo et al., (2013). "The draft genome of watermelon (*Citrullus lanatus*) and resequencing of 20 diverse accessions," Nature Genetics, 45:51-58.
Haicour et al., (2009). "Protoplast isolation and culture for banana regeneration via somatic embryogenesis," Fruits, 64(4):261-269.
Huy et al. (1997). "Protoplast isolation, culture, and cell differentiation in raspberry and blackberry cultivars (*rubus* spp.)." Angewandte-Botanik 71(3-4): 131-137.
Jansky et al., (2016). "Reinventing potato as a diploid inbred line-based crop," Crop Science, 56(4):1412-1422.
Jeong et al., (2021). "Optimization of protoplast regeneration in the model plant *Arabidopsis thaliana*," Plant Methods, 17(1):21, 16 pages.
Jiang et al., (2021). "Concerted genomic and epigenomic changes accompany stabilization of *Arabidopsis allopolyploids*," Nature Ecology & Evolution, 5:1382-1393, 22 pages.
Kouranov et al., (2022). "Demonstration of targeted crossovers in hybrid maize using CRISPR technology," Communications Biology, 5:53, 11 pages.
Li, (2013). "Aligning sequence reads, clone sequences and assembly contigs with BWA-MEM," arXiv, 1303.3997, 3 pages.
Liu et al., (2022). "Establishment of a DNA-free genome editing and protoplast regeneration method in cultivated tomato (*Solanum lycopersicum*)," Plant Cell Rep., 41(9):1843-1852.
Masters et al., (2020). "Agrobacterium Mediated Immature Embryo Transformation of Recalcitrant Maize Inbred Lines Using Morphogenic Genes," J. Vis. Exp., (156):e60782, 11 pages.
McCaw et al., (2020). "Development of a Transformable Fast-Flowering Mini-Maize as a Tool for Maize Gene Editing," Frontiers in Genome Editing, 2:622227, 14 pages.
McKenna et al., (2010). "The Genome Analysis Toolkit: a MapReduce framework for analyzing next-generation DNA sequencing data," Genome Research, 20(9):1297-1303.
Nicolia et al., (2015). "Targeted gene mutation in tetraploid potato through transient TALEN expression in protoplasts," Journal of Biotechnology, 204:17-24.
Nishiyama et al., (2007). "Embryological studies on cross-incompatibility between 2x and 4x in *Brassica*," Japanese Journal of Genetics, 41(1):27-42.
Noli et al., (2013). "Criteria for the definition of similarity thresholds for identifying essentially derived varieties," Plant Breeding, 132(6):525-531.
O'Leary et al., (2015). "Reference sequence (RefSeq) database at NCBI: current status, taxonomic expansion, and functional annotation," Nucleic Acids Res., 44(1)1):D733-D745.
Ott et al., (2017). "tGBS® genotyping-by-sequencing enables reliable genotyping of heterozygous loci," Nucleic acids research, 45(21):e178, 12 pages.
Panis et al., (1993). "Plant regeneration through direct somatic embryogenesis from protoplasts of banana (*musa* spp.)," Plant Cell Reports, 12(7):403-407.
Clot et al., (2024). "Crossover shortage in potato is caused by StMSH4 mutant alleles and leads to either highly uniform unreduced pollen or sterility," Genetics, 226(1):iyad194, 13 pages.
Peloquin et al., (1999). "Meiotic Mutants in Potato: Valuable Variants," Genetics, 153:1493-1499.
Porto et al., (2020). "Base editing: advances and therapeutic opportunities," Nature Reviews Drug Discovery, 19(12):839-859, 60 pages.
Qiu et al., (2018). "Regeneration of Blueberry Cultivars through Indirect Shoot Organogenesis," HortScience, 53(7):1045-1049.
Ren et al., (2017). "Novel technologies in doubled haploid line development," Plant Biotechnol J, 15:1361-1370.
Rizzo et al., (2022). "Climate and agronomy, not genetics, underpin recent maize yield gains in favorable environments," PNAS, 119(4):e2113629119, 6 pages.

(56) References Cited

OTHER PUBLICATIONS

Sprunck et al., (2012). "Egg cell-secreted EC1 triggers sperm cell activation during double fertilization," Science, 338(6110):1093-1097.
Tian et al. (2017. "Efficient CRISPR/Cas9-based gene knockout in watermelon" Plant Cell Rep 36:399-406.
UniProt Consortium, (2019). "UniProt: a worldwide hub of protein knowledge," Nucleic Acids Res., 47(D1):D506-D515.
University of Hohenheim, (2020). "Heterotic groups," available online at <https://weizen.uni-hohenheim.de/en/111475>, 3 pages.
VanBuren et al., (2016). "The genome of black raspberry (*Rubus occidentalis*)," The Plant Journal, 87(6):535-547.
Veillet et al., (2019). "The Solanum tuberosum GBSSI gene: a target for assessing gene and base editing in tetraploid potato," Plant Cell Reports, 38(9):1065-1080, 34 pages.
Vernet et al., (2022). "High-frequency synthetic apomixis in hybrid rice," Nature Comm, 13:7963, 13 pages.
Vijayakumar et al., (2021). "High temperature induced changes in quality and yield parameters of tomato (*Solanum lycopersicum* L.) and similarity coefficients among genotypes using SSR markers," Heliyon, 7(2):e05988, 15 pages.
Vivian-Smith et al., (1999). "Genetic analysis of growth-regulator-induced parthenocarpy in *Arabidopsis*," Plant Physiology, 121(2):437-452.
Washburn et al., (2014). "Polyploids as a "model system" for the study of heterosis," Plant Reprod, 27:1-5.
Washburn et al., (2019). "Progressive heterosis in genetically defined tetraploid maize," Journal of Genetics and Genomics, 46:389-396.
Watanabe, (2015). "Potato genetics, genomics, and applications," Breed Sci., 65(1):53-68.
Wu et al. (2018). "A Simple Method for Isolation of Soybean Protoplasts and Application to Transient Gene Expression Analyses," Journal of Visualized Experiments, 131:e57258, 7 pages.
Wu et al. (2020). "Establishment of a PEG-mediated protoplast transformation system based on DNA and CRISPR/Cas9 ribonucleoprotein complexes for banana," BMC Plant Biology, 20:425, 10 pages.
Wu et al., (2014). "Target specificity of the CRISPR-Cas9 system," Quant Biol., 2(2):59-70, 19 pages.
Wu et al., (2019). "Genome of 'Charleston Gray', the principal American watermelon cultivar, and genetic characterization of 1,365 accessions in the U.S. National Plant Germplasm System watermelon collection," Plant Biotechnol J., 17(12): 2246-2258.
Yanik et al., (2013). "TALE-Pvull fusion proteins—novel tools for gene targeting," PLoS One, 8:e82539, 13 pages.
Yoo et al., (2007). "*Arabidopsis mesophyll* protoplasts: a versatile cell system for transient gene expression analysis," Nature Protocols, 2(7):1565-1572.
Yu et al., (2011). "Generation of transgenic watermelon resistant to Zucchini yellow mosaic virus and Papaya ringspot virus type W," Plant Cell Rep, 30:359-371, 19 pages.
Arisumi, (1982). "Endosperm balance numbers among New Guinea-Indonesian Impatiens species," Journal of Heredity, 73(3):240-242.
Birchler, (1993). "Dosage analysis of maize endosperm development," Annu Rev Genet., 27:181-204.
Dalamu et al., (2023). "Genetic Diversity and Population Structure Analyses Using Simple Sequence Repeat Markers and Phenotypic Traits in Native Potato Collection in India," Potato Research: 1-25.
Dhir et al., (1992). "Regeneration of fertile plants from protoplasts of soybean (*Glycine max* L. Merr.): genotypic differences in culture response," Plant Cell Reports, 11:285-289.
Galbraith et al., (1983). "Rapid flow cytometric analysis of the cell cycle in intact plant tissues," Science, 220(4601):1049-1051.
Heslop-Harrison et al., (1970). "Evaluation of pollen viability by enzymatically induced fluorescence; intracellular hydrolysis of fluorescein diacetate," Stain Technology, 45(3):115-120.
Jarl et al., (1995). "Protoplast regeneration and fusion in Cucumis: melon x cucumber," Plant Cell, Tissue and Organ Culture, 43:259-265.

Jones et al., (2019). "Maize transformation using the morphogenic genes Baby Boom and Wuschel2," Transgenic Plants, pp. 81-93.
Klein et al., (1987). "High-velocity microprojectiles for delivering nucleic acids into living cells," Nature, 327:70-73.
Krens et al., (1982). "In vitro transformation of plant protoplasts with Ti-plasmid DNA," Nature, 296:72-74.
Larkin (1976). "Purification and viability determinations of plant protoplasts," Planta, 128(3):213-216.
Linsmaier et al., (1965). "Organic growth factor requirements of tobacco tissue cultures," Physiol. Plant., 18(1):100-127.
Lloyd et al., (1980). "Commercially-feasible micropropagation of mountain laurel, *Kalmia latifolia*, by use of shoot-tip culture," Proc. Int. Plant Prop. Soc., 30:421-427.
Masson et al., (1987). "Plant regeneration from protoplasts of diploid potato derived from crosses of Solanum tuberosum with wild Solanum species," Plant Science, 53(2):167-176.
Mok et al., (1975). "Breeding value of 2n pollen (diplandroids) in tetraploid x diploid crosses in potatoes," Theor. Appl. Genet., 46(6):307-314.
Murashige et al., (1962). "A revised medium for rapid growth and bioassays with tobacco tissue cultures," Physiologia Plantarum, 15(3):473-497.
Negrutiu et al., (1987). "Hybrid genes in the analysis of transformation conditions: I. Setting up a simple method for direct gene transfer in plant protoplasts," Plant. Mol. Biol., 8:363-373.
Ortiz et al., (1992). "The importance of Endosperm Balance Number in potato breeding and the evolution of tuber-bearing *solanum* species," Euphytica, 60:105-113.
Paz et al., (1997). "Genetic Diversity Based on Randomly Amplified Polymorphic DNA (RAPD) and Its Relationship with the Performance of Diploid Potato Hybrids," Journal of the American Society for Horticultural Sci., 122(6):740-747.
Popescu et al., (2000). "High frequency shoot regeneration from leaf-derived callus in raspberry (*Rubus idaeus* L.)," Eucarpia Symposium on Fruit Breeding and Genetics, 538:667-670.
Shahin (1985). "Totipotency of tomato protoplasts," Theoretical and Applied Genetics, 69(3):235-240.
Shillito et al., (1985). "High Efficiency Direct Gene Transfer to Plants," Bio/Technol., 3:1099-1102.
Vosman et al., (2004). "The establishment of 'essential derivation' among rose varieties, using AFLP, " Theoretical and Applied Genetics, 109:1718-1725.
Wan et al., (1989). "Efficient production of doubled haploid plants through colchicine treatment of anther-derived maize callus," Theor. Appl. Genet., 77:889-892.
Wang et al., (2020). "Biolistic DNA delivery in maize immature embryos," Biolistic DNA Delivery in Plants: Methods and Protocols, pp. 177-195.
Werner et al., (1991). "Occurrence and mechanisms of 2n egg formation in 2x potato," Genome, 34(6):975-982.
Werner et al., (2015). "Inheritance and Two Mechanisms of 2n Egg Formation in 2x Potatoes," Journal of Heredity, 81(5):371-374.
Crossway et al., (1986). "Integration of foreign DNA following microinjection of tobacco mesophyll protoplasts," Mol. Gen. Genet., 202:179-185.
GenBank, (2014). "Accession No. AC216275, *Zea maya* cultivar B73 chromosome 5 clone CH201-219E6, * Sequencing in Progress * , 5 unordered pieces," available online at <https://www.ncbi.nlm.nih.gov/nuccore/AC21 6275>, 2 pages.
GenBank, (2005). "Accession No. AC155415, *Zea mays* strain B73 clone. ZMMBBb0209O15, * Sequencing in Progress *, 19 unordered pieces," available online at <https://www.ncbi.nlm.nih.gov/nuccore/AC1 55415>, 2 pages.
GenBank, (2000). "Accession No. AC009273, Sequence of BAC T 1N6 from *Arabidopsis thaliana* chromosome 1, complete sequence," available online at <https://www.ncbi.nlm.nih.gov/nuccore/A0009273>, 2 pages.
GenBank, (2020). "Accession No. CP055239, Solanum tuberosum cultivar Solyntus chromosome 6," available online at <https://www.ncbi.nlm.nih.gov/nuccore/0P055239>, 2 pages.
GenBank, (2020). "Accession No. CP046692, Solanum tuberosum cultivar MSH/14-112 chromosome 6," available online at <https://www.ncbi.nlm.nih.gov/nuccore/CP046692>, 1 page.

(56) References Cited

OTHER PUBLICATIONS

GenBank, (2020). "Accession No. CP055240, Solanum tuberosum cultivar Solyntus chromosome 7," available online at <https://www.ncbi.nlm.nih.gov/nuccore/CP055240>, 1 page.

GenBank, (2020). "Accession No. CP046700, Solanum tuberosum cultivar MSH/14-112 chromosome 7," available online at <https://www.ncbi.nlm.nih.gov/nuccore/CP046700>, 1 page.

GenBank, (2020). "Accession No. CP055244, Solanum tuberosum cultivar Solyntus chromosome 11," available online at <https://www.ncbi.nlm.nih.gov/nuccore/CP055244>, 2 pages.

GenBank, (2020). Accession No. CP046691, Solanum tuberosum cultivar MSH/14-112 chromosome 11, available online at <https://www.ncbi.nlm.nih.gov/nuccore/0P046691>, 1 page.

International Search Report and Written Opinion received for International Patent Application No. PCT/US2023/079146 mailed on May 21, 2024, 20 pages.

Jansky et al., (2014). "M6: A Diploid Potato Inbred Line for Use in Breeding and Genetics Research," J. of Plant Registrations, doi: 10.3198/jpr2013.05.0024crg (5 total pages).

Jansky et al., (2018). "The Evolution of Potato Breeding," Plant Breeding Reviews, 41, (46 total pages).

Mahoney et al., (2019). "Sexual and Apomictic Seed Reproduction in *aronia* Species with Different Ploidy Levels," HortScience, 54(4):642-646.

Max Planck Institute for Plant Breeding Research, (2024). "Like dad and like mum . . . all in one plant," available online at <www.sciencedaily.com/releases/2024/05/240513150437.htm>, 3 pages.

Max Planck Institute for Plant Breeding Research, (2024). "Mitosis instead of Meiosis: Researchers breed tomato plants that contain the complete genetic material of both parent plants," available online at <https://www.mpipz.mpg.de/pr-underwood-2024-05-en>, 3 pages.

Wang et al., (2024). "Harnessing clonal gametes in hybrid crops to engineer polyploid genomes," Nat Genet, 56(6):1075-1079, 12 pages.

D'Erfurth et al., (2010). "The Cyclin-A CYCA1;2/TAM is Required for the Meiosis I to Meiosis II Transition and Cooperates with OSD1 for the Prophase to First Meiotic Division Transition," PLoS Genetics, 6(6):e1000989, 12 pages.

Guo et al., (2017). "Transcriptome analysis of neotetraploid rice reveals specific differential gene expressions associated with fertility and heterosis," Scientific Reports, 7:40139, 11 pages.

Kronholm et al., (2012). "Genetic basis of adaptation in *Arabidopsis thaliana*: local adaptation at the seed dormancy QTL DOG1," Evolution, 66(7):2287-302.

Qian et al., (2024). "Genetic manipulation of the genes for clonal seeds results in sterility in cotton," BMC Plant Biology, 24:946, 12 pages.

Tiwari, (2022). "Chapter 9: Conventional True Potato Seed (TPS) to Diploid Hybrid Potato Technologies," Potato Improvement in the Post-Genomics Era, pp. 231-247.

Xie et al., (2019). "A strategy for generating rice apomixis by gene editing," JIPB, 61(8):911-916.

\* cited by examiner

REC8, maize

```
Consensus                        MFYSHQLLARKAPLGQIWMAATLHSKINRKRLDKLDIIKICEEILNPSVXXXXRLSGILM  60
ZmRec8 - WT                      ..........................................PMAL........     60
ZmRec8 - B-PED2707-035 allele 1  ..........................................----........     56

Consensus                        GGVVIVYERKVKLLYTDVSRLLTEINEAWRIKPVTDPTVLPKGKTQAKYEAVTLPEINMV 120
ZmRec8 - WT                      ............................................................ 120
ZmRec8 - B-PED2707-035 allele 1  ............................................................ 116

Consensus                        VEQPMFFSEPDGAKFRRMGLEDLDEQYVQVNLDDDDFSHADDRHQAKAVNITLVDNFESG 180
ZmRec8 - WT                      ............................................................ 180
ZmRec8 - B-PED2707-035 allele 1  ............................................................ 176

Consensus                        LAETDLFNHFERFDIADDETTVNITPDEYPQVPSTLIPSPPRQEDIPQQEEPYYAAPSPV 240
ZmRec8 - WT                      ............................................................ 240
ZmRec8 - B-PED2707-035 allele 1  ............................................................ 236

Consensus                        HGEPQQGGPEDQEEQKMKQPPKASKRKARWEVPRVIMDNNQMMIPGNIYQTWLKDASSLV 300
ZmRec8 - WT                      ............................................................ 300
ZmRec8 - B-PED2707-035 allele 1  ............................................................ 296

Consensus                        SKRRKLNSNFNFIRSTKISDLMHIPPVALISHDNLFSELCYPKPLMQLWKDCTEVKSTKA 360
ZmRec8 - WT                      ............................................................ 360
ZmRec8 - B-PED2707-035 allele 1  ............................................................ 356

Consensus                        SSGGQRSSSQEPQPKNSPPQAGGEYEMETGGLPMDLTDGIEKLRANMSAKYDRAYNILHS 420
ZmRec8 - WT                      ............................................................ 420
ZmRec8 - B-PED2707-035 allele 1  ............................................................ 416

Consensus                        DHSVTPGSPAGLSRRSASSSGGSGSAFIQLDPEVQLPSGSGRSKRGQHSSARSLGNLDTV 480
ZmRec8 - WT                      ............................................................ 480
ZmRec8 - B-PED2707-035 allele 1  ............................................................ 476

Consensus                        EEDFPLEQEVRDFKMRRLSDYVPTPDLLECTEPTQTPYERRSNPMDKITETIQSHLKHF  540
ZmRec8 - WT                      ............................................................ 540
ZmRec8 - B-PED2707-035 allele 1  ............................................................ 536

Consensus                        DTPGVPQSESLSHLAHGMTKARAARLFYQIAVLATCDYIKVTQLERKGDELYGDILISRG 600
ZmRec8 - WT                      ............................................................ 600
ZmRec8 - B-PED2707-035 allele 1  ............................................................ 596

Consensus                        LKM 603
ZmRec8 - WT                      ... 603
ZmRec8 - B-PED2707-035 allele 1  ... 599
```

FIG. 23A

OSD1, maize

```
Consensus                                    MLEVRTARRPALADISGGGFFMRTVESPGAVLVNGAVKRPARQFLSPSSNKENVPPVGAF   60
ZmOsd1-chr5 - WT                             ............................................................   60
ZmOsd1-chr5 - B-PED2707-035 - allele 1       ............................................................   60
ZmOsd1-chr5 - B-PED2707-035 - allele 2       ............................................................   60

Consensus                                    RATPKRRTPLPDWYPRTPLRDITSIVKAIERRRSRLQNAAAQQQIQWTEDPSRSVDPITP  120
ZmOsd1-chr5 - WT                             ............................................................  120
ZmOsd1-chr5 - B-PED2707-035 - allele 1       ............................................................  120
ZmOsd1-chr5 - B-PED2707-035 - allele 2       ............................................................  120

Consensus                                    VQAEQGGVPTTVDGQGVGSPATCLEDGXXXXXXXXXXXXXXXXXXXXXXXXXXXXXXXX  180
ZmOsd1-chr5 - WT                             ...........................KLKTSSYPSSDCSLQATPSKPNDPALADLVEKK  180
ZmOsd1-chr5 - B-PED2707-035 - allele 1       ...........................SPIHHLTAPCRPLHPNQTIQLSQISWRRSCPAR  180
ZmOsd1-chr5 - B-PED2707-035 - allele 2       ...........................KLKI*---------------------------  180

Consensus                                    XSSSIEQIEKMVRRNLK-RTSKAAQPSKRTIQRRVLMSMR-------------------  239
ZmOsd1-chr5 - WT                             L...........................-.........................----  239
ZmOsd1-chr5 - B-PED2707-035 - allele 1       *-----------------------------------------------------------  240
ZmOsd1-chr5 - B-PED2707-035 - allele 2       ------------------------------------------------------------  240

Consensus                                    ------------------------------------------------------------  299
ZmOsd1-chr5 - WT                             ------------------------------------------------------------  299
ZmOsd1-chr5 - B-PED2707-035 - allele 1       ------------------------------------------------------------  300
ZmOsd1-chr5 - B-PED2707-035 - allele 2       ------------------------------------------------------------  300

Consensus                                    ------------------------------------------------------------  219
ZmOsd1-chr5 - WT                             ------------------------------------------------------------  219
ZmOsd1-chr5 - B-PED2707-035 - allele 1       ------------------------------------------------------------  181
ZmOsd1-chr5 - B-PED2707-035 - allele 2       ------------------------------------------------------------  152
```

FIG. 23B

SPO11-1, maize

```
Consensus              MAGRDKRRRAAPLEGDEQQLRRRLEEAALLLRRIKGLVRWIVEEVAAGRSPSIVLHRYRN  60
ZmSpo11-1 - WT         ............................................................  60
ZmSpo11-1 - B-PED2707-035 allele 1  ............................................................  60

Consensus              YCSSADSASPSPCACSYDIPVGTDVLSLLHKDYHTSXXXXLLRVLFVVQQLLQQNKHCSK  120
ZmSpo11-1 - WT         ...................................RLNV...................  120
ZmSpo11-1 - B-PED2707-035 allele 1  ...................................MCS*...................  120

Consensus              RDIYMYPSIFVEVAVVDRAINDICILFKCSRHNLNVVPVVKGLVMGWIRFMEGEKKVYC  180
ZmSpo11-1 - WT         ............................................................  180
ZmSpo11-1 - B-PED2707-035 allele 1  _____  180

Consensus              ITSVNAAFSIPVDIEAIKDVVSVAHYILVVEKETVFQRLANDKFCERNRCIVITGRGYPD  240
ZmSpo11-1 - WT         ............................................................  240
ZmSpo11-1 - B-PED2707-035 allele 1  _____  240

Consensus              IPTRRFLRYLVELLHLPAYCLVDSDPYGFDILATYKFGSLQAHDANLLRVPDIRWLGVF  300
ZmSpo11-1 - WT         ............................................................  300
ZmSpo11-1 - B-PED2707-035 allele 1  _____  300

Consensus              TSDFEEYCLPDCCLLRLSPEDRRKAEGILARCYLHREAPEWRSELEAMLQKGVKFEIEAL  360
ZmSpo11-1 - WT         ............................................................  360
ZmSpo11-1 - B-PED2707-035 allele 1  _____  360

Consensus              SANSISFLSHEYIPQKIKQGMHL  383
ZmSpo11-1 - WT         .......................  383
ZmSpo11-1 - B-PED2707-035 allele 1  _____  100
```

FIG. 23C rec8, maize

```
PRS130                                                                                              G
ZmREC8-WT                  TTTGACTGCTATTTTTGTGTTTTTTTATTTGTTTTGTTGTGTGTTCACTTTTGTTGAGTGAGGAAATTTG
ZmREC8-WT translation                                                                  -intron-[E][E][I][L]
PED-MN-MiMe                TTTGACTGCTATTTTTGTGTTTTTTTATTTGTTTTGCTGACTTTGTTGTGTGTTCACTTTTAGTGAGGAAATTTG AACCCCTCGGTGCCATGG
AACCCCTCGGTGCCGCCATGGCTCTGAGGCTCTGAATTCCATGGGTGAGTTCATTTGCTTGCGCCACCCAAAACTGTTCCTCCCATTTTTGGATAGTTTTTTTACGTTCCAA  200
[N][P][S][V][P][M][A][L][R][L][*][S][G][I][I][L][I][M][G]-intron-
AACCCCTCGGTGC--------GGCTCTGGAATCCTCATGGGTGAGTTCATTTGCTTGCGCCACCCAAAACTGTTCCTCCCATTTTTGGATAGTTTTTTTACGTTCCAA      108
```

*spo11-1*, maize

```
PR5586
ZmSPO11-1-WT            CCCTGGGCGCGGCTCGTGCGTGATTGCAGTGCCTGAGCTAGGACATCCCGTCGGCACGGACGTCTCTCTTGTTCACAAGGACTACCACACTCC
ZmSPO11-1-WT translation                     -intron-[A][C][S][Y][D][L][P][V][G][T][D][V][L][S][I][L][I][H][I][K][D][Y][I][H][T][L][S]
PED-MN-MiMe             CCCTGGCGCGGCTCGTGCGTGATTGCAGTGCCTGAGCTAGGACATCCCGTCGGCACGGACGTCTCTCTGTCCACAAGGACTACCACACTC- CGCCTCAGTACGAATACATC
ZmSPO11-1-WT            CGCCTCAGTACGAATACATCTAAATCTTTGCATTTATGTGATCACACTAATTACTTCTGATGCGTAGTGTTCATGCCTAGAGTGCTCCTGAGGGTGCTGT    200
ZmSPO11-1-WT translation [R][L]-intron-                                                    -intron-[V][L]
PED-MN-MiMe             -----AGTACGAATACATCTAAATCTTTGCATTTATGTGATCACACTAATTACTTCTGATGCGTAGTGTTCATGCCTAGAGTGCTCCTGAGGGTGCTGT    193
```

FIG. 23F

OSD1, *A. thaliana*

```
Consensus                        MPEARDRTERPVDYSTIFANPRRHGILLOEPDCPLELIESPVRPDIGSIGGTGGLVPGKP  60
AtOsd1 (Col-0) - WT              ............................................................  60
AtOsd1 (Col-0) - SB01_F3 allele 1 ............................................................  60
AtOsd1 (Col-0) - SB01_F3 allele 2 ............................................................  60

Consensus                        TTWPPGHGROGHTPFRLPQGRERMPIVTARRGPGGGLLPSWYPRTPLRDITHIVRAIERR 120
AtOsd1 (Col-0) - WT              ............................................................ 120
AtOsd1 (Col-0) - SB01_F3 allele 1 ............................................................ 120
AtOsd1 (Col-0) - SB01_F3 allele 2 ............................................................ 120

Consensus                        RGAGTGGDDGRVIEIPTHRQVGVXXXXXXXXXXXXXXXXXXXXXCXXXXNXXXNXXF   180
AtOsd1 (Col-0) - WT              .......................LESPVPLSGEHKCSMVTPQPSVGFKRS.PPSTA.VQ. 180
AtOsd1 (Col-0) - SB01_F3 allele 1 .......................PVRRTQMLDGHSWTICGIQA*------------------ 180
AtOsd1 (Col-0) - SB01_F3 allele 2 .......................LESRWSLLDHLWDSSVVAHHQLLKPKR.YLTSL.R*-  180

Consensus                        MLLDITREIAEEEAGPITPEKKLLNSIDRVEKIVMAEIQKLKSTPQARRSEPSKRVRTLN 240
AtOsd1 (Col-0) - WT              ............................................................ 240
AtOsd1 (Col-0) - SB01_F3 allele 1 ------------------------------------------------------------ 240
AtOsd1 (Col-0) - SB01_F3 allele 2 ------------------------------------------------------------ 240

Consensus                        TMR 243
AtOsd1 (Col-0) - WT              ... 243
AtOsd1 (Col-0) - SB01_F3 allele 1 --- 164
AtOsd1 (Col-0) - SB01_F3 allele 2 --- 179
```

FIG. 28A

**SPO11-1, *A. thaliana***

```
Consensus                       MEGKFAISESTELLQRIKDFTQSVVVDLAEGRSPKISINQFRHYCMHPEADCLCSSDKPR   60
AtSpo11 (Col-0) - WT            ............................................................   60
AtSpo11 (Col-0) SB01_F3 allele 1 ...........................................................   60
AtSpo11 (Col-0) SB01_F3 allele 2 ...........................................................   60

Consensus                       GQXXXXXXKXXZXXXXXMLLRVLLIVQQLLQENRHASKRDIYYMHPSAFKAQSIVDPAIG  120
AtSpo11 (Col-0) - WT            ..EIPTLK.EPQTYRID...........................................  120
AtSpo11 (Col-0) SB01_F3 allele 1 ..VLRPNH.PTESICC*------------------------------------------  120
AtSpo11 (Col-0) SB01_F3 allele 2 ..E*-------------------------------------------------------  120

Consensus                       DICILFQCSHYNLDVVSVGHGLVMGWLKFREASRKFDCLNSLNTAYSVPVLVEEVEGIVS  180
AtSpo11 (Col-0) - WT            ............................................................  180
AtSpo11 (Col-0) SB01_F3 allele 1 -----------------------------------------------------------  180
AtSpo11 (Col-0) SB01_F3 allele 2 -----------------------------------------------------------  180

Consensus                       LAEHILVYEKETVFQKLANDMFCKTHRCIVITGKGYPDVSTPRFLPLLMEKLHLPVHCLV  240
AtSpo11 (Col-0) - WT            ............................................................  240
AtSpo11 (Col-0) SB01_F3 allele 1 -----------------------------------------------------------  240
AtSpo11 (Col-0) SB01_F3 allele 2 -----------------------------------------------------------  240

Consensus                       DCDPYGFEILATYRFGSMQMAYDIESLRAPDMKWLGAFPSDSEVYSVPQCLLPLTEEDK  300
AtSpo11 (Col-0) - WT            ............................................................  300
AtSpo11 (Col-0) SB01_F3 allele 1 -----------------------------------------------------------  300
AtSpo11 (Col-0) SB01_F3 allele 2 -----------------------------------------------------------  300

Consensus                       KHIEAMLLRCYLKREMFQWRLELETMLKRGVKFEIERLSVHSLSFLSEVYIPSKIRREVS  360
AtSpo11 (Col-0) - WT            ............................................................  360
AtSpo11 (Col-0) SB01_F3 allele 1 -----------------------------------------------------------  360
AtSpo11 (Col-0) SB01_F3 allele 2 -----------------------------------------------------------  360

Consensus                       SP                                                            362
AtSpo11 (Col-0) - WT            ..                                                            362
AtSpo11 (Col-0) SB01_F3 allele 1 --                                                            77
AtSpo11 (Col-0) SB01_F3 allele 2 --                                                            64
```

FIG. 28B

REC8, *A. thaliana*

```
Consensus                               MLRLESLIVTVWGFATLLARKAPLGQIWMAATLHAKINRKKLDKLDIIQICEEILNPSVP  60
AtRec8 (Col-0) - WT                     ............................................................  60
AtRec8 (Col-0) - SB01_F3 allele 1       ............................................................  60
AtRec8 (Col-0) - SB01_F3 allele 2       ............................................................  60

Consensus                               MALRLSGILMGGVVIVYERKVKLLFDDVNRFLVEINGAWRTKSVPDPTLLPKGKTHARKE 120
AtRec8 (Col-0) - WT                     ....................RLL..................................... 120
AtRec8 (Col-0) - SB01_F3 allele 1       ....................~~~..................................... 117
AtRec8 (Col-0) - SB01_F3 allele 2       ....................R*~~~~~~~~~~~~~~~~~~~~~~~~~~~~~~~~~~~~~~ 120

Consensus                               AVTLPENEEADFGDFEQTRNVPKFGNYMDFQQTFISMRLDESHVNNNPEPEDLGQQFHQA 180
AtRec8 (Col-0) - WT                     ............................................................ 180
AtRec8 (Col-0) - SB01_F3 allele 1       ............................................................ 177
AtRec8 (Col-0) - SB01_F3 allele 2       ~~~~~~~~~~~~~~~~~~~~~~~~~~~~~~~~~~~~~~~~~~~~~~~~~~~~~~~~~~~~ 180

Consensus                               DAENITLFEYHGSFQTNNETYDRFERFDIEGDDETQMNSNPREGAEIPTTLIPSPPRHED 240
AtRec8 (Col-0) - WT                     ............................................................ 240
AtRec8 (Col-0) - SB01_F3 allele 1       ............................................................ 237
AtRec8 (Col-0) - SB01_F3 allele 2       ~~~~~~~~~~~~~~~~~~~~~~~~~~~~~~~~~~~~~~~~~~~~~~~~~~~~~~~~~~~~ 240

Consensus                               IPEGVNPTSPQRQEQQENRRDGFAEQMEEQNIPDKEEHDRPQPAKKRARKTATSAMDYEQ 300
AtRec8 (Col-0) - WT                     ............................................................ 300
AtRec8 (Col-0) - SB01_F3 allele 1       ............................................................ 297
AtRec8 (Col-0) - SB01_F3 allele 2       ~~~~~~~~~~~~~~~~~~~~~~~~~~~~~~~~~~~~~~~~~~~~~~~~~~~~~~~~~~~~ 300

Consensus                               TIIAGHVYQSWLQDTSDILCRGEKRKVRGTIRPDMESFKRANMPPTQLFEKDSSYPPQLY 360
AtRec8 (Col-0) - WT                     ............................................................ 360
AtRec8 (Col-0) - SB01_F3 allele 1       ............................................................ 357
AtRec8 (Col-0) - SB01_F3 allele 2       ~~~~~~~~~~~~~~~~~~~~~~~~~~~~~~~~~~~~~~~~~~~~~~~~~~~~~~~~~~~~ 360

Consensus                               QLWSKNTQVLQTSSSESRHPDLRAEQSPGFVQERMHNHHQTDHHERSDTSSQNLDSPAEI 420
AtRec8 (Col-0) - WT                     ............................................................ 420
AtRec8 (Col-0) - SB01_F3 allele 1       ............................................................ 417
AtRec8 (Col-0) - SB01_F3 allele 2       ~~~~~~~~~~~~~~~~~~~~~~~~~~~~~~~~~~~~~~~~~~~~~~~~~~~~~~~~~~~~ 420

Consensus                               LRTVRTGKGASVESMMAGSRASPETINRQAADIDVTTPPYSGDVRSMPSTPSARGAASIR 480
AtRec8 (Col-0) - WT                     ............................................................ 480
AtRec8 (Col-0) - SB01_F3 allele 1       ............................................................ 477
AtRec8 (Col-0) - SB01_F3 allele 2       ~~~~~~~~~~~~~~~~~~~~~~~~~~~~~~~~~~~~~~~~~~~~~~~~~~~~~~~~~~~~ 480

Consensus                               NIEIGSKSRMPNRKRPNSSPRRGLEPVAEERPWEHREYEFEFSMLPEKRFTADKEILFET 540
AtRec8 (Col-0) - WT                     ............................................................ 540
AtRec8 (Col-0) - SB01_F3 allele 1       ............................................................ 537
AtRec8 (Col-0) - SB01_F3 allele 2       ~~~~~~~~~~~~~~~~~~~~~~~~~~~~~~~~~~~~~~~~~~~~~~~~~~~~~~~~~~~~ 540

Consensus                               ASTQTQKPVCNQSDEMITDSIKSHLKTHFETPGAPQVESLNKLAVGMDRNAAAKLFFQSC 600
AtRec8 (Col-0) - WT                     ............................................................ 600
AtRec8 (Col-0) - SB01_F3 allele 1       ............................................................ 597
AtRec8 (Col-0) - SB01_F3 allele 2       ~~~~~~~~~~~~~~~~~~~~~~~~~~~~~~~~~~~~~~~~~~~~~~~~~~~~~~~~~~~~ 600

Consensus                               VLATRGVIKVNQAEPYGDILIARGPNM                                  627
AtRec8 (Col-0) - WT                     ...........................                                  627
AtRec8 (Col-0) - SB01_F3 allele 1       ...........................                                  624
AtRec8 (Col-0) - SB01_F3 allele 2       ~~~~~~~~~~~~~~~~~~~~~~~~~~~                                  83
```

FIG. 28C

*osd1* first target site, Arabidopsis

```
PRS173
AtOSD1-WT             TGGTGGAACGGGCGGGCTTGTGAGAGGCAATTTCACTACATGGAGGCCTGGTAATGGCAGAGGTGGTCACACT
AtOSD1-WT translation [G][G][T][G][G][L][V][R][G][N][F][T][T][W][R][P][G][N][G][R][G][G][H][T]
PED-AR-BC             TGGTGGAACGGGCGGGCTTGTGAGAGGCAATTTCACTACATGGAGGCCTGGTAATGGCAGAGGTGGTCACACT
PED-AR-BC             ------------------------------------AAGATCTAGAAGCGACCAACTGACTATCTTCGTTTATGATTGATT GATTGCCACAGGGAAGAGAG
                      CCATTTAGATTGCCACAGGGAAGAGAGAGAATATGCCCATAGTGACCGCTAGGCGTGGAAGAGGTGGTGGTTTGTTGCCTTCTGGTATCCAAGA
                      [P][F][R][L][I][P][I][Q][I][R][I][E][I][N][M][I][P][I][I][I][V][I][T][I][A][I][R][I][R][I][G][I][R][I][G][I][G][I][L][I][L][I][I][P][I][S][I][W][I][Y][I][P][I][R]
                      CCATTTAGATTGCCACAGGGAA------TATGCCCATAGTGACCGCTAGGCGTGGAAGAGGTGGTGGTTTGTTGCCTTCTGGTATCCAAGA
                      GGAGGTAAGCAACTACTAACCTTCTCAAAATGCCCATAGTGACCGCTAGGCGTGGAAGAGGTGGTGGTTTGTTGCCTTCTGGTATCCAAGA ACACCTCTACGCGACATAACTCATATTGTGCGGG 200
                      [T][P][L][R][D][I][I][H][I][V][R]
                      ACACCTCTACGCGACATTACTCATATTGTGCGGG 193
                      ACACCTCTACGCGACATTACTCATATTGTGCGGG 174
```

FIG. 28D

*osd1* second target site, Arabidopsis

```
PRS175                  ACAGGCTATTGAGAGAAGAAGAGGAGCTGGGACTGGAGGAGACGATGGCCGAGTTATTGAGATCCCAACTCAT
AtOSD1-WT               [A][I][E][R][R][R][G][A][G][T][G][G][D][D][G][R][V][I][E][I][I][P][T][H]
AtOSD1-WT translation   ACAGGCTATTGAGAGAAGAAGAGGAGCTGGGACTGGAGGAGACGATGGCCGAGTATTGAGATCCCAACTCAT
PED-AR-AA               ACAGGCTATTGAGAGAAGAAGAGGAGCTGGGACTGGAGGAGACGATGGCCGAGTTATTGAGATCCCAACTCAT
PED-AR-AA               ACAGGCTATTGAGAGAAGAAGAGGAGCTGGGACTGGAGGAGACGATGGCCGAGTTATTGAGATCCCAACTCAT GTACCACTGTCAGGAGAACA
                        CGACAAGTTGGTGTTCTTGAATCTCCAGTACCACTGTCAGGAGAACAACAAATGCTGATGGTCACTCTGGACCATCTGTGGGA
                        [R][Q][V][G][V][L][E][S][P][V][L][I][S][G][E][H][I][K][C][S][M][V][T][P][G][P][S][V][G]
                        CGACAAGTTGGTGTTC--------------CTGTCAGGAGAACAACAAATGCTGATGGTCACTCTGGACCATCTGTGGGA
                        CGACAAGTTGGTGTTCTTGAATCTC-------------GATGGTCACTCTGGACCATCTGTGGGA TTCAAGCGTAGTTGCCCACCATCAACTGCTAAAGTTCAAAAGA    200
                        [F][K][R][S][C][P][P][S][T][A][K][V][Q][K]
                        TTCAAGCGTAGTTGCCCACCATCAACTGCTAAAGTTCAAAAGA
                        TTCAAGCGTAGTTGCCCACCATCAACTGCTAAAGTTCAAAAGA    183
                        TTCAAGCGTAGTTGCCCACCATCAACTGCTAAAAGA            169
```

FIG. 28E

*spo11-1*, Arabidopsis

```
PRS226
AtSPO11-1-WT                  AAGGTCAACGAGTATTGAAAACTAAGACCTCATGAATTTACCATTTTATTCTGTCTATAGCTCGATAAACCAAAGGGTCAGGAAATT
AtSPO11-1-WT translation                                                         -intron-[L][C][S][D][K][P][K][G][Q][E][I]]
PED-AR-AA                     AACGTCAACGAGTATTGAAAACTAAGACCTCATGAATTTACCATTTTATTCTGTCTATAGCTTATGCGGCTCTGATAAACCAAAGGGTCAGG------
PED-AR-AA                     AACGTCAACGAGTATTGAAAACTAAGACCTCATGAATTTACCATTTTATTCTGTCTATAGCTTATGCGGCTCTGATAAACCAAAGGGTCAGGAA----

TCACTCTTAAGAAGCAACCA
TCACTCTTAAGAAGCAACCACAAAACCTACACGAATCGGTGAGTCAGGTTTCAGGATAATTCTACAAGTACATTAGTGTTATCTTAATATAGCATCACATTG    200
[F][T][L][K][K][E][P][Q][T][Y][R][I]]-intron
-------TCTTAAGAAGCAACCACAAAACCTACACGAATCGGTGAGTCAGGTTTCAGATAATTCTACAAGTACATTAGTGTTATCTTAATATAGCATCACATTG    190
---------TAAGAAGCAACCACAAAACCTACACGAATCGGTGAGTCAGGTTTCAGATAATTCTACAAGTACATTAGTGTTATCTTAATATAGCATCACATTG    189
```

FIG. 28F rec8, Arabidopsis

```
pRS205
AtREC8-WT                    GATTTTTTTTTCCTCAGTTCTTCACATTCTGGGTTCTTCAATGTTTGTTTATTCGATAGGTGGTGTGATTGTT
AtREC8-WT translation                                                              -intron-[G][V][V][I][I][V]
PED-AR-AA                    GATTTTTTTTTCCTCAGTTCTTCACATTCTGGGTTCTTCAATGTTTGTTTATTCGATAGGTGGTGTGATTGTT
PED-AR-AA                    GATTTTTTTTTCCTCAGTTCTTCACATTCTGGGTTCTTCAATGTTTGTTTATTCGATAGGTGGTGTGATTGTT
PED-AR-BC                    GATTTTTTTTTCCTCAGTTCTTCACATTCTGGGTTCTTCAATGTTTGTTTATTCGATAGGTGGTGTGATTGTT
PED-AR-BC                    GGTTTGCTACTTAGCTA-TAGATGTCTCTCTTCTGATTATCGATTCATATTCTGTGCTTGCTTTTCTTTTTGC TGAAGAAGGAAAAGTGAAAGCTCC
TATGAGAGGAAGAAAGTGAAGCTCCTATTCGGTAATTTTCTGATTCAAATCATTTTGAATTTTGGGATTTGGGATTTGAATTTTCTG
[Y][E][R][K][V][K][I][L][F]-intron-
TATGAGAGGAAGAAAG---------TATTCGGTAATTTTCTGATTCAAATCATTTTGAATTTTGGGATTTGAATTTAAGTTTACACTCTCCTCTTTTCTG
TATGAGAGGAAGAAAG---------------TCGGTAATTTTCTGATTCAAATAATAATTTTGAATTTTGGGATTTGAATTTAAGTTTACACTCTCCTCTTTTCTG
TATGAGAGGAAGAAAGT--------------------CGGTAATTTTCTGATTCAAATCATTTTGAATTTTGGGATTTGAATTTAAGTTTACACTCTCCTCTTTTCTG
ACAGAAGAATTTA-GTTCTCAGGAAAGTCGGTAATTTTCTGATTCAAATCATTTTGAATTTTGGGATTTGAATTTAAGTTTACACTCTCCTCTTTTCTG ATGAGACTCTGCTCTTTTTCTGGGTTTTA      200
ATGAGACTCTGCTCTTTTTCTGGGTTTTA      191
ATGAGACTCTGCTCTTTTTCTGGGTTTTA      189
ATGAGACTCTGCTCTTTTTCTGGGTTTTA      188
ATGAGACTCTGCTCTTTTTCTGGGTTTTA      190
```

FIG. 28G

*pair1*, Arabidopsis

```
PRS185
AtPAIR1-WT              ACTTAGCTATAGATCGTCTCTTCTTCTGATTATCGATTTCATATTTCTGTGCTTGCTTTTTGCACAGAGA
AtPAIR1-WT translation                                                                    -intron-[R]
PED-AR-BC               ACTTAGCTATAGATCGTCTCTTCTTCTGATTATCGATTTCATATTTCTGTGCTTGCTTTTTCCTTTTGCACAGAGA
PED-AR-BC               ATTTACCCGCACAATATGAGTAATGTCGCGTAGAGGTGTTCTTGGATACCAAGAAGCAACAAAACCACCACTCTT GTTCTCAGGAAGAGATCTC
TTAGTTCTCAGGAAGAGATCTCTTGAAGAAGGTTAGTAGTGCTTACCTCCAATCAATCATAAACGAGAAGATAGTCAGTTGGTCGCTTCTAGATCTCAAGTGGTCTT
[F][S][S][Q][E][R][D][I][L][S][L][K][K][V][S][S][C][L][L][P][J][P][N][H][K][R][E][D][S][Q][L][V][L][A][S][S][S][S][G][L]
--TTGAAGAAGGTTAGTAGTGCTTACCTCCAATCAATCATAAACGAGAAGATAGTCAGTTGGTCGCTTCTAGATCTCAAGTGGTCTT
CCACGCCTAGCGGTACTATGGGCATTTTGAAGAAGGTTAGTAGTGCTTACCTCCAATCAATCATAAACGAGAAGATAGTCAGTTGGTCGCTTCTAGATCTCAAGTGGTCTT
```

FIG. 28H

POLYPLOID HYBRID MAIZE BREEDING

CROSS-REFERENCE TO RELATED APPLICATIONS

This application claims the benefit of priority to U.S. Provisional Application No. 63/423,765, filed on Nov. 8, 2022, to U.S. Provisional Application No. 63/423,768, filed on Nov. 8, 2022, to U.S. Provisional Application No. 63/497,670, filed Apr. 21, 2023, to U.S. Provisional Application No. 63/461,174, filed Apr. 21, 2023, and to U.S. Provisional Application No. 63/461,170, filed Apr. 21, 2023, each of which is incorporated by reference herein in its entirety.

REFERENCE TO AN ELECTRONIC SEQUENCE LISTING

The content of the electronic sequence listing (197072000300subseqlist.xml; Size: 173,572 bytes; and Date of Creation: May 23, 2024) is herein incorporated by reference in its entirety.

FIELD

The inventions relate generally to the field of agricultural science, and specifically to crop improvement and systems of breeding novel hybrid polyploid maize cultivars. The inventions also relate to population improvement methods to desirably alter the genetic composition of diploid maize breeding populations for accelerated production of uniform hybrid polyploid maize seeds, maize plants, and maize plant parts suitable for cultivation. The inventions further relate to maize plant materials obtained by this process.

BACKGROUND

The growing human population, a desire to reduce the environmental impact of agriculture, and consumer food preferences ensure a constant need for improved varieties of crops. Crop breeding has been used as a way to improve crop characteristics, yields, and robustness to environmental pressure for millennia. Despite growth in crop yields in the $20^{th}$ century, crop yields have begun to plateau in recent decades, signaling a need for improved breeding methods (e.g., Rizzo (2021). Climate and agronomy, not genetics, underpin recent maize yield gains in favorable environments. Proceedings of the National Academy of Sciences 119(4): e2113629119). In some staple and specialty crops, the most widely-grown cultivars are polyploid. This creates immense complexity in breeding such varieties due to the increased inefficiency of artificial selection in polyploid plant species, and, in some cases, the requirement for vegetative propagation of the varieties, which is likely not even feasible in maize. In other cases reduced genetic gain in a diploid could be resolved by moving from diploid to a hybrid polyploid system.

Hybrid crops are widely grown and preferred because they tend to exhibit more robust growth, higher yields, and resilience to environmental stressors compared to their inbred or open-pollinated counterparts. This phenomenon is known as heterosis, or "hybrid vigor", and reflects the tendency of a cross-bred plant to show superior quality due to extensive heterozygosity in the plant's genome. Hybrid seed is typically produced by a single cross of fully inbred parent plants with different sets of alleles, resulting in a biallelic hybrid plant with two sets of alleles (also known as haplotypes) contributing to heterosis. In a further extension of the mechanism of heterosis, polyploid crops can exhibit progressive heterosis; for example, the additional hybrid vigor in a multiallelic double-cross tetraploid hybrid plant that is not found in its biallelic single-cross tetraploid parents or in its more inbred grandparents. Progressive heterosis has been documented in a number of tetraploid species including alfalfa, potato, and tetraploid maize (Gallais. (1984). An analysis of heterosis vs. inbreeding effects with an autotetraploid cross-fertilized plant: *Medicago sativa* L. *Genetics* 106, 123-137; Groose et al. 1989. Progressive heterosis in autotetraploid alfalfa: studies using two types of inbreds. *Crop Sci.* 29, 1173-1177; Mok and Peloquin. 1975. Breeding value of 2n pollen (diplandroids) in tetraploid x diploid crosses in potatoes. *Theor. Appl. Genet.* 46, 307-314; Washburn et al. 2013. Polyploids as a "model system" for the study of heterosis. *Plant Reprod* 27:1-5; Washburn et al. 2019. Progressive heterosis in genetically defined tetraploid maize (*J Genet Genomics*. 46(8):389-396) has resulted in increased above ground biomass and several other agronomically desirable traits. However, due to the need to cross heterozygous single-cross parents to generate double-cross polyploid hybrids, it is not feasible to generate a uniform population of true-breeding seed while taking advantage of progressive heterosis with current breeding techniques. Use of tetraploids for grain crops such as maize has also been considered undesirable due to meiotic associations that may result in non-viable gametes and reduce yield.

Prior research has established methods that allow plant geneticists to arrest meiosis in plants and replace it with a mitosis-like division in germline cells, resulting in formation of clonal gametes that contain the complete nonrecombinant genome of the parent. One such method, known as MiMe (Mitosis instead of Meiosis; d'Erfurth et al. 2009. Turning meiosis into mitosis. *PLoS Biol* 7, no. 6: e1000124.) is achieved through a triple knockout of three genes encoding gene products involved in meiosis, specifically, (1) a component of sister chromatid cohesion during the first division of meiosis, (2) a component of DNA double strand breakage during meiotic recombination, and (3) a component of progression through the second division of meiosis. This technology for MiMe is well-developed, but commercial development of MiMe has only begun in a select few applications (e.g., see US20190098858A1, US20120042408A1, and U.S. Ser. No. 10/883,112B2). These current applications of MiMe that are in development have only focused on generation of apomictic seed from diploid plants. However, the application of MiMe to develop novel and enhanced breeding techniques for plants at the polyploid level has not yet been realized.

BRIEF SUMMARY

Provided herein are novel methods of breeding polyploid maize plants and genetically uniform maize populations that apply MiMe in innovative ways to accelerate breeding and produce maize plants or maize populations that are either very difficult to produce by traditional breeding or simply cannot be produced by traditional breeding.

In particular, certain methods leverage the production of clonal gametes to unlock the potential of progressive heterosis in breeding of polyploid maize. First, a diverse set of maize lines of a given ploidy is obtained, improved using traditional breeding methods, and organized into heterotic groups based on the predicted heterotic performance of their haplotypes when combined in maize plants of higher ploidy. Then, candidate lines together comprising three or more haplotypes are selected from the set of maize lines, and one or more candidate lines are induced to form clonal gametes by a method such as MiMe. The clonal gametes are then crossed (for example, with other gametes such as clonal gametes, haploid gametes derived from a fully inbred individual, or other types of unreduced gametes that would result in three or more haplotypes) to produce a homogenous population of multiallelic polyploid maize seed comprising the three or more haplotypes of the candidate lines. The polyploid maize seed is then grown, the maize plants are evaluated for the characteristics desired in the breeding program, and the heterotic performance of the haplotypes comprised by the maize plants is used to guide the breeding and selection of maize lines for further rounds of breeding. Exemplary embodiments of these methods are depicted in FIGS. 12-20C. For many species this method allows, for the first time, the production of genetically uniform polyploid maize seed comprising three or more haplotypes, thus allowing for practical application of progressive heterosis in polyploids.

In one aspect, the present disclosure provides a population of polyploid maize seed comprising three or more haplotypes of the same or related species of maize plant, wherein at least 50% of the population of polyploid maize seed are genetically uniform, and wherein the population was obtained from a single maize plant or a set of maize plants such as, for example, a set of F1 hybrids. In some embodiments, the present disclosure provides a population of polyploid maize seed comprising a subpopulation of genetically uniform polyploid maize seed in an amount of at least 50% of the total number of seeds, the genetically uniform polyploid maize seed comprising three or more haplotypes of the same or related species of maize plant, wherein the population was obtained from a single maize plant or a set of maize plants such as, for example, of F1 hybrids. The polyploid maize seed (e.g., the subpopulation of genetically uniform polyploid maize seed) may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid maize seed are genetically uniform. In certain embodiments, the population of polyploid maize seed has an average pairwise genetic uniformity of at least 80%, at least 85%, at least 90%, at least 95%, at least 96%, at least 97%, at least 98%, at least 99%, or 100% as measured by the Jaccard similarity coefficient. In certain embodiments, the population of polyploid maize seed comprises the subpopulation of genetically uniform polyploid maize seed in an amount of at least 70%, at least 90%, at least 95%, at least 96%, at least 97%, at least 98%, or at least 99% of the total number of seeds. In certain embodiments, each pair of seeds in the subpopulation of genetically uniform polyploid maize seed has a pairwise identity of at least 95%, at least 96%, at least 97%, at least 98%, at least 99%, or 100% as measured by the Jaccard similarity coefficient. In certain embodiments, the polyploid maize seed (e.g., the subpopulation of genetically uniform polyploid maize seed) comprises four or more haplotypes of the same or related species of maize plant.

In some embodiments, the polyploid maize seed (e.g., the subpopulation of genetically uniform polyploid maize seed) comprises one or more genetic modifications resulting in decreased expression of one or more, two or more, or three or more MiMe loci. The seed may comprise one or more genetic modifications resulting in decreased expression of MiMe loci including, but not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, JASON, PC1, PC2, and FC. In some embodiments, the polyploid maize seed (e.g., the subpopulation of genetically uniform polyploid maize seed) comprises one or more genetic modifications resulting in altered activity of one or more, two or more, or three or more MiMe components. In some embodiments, the altered activity includes, for example, a dominant negative, constitutively active or null mutant of the one or more MiMe components. In one embodiment, the polyploid maize seed (e.g., the subpopulation of genetically uniform polyploid maize seed) comprises one or more genetic modifications resulting in decreased expression of REC8, SWITCH1/DYAD, or a combination thereof. In another embodiment, the polyploid maize seed (e.g., the subpopulation of genetically uniform polyploid maize seed) comprises one or more genetic modifications resulting in decreased expression of OSD1, CYCA1, TDM1, PC1, PC2, FC, or any combination thereof. In another embodiment, the polyploid maize seed (e.g., the subpopulation of genetically uniform polyploid maize seed) comprises one or more genetic modifications resulting in decreased expression of PAIR1, SPO11-1, SPO11-2, PRD1, PRD2, DFO, MTOPVIB, DSY1, SY1, SY2, SY3, SY4, or any combination thereof. In yet another embodiment, the polyploid maize seed (e.g., the subpopulation of genetically uniform polyploid maize seed) comprises one or more genetic modifications resulting in decreased expression of PS1, JASON, or a combination thereof. The polyploid maize seed may comprise genetic modifications in any combination of MiMe loci described herein. The one or more genetic modifications may include, but are not limited to, modification of an enhancer in the MiMe loci, modification of a promoter of the MiMe loci, modification of a coding region in the MiMe loci, modification of methylation status of the MiMe loci, expression of a repressor protein that targets the DNA or an mRNA of the MiMe loci, and expression of an RNA interference construct that targets an mRNA from the MiMe loci.

In certain embodiments, the population of polyploid maize seed or the subpopulation of genetically uniform polyploid maize seed has a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, the population of polyploid or the subpopulation of genetically uniform polyploid maize seed has a partial MiMe genotype comprising (a) one or more MiMe alleles conferring decreased expression of one or more MiMe loci of each of the first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof.

In certain embodiments, the population of polyploid maize seed or the subpopulation of genetically uniform polyploid maize seed has a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In other embodiments, the population of polyploid maize seed or the subpopulation of genetically uniform polyploid maize seed has a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis comprise PS1, JASON, or a combination thereof.

In certain embodiments, the population of polyploid maize seed or the subpopulation of genetically uniform polyploid maize seed has (i) at least a first and second haplotype, each comprising one or more MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the MiMe locus of the component of progression through the first division of meiosis of the third haplotype is PS1 or JASON. In still additional variations, the one or more MiMe loci of the component of progression through the second division of meiosis of the first and second haplotype comprise OSD1, CYCA1, TDM1, PC1, PC2, FC, or any combination thereof. In yet additional variations, the locus of the component of progression through the second division of meiosis of the third haplotype is OSD1, CYCA1, TDM1, PC1, PC2, or FC.

In certain embodiments, the population of polyploid maize seed or the subpopulation of genetically uniform polyploid maize seed has (i) at least a first and second haplotype, each comprising one or more MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis of the first and second haplotype comprise PS1, JASON, or a combination thereof. In still additional variations, the MiMe locus of the component of progression through the first division of meiosis of the third haplotype is PS1 or JASON. In yet additional variations, the MiMe locus of the component of progression through the second division of meiosis of the third haplotype is OSD1, CYCA1, TDM1, PC1, PC2 or FC.

In some embodiments, the population of polyploid maize seed or the subpopulation of genetically uniform polyploid maize seed has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the population of polyploid maize seed or the subpopulation of genetically uniform polyploid maize seed has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the population of polyploid maize seed or the subpopulation of genetically uniform polyploid maize seed has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid maize seed or the subpopulation of genetically uniform polyploid maize seed has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid maize seed or the subpopulation of genetically uniform polyploid maize seed has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid maize seed or the subpopulation of genetically uniform polyploid maize seed has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid maize seed or the subpopulation of genetically uniform polyploid maize seed has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the population of polyploid maize seed or the subpopulation of genetically uniform polyploid maize seed has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the population of polyploid maize seed or the subpopulation of genetically uniform polyploid maize seed has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid maize seed or the subpopulation of genetically uniform polyploid maize seed has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid maize seed or the subpopulation of genetically uniform polyploid maize seed has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the population of polyploid maize seed or the subpopulation of genetically uniform polyploid maize seed has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In another aspect, the present disclosure provides a population of polyploid maize seed having a partially-complemented MiMe genotype comprising (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component, wherein at least 50% of the population of polyploid maize seed are genetically uniform, and wherein the population was obtained from a single maize plant or a set of maize plants such as, for example, a set of F1 hybrids. In some embodiments, the present disclosure provides a population of polyploid maize seed comprising a subpopulation of genetically uniform polyploid maize seed in an amount of at least 50% of the total number of seeds, the genetically uniform polyploid maize seed comprising a partially-complemented MiMe genotype comprising (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component, and wherein the population was obtained from a single maize plant or a set of maize plants such as, for example, a set of F1 hybrids. The polyploid maize seed (e.g., the subpopulation of genetically uniform polyploid maize seed) may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid maize seed are genetically uniform. In certain embodiments, the population of polyploid maize seed has an average pairwise genetic uniformity of at least 80%, at least 85%, at least 90%, at least 95%, at least 96%, at least 97%, at least 98%, at least 99%, or 100% as measured by the Jaccard similarity coefficient. In certain embodiments, the population of polyploid maize seed comprises the subpopulation of genetically uniform polyploid maize seed in an amount of at least 70%, at least 90%, at least 95%, at least 96%, at least 97%, at least 98%, or at least 99% of the total number of seeds. In certain embodiments, each pair of seeds in the subpopulation of genetically uniform polyploid maize seed has a pairwise identity of at least 95%, at least 96%, at least 97%, at least 98%, at least 99%, or 100% as measured by the Jaccard similarity coefficient. In some embodiments, the partially-complemented genotype comprises only MiMe alleles at one or more MiMe loci of a third MiMe component. In other embodiments, the partially-complemented genotype comprises one or more MiMe alleles and one or more non-MiMe alleles at a first MiMe locus of the third MiMe component, and one or more MiMe alleles and one or more non-MiMe alleles at a second MiMe locus of the third MiMe component. In certain embodiments, the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

In another aspect, the present disclosure provides a population of polyploid maize seed having a partially-complemented MiMe genotype comprising (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein at least 50% of the population of polyploid maize seed are genetically uniform, and wherein the population was obtained from a single parent maize plant or a set of maize plants, such as, for example, a set of F1 hybrids. In some embodiments, the present disclosure provides a population of polyploid maize seed comprising a subpopulation of genetically uniform polyploid maize seed in an amount of at least 50% of the total number of seeds, the genetically uniform polyploid maize seed comprising a partially-complemented MiMe genotype comprising (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, and wherein the population was obtained from a single parent maize plant or a set of maize plants, such as, for example, a set of F1 hybrids. The polyploid maize seed (e.g., the subpopulation of genetically uniform polyploid maize seed) may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid maize seed are genetically uniform. In certain embodiments, the population of polyploid maize seed has an average pairwise genetic uniformity of at least 80%, at least 85%, at least 90%, at least 95%, at least 96%, at least 97%, at least 98%, at least 99%, or 100% as measured by the Jaccard similarity coefficient. In certain embodiments, the population of polyploid maize seed comprises the subpopulation of genetically uniform polyploid maize seed in an amount of at least 70%, at least 90%, at least 95%, at least 96%, at least 97%, at least 98%, or at least 99% of the total number of seeds. In certain embodiments, each pair of seeds in the subpopulation of genetically uniform polyploid maize seed has a pairwise identity of at least 95%, at least 96%, at least 97%, at least 98%, at least 99%, or 100% as measured by the Jaccard similarity coefficient. In some embodiments, the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components.

In another aspect, the present disclosure provides a population of polyploid maize seed having a partially-complemented MiMe genotype comprising (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein at least 50% of the population of polyploid maize seed are genetically uniform, and wherein the population was obtained from a single parent maize plant or a set of maize plants, such as, for example, a set of F1 hybrids. In some embodiments, the present disclosure provides a population of polyploid maize seed comprising a subpopulation of genetically uniform polyploid maize seed in an amount of at least 50% of the total number of seeds, the genetically uniform polyploid maize seed comprising a partially-complemented MiMe genotype comprising (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, and wherein the population was obtained from a single parent maize plant or a set of maize plants, such as, for example, a set of F1 hybrids. The polyploid maize seed (e.g., the subpopulation of genetically uniform polyploid maize seed) may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid maize seed are genetically uniform. In certain embodiments, the population of polyploid maize seed has an average pairwise genetic uniformity of at least 80%, at least 85%, at least 90%, at least 95%, at least 96%, at least 97%, at least 98%, at least 99%, or 100% as measured by the Jaccard similarity coefficient. In certain embodiments, the population of polyploid maize seed comprises the subpopulation of genetically uniform polyploid maize seed in an amount of at least 70%, at least 90%, at least 95%, at least 96%, at least 97%, at least 98%, or at least 99% of the total number of seeds. In certain embodiments, each pair of seeds in the subpopulation of genetically uniform polyploid maize seed has a pairwise identity of at least 95%, at least 96%, at least 97%, at least 98%, at least 99%, or 100% as measured by the Jaccard similarity coefficient. In some embodiments, the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

In some embodiments of the foregoing aspects, the first MiMe component is a component of sister chromatid cohesion during the first division of meiosis. In some variations, the one or more MiMe loci of the first MiMe component comprise REC8, SWITCH1/DYAD, or a combination thereof. In one variation, the MiMe locus of the first MiMe component is REC8. In certain embodiments, the second MiMe component is a component of DNA double strand breakage during meiotic recombination. In some variations, the first MiMe locus and the second MiMe locus of the second MiMe component comprise PAIR1, SPO11-1, SPO11-2, PRD1, PRD2, DFO, MTOPVIB, DSY1, SY1, SY2, SY3, SY4, or any combination thereof. In one variation, the first MiMe locus of the second MiMe component is PAIR1 and the second MiMe locus of the second MiMe component is SPO11-1. In further embodiments, the third MiMe component is a component of progression through the second division of meiosis. In some embodiments, the partially-complemented MiMe genotype comprises only MiMe alleles at one or more MiMe loci of the third MiMe component. In some variations, the one or more MiMe loci of the third MiMe component comprise OSD1, CYCA1, TDM1, PC1, PC2, FC, or any combination thereof. In one variation, the MiMe locus of the third MiMe component is OSD1. In other embodiments, the partially-complemented MiMe genotype comprises one or more MiMe alleles and one or more non-MiMe alleles at a first MiMe locus of the third MiMe component, and one or more MiMe alleles and one or more non-MiMe alleles at a second MiMe locus of the third MiMe component. In some variations, the first MiMe locus and the second MiMe locus of the third MiMe component comprise OSD1, CYCA1, TDM1, PC1, PC2, FC, or any combination thereof. In one embodiment, the partially-complemented MiMe genotype comprises only MiMe alleles at one or more MiMe loci of the third MiMe component, wherein the one or more MiMe loci having only MiMe alleles of the first MiMe component comprise REC8, the first MiMe locus of the second MiMe component is PAIR1, the second MiMe locus of the second MiMe component is SPO11-1, and the one or more MiMe loci having only MiMe alleles of the third MiMe component comprise OSD1. In some embodiments, the polyploid maize seed (e.g., the subpopulation of genetically uniform polyploid maize seed) comprises one or more genetic modifications resulting in altered activity of one or more, two or more, or three or more MiMe components. In some embodiments, the altered activity includes, for example, a dominant negative, constitutively active or null mutant of the one or more MiMe components In some embodiments of the foregoing aspects, the population of polyploid maize seed or the subpopulation of genetically uniform polyploid maize seed has a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more only MiMe alleles at one or more SPO11-1 loci, wherein each of the MiMe alleles at the SPO11-1 locus comprise one or more genetic modifications resulting in decreased expression of SPO11-1.

In some embodiments of the foregoing aspects, the population of polyploid maize seed or the subpopulation of genetically uniform polyploid maize seed has a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

In some embodiments of the foregoing aspects, the population of polyploid maize seed or the subpopulation of genetically uniform polyploid maize seed has a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

In another aspect, the present disclosure provides a method of producing a population of polyploid maize seed described herein, the method comprising: (a) providing clonal gametes from a pair of parent MiMe maize plants that together comprise three or more haplotypes; and (b) crossing the clonal gametes to produce the population of polyploid maize seed. In some embodiments, at least 50% of the population of polyploid maize seed are genetically uniform and comprise three or more haplotypes. In some embodiments, at least 70%, at least 90%, at least 95%, at least 96%, at least 97%, at least 98%, or at least 99% of the population of polyploid maize seed produced by said method are genetically uniform. In some embodiments, the population of polyploid maize seed comprises a subpopulation of genetically uniform polyploid maize seed in an amount of at least 50% of the total number of seeds, the subpopulation of genetically uniform polyploid maize seed comprising three or more haplotypes. In certain embodiments, the population of polyploid maize seed comprises a subpopulation of genetically uniform polyploid maize seed in an amount of at least 70%, at least 90%, at least 95%, at least 96%, at least 97%, at least 98%, or at least 99% of the total number of seeds. In certain embodiments, the polyploid maize seed (e.g., the subpopulation of genetically uniform polyploid maize seed) produced by said method comprises four or more haplotypes of the same or related species of maize plant. The population of polyploid maize seed or the subpopulation of genetically uniform polyploid maize seed may be, for example, triploid, tetraploid, pentaploid, hexaploid, heptaploid, or octoploid.

In some embodiments, the method of producing the population of polyploid seeds comprises producing a population of polyploid maize seed comprising one or more genetic modifications resulting in decreased expression of one or more, two or more, or three or more MiMe loci. The population of polyploid maize seed or the subpopulation of genetically uniform polyploid maize seed may comprise one or more genetic modifications resulting in decreased expression of MiMe loci including, but not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, JASON, PC1, PC2, and FC. In one embodiment, the polyploid maize seed produced by said method, or the subpopulation of genetically uniform polyploid maize seed, comprises one or more genetic modifications resulting in decreased expression of REC8, SWITCH1/DYAD, or a combination thereof. In another embodiment, the polyploid maize seed produced by said method, or the subpopulation of genetically uniform polyploid maize seed, comprises one or more genetic modifications resulting in decreased expression of OSD1, CYCA1, TDM1, PC1, PC2, FC, or a combination thereof. In another embodiment, the polyploid maize seed produced by said method, or the subpopulation of genetically uniform polyploid maize seed, comprises one or more genetic modifications resulting in decreased expression of PAIR1, SPO11-1, SPO11-2, PRD1, PRD2, DFO, MTOPVIB, DSY1, SY1, SY2, SY3, SY4, or a combination thereof. In yet another embodiment, the polyploid maize seed produced by said method comprises one or more genetic modifications resulting in decreased expression of PS1, JASON, or a combination thereof. The polyploid maize seed produced by said method, or the subpopulation of genetically uniform polyploid maize seed, may comprise genetic modifications in any combination of MiMe loci described herein. The genetic modifications may include, but are not limited to, modification of an enhancer in the MiMe loci, modification of a promoter of the MiMe loci, modification of a coding region in the MiMe loci, modification of methylation status of the MiMe loci, expression of a repressor protein that targets the DNA or an mRNA of the MiMe loci, and expression of an RNA interference construct that targets an mRNA from the MiMe loci.

In certain embodiments, the population of polyploid maize seed produced by said method, or the subpopulation of genetically uniform polyploid maize seed, comprises a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, the population of polyploid maize seed produced by said method, or the subpopulation of genetically uniform polyploid maize seed, comprises a partial MiMe genotype comprising (a) one or more MiMe alleles conferring decreased expression of one or more MiMe loci of each of the first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof.

In certain embodiments, the population of polyploid maize seed produced by said method, or the subpopulation of genetically uniform polyploid maize seed, has a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In other embodiments, the population of polyploid maize seed produced by said method, or the subpopulation of genetically uniform polyploid maize seed, has a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis comprise PS1, JASON, or a combination thereof.

In another aspect, the present disclosure provides a method of producing a population of polyploid maize seed described herein having a partially-complemented MiMe genotype, the method comprising (a) providing clonal gametes from a first parent MiMe maize plant, wherein the first parent MiMe maize plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; (b) providing clonal gametes from a second parent MiMe maize plant, wherein the second parent MiMe maize plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component; and (c) crossing the clonal gametes from the first and second parent MiMe maize plants to produce the population of polyploid maize seed having a partially-complemented MiMe genotype. In some embodiments, at least 50% of the population of polyploid maize seed are genetically uniform and comprise two, three, or more haplotypes. In some embodiments, the population of polyploid maize seed comprises a subpopulation of genetically uniform polyploid maize seed in an amount of at least 50% of the total number of seeds, the subpopulation of genetically uniform polyploid maize seed comprising the partially-complemented MiMe genotype. In certain embodiments, at least one of the MiMe loci having only MiMe alleles of the first MiMe component of the first parent MiMe maize plant is the same as at least one of the MiMe loci having only MiMe alleles of the first MiMe component of the second parent MiMe maize plant. In some embodiments, at least one of the MiMe loci having only MiMe alleles of the third MiMe component of the first parent MiMe maize plant is the same as at least one of the MiMe loci having only MiMe alleles of the third MiMe component of the second parent MiMe maize plant. In other embodiments, the one or more MiMe loci having only MiMe alleles of the third MiMe component of the first parent MiMe maize plant are distinct from the one or more MiMe loci having only MiMe alleles of the third MiMe component of the second parent MiMe maize plant. In some embodiments, the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

In another aspect, the present disclosure provides a method of producing a population of polyploid maize seed having a partially-complemented MiMe genotype described herein, the method comprising (a) providing clonal gametes from a first parent MiMe maize plant, wherein the first parent MiMe maize plant has only MiMe alleles at one or more MiMe loci of a first MiMe component, only MiMe alleles at a first MiMe locus of a second MiMe component, and only non-MiMe alleles at a second MiMe locus of the second MiMe component; (b) providing clonal gametes from a second parent MiMe maize plant, wherein the second parent MiMe maize plant has only MiMe alleles at one or more MiMe loci of the first MiMe component, only non-MiMe alleles at the first MiMe locus of the second MiMe component, and only MiMe alleles at the second MiMe locus of the second MiMe component; and (c) crossing the clonal gametes from the first and second parent MiMe maize plants to produce the population of polyploid maize seed having a partially-complemented MiMe genotype. In some embodiments, at least 50% of the population of polyploid maize seed are genetically uniform and comprise two, three, or more haplotypes. In some embodiments, the population of polyploid maize seed comprises a subpopulation of genetically uniform polyploid maize seed in an amount of at least 50% of the total number of seeds, the subpopulation of genetically uniform polyploid maize seed comprising the partially-complemented MiMe genotype. In some embodiments at least one of the MiMe loci having only MiMe alleles of the first MiMe component of the first parent MiMe maize plant is the same as at least one of the MiMe loci having only MiMe alleles of the first MiMe component of the second parent MiMe maize plant. In certain embodiments, the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components.

In yet another aspect, the present disclosure provides a method of producing a population of polyploid maize seed having a partially-complemented MiMe genotype described herein, the method comprising (a) providing clonal gametes from a first parent MiMe maize plant, wherein the first parent MiMe maize plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination; (b) providing clonal gametes from a second parent MiMe maize plant, wherein the second parent MiMe maize plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and (c) crossing the clonal gametes from the first and second parent MiMe maize plants to produce the population of polyploid maize seed having a partially-complemented MiMe genotype. In some embodiments, at least 50% of the population of polyploid maize seed are genetically uniform and comprise two, three, or more haplotypes. In some embodiments, the population of polyploid maize seed comprises a subpopulation of genetically uniform polyploid maize seed in an amount of at least 50% of the total number of seeds, the subpopulation of genetically uniform polyploid maize seed comprising the partially-complemented MiMe genotype. In some embodiments, at least one of the MiMe loci having only MiMe alleles of the first MiMe component of the first parent MiMe maize plant is the same as at least one of the MiMe loci having only MiMe alleles of the first MiMe component of the second parent MiMe maize plant. In certain embodiments, the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

In some embodiments of the foregoing methods, the first MiMe component is a component of sister chromatid cohesion during the first division of meiosis. In some variations of said method, the MiMe loci of the first MiMe component of both the first and second parent MiMe maize plants comprise REC8. In certain embodiments of said method, the second MiMe component is a component of DNA double strand breakage during meiotic recombination. In some variations of said method, the first MiMe locus and the second MiMe locus of the second MiMe component comprise PAIR1, SPO11-1, SPO11-2, PRD1, PRD2, DFO, MTOPVIB, DSY1, SY1, SY2, SY3, SY4, or any combination thereof. In one variation of said method, the first MiMe locus of the second MiMe component is PAIR1 and the second MiMe locus of the second MiMe component is SPO11-1. In further embodiments of said method, the third MiMe component is a component of progression through the second division of meiosis. In some embodiments of said method, at least one of the MiMe loci having only MiMe alleles of the third MiMe component of the first parent MiMe maize plant is the same as at least one of the MiMe loci having only MiMe alleles of the third MiMe component of the second parent MiMe maize plant. In some variations, the MiMe loci having only MiMe alleles of the component of progression through the second division of meiosis comprise OSD1, CYCA1, TDM1, PC1, PC2, FC, or any combination thereof. In one variation, the MiMe locus having only MiMe alleles of the third MiMe component is OSD1. In other embodiments of said method, the one or more MiMe loci having only MiMe alleles of the third MiMe component of the first parent MiMe maize plant are distinct from the one or more MiMe loci having only MiMe alleles of the third MiMe component of the second parent MiMe maize plant. In some variations, the MiMe loci having only MiMe alleles of the third MiMe component comprise OSD1, CYCA1, TDM1, PC1, PC2, FC, or any combination thereof. In one variation of said method, the MiMe loci having only MiMe alleles of the first MiMe component comprise REC8, the first MiMe locus of the second MiMe component is PAIR1, the second MiMe locus of the second MiMe component is SPO11-1, and the MiMe loci having only MiMe alleles of the third MiMe component comprise OSD1.

In another aspect, the present disclosure provides a method of breeding a polyploid hybrid maize line, comprising: (a) obtaining a set of maize lines; (b) breeding the maize lines using traditional plant breeding methods to produce a set of candidate maize lines of the maize; (c) selecting two or more candidate maize lines together comprising three or more haplotypes; (d) generating two parent MiMe maize plants from the two or more candidate maize lines that together comprise the three or more haplotypes; (e) providing clonal gametes from each of the parent MiMe maize plants; (f) crossing the clonal gametes to produce a hybrid polyploid maize seed comprising the three or more haplotypes; (g) growing the hybrid polyploid maize seed to produce a hybrid polyploid maize plant comprising three or more haplotypes; and (h) evaluating one or more characteristics of the hybrid polyploid maize plant. The candidate maize lines and the parent MiMe maize plants may be any ploidy, including, but not limited to, haploid, monoploid, diploid, triploid, or tetraploid. In additional embodiments of said breeding method, the hybrid polyploid maize plant is tetraploid, pentaploid, hexaploid, heptaploid, or octoploid.

In some embodiments of said breeding method, step (d) comprises introducing a complete MiMe genotype directly into two candidate maize lines to produce the two parent MiMe maize plants. In other embodiments of said breeding method, step (d) comprises introducing a partial MiMe genotype into two candidate maize lines to produce two grandparent non-MiMe maize plants each having a partial MiMe genotype, crossing said grandparent non-MiMe maize plants each having a partial MiMe genotype to produce the first parent MiMe maize plant, and introducing a complete MiMe genotype directly into a third candidate maize line to produce the second parent MiMe maize plant. In yet other embodiments of said breeding method, step (d) comprises introducing a partial MiMe genotype into four candidate maize lines to produce four grandparent non-MiMe maize plants each having a partial MiMe genotype, and crossing pairs of said grandparent non-MiMe maize plants each having a partial MiMe genotype to produce the two parent MiMe maize plants. In certain embodiments, step (d) further comprises propagating parent MiMe maize plants to scale production of homogenous seed.

In some embodiments of said breeding method, the parent MiMe maize plants of step (d) each have a complete MiMe genotype comprising MiMe alleles that are naturally-occurring, introduced via genetic modification, or a combination thereof. In certain embodiments, the genetic modifications result in decreased expression of one or more, two or more, or three or more MiMe loci including, but not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, JASON, PC1, PC2, and FC. In one embodiment, the genetic modifications result in decreased expression of REC8, SWITCH1/DYAD, or a combination thereof. In another embodiment, the genetic modifications result in decreased expression of OSD1, CYCA1, TDM1, PC1, PC2, FC, or any combination thereof. In another embodiment, the genetic modifications result in decreased expression of PAIR1, SPO11-1, SPO11-2, PRD1, PRD2, DFO, MTOPVIB, DSY1, SY1, SY2, SY3, SY4, or any combination thereof. In yet another embodiment, the genetic modifications result in decreased expression of PS1, JASON, or a combination thereof. In some embodiments, the one or more genetic modifications are introduced by gene editing, transgenesis, or a combination thereof. The genetic modifications may be achieved by any methods described herein, including, but not limited to, gene disruption, gene knockout, gene knockdown, gene silencing, RNA interference, induction of methylation, or any combination thereof.

In certain embodiments, the population of polyploid maize seed produced by said breeding method comprises a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, the population of polyploid maize seed produced by said breeding method comprises a partial MiMe genotype comprising (a) one or more MiMe alleles conferring decreased expression of one or more MiMe loci of each of the first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof.

In certain embodiments, the population of polyploid maize seed produced by said breeding method has a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In other embodiments, the population of polyploid maize seed produced by said breeding method has a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis comprise PS1, JASON, or a combination thereof.

In certain embodiments of said breeding method, the method of breeding a population of polyploid maize seed further comprises (i) repeating steps (b)-(h) or steps (c)-(h) using the one or more characteristics of the hybrid polyploid maize plant evaluated in step (h) to guide the breeding of maize lines of step (b), the selecting of candidate maize lines of step (c), or both. In some variations, the one or more characteristics includes the heterotic performance of the three or more haplotypes of the polyploid hybrid maize plant evaluated in step (h).

In some embodiments of said breeding method, the set of maize lines in step (a) are obtained from one or more of natural diversity or existing breeding programs. In certain embodiments of said breeding method, step (a) further comprises organizing the set of maize lines into three or more heterotic groups, wherein each heterotic group comprises a haplotype, and wherein the haplotypes are grouped based on observed or predicted heterotic performance when combined in the hybrid polyploid maize plant of step (g). In one variation, step (a) comprises organizing the set of maize lines into four or more heterotic groups. In certain embodiments, heterotic performance is predicted via genome prediction modeling. In some embodiments of said breeding method, step (b) comprises reciprocal recurrent selection, inbreeding one or more of the maize lines to homozygosity, production of a doubled haploid maize line (e.g., a doubled monoploid maize line), backcrossing, or any other method known in the art for creating maize lines with high degrees of homozygosity, or a combination thereof. The candidate maize lines of step (c) may be inbred maize lines, hybrid maize lines, or a combination thereof.

In another aspect, the present disclosure provides a method of producing a population of polyploid maize seed comprising: (a) providing clonal gametes from a pair of parent MiMe maize plants that together comprise three or more haplotypes that were selected using the methods of breeding described herein based upon the polyploid maize plant comprising said three or more haplotypes having one or more desired characteristics; and (b) crossing the clonal gametes to produce the population of polyploid maize seed, wherein at least 50% of the population of polyploid maize seed are genetically uniform and comprise three or more haplotypes. The polyploid maize seed produced by said method may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid maize seed produced by said method are genetically uniform. In certain embodiments, the polyploid maize seed produced by said method comprises four or more haplotypes of the same or related species of maize. In some variations of said method, maize lines are maintained via vegetative propagation, selfing, apomixis, cell culture, or any combination thereof. In some embodiments, said method further comprises maintaining an inventory of maize lines from which haplotypes may be selected for rapid deterministic stacking of the haplotypes. In some variations, the inventory of maize lines comprises one or more maize lines having a complete MiMe genotype that is maintained through vegetative propagation, hybridization with a haploid inducer, or a combination thereof. In additional variations, the inventory of maize lines comprises one or more maize lines having a partial MiMe genotype.

In another aspect, the present disclosure provides a method of producing a population of polyploid maize seed comprising: (a) providing clonal gametes from a parent MiMe maize plant; (b) providing haploid (e.g., monoploid) gametes from a homozygous parent non-MiMe maize plant; and (c) crossing the clonal gametes with the haploid (e.g., monoploid) gametes to produce the population of polyploid maize seed, wherein the clonal gametes and the haploid (e.g., monoploid) gametes together comprise three or more haplotypes, and wherein at least 50% of the population of polyploid maize seed are genetically uniform and comprise three or more haplotypes. The parent MiMe maize plant may be, for example, diploid, triploid, or tetraploid. The homozygous parent non-MiMe maize plant may be, for example, diploid or tetraploid. The polyploid maize seed produced by said method may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid maize seed produced by said method are genetically uniform. In certain embodiments, the polyploid maize seed produced by said method comprises four or more haplotypes of the same or related species of maize plant.

In some embodiments, the method of producing a population of polyploid maize seed comprises producing a population of polyploid maize seed comprising one or more genetic modifications resulting in decreased expression of one or more, two or more, or three or more MiMe loci. The seed may comprise one or more genetic modifications resulting in decreased expression of MiMe loci including, but not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, JASON, PC1, PC2, and FC. In one embodiment, the polyploid maize seed produced by said method comprises one or more genetic modifications resulting in decreased expression of REC8, SWITCH1/DYAD, or a combination thereof. In another embodiment, the polyploid maize seed produced by said method comprises one or more genetic modifications resulting in decreased expression of OSD1, CYCA1, TDM1, PC1, PC2, FC, or a combination thereof. In another embodiment, the polyploid maize seed produced by said method comprises one or more genetic modifications resulting in decreased expression of PAIR1, SPO11-1, SPO11-2, PRD1, PRD2, DFO, MTOPVIB, DSY1, SY1, SY2, SY3, SY4, or a combination thereof. In yet another embodiment, the polyploid maize seed produced by said method comprises one or more genetic modifications resulting in decreased expression of PS1, JASON, or a combination thereof. The polyploid maize seed produced by said method may comprise genetic modifications in any combination of MiMe loci described herein. The genetic modifications may include, but are not limited to, modification of an enhancer in the MiMe loci, modification of a promoter of the MiMe loci, modification of a coding region in the MiMe loci, modification of methylation status of the MiMe loci, expression of a repressor protein that targets the DNA or an mRNA of the MiMe loci, and expression of an RNA interference construct that targets an mRNA from the MiMe loci.

In certain embodiments, the population of polyploid maize seed produced by said method comprises a partial MiMe genotype comprising (a) one or more MiMe alleles conferring decreased expression of one or more MiMe loci of each of the first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof.

In certain embodiments, the population of polyploid maize seed produced by said method has a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis comprise PS1, JASON, or a combination thereof.

In another aspect, the present disclosure provides a method of breeding a polyploid hybrid maize line, comprising: (a) obtaining a set of maize lines; (b) breeding the maize lines using traditional plant breeding methods to produce a set of candidate maize lines of maize; (c) selecting two or more candidate maize lines together comprising three or more haplotypes; (d) generating a parent MiMe maize plant from one of the two or more candidate maize lines; (e) providing clonal gametes from the parent MiMe maize plant; (f) providing haploid (e.g., monoploid) gametes from a homozygous parent non-MiMe maize plant of one of the two or more candidate maize lines; (g) crossing the clonal gametes with the haploid (e.g., monoploid) gametes to produce a hybrid polyploid maize seed; (h) growing the hybrid polyploid maize seed to produce a hybrid polyploid maize plant; and (i) evaluating one or more characteristics of the hybrid polyploid maize plant, wherein the parent MiMe maize plant and the homozygous parent non-MiMe maize plant together comprise three or more haplotypes, wherein the crossing of step (g) results in the hybrid polyploid maize seed comprising three or more haplotypes, and wherein the growing of step (h) results in the hybrid polyploid maize plant comprising three or more haplotypes. The candidate maize lines, parent MiMe maize plant, and the homozygous parent non-MiMe maize plant may be any ploidy, including, but not limited to, haploid, monoploid, diploid, triploid, or tetraploid. In some embodiments of said breeding method, the hybrid polyploid maize plant is tetraploid, pentaploid, hexaploid, heptaploid, or octoploid.

In some embodiments of said breeding method, step (d) comprises introducing a complete MiMe genotype directly into a candidate maize line to produce the parent MiMe maize plant. In further embodiments of said breeding method, step (d) comprises introducing a partial MiMe genotype into two candidate maize lines to produce two grandparent non-MiMe maize plants each having a partial MiMe genotype, crossing said grandparent non-MiMe maize plants each having a partial MiMe genotype to produce the parent MiMe maize plant. In certain embodiments, step (d) further comprises propagating the parent MiMe maize plant to scale production of homogenous seed.

In some embodiments of said breeding method, the parent MiMe maize plant of step (d) has a complete MiMe genotype comprising MiMe alleles that are naturally-occurring, introduced via genetic modification, or a combination thereof. In certain embodiments, the genetic modifications result in decreased expression of one or more, two or more, or three or more MiMe loci including, but not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, JASON, PC1, PC2, and FC. In one embodiment, the genetic modifications result in decreased expression of REC8, SWITCH1/DYAD, or a combination thereof. In another embodiment, the genetic modifications result in decreased expression of OSD1, CYCA1, TDM1, PC1, PC2, FC, or any combination thereof. In another embodiment, the genetic modifications result in decreased expression of PAIR1, SPO11-1, SPO11-2, PRD1, PRD2, DFO, MTOPVIB, DSY1, SY1, SY2, SY3, SY4, or any combination thereof. In yet another embodiment, the genetic modifications result in decreased expression of PS1, JASON, or a combination thereof. In some embodiments, the one or more genetic modifications are introduced by gene editing, transgenesis, or a combination thereof. The genetic modifications may be achieved by any methods described herein, including, but not limited to, gene disruption, gene knockout, gene knockdown, gene silencing, RNA interference, induction of methylation, or any combination thereof.

In certain embodiments, the population of polyploid maize seed produced by said breeding method comprises a partial MiMe genotype comprising (a) one or more MiMe alleles conferring decreased expression of one or more MiMe loci of each of the first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof.

In certain embodiments, the population of polyploid maize seed produced by said breeding method has a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis comprise PS1, JASON, or a combination thereof.

In certain embodiments of said breeding method, the method of breeding a population of polyploid maize seed further comprises j) repeating steps (b)-(i) or steps (c)-(i) using the one or more characteristics of the hybrid polyploid maize plant evaluated in step (i) to guide the breeding of maize lines of step (b), the selecting of candidate maize lines of step (c), or both. In some variations, the one or more characteristics includes the heterotic performance of the three or more haplotypes of the polyploid hybrid maize plant evaluated in step (i).

In some embodiments of said breeding method, the set of maize lines in step (a) are obtained from one or more of natural diversity or existing breeding programs. In certain embodiments of said breeding method, step (a) further comprises organizing the set of maize lines into three or more heterotic groups, wherein each heterotic group comprises a haplotype, and wherein the haplotypes are grouped based on observed or predicted heterotic performance when combined in the hybrid polyploid maize plant of step (h). In one variation, step (a) comprises organizing the set of maize lines into four or more heterotic groups. In certain embodiments, heterotic performance is predicted via genome prediction modeling. In some embodiments of said breeding method, step (b) comprises reciprocal recurrent selection, inbreeding one or more of the maize lines to homozygosity, production of a doubled haploid maize line (e.g., a doubled monoploid maize line), backcrossing, or any other method known in the art for creating maize lines with high degrees of homozygosity, or a combination thereof. The candidate maize lines of step (c) may be inbred maize lines, hybrid maize lines, or a combination thereof.

In another aspect, the present disclosure provides a method of producing a population of polyploid maize seed comprising: (a) selecting three or more haplotypes using the method of breeding described herein based upon the polyploid maize plant comprising said three or more haplotypes having one or more desired characteristics; (b) providing clonal gametes from a parent MiMe maize plant; (c) providing haploid (e.g., monoploid) gametes from a homozygous parent non-MiMe maize plant; (d) crossing the clonal gametes with the haploid (e.g., monoploid) gametes to produce the population of polyploid maize seed; wherein the parent MiMe maize plant and the homozygous parent non-MiMe maize plant together comprise the three or more haplotypes selected in step (a), wherein the crossing of step (d) results in a population of polyploid maize seed comprising the three or more haplotypes selected in step (a), and wherein at least 50% of the population of polyploid maize seed are genetically uniform and comprise three or more haplotypes. The polyploid maize seed produced by said method may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid maize seed produced by said method are genetically uniform. In certain embodiments, the polyploid maize seed produced by said method comprises four or more haplotypes of the same or related species of maize. In some variations of said method, maize lines are maintained via vegetative propagation, selfing, apomixis, cell culture, or any combination thereof. In some embodiments, said method further comprises maintaining an inventory of maize lines of maize from which haplotypes may be selected for rapid deterministic stacking of the haplotypes. In some variations, the inventory of maize lines comprises one or more maize lines having a complete MiMe genotype that is maintained through vegetative propagation, hybridization with a haploid inducer, or a combination thereof. In additional variations, the inventory of maize lines comprises one or more maize lines having a partial MiMe genotype.

In another aspect, the present disclosure provides a method of breeding a polyploid maize plant, comprising (a) obtaining a set of maize lines; (b) breeding the maize lines using traditional plant breeding methods to produce a set of candidate maize lines of maize; (c) selecting one or more candidate maize lines; (d) generating a first parent MiMe maize plant from one of the candidate maize lines, wherein the first parent MiMe maize plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; (e) generating a second parent MiMe maize plant from one of the candidate maize lines, wherein the second parent MiMe maize plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component, wherein at least one of the MiMe loci having only MiMe alleles of the first MiMe component of the first parent MiMe maize plant is the same as at least one of the MiMe loci having only MiMe alleles of the first MiMe component of the second parent MiMe maize plant; (f) providing clonal gametes from each of the parent MiMe maize plants; (g) crossing the clonal gametes to produce a polyploid maize seed; (h) growing the polyploid maize seed to produce a polyploid maize plant; and (i) evaluating one or more characteristics of the polyploid maize plant. In some embodiments, at least one of the MiMe loci having only MiMe alleles of the third MiMe component of the first parent MiMe maize plant is the same as at least one of the MiMe loci having only MiMe alleles of the third MiMe component of the second parent MiMe maize plant. In other embodiments, the one or more MiMe loci having only MiMe alleles of the third MiMe component of the first parent MiMe maize plant are distinct from the one or more MiMe loci having only MiMe alleles of the third MiMe component of the second parent MiMe maize plant. In certain embodiments, the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

In some embodiments of said breeding method, the first MiMe component is a component of sister chromatid cohesion during the first division of meiosis. In some variations of said breeding method, the MiMe loci of the first MiMe component of both the first and second parent MiMe maize plants comprise REC8. In certain embodiments of said breeding method, the second MiMe component is a component of DNA double strand breakage during meiotic recombination. In some variations of said breeding method, the first MiMe locus and the second MiMe locus of the second MiMe component comprise PAIR1, SPO11-1, SPO11-2, PRD1, PRD2, DFO, MTOPVIB, DSY1, SY1, SY2, SY3, SY4, or any combination thereof. In one variation of said breeding method, the first MiMe locus of the second MiMe component is PAIR1 and the second MiMe locus of the second MiMe component is SPO11-1. In further embodiments of said breeding method, the third MiMe component is a component of progression through the second division of meiosis. In some embodiments of said breeding method, at least one of the MiMe loci having only MiMe alleles of the third MiMe component of the first parent MiMe maize plant is the same as at least one of the MiMe loci having only MiMe alleles of the third MiMe component of the second parent MiMe maize plant. In some variations, the MiMe loci having only MiMe alleles of the component of progression through the second division of meiosis comprise OSD1, CYCA1, TDM1, PC1, PC2, FC, or any combination thereof. In one variation, the MiMe locus having only MiMe alleles of the third MiMe component is OSD1. In other embodiments of said breeding method, the one or more MiMe loci having only MiMe alleles of the third MiMe component of the first parent MiMe maize plant are distinct from the one or more MiMe loci having only MiMe alleles of the third MiMe component of the second parent MiMe maize plant. In some variations, the MiMe loci having only MiMe alleles of the third MiMe component comprise OSD1, CYCA1, TDM1, PC1, PC2, FC, or any combination thereof. In one variation of said breeding method, the MiMe loci having only MiMe alleles of the first MiMe component comprise REC8, the first MiMe locus of the second MiMe component is PAIR1, the second MiMe locus of the second MiMe component is SPO11-1, and the one or more MiMe loci having only MiMe alleles of the third MiMe component comprise OSD1.

In another aspect, the present disclosure provides a method of producing a population of polyploid maize seed comprising (a) providing clonal gametes from a pair of parent MiMe maize plants together comprising two or more haplotypes that were selected using the foregoing method of breeding based upon the polyploid maize plant comprising said two or more haplotypes having one or more desired characteristics, wherein: (i) the first parent MiMe maize plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; (ii) the second parent MiMe maize plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component; and (iii) at least one of the MiMe loci having only MiMe alleles of the first MiMe component of the first parent MiMe maize plant is the same as at least one of the MiMe loci having only MiMe alleles of the first MiMe component of the second parent MiMe maize plant; and (b) crossing the clonal gametes to produce the population of polyploid maize seed, wherein at least 50% of the population of polyploid maize seed are genetically uniform and comprise two or more haplotypes. In some embodiments, at least one of the MiMe loci having only MiMe alleles of the third MiMe component of the first parent MiMe maize plant is the same as at least one of the MiMe loci having only MiMe alleles of the third MiMe component of the second parent MiMe maize plant. In other embodiments, the one or more MiMe loci having only MiMe alleles of the third MiMe component of the first parent MiMe maize plant are distinct from the one or more MiMe loci having only MiMe alleles of the third MiMe component of the second parent MiMe maize plant.

In another aspect, the present disclosure provides a method of breeding a polyploid maize plant, comprising (a) obtaining a set of maize lines; (b) breeding the maize lines using traditional plant breeding methods to produce a set of candidate maize lines of maize; (c) selecting one or more candidate maize lines; (d) generating a first parent MiMe maize plant from one of the candidate maize lines, wherein the first parent MiMe maize plant has only MiMe alleles at one or more MiMe loci of a first MiMe component, only MiMe alleles at a first MiMe locus of a second MiMe component, and only non-MiMe alleles at a second MiMe locus of the second MiMe component; (e) generating a second parent MiMe maize plant from one of the candidate maize lines, wherein the second parent MiMe maize plant has only MiMe alleles at one or more MiMe loci of the first MiMe component, only non-MiMe alleles at the first MiMe locus of the second MiMe component, and only MiMe alleles at the second MiMe locus of the second MiMe component, and at least one of the MiMe loci having only MiMe alleles of the first MiMe component of the first parent MiMe maize plant is the same as at least one of the MiMe loci having only MiMe alleles of the first MiMe component of the second parent MiMe maize plant; (f) providing clonal gametes from each of the parent MiMe maize plants; (g) crossing the clonal gametes to produce a polyploid maize seed; (h) growing the polyploid maize seed to produce a polyploid maize plant; and (i) evaluating one or more characteristics of the polyploid maize plant. In some embodiments of said breeding method, the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components.

In another aspect, the present disclosure provides a method of producing a population of polyploid maize seed comprising (a) providing clonal gametes from a pair of parent MiMe maize plants together comprising two or more haplotypes that were selected using the foregoing method of breeding based upon the polyploid maize plant comprising said two or more haplotypes having one or more desired characteristics, wherein: (i) the first parent MiMe maize plant has only MiMe alleles at one or more MiMe loci of a first MiMe component, only MiMe alleles at a first MiMe locus of a second MiMe component, and only non-MiMe alleles at a second MiMe locus of the second MiMe component; (ii) the second parent MiMe maize plant has only MiMe alleles at one or more MiMe loci of the first MiMe component, only non-MiMe alleles at the first MiMe locus of the second MiMe component, and only MiMe alleles at the second MiMe locus of the second MiMe component; and (iii) at least one of the MiMe loci having only MiMe alleles of the first MiMe component of the first parent MiMe maize plant is the same as at least one of the MiMe loci having only MiMe alleles of the first MiMe component of the second parent MiMe maize plant; and (b) crossing the clonal gametes to produce the population of polyploid maize seed wherein at least 50% of the population of polyploid maize seed are genetically uniform and comprise two or more haplotypes.

In another aspect, the present disclosure provides a method of breeding a polyploid maize plant, comprising (a) obtaining a set of maize lines; (b) breeding the maize lines using traditional plant breeding methods to produce a set of candidate maize lines; (c) selecting one or more candidate maize lines; (d) generating a first parent MiMe maize plant from one of the candidate maize lines, wherein the first parent MiMe maize plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination; (e) generating a second parent MiMe maize plant from one of the candidate maize lines, wherein the second parent MiMe maize plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component, and at least one of the MiMe loci having only MiMe alleles of the first MiMe component of the first parent MiMe maize plant is the same as at least one of the MiMe loci having only MiMe alleles of the first MiMe component of the second parent MiMe maize plant; (f) providing clonal gametes from each of the parent MiMe maize plants; (g) crossing the clonal gametes to produce a polyploid maize seed; (h) growing the polyploid maize seed to produce a polyploid maize plant; and (i) evaluating one or more characteristics of the polyploid maize plant. In some embodiments of said breeding method, the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

In another aspect, the present disclosure provides a method of producing a population of polyploid maize seed comprising (a) providing clonal gametes from a pair of parent MiMe maize plants together comprising two or more haplotypes that were selected using the foregoing method of breeding based upon the polyploid maize plant comprising said two or more haplotypes having one or more desired characteristics, wherein: (i) the first parent MiMe maize plant has only MiMe alleles at one or more MiMe loci of a first MiMe component, only MiMe alleles at a first MiMe locus of a second MiMe component, and only non-MiMe alleles at a second MiMe locus of the second MiMe component; (ii) the second parent MiMe maize plant has only MiMe alleles at one or more MiMe loci of the first MiMe component, only non-MiMe alleles at the first MiMe locus of the second MiMe component, and only MiMe alleles at the second MiMe locus of the second MiMe component; and (iii) at least one of the MiMe loci having only MiMe alleles of the first MiMe component of the first parent MiMe maize plant is the same as at least one of the MiMe loci having only MiMe alleles of the first MiMe component of the second parent MiMe maize plant; and (b) crossing the clonal gametes to produce the population of polyploid maize seed, wherein at least 50% of the population of polyploid maize seed are genetically uniform and comprise two or more haplotypes.

In some embodiments of the foregoing breeding methods, steps (d) and (e) comprise introducing a complete MiMe genotype directly into two candidate maize lines to produce the two parent MiMe maize plants. In further embodiments of the foregoing breeding methods, steps (d) and (e) comprise introducing a partial MiMe genotype into two candidate maize lines to produce two grandparent non-MiMe maize plants each having a partial MiMe genotype, crossing said grandparent non-MiMe maize plants each having a partial MiMe genotype to produce the first parent MiMe maize plant, and introducing a complete MiMe genotype directly into a third candidate maize line to produce the second parent MiMe maize plant. In yet further embodiments of the foregoing breeding methods, steps (d) and (e) comprise introducing a partial MiMe genotype into four candidate maize lines to produce four grandparent non-MiMe maize plants each having a partial MiMe genotype, and crossing pairs of said grandparent non-MiMe maize plants each having a partial MiMe genotype to produce the two parent MiMe maize plants. In certain embodiments of the foregoing breeding methods, steps (d) and (e) further comprise propagating parent MiMe maize plants to scale production of homogenous seed.

In some embodiments of the foregoing breeding methods, the method further comprises (j) repeating steps (b)-(i) or steps (c)-(i) using the one or more characteristics of the polyploid maize plant evaluated in step (i) to guide the breeding of the maize lines of step (b), the selecting of candidate maize lines of step (c), or both. In certain embodiments of the foregoing breeding methods, the one or more characteristics includes the heterotic performance of the two, three, four, or more haplotypes of the polyploid maize plant evaluated in step (i). In some embodiments of the foregoing breeding methods, the set of maize lines in step (a) are obtained from one or more of: natural diversity or existing breeding programs. In certain embodiments of the foregoing breeding methods, step (a) further comprises organizing the set of maize lines into two, three, four, or more heterotic groups, wherein each heterotic group comprises a haplotype, and wherein the haplotypes are grouped based on observed or predicted heterotic performance when combined in the polyploid maize plant of step (i). In some variations, heterotic performance is predicted via genome prediction modeling. In some embodiments of the foregoing breeding methods, step (b) comprises reciprocal recurrent selection, inbreeding one or more of the maize lines to homozygosity, production of a doubled haploid maize line (e.g., a doubled monoploid maize line), backcrossing, or any other method known in the art for creating maize lines with high degrees of homozygosity, or a combination thereof. In some embodiments of the foregoing breeding methods, one or more of the candidate maize lines of step (c) are inbred maize lines. In further embodiments of the foregoing breeding methods, one or more of the candidate maize lines of step (c) are hybrid maize lines.

In some embodiments of any of the forgoing breeding methods, the first and second parent MiMe maize plants together comprise two, three, four, or more haplotypes, resulting in a polyploid maize plant comprising two, three, four, or more haplotypes. In some embodiments of the foregoing breeding methods, the maize lines are maintained via vegetative propagation, selfing, apomixis, cell culture, or any combination thereof. In further embodiments of the forgoing methods, the method further comprises maintaining an inventory of maize lines from which haplotypes may be selected for rapid deterministic stacking of the haplotypes. In some variations, the inventory of maize lines comprises one or more maize lines having a complete MiMe genotype that is maintained through vegetative propagation, hybridization with a haploid inducer, or a combination thereof. In additional variations, the inventory of maize lines comprises one or more maize lines having a partial MiMe genotype.

In some embodiments of the foregoing aspects and embodiments, the one or more MiMe loci of the component of sister chromatid cohesion during the first division of meiosis comprise REC8, SWITCH1/DYAD, or a combination thereof. In some embodiments of the foregoing aspects and embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In some embodiments of the foregoing aspects and embodiments, the one or more MiMe loci of the component of progression through the second division of meiosis comprise OSD1, CYCA1, TDM1, PC1, PC2, FC, or any combination thereof. In some embodiments of the foregoing aspects and embodiments, the one or more MiMe loci of the component of progression through the first division of meiosis comprise PS1, JASON, or a combination thereof.

In some embodiments of any of the foregoing aspects and embodiments, the MiMe alleles comprise alleles that are naturally-occurring, introduced via genetic modification, or a combination thereof. In certain embodiments of the foregoing aspects and embodiments, the MiMe alleles comprise one or more genetic modifications. In further embodiments of the foregoing aspects and embodiments, one or more of the genetic modifications are at MiMe loci encoding gene products of the MiMe components. In some variations, the genetic modifications comprise modification of an enhancer in the MiMe loci, modification of a promoter of the MiMe loci, modification of a coding region in the MiMe loci, modification of methylation status of the MiMe loci, expression of a repressor protein that targets the DNA or an mRNA of the MiMe loci, and expression of an RNA interference construct that targets an mRNA from the MiMe loci, or any combination thereof. In some embodiments of the foregoing aspects and embodiments, one or more genetic modifications are introduced by gene editing, transgenesis, or a combination thereof. In further embodiments of the foregoing aspects and embodiments, the decreased expression of the one or more MiMe loci is achieved by gene disruption, gene knockout, gene knockdown, gene silencing, RNA interference, induction of methylation, or any combination thereof.

In any of the foregoing aspects and embodiments, the population of polyploid maize seed may be, for example, triploid, tetraploid, pentaploid, hexaploid, heptaploid, or octoploid. In some embodiments of the foregoing aspects and embodiments, at least 50%, at least 70%, at least 80%, at least 90%, at least 95%, at least 96%, at least 97%, at least 98%, or at least 99% of the population of polyploid maize seed are genetically uniform. In some embodiments of the foregoing aspects and embodiments, the population of polyploid maize seed comprises a subpopulation of genetically uniform polyploid maize seed in an amount of at least 50%, at least at least 70%, at least 75%, at least 80%, at least 90%, at least 95%, at least 96%, at least 97%, at least 98%, or at least 99% of the total number of seeds. In certain embodiments of the foregoing aspects and embodiments, the polyploid maize seed (e.g., the subpopulation of genetically uniform polyploid maize seed) comprises two, three, four, or more haplotypes of the same or related species of maize.

In another aspect, the present disclosure provides a genetically modified maize plant, plant part, or plant cell. In some embodiments, the genetically modified maize plant, plant part, or plant cell comprises: i) three or more haplotypes; and ii) a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, the genetically modified maize plant, plant part, or plant cell comprises: i) three or more haplotypes; and ii) a partial MiMe genotype comprising: (a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations of the foregoing embodiments, the one or more MiMe loci of the component of sister chromatid cohesion during the first division of meiosis comprise REC8, SWITCH1/DYAD, or a combination thereof. In additional variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations of the foregoing embodiments, the one or more MiMe loci of the component of progression through the second division of meiosis comprise OSD1, CYCA1, TDM1, PC1, PC2, FC, or any combination thereof.

In some embodiments of said genetically modified maize plant, plant part, or plant cell, the present disclosure provides a genetically modified maize plant, plant part, or plant cell comprising: i) three or more haplotypes; and ii) a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In other embodiments of this aspect, the genetically modified maize plant, plant part, or plant cell comprising: i) three or more haplotypes; and ii) a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiments, the one or more MiMe loci of the component of progression through the first division of meiosis comprise PS1, JASON, or a combination thereof.

In some embodiments of said genetically modified maize plant, plant part, or plant cell, the genetically modified maize plant, plant part, or plant cell comprises: (i) at least a first and second haplotype, each comprising one or more MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations of the foregoing embodiments, the one or more MiMe loci of the component of sister chromatid cohesion during the first division of meiosis comprise REC8, SWITCH1/DYAD, or a combination thereof. In additional variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations of the foregoing embodiments, the MiMe locus of the component of progression through the first division of meiosis of the third haplotype is PS1 or JASON. In still additional variations of the foregoing embodiments, the one or more MiMe loci of the component of progression through the second division of meiosis of the first and second haplotype comprise OSD1, CYCA1, TDM1, PC1, PC2, FC, or any combination thereof. In yet additional variations of the foregoing embodiments, the locus of the component of progression through the second division of meiosis of the third haplotype is OSD1, CYCA1, TDM1, PC1, PC2, or FC.

In some embodiments of said genetically modified maize plant, plant part, or plant cell, the genetically modified maize plant, plant part, or plant cell comprises: (i) at least a first and second haplotype, each comprising one or more MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiments, the one or more MiMe loci of the component of progression through the first division of meiosis of the first and second haplotype comprise PS1, JASON, or a combination thereof. In yet additional variations of the foregoing embodiments, the MiMe locus of the component of progression through the first division of meiosis of the third haplotype is PS1 or JASON. In still additional variations of the foregoing embodiments, the MiMe locus of the component of progression through the second division of meiosis of the third haplotype is OSD1, CYCA1, TDM1, PC1, PC2 or FC.

In some embodiments, the genetically modified maize plant, plant part, or plant cell has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the genetically modified maize plant, plant part, or plant cell has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the genetically modified maize plant, plant part, or plant cell has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the genetically modified maize plant, plant part, or plant cell has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the genetically modified maize plant, plant part, or plant cell has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1 In some embodiments, the genetically modified maize plant, plant part, or plant cell has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the genetically modified maize plant, plant part, or plant cell has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the genetically modified maize plant, plant part, or plant cell has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the genetically modified maize plant, plant part, or plant cell has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the genetically modified maize plant, plant part, or plant cell has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the genetically modified maize plant, plant part, or plant cell has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the genetically modified maize plant, plant part, or plant cell has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some aspects, provided herein is a genetically modified maize plant, plant part, or plant cell having a partially-complemented MiMe genotype. In some embodiments, the genetically modified maize plant, plant part, or plant cell has a partially-complemented MiMe genotype comprising: (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some embodiments, the first MiMe component is a component of sister chromatid cohesion during the first division of meiosis. In some variations, the one or more MiMe loci of the first MiMe component comprise REC8, SWITCH1/DYAD, or a combination thereof. In one variation, the MiMe locus of the first MiMe component is REC8. In certain embodiments, the second MiMe component is a component of DNA double strand breakage during meiotic recombination. In some variations, the first MiMe locus and the second MiMe locus of the second MiMe component comprise PAIR1, SPO11-1, SPO11-2, PRD1, PRD2, DFO, MTOPVIB, DSY1, SY1, SY2, SY3, SY4, or any combination thereof. In one variation, the first MiMe locus of the second MiMe component is PAIR1 and the second MiMe locus of the second MiMe component is SPO11-1. In further embodiments, the third MiMe component is a component of progression through the second division of meiosis. In some embodiments, the partially-complemented MiMe genotype comprises only MiMe alleles at one or more MiMe loci of the third MiMe component. In some variations, the one or more MiMe loci of the third MiMe component comprise OSD1, CYCA1, TDM1, PC1, PC2, FC, or any combination thereof. In one variation, the MiMe locus of the third MiMe component is OSD1. In other embodiments, the partially-complemented MiMe genotype comprises one or more MiMe alleles and one or more non-MiMe alleles at a first MiMe locus of the third MiMe component, and one or more MiMe alleles and one or more non-MiMe alleles at a second MiMe locus of the third MiMe component. In some variations, the first MiMe locus and the second MiMe locus of the third MiMe component comprise OSD1, CYCA1, TDM1, PC1, PC2, FC, or any combination thereof. In one embodiment, the partially-complemented MiMe genotype comprises only MiMe alleles at one or more MiMe loci of the third MiMe component, wherein the one or more MiMe loci having only MiMe alleles of the first MiMe component comprise REC8, the first MiMe locus of the second MiMe component is PAIR1, the second MiMe locus of the second MiMe component is SPO11-1, and the one or more MiMe loci having only MiMe alleles of the third MiMe component comprise OSD1.

In some embodiments, the present disclosure provides a genetically modified maize plant, plant part, or plant cell having a partially-complemented MiMe genotype comprising: (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiment, the one or more MiMe loci of the component of progression through the first division of meiosis comprise PS1, JASON, or a combination thereof.

In some embodiments, the present disclosure provides a genetically modified maize plant, plant part, or plant cell having a partially-complemented MiMe genotype comprising: (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiments, the one or more MiMe loci of the component of sister chromatid cohesion during the first division of meiosis comprise REC8, SWITCH1/DYAD, or a combination thereof. In yet additional variations of the foregoing embodiments, the one or more MiMe loci of the component of progression through the second division of meiosis comprise OSD1, CYCA1, TDM1, PC1, PC2, FC, or any combination thereof. In still additional variations of the foregoing embodiments, the one or more MiMe loci of the component of progression through the first division of meiosis comprise PS1, JASON, or a combination thereof.

In some embodiments, the genetically modified maize plant, plant part, or plant cell has a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more only MiMe alleles at one or more SPO11-1 loci, wherein each of the MiMe alleles at the SPO11-1 locus comprise one or more genetic modifications resulting in decreased expression of SPO11-1.

In some embodiments, the genetically modified maize plant, plant part, or plant cell has a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

In some embodiments, the genetically modified maize plant, plant part, or plant cell has a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

In some embodiments of said genetically modified maize plant, plant part, or plant cell, which may be combined with any of the preceding embodiments, the genetically modified maize plant, plant part, or plant cell is diploid, triploid, tetraploid, pentaploid, hexaploid, heptaploid, or octaploid. In additional embodiments which may be combined with any of the preceding embodiments, the genetically modified maize plant, plant part, or plant cell comprises two, three, four, or more haplotypes of the same or related species of maize. In certain embodiments, which may be combined with any of the preceding embodiments, the genetically modified maize plant part is a non-regenerable plant part. In certain embodiments, which may be combined with any of the preceding embodiments, the genetically modified maize plant cell is a non-regenerable maize plant cell. In certain embodiments, which may be combined with any of the preceding embodiments, the maize plant part is a flower, a pistil, a stamen, a leaf, a stem, a cutting, a tissue, a seed coat, an ovule, a pollen, a root, a rootstock, a scion, a pericarp, a cotyledon, a hypocotyl, a protoplast, an embryo, an endosperm, an anther, a seed, a cob, a glume, a husk, a leaf sheath, a ligule, a trichome, or a portion thereof.

In another aspect, provided herein is a processed maize product derived from any of the foregoing embodiments of genetically modified maize plants, plant parts, or plant cells, wherein the processed maize product comprises a detectable amount of the one or more MiMe alleles of the genetically modified maize plant, plant part, or plant cell. In some embodiments, the maize product is selected from the group consisting of maize plant parts, fresh corn, canned corn, dehydrated corn, starch, hulls, hominy, popcorn, cereal, grain, margarine, fermented alcoholic beverage, biofuel, gluten, corn syrup, table syrup, candy, confections, soft drinks, ice cream, shoe polish, corn sugar, infant formulas, dietetic foods, caramel coloring, vinegar, lactic acid, tanning mixtures, brewing additive, artificial silk, edible starch, dextrin, mucilage, glue, textile sizing, food sauces, fireworks, industrial starch, laundry starch, filler in paper, cosmetics, explosives, germ, oil cake or meal, cattle feed, plastic resin, rubber substitutes, erasers, elastic heels, soap, glycerin, soluble corn oil, cloth coloring, salad oils, cooking oils, medicinal oils, animal feed, paper, wallboard, filling material, fuel, charcoal, industrial solvent, biomass, oil, meal, food starch, syrup, sugar, animal feed, flour, flakes, bran, processed seed, and seed. In certain embodiments, the processed maize product is non-regenerable.

DESCRIPTION OF THE FIGURES

The present application can be understood by reference to the following description taken in conjunction with the accompanying figures.

FIG. 1 depicts a phylogenetic tree of REC8 protein sequences from monocotyledonous plants.

FIG. 2 depicts a phylogenetic tree of SPO11-1 protein sequences from monocotyledonous plants.

FIG. 3 depicts a phylogenetic tree of PAIR1 protein sequences from monocotyledonous plants.

FIG. 20A illustrates generation of a plant having a first exemplary partially-complemented MiMe genotype where MiMe loci are propagated at the parent stage and each parent has a different set of edited MiMe loci. FIG. 20B illustrates generation of a plant having a second exemplary partially-complemented MiMe genotype where MiMe loci are propagated at the parent stage and each parent has a different set of edited MiMe loci. FIG. 20C illustrates generation of a plant having a third exemplary partially-complemented MiMe genotype where MiMe loci are propagated at the parent stage and each parent has a different set of edited MiMe loci.

FIG. 22A shows the screening results where editing efficiency is displayed as the proportion of sequence reads edited compared to wild-type (vertical axis, in percentage) across a range of selected protospacers (horizontal axis) across four different genes (horizontal axis, grey boxes). From left to right, the maize orthologs are listed for OSD1 on chromosome 2 ("ZmOsd1-chr2"), OSD1 on chromosome 5 ("ZmOsd1-chr5-1") and OSD1 duplication on chromosome 5 ("ZmOsd1-chr5-2"), CYCA1 on chromosome 3 ("ZmTAM-chr3"), and CYCA1 on chromosome 8 ("ZmTAM-chr8"). FIG. 22B shows further results of screening, as in FIG. 22A, with the exception that the exhibited genes are the maize orthologs of PAIR1 ("ZmPairl-1" and "ZmPairl-9"), REC8 ("ZmRec8"), and SPO11-1 ("ZmSpo11-1").

FIGS. 23A-23F show the resultant editing of MiMe alleles and disruption of MiMe components in edited maize lines. FIG. 23A shows that four conserved amino acids in the REC8 protein are deleted as a result of the edited rec8 allele. FIG. 23B shows the truncated, inactivated OSD1 proteins resulting from frameshift edits that result in premature stop codons in the edited osd1 alleles. FIG. 23C shows the truncated, inactivated SPO11-1 protein resulting from a frameshift edit that results in a premature stop codon in the edited spo11-1 allele. FIG. 23D shows an alignment of edited "scar" nucleotide sequence of the edited rec8 allele (bottom portion continues from the top portion). FIG. 23E shows an alignment of edited "scar" nucleotide sequences of edited osd1 alleles (bottom portion continues from the top portion). FIG. 23F shows an alignment of edited "scar" nucleotide sequences of edited spo11-1 alleles (bottom portion continues from the top portion).

FIG. 26A shows multiple rows of BMP plants. FIG. 26B shows a close-up of the right-hand side of FIG. 26A, displaying a close-up view of three BMP plants. FIG. 26C shows healthy BMP plants readily producing ears. FIG. 26D shows a close-up view of the ears of BMP plants as shown in FIG. 26C.

FIGS. 28A-28H show the resultant editing of MiMe alleles and disruption of MiMe components in edited Arabidopsis lines. FIG. 28A shows the truncated, inactivated proteins resulting from premature stop codons that result from the edited osdi alleles. FIG. 28B shows the truncated, inactivated proteins resulting from insertion of a premature stop codon in edited spo11-1 alleles. FIG. 28C shows a truncated, inactivated protein resulting from a premature stop codon in one of the edited rec8 alleles, and the deletion of three conserved amino acids resulting from the other edited rec8 allele. FIG. 28D shows an alignment of edited "scar" nucleotide sequences of edited osdi alleles targeted at a first target site (bottom portion continues from the top portion). FIG. 28E shows an alignment of edited "scar" nucleotide sequences of edited osdi alleles targeted at a second target site (bottom portion continues from the top portion). FIG. 28F shows an alignment of edited "scar" nucleotide sequences of edited spo11-1 alleles (bottom portion continues from the top portion). FIG. 28G shows an alignment of edited "scar" nucleotide sequences of edited rec8 alleles. FIG. 28H shows an alignment of edited "scar" nucleotide sequences of edited pair1 alleles (bottom portion continues from the top portion).

FIG. 29A illustrates a summary of the genotyping results at 58 triallelic markers across 99 progeny comprising the Boosted Arabidopsis Population 1 (BAP1). The horizontal-axis corresponds to individual tetraploid progeny as well as the two diploid parent plants for reference. The vertical-axis corresponds to individual triallelic markers distributed across 4 separate chromosomes. When referring to the axis, vertical and horizontal are in respect to the legend text for their respective figure. The coloration of each cell denotes the specific configuration of haplotypes observed at that marker (where A=Shahdara, B=Col-0, and C=HR-10). Samples with markers that are "AABC" have three haplotypes. Marker design was limited to regions of the genome where heterozygous parental SNPs were present. No usable markers were found on chromosome 3. The parent genotypes are displayed in the two left-most columns. FIG. 29B illustrates a summary of the genotyping results at 57 triallelic markers across 9 progeny of the Standard Arabidopsis Population (SAP, top).

The vertical-axis corresponds to individual tetraploid progeny as well as the two tetraploid parent plants for reference. The horizontal-axis corresponds to individual triallelic markers distributed across 5 separate chromosomes. The coloration of each cell denotes the specific configuration of haplotypes observed at that marker (where A=Shahdara, B=Col-0, and C=HR-10). 9 representative individuals from BAP1 (FIG. 29A) are shown for comparison (bottom). FIG. 29C shows a matrix illustrating pairwise identity as estimated by the Jaccard similarity coefficient of 57 molecular markers genotyped between 9 tetraploid *Arabidopsis* plants in the Standard *Arabidopsis* Population (SAP). FIG. 29D shows a matrix for pairwise identity as estimated by the Jaccard similarity coefficient of 58 molecular markers genotyped between 99 tetraploid *Arabidopsis* plants in Boosted *Arabidopsis* Population 1 (BAP1).

FIG. 30A shows a top-down view of BAP1 plants at 48 days after planting. FIG. 30B shows a subset of FIG. 30A's BAP1 plants, at a closer proximity and an oblique view, also at 48 days after planting.

FIG. 31A shows seedless fruit from BAP1 plants whose pistils were treated, untreated, or mock-treated with gibberellic acid ("GA3") to induce fruit development, compared to fruit resulting from pistils treated or mock-treated from fertile *Arabidopsis* control plants. FIG. 31B shows comparison of the average number of seeds per silique (vertical axis) between BAP1 plants, the doubled version of the parent MiMe plant PED-AR-BC (doubled as "PED-AR-BCBC") plants, and the doubled version of the parent MiMe plant PED-AR-AA (doubled as "PED-AR-AAAA") plants, all along the horizontal axis. The population means and standard deviations are represented in the graph by crosses and error bars, respectively FIG. 31C shows comparison of the silique lengths (vertical axis) between the same plant groups in FIG. 31B (horizontal axis). The length of fruit (siliques) resulting from GA3-treated pistils, mock-treated pistils ("mock"), and untreated pistils was measured across the respective plant groups at 8 days after GA3 application. The population means and standard deviations are represented in the graph by crosses and error bars, respectively. FIG. 31D illustrates a comparison of the average number of seeds per silique (vertical axis) between BAP2 plants, the doubled version of the parent MiMe plant PED-AR-BC (doubled as "PED-AR-BCBC"), and the doubled version of the parent MiMe plant PED-AR-DE (doubled as "PED-AR-DEDE"), all along the horizontal axis. The population means and standard deviations are represented in the graph by crosses and error bars, respectively.

DETAILED DESCRIPTION

Figure 4:
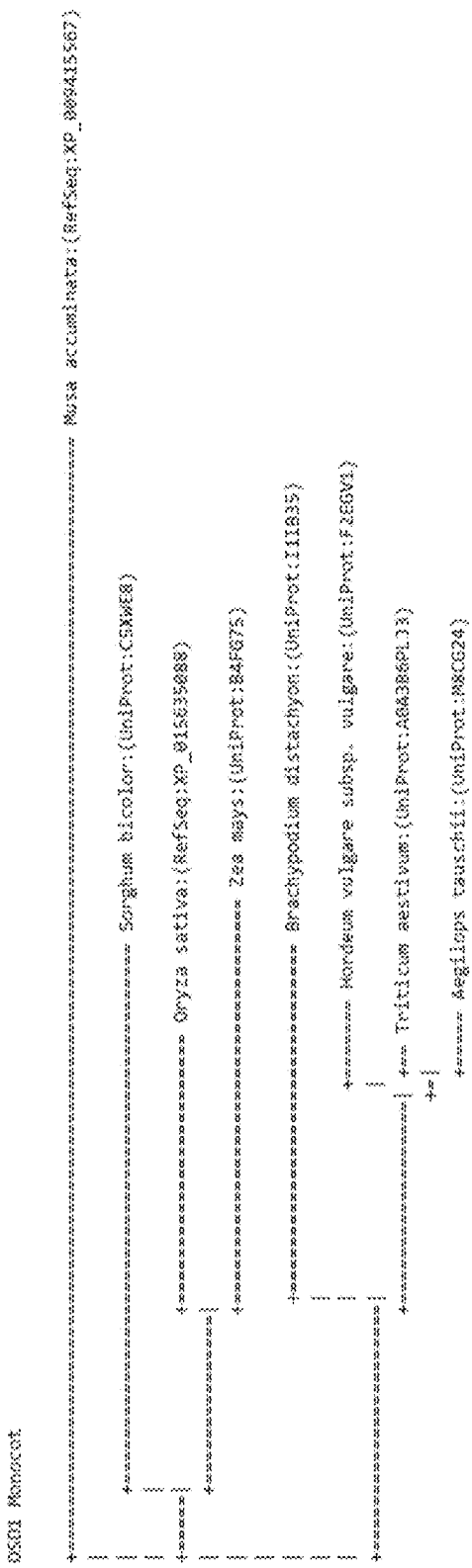
FIG. 4 depicts a phylogenetic tree of OSD1 protein sequences from monocotyledonous plants.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Overview

In one aspect, described herein is a population of polyploid maize seed comprising three or more haplotypes of the same or related species of maize, wherein at least 50% of the population of polyploid maize seed is genetically uniform, and wherein the population was obtained from a single maize plant or a set of maize plants such as, for example, a set of genetically uniform F1 hybrids. In some embodiments, the population of polyploid maize seed comprises a subpopulation of genetically uniform polyploid maize seed in an amount of at least 50% of the total number of seed, the genetically uniform polyploid maize seed comprising three or more haplotypes of the same or related species of maize. The genetic uniformity of the seeds of the population addresses a long-felt need for genetically uniform populations of polyploid maize seed comprising three or more haplotypes with improved heterotic performance over the pairs of haplotypes present in existing hybrid maize plants. In some embodiments, the population of polyploid maize seed and/or the subpopulation of genetically uniform polyploid maize seed comprises one or more genetic modifications resulting in decreased expression of one or more MiMe loci. The population of polyploid maize seed and/or the subpopulation of genetically uniform polyploid maize seed may have a complete or partial MiMe genotype comprising MiMe alleles conferring decreased expression of MiMe loci of one or more MiMe components.

In another aspect, provided herein are methods of producing a population of polyploid maize seed comprising three or more haplotypes wherein at least 50% of the population of polyploid maize seed are genetically uniform. In some embodiments, the population of polyploid maize seed comprises a subpopulation of genetically uniform polyploid maize seed in an amount of at least 50% of the total number of seed, the genetically uniform polyploid maize seed comprising three or more haplotypes of the same or related species of maize. In some embodiments, the method comprises (a) providing clonal gametes from a pair of parent MiMe maize plants that together comprise three or more haplotypes; and (b) crossing the clonal gametes to produce the population of polyploid maize seed. In other embodiments, the method comprises (a) providing clonal gametes from a parent MiMe maize plant; (b) providing haploid (e.g., monoploid, dihaploid, or higher ploidy) gametes from a homozygous parent non-MiMe maize plant; and (c) crossing the clonal gametes with the haploid (e.g., monoploid) gametes to produce the population of polyploid maize seed.

In yet another aspect, provided herein are methods of breeding a polyploid hybrid maize line comprising three or more haplotypes, the methods comprising: obtaining a set of maize lines; breeding the maize lines using traditional plant breeding methods to produce a set of candidate maize lines; and selecting two or more candidate maize lines, together comprising three or more haplotypes, for crossing. In some embodiments, after the selection of candidate maize lines, the methods further comprise generating two parent MiMe maize plants from the two or more candidate maize lines; providing clonal gametes from each of the parent MiMe maize plants; and crossing the clonal gametes to produce a hybrid polyploid maize seed comprising the three or more haplotypes. In alternative embodiments, after the selection of candidate maize lines, the methods further comprise generating a single parent MiMe maize plant from one of the two or more candidate maize lines; providing clonal gametes from the parent MiMe maize plant; providing haploid (e.g., monoploid) gametes from a homozygous parent non-MiMe maize plant of one of the two or more candidate maize lines; and crossing the clonal gametes with the haploid (e.g., monoploid) gametes to produce a hybrid polyploid maize seed. In some embodiments, after the crossing of the clonal gametes or the crossing of the clonal gametes with the haploid (e.g., monoploid) gametes, the methods further comprise growing the hybrid polyploid maize seed to produce a hybrid polyploid maize plant and evaluating one or more characteristics of the hybrid polyploid maize plant.

In another aspect, described herein is a population of polyploid maize seed comprising a partially-complemented MiMe genotype, wherein at least 50% of the population of polyploid maize seed is genetically uniform, and wherein the population was obtained from a single maize plant or a set of maize plants such as, for example, a set of genetically uniform F1 hybrids. In some embodiments, the population of polyploid maize seed comprises a subpopulation of genetically uniform polyploid maize seed in an amount of at least 50% of the total number of seed, the genetically uniform polyploid maize seed comprising the partially-complemented MiMe genotype. The polyploid maize seed comprising the partially-complemented MiMe genotype may comprise one, two, three, or more haplotypes. The partially-complemented MiMe genotype of the population of polyploid maize seed results in a maize plant having neither a wild-type meiosis phenotype nor a MiMe phenotype. Thus, in some embodiments, germination of a seed of the population of polyploid maize seed or the subpopulation of genetically uniform polyploid maize seed results in a maize plant that produces inviable gametes. The genetic uniformity of the seeds of the population addresses a long-felt need for genetically uniform populations of polyploid maize seed of plants. In some embodiments, the partially-complemented MiMe genotype comprises (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component. In certain embodiments, the partially-complemented MiMe genotype further comprises (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component.

In another aspect, provided herein are methods of producing a population of polyploid maize seed comprising a partially-complemented MiMe genotype wherein at least 50% of the population of polyploid maize seed are genetically uniform. In some embodiments, the population of polyploid maize seed comprises a subpopulation of genetically uniform polyploid maize seed in an amount of at least 50% of the total number of seed, the genetically uniform polyploid maize seed comprising the partially-complemented MiMe genotype. The polyploid maize seed comprising the partially-complemented MiMe genotype may comprise one, two, three, or more haplotypes. In some embodiments, the method comprises: (a) providing clonal gametes from a first parent MiMe maize plant; (b) providing clonal gametes from a second parent MiMe maize plant; and (c) crossing the clonal gametes to produce the population of polyploid maize seed comprising a partially-complemented MiMe genotype. In some embodiments, the first parent MiMe maize plant has only MiMe alleles at one or more MiMe loci of a first MiMe component, only MiMe alleles at a first MiMe locus of a second MiMe component, and only non-MiMe alleles at a second MiMe locus of the second MiMe component; and the second parent MiMe maize plant has only MiMe alleles at one or more MiMe loci of the first MiMe component, only non-MiMe alleles at the first MiMe locus of the second MiMe component, and only MiMe alleles at the second MiMe locus of the second MiMe component. In certain embodiments, at least one of the MiMe loci having only MiMe alleles of the first MiMe component of the first parent MiMe maize plant is the same as at least one of the MiMe loci having only MiMe alleles of the first MiMe component of the second parent MiMe maize plant. In some embodiments, the first and second parent MiMe maize plants further have only MiMe alleles at one or more MiMe loci of a third MiMe component, wherein the one or more MiMe loci having only MiMe alleles of the third MiMe component of the first and second parent MiMe maize plants are the same or different.

In yet another aspect, provided herein are methods of breeding a polyploid maize plant, the methods comprising: obtaining a set of maize lines; breeding the maize lines using traditional plant breeding methods to produce a set of candidate maize lines; and selecting two or more candidate maize lines for crossing. In some embodiments, after the selection of candidate maize lines, the methods further comprise generating two parent MiMe maize plants from the two or more candidate maize lines. In some embodiments, the first parent MiMe maize plant has only MiMe alleles at one or more MiMe loci of a first MiMe component, only MiMe alleles at a first MiMe locus of a second MiMe component, and only non-MiMe alleles at a second MiMe locus of the second MiMe component; and the second parent MiMe maize plant has only MiMe alleles at one or more MiMe loci of the first MiMe component, only non-MiMe alleles at the first MiMe locus of the second MiMe component, and only MiMe alleles at the second MiMe locus of the second MiMe component. In certain embodiments, at least one of the MiMe loci having only MiMe alleles of the first MiMe component of the first parent MiMe maize plant is the same as at least one of the MiMe loci having only MiMe alleles of the first MiMe component of the second parent MiMe maize plant. In some embodiments, the first and second parent MiMe maize plants further have only MiMe alleles at one or more MiMe loci of a third MiMe component, wherein the one or more MiMe loci having only MiMe alleles of the third MiMe component of the first and second parent MiMe maize plants are the same or different. In some embodiments, the method further comprises providing clonal gametes from each of the parent MiMe maize plants, crossing the clonal gametes to produce a polyploid maize seed, growing the polyploid maize seed to produce a polyploid maize plant, and evaluating one or more characteristics of the polyploid maize plant.

In some variations of the methods of breeding, the methods may further comprise repeating the steps of the method, using the one or more characteristics of the hybrid polyploid maize plant evaluated to guide the breeding of maize lines, the selecting of candidate maize lines, or both. In additional variations, the methods may further comprise organizing the set of maize lines into three or more heterotic groups, wherein each heterotic group comprises a haplotype, and wherein the haplotypes are grouped based on observed or predicted heterotic performance when combined in the hybrid polyploid maize plant. This method allows for deterministic combination of three or more haplotypes in a polyploid maize plant, addressing the need for maize plant breeding methods that yield predictable results on time scales shorter than those required for traditional breeding methods.

Definitions

As used herein, the terms "maize" and "maize plant" include the whole maize plant or any parts or derivatives thereof, such as plant organs (e.g., harvested or non-harvested flowers, leaves, etc.), plant cells, plant protoplasts, plant cell or tissue cultures from which whole plants can be regenerated, regenerable or non-regenerable plant cells, plant calli, plant cell clumps, and plant cells that are intact in plants, or parts of plants, such as embryos, pollen, ovules, ovaries (e.g., harvested tissues or organs), flowers, leaves, seeds, clonally propagated plants, roots, stems, cotyledons, hypocotyls, root tips and the like. The plant parts or derivatives thereof can also include any of the aforementioned plant parts in an encapsulated form such as, for example, shoot meristems, nodes, stolon tips, and the like, encapsulated in alginate, e.g., in a synthetic seed. Any developmental stage is also included, such as seeds, seedlings, immature and mature, etc. As used herein, the term "non-regenerable" generally refers to a maize plant part, a plant cell, a processed maize product, or a portion of any of the foregoing, that cannot be induced to form a whole maize plant or that cannot be induced to form a whole maize plant that is capable of sexual and/or asexual reproduction.

As used herein, the term "seed" typically refers to a true seed rather than another plant part used for propagation.

As used herein, the term "non-regenerable" generally refers to a plant part, a plant cell, a processed plant product, or a portion of any of the foregoing, that cannot be induced to form a whole plant or that cannot be induced to form a whole plant that is capable of sexual and/or asexual reproduction.

As used herein, "ploidy" refers to the number of complete sets of chromosomes in a cell or organism. Ploidy may be annotated using "n" as the unit of complete sets of chromosomes. For example, a cell or organism with a single set of chromosomes may be referred to as "1n", or the single set of chromosomes itself may be referred to as "1n". A diploid cell or organism with two sets of chromosomes may be referred to as "2n"; a triploid cell or organism with three sets of chromosomes may be referred to as "3n"; and so on.

As used herein, "monoploid" refers to a cell or organism with a ploidy of 1n.

As used herein, "diploid" refers to a cell or organism with a ploidy of 2n.

As used herein, "polyploid" refers to a cell or organism with a ploidy of greater than 2n. "Polyploid" may refer to organisms which are triploid (3n), tetraploid (4n), pentaploid (5n), hexaploid (6n), heptaploid (7n), octoploid (8n), or higher ploidies (greater than 8n).

As used herein, "allele" refers to one of two or more alternative forms of a single gene or locus within the genome. As used herein, "monoallelic" typically describes the presence of a single allele at a given locus or set of loci within a cell or organism. As used herein, "biallelic" typically describes the presence of two different alleles at a given locus or set of loci within a cell or organism. As used herein, "multiallelic" typically describes the presence of three or more alleles at a given locus or set of loci within a cell or organism.

As used herein, "haplotype" refers to a distinct 1n set of chromosomes with a unique set of alleles. As used herein, each haplotype is distinct from other haplotypes in that it contains a set of alleles that confers a unique set of characteristics not conferred by other haplotypes. As used herein, as a feature of the present disclosure, each distinct haplotype need not be inherited from a different parent—a polyploid organism of the present disclosure may comprise three or more haplotypes inherited from two parents. As used herein, "monoallelic plant" typically refers to a plant line containing a single haplotype, "biallelic plant" typically refers to a plant line containing two haplotypes, and "multiallelic plant" typically refers to a plant line containing three or more haplotypes. In the case of allopolyploid maize plants that contain multiple subgenomes between which there is little to no recombination, as used herein, the term "three or more haplotypes" typically refers to three or more haplotypes of the same subgenome.

As used herein, "clonal" describes a body of DNA that is substantially identical to another body of DNA; or a set of cells or organisms that comprise such DNA. For example, mitosis results in two clonal genomes comprised by two clonal cells. Due to random errors in natural DNA replication, clonal bodies of DNA, clonal cells, or clonal organisms may not be completely identical. "Clonal" may describe two genomes that are not completely identical in sequence but that contain the same set of alleles.

As used herein, "genetically uniform" typically describes a set of individual plants, plant parts (e.g., seeds), or plant cells whose genomes are identical across at least 80% of loci, or are clonal. Genetic uniformity of a set of individual plants, plant parts (e.g., seeds), or plant cells may be measured using methods known in the art and described herein. For example, a set of genetic markers may be identified and used to determine the estimated pairwise identity of a pair of individuals, or to determine the average pairwise genetic uniformity of a population of individuals, using the Jaccard similarity coefficient. For example, a population of genetically uniform plants or seeds may consist of plants or seeds having genomes that are identical to one another across at least 80%, at least 85%, at least 90%, at least 95%, at least 96%, at least 97%, at least 98%, at least 99%, or 100% of genetic markers analyzed, or may consist of seeds having an average pairwise genetic uniformity of at least 80%, at least 85%, at least 90%, at least 95%, at least 96%, at least 97%, at least 98%, at least 99%, or 100% as measured by the Jaccard similarity coefficient. Additionally, each pair of seeds in a population of genetically uniform plants or seed may have genomes that have a pairwise identity of at least 95%, at least 96%, at least 97%, at least 98%, at least 99%, or 100% as measured by the Jaccard similarity coefficient.

As used herein, "expression" and "expression level" refer to the relative or absolute amount of a functional gene product present in a cell. As used herein, "gene products" include, but are not limited to, nucleic acids (e.g., RNA), post-transcriptionally modified nucleic acids (e.g., spliced RNA, poly-adenylated mRNA), proteins (e.g., enzymes, structural proteins, etc.), and post-translationally modified proteins (e.g., glycoproteins, lipoproteins, etc.). The function of the gene product refers to the wild-type, unmodified, uninhibited function of the gene product. As used herein, "decreased expression" refers to a relative decrease in the amount of a functional gene product of a gene or genetic locus, such as a MiMe locus, present in a cell. The decreased expression may refer to a decrease in the total amount of a gene product present in a cell (e.g., a decrease in the amount of a protein) or to a decrease in the amount of functional gene products present in a cell (e.g., a decrease in the percentage of proteins with wild-type function, e.g., an altered activity of the protein) or to a decrease in the function of gene products present in a cell (e.g., a decrease in the activity of proteins as compared to proteins with wild-type function, e.g., elimination of activity). The decreased expression may be of a gene product encoded at a certain genomic locus. Decreased expression also includes "non-expression" and "eliminated expression." As used herein, "non-expression" or "eliminated expression" refers to the absence of a functional gene product present in a cell, or to an expression level insufficient for detection of the gene product in the cell, or to an expression level insufficient to result in the function of the gene product within the cell, or to an activity level insufficient to result in the detectable activity of the gene product within the cell.

As used herein, "homozygous" describes a cell or organism in which all sets of chromosomes encode the same allele or set of alleles at a certain chromosomal locus, a set of chromosomal loci, or at all chromosomal loci. For example, a triploid cell or organism with the same allele at a specific locus in all three sets of chromosomes is homozygous for that allele. An organism may be homozygous for a specific allele or set of alleles at a certain chromosomal locus or set of chromosomal loci, or an organism may be homozygous for a haplotype. For example, a triploid cell or organism containing three copies of the same haplotype is homozygous for that haplotype. As used herein, "homozygous plant" typically refers to an inbred plant or plant line, a monoallelic plant or plant line, or a plant or plant line which is homozygous at all loci within its genome.

As used herein, "heterozygous" describes a cell or organism in which at least one set of chromosomes encodes an allele or set of alleles at a certain chromosomal locus or set of chromosomal loci that is distinct from those of the other sets of chromosomes within the cell or organism. For example, a triploid cell or organism having allele $a_1$ at locus A in two sets of chromosomes and having allele $a_2$ at locus A in the third set of chromosomes is heterozygous for alleles $a_1$ and $a_2$. An organism may be heterozygous for a specific set of alleles at a certain chromosomal locus or set of chromosomal loci, or an organism may be heterozygous for a haplotype. For example, a triploid cell or organism containing two copies of one first haplotype and one copy of a second haplotype is heterozygous for the first and second haplotype. As used herein, "heterozygous plant" typically refers to a biallelic or multiallelic plant or plant line containing two or more haplotypes.

As used herein, "crossing" refers to the act of forming a zygote from gametes of two distinct plants or plant lines. Crossing may refer to pollinating a plant or plant line using the pollen of a different plant or plant line.

As used herein, "related species of maize" refers to two or more species of maize (e.g., two or more species of the genus *Zea*) that, when crossed, result in viable seed.

As used herein, "hybrid" describes a plant comprising two or more haplotypes from the same or related species of plant.

As used herein, "F1 hybrid" refers to the first filial generation of hybrid seeds or plants resulting from the cross of parents comprising two or more haplotypes. For clarity, this refers to the first filial generation of the cross and not the first filial generation of the hybrids of a cross.

As used herein, "heterotic performance" refers to the performance of a set of two or more haplotypes in conferring certain desirable characteristics when combined in a hybrid plant. The desired characteristics of heterotic performance may include characteristics of plant vigor including, but not limited to, plant size, hardiness, grain yield, and the like.

As used herein, "MiMe" typically refers to a phenotype of a plant wherein the wild-type meiosis phenotype of the plant is disrupted in such a way that results in the formation of clonal female gametes and/or clonal male gametes. "MiMe" may refer to any one of several known methods to promote the formation of clonal female gametes and/or clonal male gametes in plants including, but not limited to, Mitosis instead of Meiosis as disclosed in d'Erfurth et al. (2009. Turning meiosis into mitosis. *PLoS Biol* 7, e1000124) and first division restitution without crossing over (FDR-NCO) as disclosed in Peloquin et al. (1999. Meiotic mutants in potato: valuable variants. *Genetics* 153: 1493-1499), a prime example of FDR-NCO being spo11-1, ps1 mutants as disclosed in Brownfield and Kohler (2010. Unreduced gamete formation in plants: mechanisms and prospects. *J Exp Bot* 62:5, 1659-1668).

In organisms with a wild-type meiosis phenotype, meiosis in germline cells results in haploid gametes. As used herein, "haploid" typically refers to a cell or organism with a ploidy half that of the parent organism. As used herein, "haploid gametes" typically refers to gamete cells with a ploidy half that of the parent organism. For example, in a diploid (2n) organism with a wild-type meiosis phenotype, meiosis in germline cells results in 1n haploid gametes. In another example, in a tetraploid (4n) organism with a wild-type meiosis phenotype, meiosis in germline cells results in 2n haploid gametes. As used herein, "parent non-MiMe plant" typically refers to a plant with the wild-type meiosis phenotype wherein meiosis in germline cells results in haploid gametes (pollen and egg cells). As used herein, "homozygous parent non-MiMe plant" typically refers to an inbred parent non-MiMe parent, a monoallelic parent non-MiMe plant, or a parent non-MiMe plant which is homozygous at all loci within its genome. A homozygous parent non-MiMe plant may be produced through inbreeding, production of a doubled haploid line (e.g., a doubled monoploid line), or any other method known in the art for creating plant lines with high degrees of homozygosity.

In plants with the MiMe phenotype, meiosis is replaced by a mitosis-like process in male and/or female germline cells, resulting in clonal gametes. As used herein, "clonal gametes" typically refers to gametes which comprise unreduced, unrecombined copies of the parent plant's genome and, therefore, have the same ploidy as, and are typically genetically identical to, the parent plant. Clonal gametes are produced when germline cells in the parent plant do not undergo recombination as they would in a normal meiotic process, and also undergo a first division restitution or a second division restitution, resulting in unreduced gametes. As a result, clonal gametes are typically both unreduced and unrecombined and therefore typically genetically identical to the parent plant. For example, in a diploid (2n) plant with a MiMe phenotype, germline cells undergo mitosis instead of meiosis, typically resulting in 2n unrecombined gametes, i.e., clonal gametes. In another example, in a tetraploid (4n) plant with a MiMe phenotype, germline cells undergo mitosis instead of meiosis, typically resulting in 4n unrecombined gametes, i.e., clonal gametes. Clonal gametes may refer to female clonal gametes, male clonal gametes, or a combination thereof.

As used herein, "unreduced, non-clonal gametes" typically refers to gametes which comprise unreduced, yet recombined, copies of the parent plant's genome and, therefore, have the same ploidy as the parent plant, but are not genetically identical to the parent plant. Unreduced, non-clonal gametes are produced when germline cells in the parent plant undergo recombination as they would in a normal meiotic process, but undergo a first division restitution or a second division restitution, resulting in unreduced gametes. Therefore, even though unreduced, non-clonal gametes are unreduced, they are the result of a normal recombination process, and are therefore not genetically identical to the parent plant. For example, germline cells in a diploid (2n) plant that undergo a normal recombination process but undergo a first division restitution or a second division restitution result in 2n, recombined gametes, i.e., unreduced, non-clonal gametes. In another example, germline cells in a tetraploid (4n) plant that undergo a normal recombination process but undergo a first division restitution or a second division restitution result in 4n, recombined gametes, i.e., unreduced, non-clonal gametes. Unreduced, non-clonal gametes may refer to female clonal gametes, male clonal gametes, or a combination thereof.

As used herein, "MiMe component" typically refers to a gene function that contributes to a MiMe phenotype, including, but not limited to, genes and gene products involved in meiosis that may be modified or altered to disrupt a wild-type meiotic phenotype in a manner relevant to the formation of clonal female gametes and/or clonal male gametes via MiMe. MiMe components include (1) a component of sister chromatid cohesion during the first division of meiosis, (2) a component of DNA double strand breakage during meiotic recombination, (3) a component of progression through the second division of meiosis, and (4) a component of progression through the first division of meiosis. In general, each MiMe component includes one or more MiMe loci discussed further below. Further, generally, each MiMe locus may have MiMe alleles and non-MiMe alleles.

As used herein, "MiMe allele" typically refers to an allele at a MiMe locus that disrupts the normal meiotic function of a MiMe component (e.g., an allele that disrupts sister chromatid cohesion during the first division of meiosis). MiMe alleles may be naturally occurring MiMe alleles, or may be introduced into a plant line via genetic modification using the methods described herein.

As used herein, "non-MiMe allele" typically refers to any allele that contributes to wild-type function of a MiMe component that therefore does not contribute to conferring a MiMe phenotype in a plant. A non-MiMe allele typically refers to an allele at a MiMe locus that contributes to the wild-type meiotic function of a MiMe component (e.g., an allele that provides the wild-type function that contributes to sister chromatid cohesion during the first division of meiosis).

As used herein, "complete MiMe genotype" typically refers to any set of alleles that confers the MiMe phenotype in a plant. The individual alleles that make up the complete MiMe genotypes are referred to as MiMe alleles. The complete MiMe genotype may be naturally present in a plant or may be introduced via, for example, plant breeding, transgenic techniques, gene-editing techniques, or any combination thereof to introduce one or more naturally-occurring alleles, non-naturally-occurring alleles, or a combination thereof. A complete MiMe genotype may comprise any number of MiMe alleles that results in a MiMe phenotype, such as one, two, three, or more MiMe alleles. As used herein, "MiMe locus" and "MiMe loci" typically refers to any chromosomal locus or loci which may be the site of MiMe alleles, including genes and intergenic loci. A MiMe locus or MiMe loci may correspond to a specific MiMe component, for example, if the MiMe locus encodes a MiMe component gene product. A complete MiMe genotype may comprise MiMe alleles at any number of MiMe loci, such as one, two, three, or more MiMe loci. A complete MiMe genotype may comprise different alleles at the same MiMe locus on different sets of chromosomes and need not be homozygous to confer a MiMe phenotype. For example, a diploid plant with a complete MiMe genotype may have two different REC8 alleles each of which reduces or eliminates REC8 expression or activity such that the plant has two MiMe alleles for REC8 and thus exhibits disruption of sister chromatid cohesion during the first division of meiosis. Specific examples of complete MiMe genotypes are described in detail herein.

As used herein, "partial MiMe genotype" typically refers to a set of alleles that comprises both MiMe and non-MiMe alleles at one or more MiMe loci such that a plant with a partial MiMe genotype exhibits a wild-type meiosis phenotype. Two plants having compatible partial MiMe genotypes each exhibit a wild-type meiosis phenotype and may be crossed to produce F1 offspring having a complete MiMe genotype and, thus, a MiMe phenotype. As used herein, "compatible partial MiMe genotypes" typically refers to two or more partial MiMe genotypes that comprise sets of MiMe alleles at the same MiMe loci. For example, a partial MiMe genotype comprising MiMe alleles of REC8, SPO11-1, and OSD1 is compatible with another partial MiMe genotype that comprises the same or different MiMe alleles of REC8, SPO11-1, and OSD1. The MiMe alleles of a partial MiMe genotype may be combined with the MiMe alleles of the same or different partial MiMe genotype in a single cross to create a complete MiMe genotype and confer a MiMe phenotype in the F1 offspring. In general, where MiMe alleles and non-MiMe alleles are referred to together they are alleles of the same MiMe loci. The partial MiMe genotype may be naturally present in a plant or may be introduced via, for example, plant breeding, transgenic techniques, gene-editing techniques, or any combination thereof to introduce one or more naturally-occurring alleles, non-naturally-occurring alleles, or a combination thereof. A partial MiMe genotype may comprise any number of alleles, such as one, two, three, or more alleles. Further, a partial MiMe genotype may comprise MiMe alleles at any number of MiMe loci, such as one, two, three, or more MiMe loci. Specific examples of partial MiMe genotypes are described in detail herein.

Figure 20A:
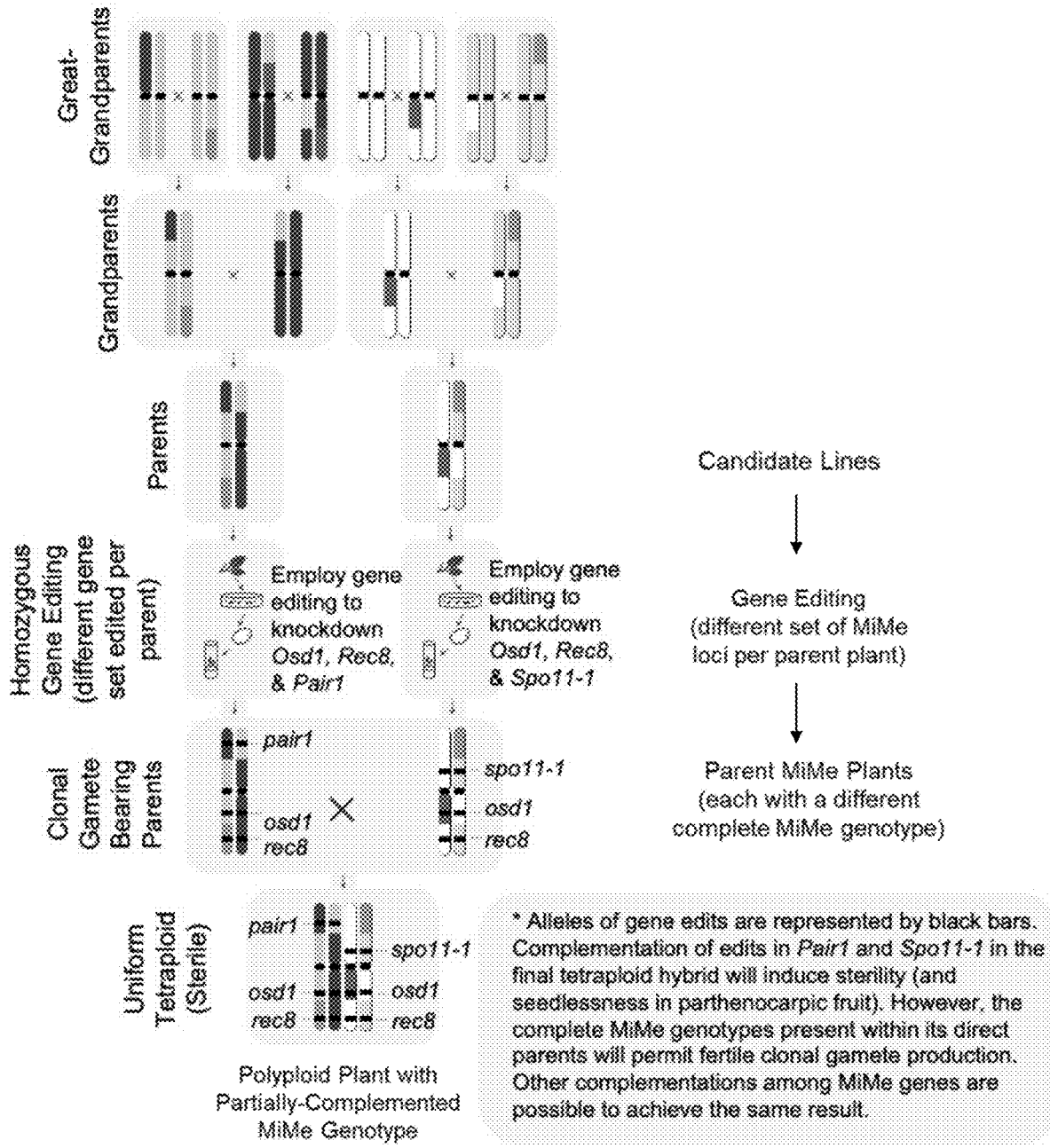
FIGS. 20A-20C illustrate embodiments where sterility of the polyploid hybrid seed is induced via complementation of one of the MiMe loci.
Figure 20B:
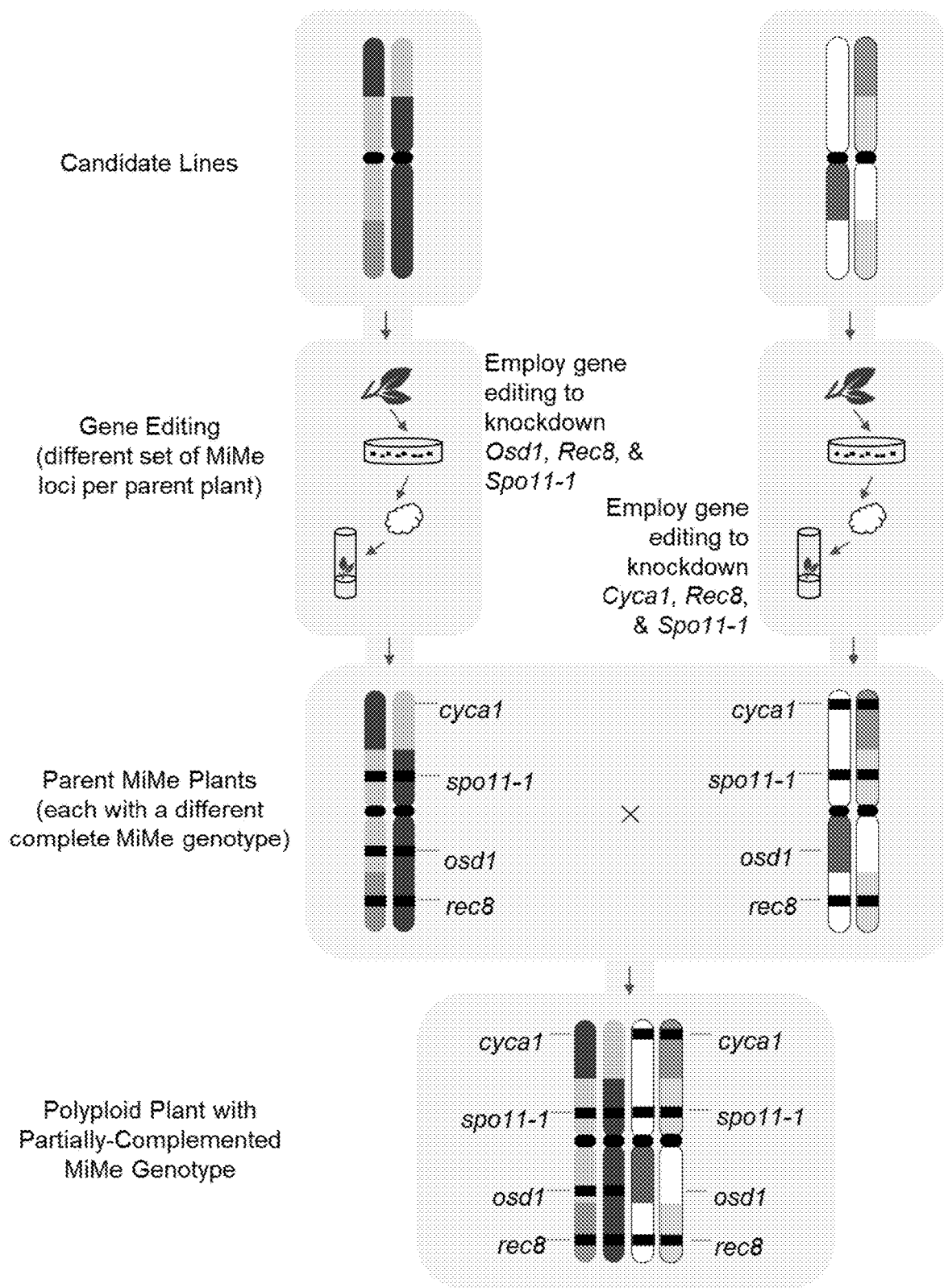
Figure 20C:
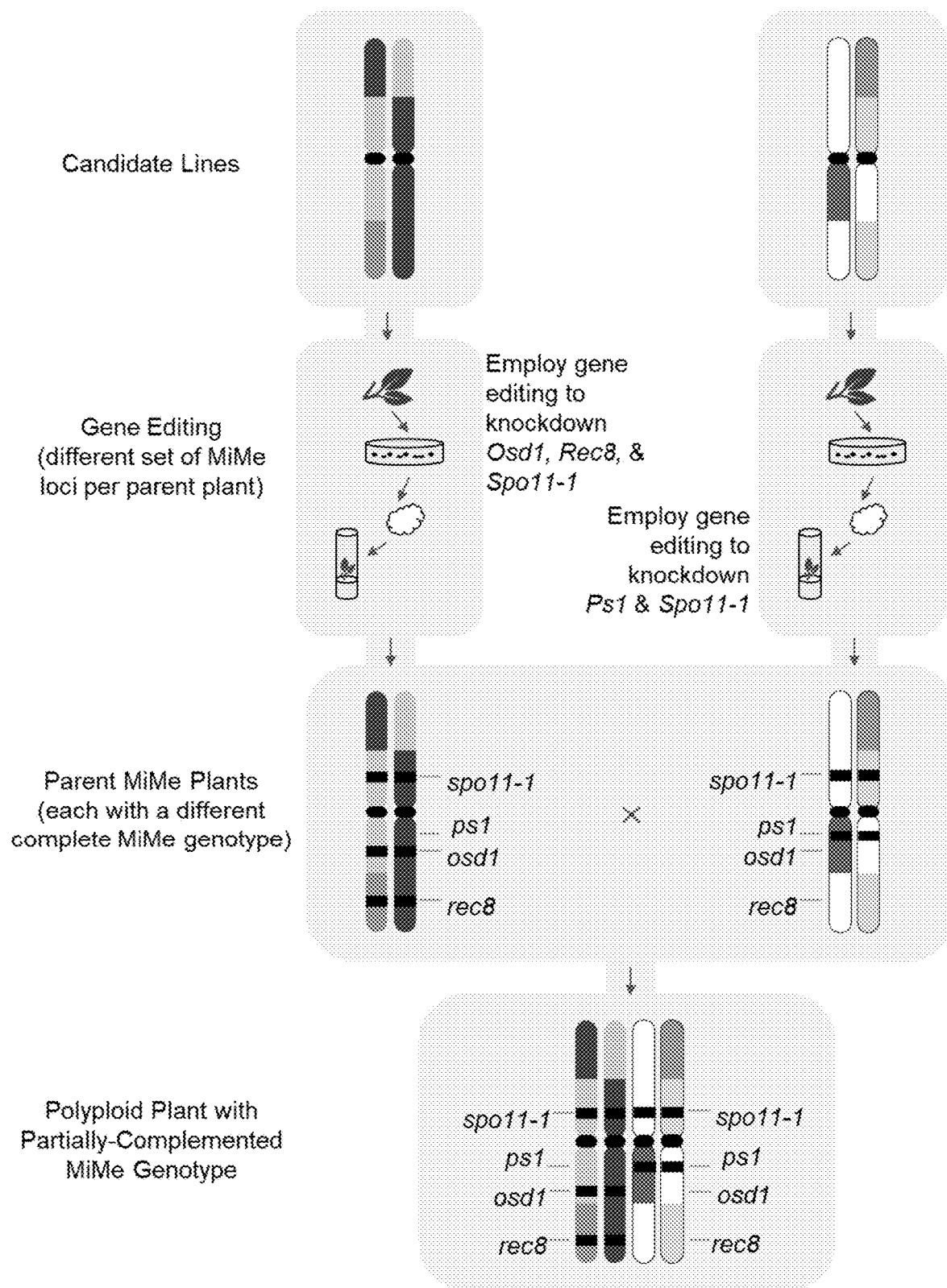

As used herein, "partially-complemented MiMe genotype" typically refers to a set of alleles that comprises only MiMe alleles at each of one or more MiMe loci of a first MiMe component, both MiMe and non-MiMe alleles at a first MiMe locus of a second MiMe component, and both MiMe and non-MiMe alleles at a second MiMe locus of the second MiMe component. A plant with a partially-complemented MiMe genotype typically does not exhibit a wild-type meiosis phenotype because the first MiMe component has only MiMe alleles at each of one or more MiMe loci, disrupting wild-type meiosis. The plant will also not exhibit a MiMe phenotype due to the complementation of the MiMe alleles by the non-MiMe alleles of each of the first and second MiMe loci of the second MiMe component. Therefore, a plant with a partially-complemented MiMe genotype exhibits neither a wild-type meiosis phenotype nor a MiMe phenotype. A partially-complemented MiMe genotype may also include MiMe alleles for a third MiMe component, e.g., only MiMe alleles at each of one or more MiMe loci of a third MiMe component, or both MiMe and non-MiMe alleles at a first MiMe locus of a third MiMe component and both MiMe and non-MiMe alleles at a second MiMe locus of the third MiMe component. As used herein, a plant or genotype "comprising only MiMe alleles at a MiMe locus" is a plant or genotype wherein each set of chromosomes has a MiMe allele at said locus, thus conferring decreased expression (including non-expression or altered activity) of the functional gene product of said locus. Exemplary partially-complemented MiMe genotypes are shown in FIGS. 20A-20C and described in detail herein. The MiMe alleles of each MiMe locus having only MiMe alleles of the first MiMe component may comprise any number of distinct MiMe alleles on different sets of chromosomes and need not be homozygous, as long as there are no non-MiMe alleles at that locus on any set of chromosomes. The partially-complemented MiMe genotype may comprise, for example, one, two, three, or more MiMe alleles and one, two, three, or more non-MiMe alleles at each of the first and second MiMe loci of the second MiMe component, as long as at least one MiMe allele and at least one non-MiMe allele are present at each of the first and second MiMe loci of the second MiMe component. Further, a partially-complemented MiMe genotype may comprise MiMe alleles at more than three MiMe loci, such as four, five, or more MiMe loci. Specific examples of partially-complemented MiMe genotypes are described in detail herein.

As used herein, "parent MiMe plant" typically refers to a plant which has a complete MiMe genotype and exhibits a MiMe phenotype, and which may be a source of clonal gametes (pollen and/or egg cells).

As used herein, "introducing a complete MiMe genotype directly" typically refers to introducing genetic modifications resulting in a complete MiMe genotype into a plant or plant cell including using the methods described herein, selecting a plant or plant cell that has a complete MiMe genotype, if needed, and regenerating the cell that has the complete MiMe genotype into a plant that exhibits a MiMe phenotype, if needed.

As used herein, "grandparent non-MiMe plant having a partial MiMe genotype" typically refers to a plant which has a partial MiMe genotype and exhibits a wild-type meiosis phenotype. A grandparent non-MiMe plant having a partial MiMe genotype produces haploid gametes that may be crossed with haploid gametes from the same or another grandparent non-MiMe plant having a partial MiMe genotype to produce one or more seeds that have a complete MiMe genotype and can be grown to produce one or more parent MiMe plants.

As used herein, "introducing a partial MiMe genotype" refers to introducing genetic modifications resulting in a partial MiMe genotype into a plant or plant cell including using the methods described herein, selecting a plant or plant cell that has a partial MiMe genotype, if needed, and regenerating the cell that has a partial MiMe genotype into a plant that exhibits a wild-type meiosis phenotype. For example, introducing a partial MiMe genotype could include crossing a plant with a MiMe and a non-MiMe allele for a component of sister chromatid cohesion during the first division of meiosis and a MiMe and a non-MiMe allele for a component of DNA double strand breakage during meiotic recombination with a plant that has a MiMe and a non-MiMe allele for a component of progression through the second division of meiosis, and then selecting for offspring that are heterozygous for all three of the parental MiMe alleles and therefore have a partial MiMe genotype.

As used herein, "genetic modification" typically refers to any sequence or portion thereof within a nucleic acid molecule that differs from the sequence of an ancestral nucleic acid molecule. For example, a seed that contains an inserted or deleted genomic sequence that is not present in one of its parent plants comprises a genetic modification. A genetic modification may be naturally occurring or introduced. A genetic modification may be introduced via, for example: plant breeding to introduce a naturally-occurring genetic modification of one plant line into another plant line; transgenic methods; gene editing; chemical mutagenesis; and the like.

As used herein, "transgenesis" refers to the insertion of an exogenous genetic element into the genome of an organism. Any exogenous genetic element may be inserted via transgenesis, including, but not limited to, genes, protein coding sequences, non-protein coding sequences, regulatory sequences, spacer DNA, and the like.

As used herein, "gene editing" refers to a type of genetic modification in which DNA is inserted, deleted or substituted in the genome of an organism using one or more natural or engineered nucleases. Gene editing may be carried out using site-specific nucleases, guided nucleases, or a combination thereof. The nuclease creates one or more site-specific breaks, such as double-strand breaks (DSBs) at target loci in the genome. Each site-specific break may be repaired, for example via non-homologous end joining (NHEJ), resulting in a genetic modification in the genome at the target locus; or via homologous recombination of the target locus with a provided repair nucleic acid molecule comprising homology to the target genomic sequence and the desired genetic modification.

Populations of Polyploid Seed

In one aspect, described herein is a population of polyploid maize seed comprising three or more haplotypes of the same or related species of maize wherein at least 50% of the population of polyploid seed are genetically uniform, and wherein the population was obtained from a single maize plant or a set of maize plants (e.g., a set of genetically uniform maize plants, e.g., a set of genetically uniform F1 maize hybrids). In some embodiments, the population of polyploid maize seed comprises a subpopulation of genetically uniform polyploid maize seed in an amount of at least 50% of the total number of maize seed, the genetically uniform polyploid maize seed comprising three or more haplotypes of the same or related species of maize. In some embodiments, the population of polyploid seed may have a complete MiMe genotype or a partial MiMe genotype.

In another aspect, described herein is a population of polyploid maize seed comprising a partially-complemented MiMe genotype, wherein at least 50% of the population of polyploid maize seed are genetically uniform, and wherein the population was obtained from a single maize plant or a set of maize plants (e.g., a set of genetically uniform maize plants, e.g., a set of genetically uniform F1 maize hybrids). In some embodiments, the population of polyploid maize seed comprises a subpopulation of genetically uniform polyploid maize seed in an amount of at least 50% of the total number of seed, the genetically uniform polyploid maize seed comprising the partially-complemented MiMe genotype. In some embodiments, the population of polyploid maize seed comprising the partially-complemented MiMe genotype may comprise one, two, three, or more haplotypes.

Haplotypes

In some embodiments, the population of polyploid maize seed or the subpopulation of genetically uniform polyploid maize seed comprises one, two, three, or more haplotypes. In some variations, the population of polyploid maize seed or the subpopulation of genetically uniform polyploid maize seed comprises two or more haplotypes, three or more haplotypes, four or more haplotypes, five or more haplotypes, six or more haplotypes, seven or more haplotypes, or eight or more haplotypes. In additional variations, the population of polyploid maize seed or the subpopulation of genetically uniform polyploid maize seed comprises two, three, four, five, six, seven, or eight haplotypes. In some embodiments wherein the polyploid maize seed is from an allopolyploid maize plant having multiple subgenomes, the two, three, or more haplotypes are two, three, or more haplotypes of the same subgenome.

Maize Plants

In some embodiments, the population of polyploid maize seed can be any species of maize plant including, but not limited to, *Zea* spp. including *Z. diploperennis, Z. luxurians, Z. nicaraguensis,* and *Z. perennis, Zea mays* including *Z. mays* spp. mays (modern maize), *Z. mays* spp. *Parviglumis,* and *Z. mays* spp. *mexicana.*

In some embodiments, the population of polyploid seed comprises two, three, or more haplotypes of the same or related species of maizeplant. In another embodiment, the population of polyploid maize seed comprises two, three, or more haplotypes of related species of maize plant. In some embodiments, related species of maize plant are species of plant within the Poaceae family. In other embodiments, related species of maize plant are species of plant within the genus *Zea.*

In some embodiments, the population of polyploid maize seed is a population of seed of the family Poaceae comprising two, three, or more haplotypes from one or more species within the family Poaceae. In some embodiments, the population of polyploid maize seed comprises two, three, or more haplotypes of maize. In some variations, the two, three, or more haplotypes may be from different subspecies of maize. In some embodiments, the population of polyploid seed is a population of seed of the genus *Zea* comprising two, three, or more haplotypes from one or more species within the genus *Zea.* The population of polyploid seed of the genus *Zea* may be a population of seed of any plant within the genus *Zea* including, but not limited to, maize and teosinte. In some variations, the two, three, or more haplotypes may be from any species or subspecies in the genus *Zea* including, but not limited to, *Zea mays, Zea diploperennis, Zea nicaraguensis, Zea perennis,* and *Zea* spp. In certain embodiments, the population of polyploid seed is a population of maize seed comprising two, three, or more haplotypes from the same or related species of maize or teosinte including, but not limited to, the species of *Zea* described herein.

Genetic Uniformity, Ploidy, and Origin

In some embodiments, at least 50% of the population of polyploid maize seed comprising two, three, or more haplotypes are genetically uniform. In some variations, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the population of polyploid maize seed comprising two, three, or more haplotypes are genetically uniform. In some embodiments, at least 50% of the population of polyploid maize seed produced are genetically uniform, wherein the polyploid maize seed comprises three or more haplotypes. In some variations, at least 60%, least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the population of polyploid maize seed produced are genetically uniform, wherein the polyploid maize seed comprises three or more haplotypes. In some embodiments, the population of polyploid maize seed has an average pairwise genetic uniformity of at least 80% as measured by the Jaccard similarity coefficient.

In some variations, the population of polyploid maize seed has an average pairwise genetic uniformity of at least 80%, at least 85%, at least 90%, at least 91%, at least 92%, at least 93%, at least 94%, at least 95%, at least 96%, at least 97%, at least 98%, at least 99%, or 100% as measured by the Jaccard similarity coefficient. In one variation, the population of polyploid maize seed has an average pairwise genetic uniformity of at least 85% as measured by the Jaccard similarity coefficient. In another variation, the population of polyploid maize seed has an average pairwise identity of at least 90% as measured by the Jaccard similarity coefficient.

In some embodiments, the population of polyploid maize seed comprises a subpopulation of genetically uniform polyploid maize seed in an amount of at least 50% of the total number of maize seeds. In some variations, the population of polyploid maize seed comprises a subpopulation of genetically uniform polyploid maize seed in an amount of at least 60%, least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the total number of maize seeds. In some embodiments, each pair of the subpopulation of genetically uniform polyploid maize seed has a pairwise identity of at least about 90% as measured by the Jaccard similarity coefficient. In some embodiments, each pair of the subpopulation of genetically uniform polyploid maize maize seed has a pairwise identity of at least about 90%, at least about 95%, at least about 96%, at least about 97%, at least about 98%, at least about 99%, or about 100% as measured by the Jaccard similarity coefficient.

In some embodiments, the population of polyploid maize seed or the subpopulation of genetically uniform polyploid maize seed comprising two, three, or more haplotypes is triploid, tetraploid, pentaploid, hexaploid, heptaploid, or octoploid. In other embodiments, the population of polyploid maize seed or the subpopulation of genetically uniform polyploid maize seed comprising two, three, or more haplotypes has a ploidy of 9n, 10n, 11n, 12n, 13n, 14n, 15n, 16n, or higher.

In some embodiments, the population of polyploid maize seed was obtained from a single maize plant or a set of maize plants such as, for example, a set of F1 hybrids. In some embodiments, the population of polyploid maize seed was obtained from a single maize plant. In other embodiments, the population of polyploid maize seed was obtained from a set of F1 hybrids. In some variations, the population of polyploid maize seed was obtained from a set of two, three, four, five, 10, 20, 50, 100, or more F1 hybrids. In some additional variations, the population of polyploid maize seed was obtained from a set of genetically uniform maize plants, e.g., a set of F1 hybrids derived from the same inbred parents. In yet additional variations, the population of polyploid maize seed was obtained from a set of two, three, four, five, 10, 20, 50, 100, or more genetically uniform maize plants, e.g., genetically uniform F1 hybrids. In certain embodiments, the genetically uniform set of maize plants (e.g., the genetically uniform set of F1 hybrids) has an average pairwise genetic uniformity of at least 80%, at least 85%, at least 90%, at least 91%, at least 92%, at least 93%, at least 94%, at least 95%, at least 96%, at least 97%, at least 98%, at least 99%, or 100% as measured by the Jaccard similarity coefficient. In certain embodiments, each pair of the genetically uniform set of maize plants (e.g., the genetically uniform set of F1 hybrids) has a pairwise identity of at least about 90%, at least about 95%, at least about 96%, at least about 97%, at least about 98%, at least about 99%, or about 100% as measured by the Jaccard similarity coefficient.

Methods of measuring genetic uniformity are known in the art. One exemplary method of measuring genetic uniformity is by using the Jaccard similarity coefficient, also known as the Jaccard index or Jacard similarity index. In the context of molecular plant genetics, the Jaccard index, Jaccard similarity index, or Jaccard similarity coefficient (Jaccard, P. (1908) Nouvelles Recherches sur la Distribution Florale. Bulletin de la Société Vaudoise des Sciences Naturelles. Vol. 44), is commonly applied to quantify the pairwise genetic similarity or uniformity of plants based on the presence or absence of shared alleles at loci spread throughout the genome. Exemplary methods f using the Jaccard similarity coefficient to measure genetic uniformity between two plants are described in Example 1 below and, for example, in Paz and Veilleux (1997. Genetic diversity based on randomly amplified polymorphic DNA (RAPD) and its relationship with the performance of diploid potato hybrids. Journal of the American Society for Horticultural Sci. 122(6): 740-747), Vosman et al. (2004. The establishment of 'essential derivation' among rose varieties, using AFLP. Theoretical and Applied Genetics. 109: 1718-1725), Noli et al. (2013. Criteria for the definition of similarity thresholds for identifying essentially derived varieties. Plant Breeding. 132(6): 525-531), Vijayakumar et al. (2021. High temperature induced changes in quality and yield parameters of tomato (Solanum lycopersicum L.) and similarity coefficients among genotypes using SSR markers. Heliyon. 7(2)), and Dalamu et al. (2023. Genetic Diversity and Population Structure Analyses Using Simple Sequence Repeat Markers and Phenotypic Traits in Native Potato Collection in India. Potato Research: 1-25). The Jaccard similarity coefficient is defined as the ratio of the number of shared items to the total number of distinct items in the two sets. In the context of molecular plant genetics, it quantifies the proportion of shared alleles between two plants. The formula for calculating the Jaccard similarity coefficient is:

$$J(A,B)=|A \cap B|/|A \cup B|$$

Where A represents the unique set of alleles without duplicates in one plant, B the unique set of alleles without duplicates in the other plant, $|A \cap B|$ represents the number of shared alleles (the cardinality of the intersection) between the plants, and $|A \cup B|$ represents the number of distinct alleles (the cardinality of the union) between the plants. This formula computes the cardinality of the intersection (common elements) of two sets (the shared alleles) divided by the cardinality of the union (all alleles) of the two sets (all distinct alleles present). The resulting value of the Jaccard similarity coefficient ranges from 0 to 1, where 0 indicates no shared alleles, and 1 indicates complete uniformity. The average pairwise genetic uniformity of the populations was calculated as the average Jaccard similarity of all possible pairs of plants within the population. We note that in the context of genetic pairwise similarity estimations, the size of A should be the same as, or very close to the size of B to avoid misinterpretation.

Genetic Modifications

In some embodiments, the polyploid maize seed (e.g., the subpopulation of genetically uniform polyploid maize seed) comprises one or more genetic modifications. Genetic modifications may be generated by modification of any nucleic acid sequence or genetic element by insertion, deletion, or substitution of one or more nucleotides in a nucleic acid molecule. This can occur by a replacement of at least one nucleotide, a deletion of at least one nucleotide, an insertion of at least one nucleotide, a chemical alteration of at least one nucleotide, or a combination thereof as long as the result is a detectable (e.g., by PCR, DNA sequencing, chromatography, etc.) change of nucleotide sequence compared to the sequence of the nucleic acid molecule prior to modification. Such modifications can be achieved by any of several well-known methods known in the art including, but not limited to, random mutagenesis, genome editing, insertion of a recombinant nucleic acid, crossing of an unmodified maize plant with a modified maize plant to introduce the modification of the modified maize plant into the unmodified maize plant, and the like. A genetic modification may be naturally occurring or non-naturally occurring.

The genetic modifications described herein may be present in any known genetic element including, but not limited to, protein-coding sequences, non-protein-coding sequences, promoter regions, 5' untranslated leaders, genes, exons, introns, poly-A signal sequences, 3' untranslated regions, regions encoding small RNAs (such as microRNAs and small-interfering RNAs), and any other sequences that affect transcription or translation of one or more nucleic acid sequences. In some embodiments, genetic modifications may include, but are not limited to, modifying or replacing nucleotide sequences of interest (such as a regulatory elements), gene disruption, gene knockout, gene knockdown, gene knock-in, gene silencing (including, e.g., by expressing an inverted repeat into a gene of interest), RNA interference (including, e.g., by insertion and/or expression of an RNA interference construct), modification of methylation status, modification of splicing sites, introducing alternate splicing sites, or any combination thereof. As used herein, gene disruption refers to the alteration or insertion of a sequence into a gene or locus that results in decreased expression (including non-expression or altered activity) of a functional protein gene product. A gene disruption may be achieved by introduction of a genetic modification in a protein-coding sequence, including, but not limited to, as a mis-sense or non-sense mutation, or an insertion, deletion, or substitution. As used herein, a knockout is a genetic modification wherein a gene or gene product has been rendered completely inoperative. A knockout of a gene product may be achieved by introduction of a genetic modification in a protein-coding sequence of a gene or any non-protein-coding or regulatory sequence described herein. As used herein, a knockdown is a genetic modification wherein a gene or gene product has been rendered partially inoperative. A knockdown of a gene product may be achieved by introduction of a genetic modification in a protein-coding sequence of a gene or in a non-protein-coding or regulatory sequence, or insertion of a trans-acting element, such as a construct that expresses an inverted repeat of the gene product or a construct that expresses a DNA- or RNA-binding protein such as a transcriptional repressor which may include, for example, a deactivated targeted nuclease such as deactivated Cas9 (dCas9). As used herein, knock-in represents the replacement or insertion of a DNA sequence at a specific DNA locus in a cell. Knock-ins may include, but are not limited to, specific insertion of a heterologous amino acid coding sequence in a coding region of a gene, an insertion of a transcriptional regulatory element in a genetic locus, or any of several methods of inserting a DNA sequence into a cell that are known to one of ordinary skill in the art.

In certain embodiments, the polyploid maize seed (e.g., the subpopulation of genetically uniform polyploid maize seed) comprises one or more genetic modifications resulting in decreased expression (including non-expression or altered activity) of a gene product of a genomic locus. In some embodiments, genetic modifications resulting in decreased expression (including non-expression or altered activity) of a gene product or locus may include, but are not limited to, modification of an enhancer, modification of a promoter, modification of a 5' untranslated leader, modification of a coding region, modification of a non-coding region, insertion and/or expression of an RNA interference construct that targets an mRNA, modification of a region encoding a small RNA, modification of methylation status of a genomic locus, expression of a repressor protein that targets a DNA or mRNA sequence, and any other sequences that affect transcription or translation of one or more nucleic acid sequences. In some embodiments, genetic modifications resulting in decreased expression (including non-expression or altered activity) of a gene product or locus may include, but are not limited to, modifying or replacing nucleotide sequences of interest (such as a regulatory elements), gene disruption, gene knockout, gene knockdown, gene knock-in, gene silencing (including, e.g., by inserting and/or expressing an inverted repeat into a gene of interest), RNA interference (including, e.g., by insertion and/or expression of an RNA interference construct), expression of a repressor protein (e.g. dCas9), modification of methylation status of gene loci, modification of splicing sites, introducing alternate splicing sites, or any combination thereof. In some variations, the genetic modification is positioned in the first 70%, the first 60%, the first 50%, the first 40%, the first 30%, the first 20%, or the first 10% of the nucleotides of the coding sequence of the genomic locus following the start codon in the 3' direction. In certain variations, the genetic modification is positioned in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the genomic locus following the start codon in the 3' direction.

In some embodiments, one or more genetic modifications each independently comprise an insertion, a deletion, one or more nucleotide changes, or an inversion that results in decreased expression of the one or more genomic loci (e.g., MiMe loci). In some variations, the insertion, the deletion, the one or more nucleotide changes, or the inversion eliminates expression (e.g., eliminates activity) of the genomic locus. In some variations, the insertion, the deletion, the one or more nucleotide changes, or the inversion is positioned in the first 70%, the first 60%, the first 50%, the first 40%, the first 30%, the first 20%, or the first 10% of the nucleotides of the coding sequence of the genomic locus following the start codon in the 3' direction. In certain variations, the insertion, the deletion, the one or more nucleotide changes, or the inversion is positioned in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the genomic locus following the start codon in the 3' direction. In some embodiments, the insertion, the deletion, the one or more nucleotide changes, or the inversion eliminates expression (e.g., eliminates activity) of the genomic locus. In some variations, the insertion, the deletion, the one or more nucleotide changes, or the inversion results in a premature stop codon present in the first 70%, the first 60%, the first 50%, the first 40%, the first 30%, the first 20%, or the first 10% of the nucleotides of the coding sequence of the MiMe locus following the start codon in the 3' direction, thereby eliminating expression (e.g., activity) of the genomic locus.

In some variations, the insertion, the deletion, the one or more nucleotide changes, or the inversion results in a premature stop codon present in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the genomic locus following the start codon in the 3' direction, thereby eliminating expression (e.g., activity) of the genomic locus.

In some embodiments, the one or more genetic modifications comprise one or more polynucleotide sequences selected from the group consisting of SEQ ID NOs: 108-111. In certain embodiments, the one or more genetic modifications comprise one or more polynucleotide sequences each having at least 80%, at least 85%, at least 90%, at least 95%, at least 96%, at least 97%, at least 98%, or at least 99% identity or complementarity to a nucleotide sequence selected from the group consisting of SEQ ID NOs: 108-111.

MiMe Loci, MiMe Genotypes, and MiMe Components

In some embodiments, the polyploid maize seed (e.g., the subpopulation of genetically uniform polyploid maize seed) comprises one or more genetic modifications resulting in decreased expression (including non-expression or altered activity) of one or more MiMe loci. In some variations, the polyploid maize seed (e.g., the subpopulation of genetically uniform polyploid maize seed) comprises one or more genetic modifications resulting in a decreased amount of a functional gene product encoded at one or more MiMe loci. The gene products at the MiMe loci may include, but are not limited to, nucleic acids (e.g. RNA), post-transcriptionally modified nucleic acids (e.g. spliced RNA, poly-adenylated mRNA), proteins (e.g. enzymes, structural proteins, etc.), and post-translationally modified proteins (e.g. glycoproteins, lipoproteins, etc.). The function of the gene product at the MiMe locus refers to the wild-type, unmodified function of the gene product. The decreased expression of a MiMe locus may refer to a decrease in the total amount of a gene product encoded at a MiMe locus present in a cell (e.g. a decrease in the amount of a protein, including up to no detectable expression) or to a decrease in the amount of a functional gene product encoded at a MiMe locus present in a cell (e.g. a decrease in the percentage of proteins with wild-type function, or an increase in the percentage of proteins with altered activity). In some embodiments, the one or more genetic modifications resulting in decreased expression of one or more MiMe loci may include, but are not limited to, modification of an enhancer in the MiMe loci, modification of a promoter of the MiMe loci, modification of a coding region in the MiMe loci, modification of methylation status of the MiMe loci, expression of a repressor protein that targets the DNA or an mRNA of the MiMe loci, and expression of an RNA interference construct that targets an mRNA from the MiMe loci. In some embodiments, the polyploid maize seed (e.g., the subpopulation of genetically uniform polyploid maize seed) may comprise one or more genetic modifications resulting in non-expression of one or more MiMe loci. In some embodiments, the polyploid maize seed (e.g., the subpopulation of genetically uniform polyploid maize seed) may comprise one or more genetic modifications resulting in decreased expression (including non-expression or altered activity) of a combination of two or more MiMe loci.

In some embodiments, the polyploid maize seed comprises one or more genetic modifications resulting in decreased expression of one or more MiMe loci. In other embodiments, the polyploid maize seed (e.g., the subpopulation of genetically uniform polyploid maize seed) comprises one or more genetic modifications resulting in decreased expression of two or more MiMe loci. In yet another embodiment, the polyploid maize seed (e.g., the subpopulation of genetically uniform polyploid maize seed) comprises one or more genetic modifications resulting in decreased expression of three or more MiMe loci. In some variations, the MiMe loci may include, but are not limited to, REC8, OSD1 (e.g., OSD1-1, OSD1-2, and/or OSD1-3 in maize), CYCA1, TDM1, PAIR1 (e.g., PAIR1-1 and/or PAIR1-2 in maize), SPO11-1, SPO11-2, PRD1, PRD2, DFO, MTOPVIB, DSY1, SY1, SY2, SY3, SY4, SWITCH1/DYAD, PS1, PS1-LIKE PROTEIN, JASON (e.g., JASON-1 and/or JASON-2 in maize), PC1, PC2, and FC. In one variation, the polyploid maize seed (e.g., the subpopulation of genetically uniform polyploid maize seed) comprises one or more genetic modifications resulting in decreased expression of REC8. In a second variation, the polyploid maize seed (e.g., the subpopulation of genetically uniform polyploid maize seed) comprises one or more genetic modifications resulting in decreased expression of OSD1 (e.g., OSD1-1, OSD1-2, and/or OSD1-3 in maize). In a third variation, the polyploid maize seed (e.g., the subpopulation of genetically uniform polyploid maize seed) comprises one or more genetic modifications resulting in decreased expression of PAIR1 (e.g., PAIR1-1 and/or PAIR1-2 in maize). In a fourth variation, the polyploid maize seed (e.g., the subpopulation of genetically uniform polyploid maize seed) comprises one or more genetic modifications resulting in decreased expression of SPO11-1, SPO11-2, or a combination thereof. In a fifth variation, the polyploid maize seed (e.g., the subpopulation of genetically uniform polyploid maize seed) comprises one or more genetic modifications resulting in decreased expression of REC8 and SPO11-1. In a sixth variation, the polyploid maize seed (e.g., the subpopulation of genetically uniform polyploid maize seed) comprises one or more genetic modifications resulting in decreased expression of REC8 and OSD1 (e.g., OSD1-1, OSD1-2, and/or OSD1-3 in maize). In a seventh variation, the polyploid maize seed (e.g., the subpopulation of genetically uniform polyploid maize seed) comprises one or more genetic modifications resulting in decreased expression of REC8 and PAIR1 (e.g., PAIR1-1 and/or PAIR1-2 in maize). In an eighth variation, the polyploid maize seed (e.g., the subpopulation of genetically uniform polyploid maize seed) comprises one or more genetic modifications resulting in decreased expression of OSD1 (e.g., OSD1-1, OSD1-2, and/or OSD1-3 in maize) and SPO11-1. In a ninth variation, the polyploid maize seed (e.g., the subpopulation of genetically uniform polyploid maize seed) comprises one or more genetic modifications resulting in decreased expression of OSD1 (e.g., OSD1-1, OSD1-2, and/or OSD1-3 in maize) and PAIR1 (e.g., PAIR1-1 and/or PAIR1-2 in maize). In a tenth variation, the polyploid maize seed (e.g., the subpopulation of genetically uniform polyploid maize seed) comprises one or more genetic modifications resulting in decreased expression of REC8, OSD1 (e.g., OSD1-1, OSD1-2, and/or OSD1-3 in maize), and PAIR1 (e.g., PAIR1-1 and/or PAIR1-2 in maize). In an eleventh variation, the polyploid maize seed (e.g., the subpopulation of genetically uniform polyploid maize seed) comprises one or more genetic modifications resulting in decreased expression of REC8, OSD1 (e.g., OSD1-1, OSD1-2, and/or OSD1-3 in maize), and SPO11-1. In a twelfth variation, the polyploid maize seed (e.g., the subpopulation of genetically uniform polyploid maize seed) comprises one or more genetic modifications resulting in decreased expression of PS1 and SPO11-1. In a thirteenth variation, the polyploid maize seed (e.g., the subpopulation of genetically uniform polyploid maize seed) comprises one or more genetic modifications resulting in decreased expression of PS1 and SY3. In a fourteenth variation, the polyploid maize seed (e.g., the subpopulation of genetically uniform polyploid maize seed) comprises one or more genetic modifications resulting in decreased expression of OSD1 (e.g., OSD1-1, OSD1-2, and/or OSD1-3 in maize), SPO11-1, and REC8. In a fifteenth variation, the polyploid maize seed (e.g., the subpopulation of genetically uniform polyploid maize seed) comprises one or more genetic modifications resulting in decreased expression of REC8, OSD1 (e.g., OSD1-1, OSD1-2, and/or OSD1-3 in maize), SPO11-1, and PAIR1 (e.g., PAIR1-1 and/or PAIR1-2 in maize). In a sixteenth variation, the polyploid maize seed (e.g., the subpopulation of genetically uniform polyploid maize seed) comprises one or more genetic modifications resulting in decreased expression of PS1 or PS1-LIKE PROTEIN, SY3, and SPO11-1. The polyploid maize seed (e.g., the subpopulation of genetically uniform polyploid maize seed) may comprise one or more genetic modifications resulting in decreased expression of any combination of MiMe loci described herein or known in the art. In some embodiments, the polyploid maize seed (e.g., the subpopulation of genetically uniform polyploid maize seed) may comprise one or more genetic modifications resulting in non-expression of any combination of MiMe loci described here or known in the art. In further embodiments, the polyploid maize seed (e.g., the subpopulation of genetically uniform polyploid maize seed) may comprise one or more genetic modifications resulting in decreased expression (including non-expression or altered activity) of a combination of two or more MiMe loci described here or known in the art.

In some embodiments, the polyploid maize seed (e.g., the subpopulation of genetically uniform polyploid maize seed) comprises one or more genetic modifications resulting in decreased expression of REC8, SWITCH1/DYAD, or a combination thereof. In some variations, the polyploid maize seed (e.g., the subpopulation of genetically uniform polyploid maize seed) comprises one or more genetic modifications resulting in decreased expression of REC8, SWITCH1/DYAD, or a combination thereof and one or more genetic modifications resulting in decreased expression of one or more additional MiMe loci. In additional variations, the polyploid maize seed (e.g., the subpopulation of genetically uniform polyploid maize seed) comprises one or more genetic modifications resulting in decreased expression of REC8, SWITCH1/DYAD, or a combination thereof and one or more genetic modifications resulting in decreased expression of one or more additional MiMe loci which may include, but are not limited to, OSD1 (e.g., OSD1-1, OSD1-2, and/or OSD1-3 in maize), CYCA1, TDM1, PC1, PC2, and FC. In yet additional variations, the polyploid maize seed (e.g., the subpopulation of genetically uniform polyploid maize seed) comprises one or more genetic modifications resulting in decreased expression of REC8, SWITCH1/DYAD, or a combination thereof; one or more genetic modifications resulting in decreased expression of OSD1 (e.g., OSD1-1, OSD1-2, and/or OSD1-3 in maize), CYCA1, TDM1, PC1, PC2, FC, or any combination thereof; and one or more genetic modifications resulting in decreased expression of one or more additional MiMe loci, which may include, but are not limited to, PAIR1 (e.g., PAIR1-1 and/or PAIR1-2 in maize), SPO11-1, SPO11-2, PRD1, PRD2, DFO, MTOPVIB, DSY1, SY1, SY2, SY3, and SY4.

In some embodiments, the polyploid maize seed (e.g., the subpopulation of genetically uniform polyploid maize seed) comprises one or more genetic modifications resulting in decreased expression of one or more MiMe loci which may include, but are not limited to, OSD1 (e.g., OSD1-1, OSD1-2, and/or OSD1-3 in maize), CYCA1, TDM1, PC1, PC2, and FC. In some variations, the polyploid maize seed (e.g., the subpopulation of genetically uniform polyploid maize seed) comprises one or more genetic modifications resulting in decreased expression of OSD1 (e.g., OSD1-1, OSD1-2, and/or OSD1-3 in maize), CYCA1, TDM1, PC1, PC2, FC, or any combination thereof and further comprises one or more genetic modifications resulting in decreased expression of one or more additional MiMe loci, which may include, but are not limited to, PAIR1 (e.g., PAIR1-1 and/or PAIR1-2 in maize), SPO11-1, SPO11-2, PRD1, PRD2, DFO, MTOPVIB, DSY1, SY1, SY2, SY3, and SY4.

In some embodiments, the polyploid maize seed (e.g., the subpopulation of genetically uniform polyploid maize seed) comprises one or more genetic modifications resulting in decreased expression of one or more MiMe loci which may include, but are not limited to, PAIR1 (e.g., PAIR1-1 and/or PAIR1-2 in maize), SPO11-1, SPO11-2, PRD1, PRD2, DFO, MTOPVIB, DSY1, SY1, SY2, SY3, and SY4. In some variations, the polyploid maize seed (e.g., the subpopulation of genetically uniform polyploid maize seed) comprises one or more genetic modifications resulting in decreased expression of PAIR1 (e.g., PAIR1-1 and/or PAIR1-2 in maize), SPO11-1, SPO11-2, PRD1, PRD2, DFO, MTOPVIB, DSY1, SY1, SY2, SY3, SY4, or any combination thereof, and further comprises one or more genetic modifications resulting in decreased expression of one or more additional MiMe loci, which may include, but are not limited to PS1, PS1-LIKE PROTEIN, and JASON (e.g., JASON-1 and/or JASON-2 in maize).

In some embodiments, each of the one or more MiMe loci encodes a protein of a MiMe component as described herein. In certain embodiments, each of the one or more MiMe loci encodes a protein having an amino acid sequence selected from the group consisting of SEQ ID NOs: 1-12. In some variations, each of the one or more MiMe loci encodes a protein having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to an amino acid sequence selected from the group consisting of SEQ ID NOs: 1-12.

In some embodiments, the population of polyploid maize seed or the subpopulation of genetically uniform polyploid maize seed has a complete MiMe genotype. In alternative embodiments, the population of polyploid maize seed or the subpopulation of genetically uniform polyploid maize seed has a partial MiMe genotype. In still other embodiments, the population of polyploid maize seed or the subpopulation of genetically uniform polyploid maize seed has a partially-complemented MiMe genotype. In certain embodiments, the complete, partial, or partially-complemented MiMe genotype comprises one or more genetic modifications resulting in decreased expression of one or more MiMe loci. In other embodiments, the complete, partial, or partially-complemented MiMe genotype comprises one or more genetic modifications resulting in decreased expression of two or more MiMe loci. In yet another embodiment, the complete, partial, or partially-complemented MiMe genotype comprises one or more genetic modifications resulting in decreased expression of three or more MiMe loci. In some variations, the MiMe loci may include, but are not limited to, REC8, OSD1 (e.g., OSD1-1, OSD1-2, and/or OSD1-3 in maize), CYCA1, TDM1, PAIR1 (e.g., PAIR1-1 and/or PAIR1-2 in maize), SPO11-1, SPO11-2, PRD1, PRD2, DFO, MTOPVIB, DSY1, SY1, SY2, SY3, SY4, SWITCH1/DYAD, PS1, PS1-LIKE PROTEIN, JASON (e.g., JASON-1 and/or JASON-2 in maize), PC1, PC2, and FC. In one variation, the complete, partial, or partially-complemented MiMe genotype comprises one or more genetic modifications resulting in decreased expression of REC8. In a second variation, the complete, partial, or partially-complemented MiMe genotype comprises one or more genetic modifications resulting in decreased expression of OSD1 (e.g., OSD1-1, OSD1-2, and/or OSD1-3 in maize). In a third variation, the complete, partial, or partially-complemented MiMe genotype comprises one or more genetic modifications resulting in decreased expression of PAIR1 (e.g., PAIR1-1 and/or PAIR1-2 in maize). In a fourth variation, the complete, partial, or partially-complemented MiMe genotype comprises one or more genetic modifications resulting in decreased expression of SPO11-1, SPO11-2, or a combination thereof. In a fifth variation, the complete, partial, or partially-complemented MiMe genotype comprises one or more genetic modifications resulting in decreased expression of REC8 and SPO11-1. In a sixth variation, the complete, partial, or partially-complemented MiMe genotype comprises one or more genetic modifications resulting in decreased expression of REC8 and OSD1 (e.g., OSD1-1, OSD1-2, and/or OSD1-3 in maize). In a seventh variation, the complete, partial, or partially-complemented MiMe genotype comprises one or more genetic modifications resulting in decreased expression of REC8 and PAIR1 (e.g., PAIR1-1 and/or PAIR1-2 in maize). In an eighth variation, the complete, partial, or partially-complemented MiMe genotype comprises one or more genetic modifications resulting in decreased expression of OSD1 (e.g., OSD1-1, OSD1-2, and/or OSD1-3 in maize) and SPO11-1. In a ninth variation, the complete, partial, or partially-complemented MiMe genotype comprises one or more genetic modifications resulting in decreased expression of OSD1 (e.g., OSD1-1, OSD1-2, and/or OSD1-3 in maize) and PAIR1 (e.g., PAIR1-1 and/or PAIR1-2 in maize). In a tenth variation, the complete, partial, or partially-complemented MiMe genotype comprises one or more genetic modifications resulting in decreased expression of REC8, OSD1 (e.g., OSD1-1, OSD1-2, and/or OSD1-3 in maize), and PAIR1 (e.g., PAIR1-1 and/or PAIR1-2 in maize). In an eleventh variation, the complete, partial, or partially-complemented MiMe genotype comprises one or more genetic modifications resulting in decreased expression of REC8, OSD1 (e.g., OSD1-1, OSD1-2, and/or OSD1-3 in maize), and SPO11-1. In a twelfth variation, the complete, partial, or partially-complemented MiMe genotype comprises one or more genetic modifications resulting in decreased expression of PS1 and SPO11-1. In a thirteenth variation, the complete, partial, or partially-complemented MiMe genotype comprises one or more genetic modifications resulting in decreased expression of PS1 and SY3. In a fourteenth variation, the complete, partial, or partially-complemented MiMe genotype comprises one or more genetic modifications resulting in decreased expression of OSD1 (e.g., OSD1-1, OSD1-2, and/or OSD1-3), SPO11-1, and REC8. In a fifteenth variation, the complete, partial, or partially-complemented MiMe genotype comprises one or more genetic modifications resulting in decreased expression of REC8, OSD1 (e.g., OSD1-1, OSD1-2, and/or OSD1-3 in maize), SPO11-1, and PAIR1 (e.g., PAIR1-1 and/or PAIR1-2 in maize). In a sixteenth variation, the complete, partial, or partially-complemented MiMe genotype comprises one or more genetic modifications resulting in decreased expression of PS1 or PS1-LIKE PROTEIN, SY3, and SPO11-1. The complete, partial, or partially-complemented MiMe genotype may comprise one or more genetic modifications resulting in decreased expression of any combination of MiMe loci described herein or known in the art, wherein a maize plant that has the complete MiMe genotype exhibits a MiMe phenotype. In some embodiments, the complete, partial, or partially-complemented MiMe genotype may comprise one or more genetic modifications resulting in non-expression of any combination of MiMe loci described here or known in the art wherein a maize plant that has the complete MiMe genotype exhibits a MiMe phenotype. In further embodiments, the complete, partial, or partially-complemented MiMe genotype may comprise one or more genetic modifications resulting in decreased expression (including non-expression or altered activity) of a combination of two or more MiMe loci described here or known in the art, wherein a maize plant that has the complete MiMe genotype exhibits a MiMe phenotype. Specific examples of complete MiMe genotypes are shown in Table 6.

In some embodiments, the complete, partial, or partially-complemented MiMe genotype comprises one or more genetic modifications resulting in decreased expression of REC8, SWITCH1/DYAD, or a combination thereof. In some variations, the complete, partial, or partially-complemented MiMe genotype comprises one or more genetic modifications resulting in decreased expression of REC8, SWITCH1/DYAD, or a combination thereof and one or more genetic modifications resulting in decreased expression of one or more additional MiMe loci. In additional variations, the complete, partial, or partially-complemented MiMe genotype comprises one or more genetic modifications resulting in decreased expression of REC8, SWITCH1/DYAD, or a combination thereof and one or more genetic modifications resulting in decreased expression of one or more additional MiMe loci, including, but not limited to, OSD1 (e.g., OSD1-1, OSD1-2, and/or OSD1-3 in maize), CYCA1, TDM1, PC1, PC2, and FC. In yet additional variations, the complete, partial, or partially-complemented MiMe genotype comprises one or more genetic modifications resulting in decreased expression of REC8, SWITCH1/DYAD, or a combination thereof; one or more genetic modifications resulting in decreased expression of OSD1 (e.g., OSD1-1, OSD1-2, and/or OSD1-3 in maize), CYCA1, TDM1, PC1, PC2, FC, or any combination thereof; and one or more genetic modifications resulting in decreased expression of one or more additional MiMe loci, including, but not limited to, PAIR1 (e.g., PAIR1-1 and/or PAIR1-2 in maize), SPO11-1, SPO11-2, PRD1, PRD2, DFO, MTOPVIB, DSY1, SY1, SY2, SY3, and SY4.

In some embodiments, the complete, partial, or partially-complemented MiMe genotype comprises one or more genetic modifications resulting in decreased expression of one or more MiMe loci including, but not limited to, OSD1 (e.g., OSD1-1, OSD1-2, and/or OSD1-3 in maize), CYCA1, TDM1, PC1, PC2, and FC. In some variations, the complete, partial, or partially-complemented MiMe genotype comprises one or more genetic modifications resulting in decreased expression of OSD1 (e.g., OSD1-1, OSD1-2, and/or OSD1-3 in maize), CYCA1, TDM1, PC1, PC2, FC, or any combination thereof and further comprises one or more genetic modifications resulting in decreased expression of one or more additional MiMe loci, including, but not limited to, PAIR1 (e.g., PAIR1-1 and/or PAIR1-2 in maize), SPO11-1, SPO11-2, PRD1, PRD2, DFO, MTOPVIB, DSY1, SY1, SY2, SY3, and SY4.

In some embodiments, the complete, partial, or partially-complemented MiMe genotype comprises one or more genetic modifications resulting in decreased expression of one or more MiMe loci including, but not limited to, PAIR1 (e.g., PAIR1-1 and/or PAIR1-2 in maize), SPO11-1, SPO11-2, PRD1, PRD2, DFO, MTOPVIB, DSY1, SY1, SY2, SY3, and SY4. In some variations, the complete, partial, or partially-complemented MiMe genotype comprises one or more genetic modifications resulting in decreased expression of PAIR1 (e.g., PAIR1-1 and/or PAIR1-2 in maize), SPO11-1, SPO11-2, PRD1, PRD2, DFO, MTOPVIB, DSY1, SY1, SY2, SY3, SY4, or any combination thereof, and further comprises one or more genetic modifications resulting in decreased expression of one or more additional MiMe loci, which may include, but are not limited to PS1, PS1-LIKE PROTEIN, and JASON (e.g., JASON-1 and/or JASON-2 in maize).

In some embodiments, the population of polyploid maize seed or the subpopulation of genetically uniform polyploid maize seed has a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

In other embodiments, the population of polyploid maize seed or the subpopulation of genetically uniform polyploid maize seed has a partial MiMe genotype comprising (a) one or more MiMe alleles conferring decreased expression of one or more MiMe loci of each of a first, second, and third MiMe component; and (b) one or more non-MiMe alleles at the one or more MiMe loci of each of the first, second, and third MiMe components wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the partial MiMe genotype comprises one or more non-MiMe alleles at the one or more MiMe loci of each of the first, second, and third MiMe components. In other variations, the partial MiMe genotype comprises two or more non-MiMe alleles at the one or more MiMe loci of each of the first, second, and third MiMe components.

In some embodiments, the population of polyploid maize seed or the subpopulation of genetically uniform polyploid maize seed has a complete MiMe genotype comprising MiMe alleles conferring decreased expression of one or more MiMe loci each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In some variations, the population of polyploid maize seed or the subpopulation of genetically uniform polyploid maize seed having a complete MiMe genotype comprising MiMe alleles conferring decreased expression of MiMe loci of (2) a component of DNA double strand breakage during meiotic recombination and (4) a component of progression through the first division of meiosis exhibits a MiMe phenotype in male germline cells and/or produces clonal male gametes, and exhibits a wild-type meiosis phenotype in female germline cells and/or produces haploid female gametes.

In other embodiments, the population of polyploid maize seed or the subpopulation of genetically uniform polyploid maize seed has a partial MiMe genotype comprising (a) one or more MiMe alleles conferring decreased expression of one or more MiMe loci of each of a first and second MiMe component; and (b) one or more non-MiMe alleles at the one or more MiMe loci of each of the first and second MiMe components wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In some variations, the partial MiMe genotype comprises one or more non-MiMe alleles at the one or more MiMe loci of each of the first and second MiMe components. In other variations, the partial MiMe genotype comprises two or more non-MiMe alleles at the one or more MiMe loci of each of the first and second MiMe components.

In yet other embodiments, the population of polyploid maize seed or the subpopulation of genetically uniform polyploid maize seed has (i) at least a first and second haplotype, each comprising one or more MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the third haplotype comprises a non-MiMe allele at the one or more MiMe loci of one or more of the first, second, and third MiMe components.

In still other embodiments, the population of polyploid maize seed or the subpopulation of genetically uniform polyploid maize seed has (i) at least a first and second haplotype, each comprising one or more MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the third haplotype comprises a non-MiMe allele at the one or more MiMe loci of one or more of the first and second MiMe components.

In some embodiments, the population of polyploid maize seed or the subpopulation of genetically uniform polyploid maize seed has a partially-complemented MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the partially-complemented MiMe genotype comprises (a) only MiMe alleles at one or more MiMe loci of the first MiMe component; (b) one or more MiMe alleles and one or more non-MiMe alleles at a first MiMe locus of the second MiMe component, and one or more MiMe alleles and one or more non-MiMe alleles at a second MiMe locus of the second MiMe component; and (c) either (i) only MiMe alleles at one or more MiMe loci of the third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component. In some embodiments, the partially-complemented MiMe genotype comprises (a) only MiMe alleles at one or more MiMe loci of a component of sister chromatid cohesion during the first division of meiosis; (b) one or more MiMe alleles and one or more non-MiMe alleles at a first MiMe locus of a component of DNA double strand breakage during meiotic recombination, and one or more MiMe alleles and one or more non-MiMe alleles at a second MiMe locus of the component of DNA double strand breakage during meiotic recombination; and (c) either (i) only MiMe alleles at one or more MiMe loci of a component of progression through the second division of meiosis, or (ii) one or more MiMe alleles and one or more non-MiMe alleles at a first MiMe locus of a component of progression through the second division of meiosis, and one or more MiMe alleles and one or more non-MiMe alleles at a second MiMe locus of the component of progression through the second division of meiosis. Exemplary MiMe loci of each of said MiMe components are extensively described herein below. In one embodiment, the partially-complemented MiMe genotype comprises (a) only MiMe alleles of REC8; (b) one or more MiMe alleles and one or more non-MiMe alleles of SPO11-1, and one or more MiMe alleles and one or more non-MiMe alleles of PAIR1; and (c) only MiMe alleles of OSD1.

In other embodiments, the population of polyploid maize seed or the subpopulation of genetically uniform polyploid maize seed has a partially-complemented MiMe genotype comprising MiMe alleles conferring decreased expression of one or more MiMe loci each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In some variations, the population of polyploid maize seed or the subpopulation of genetically uniform polyploid maize seed having a partially-complemented MiMe genotype comprising MiMe alleles conferring decreased expression of MiMe loci of (2) a component of DNA double strand breakage during meiotic recombination and (4) a component of progression through the first division of meiosis exhibits neither a MiMe phenotype nor a wild-type meiosis phenotype in male germline cells and does not produce viable male gametes, and exhibits a wild-type meiosis phenotype in female germline cells and/or produces viable haploid female gametes. In some embodiments, the partially-complemented MiMe genotype comprises (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component. In certain embodiments, the partially-complemented MiMe genotype comprises (a) only MiMe alleles at one or more MiMe loci of a component of DNA double strand breakage during meiotic recombination; and (b) one or more MiMe alleles and one or more non-MiMe alleles at a first MiMe locus of a component of progression through the first division of meiosis, and one or more MiMe alleles and one or more non-MiMe alleles at a second MiMe locus of the component of progression through the first division of meiosis. In other embodiments, the partially-complemented MiMe genotype comprises (a) only MiMe alleles at one or more MiMe loci of a component of progression through the first division of meiosis; and (b) one or more MiMe alleles and one or more non-MiMe alleles at a first MiMe locus of a component of DNA double strand breakage during meiotic recombination and one or more MiMe alleles and one or more non-MiMe alleles at a second MiMe locus of the component of DNA double strand breakage during meiotic recombination. Exemplary MiMe loci of each of said MiMe components are extensively described below.

In some embodiments, the population of polyploid maize seed or the subpopulation of genetically uniform polyploid maize seed has a partially-complemented MiMe genotype comprising MiMe alleles conferring decreased expression of one or more MiMe loci of a first, second, third, and fourth MiMe component are selected from the group consisting of (1) a component of sister chromatid cohesion during the first division of meiosis, (2) a component of DNA double strand breakage during meiotic recombination, (3) a component of progression through the second division of meiosis, and (4) a component of progression through the first division of meiosis. In certain embodiments, the partially-complemented genotype comprises (a) only MiMe alleles at one or more MiMe loci of the first MiMe component, wherein the first MiMe component is a component of DNA double strand breakage during meiotic recombination; (b) one or more MiMe alleles and one or more non-MiMe alleles at one or more MiMe loci of the second MiMe component; (c) one or more MiMe alleles and one or more non-MiMe alleles at one or more MiMe loci of the third MiMe component; (d) one or more MiMe alleles and one or more non-MiMe alleles at one or more MiMe loci of the fourth MiMe component. In some embodiments, the partially-complemented genotype comprises (a) only MiMe alleles at one or more MiMe loci of a component of DNA double strand breakage during meiotic recombination; (b) one or more MiMe alleles and one or more non-MiMe alleles at one or more MiMe loci of a component of sister chromatid cohesion during the first division of meiosis; (c) one or more MiMe alleles and one or more non-MiMe alleles at one or more MiMe loci of a component of progression through the second division of meiosis; (d) one or more MiMe alleles and one or more non-MiMe alleles at one or more MiMe loci of a component of progression through the first division of meiosis. Exemplary MiMe loci of each of said MiMe components are extensively described below. In one variation, the partially-complemented genotype comprises (a) only MiMe alleles at SPO11-1; (b) one or more MiMe alleles and one or more non-MiMe alleles at REC8; (c) one or more MiMe alleles and one or more non-MiMe alleles at OSD1; (d) one or more MiMe alleles and one or more non-MiMe alleles at PS1 or JASON.

In some embodiments, the population of polyploid maize seed or the subpopulation of genetically uniform polyploid maize seed has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the population of polyploid maize seed or the subpopulation of genetically uniform polyploid maize seed has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In some variations, the one or more OSD1 loci comprise OSD1-1, OSD1-2, and/or OSD1-3, and/or the one or more PAIR1 loci comprise PAIR1-1 and/or PAIR1-2.

In some embodiments, the population of polyploid maize seed or the subpopulation of genetically uniform polyploid maize seed has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid maize seed or the subpopulation of genetically uniform polyploid maize seed has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In some variations, the one or more OSD1 loci comprise OSD1-1, OSD1-2, and/or OSD1-3.

In some embodiments, the population of polyploid maize seed or the subpopulation of genetically uniform polyploid maize seed has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid maize seed or the subpopulation of genetically uniform polyploid maize seed has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid maize seed or the subpopulation of genetically uniform polyploid maize seed has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the population of polyploid maize seed or the subpopulation of genetically uniform polyploid maize seed has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In some variations, the one or more PAIR1 loci comprise PAIR1-1 and/or PAIR1-2.

In some embodiments, the population of polyploid maize seed or the subpopulation of genetically uniform polyploid maize seed has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid maize seed or the subpopulation of genetically uniform polyploid maize seed has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid maize seed or the subpopulation of genetically uniform polyploid maize seed has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the population of polyploid maize seed or the subpopulation of genetically uniform polyploid maize seed has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In some variations, the one or more PAIR1 loci comprise PAIR1-1 and/or PAIR1-2.

In some embodiments, the population of polyploid maize seed or the subpopulation of genetically uniform polyploid maize seed has a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more only MiMe alleles at one or more SPO11-1 loci, wherein each of the MiMe alleles at the SPO11-1 locus comprise one or more genetic modifications resulting in decreased expression of SPO11-1. In some variations, the one or more OSD1 loci comprise OSD1-1, OSD1-2, and/or OSD1-3, and/or the one or more PAIR1 loci comprise PAIR1-1 and/or PAIR1-2.

In some embodiments, the population of polyploid maize seed or the subpopulation of genetically uniform polyploid maize seed has a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

In some embodiments, the population of polyploid maize seed or the subpopulation of genetically uniform polyploid maize seed has a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1. In some variations, the one or more PAIR1 loci comprise PAIR1-1 and/or PAIR1-2.

In some embodiments, the subpopulation of genetically uniform polyploid maize seed comprises one or more polynucleotide sequences selected from the group consisting of SEQ ID NOs: 108-111. In certain embodiments, the subpopulation of genetically uniform polyploid maize seed comprises a) a MiMe allele at one or more OSD~2 loci, each independently comprising a polynucleotide sequence selected from the group consisting of SEQ ID NOs: 108 and 109: b) a MiMe allele at a REC8 locus comprising the polynucleotide sequence of SEQ ID NO: 110; and/or c) a MiMe allele at a SPO11-1 locus comprising the polynucleotide sequence of SEQ ID NO: 111 In some variations, each the one or more OSD1-2 loci, each of the one or more REC8 loci, and/or each of the one or more SPO11-1 loci are present on a different homologous chromosome.

In some embodiments, the population of polyploid maize seed comprises one or more genetic modifications resulting in decreased expression of one or more MiMe loci. In certain embodiments, the genetic modification resulting in decreased expression of a MiMe locus is positioned in the first 70%, the first 60%, the first 50%, the first 40%, the first 30%, the first 20%, or the first 10% of the nucleotides of the coding sequence of the MiMe locus following the start codon in the 3' direction. In some embodiments, the genetic modification resulting in decreased expression of a MiMe locus is positioned in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the MiMe locus following the start codon in the 3' direction. In some embodiments, the genetic modification resulting in decreased expression of a MiMe locus is an insertion, a deletion, one or more nucleotide changes, or an inversion. In some variations, the insertion, the deletion, the one or more nucleotide changes, or the inversion eliminates expression (e.g., eliminates activity) of the MiMe locus. In certain embodiments, the insertion, the deletion, the one or more nucleotide changes, or the inversion is positioned in the first 70%, the first 60%, the first 50%, the first 40%, the first 30%, the first 20%, or the first 10% of the nucleotides of the coding sequence of the MiMe locus following the start codon in the 3' direction. In certain embodiments, the insertion, the deletion, the one or more nucleotide changes, or the inversion is positioned in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the MiMe locus following the start codon in the 3' direction. In certain embodiments, the insertion, the deletion, the one or more nucleotide changes, or the inversion results in a premature stop codon present in the first 70%, the first 60%, the first 50%, the first 40%, the first 30%, the first 20%, or the first 10% of the nucleotides of the coding sequence of the MiMe locus following the start codon in the 3' direction, thereby eliminating expression (e.g., activity) of the MiMe locus. In certain embodiments, the insertion, the deletion, the one or more nucleotide changes, or the inversion results in a premature stop codon present in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the MiMe locus following the start codon in the 3' direction, thereby eliminating expression (e.g., activity) of the MiMe locus.

In some embodiments, the one or more genetic modifications resulting in decreased expression of one or more MiMe loci comprise one or more sequences selected from the group consisting of SEQ ID NOs: 108-111.

Components of Sister Chromatid Cohesion During the First Division of Meiosis

Figure 1:
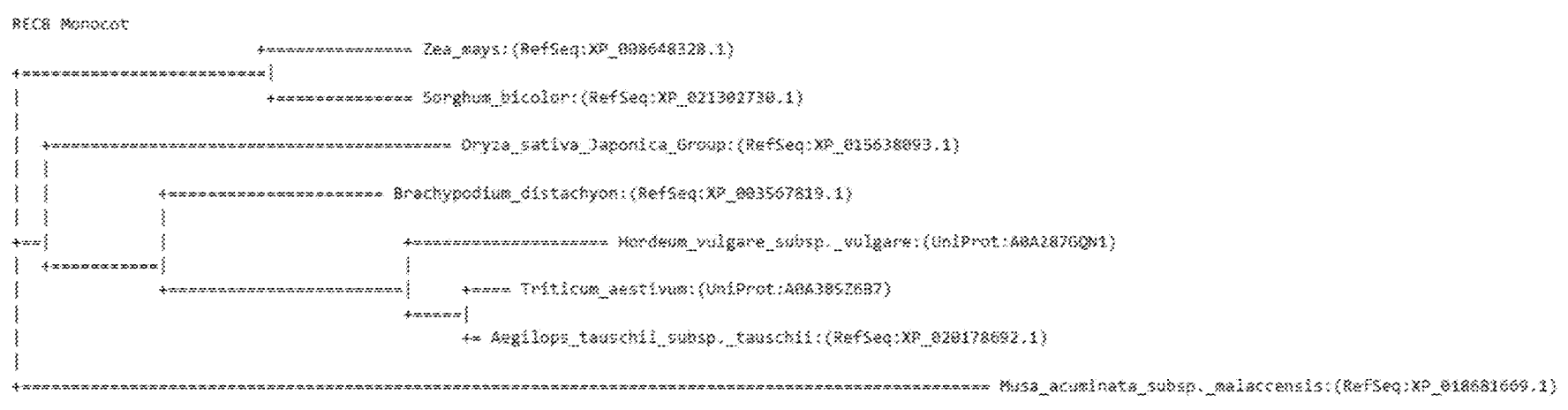

In some embodiments, the complete, partial, or partially-complemented MiMe genotype comprises one or more MiMe alleles conferring decreased expression of one or more MiMe loci of a component of sister chromatid cohesion during the first division of meiosis. In certain embodiments, the one or more MiMe loci of the component of sister chromatid cohesion during the first division of meiosis comprise REC8, SWITCH1/DYAD, or a combination thereof. One of skill in the art will understand that MiMe loci that are components of sister chromatid cohesion during the first division of meiosis are not limited to REC8 and SWITCH1/DYAD, and may include any loci encoding gene products required for sister chromatid cohesion during the first division of meiosis. By way of example only, a gene product of the component of sister chromatid cohesion during the first division of meiosis is exemplified by a REC8 protein and specifically by the REC8 protein sequences, sequence alignments, and percent identities described in "MiMe Gene Product Sequences" below. A representative REC8 protein sequence from maize (SEQ ID NO: 1) is provided in the sequence listing as outlined in Table 5, including eight native sequences and a consensus sequence identified by multiple sequence alignment of the eight native sequences (Sequence Alignment 1). Table 1 shows a matrix of percent identities of the REC8 protein sequences from monocotyledonous plants, and a phylogenetic tree showing the relationship between the sequences is shown in FIG. 1. The gene products of MiMe loci of the component of sister chromatid cohesion during the first division of meiosis include REC8 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the REC8 protein of SEQ ID NO: 1.

There is an abundance of known REC8 gene products frommaize including all of the following, which sequences are hereby incorporated by reference in their form as of the effective filing date. Exemplary REC8 gene products from maize include those of, by way of example, *Zea mays* (NP 001105829.1, XP 008648327.1, XP 008648329.1, and XP 008648328.1.

A gene product of the component of sister chromatid cohesion during the first division of meiosis is also exemplified by a SWITCH1 protein. There is an abundance of known SWITCH1 gene products from maize including all of the following, which sequences are hereby incorporated by reference in their form as of the effective filing date. Exemplary SWITCH1 gene products from maize include those of, by way of example, *Zea mays* (NP_001139538.1, XP 008662288.1 and C0RWW9).

Components of DNA Double Strand Breakage during Meiotic Recombination

Figure 2:
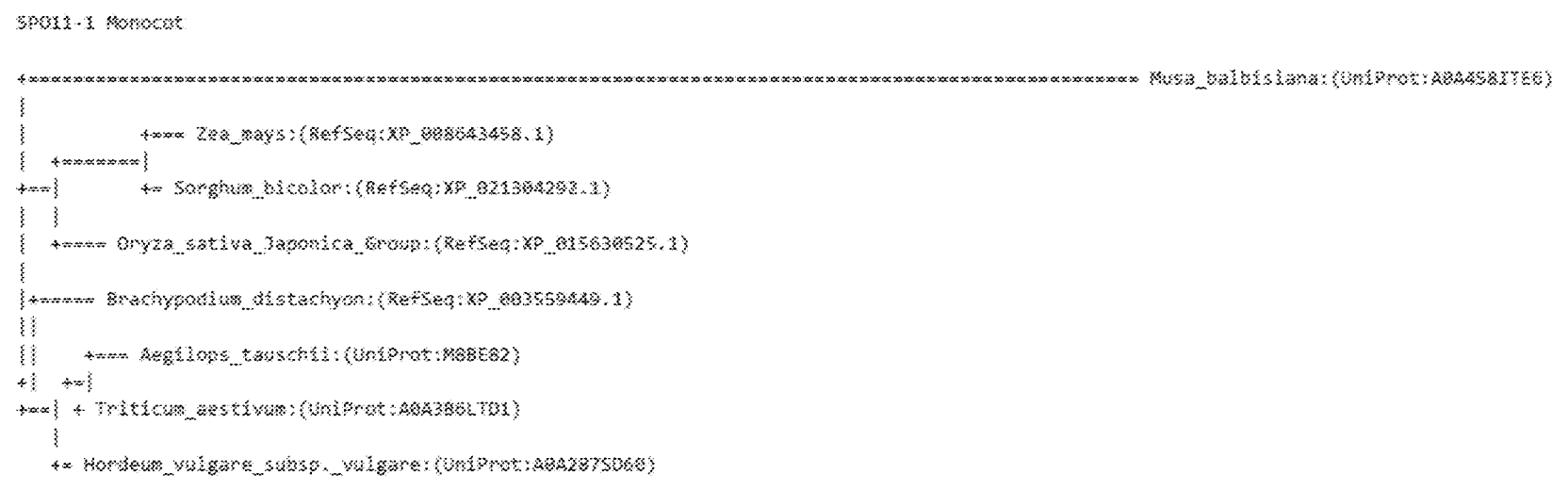

In some embodiments, the complete, partial, or partially-complemented MiMe genotype comprises one or more MiMe alleles conferring decreased expression of one or more MiMe loci of a component of DNA double strand breakage during meiotic recombination. In certain embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. One of skill in the art will understand that MiMe loci of the component of DNA double strand breakage during meiotic recombination are not limited to PAIR1, SPO11-1, SPO11-2, PRD1, PRD2, DFO, MTOPVIB, DSY1, SY1, SY2, SY3, and SY4 and may include any loci encoding gene products required for DNA double strand breakage during meiotic recombination. By way of example only, a gene product of the component of DNA double strand breakage during meiotic recombination is exemplified by a SPO11-1 protein and specifically by the SPO11-1 protein sequences, sequence alignments, and percent identities described in "MiMe Gene Product Sequences" below. A representative SPO11-1 protein sequences from maize (SEQ ID NO: 2) is provided in the sequence listing as outlined in Table 5, including eight native sequences and a consensus sequence identified by multiple sequence alignment of the eight native sequences (Sequence Alignment 2). Table 2 shows a matrix of percent identities of the SPO11-1 protein sequences from monocotyledonous plants, and a phylogenetic tree showing the relationship between the sequences is shown in FIG. 2. The gene products of MiMe loci of the component of DNA double strand breakage during meiotic recombination include SPO11-1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to any one of the SPO11-1 proteins of SEQ ID NO: 2.

There is an abundance of known SPO11-1 gene products from maize including all of the following, which sequences are hereby incorporated by reference in their form as of the effective filing date. Exemplary SPO11-1 gene products from maize include those of, by way of example, *Zea luxurians* (AOA1P8W173), *Zea mays* (NP 001347894.1, XP 008643457.1, XP 008643458.1, XP 008643459.1, XP 020408860.1, and XP 008643458.1), *Zea mays* subsp. huehuetenangensis (AOA1P8W126), *Zea mays* subsp. *mays* (AOA1P8W137 and AOA1P8W169), *Zea mays* subsp. *mexicana* (AOA1P8W110), *Zea mays* subsp. *parviglumis* (AOA1P8WOZ9, AOA1P8W103, AOA1P8W125, and AOA1P8W189).

A gene product of the component of DNA double strand breakage during meiotic recombination is also exemplified by a SPO11-2 protein. There is an abundance of known SPO11-2 gene products from maize including all of the following, which sequences are hereby incorporated by reference in their form as of the effective filing date. Exemplary SPO11-2 gene products from maize include those of, by way of example, *Zea mays* (XP 020406911.1, NP_001298099.1 and NP_001141583.1), *Zea mays* (AOA1P8W150, AOA1P8W149 and AOA1P8W163), *Zea mays* (AOA1P8W133, AOA1P8W171 and AOA1P8W158), *Zea diploperennis* (AOA1P8W179), *Zea mays* (AOA1P8W114), *Zea luxurians* (AOA1P8W147), and *Zea mays* (AOA1P8W1E8).

Figure 3:
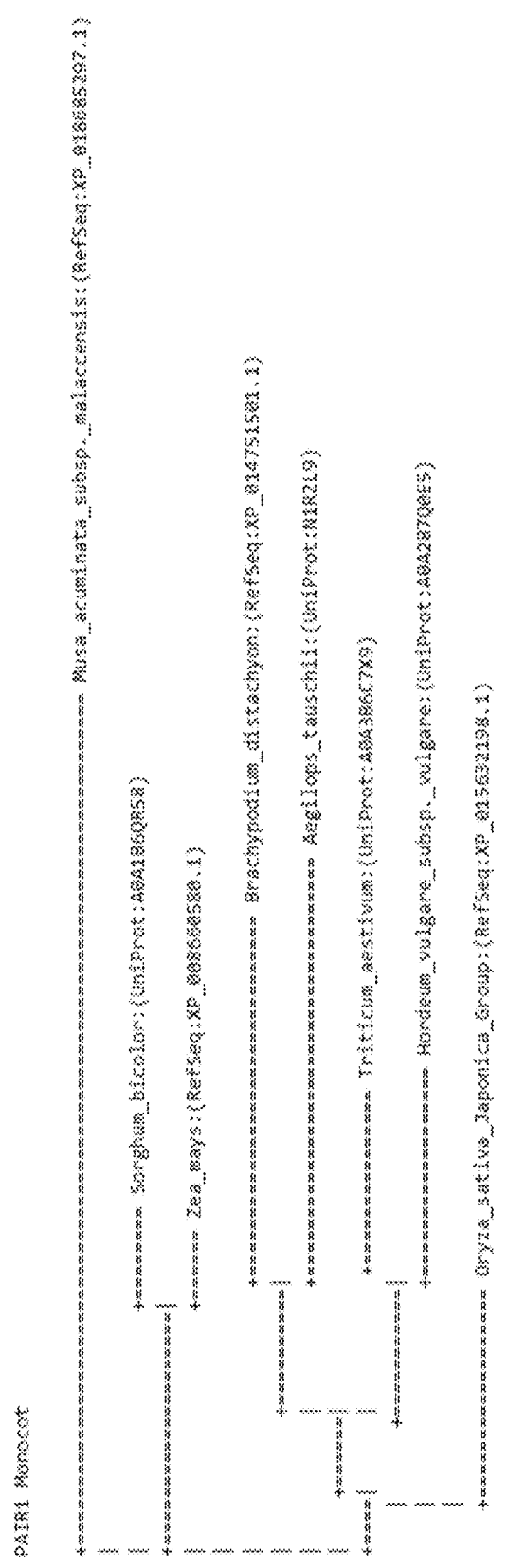

A gene product of the component of DNA double strand breakage during meiotic recombination is also exemplified by a PAIR1 protein (e.g., a PAIR1-1 protein or a PAIR1-2 protein) and specifically by the PAIR1 protein sequences, sequence alignments, and percent identities described in "MiMe Gene Product Sequences" below. Representative PAIR1 protein sequences from maize (SEQ ID NOs: 3 and 5), including a representative PAIR1-1 protein sequence from maize (SEQ ID NO: 3) and a representative PAIR1-2 protein sequence from maize (SEQ ID NO: 5), are provided in the sequence listing as outlined in Table 5, including eight native sequences and a consensus sequence identified by multiple sequence alignment of the eight native sequences (Sequence Alignment 3). Table 3 shows a matrix of percent identities of the PAIR1 protein sequences from monocotyledonous plants, and a phylogenetic tree showing the relationship between the sequences is shown in FIG. 3. The gene products of MiMe loci of the component of DNA double strand breakage during meiotic recombination includes PAIR1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to any one of the PAIR1 proteins of SEQ ID NOs: 3 and 5. The gene products of MiMe loci of the component of DNA double strand breakage during meiotic recombination also include: a) PAIR1-1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the PAIR1-1 protein of SEQ ID NO: 3; and b) PAIR1-2 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the PAIR1-2 protein of SEQ ID NO: 5.

There is an abundance of known PAIR1 gene products maize including all of the following, which sequences are hereby incorporated by reference in their form as of the effective filing date. Exemplary PAIR1 gene products from maize include those of, by way of example, Zea mays (XP 008660580.1, AOA1D6JK92, AOA1D6JK93, AOA1D6JK94, and AOA1D6PM18.

A gene product of the component of DNA double strand breakage during meiotic recombination is also exemplified by a PRD1 protein. There is an abundance of known PRD1 gene products from maize including all of the following, which sequences are hereby incorporated by reference in their form as of the effective filing date. Exemplary PRD1 gene products from maize include those of, by way of example, Zea mays (XP 020399554.1, XP 020399553.1 and AOA1D6P5Q4).

A gene product of the component of DNA double strand breakage during meiotic recombination is also exemplified by a PRD2 protein. There is an abundance of known PRD2 gene products from maize including all of the following, which sequences are hereby incorporated by reference in their form as of the effective filing date. Exemplary PRD2 gene products from maize include those of, by way of example, Zea mays (NP_001130070.1, XP 035822500.1 and AOA3L6F902), Setaria viridis (XP 034583479.1, XP 034583480.1 and XP 034600292.1).

A gene product of the component of DNA double strand breakage during meiotic recombination is also exemplified by a DFO protein. There is an abundance of known DFO gene products from maize including all of the following, which sequences are hereby incorporated by reference in their form as of the effective filing date. Exemplary DFO gene products from dicots include those of, by way of example, Zea mays (XP 020397706.1, AOA1D6QG87 and AOA3L6EXP8).

A gene product of the component of DNA double strand breakage during meiotic recombination is also exemplified by a MTOPVIB protein. There is an abundance of known MTOPVIB gene products from maize including all of the following, which sequences are hereby incorporated by reference. Exemplary MTOPVIB gene products from maize include those of, by way of example, Zea mays (XP 008645058.1, AOA3L6EMU7 and AOA1D6GVU9).

Components of Progression Through the Second Division of Meiosis

In some embodiments, the complete, partial, or partially-complemented MiMe genotype comprises one or more MiMe alleles conferring decreased expression of one or more MiMe loci of a component of progression through the second division of meiosis. Components of progression through the second division of meiosis include, for example, both (a) MiMe loci that encode gene products that are required for progression through the second division of meiosis and (b) MiMe loci that that are associated with second division restitution mechanisms, since the effective end result of both is as if the second division of meiosis did not occur, with the resulting gametes of each containing sister chromatids. Second division restitution (also known as nuclear restitution) mechanisms are known in the art and described in Brownfield and Kohler (2010. Unreduced gamete formation in plants: mechanisms and prospects. J Exp Bot 62:5, 1659-1668). In certain embodiments, the one or more MiMe loci of the component of progression through the second division of meiosis comprise OSD1, CYCA1, TDM1, PC1, PC2, FC, or any combination thereof. One of skill in the art will understand that MiMe loci of the component of progression through the second division of meiosis are not limited to OSD1, CYCA1, TDM1, PC1, PC2, and FC, and may include any loci encoding gene products required for progression through the second division of meiosis or associated with second division restitution mechanisms. By way of example only, a gene product of the component of progression through the second division of meiosis of the first division sister chromatid segregation is exemplified by an OSD1 protein (e.g., an OSD1-1 protein, an OSD1-2 protein, or an OSD1-3 protein) and specifically by the OSD1 protein sequences, sequence alignments, and percent identities described in "MiMe Gene Product Sequences" below. Representative OSD1 protein sequences from maize (SEQ ID NOs: 4, 6, and 7) are provided in the sequence listing as outlined in Table 5, including eight native sequences and a consensus sequence identified by multiple sequence alignment of the eight native sequences (Sequence Alignment 4), as well as OSD1-1, OSD1-2, and OSD1-3 protein sequences from maize. OSD1 homologues present in the maize genome include, for example, OSD1-1 on chromosome 2 (SEQ ID NO: 4), OSD1-2 on chromosome 5 (SEQ ID NO: 6), and OSD1-3 on chromosome 5 (SEQ ID NO: 7). Table 4A shows a matrix of percent identities of the OSD1 protein sequences from monocotyledonous plants, and a phylogenetic tree showing the relationship between the sequences is shown in FIG. 4. The gene products of MiMe loci of the component of progression through the second division of meiosis include OSD1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to any one of the OSD1 proteins of SEQ ID NOs: 4 and 6-7. The gene products of MiMe loci of the component of progression through the second division of meiosis also include: a) OSD1-1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to any one of the OSD1-1 protein of SEQ ID NO: 4; b) OSD1-2 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the OSD1-2 protein of SEQ ID NO: 6; a) OSD1-3 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the OSD1-3 protein of SEQ ID NO: 7.

There is an abundance of known OSD1 gene products from maize including all of the following, which sequences are hereby incorporated by reference in their form as of the effective filing date. Exemplary OSD1 gene products from maize include those of, by way of example, *Zea mays* (AOA1D6HBV9, AOA1D6HBW0, B4FCP3, B4FG75, and B6T7U1).

By way of example only, a gene product of the component of progression through the second division of meiosis is also exemplified by a CYCA1 protein, also known as CYCLIN-A1 or TARDY ASYNCHRONOUS MEIOSIS (TAM), and specifically by the CYCA1 protein sequences, sequence alignments, and percent identities described in "MiMe Gene Product Sequences" below. A representative CYCA1 protein sequence from maize (SEQ ID NOs: 10 and 13) are provided in the sequence listing as outlined in Table 5, including native sequences and a consensus sequence identified by multiple sequence alignment of the native sequences (Sequence Alignment 5). Table 4B shows a matrix of percent identities of the OSD1 protein sequences from monocotyledonous plants. The gene products of MiMe loci of the component of progression through the second division of meiosis include CYCA1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the CYCA1 protein of SEQ ID NOs: 10 and 13.

There is an abundance of known CYCA1 gene products from maize including all of the following, which sequences are hereby incorporated by reference in their form as of the effective filing date. Exemplary CYCA1 gene products from maize include those of, by way of example, *Zea mays* (NP_001105387.2, NP_001288521.1 and XP 008656316.2).

By way of example only, a gene product of the component of progression through the second division of meiosis is also exemplified by a TDM1 protein, and specifically by the TDM1 protein sequences and percent identities described herein. A representative TDM1 protein sequence from maize (SEQ ID NO: 11) is provided in Table 5. The gene products of MiMe loci of the component of progression through the second division of meiosis include TDM1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the TDM1 protein of SEQ ID NO: 11. The gene products of MiMe loci of the component of progression through the second division of meiosis also include TDM1-1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the protein of SEQ ID NO: 11.

There is an abundance of known TDM1 gene products from maize including all of the following, which sequences are hereby incorporated by reference in their form as of the effective filing date. Exemplary TDM1 gene products from maize include those of, by way of example, *Zea mays* (NP_001170740.1, NP_001141607.1 and XP 008651103.1).

Components of Progression Through the First Division of Meiosis

In some embodiments, the complete, partial, or partially-complemented MiMe genotype comprises one or more MiMe alleles conferring decreased expression of one or more MiMe loci of a component of progression through the first division of meiosis. Components of progression through the first division of meiosis include, for example, both (a) MiMe loci that encode gene products that are required for progression through the first division of meiosis and (b) MiMe loci that that are associated with first division restitution mechanisms, since the effective end result of both is as if the first division of meiosis did not occur, with the resulting gametes of each containing non-sister chromatids. First division restitution (also known as nuclear restitution) mechanisms are known in the art and described in Peloquin et al. (1999. Meiotic mutants in potato: valuable variants. *Genetics* 153: 1493-1499) and Brownfield and Kohler (2010. Unreduced gamete formation in plants: mechanisms and prospects. *J Exp Bot* 62:5, 1659-1668). In certain embodiments, the one or more MiMe loci of the component of progression through the first division of meiosis comprise PS1, JASON, or a combination thereof. One of skill in the art will understand that MiMe loci of the component of progression through the first division of meiosis are not limited to PS1 and JASON, and may include any loci encoding gene products required for progression through the first division of meiosis or associated with first division restitution mechanisms. By way of example only, a gene product of the component of progression through the first division of meiosis is exemplified by PS1 protein or a PS1-like protein, and specifically by the PS1 and PS1-like protein sequences and percent identities described herein. A representative PS1 protein sequence (SEQ ID NO: 12) is provided in the sequence listing as outlined in Table 5. The gene products of MiMe loci of the component of progression through the first division of meiosis include: a) PS1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the PS1 protein of SEQ ID NO:12

There is an abundance of known PS1 gene products from maize including all of the following, which sequences are hereby incorporated by reference in their form as of the effective filing date. Exemplary PS1 gene products from maize include those of, by way of example, *Zea mays* (NP_001348386.1, XP 035820777.1 and XP 008668271.1).

By way of example only, a gene product of the component of progression through the first division of meiosis is also exemplified by a JASON protein (e.g., a JASON-1 or a JASON-2 protein), and specifically by the JASON protein sequences and percent identities described herein. Representative JASON protein sequences (SEQ ID. 8 and 9), including a representative JASON-1 protein sequence (SEQ ID NO: 8) and a representative JASON-2 protein sequence (SEQ ID NO: 9), are provided in the sequence listing as outlined in Table 5. The gene products of MiMe loci of the component of progression through the first division of meiosis include: a) JASON-1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the JASON-1 protein of SEQ ID NO: 8; b) JASON-2 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the JASON-2 protein of SEQ ID NO: 9.

There is an abundance of known JASON gene products from maize including all of the following, which sequences are hereby incorporated by reference in their form as of the effective filing date. Exemplary JASON gene products from maize include those of, by way of example, *Zea mays* (NP_001132267.1, XP 008647301.1 and NP_001130670.1).

The sequences of the gene products listed above may be accessed using the given accession numbers in the RefGen, UniProt, and RefSeq databases.

Exemplary Populations of Polyploid Seed

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize. In certain embodiments, the population was obtained from a single maize plant or a set of maize plants (e.g., a set of genetically uniform maize plants, e.g., a set of genetically uniform F1 hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, or at least about 95%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. The subpopulation of genetically uniform polyploid maize seed may have any complete MiMe genotype, partial MiMe genotype, or partially-complemented MiMe genotype described herein. In certain embodiments, the subpopulation of genetically uniform polyploid maize seed has a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the subpopulation of genetically uniform polyploid maize seed has a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In certain embodiments, the subpopulation of genetically uniform polyploid maize seed has a partial MiMe genotype comprising (a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the subpopulation of genetically uniform polyploid maize seed has a partial MiMe genotype comprising (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In certain embodiments, the subpopulation of genetically uniform polyploid maize seed has a partially-complemented MiMe genotype comprising (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the subpopulation of genetically uniform polyploid maize seed has a partially-complemented MiMe genotype comprising (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In certain embodiments, the subpopulation of genetically uniform polyploid maize seed has a partially-complemented MiMe genotype comprising (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components. In some variations, the one or more MiMe loci of the component of sister chromatid cohesion during the first division of meiosis comprise REC8, SWITCH1/DYAD, or a combination thereof; the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof; the one or more MiMe loci of the component of progression through the second division of meiosis comprise OSD1, CYCA1, TDM1, PC1, PC2, FC, or any combination thereof; and/or the one or more MiMe loci of the component of progression through the first division of meiosis comprise PS1, JASON, or a combination thereof. In other variations, the one or more MiMe loci of the component of sister chromatid cohesion during the first division of meiosis comprise REC8; the one or more MiMe loci of the component of DNA double strand breakage during meiotic recombination comprise PAIR1, SPO11-1, SPO11-2, or any combination thereof; the one or more MiMe loci of the component of progression through the second division of meiosis comprise OSD1, CYCA1, TDM1, or any combination thereof; and/or the one or more MiMe loci of the component of progression through the first division of meiosis comprise PS1. In some embodiments, the subpopulation of genetically uniform polyploid maize seed comprises one or more polynucleotide sequences selected from the group consisting of SEQ ID NOs: 108-111. In certain embodiments, the subpopulation of genetically uniform polyploid maize seed comprises a) a MiMe allele at one or more OSD1-2 loci, each independently comprising a polynucleotide sequence selected from the group consisting of SEQ ID NOs: 108 and 109; b) a MiMe allele at a REC8 locus comprising the polynucleotide sequence of SEQ ID NO: 110; and/or c) a MiMe allele at a SPO11-1 locus comprising the polynucleotide sequence of SEQ ID NO: 111 In some variations, each the one or more OSD1-2 loci, each of the one or more REC8 loci, and/or each of the one or more SPO11-1 loci are present on a different homologous chromosome.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize. In certain embodiments, the population of maize seed was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, or at least about 95%) as measured by the Jaccard similarity coefficient. In one embodiment, the population of polyploid maize seed has an average pairwise genetic uniformity of at least 99% or about 100% as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In one embodiment, the population of polyploid maize seed comprises the subpopulation of genetically uniform polyploid maize seed in an amount of at least about 98% of the total number of seeds, wherein each pair of seeds in the subpopulation of genetically uniform polyploid maize seed has a pairwise identity of 100%. The subpopulation of genetically uniform polyploid maize seed may have any complete MiMe genotype, partial MiMe genotype, or partially-complemented MiMe genotype described herein. In certain embodiments, the subpopulation of genetically uniform polyploid maize seed has a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the subpopulation of genetically uniform polyploid maize seed has a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In certain embodiments, the subpopulation of genetically uniform polyploid maize seed has a partial MiMe genotype comprising (a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the subpopulation of genetically uniform polyploid maize seed has a partial MiMe genotype comprising (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In certain embodiments, the subpopulation of genetically uniform polyploid maize seed has a partially-complemented MiMe genotype comprising (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the subpopulation of genetically uniform polyploid maize seed has a partially-complemented MiMe genotype comprising (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In certain embodiments, the subpopulation of genetically uniform polyploid maize seed has a partially-complemented MiMe genotype comprising (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components. In some variations, the one or more MiMe loci of the component of sister chromatid cohesion during the first division of meiosis comprise REC8; the one or more MiMe loci of the component of DNA double strand breakage during meiotic recombination comprise PAIR1, SPO11-1, SPO11-2, or any combination thereof; the one or more MiMe loci of the component of progression through the second division of meiosis comprise OSD1, CYCA1, or a combination thereof; and/or the one or more MiMe loci of the component of progression through the first division of meiosis comprise PS1. In some embodiments, the subpopulation of genetically uniform polyploid maize seed comprises one or more polynucleotide sequences selected from the group consisting of SEQ ID NOs: 108-111. In certain embodiments, the subpopulation of genetically uniform polyploid maize seed comprises a) a MiMe allele at one or more OSD1-2 loci, each independently comprising a polynucleotide sequence selected from the group consisting of SEQ ID NOs: 108 and 109; b) a MiMe allele at a REC8 locus comprising the polynucleotide sequence of SEQ ID NO: 110: and/or c) a MiMe allele at a SPO11-1 locus comprising the polynucleotide sequence of SEQ ID NO: 111. In some variations, each the one or more OSD1-2 loci, each of the one or more REC8 loci, and/or each of the one or more SPO11-1 loci are present on a different homologous chromosome.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the one or more OSD1 loci comprise OSD1-1, OSD1-2, and/or OSD1-3, and/or the one or more PAIR1 loci comprise PAIR1-1 and/or PAIR1-2. In certain variations, the one or more OSD1 loci comprise OSD1-1 and OSD1-2. In some variations, the subpopulation of genetically uniform polyploid maize seed comprises a) a rec8 allele comprising the polynucleotide sequence of SEQ ID NO: 110; and/or b) one or more osd1 alleles, each comprising a polynucleotide sequence selected from the group consisting of SEQ ID NOS: 108 and 109.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the one or more OSD1 loci comprise OSD1-1, OSD1-2, and/or OSD1-3, and/or the one or more PAIR1 loci comprise PAIR1-1 and/or PAIR1-2. In certain variations, the one or more OSD1 loci comprise OSD1-1 and OSD1-2. In some variations, the subpopulation of genetically uniform polyploid maize seed comprises a) a rec8 allele comprising the polynucleotide sequence of SEQ ID NO: 110; and/or b) one or more osd1 alleles, each comprising a polynucleotide sequence selected from the group consisting of SEQ ID NOS: 108 and 109.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient In some variations, the one or more OSD1 loci comprise OSD1-1, OSD1-2, and/or OSD1-3. In certain variations, the one or more OSD1 loci comprise OSD1-1 and OSD1-2. In some variations, the subpopulation of genetically uniform polyploid maize seed comprises a) a rec8 allele comprising the polynucleotide sequence of SEQ ID NO: 110; b) one or more osd1 alleles, each comprising a polynucleotide sequence selected from the group consisting of SEQ ID NOS: 108 and 109; and/or c) a spo11-1 allele comprising the polynucleotide sequence of SEQ ID NO: 111.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient In some variations, the one or more OSD1 loci comprise OSD1-1, OSD1-2, and/or OSD1-3. In certain variations, the one or more OSD1 loci comprise OSD1-1 and OSD1-2. In some variations, the subpopulation of genetically uniform polyploid maize seed comprises a) a rec8 allele comprising the polynucleotide sequence of SEQ ID NO: 110; b) one or more osd1 alleles, each comprising a polynucleotide sequence selected from the group consisting of SEQ ID NOS: 108 and 109; and/or c) a spo11-1 allele comprising the polynucleotide sequence of SEQ ID NO: 111.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the subpopulation of genetically uniform polyploid maize seed comprises a) a rec8 allele comprising the polynucleotide sequence of SEQ ID NO: 110; and/or b) a spo11-1 allele comprising the polynucleotide sequence of SEQ ID NO: 111.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the subpopulation of genetically uniform polyploid maize seed comprises a) a rec8 allele comprising the polynucleotide sequence of SEQ ID NO: 110; and/or b) a spo11-1 allele comprising the polynucleotide sequence of SEQ ID NO: 111.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the one or more PAIR1 loci comprise PAIR1-1 and/or PAIR1-2. In some variations, the subpopulation of genetically uniform polyploid maize seed comprises a rec8 allele comprising the polynucleotide sequence of SEQ ID NO: 110.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the one or more PAIR1 loci comprise PAIR1-1 and/or PAIR1-2. In some variations, the subpopulation of genetically uniform polyploid maize seed comprises a rec8 allele comprising the polynucleotide sequence of SEQ ID NO: 110.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the subpopulation of genetically uniform polyploid maize seed comprises a) a rec8 allele comprising the polynucleotide sequence of SEQ ID NO: 110; and/or b) a spo11-1 allele comprising the polynucleotide sequence of SEQ ID NO: 111.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the subpopulation of genetically uniform polyploid maize seed comprises a) a rec8 allele comprising the polynucleotide sequence of SEQ ID NO: 110; and/or b) a spo11-1 allele comprising the polynucleotide sequence of SEQ ID NO: 111.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the one or more PAIR1 loci comprise PAIR1-1 and/or PAIR1-2. In some variations, subpopulation of genetically uniform polyploid maize seed comprises a rec8 allele comprising the polynucleotide sequence of SEQ ID NO: 110.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the one or more PAIR1 loci comprise PAIR1-1 and/or PAIR1-2. In some variations, the subpopulation of genetically uniform polyploid maize seed comprises a rec8 allele comprising the polynucleotide sequence of SEQ ID NO: 110.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more only MiMe alleles at one or more SPO11-1 loci, wherein each of the MiMe alleles at the SPO11-1 locus comprise one or more genetic modifications resulting in decreased expression of SPO11-1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the one or more PAIR1 loci comprise PAIR1-1 and/or PAIR1-2. In some variations, the subpopulation of genetically uniform polyploid maize seed comprises a) a rec8 allele comprising the polynucleotide sequence of SEQ ID NO: 110; and/or b) a spo11-1 allele comprising the polynucleotide sequence of SEQ ID NO: 111.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the one or more PAIR1 loci comprise PAIR1-1 and/or PAIR1-2. In some variations, the subpopulation of genetically uniform polyploid maize seed comprises a) a rec8 allele comprising the polynucleotide sequence of SEQ ID NO: 110; and/or b) a spo11-1 allele comprising the polynucleotide sequence of SEQ ID NO: 111.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In some variations, the one or more PAIR1 loci comprise PAIR1-1 and/or PAIR1-2. In some variations, the subpopulation of genetically uniform polyploid maize seed comprises a) a rec8 allele comprising the polynucleotide sequence of SEQ ID NO: 110; and/or b) a spo11-1 allele comprising the polynucleotide sequence of SEQ ID NO: 111.

In some embodiments, provided herein is a population of polyploid maize seed comprising a subpopulation of genetically uniform polyploid maize seed in an amount of at least 50% of the total number of seeds, the genetically uniform polyploid maize seed comprising three or more haplotypes of the same or related species of maize and one or more polynucleotide sequences selected from the group consisting of SEQ ID NOs: 108-111. In certain embodiments, the population was obtained from a single maize plant or a set of maize plants (e.g., a set of genetically uniform maize plants, e.g., a set of genetically uniform F1 maize hybrids). In certain embodiments, the subpopulation of genetically uniform polyploid maize seed is triploid, tetraploid, or pentaploid. In one embodiment, the subpopulation of genetically uniform polyploid maize seed is tetraploid. In certain embodiments, the population of polyploid maize seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid maize seed comprises the subpopulation of genetically uniform polyploid maize seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid maize seed has a pairwise identity of at least about 95% (e.g., at least about 95%, at least about 96%, at least about 97%, at least about 98%, at least about 99%, or about 100%) as measured by the Jaccard similarity coefficient. In certain embodiments, the subpopulation of genetically uniform polyploid maize seed comprises a) a MiMe allele at each of one or more OSD1-2 loci, each independently comprising a polynucleotide sequence selected from the group consisting of SEQ ID NOs: 108 and 109; b) a MiMe allele at a REC8 locus comprising the polynucleotide sequence of SEQ ID NO: 110; and/or c) a MiMe allele at a SPO11-1 locus comprising the polynucleotide sequence of SEQ ID NO: 111. In some variations, each the one or more OSD1-2 loci, each of the one or more REC8 loci, and/or each of the one or more SPO11-1 loci are present on a different homologous chromosome.

Methods of Producing Populations of Polyploid Maize Seed

In another aspect, provided herein are methods of producing a population of polyploid maize seed comprising three or more haplotypes wherein at least 50% of the population of polyploid maize seed are genetically uniform. In some embodiments, the population of polyploid maize seed comprises a subpopulation of genetically uniform polyploid maize seed in an amount of at least 50%, the genetically uniform polyploid maize seed comprising the three or more haplotypes. In some embodiments, the method comprises (a) providing clonal gametes from a pair of parent MiMe maize plants that together comprise three or more haplotypes; and (b) crossing the clonal gametes to produce the population of polyploid maize seed. In other embodiments, the method comprises (a) providing clonal gametes from a parent MiMe maize plant; (b) providing haploid gametes from a homozygous parent non-MiMe maize plant; and (c) crossing the clonal gametes with the haploid gametes to produce the population of polyploid maize seed. In other embodiments, the method comprises (a) providing clonal gametes from a parent MiMe maize plant; (b) providing haploid gametes from a homozygous parent non-MiMe maize plant; and (c) crossing the clonal gametes with the haploid gametes to produce the population of polyploid maize seed; wherein the clonal gametes and the haploid gametes together comprise three or more haplotypes. In still other embodiments, the method comprises (a) providing clonal gametes from a parent MiMe maize plant; (b) providing unreduced, non-clonal gametes from a homozygous parent maize plant; and (c) crossing the clonal gametes with the unreduced, non-clonal gametes to produce the population of polyploid maize seed; wherein the clonal gametes and the unreduced, non-clonal gametes together comprise three or more haplotypes.

In another aspect, provided herein are methods of producing a population of polyploid maize seed comprising a partially-complemented MiMe genotype wherein at least 50% of the population of polyploid maize seed are genetically uniform. In some embodiments, provided herein are methods of producing a population of polyploid maize seed comprising a subpopulation of genetically uniform polyploid maize seed in an amount of at least 50% of the total number of seeds, the subpopulation of genetically uniform polyploid maize seed comprising a partially-complemented MiMe genotype wherein at least 50% of the population of polyploid maize seed are genetically uniform. In some embodiments, the method comprises (a) providing clonal gametes from a first parent MiMe maize plant; (b) providing clonal gametes from a second parent MiMe maize plant; and (c) crossing the clonal gametes to produce the population of polyploid maize seed comprising a partially-complemented MiMe genotype. In certain embodiments, the polyploid maize seed (e.g., the subpopulation of genetically uniform polyploid maize seed) comprises one, two, three, or more haplotypes.

In some embodiments, at least 50% of the population of polyploid maize seed produced are genetically uniform. In some variations, at least 60%, least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the population of polyploid maize seed produced are genetically uniform. In some embodiments, at least 50% of the population of polyploid maize seed produced are genetically uniform, wherein the polyploid maize seed comprises two, three, or more haplotypes. In some variations, at least 60%, least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the population of polyploid maize seed produced are genetically uniform, wherein the polyploid maize seed comprises two, three, or more haplotypes.

In some embodiments, the population of polyploid maize seed comprises a subpopulation of genetically uniform polyploid maize seed in an amount of at least 50% of the total number of seeds. In some variations, the population of polyploid maize seed comprises a subpopulation of genetically uniform polyploid maize seed in an amount of at least 60%, least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the total number of seeds. In some embodiments, the subpopulation of genetically uniform polyploid maize seed comprises two, three, or more haplotypes. In some variations, the population of polyploid maize seed comprises a subpopulation of genetically uniform polyploid maize seed in an amount of at least 60%, least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the total number of seeds, wherein the genetically uniform polyploid maize seed comprises two, three, or more haplotypes. In certain variations, the subpopulation of genetically uniform polyploid maize seed has a complete MiMe genotype, a partial MiMe genotype, or a partially-complemented MiMe genotype.

Providing Clonal Gametes

In some embodiments, the method of producing a population of polyploid maize seed comprises providing clonal gametes. In some embodiments, providing clonal gametes comprises growing a maize plant with a complete MiMe genotype that exhibits a MiMe phenotype and allowing the maize plant to grow to a reproductive stage until clonal gametes form. In other embodiments, providing clonal gametes comprises generating a maize plant with a complete MiMe genotype that exhibits a MiMe phenotype and growing said maize plant to a reproductive stage until clonal gametes form. In some variations, providing clonal gametes further comprises collecting pollen comprising clonal gametes from a maize plant with a complete MiMe genotype that exhibits a MiMe phenotype.

In some embodiments, the method of producing a population of polyploid maize seed comprises providing clonal gametes from one or more parent MiMe maize plants. In some variations, the method of producing a population of polyploid maize seed comprises providing clonal gametes from a pair of parent MiMe maize plants. In some embodiments, providing clonal gametes comprises growing one or more parent MiMe maize plants and allowing them to grow to a reproductive stage until clonal gametes form. In other embodiments, providing clonal gametes comprises generating one or more parent MiMe maize plants and growing them to a reproductive stage until clonal gametes form. In some variations, providing clonal gametes further comprises collecting pollen comprising clonal gametes from one or more parent MiMe maize plants. In some additional variations, the pair of parent MiMe maize plants are diploid, triploid, tetraploid, pentaploid, hexaploid, heptaploid, octaploid, or any combination thereof.

In some embodiments, the method of producing a population of polyploid maize seed comprises providing clonal gametes from a pair of parent MiMe maize plants that together comprise three or more haplotypes. In some variations, the pair of parent MiMe maize plants together comprise three or more haplotypes, four or more haplotypes, five or more haplotypes, six or more haplotypes, seven or more haplotypes, or eight or more haplotypes. In additional variations, the pair of parent MiMe maize plants together comprise three, four, five, six, seven, or eight haplotypes. In some embodiments, the first parent MiMe maize plant comprises one or more haplotypes and the second parent MiMe maize plant comprises one or more haplotypes, wherein the parent MiMe maize plants together comprise two or more haplotypes. In some embodiments, the first parent MiMe maize plant comprises one haplotype and the second parent MiMe maize plant comprises two or more haplotypes, wherein the parent MiMe maize plants together comprise three or more haplotypes. In other embodiments, each of the parent MiMe maize plants comprises two or more haplotypes, wherein the parent MiMe maize plants together comprise four or more haplotypes.

Parent MiMe Maize Plant Genotypes

In some embodiments, each of the parent MiMe maize plants has a complete MiMe genotype. In certain embodiments, the complete MiMe genotype comprises one or more genetic modifications resulting in decreased expression of one or more MiMe loci. In other embodiments, the complete MiMe genotype comprises one or more genetic modifications resulting in decreased expression of two or more MiMe loci. In yet another embodiment, the complete MiMe genotype comprises one or more genetic modifications resulting in decreased expression of three or more MiMe loci. In some variations, the MiMe loci may include, but are not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, JASON, PC1, PC2, and FC. In one variation, the complete MiMe genotype comprises one or more genetic modifications resulting in decreased expression of REC8. In a second variation, the complete MiMe genotype comprises one or more genetic modifications resulting in decreased expression of OSD1. In a third variation, the complete MiMe genotype comprises one or more genetic modifications resulting in decreased expression of PAIR1. In a fourth variation, the complete MiMe genotype comprises one or more genetic modifications resulting in decreased expression of SPO11-1, SPO11-2, or a combination thereof. In a fifth variation, the complete MiMe genotype comprises one or more genetic modifications resulting in decreased expression of REC8 and SPO11-1. In a sixth variation, the complete MiMe genotype comprises one or more genetic modifications resulting in decreased expression of REC8 and OSD1. In a seventh variation, the complete MiMe genotype comprises one or more genetic modifications resulting in decreased expression of REC8 and PAIR1. In an eighth variation, the complete MiMe genotype comprises one or more genetic modifications resulting in decreased expression of OSD1 and SPO11-1. In a ninth variation, the complete MiMe genotype comprises one or more genetic modifications resulting in decreased expression of OSD1 and PAIR1. In a tenth variation, the complete MiMe genotype comprises one or more genetic modifications resulting in decreased expression of REC8, OSD1, and PAIR1. In an eleventh variation, the complete MiMe genotype comprises one or more genetic modifications resulting in decreased expression of REC8, OSD1, and SPO11-1. In a twelfth variation, the complete MiMe genotype comprises one or more genetic modifications resulting in decreased expression of PS1 and SPO11-1. In a thirteenth variation, the complete MiMe genotype comprises one or more genetic modifications resulting in decreased expression of PS1 and SY3. The complete MiMe genotype may comprise one or more genetic modifications resulting in decreased expression of any combination of MiMe loci described herein or known in the art, wherein a maize plant that has the complete MiMe genotype exhibits a MiMe phenotype. In some embodiments, the complete MiMe genotype may comprise one or more genetic modifications resulting in non-expression of any combination of MiMe loci described here or known in the art wherein a maize plant that has the complete MiMe genotype exhibits a MiMe phenotype. In further embodiments, the complete MiMe genotype may comprise one or more genetic modifications resulting in decreased expression, non-expression, or a combination thereof of any combination of MiMe loci described here or known in the art, wherein a maize plant that has the complete MiMe genotype exhibits a MiMe phenotype. The parent MiMe maize plant may have any complete MiMe genotype known in the art or described herein, including, but not limited to, complete MiMe genotypes comprising MiMe alleles resulting in decreased expression of any of the MiMe loci described herein. Specific examples of complete MiMe genotypes are shown in Table 6.

In some embodiments, the complete MiMe genotype comprises one or more genetic modifications resulting in decreased expression of REC8, SWITCH1/DYAD, or a combination thereof. In some variations, the complete MiMe genotype comprises one or more genetic modifications resulting in decreased expression of REC8, SWITCH1/DYAD, or a combination thereof and one or more genetic modifications resulting in decreased expression of one or more additional MiMe loci. In additional variations, the complete MiMe genotype comprises one or more genetic modifications resulting in decreased expression of REC8, SWITCH1/DYAD, or a combination thereof and one or more genetic modifications resulting in decreased expression of one or more additional MiMe loci, including, but not limited to, OSD1, CYCA1, TDM1, PC1, PC2, and FC. In yet additional variations, the complete MiMe genotype comprises one or more genetic modifications resulting in decreased expression of REC8, SWITCH1/DYAD, or a combination thereof; one or more genetic modifications resulting in decreased expression of OSD1, CYCA1, TDM1, PC1, PC2, FC, or any combination thereof; and one or more genetic modifications resulting in decreased expression of one or more additional MiMe loci, including, but not limited to, PAIR1, SPO11-1, SPO11-2, PRD1, PRD2, DFO, MTOPVIB, DSY1, SY1, SY2, SY3, and SY4.

In some embodiments, the complete MiMe genotype comprises one or more genetic modifications resulting in decreased expression of one or more MiMe loci including, but not limited to, OSD1, CYCA1, TDM1, PC1, PC2, and FC. In some variations, the complete MiMe genotype comprises one or more genetic modifications resulting in decreased expression of OSD1, CYCA1, TDM1, PC1, PC2, FC, or any combination thereof and further comprises one or more genetic modifications resulting in decreased expression of one or more additional MiMe loci, including, but not limited to, PAIR1, SPO11-1, SPO11-2, PRD1, PRD2, DFO, MTOPVIB, DSY1, SY1, SY2, SY3, and SY4.

In some embodiments, the complete MiMe genotype comprises one or more genetic modifications resulting in decreased expression of one or more MiMe loci including, but not limited to, PAIR1, SPO11-1, SPO11-2, PRD1, PRD2, DFO, MTOPVIB, DSY1, SY1, SY2, SY3, and SY4. In some variations, the complete MiMe genotype comprises one or more genetic modifications resulting in decreased expression of PAIR1, SPO11-1, SPO11-2, PRD1, PRD2, DFO, MTOPVIB, DSY1, SY1, SY2, SY3, SY4, or any combination thereof, and further comprises one or more genetic modifications resulting in decreased expression of one or more additional MiMe loci, which may include, but are not limited to PS1 and JASON.

In some embodiments, the parent MiMe maize plant has a complete MiMe genotype comprising MiMe alleles conferring decreased expression of MiMe loci of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, the parent MiMe maize plant has a complete MiMe genotype comprising MiMe alleles conferring decreased expression of MiMe loci of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In some variations, the parent MiMe maize plant having a complete MiMe genotype comprising MiMe alleles conferring decreased expression of MiMe loci of (2) a component of DNA double strand breakage during meiotic recombination and (4) a component of progression through the first division of meiosis exhibits a MiMe phenotype in male germline cells and/or produces clonal male gametes, and exhibits a wild-type meiosis phenotype in female germline cells and/or produces haploid female gametes. The parent MiMe maize plant may have any complete MiMe genotype known in the art or described herein, including, but not limited to, complete MiMe genotypes comprising MiMe alleles resulting in decreased expression of any of the MiMe loci described herein.

Parent MiMe Maize Plant Complementary Genotypes

In some embodiments, each of the parent MiMe maize plants has a complete MiMe genotype comprising MiMe alleles conferring decreased expression of MiMe loci of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some embodiments, (a) the first parent MiMe maize plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; (b) the second parent MiMe maize plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component; and (c) at least one of the MiMe loci having only MiMe alleles of the first MiMe component of the first parent MiMe maize plant is the same as at least one of the MiMe loci having only MiMe alleles of the first MiMe component of the second parent MiMe maize plant. In some variations, at least one of the MiMe loci having only MiMe alleles of the third MiMe component of the first parent MiMe maize plant is the same as at least one of the MiMe loci having only MiMe alleles of the third MiMe component of the second parent MiMe maize plant. In other variations, the one or more MiMe loci having only MiMe alleles of the third MiMe component of the first parent MiMe maize plant are distinct from the one or more MiMe loci having only MiMe alleles of the third MiMe component of the second parent MiMe maize plant. In some embodiments, (a) the first parent MiMe maize plant has only MiMe alleles at one or more MiMe loci of a component of sister chromatid cohesion during the first division of meiosis, only MiMe alleles at a first MiMe locus of a component of DNA double strand breakage during meiotic recombination, only non-MiMe alleles at a second MiMe locus of the component of DNA double strand breakage during meiotic recombination, and only MiMe alleles at one or more MiMe loci of a component of progression through the second division of meiosis; (b) the second parent MiMe maize plant has only MiMe alleles at one or more MiMe loci of the component of sister chromatid cohesion during the first division of meiosis, only non-MiMe alleles at the first MiMe locus of the component of DNA double strand breakage during meiotic recombination, only MiMe alleles at the second MiMe locus of component of DNA double strand breakage during meiotic recombination, and only MiMe alleles at one or more MiMe loci of the of a component of progression through the second division of meiosis; and (c) at least one of the MiMe loci having only MiMe alleles of the component of sister chromatid cohesion during the first division of meiosis of the first parent MiMe maize plant is the same as at least one of the MiMe loci having only MiMe alleles of the component of sister chromatid cohesion during the first division of meiosis of the second parent MiMe maize plant. In some variations, at least one of the MiMe loci having only MiMe alleles of the component of progression through the second division of meiosis of the first parent MiMe maize plant is the same as at least one of the MiMe loci having only MiMe alleles of the component of progression through the second division of meiosis of the second parent MiMe maize plant. In other variations, the one or more MiMe loci having only MiMe alleles of the component of progression through the second division of meiosis of the first parent MiMe maize plant are distinct from the one or more MiMe loci having only MiMe alleles of the component of progression through the second division of meiosis of the second parent MiMe maize plant. Exemplary MiMe loci of each of said MiMe components are extensively described below. In certain embodiments, (a) the first parent MiMe maize plant has only MiMe alleles at REC8, only MiMe alleles at SPO11-1, only non-MiMe alleles at PAIR1, and only MiMe alleles at OSD1; and (b) the second parent MiMe maize plant has only MiMe alleles at REC8, only non-MiMe alleles at SPO11-1, only MiMe alleles at PAIR1, and only MiMe alleles at OSD1.

In other embodiments, each of the parent MiMe maize plants has a complete MiMe genotype comprising MiMe alleles conferring decreased expression of MiMe loci of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In some variations, the parent MiMe maize plant having a complete MiMe genotype comprising MiMe alleles conferring decreased expression of MiMe loci of (2) a component of DNA double strand breakage during meiotic recombination and (4) a component of progression through the first division of meiosis exhibits a MiMe phenotype in male germline cells and/or produces clonal male gametes, and exhibits a wild-type meiosis phenotype in female germline cells and/or produces haploid female gametes. In some embodiments, (a) the first parent MiMe maize plant has only MiMe alleles at one or more MiMe loci of a first MiMe component, only MiMe alleles at a first MiMe locus of a second MiMe component, and only non-MiMe alleles at a second MiMe locus of the second MiMe component; (b) the second parent MiMe maize plant has only MiMe alleles at one or more MiMe loci of the first MiMe component, only non-MiMe alleles at the first MiMe locus of the second MiMe component, and only MiMe alleles at the second MiMe locus of the second MiMe component; and (c) at least one of the MiMe loci having only MiMe alleles of the first MiMe component of the first parent MiMe maize plant is the same as at least one of the MiMe loci having only MiMe alleles of the first MiMe component of the second parent MiMe maize plant. In certain embodiments, (a) the first parent MiMe maize plant has only MiMe alleles at one or more MiMe loci of a component of DNA double strand breakage during meiotic recombination, only MiMe alleles at a first MiMe locus of a component of progression through the first division of meiosis, and only non-MiMe alleles at a second MiMe locus of the component of progression through the first division of meiosis; (b) the second parent MiMe maize plant has only MiMe alleles at one or more MiMe loci of the component of DNA double strand breakage during meiotic recombination, only non-MiMe alleles at the first MiMe locus of the component of progression through the first division of meiosis, and only MiMe alleles at the second MiMe locus of the component of progression through the first division of meiosis; and (c) at least one of the MiMe loci having only MiMe alleles of the component of DNA double strand breakage during meiotic recombination of the first parent MiMe maize plant is the same as at least one of the MiMe loci having only MiMe alleles of the component of DNA double strand breakage during meiotic recombination of the second parent MiMe maize plant. In certain embodiments, (a) the first parent MiMe maize plant has only MiMe alleles at one or more MiMe loci of a component of progression through the first division of meiosis, only MiMe alleles at a first MiMe locus of a the component of DNA double strand breakage during meiotic recombination, and only non-MiMe alleles at a second MiMe locus of the component of DNA double strand breakage during meiotic recombination; (b) the second parent MiMe maize plant has only MiMe alleles at one or more MiMe loci of the component of progression through the first division of meiosis, only non-MiMe alleles at the first MiMe locus of the component of DNA double strand breakage during meiotic recombination, and only MiMe alleles at the second MiMe locus of the component of DNA double strand breakage during meiotic recombination; and (c) at least one of the MiMe loci having only MiMe alleles of the component of progression through the first division of meiosis of the first parent MiMe maize plant is the same as at least one of the MiMe loci having only MiMe alleles of the component of progression through the first division of meiosis of the second parent MiMe maize plant. Exemplary MiMe loci of each of said MiMe components are extensively described below. The parent MiMe maize plant may have any complete MiMe genotype known in the art or described herein, including, but not limited to, complete MiMe genotypes comprising MiMe alleles resulting in decreased expression of any of the MiMe loci described herein.

In some embodiments, the first parent MiMe maize plant has a complete MiMe genotype comprising MiMe alleles conferring decreased expression of one or more MiMe loci of a first, second, and third MiMe component, wherein the first MiMe component is (2) a component of DNA double strand breakage during meiotic recombination, the second MiMe component is (1) a component of sister chromatid cohesion during the first division of meiosis and the third MiMe component is (3) a component of progression through the second division of meiosis, and the second parent MiMe maize plant has a complete MiMe genotype comprising MiMe alleles conferring decreased expression of MiMe loci of the first MiMe component and a fourth MiMe component, wherein the fourth MiMe component is (4) a component of progression through the first division of meiosis. In some variations, the second parent MiMe maize plant having a complete MiMe genotype comprising MiMe alleles conferring decreased expression of MiMe loci of (2) a component of DNA double strand breakage during meiotic recombination and (4) a component of progression through the first division of meiosis exhibits a MiMe phenotype in male germline cells and/or produces clonal male gametes, and exhibits a wild-type meiosis phenotype in female germline cells and/or produces haploid female gametes. In certain embodiments, (a) the first parent MiMe maize plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination; (b) the second parent MiMe maize plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of a fourth MiMe component; and (c) at least one of the MiMe loci having only MiMe alleles of the first MiMe component of the first parent MiMe maize plant is the same as at least one of the MiMe loci having only MiMe alleles of the first MiMe component of the second parent MiMe maize plant. In some variations, (a) the first parent MiMe maize plant has only MiMe alleles at one or more MiMe loci of a component is a component of DNA double strand breakage during meiotic recombination, only MiMe alleles one or more MiMe loci of a component of sister chromatid cohesion during the first division of meiosis, only MiMe alleles at one or more MiMe loci of a component of progression through the second division of meiosis, and only non-MiMe alleles at one or more MiMe loci of a component of progression through the first division of meiosis; and (b) the second parent MiMe maize plant has only MiMe alleles at the one or more MiMe loci of the component of DNA double strand breakage during meiotic recombination, only non-MiMe alleles at the one or more MiMe loci of the component of sister chromatid cohesion during the first division of meiosis, only non-MiMe alleles at the one or more MiMe loci of the component of progression through the second division of meiosis, and only MiMe alleles at the one or more MiMe loci of the component of progression through the first division of meiosis. Exemplary MiMe loci of each of said MiMe components are extensively described below. In one variation, (a) the first parent MiMe maize plant has only MiMe alleles at SPO11-1, only MiMe alleles at REC8, only MiMe alleles at OSD1, and only non-MiMe alleles at PS1 and JASON; (b) the second parent MiMe maize plant has only MiMe alleles at SPO11-1, only non-MiMe alleles at REC8, only non-MiMe alleles at OSD1, and only MiMe alleles at PS1 or JASON.

In some embodiments, the first parent MiMe maize plant, the second parent MiMe maize plant, or both has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some variations, the one or more OSD1 loci comprise OSD1-1, OSD1-2, and/or OSD1-3, and/or the one or more PAIR1 loci comprise PAIR1-1 and/or PAIR1-2.

In some embodiments, the first parent MiMe maize plant, the second parent MiMe maize plant, or both has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some variations, the one or more OSD1 loci comprise OSD1-1, OSD1-2, and/or OSD1-3.

In some embodiments, the first parent MiMe maize plant, the second parent MiMe maize plant, or both has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1.

In some embodiments, the first parent MiMe maize plant, the second parent MiMe maize plant, or both has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some variations, the one or more PAIR1 loci comprise PAIR1-1 and/or PAIR1-2.

In some embodiments, the first parent MiMe maize plant, the second parent MiMe maize plant, or both has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1.

In some embodiments, the first parent MiMe maize plant, the second parent MiMe maize plant, or both has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some variations, the one or more PAIR1 loci comprise PAIR1-1 and/or PAIR1-2.

In some embodiments, the first parent MiMe maize plant, the second parent MiMe maize plant, or both comprise one or more polynucleotide sequences selected from the group consisting of SEQ ID NOs: 108-111. In certain embodiments the first parent MiMe maize plant, the second parent MiMe maize plant, or both comprises a) a MiMe allele at one or more OSD1-2 loci, each independently comprising a polynucleotide sequence selected from the group consisting of SEQ ID NOs: 108 and 109; b) a MiMe allele at a REC3 locus comprising the polynucleotide sequence of SEQ ID NO: 110; and/or c) a MiMe allele at a SPO11-1 locus comprising the polynucleotide sequence of SEQ ID NO: 111. In some variations, each the one or more OSD1-3 loci, each of the one or more REC8 loci, and/or each of the one or more SPO11-1 loci are present on a different homologous chromosome.

Providing Haploid Gametes

In some embodiments, the method of producing a population of polyploid maize seed comprises providing haploid gametes from a homozygous parent non-MiMe maize plant. In some embodiments, providing haploid gametes comprises growing one or more homozygous parent non-MiMe maize plants and allowing them to grow to a reproductive stage until haploid gametes form. In some variations, providing haploid gametes further comprises collecting haploid pollen from one or more homozygous parent non-MiMe maize plants. In some additional variations, the one or more homozygous parent non-MiMe maize plants may be haploid, monoploid, diploid, triploid, tetraploid, pentaploid, hexaploid, heptaploid, octaploid, or any combination thereof. In some embodiments, the homozygous parent non-MiMe maize plant is diploid and the haploid gametes are monoploid gametes.

In some embodiments, the method of producing a population of polyploid maize seed comprises (a) providing clonal gametes from a parent MiMe maize plant; and (b) providing haploid (e.g., monoploid) gametes from a homozygous parent non-MiMe maize plant, wherein the clonal gametes and the haploid (e.g., monoploid) gametes together comprise three or more haplotypes. In some variations, the clonal gametes and the haploid gametes together comprise three or more haplotypes, four or more haplotypes, five or more haplotypes, six or more haplotypes, seven or more haplotypes, or eight or more haplotypes. In additional variations the clonal gametes and the haploid gametes together comprise three, four, five, six, seven, or eight haplotypes. In some embodiments, the haploid gametes comprise one haplotype and the clonal gametes comprise two or more haplotypes, wherein the clonal gametes and the haploid gametes together comprise three or more haplotypes.

Providing Unreduced, Non-Clonal Gametes

In some embodiments, the method of producing a population of polyploid maize seed comprises providing unreduced, non-clonal gametes. In some embodiments, the method of producing a population of polyploid maize seed comprises providing unreduced, non-clonal gametes from one or more parent maize plants. In certain embodiments, providing unreduced, non-clonal gametes comprises: growing a parent maize plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis; and allowing the parent maize plant to grow to a reproductive stage until unreduced, non-clonal gametes form. In other embodiments, providing unreduced, non-clonal gametes comprises: generating a parent maize plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis; and growing said parent maize plant to a reproductive stage until unreduced, non-clonal gametes form. In some variations, providing unreduced, non-clonal gametes further comprises collecting pollen comprising unreduced, non-clonal gametes from a parent maize plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis. The MiMe loci of a of a component of progression through the first division of meiosis may be any loci of a component of progression through the first division of meiosis known in the art or described herein, including, but not limited to, PS1 and JASON. The MiMe loci of a component of a component of progression through the second division of meiosis may be any loci of a component of a component of progression through the second division of meiosis known in the art or described herein, including, but not limited to, OSD1, CYCA1, TDM1, PC1, PC2, and FC. In certain embodiments, the parent maize plant is a plant of an inbred maize line. In some variations, the parent maize plant is diploid, triploid, tetraploid, pentaploid, hexaploid, heptaploid, octaploid, or any combination thereof.

Crossing Clonal Gametes

In some embodiments, the method of producing a population of polyploid maize seed comprises crossing the clonal gametes to produce the population of polyploid maize seed. In some variations, crossing the clonal gametes to produce the population of polyploid maize seed comprises contacting pollen comprising clonal gametes with the stigma of a pistil comprising clonal gametes. In some variations, crossing the clonal gametes to produce the population of polyploid maize seed comprises contacting pollen comprising clonal gametes of a first maize plant with the stigma of a pistil comprising clonal gametes of a second maize plant. In some embodiments, crossing the clonal gametes to produce the population of polyploid maize seed comprises contacting pollen comprising clonal gametes from a first parent MiMe maize plant with the stigma of a pistil comprising clonal gametes of a second parent MiMe maize plant. In some embodiments, the population of polyploid maize seed is produced by crossing the clonal gametes and allowing seeds to form.

In other embodiments, the method of producing a population of polyploid maize seed comprises crossing clonal gametes with haploid gametes to produce the population of polyploid maize seed. In one variation, crossing the clonal gametes with the haploid gametes to produce the population of polyploid maize seed comprises contacting pollen comprising clonal gametes with the stigma of a pistil comprising haploid gametes. In another variation, crossing the clonal gametes with the haploid gametes to produce the population of polyploid maize seed comprises contacting pollen comprising haploid gametes with the stigma of a pistil comprising clonal gametes. In some embodiments, crossing the clonal gametes with the haploid gametes to produce the population of polyploid maize seed comprises contacting pollen comprising clonal gametes from a parent MiMe maize plant with the stigma of a pistil comprising haploid gametes of a homozygous parent non-MiMe maize plant. In other embodiments, crossing the clonal gametes with the haploid gametes to produce the population of polyploid maize seed comprises contacting pollen comprising haploid gametes from a homozygous parent non-MiMe maize plant with the stigma of a pistil comprising clonal gametes of a parent MiMe maize plant. In some variations, the homozygous parent non-MiMe maize plant and the haploid gametes are monoploid gametes. In some embodiments, the population of polyploid maize seed is produced by crossing the clonal gametes with the haploid gametes and allowing seeds to form.

In yet other embodiments, the method of producing a population of polyploid maize seed comprises crossing clonal gametes with unreduced, non-clonal gametes to produce the population of polyploid maize seed. In one variation, crossing the clonal gametes with the unreduced, non-clonal gametes to produce the population of polyploid maize seed comprises contacting pollen comprising clonal gametes with the stigma of a pistil comprising unreduced, non-clonal gametes. In another variation, crossing the clonal gametes with the unreduced, non-clonal gametes to produce the population of polyploid maize seed comprises contacting pollen comprising unreduced, non-clonal gametes with the stigma of a pistil comprising clonal gametes. In some embodiments, crossing the clonal gametes with the unreduced, non-clonal gametes to produce the population of polyploid maize seed comprises contacting pollen comprising clonal gametes from a parent MiMe maize plant with the stigma of a pistil comprising unreduced, non-clonal gametes of a homozygous parent maize plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis. In some embodiments, crossing the clonal gametes with the unreduced, non-clonal gametes to produce the population of polyploid maize seed comprises contacting the stigma of a pistil comprising clonal gametes from a parent MiMe maize plant with pollen comprising unreduced, non-clonal gametes of a homozygous parent maize plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis. In some embodiments, the population of polyploid maize seed is produced by crossing the clonal gametes with the unreduced, non-clonal gametes and allowing seeds to form.

In some embodiments, crossing clonal gametes to produce the population of polyploid seed comprises (a) collecting pollen from a first parent MiMe maize plant having only MiMe alleles at the one or more MiMe loci of the component of DNA double strand breakage during meiotic recombination, only non-MiMe alleles at the one or more MiMe loci of the component of sister chromatid cohesion during the first division of meiosis, only non-MiMe alleles at the one or more MiMe loci of the component of progression through the second division of meiosis, and only MiMe alleles at the one or more MiMe loci of the component of progression through the first division of meiosis; and (b) contacting the pollen from the first parent MiMe maize plant with a stigma of a second parent MiMe maize plant having only MiMe alleles at one or more MiMe loci of a component is a component of DNA double strand breakage during meiotic recombination, only MiMe alleles one or more MiMe loci of a component of sister chromatid cohesion during the first division of meiosis, only MiMe alleles at one or more MiMe loci of a component of progression through the second division of meiosis, and only non-MiMe alleles at one or more MiMe loci of a component of progression through the first division of meiosis.

Methods of Breeding Polyploid Hybrid Maize Lines Comprising Three or More Haplotypes In yet another aspect, provided herein are methods of breeding a polyploid hybrid maize line comprising three or more haplotypes, comprising obtaining a set of maize lines; breeding the lines using traditional maize breeding methods to produce a set of candidate maize lines; and selecting two or more candidate maize lines together comprising three or more haplotypes for crossing. In some embodiments, after the selection of candidate maize lines, the methods further comprise generating two parent MiMe maize plants from the two or more candidate maize lines; providing clonal gametes from each of the parent MiMe maize plants; and crossing the clonal gametes to produce a hybrid polyploid seed comprising the three or more haplotypes. In alternative embodiments, after the selection of candidate maize lines, the methods further comprise generating a single parent MiMe maize plant from one of the two or more candidate maize lines; providing clonal gametes from the parent MiMe maize plant; providing haploid (e.g., monoploid) gametes from a homozygous parent non-MiMe maize plant of one of the two or more candidate maize lines; and crossing the clonal gametes with the haploid (e.g., monoploid) gametes to produce a hybrid polyploid seed. In yet additional embodiments, after the selection of candidate maize lines, the methods further comprise generating a single parent MiMe maize plant from one of the two or more candidate maize lines; providing clonal gametes from the parent MiMe maize plant; providing unreduced, non-clonal gametes from homozygous parent maize plant of one of the two or more candidate maize lines; and crossing the clonal gametes with the unreduced, non-clonal gametes to produce a hybrid polyploid seed. In some embodiments, after the crossing of the clonal gametes or the crossing of the clonal gametes with the haploid (e.g., monoploid) gametes, or crossing of the clonal gametes with unreduced, non-clonal gametes, the methods further comprise growing the hybrid polyploid seed to produce a hybrid polyploid maize plant and evaluating one or more characteristics of the hybrid polyploid maize plant.

In still another aspect, provided herein are methods of breeding hybrid polyploid maize plants, comprising obtaining a set of maize lines; breeding the lines using traditional maize breeding methods to produce a set of candidate maize lines; selecting two or more candidate maize lines for crossing; and generating a first parent MiMe maize plant and a second parent MiMe maize plants from the two or more candidate maize lines. In some embodiments, the first parent MiMe maize plant has only MiMe alleles at one or more MiMe loci of a first MiMe component, only MiMe alleles at a first MiMe locus of a second MiMe component, and only non-MiMe alleles at a second MiMe locus of the second MiMe component; and the second parent MiMe maize plant has only MiMe alleles at one or more MiMe loci of the first MiMe component, only non-MiMe alleles at the first MiMe locus of the second MiMe component, and only MiMe alleles at the second MiMe locus of the second MiMe component. In certain embodiments, at least one of the MiMe loci having only MiMe alleles of the first MiMe component of the first parent MiMe maize plant is the same as at least one of the MiMe loci having only MiMe alleles of the first MiMe component of the second parent MiMe maize plant. In some embodiments, the first and second parent MiMe maize plants further have only MiMe alleles at one or more MiMe loci of a third MiMe component, wherein the one or more MiMe loci having only MiMe alleles of the third MiMe component of the first and second parent MiMe maize plants are the same or different. In certain embodiments, the parent MiMe maize plants together comprise two, three, or more haplotypes. In some embodiments, the methods further comprise providing clonal gametes from each of the parent MiMe maize plants; crossing the clonal gametes to produce a polyploid seed; growing the polyploid seed to produce a hybrid polyploid maize plant; and evaluating one or more characteristics of the hybrid polyploid maize plant.

Obtaining Maize Lines

In some embodiments, the method of breeding a polyploid hybrid maize line comprising two, three, or more haplotypes comprises obtaining a set of maize lines. In preferred embodiments, the set of maize lines is genetically diverse and comprises a large and diverse pool of haplotypes. In some embodiments, the method of breeding a polyploid hybrid maize line comprising two, three, or more haplotypes comprises obtaining a set of maize lines of the same or related species of maize plant. The set of maize lines may be obtained from any source and by any methods known in the art. In some embodiments, the set of maize lines is obtained from sources including, but not limited to, natural diversity, existing breeding programs, or any combination thereof.

In some embodiments, the set of maize plant lines is a genetically diverse founder population of maize plants. These maize plants may be collected from existent diploid germplasm sources such as wild species, progenitor species and landraces or from recent diploid inbred line-based breeding efforts (Jansky et al. 2016. Reinventing potato as a diploid inbred line-based crop. Crop Science 56, no. 4: 1412-1422). In some instances, these maize plants may have high genetic load and may not have undergone the narrowing of genetic variability attributable to the elite selection practices imposed on modern cultivated materials. As such, many possess traits promoting their fitness within non-agrarian environments in the case of wild progenitors, or have been adapted to vastly differing cultivation practices and agricultural environments in the case of landraces. In either instance, these founding maize plant materials may contain suites of both desirable and undesirable agronomic characteristics that may be recombined, selected, and complemented to develop a commercially viable product.

In some embodiments, the method of breeding a polyploid hybrid maize line comprising two, three, or more haplotypes comprises obtaining a set of diploid maize lines. The diploid maize lines may be obtained by any methods known in the art or described herein.

In certain embodiments, the obtaining a set of maize lines comprises creating reduced-ploidy maize lines by haploid induction of polyploid maize lines. Haploid induction may be achieved maize by, for example, interspecific hybridization with a haploid inducer, intraspecific hybridization with a haploid inducer, or modification of CENH3 activity or expression (e.g. by RNA interference and/or expression of a modified CENH3 protein). Methods of haploid induction are well known in the literature, and examples are described Wan, et al. (1989. Efficient production of doubled haploid plants through colchicine treatment of anther-derived maize callus. Theor. Appl. Genet., 77:889-892.) and Ren et al. (2017. Novel technologies in doubled haploid line development. Plant Biotechnol J 15, 1361-1370.) and references cited therein. In some variations, the obtaining a set of maize lines comprises haploid induction of one or more tetraploid lines to create one or more diploid lines. In other variations, the obtaining a set of maize lines comprises haploid induction of hexaploid, octaploid, or higher even-ploidy lines to create one or more lines of half the original ploidy.

Heterotic Groups

In some embodiments, the method of breeding a polyploid hybrid maize line comprises organizing the set of maize lines into two, three, or more heterotic groups, wherein each heterotic group comprises a haplotype, and wherein the haplotypes are grouped based on observed or predicted heterotic performance when combined in the hybrid polyploid maize plant. In some embodiments, the method of breeding a polyploid hybrid maize line comprises organizing the set of maize lines into four or more heterotic groups. In some variations, the method of breeding a polyploid hybrid maize line comprises organizing the set of maize lines into five or more heterotic groups, six or more heterotic groups, seven or more heterotic groups, or eight or more heterotic groups.

The obtained set of maize lines may be organized by assigning their membership into complementary heterotic groups based upon both their empirically-defined Endosperm Balance Number for the genus in question (Ortiz and Ehlenfeldt. 1992. The importance of Endosperm Balance Number in potato breeding and the evolution of tuber-bearing Solanum species. Euphytica 60, 105-113; Arisumi. 1982. Endosperm balance numbers among New Guinea-Indonesian Impatiens species, Journal of Heredity, 73:3, 240-242; Birchler. 1993. Dosage analysis of maize endosperm development. Annu Rev Genet. 27:181-204; Nishiyama et al. 2007. Embryological studies on cross-incompatibility between 2× and 4× in *Brassica*, Japanese Journal of Genetics, 41:1, 27-42) and heterotic patterns observed from preliminary estimation or prediction of their combining ability for traits and environments of interest at the diploid and polyploid levels. In this context, the combining ability is an estimation of the value of a plant as a parent as inferred by progeny testing in an established factorial or hierarchical mating design. Combining ability at the polyploid hybrid level is of primary importance; however, sufficient diploid hybrid performance is necessary to permit the diploid hybrid to serve as a parent for seed production. Furthermore, assessment of combining abilities at the simplified diploid level will better inform predictive models of genetic architecture.

In defining heterotic groups, the main goal is identifying subpopulations of the set of maize lines based on employment of a clustering procedure that maximizes some measure of interpopulation combining ability. Exhaustive evaluation of all possible parental combinations for the final polyploid hybrid, as in the case of a factorial mating scheme, is infeasible for all but a trivial number of potential parents (i.e. even a partial diallel ignoring reciprocal crosses scales at $(n+3)!/(4!(n-1)!)$ crosses per n parents). Yet, hierarchical mating schemes necessitate an understanding and judgment of which set of "testers" or analogous constructs should serve as a relevant and efficient basis or frame of reference for inferring combining ability. The sample of testers selected invariably biases perceptions of existing heterotic patterns. Furthermore, the relative importances of traits and environments of interest used to infer these combining abilities are dynamic and depend upon market trends. As such, predictive modeling is essential and the process of assigning and refining heterotic groups and testers to represent them is one of iterative improvement and refinement throughout repeated cycles of the breeding process. Nonetheless, once preliminary heterotic group membership is assigned, interpopulation improvement of the diploid germplasm and development of polyploid hybrid maize plants may proceed.

Breeding Maize Lines

In some embodiments, the method of breeding a polyploid hybrid maize line comprising three or more haplotypes comprises breeding the lines using traditional plant breeding methods to produce a set of candidate lines of maize. The method may comprise breeding the lines using any traditional plant breeding method known in the art or described herein. In some embodiments, the breeding of the lines comprises reciprocal recurrent selection. In additional embodiments, the breeding of the lines comprises inbreeding one or more of the lines to homozygosity. In some variations, the breeding of the lines comprises crossing, selfing (self-pollinating), and backcrossing the lines to produce candidate lines. In additional variations, the breeding of the lines comprises crossing pairs of the lines to generate an F1 (first filial) generation, followed by several generations of selfing (generating F2, F3, etc.). In yet additional variations, the breeding of the lines comprises backcrossing (BC) steps, whereby the offspring is backcrossed to one of the parental lines, termed the recurrent parent.

There are numerous steps that may be taken in breeding the lines of maize using traditional plant breeding methods to produce a set of candidate lines of maize. The choice of breeding method depends on the mode of plant reproduction and the heritability of the trait(s) being improved. Backcross breeding may be used to transfer one or a few favorable genes for a highly heritable trait into a desirable line. This approach has been used extensively for breeding disease-resistant lines. Various recurrent selection techniques may be used to improve quantitatively inherited traits controlled by numerous genes. The use of recurrent selection in self-pollinating crops depends on the ease of pollination, the frequency of successful hybrids from each pollination, and the number of hybrid offspring from each successful cross. A breeder can initially select and cross two or more parental lines, followed by repeated selfing and selection, producing many new genetic combinations. Moreover, a breeder can generate multiple different genetic combinations by crossing, selfing, generating mutations, or any combination thereof. A plant breeder can then select which lines to select as candidate lines. Recurrent selection techniques are reviewed in Vasal et al. (2004. Population Improvement Strategies for Crop Improvement. In: *Plant Breeding*. Springer, p 391-406).

The development of candidate lines for the methods described herein may include obtaining parental lines, crossing of these lines, and evaluating the crosses. Pedigree breeding and recurrent selection breeding methods may be used to develop candidate lines from breeding populations. Breeding programs may combine desirable traits from two or more varieties or various broad-based sources into breeding pools from which lines are developed by selfing and selection of desired phenotypes. The new lines may be further crossed with other lines and the hybrids from these crosses may be evaluated for potential selection as candidate lines.

Choice of breeding or selection methods depends on the mode of plant reproduction and the heritability of the trait(s) being improved. For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

In some embodiments, the breeding of the maize lines comprises inbreeding one or more of the lines to homozygosity. In some variations, inbreeding a maize line to homozygosity may comprise selfing plants of the line for two or more generations, such as for five to seven generations, to produce an inbred or homozygous maize line. Homozygous maize lines may also be developed by the production of double haploids. Double haploids are produced by generating a haploid plant from a heterozygous plant and the doubling of the genome of the haploid plant to produce a completely homozygous individual. The process of generating a haploid plant is also known as haploid induction. Haploid induction can be achieved in a variety of plants using methods well-known in the art and described herein. After a haploid plant is generated, genome doubling may occur spontaneously or may be achieved artificially using, for example, colchicine, amiprophos-mehtyl (APM), oryzalin, pronamide, trifluralin, or nitrous oxide. Methods of producing double haploids are well known in the literature, and examples are described Wan, et al. (1989. Efficient production of doubled haploid plants through colchicine treatment of anther-derived maize callus. *Theor. Appl. Genet.*, 77:889-892.) and Ren et al. (2017. Novel technologies in doubled haploid line development. *Plant Biotechnol J* 15, 1361-1370.) and references cited therein.

Pedigree breeding is used commonly for the improvement of self-pollinating crops or inbred lines of cross-pollinating crops. Two parents which possess favorable, complementary traits are crossed to produce an F1 population. An F2 population is produced by selfing one or several F1s or by intercrossing two F1s (sib mating). Selection of the best individuals may begin in the F2 population; then, beginning in the F3, the best individuals in the best families may be selected. Replicated testing of families, or hybrid combinations involving individuals of these families, may follow in the F4 generation to improve the effectiveness of selection for traits with low heritability. At an advanced stage of inbreeding (i.e., F6 and F7), the best lines or mixtures of phenotypically similar lines may be tested for potential selection as candidate lines.

Mass and recurrent selections can be used to improve lines of either self- or cross-pollinating crops. A genetically variable population of heterozygous individuals may be either identified or created by intercrossing several different parents. The best plants are selected based on individual superiority, outstanding progeny, or heterotic performance. The selected plants are intercrossed to produce a new population in which further cycles of selection are continued.

Backcross breeding may be used to transfer genes for a simply inherited, highly heritable trait into a desirable homozygous line that is the recurrent parent. The source of the trait to be transferred is called the donor parent. The resulting plant is expected to have the attributes of the recurrent parent and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generational advancement is completed.

In addition to phenotypic observations, the genotype of a plant can also be examined during breeding to produce candidate lines. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs-which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of lines as parental varieties or ancestors of a plant by providing a means of tracking genetic profiles through crosses.

Mutation breeding may also be used in the breeding of maize lines to produce candidate lines. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into an existing line by traditional breeding techniques. Details of mutation breeding can be found in Principles of Cultivar Development by Fehr, Macmillan Publishing Company, 1993.

Additional non-limiting examples of breeding methods that may be used include, without limitation, those found in Allard (1960. *Principles of Plant Breeding*, John Wiley and Son, pp. 115-161). Simmonds (1979. *Principles of Crop Improvement*, Longman Group Limited), Sneep (1979. *Plant Breeding Perspectives*, Unipub), and Fehr and Walt (1987. *Principles of Cultivar Development*, pp. 261-286).

In certain embodiments, breeding the lines of maize comprises generating and maintaining one or more maize lines having complete or partial MiMe genotypes. The one or more maize lines having complete or partial MiMe genotypes may be maintained via selfing, apomixis, cell culture, or any combination thereof. The MiMe alleles of the one or more maize lines having partial MiMe genotypes may be propagated across breeding cycles to reduce the number of required editing or transgenesis events to introduce partial or complete MiMe genotypes into candidate lines of maize. In some embodiments, each of the heterotic groups may be further divided into two subgroups, resulting in each heterotic group containing a small subgroup of maize lines having a partial MiMe genotype, maintained through outbreeding and stabilizing selection for the partial MiMe genotype and a wild-type meiosis phenotype, and another larger subgroup of maize lines that do not comprise MiMe alleles. The subgroup containing the maize lines having a partial MiMe genotype may be slower-cycling during breeding, as genotyping and stabilizing selection for the partial MiMe genotype and wild-type meiosis phenotype may be undertaken in some or all progeny. Within this subgroup, a subset of all possible intragroup crosses, which are expected to bear some offspring possessing the partial MiMe genotype and a wild-type meiosis phenotype, is selected and realized by considering the following criteria: 1) per se performance of the maize line, 2) genotype or pedigree-based estimation or prediction of breeding value and combining ability with regard to complementing the alternate subgroup within the heterotic group as well as the other heterotic groups at the polyploid hybrid level, and 3) management of inbreeding with respect to both subgroups of the heterotic group. After genotyping and selecting the subset of realized recombinant diploid progeny having a partial MiMe genotype and a wild-type meiosis phenotype, these maize plants may serve in the following breeding roles: 1) field evaluations to improve the estimation or prediction of breeding values and combining abilities, 2) testers to aid heterotic group (re)assignment, 3) progenitors in recurrent cycles of diploid intergroup improvement to increase desirable allele frequencies and linkage disequilibria, and/or 4) great-grandparents in tetraploid hybrid maize development.

In some embodiments, breeding the lines of maize comprises (i) introducing a partial MiMe genotype into one or more lines of maize within a heterotic group to produce a maize line having a partial MiMe genotype, wherein the maize line having a partial MiMe genotype comprises one or more haplotypes, (ii) crossing the maize line having the partial MiMe genotype with itself or another maize line, and (iii) propagating the maize line having the partial MiMe genotype by selecting for the partial MiMe genotype in the offspring of the cross of step (ii). In some variations, step (ii) comprises crossing the maize line having the partial MiMe genotype with itself. In other variations, step (ii) comprises crossing the maize line having the partial MiMe genotype with another plant within the same heterotic group or a different heterotic group.

In some embodiments, haploid induction may be used to maintain haploid, diploid, or polyploid maize lines having a complete MiMe genotype. In certain embodiments, maintaining a polyploid maize line having a complete MiMe genotype comprises crossing a polyploid maize having a complete MiMe genotype with a haploid inducer to produce progeny of the same ploidy as the plant having the complete MiMe genotype. In one variation, maintaining a polyploid maize line having a complete MiMe genotype comprises crossing a tetraploid maize plant having a complete MiMe genotype with a haploid inducer to produce tetraploid progeny.

Selecting Candidate Maize Lines

In some embodiments, the method of breeding a polyploid hybrid maize line comprising two, three, or more haplotypes comprises selecting two or more candidate maize lines together comprising two, three, or more haplotypes. In some variations, the method of breeding a hybrid polyploid plant comprises selecting two or more candidate maize lines together comprising three or more haplotypes or four or more haplotypes. In some embodiments, one or more of the candidate maize lines are inbred maize lines. In additional embodiments, one or more of the candidate maize lines are hybrid maize lines. In certain embodiments, the selecting of candidate maize lines is guided by the one or more characteristics of a hybrid polyploid plant comprising the two, three, or more haplotypes comprised by the two or more candidate maize lines. In certain embodiments, the selecting of candidate maize lines is guided by the one or more characteristics of a hybrid polyploid plant comprising the two or more haplotypes, three or more haplotypes, or four or more haplotypes comprised by the two or more candidate maize lines. In some variations, the selecting of candidate maize lines is guided by the observed or predicted heterotic performance of the two or more haplotypes, three or more haplotypes, or four or more haplotypes comprised by the two or more candidate maize lines.

Generating Parent MiMe plants

In some embodiments, the method of breeding a polyploid hybrid maize line comprising two, three, or more haplotypes comprises generating one or more parent MiMe maize plants from one or more of the two or more candidate maize lines, wherein the parent MiMe maize plant has a complete MiMe genotype. In some variations, the method of breeding a polyploid hybrid maize line comprising two, three, or more haplotypes comprises generating two parent MiMe maize plants from two of the two or more candidate maize lines, wherein each of the parent MiMe maize plants has a complete MiMe genotype. In some embodiments, the method of breeding a hybrid polyploid maize plant comprises generating a first parent MiMe maize plant from one of the candidate maize lines and generating a second parent MiMe maize plant from one of the candidate maize lines, wherein the parent MiMe maize plant has a complete MiMe genotype. In some variations, the method of breeding a hybrid polyploid maize plant comprises generating two parent MiMe maize plants from two of the two or more candidate maize lines, wherein the parent MiMe maize plant has a complete MiMe genotype. In some embodiments, the complete MiMe genotypes of the one or more parent MiMe maize plants comprise alleles that are naturally-occurring, introduced via genetic modification, or a combination thereof. The one or more parent MiMe maize plants may have any complete MiMe genotype known in the art or described herein. The generating of the parent MiMe maize plants may comprise introducing any of the parent MiMe maize plant genotypes described herein (see "Parent MiMe Maize Plant Genotypes" and "Parent MiMe Maize Plant Complementary Genotypes").

Figure 12:
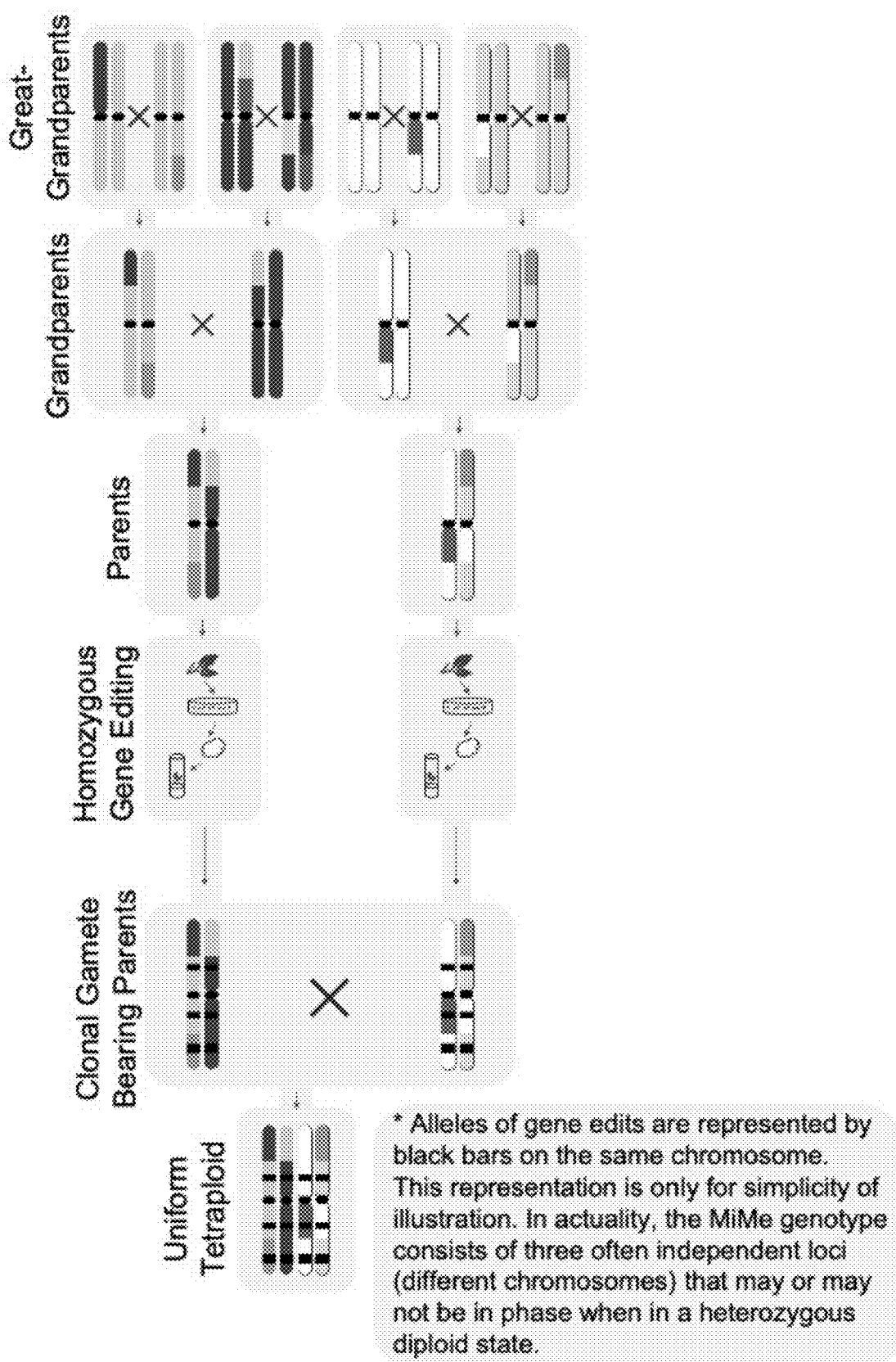
FIG. 12 illustrates an embodiment where homozygous gene editing occurs at the parent stage.
Figure 13:
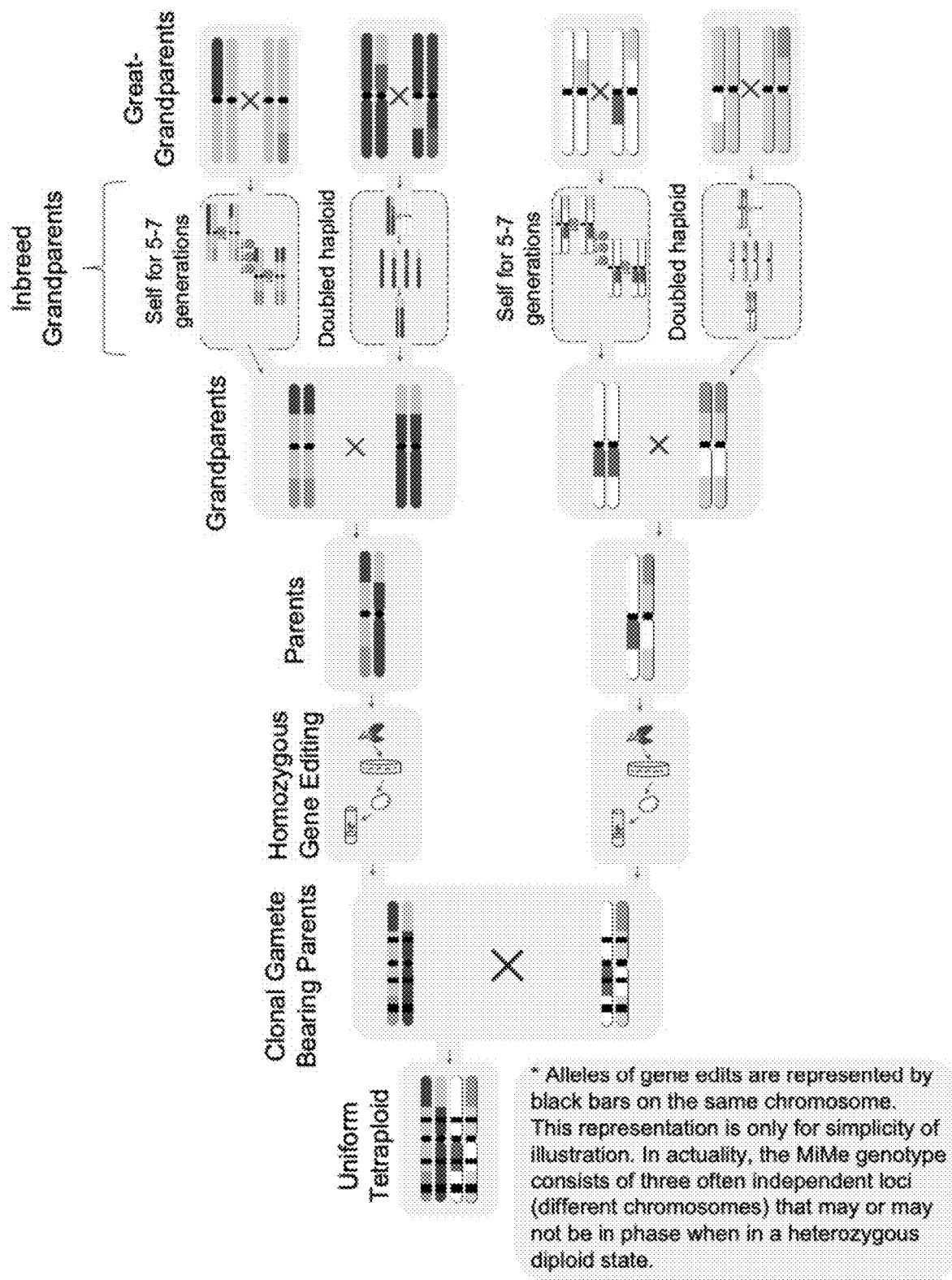
FIG. 13 illustrates an embodiment where grandparents are inbred and homozygous gene editing occurs at the parent stage.
Figure 19:
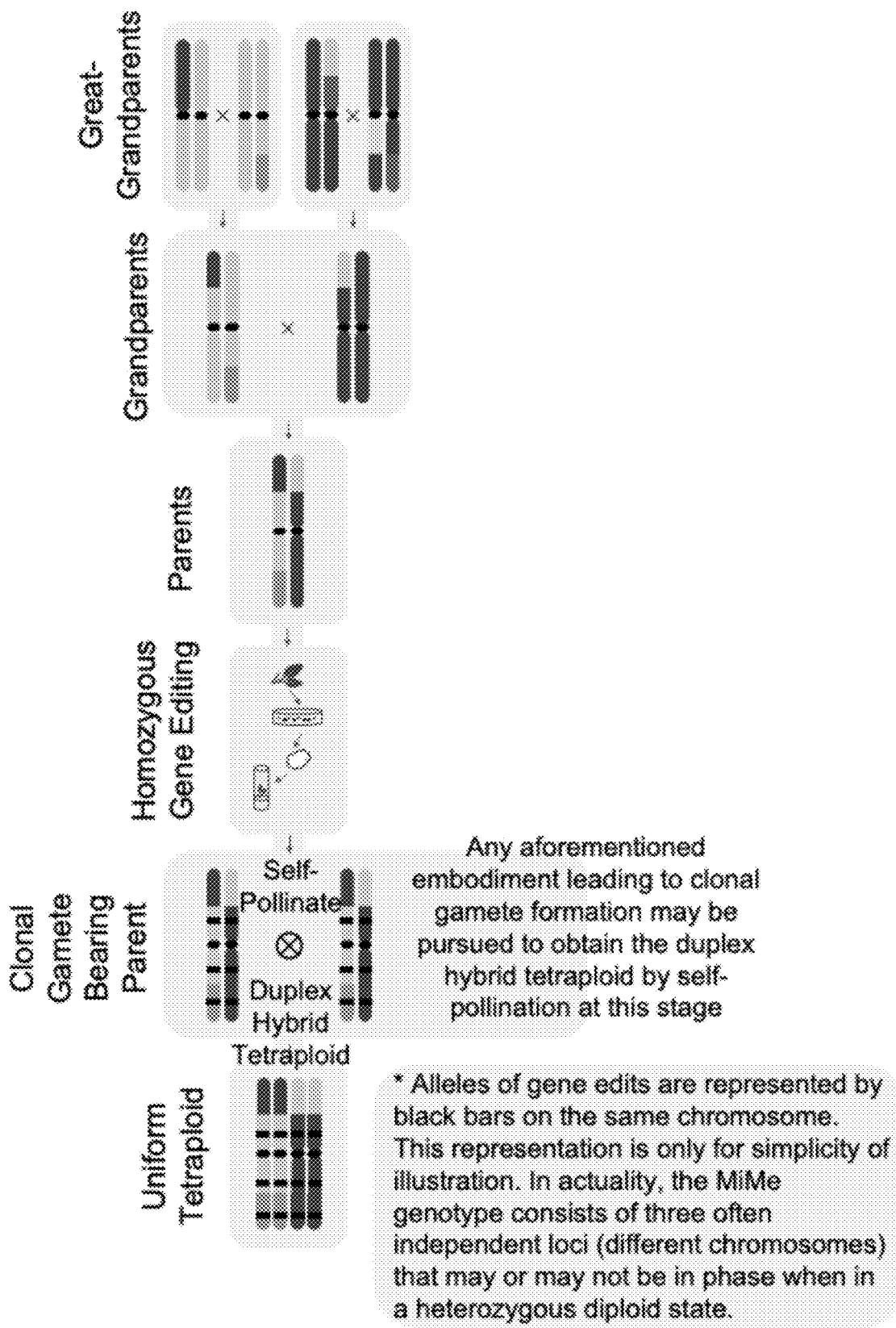
FIG. 19 illustrates an embodiment where unilateral editing results in sexual tetraploidization.

In certain embodiments, the generating of the one or more parent MiMe maize plants comprises introducing a complete MiMe genotype directly into one or more candidate maize lines to produce the one or more parent MiMe maize plants. In some variations, the generating of the two parent MiMe maize plants comprises introducing a complete MiMe genotype directly into two or more candidate maize lines to produce the two parent MiMe maize plants, for example, as shown in FIG. 12, 13, or 19.

Figure 14:
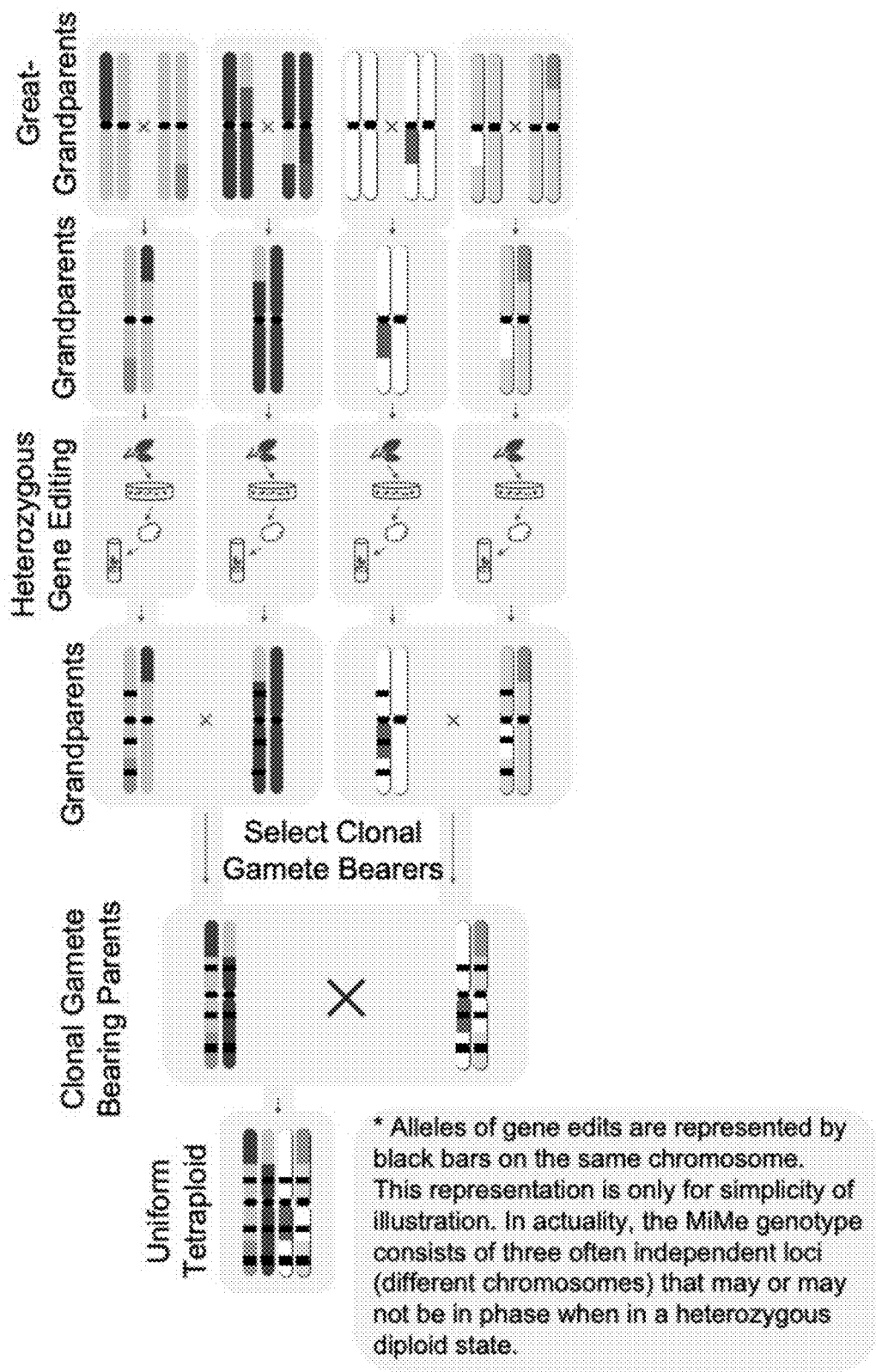
FIG. 14 illustrates an embodiment where heterozygous gene editing occurs at the grandparent stage.
Figure 15:
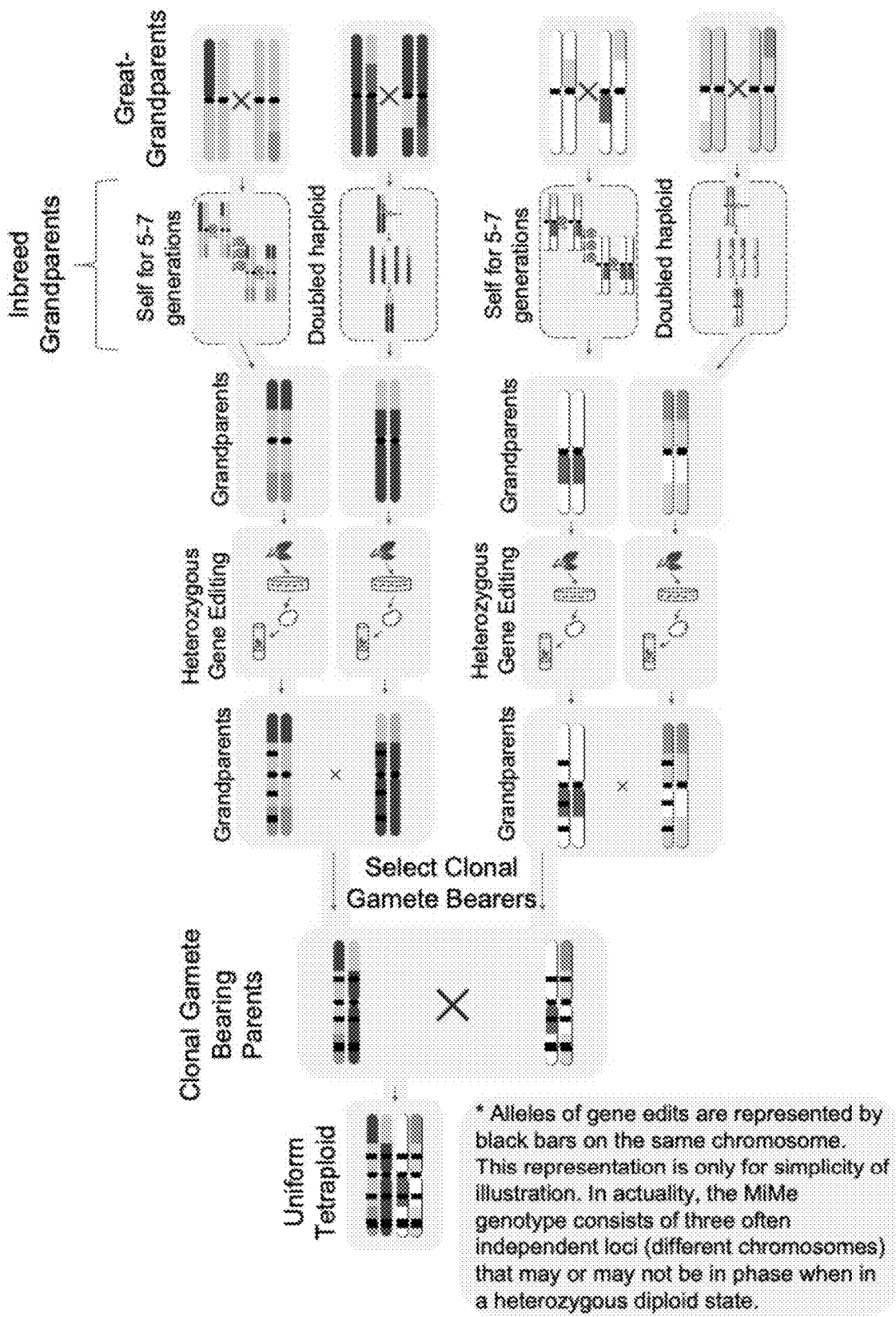
FIG. 15 illustrates an embodiment where grandparents are inbred and heterozygous gene editing at the grandparent stage.
Figure 16:
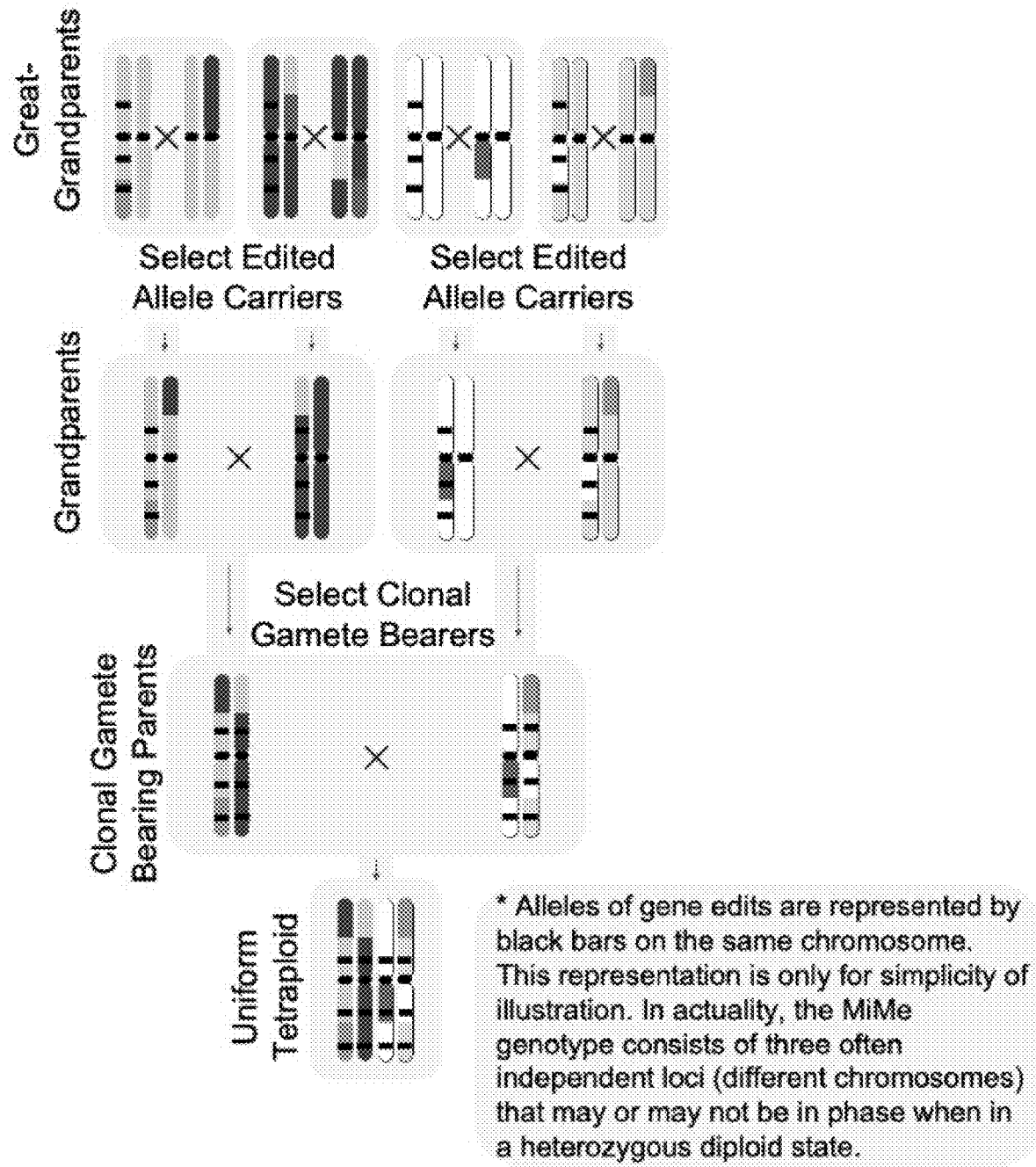
FIG. 16 illustrates an embodiment where MiMe loci are propagated at the grandparent stage.
Figure 17:
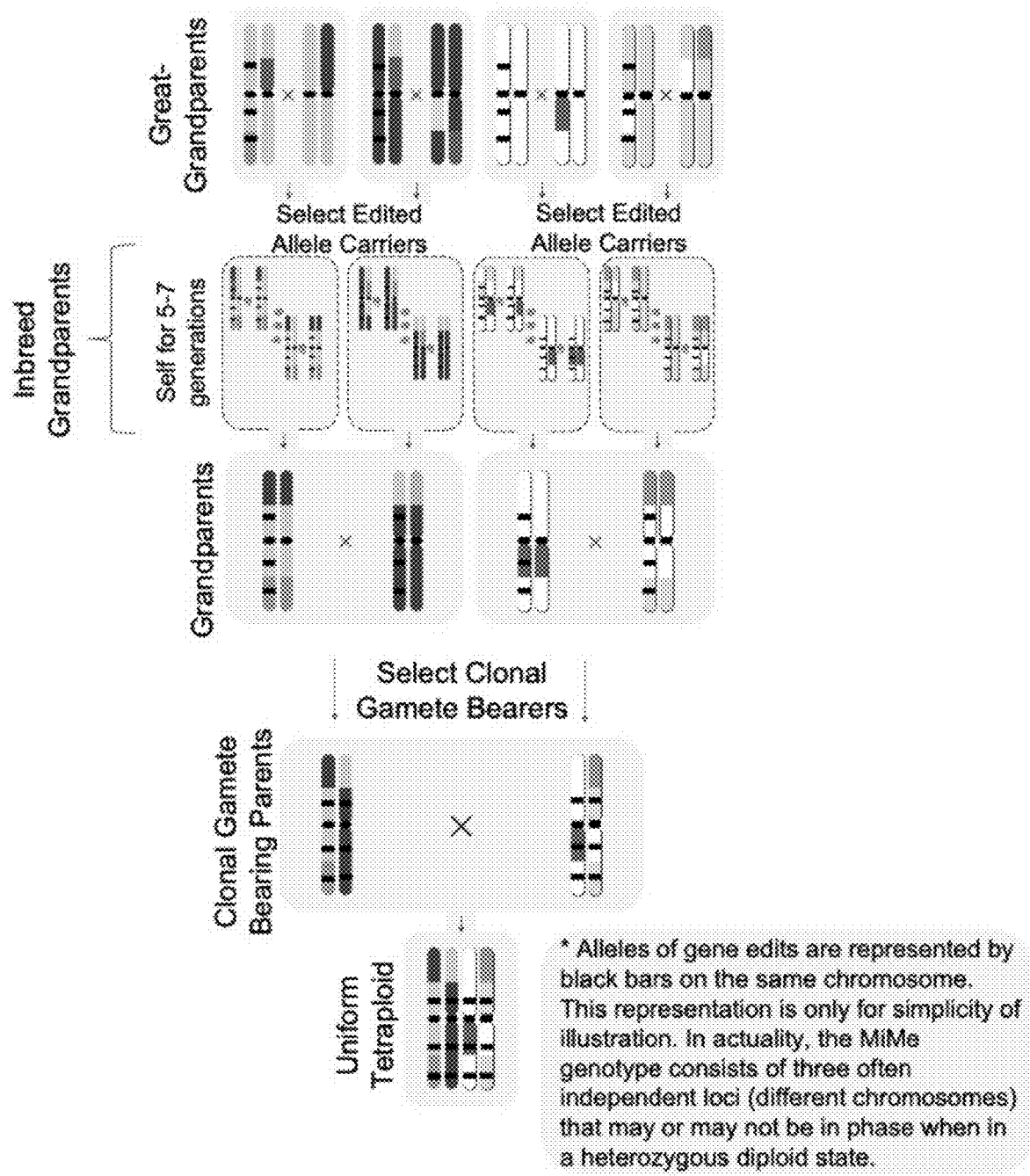
FIG. 17 illustrates an embodiment where grandparents are inbred and MiMe loci are propagated at the grandparent stage.
Figure 18:
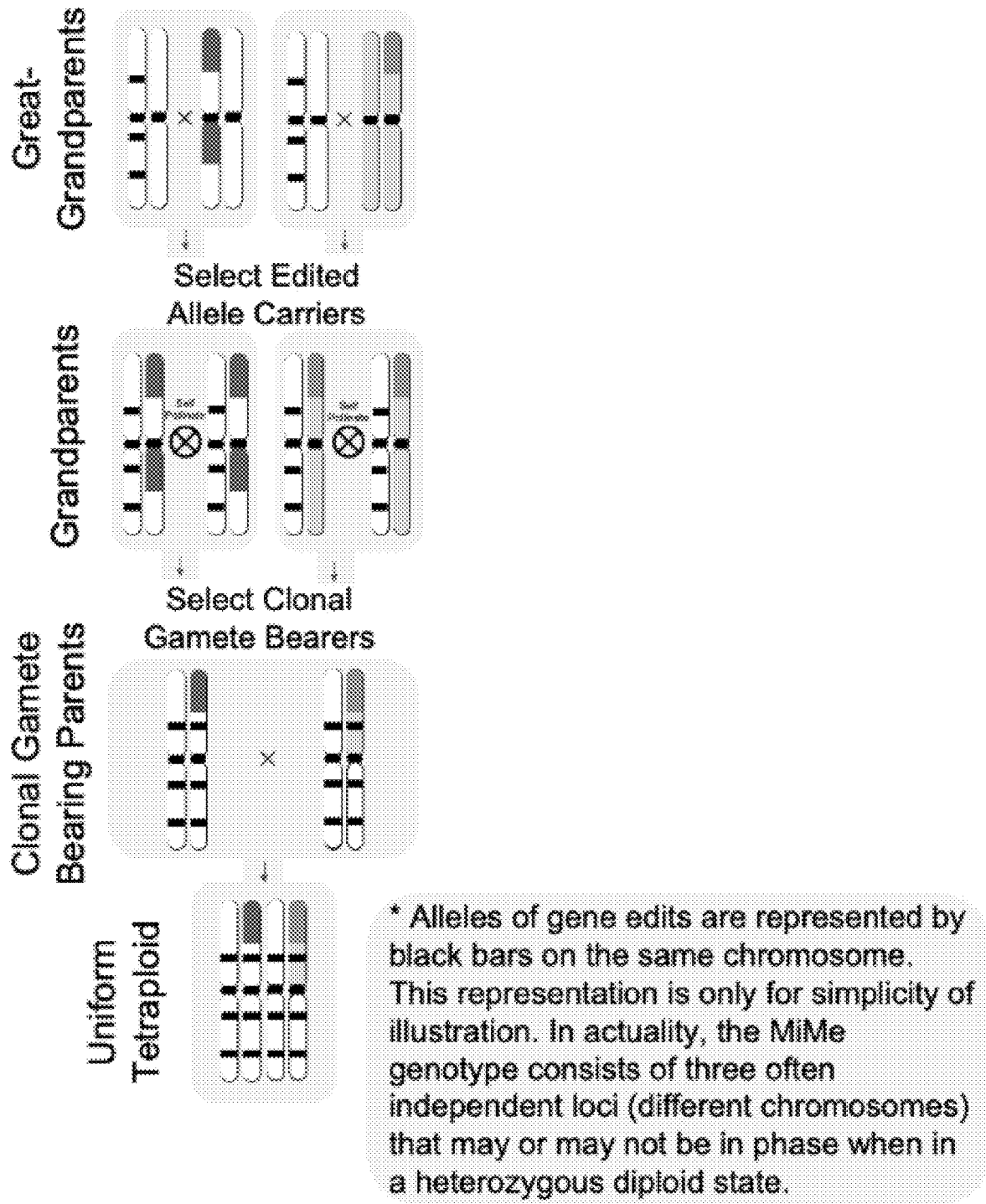
FIG. 18 illustrates an embodiment where MiMe loci are propagated at the great-grandparent stage.

In certain embodiments, the generating of the one or more parent MiMe maize plants comprises introducing a partial MiMe genotype into two or more candidate maize lines to produce two or more grandparent non-MiMe maize plants each having a partial MiMe genotype and crossing said grandparent non-MiMe maize plants each having a partial MiMe genotype to produce the one or more parent MiMe maize plants, for example, as shown in FIG. 14 or 15. In some embodiments, the generating of the two parent MiMe maize plants comprises introducing a partial MiMe genotype into four candidate maize lines to produce four grandparent non-MiMe maize plants each having a partial MiMe genotype, and crossing pairs of said grandparent non-MiMe maize plants each having a partial MiMe genotype to produce the two parent MiMe maize plants, for example, as shown in FIG. 14 or 15. In other embodiments, the generating of the two parent MiMe maize plants comprises introducing a partial MiMe genotype into two candidate maize lines to produce two grandparent non-MiMe maize plants each having a partial MiMe genotype, crossing said grandparent non-MiMe maize plants each having a partial MiMe genotype to produce the first parent MiMe maize plant, and introducing a complete MiMe genotype directly into a third candidate maize line to produce the second parent MiMe maize plant. In additional embodiments, the generating of the one or more parent MiMe maize plants comprises introducing a partial MiMe genotype into a candidate line to produce a great-grandparent non-MiMe maize plant having a partial MiMe genotype, crossing the great-grandparent non-MiMe maize plant having a partial MiMe genotype with one or more candidate maize lines together comprising one or more haplotypes to produce a grandparent non-MiMe maize plant having a partial MiMe genotype and comprising two or more haplotypes, and crossing or selfing the grandparent non-MiMe maize plant having the partial MiMe genotype and comprising two or more haplotypes to produce a parent MiMe maize plant comprising two or more haplotypes, for example, as shown in any one of FIGS. 16-18. In one variation, the generating of the two parent MiMe maize plants comprises introducing a partial MiMe genotype into a candidate maize line to produce a great-grandparent non-MiMe maize plant having a partial MiMe genotype, crossing the great-grandparent non-MiMe maize plant having a partial MiMe genotype with two candidate maize lines together comprising two or more haplotypes to produce two grandparent non-MiMe maize plants together comprising three or more haplotypes, and selfing each of the grandparent non-MiMe maize plants together comprising three or more haplotypes to produce two parent MiMe maize plants together comprising three or more haplotypes, for example, as shown in FIG. 17 or 18. In one variation, the generating of the two parent MiMe maize plants comprises introducing a partial MiMe genotype into a candidate maize line to produce a great-grandparent non-MiMe maize plant having a partial MiMe genotype, crossing the great-grandparent non-MiMe maize plant having a partial MiMe genotype with two candidate maize lines together comprising two or more haplotypes to produce two grandparent non-MiMe maize plants together comprising three or more haplotypes, and crossing pairs of the grandparent non-MiMe maize plants together comprising three or more haplotypes to produce two parent MiMe maize plants together comprising three or more haplotypes, for example, as shown in FIG. 16. Any combination of methods for generating one or more parent MiMe maize plants described herein can be used in any combination to generate parent MiMe maize plants for use in the methods described herein. The grandparent non-MiMe maize plant or great-grandparent non-MiMe maize plant may have any partial MiMe genotype known in the art or described herein, including, but not limited to, partial MiMe genotypes comprising MiMe alleles resulting in decreased expression of any of the MiMe loci described herein.

In some embodiments, the grandparent non-MiMe maize plant has a partial MiMe genotype comprising (a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, the grandparent non-MiMe maize plant has a partial MiMe genotype comprising (a) one or more MiMe alleles conferring decreased expression of one or more MiMe loci of each of a first and second MiMe component; and (a) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. The grandparent non-MiMe maize plant or great-grandparent non-MiMe maize plant may have any partial MiMe genotype known in the art or described herein, including, but not limited to, partial MiMe genotypes comprising MiMe alleles resulting in decreased expression of any of the MiMe loci described herein.

In some embodiments, the generating of the parent MiMe maize plants comprises introducing a complete MiMe genotype into two candidate maize lines wherein (a) the first parent MiMe maize plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; (b) generating a second parent MiMe maize plant from one of the candidate maize lines, wherein the second parent MiMe maize plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component; (c) at least one of the MiMe loci having only MiMe alleles of the first MiMe component of the first parent MiMe maize plant is the same as at least one of the MiMe loci having only MiMe alleles of the first MiMe component of the second parent MiMe maize plant; and (d) either (1) at least one of the MiMe loci having only MiMe alleles of the third MiMe component of the first parent MiMe maize plant is the same as at least one of the MiMe loci having only MiMe alleles of the third MiMe component of the second parent MiMe maize plant, or (2) the one or more MiMe loci having only MiMe alleles of the third MiMe component of the first parent MiMe maize plant are distinct from the one or more MiMe loci having only MiMe alleles of the third MiMe component of the second parent MiMe maize plant. In some embodiments, the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. Exemplary MiMe loci of each of said MiMe components are extensively described herein.

In other embodiments, the generating of the parent MiMe maize plants comprises introducing a complete MiMe genotype into two candidate maize lines wherein (a) the first parent MiMe maize plant has only MiMe alleles at one or more MiMe loci of a first MiMe component, only MiMe alleles at a first MiMe locus of a second MiMe component, and only non-MiMe alleles at a second MiMe locus of the second MiMe component; (b) the second parent MiMe maize plant has only MiMe alleles at one or more MiMe loci of the first MiMe component, only non-MiMe alleles at the first MiMe locus of the second MiMe component, and only MiMe alleles at the second MiMe locus of the second MiMe component; and (c) at least one of the MiMe loci having only MiMe alleles of the first MiMe component of the first parent MiMe maize plant is the same as at least one of the MiMe loci having only MiMe alleles of the first MiMe component of the second parent MiMe maize plant. In some embodiments, the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. Exemplary MiMe loci of each of said MiMe components are extensively described herein.

In some embodiments, the grandparent non-MiMe maize plant or the great-grandparent non-MiMe maize plant has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In some variations, the one or more OSD1 loci comprise OSD1-1, OSD1-2, and/or OSD1-3, and/or the one or more PAIR1 loci comprise PAIR1-1 and/or PAIR1-2.

In some embodiments, the grandparent non-MiMe maize plant or the great-grandparent non-MiMe maize plant has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In some variations, the one or more OSD1 loci comprise OSD1-1, OSD1-2, and/or OSD1-3.

In some embodiments, the grandparent non-MiMe maize plant or the great-grandparent non-MiMe maize plant has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the grandparent non-MiMe maize plant or the great-grandparent non-MiMe maize plant has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In some variations, the one or more PAIR1 loci comprise PAIR1-1 and/or PAIR1-2.

In some embodiments, the grandparent non-MiMe maize plant or the great-grandparent non-MiMe maize plant has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the grandparent non-MiMe maize plant or the great-grandparent non-MiMe maize plant has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In some variations, the one or more PAIR1 loci comprise PAIR1-1 and/or PAIR1-2.

In some embodiments, the grandparent non-MiMe maize plant or the great-grandparent non-MiMe maize plant comprises one or more polynucleotide sequences selected from the group consisting of SEQ ID NOS: 108-111. In certain embodiments the grandparent non-MiMe maize plant or the great-grandparent non-MiMe maize plant comprises a) a MiMe allele at one or more OSD1-2 loci, each independently comprising a polynucleotide sequence selected from the group consisting of SEQ ID NOs: 108 and 109; b) a MiMe allele at a REC8 locus comprising the polynucleotide sequence of SEQ ID NO: 110; and/or e) a MiMe allele at a SPO11-1 locus comprising the polynucleotide sequence of SEQ ID NO: 111. In some variations, each the one or more OSD1-2 loci, each of the one or more REC8 loci, and/or each of the one or more SPO11-1 loci are present on a different homologous chromosome.

Methods of Introducing Genetic Modifications

In some embodiments, the method of breeding a polyploid hybrid maize line comprising two, three, or more haplotypes comprises generating one or more parent MiMe maize plants from one or more of the two or more candidate maize lines, wherein the parent MiMe maize plant has a complete MiMe genotype, and wherein the complete MiMe genotype comprises alleles that are introduced via genetic modification. Generating a parent MiMe maize plant having a complete MiMe genotype may comprise introducing a complete MiMe genotype via genetic modification directly into a candidate maize line to produce the parent MiMe maize plant; introducing a partial MiMe genotype via genetic modification into two candidate maize lines to produce two grandparent non-MiMe maize plants each having a partial MiMe genotype, and crossing the grandparent non-MiMe maize plants each having a partial MiMe genotype to produce the parent MiMe maize plant; or a combination thereof. The MiMe alleles of a complete or partial MiMe genotype may be introduced via genetic modification by any means known in the art. In some embodiments, the genetic modifications are introduced by gene editing, transgenesis, or a combination thereof.

In some embodiments, the methods described herein comprise introducing one or more genetic modifications into one or more MiMe loci that result in the decreased expression of the one or more MiMe loci. In some embodiments, decreased expression a MiMe locus may be achieved by modifying or replacing nucleotide sequences of interest (such as a regulatory elements), gene disruption, gene knockout, gene knockdown, gene knock-in, gene silencing (including, e.g., by inserting and/or expressing an inverted repeat into a gene of interest), RNA interference (including, e.g., by insertion and/or expression of an RNA interference construct), expression of a repressor protein (e.g. dCas9), modification of methylation status of gene loci, modification of splicing sites, introducing alternate splicing sites, or any combination thereof. In some variations, the genetic modification is introduced into the first 70%, the first 60%, the first 50%, the first 40%, the first 30%, the first 20%, or the first 10% of the nucleotides of the coding sequence of the MiMe locus following the start codon in the 3' direction. In certain variations, the genetic modification is introduced into the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the MiMe locus following the start codon in the 3' direction. In certain variations, the genetic modification is introduced into a non-coding element of the MiMe locus (e.g., a promoter, an enhancer, a terminator, an intron, or the like).

In some embodiments, the decreased expression of each of the one or more of the MiMe loci is independently achieved by introducing an insertion, a deletion, one or more nucleotide changes, or an inversion into the MiMe locus that that results in decreased expression of the MiMe locus. In some variations, the insertion, the deletion, the one or more nucleotide changes, or the inversion is introduced into the first 70%, the first 60%, the first 50%, the first 40%, the first 30%, the first 20%, or the first 10% of the nucleotides of the coding sequence of the MiMe locus following the start codon in the 3' direction. In certain variations, the insertion, the deletion, the one or more nucleotide changes, or the inversion is introduced into the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the genomic locus following the start codon in the 3' direction. In some variations, the insertion, the deletion, the one or more nucleotide changes, or the inversion eliminates expression (e.g., eliminates activity) of the MiMe locus. In some variations, the activity of the MiMe locus is eliminated by a premature stop codon introduced into the first 70%, the first 60%, the first 50%, the first 40%, the first 30%, the first 20%, or the first 10% of the nucleotides of the coding sequence of the MiMe locus following the start codon in the 3' direction. In certain variations, the activity of the MiMe locus is eliminated by a premature stop codon introduced into the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the MiMe locus following the start codon in the 3' direction.

In certain embodiments, the genetic modifications are introduced by gene editing. Any of several gene editing methods known in the art may be used to introduce the genetic modifications of the complete or partial MiMe genotype. In some variations, gene editing is performed with one or more natural or engineered nucleases including, but not limited to, RNA-guided nucleases, meganucleases, zinc finger nucleases (ZFNs), and transcription activator-like effector-based nucleases (TALENs). In further variations, gene editing is performed with RNA-guided nucleases including, but not limited to, Clustered Regularly Interspaced Short Palindromic Repeats (CRISPR) associated nucleases. Methods of gene editing are numerous, well-known and routine in the art, and are described in U.S. Ser. No. 17/045,747, U.S. Ser. No. 16/977,020, and U.S. Ser. No. 16/961,396, which are herein incorporated in their entirety.

An engineered nuclease may be a guided nuclease, which may function as a ribonucleoprotein (RNP) complex with a guide RNA. According to some embodiments, a guided nuclease may be selected from the group consisting of Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csxl, Csx15, Csf1, Csf2, Csf3, Csf4, Cpf1, CasX, CasY, CasZ, and homologs or modified versions thereof, Argonaute (non-limiting examples of Argonaute proteins include Thermus thermophilus Argonaute (TtAgo), Pyrococcus furiosus Argonaute (PfAgo), Natronobacterium gregoryi Argonaute (NgAgo), and homologs or modified versions thereof). According to some embodiments, a guided nuclease is a Cas9 or Cpf1 enzyme. The DNA construct or molecule encoding a guided nuclease, or the guided nuclease itself, may be delivered with or without a guide nucleic acid.

For guided nucleases, a guide nucleic acid molecule may be further provided to direct the guided nuclease to a target site in the genome of the plant via base-pairing or hybridization to cause a DSB or nick at or near the target site. The guide nucleic acid may be transformed or introduced into a plant cell or tissue as a guide nucleic acid molecule, or as a recombinant DNA molecule, construct or vector comprising a transcribable DNA sequence encoding the guide nucleic acid operably linked to a promoter or plant-expressible promoter (e.g., a maize-expressible promoter). The promoter may be a constitutive promoter, a tissue-specific or tissue-preferred promoter, a developmental stage promoter, or an inducible promoter.

In some embodiments, the guide nucleic acid comprises a first segment comprising a nucleotide sequence that is complementary to a sequence in a target nucleic acid and a second segment that interacts with a guided nuclease protein. In some embodiments, the first segment of a guide comprising a nucleotide sequence that is complementary to a sequence in a target nucleic acid corresponds to a CRISPR RNA (crRNA or crRNA repeat). In some embodiments, the second segment of a guide comprising a nucleic acid sequence that interacts with a guided nuclease protein corresponds to a trans-acting CRISPR RNA (tracrRNA). In some embodiments, the guide nucleic acid comprises two separate nucleic acid molecules (a polynucleotide that is complementary to a sequence in a target nucleic acid and a polynucleotide that interacts with a guided nuclease protein) that hybridize with one another. In other embodiments, the guide nucleic acid is a single polynucleotide. In some embodiments, the guide nucleic acid may comprise DNA, RNA or a combination of DNA and RNA.

A protospacer-adjacent motif (PAM) may be present in the genome immediately adjacent and upstream to the 5' end of the genomic target site sequence complementary to the targeting sequence of the guide RNA, immediately downstream (3') to the sense (+) strand of the genomic target site (relative to the targeting sequence of the guide RNA) as known in the art. See, e.g., Wu, X. et al. 2014. Target specificity of the CRISPR-Cas9 system, Quant Biol. 2(2): 59-70. The genomic PAM sequence on the sense (+) strand adjacent to the target site (relative to the targeting sequence of the guide RNA) may comprise any known PAM sequence, including, for example, 5'-NGG-3'. However, the corresponding sequence of the guide nucleic acid (immediately downstream (3') to the targeting sequence of the guide RNA) may generally not be complementary to the genomic PAM sequence.

The guide nucleic acid may typically be a non-coding RNA molecule that does not encode a protein. The targeting sequence of the guide nucleic acid may be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The targeting sequence may be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

In addition to the targeting sequence, a guide nucleic acid may further comprise one or more other structural or scaffold sequence(s), which may bind or interact with an RNA-guided endonuclease. Such scaffold or structural sequences may further interact with other RNA molecules (e.g., tracrRNA). Methods and techniques for designing targeting constructs and guide nucleic acids for genome editing and site-directed integration at a target site within the genome of a maize plant using a guided nuclease are known in the art.

An engineered nuclease may be a site-specific nuclease. Several site-specific nucleases, such as recombinases, zinc finger nucleases (ZFNs), meganucleases, and TALENs, are not nucleic acid-guided and instead rely on their protein structure to determine their target site for causing the DSB or nick, or they are fused, tethered or attached to a DNA-binding protein domain or motif. The protein structure of the site-specific nuclease (or the fused/attached/tethered DNA binding domain) may target the site-specific nuclease to the target site. According to many of these embodiments, non-nucleic acid-guided site-specific nucleases, such as recombinases, zinc finger nucleases (ZFNs), meganucleases, and TALENs, may be designed, engineered and constructed according to known methods to target and bind to a target site at or near the genomic locus of an endogenous gene of a plant to create a DSB or nick at such genomic locus to knockout or knockdown expression of the gene via repair of the DSB or nick, which may lead to the creation of a mutation or insertion of a sequence at the site of the DSB or nick, through cellular repair mechanisms, which may be guided by a donor template molecule.

In some embodiments, a site-specific nuclease is a recombinase. A recombinase may be a serine recombinase attached to a DNA recognition motif, a tyrosine recombinase attached to a DNA recognition motif, or other recombinase enzyme known in the art. A recombinase or transposase may be a DNA transposase or recombinase attached or fused to a DNA binding domain. Non-limiting examples of recombinases include a tyrosine recombinase attached, etc., to a DNA recognition motif provided herein is selected from the group consisting of a Cre recombinase, a gin recombinase, a Flp recombinase, and a Tnpl recombinase. In an aspect, a Cre recombinase or a Gin recombinase provided herein is tethered to a zinc-finger DNA-binding domain, or a transcription activator-like effector (TALE) DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

A site-specific nuclease may be a zinc finger nuclease (ZFN). ZFNs are synthetic proteins consisting of an engineered zinc finger DNA-binding domain fused to a cleavage domain (or a cleavage half-domain), which may be derived from a restriction endonuclease (e.g., FokI). The DNA binding domain may be canonical (C2H2) or non-canonical (e.g., C3H or C4). The DNA-binding domain can comprise one or more zinc fingers (e.g., 2, 3, 4, 5, 6, 7, 8, 9 or more zinc fingers) depending on the target site. Multiple zinc fingers in a DNA-binding domain may be separated by linker sequence(s). ZFNs can be designed to cleave almost any stretch of double-stranded DNA by modification of the zinc finger DNA-binding domain. ZFNs form dimers from monomers composed of a non-specific DNA cleavage domain (e.g., derived from the FokI nuclease) fused to a DNA-binding domain comprising a zinc finger array engineered to bind a target site DNA sequence. The DNA-binding domain of a ZFN may typically be composed of 3-4 (or more) zinc-fingers. The amino acids at positions −1, +2, +3, and +6 relative to the start of the zinc finger alpha-helix, which contribute to site-specific binding to the target site, can be changed and customized to fit specific target sequences. The other amino acids may form a consensus backbone to generate ZFNs with different sequence specificities.

Methods and rules for designing ZFNs for targeting and binding to specific target sequences are known in the art. See, e.g., US Patent App. Nos. 2005/0064474, 2009/0117617, and 2012/0142062. The FokI nuclease domain may require dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. A ZFN, as used herein, is broad and includes a monomeric ZFN that can cleave double stranded DNA without assistance from another ZFN. The term ZFN may also be used to refer to one or both members of a pair of ZFNs that are engineered to work together to cleave DNA at the same site. Without being limited by any theory, because the DNA-binding specificities of zinc finger domains can be re-engineered using one of various methods, customized ZFNs can theoretically be constructed to target nearly any target sequence (e.g., at or near a gene in a maize plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick.

A site-specific nuclease may be a TALEN enzyme. TALENs are artificial restriction enzymes generated by fusing the TALE DNA binding domain to a nuclease domain (e.g., FokI). When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the TALE DNA binding domain to a nuclease domain. In some aspects, the nuclease is selected from a group consisting of PvuII, MutH, TevI, FokI, AlwI, MlyI, SbfI, SdaI, StsI, CleDORF, Clo051, and Pept071. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN also refers to one or both members of a pair of TALENs that work together to cleave DNA at the same site.

Transcription activator-like effectors (TALEs) can be engineered to bind practically any DNA sequence, such as at or near the genomic locus of a gene in a maize plant. TALEs have a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. PLoS One. 8: e82539). MutH is capable of introducing strand-specific nicks in DNA (see Gabsalilow et al. 2013. Nucleic Acids Research. 41: e83). TevI introduces double-stranded breaks in DNA at targeted sites (see Beurdeley et al., 2013. Nature Communications. 4: 1762).

The relationship between amino acid sequence and DNA recognition of the TALE binding domain allows for designable proteins. Software programs such as DNAWorks can be used to design TALE constructs. Other methods of designing TALE constructs are known to those of skill in the art. See Doyle et al., *Nucleic Acids Research* (2012) 40: W117-122; Cermak et al., *Nucleic Acids Research* (2011) 39:e82; and tale-nt.cac.cornelledu/about. In another aspect, a TALEN provided herein is capable of generating a targeted DSB.

A site-specific nuclease may be a meganuclease. Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some embodiments, a meganuclease may comprise a scaffold or base enzyme selected from the group consisting of I-CreI, I-CeuI, I-MsoI, I-SceI, I-AniI, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease may be selected or engineered to bind to a genomic target sequence in a maize plant, such as at or near the genomic locus of a gene. In another aspect, a meganuclease provided herein is capable of generating a targeted DSB.

In some embodiments, gene editing comprises (a) inducing a DSB in the genome of a cell at a cleavage site at or near a recognition site for a natural or engineered nuclease by expressing in the cell the natural or engineered nuclease recognizing said recognition site and inducing said DSB at the cleavage site; (b) introducing into the cell a repair nucleic acid molecule comprising an upstream flanking region having homology to the DNA region upstream of the preselected site and/or a downstream flanking DNA region having homology to the DNA region downstream of the preselected site for allowing homologous recombination between said flanking region or regions and said DNA region or regions flanking said preselected site; and (c) selecting a cell wherein said repair nucleic acid molecule has been used as a template for making a modification of said genome at said preselected site. In other embodiments, gene editing comprises (a) inducing a DSB in the genome of a cell at a cleavage site at or near a recognition site for a natural or engineered nuclease by introducing into the cell the natural or engineered nuclease recognizing said recognition site and inducing said DSB at the cleavage site; (b) introducing into the cell a repair nucleic acid molecule comprising an upstream flanking region having homology to the DNA region upstream of the preselected site and/or a downstream flanking DNA region having homology to the DNA region downstream of the preselected site for allowing homologous recombination between said flanking region or regions and said DNA region or regions flanking said preselected site; and (c) selecting a cell wherein said repair nucleic acid molecule has been used as a template for making a modification of said genome at said preselected site.

As used herein, a repair nucleic acid molecule is a single-stranded or double-stranded DNA molecule or RNA molecule that is used as a template for modification of the genomic DNA at the preselected site in the vicinity of or at the cleavage site. As used herein, use as a template for modification of the genomic DNA, means that the repair nucleic acid molecule is copied or integrated at the preselected site by homologous recombination between the flanking region(s) and the corresponding homology region(s) in the target genome flanking the preselected site, optionally in combination with non-homologous end-joining (NHEJ) at one of the two ends of the repair nucleic acid molecule (e.g. in case there is only one flanking region). Integration by homologous recombination will allow precise joining of the repair nucleic acid molecule to the target genome up to the nucleotide level, while NHEJ may result in small insertions/deletions at the junction between the repair nucleic acid molecule and genomic DNA.

In some embodiments, gene editing comprises base editing. As used herein, base editing refers to the chemical modification of at least one nucleotide in a DNA or RNA sequence, resulting in an altered DNA sequence. Base editing may be achieved using a fusion protein, referred to as a base editor, comprising a site-specific nuclease and a base-editing enzyme. The base editor may comprise any suitable site-specific nuclease, such as the site-specific nucleases described herein, which has been modified to reduce or abolish nuclease activity of the site-specific nuclease. The base-editing enzyme may be any enzyme capable of chemically modifying a nucleotide, including, for example, a deaminase such as a cytidine deaminase, a cytosine deaminase, an adenosine deaminase, an adenine deaminase, or variants thereof. The base editor may also comprise one or more additional protein domains and/or one or more linker sequences linking the site-directed nuclease, the base-editing enzyme, and any other additional protein domains. Base editing is reviewed, for example, in Porto et al. 2020 ("Base editing: advances and therapeutic opportunities." Nature Reviews Drug Discovery 19.12: 839-859).

In some embodiments, the genetic modifications introduced by gene editing result in the decreased expression (including non-expression or altered activity) of one or more MiMe loci. In gene editing, the introduction of a DSB or nick may be used to introduce targeted genetic modifications in the genome of a maize plant. According to this approach, genetic modifications, such as deletions, insertions, inversions and/or substitutions may be introduced at a target site via imperfect repair of the DSB or nick to produce a knock-out or knock-down of a gene, or to produce a MiMe component with altered activity. Such genetic modifications may be generated by imperfect repair of the targeted locus even without the use of a donor template molecule, and can result in decreased expression (including non-expression or altered activity) of an endogenous gene product. For example, genetic modifications may be produced by an indel (insertion or deletion of nucleotide bases in a target DNA sequence through NHEJ), or by specific removal of sequence that reduces or completely destroys the function of a sequence or motif at or near the targeting site, or which results in an altered activity of a MiMe component such as the production of a dominant-negative MiMe component, a constitutively active MiMe component, a null mutant, or the like. Such embodiments may comprise a deletion or insertion which alters one or more post-translational modifications on the one or more MiMe components. The post-translational modifications can include phosphorylation, glycosylation, ubiquitination, nitrosylation, methylation, acetylation, lipidation and the like. Altered activity in a MiMe component can be achieved, for example, by deleting or otherwise disrupting one or more phosphorylation sites (e.g., Tyrosine phosphorylation site or Serine/Threonine phosphorylation site). In further embodiments, the motif which is disrupted is a proteolytic cleavage site. A knockout of a gene may be achieved by inducing a DSB or nick at or near the endogenous locus of the gene that results in non-expression of the gene product, whereas a knockdown of a gene may be achieved in a similar manner by inducing a DSB or nick at or near the endogenous locus of the gene that is repaired imperfectly at a site that does not affect the coding sequence of the gene in a manner that would eliminate the function of the gene product. For example, the site of the DSB or nick within the endogenous locus may be in the upstream or 5' region of the gene (e.g., a promoter and/or enhancer sequence) to affect or reduce its level of expression. Similarly, such targeted knockout or knockdown mutations of a gene may be generated with a donor template molecule to direct a particular or desired mutation at or near the target site via repair of the DSB or nick. The donor template molecule may comprise a homologous sequence with or without an insertion sequence and comprising one or more mutations, such as one or more deletions, insertions, inversions and/or substitutions, relative to the targeted genomic sequence at or near the site of the DSB or nick. For example, targeted knockout mutations of a gene may be achieved by substituting, inserting, deleting or inverting at least a portion of the gene, including, but not limited to, by introducing a frame shift or premature stop codon into a protein coding sequence of the gene. A deletion of a portion of a gene may also be introduced by generating DSBs or nicks at two target sites and causing a deletion of the intervening target region flanked by the target sites.

In some embodiments, the genetic modifications are introduced by transgenesis. Transgenes may include, but are not limited to, one or more protein-coding sequences operably linked to a plant-expressible promoter (e.g., a maize expressible promoter), one or more transcribable DNA sequences encoding an RNA molecule operably linked to a plant-expressible promoter (e.g., a maize expressible promoter), a gene of interest, a marker gene, or any combination thereof. Methods for the introduction of transgenes in maize plants are well-known and routine in the art. In some embodiments, transgenesis comprises (a) inducing a DSB in the genome of a cell at a cleavage site at or near a recognition site for a natural or engineered nuclease by expressing in the cell the natural or engineered nuclease recognizing said recognition site and inducing said DSB at the cleavage site; (b) introducing into the cell a repair nucleic acid molecule comprising an upstream flanking region having homology to the DNA region upstream of the preselected site, a downstream flanking DNA region having homology to the DNA region downstream of the preselected site, and a transgene region flanked by the upstream and downstream flanking DNA regions and comprising the transgene to be inserted at the preselected site; and (c) selecting a cell wherein said repair nucleic acid molecule has been used as a template for making a modification of said genome at said preselected site. In other embodiments, transgenesis comprises (a) inducing a DSB in the genome of a cell at a cleavage site at or near a recognition site for a natural or engineered nuclease by introducing into the cell the natural or engineered nuclease recognizing said recognition site and inducing said DSB at the cleavage site; (b) introducing into the cell a repair nucleic acid molecule comprising an upstream flanking region having homology to the DNA region upstream of the preselected site, a downstream flanking DNA region having homology to the DNA region downstream of the preselected site, and a transgene region flanked by the upstream and downstream flanking DNA regions and comprising the transgene to be inserted at the preselected site; and (c) selecting a cell wherein said repair nucleic acid molecule has been used as a template for making a modification of said genome at said preselected site.

In some embodiments, the genetic modification comprises introducing proteins, nucleic acids, or a combination thereof into a maize cell. The introduction of the proteins, nucleic acids, or combination thereof into the maize cell may be achieved by any of several means known and routinely-used in the art. In some embodiments, the introduction of the proteins, nucleic acids, or combination thereof into the maize cell comprises isolating protoplasts, transfecting the protoplasts, encapsulating the protoplasts, and regenerating maize plants from the protoplasts. In other embodiments, the introduction of the proteins, nucleic acids, or combination thereof into the maize cell comprises biolistic transformation. In certain embodiments, the introduction of the proteins, nucleic acids, or combination thereof into the maize cell comprises isolating immature maize embryos, bombarding the embryos with particles comprising nucleic acids, and regenerating maize plants from the immature embryos. Numerous additional transformation methods may be used to introduce the proteins, nucleic acids, or combination thereof into a suitable maize plant or maize cell. Transformation methods include the use of liposomes, electroporation, chemicals that increase free DNA uptake, injection of the DNA directly into the maize plant (cell) such as microinjection, particle gun bombardment, transformation using viruses or pollen and microprojection. Methods may be selected from the calcium/polyethylene glycol method for protoplasts (Krens et al. (1982) Nature 296: 72-74; Negrutiu et al. (1987) Plant. Mol. Biol. 8: 363-373); electroporation of protoplasts (Shillito et al. (1985) Bio/Technol. 3: 1099-1102); microinjection into plant material (Crossway et al. (1986) Mol. Gen. Genet. 202: 179-185); DNA or RNA-coated particle bombardment (Klein et al. (1987) Nature 327: 70) infection with (non-integrative) viruses and the like.

In some embodiments, generating the parent MiMe maize plant, the grandparent non-MiMe maize plant, the great-grandparent non-MiMe maize plant, or any combination thereof comprises introducing an RNA-guided nuclease system (e.g., a CRISPR system) into a cell of a candidate maize line, wherein the RNA-guided nuclease system (e.g., a CRISPR system) is configured to bind to one or more target sequences of each of one or more MiMe loci. Exemplary target sequences for specific MiMe loci are provided in the sequence listing as outlined in Table 5, and also in Examples 2 and 3. In certain embodiments, the one or more target sequences comprise a polynucleotide sequence selected from the group consisting of SEQ ID NOs: 14-60, or a variant thereof comprising 1, 2, 3, 4, or 5 nucleotide substitutions.

In certain embodiments, the CRISPR system comprises one or more nucleic acid molecules (e.g., one or more plasmids) encoding an expression cassette for expressing a Cas enzyme, and expression cassette for expressing a targeting RNA (e.g., a crRNA or gRNA molecule), or a combination thereof. In some variations, the targeting RNA and the Cas enzyme are encoded on separate nucleic acid molecules (e.g., separate plasmids). In other variations, the targeting RNA and the Cas enzyme are encoded on the same nucleic acid molecule (e.g., the same plasmid). In certain embodiments, the CRISPR system comprises ribonucleoproteins (RNPs) comprising a Cas enzyme complexed with a targeting RNA (e.g., a crRNA or gRNA molecule). Exemplary gRNA protospacer sequences for specific MiMe loci are provided in the sequence listing as outlined in Table 5, and also in Example 2. In certain embodiments, the targeting RNA (e.g., crRNA or gRNA) comprises a polynucleotide sequence selected from the group consisting of SEQ ID NOs: 61-107, or a variant thereof comprising 1, 2, 3, 4, or 5 nucleotide substitutions.

In some embodiments, introducing the CRISPR system into the cell of the candidate maize line results in an insertion, a deletion, one or more nucleotide changes, or an inversion that results in decreased expression of the targeted MiMe locus. The one or more MiMe loci may comprise any MiMe loci known in the art or described herein. In some variations, the insertion, the deletion, the one or more nucleotide changes, or the inversion is positioned in the first 70%, the first 60%, the first 50%, the first 40%, the first 30%, the first 20%, or the first 10% of the nucleotides of the coding sequence of the genomic locus following the start codon in the 3' direction. In certain variations, the insertion, the deletion, the one or more nucleotide changes, or the inversion is positioned in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the genomic locus following the start codon in the 3' direction. In some variations, the insertion, the deletion, the one or more nucleotide changes, or the inversion results in a premature stop codon present in the first 70%, the first 60%, the first 50%, the first 40%, the first 30%, the first 20%, or the first 10% of the nucleotides of the coding sequence of the MiMe locus following the start codon in the 3' direction, thereby eliminating expression (e.g., activity) of the genomic locus. In some variations, the insertion, the deletion, the one or more nucleotide changes, or the inversion results in a premature stop codon present in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the genomic locus following the start codon in the 3' direction, thereby eliminating expression (e.g., activity) of the genomic locus.

Crossing Clonal Gametes to Produce Hybrid Polyploid Seed

In some embodiments, the method of breeding a polyploid hybrid maize line comprises providing clonal gametes from two parent MiMe maize plants and crossing the clonal gametes to produce a hybrid polyploid seed comprising two, three, or more haplotypes. In other embodiments, the method of breeding a polyploid hybrid maize line comprises providing clonal gametes from a parent MiMe maize plant, providing haploid gametes from a homozygous parent non-MiMe maize plant, and crossing the clonal gametes with the haploid gametes to produce a hybrid polyploid seed. In some variations, the homozygous parent non-MiMe maize plant is diploid and the haploid gametes are monoploid gametes. In yet other embodiments, the method of breeding a polyploid hybrid maize line comprises providing clonal gametes from a parent MiMe maize plant, providing unreduced, non-clonal gametes from a homozygous parent maize plant, and crossing the clonal gametes with the unreduced, non-clonal gametes to produce a hybrid polyploid seed. Methods for providing clonal gametes, providing haploid gametes, providing unreduced, non-clonal gametes, crossing clonal gametes, crossing clonal gametes with haploid gametes, and crossing clonal gametes with unreduced, non-clonal gametes are described herein. In some embodiments, the method of breeding a polyploid hybrid maize line comprises growing the hybrid polyploid seed to produce a hybrid polyploid maize plant.

In some embodiments, the method of breeding a polyploid hybrid maize line comprises crossing the clonal gametes to produce the hybrid polyploid seed. In some variations, crossing the clonal gametes to produce the hybrid polyploid seed comprises contacting pollen comprising clonal gametes with the stigma of a pistil comprising clonal gametes. In some variations, crossing the clonal gametes to produce the hybrid polyploid seed comprises contacting pollen comprising clonal gametes of a first maize plant with the stigma of a pistil comprising clonal gametes of a second maize plant. In some embodiments, crossing the clonal gametes to produce the hybrid polyploid seed comprises contacting pollen comprising clonal gametes from a first parent MiMe maize plant with the stigma of a pistil comprising clonal gametes of a second parent MiMe maize plant. In some variations, the homozygous parent non-MiMe maize plant is diploid and the haploid gametes are monoploid gametes. In some embodiments, the hybrid polyploid seed is produced by crossing the clonal gametes and allowing seeds to form.

In other embodiments, the method of breeding a polyploid hybrid maize line comprises crossing the clonal gametes with the haploid gametes to produce the hybrid polyploid seed. In one variation, crossing the clonal gametes with the haploid gametes to produce the hybrid polyploid seed comprises contacting pollen comprising clonal gametes with the stigma of a pistil comprising haploid gametes. In another variation, crossing the clonal gametes with the haploid gametes to produce the hybrid polyploid seed comprises contacting pollen comprising haploid gametes with the stigma of a pistil comprising clonal gametes. In some embodiments, crossing the clonal gametes with the haploid gametes to produce the hybrid polyploid seed comprises contacting pollen comprising clonal gametes from a parent MiMe maize plant with the stigma of a pistil comprising haploid gametes of a homozygous parent non-MiMe maize plant. In other embodiments, crossing the clonal gametes with the haploid gametes to produce the hybrid polyploid seed comprises contacting pollen comprising haploid gametes from a homozygous parent non-MiMe maize plant with the stigma of a pistil comprising clonal gametes of a parent MiMe maize plant. In some embodiments, the population of polyploid seed is produced by crossing the clonal gametes with the haploid gametes and allowing seeds to form.

In yet other embodiments, the method of breeding a polyploid hybrid maize line comprises crossing clonal gametes with unreduced, non-clonal gametes to produce the hybrid polyploid seed. In one variation, crossing the clonal gametes with the unreduced, non-clonal gametes to produce the hybrid polyploid seed comprises contacting pollen comprising clonal gametes with the stigma of a pistil comprising unreduced, non-clonal gametes. In another variation, crossing the clonal gametes with the unreduced, non-clonal gametes to produce the hybrid polyploid seed comprises contacting pollen comprising unreduced, non-clonal gametes with the stigma of a pistil comprising clonal gametes. In some embodiments, crossing the clonal gametes with the unreduced, non-clonal gametes to produce the hybrid polyploid seed comprises contacting pollen comprising clonal gametes from a parent MiMe maize plant with the stigma of a pistil comprising unreduced, non-clonal gametes of a homozygous parent maize plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis. In some embodiments, crossing the clonal gametes with the unreduced, non-clonal gametes to produce the hybrid polyploid seed comprises contacting the stigma of a pistil comprising clonal gametes from a parent MiMe maize plant with pollen comprising unreduced, non-clonal gametes of a homozygous parent maize plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis. In some embodiments, the hybrid polyploid seed is produced by crossing the clonal gametes with the unreduced, non-clonal gametes and allowing seeds to form.

Evaluating Characteristics and Heterotic Performance

In some embodiments, the method of breeding a polyploid hybrid maize line comprises evaluating one or more characteristics of the hybrid polyploid maize plant. Methods for evaluating maize plant characteristics are numerous and well-known in the art. The one or more characteristics evaluated may include, but are not limited to, plant height, plant size, plant vigor, fruit yield, crop yield, disease resistance, pest resistance, and the like. The maize plants to be evaluated may then be grown under different geographical, climatic, and soil conditions, and further selections can be made during, and at the end of, the growing season. Promising advanced breeding lines are thoroughly tested and compared to appropriate standards in environments representative of the commercial target area(s) for three years at least. The best lines are candidates for new commercial cultivars. These processes, which lead to the final step of marketing and distribution, usually take from five to ten years from the time the first cross or selection is made.

In some embodiments, the one or more characteristics includes the heterotic performance of the two, three, or more haplotypes of the polyploid hybrid maize plant. In some embodiments, the heterotic performance of the two, three, or more haplotypes of the polyploid hybrid maize plant is used to guide the breeding of maize lines, the selecting of candidate maize lines, or both. In some embodiments, the heterotic performance is predicted via genome prediction modeling.

In some embodiments, the method of breeding a polyploid hybrid maize line comprises repeating the steps of the method using the one or more characteristics of the hybrid polyploid maize plant evaluated to guide the breeding of, the selecting of candidate maize lines, or both. In some variations, the method comprises repeating the steps of the method two, three, four, five, six, seven, eight, nine, or ten times or more. In additional variations, the repeating of the steps of the method iteratively informs a genome prediction model for improved prediction of heterotic performance. In certain variations, the improved prediction of heterotic performance allows for rapid combination of haplotypes with strong heterotic performance and acceleration of breeding programs.

Inventory and Maintenance of Maize Lines

In some embodiments, the method of breeding a polyploid maize line comprises maintaining the lines of maize. In some variations, the lines of maize are maintained via selfing, apomixis, cell culture, or any combination thereof. Additional methods of maintaining lines of maize are well-known in the art. In some embodiments, the method of breeding a polyploid maize line comprises maintaining an inventory of lines of maize from which haplotypes may be selected for rapid deterministic stacking of the haplotypes. In some variations, the inventory of lines comprises one or more maize lines having complete or partial MiMe genotypes that are maintained through hybridization with a haploid inducer, or a combination thereof. In additional variations, the inventory of lines may include, but is not limited to, the set of lines, candidate lines, lines comprising one or more MiMe alleles, lines having a partial MiMe genotype, lines having a complete MiMe genotype, grandparent non-MiMe maize plants having a partial MiMe genotype, parent MiMe maize plants, homozygous parent non-MiMe maize plants, or any combination thereof maintained by seed propagation, tissue culture, hybridization with a haploid inducer or any combination thereof.

In some embodiments, haploid induction may be used to maintain polyploid maize lines having a complete MiMe genotype. In certain embodiments, maintaining the inventory of lines of maize comprises crossing a polyploid maize plant having a complete MiMe genotype with a haploid inducer to produce progeny of the same ploidy as the maize plant having the complete MiMe genotype. In one variation, maintaining the inventory of lines of maize comprises crossing a tetraploid maize plant having a complete MiMe genotype with a haploid inducer to produce tetraploid progeny.

Genetically Modified Plants, Plant Parts, Plant Cells, and Processed Plant Products In some aspects, provided herein are genetically modified maize plants, plant parts, and plant cells grown from a population of polyploid maize seed or a subpopulation of genetically uniform polyploid maize seed described herein. Also provided herein are processed maize products derived from the genetically modified maize plants, plant parts, or plant cells provided herein. In some embodiments, the genetically modified maize plant parts, genetically modified plant cells, and processed maize products provided herein are non-regenerable.

In some embodiments, genetically modified maize plants and genetically modified plant parts are provided herein. The genetically modified maize plants and plant parts may be grown from a population of polyploid maize seed or a subpopulation of genetically uniform polyploid maize seed comprising three or more haplotypes and one or more genetic modifications resulting in decreased expression of one or more MiMe loci described herein. Alternatively, the genetically modified maize plants and plant parts may be regenerated from a genetically modified maize plant cell wherein the genetically modified maize plant cell comprises three or more haplotypes and one or more genetic modifications resulting in decreased expression of one or more MiMe loci. Genetically modified maize plants can be obtained from a genetically modified maize seed. Genetically modified maize plant parts can be obtained by cutting, snapping, grinding or otherwise disassociating the part from the maize plant. The maize plant part may be any plant part known in the art, including, but not limited to, a flower, a pistil, a stamen, a leaf, a stem, a cutting, a tissue, a seed coat, an ovule, pollen, a root, a rootstock, a scion, a pericarp, a cotyledon, a hypocotyl, a protoplast, an embryo, an endosperm, an anther, a seed, a cob, a glume, a husk, a leaf sheath, a ligule, a trichome, or a portion thereof. In certain embodiments, a genetically modified maize plant part provided herein is a non-regenerable portion of a genetically modified maize plant part. As used in this context, a "non-regenerable" portion of a genetically modified maize plant part refers to a portion that cannot be induced to form a whole maize plant (e.g., through in vitro culture) or that cannot be induced to form a whole maize plant that is capable of sexual and/or asexual reproduction. A non-regenerable portion of a genetically modified maize plant part may be a portion of a flower, a pistil, a stamen, a leaf, a stem, a cutting, a tissue, a seed coat, an ovule, pollen, a root, a rootstock, a scion, a pericarp, a cotyledon, a hypocotyl, a protoplast, an embryo, an endosperm, an anther, a cob, a glume, a husk, a leaf sheath, a ligule, a trichome, or a portion thereof.

In some embodiments, a non-regenerable or non-propagating maize plant cell is provided herein. As used in this context, a "non-regenerable maize plant cell" is a cell which cannot be regenerated into a whole maize plant that is capable of sexual and/or asexual reproduction through in vitro culture. The non-regenerable maize cell may be in a maize plant or plant part described herein. The non-regenerable maize cell may be a cell in a seed, or in the seedcoat of said seed. Mature maize plant organs, including a mature leaf, a mature stem or a mature root, contain at least one non-regenerable cell. In certain embodiments, the non-regenerable maize plant cell is a somatic cell.

Also provided herein is a maize cell culture or tissue culture of non-regenerable or regenerable maize cells or tissue of a genetically modified maize plant or genetically modified plant part described herein, wherein the non-regenerable or regenerable maize cells comprise three or more haplotypes and one or more genetic modifications resulting in decreased expression of one or more MiMe loci described herein. Preferably, the regenerable maize cells are derived from embryos, protoplasts, meristematic cells, callus, pollen, leaves, anthers, stems, pericarps, roots, root tips, seeds, flowers, cotyledons, and/or hypocotyls of a genetically modified maize plant or a genetically modified plant part grown from a population of polyploid maize seed or a subpopulation of genetically uniform polyploid maize seed described herein.

In some embodiments, provided herein is a processed maize product derived from a genetically modified maize plant, plant part, or plant cell described herein comprising three or more haplotypes and one or more genetic modifications resulting in decreased expression of one or more MiMe loci. In certain embodiments, the processed maize product contains sufficient nucleic acid (e.g., DNA or RNA) and/or protein material from the genetically modified maize plant, plant part, or plant cell to detect nucleic acid and/or protein sequences corresponding to the three haplotypes, the one or more genetic modifications resulting in decreased expression of one or more MiMe loci, or both. In some embodiments, the processed maize product is non-regenerable, i.e., cannot be induced to form a whole maize plant or that cannot be induced to form a whole maize plant that is capable of sexual and/or asexual reproduction.

A processed maize product may be a seed, a grain, a root, a vegetable, or any maize plant part described herein, and may be blended as a commodity or other product which moves through commerce and is derived from a genetically modified maize plant or a genetically modified plant part. In some embodiments, the commodity or other product can be tracked through commerce by detecting nucleic acid and/or protein sequences of the genetically modified maize plant or plant part from which they were obtained. In certain embodiments, the processed maize product comprises a detectable amount of nucleotide and/or protein sequences corresponding to the three or more haplotypes and/or to the one or more genetic modifications resulting in decreased expression of one or more MiMe loci. In certain embodiments, the commodity or other maize product is produced in or maintained in the genetically modified maize plant or plant part from which the commodity or other product has been obtained. Such commodities or other products of commerce include, but are not limited to, maize plant parts, fresh corn, canned corn, dehydrated corn, starch, hulls, hominy, popcorn, cereal, grain, margarine, fermented alcoholic beverage, biofuel, gluten, corn syrup, table syrup, candy, confections, soft drinks, ice cream, shoe polish, corn sugar, infant formulas, dietetic foods, caramel coloring, vinegar, lactic acid, tanning mixtures, brewing additive, artificial silk, edible starch, dextrin, mucilage, glue, textile sizing, food sauces, fireworks, industrial starch, laundry starch, filler in paper, cosmetics, explosives, germ, oil cake or meal, cattle feed, plastic resin, rubber substitutes, erasers, elastic heels, soap, glycerin, soluble corn oil, cloth coloring, salad oils, cooking oils, medicinal oils, animal feed, paper, wallboard, filling material, fuel, charcoal, industrial solvent, biomass, oil, meal, food starch, syrup, sugar, animal feed, flour, flakes, bran, processed seed, and seed. The processed maize product may be a food product that is processed by any means known in the art, e.g., canned, steamed, boiled, fried, blanched and/or frozen etc. The maize product may be produced for any purpose(s) or industry, including but not limited to human consumption, agriculture, animal consumption, dietary supplement, food product ingredient, pharmaceutical, textile, wood, paper, adhesive, binder, texture agent, filler, biofuel production.

In some embodiments, provided herein is a genetically modified maize plant, plant part, or plant cell comprising: i) three or more haplotypes; and ii) a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, provided herein is a genetically modified maize plant, plant part, or plant cell comprising: i) three or more haplotypes; and ii) a partial MiMe genotype comprising: (a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof. In certain embodiments, the genetically modified maize plant part is a non-regenerable plant part. In certain embodiments, the genetically modified maize plant cell is a non-regenerable plant cell. Also provided herein is germplasm of the genetically modified maize plant, the germplasm comprising the complete or partial MiMe genotype. Further provided herein is a genetically altered plant genome derived from the genetically modified maize plant, the genetically altered plant genome comprising the complete or partial MiMe genotype.

In some embodiments, provided herein is a genetically modified maize plant, plant part, or plant cell comprising: i) three or more haplotypes; and ii) a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In other embodiments, provided herein is a genetically modified maize plant, plant part, or plant cell comprising: i) three or more haplotypes; and ii) a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In other variations, the one or more MiMe loci of the component of progression through the first division of meiosis comprise PS1, JASON, or a combination thereof. In certain embodiments, the genetically modified maize plant part is a non-regenerable plant part. In certain embodiments, the genetically modified maize plant cell is a non-regenerable plant cell. Also provided herein is germplasm of the genetically modified maize plant, the germplasm comprising the complete or partial MiMe genotype. Further provided herein is a genetically altered plant genome derived from the genetically modified maize plant, the genetically altered plant genome comprising the complete or partial MiMe genotype.

In some embodiments, provided herein is a genetically modified maize plant, plant part, or plant cell comprising: (i) at least a first and second haplotype, each comprising one or more MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the MiMe locus of the component of progression through the first division of meiosis of the third haplotype is PS1 or JASON. In still additional variations, the one or more MiMe loci of the component of progression through the second division of meiosis of the first and second haplotype comprise OSD1, CYCA1, TDM1, PC1, PC2, FC, or any combination thereof. In yet additional variations, the locus of the component of progression through the second division of meiosis of the third haplotype is OSD1, CYCA1, TDM1, PC1, PC2, or FC. In certain embodiments, the genetically modified maize plant part is a non-regenerable plant part. In certain embodiments, the genetically modified maize plant cell is a non-regenerable plant cell. Also provided herein is germplasm of the genetically modified maize plant, the germplasm comprising the MiMe alleles of the genetically modified maize plant. Further provided herein is a genetically altered plant genome derived from the genetically modified maize plant, the genetically altered plant genome comprising the germplasm comprising the MiMe alleles of the genetically modified maize plant.

In some embodiments, provided herein is a genetically modified maize plant, plant part, or plant cell comprising: (i) at least a first and second haplotype, each comprising one or more MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis of the first and second haplotype comprise PS1, JASON, or a combination thereof. In yet additional variations, the MiMe locus of the component of progression through the first division of meiosis of the third haplotype is PS1 or JASON. In still additional variations, the MiMe locus of the component of progression through the second division of meiosis of the third haplotype is OSD1, CYCA1, TDM1, PC1, PC2 or FC. In certain embodiments, the genetically modified maize plant part is a non-regenerable plant part. In certain embodiments, the genetically modified plant cell is a non-regenerable plant cell. Also provided herein is germplasm of the genetically modified maize plant, the germplasm comprising the MiMe alleles of the genetically modified maize plant. Further provided herein is a genetically altered plant genome derived from the genetically modified maize plant, the genetically altered plant genome comprising the germplasm comprising the MiMe alleles of the genetically modified maize plant.

In some embodiments, provided herein is a genetically modified maize plant, plant part, or plant cell having a partially-complemented MiMe genotype. In some embodiments, the genetically modified maize plant, plant part, or plant cell has a partially-complemented MiMe genotype comprising: (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some embodiments, the first MiMe component is a component of sister chromatid cohesion during the first division of meiosis. In some variations, the one or more MiMe loci of the first MiMe component comprise REC8, SWITCH1/ DYAD, or a combination thereof. In one variation, the MiMe locus of the first MiMe component is REC8. In certain embodiments, the second MiMe component is a component of DNA double strand breakage during meiotic recombination. In some variations, the first MiMe locus and the second MiMe locus of the second MiMe component comprise PAIR1, SPO11-1, SPO11-2, PRD1, PRD2, DFO, MTOPVIB, DSY1, SY1, SY2, SY3, SY4, or any combination thereof. In one variation, the first MiMe locus of the second MiMe component is PAIR1 and the second MiMe locus of the second MiMe component is SPO11-1. In further embodiments, the third MiMe component is a component of progression through the second division of meiosis. In some embodiments, the partially-complemented MiMe genotype comprises only MiMe alleles at one or more MiMe loci of the third MiMe component. In some variations, the one or more MiMe loci of the third MiMe component comprise OSD1, CYCA1, TDM1, PC1, PC2, FC, or any combination thereof. In one variation, the MiMe locus of the third MiMe component is OSD1. In other embodiments, the partially-complemented MiMe genotype comprises one or more MiMe alleles and one or more non-MiMe alleles at a first MiMe locus of the third MiMe component, and one or more MiMe alleles and one or more non-MiMe alleles at a second MiMe locus of the third MiMe component. In some variations, the first MiMe locus and the second MiMe locus of the third MiMe component comprise OSD1, CYCA1, TDM1, PC1, PC2, FC, or any combination thereof. In one embodiment, the partially-complemented MiMe genotype comprises only MiMe alleles at one or more MiMe loci of the third MiMe component, wherein the one or more MiMe loci having only MiMe alleles of the first MiMe component comprise REC8, the first MiMe locus of the second MiMe component is PAIR1, the second MiMe locus of the second MiMe component is SPO11-1, and the one or more MiMe loci having only MiMe alleles of the third MiMe component comprise OSD1. Also provided herein is germplasm of the genetically modified maize plant, the germplasm comprising the partially-complemented MiMe genotype. Further provided herein is a genetically altered plant genome derived from the genetically modified maize plant, the genetically altered plant genome comprising the germplasm comprising the partially-complemented MiMe genotype.

In some embodiments, provided herein is a genetically modified maize plant, plant part, or plant cell having a partially-complemented MiMe genotype comprising: (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiment, the one or more MiMe loci of the component of progression through the first division of meiosis comprise PS1, JASON, or a combination thereof. Also provided herein is germplasm of the genetically modified maize plant, the germplasm comprising the partially-complemented MiMe genotype. Further provided herein is a genetically altered plant genome derived from the genetically modified maize plant, the genetically altered plant genome comprising the germplasm comprising the partially-complemented MiMe genotype.

In some embodiments, provided herein is a genetically modified maize plant, plant part, or plant cell having a partially-complemented MiMe genotype comprising: (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiments, the one or more MiMe loci of the component of sister chromatid cohesion during the first division of meiosis comprise REC8, SWITCH1/DYAD, or a combination thereof. In yet additional variations of the foregoing embodiments, the one or more MiMe loci of the component of progression through the second division of meiosis comprise OSD1, CYCA1, TDM1, PC1, PC2, FC, or any combination thereof. In still additional variations of the foregoing embodiments, the one or more MiMe loci of the component of progression through the first division of meiosis comprise PS1, JASON, or a combination thereof. Also provided herein is germplasm of the genetically modified maize plant, the germplasm comprising the partially-complemented MiMe genotype. Further provided herein is a genetically altered plant genome derived from the genetically modified maize plant, the genetically altered plant genome comprising the germplasm comprising the partially-complemented MiMe genotype.

In some embodiments which may be combined with any of the preceding embodiments, the genetically modified maize plant, plant part, or plant cell is diploid, triploid, tetraploid, pentaploid, hexaploid, heptaploid, or octaploid. In additional embodiments which may be combined with any of the preceding embodiments, the genetically modified maize plant, plant part, or plant cell comprises two, three, four, or more haplotypes of the same or related species of maize.

In certain embodiments, which may be combined with any of the previous embodiments, the maize plant part is a flower, a pistil, a stamen, a leaf, a stem, a cutting, a tissue, a seed coat, an ovule, pollen, a root, a rootstock, a scion, a pericarp, a cotyledon, a hypocotyl, a protoplast, an embryo, an endosperm, an anther, a seed, a cob, a glume, a husk, a leaf sheath, a ligule, a trichome, or a portion thereof.

In some embodiments, provided herein is a processed maize product derived from the genetically modified maize plant, plant part, or plant cell of any one of the preceding embodiments. In certain embodiments, the processed maize product comprises a detectable amount of the one or more MiMe alleles of the genetically modified maize plant, plant part, or plant cell. In certain embodiments, the maize product is selected from the group consisting of plant biomass, oil, meal, food starch, syrup, animal feed, flour, flakes, bran, lint, hulls, processed seed, puree, juice, juice concentrate, pulp, pomace, preserve, or sauce. In some embodiments, the processed maize product is non-regenerable. In certain embodiments, the processed maize product contains sufficient nucleic acid (e.g., DNA or RNA) and/or protein material from the genetically modified maize plant, plant part, or plant cell to detect nucleic acid and/or protein sequences corresponding to the three haplotypes, the one or more genetic modifications resulting in decreased expression of one or more MiMe loci, or both.

In some embodiments, provided herein is a processed maize product derived from a genetically modified maize plant, plant part, or plant cell comprising: i) three or more haplotypes; and ii) a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, provided herein is a processed maize product derived from a genetically modified maize plant, plant part, or plant cell comprising: i) three or more haplotypes; and ii) a partial MiMe genotype comprising: (a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof. In certain embodiments, the processed maize product comprises sufficient nucleic acid (e.g., DNA or RNA) and/or protein material from the genetically modified maize plant, plant part, or plant cell to detect nucleic acid and/or protein sequences corresponding to the three haplotypes, the MiMe alleles, or both in the processed maize product. In certain embodiments, the processed maize product is non-regenerable.

In some embodiments, provided herein is a processed maize product derived from a genetically modified maize plant, plant part, or plant cell comprising: i) three or more haplotypes; and ii) a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In other embodiments, provided herein is a processed maize product derived from a genetically modified maize plant, plant part, or plant cell comprising: i) three or more haplotypes; and ii) a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In other variations, the one or more MiMe loci of the component of progression through the first division of meiosis comprise PS1, JASON, or a combination thereof. In certain embodiments, the processed maize product comprises sufficient nucleic acid (e.g., DNA or RNA) and/or protein material from the genetically modified maize plant, plant part, or plant cell to detect nucleic acid and/or protein sequences corresponding to the three haplotypes, the MiMe alleles, or both in the processed maize product. In certain embodiments, the processed maize product is non-regenerable.

In some embodiments, provided herein is a processed maize product derived from a genetically modified maize plant, plant part, or plant cell comprising: (i) at least a first and second haplotype, each comprising one or more MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the MiMe locus of the component of progression through the first division of meiosis of the third haplotype is PS1 or JASON. In still additional variations, the one or more MiMe loci of the component of progression through the second division of meiosis of the first and second haplotype comprise OSD1, CYCA1, TDM1, PC1, PC2, FC, or any combination thereof. In yet additional variations, the locus of the component of progression through the second division of meiosis of the third haplotype is OSD1, CYCA1, TDM1, PC1, PC2, or FC. In certain embodiments, the processed maize product comprises sufficient nucleic acid (e.g., DNA or RNA) and/or protein material from the genetically modified maize plant, plant part, or plant cell to detect nucleic acid and/or protein sequences corresponding to the three haplotypes, the MiMe alleles, or both in the processed maize product. In certain embodiments, the processed maize product is non-regenerable.

In some embodiments, provided herein is a processed maize product derived from a genetically modified maize plant, plant part, or plant cell comprising: (i) at least a first and second haplotype, each comprising one or more MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis of the first and second haplotype comprise PS1, JASON, or a combination thereof. In yet additional variations, the MiMe locus of the component of progression through the first division of meiosis of the third haplotype is PS1 or JASON. In still additional variations, the MiMe locus of the component of progression through the second division of meiosis of the third haplotype is OSD1, CYCA1, TDM1, PC1, PC2 or FC. In certain embodiments, the processed maize product comprises sufficient nucleic acid (e.g., DNA or RNA) and/or protein material from the genetically modified maize plant, plant part, or plant cell to detect nucleic acid and/or protein sequences corresponding to the three haplotypes, the MiMe alleles, or both in the processed maize product. In certain embodiments, the processed plant product is non-regenerable.

In some embodiments, provided herein is a processed maize product derived from a genetically modified maize plant, plant part, or plant cell having a partially-complemented MiMe genotype. In some embodiments, a processed maize product derived from a genetically modified maize plant, plant part, or plant cell having a partially-complemented MiMe genotype comprising: (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some embodiments, the first MiMe component is a component of sister chromatid cohesion during the first division of meiosis. In some variations, the one or more MiMe loci of the first MiMe component comprise REC8, SWITCH1/DYAD, or a combination thereof. In one variation, the MiMe locus of the first MiMe component is REC8. In certain embodiments, the second MiMe component is a component of DNA double strand breakage during meiotic recombination. In some variations, the first MiMe locus and the second MiMe locus of the second MiMe component comprise PAIR1, SPO11-1, SPO11-2, PRD1, PRD2, DFO, MTOPVIB, DSY1, SY1, SY2, SY3, SY4, or any combination thereof. In one variation, the first MiMe locus of the second MiMe component is PAIR1 and the second MiMe locus of the second MiMe component is SPO11-1. In further embodiments, the third MiMe component is a component of progression through the second division of meiosis. In some embodiments, the partially-complemented MiMe genotype comprises only MiMe alleles at one or more MiMe loci of the third MiMe component. In some variations, the one or more MiMe loci of the third MiMe component comprise OSD1, CYCA1, TDM1, PC1, PC2, FC, or any combination thereof. In one variation, the MiMe locus of the third MiMe component is OSD1. In other embodiments, the partially-complemented MiMe genotype comprises one or more MiMe alleles and one or more non-MiMe alleles at a first MiMe locus of the third MiMe component, and one or more MiMe alleles and one or more non-MiMe alleles at a second MiMe locus of the third MiMe component. In some variations, the first MiMe locus and the second MiMe locus of the third MiMe component comprise OSD1, CYCA1, TDM1, PC1, PC2, FC, or any combination thereof. In one embodiment, the partially-complemented MiMe genotype comprises only MiMe alleles at one or more MiMe loci of the third MiMe component, wherein the one or more MiMe loci having only MiMe alleles of the first MiMe component comprise REC8, the first MiMe locus of the second MiMe component is PAIR1, the second MiMe locus of the second MiMe component is SPO11-1, and the one or more MiMe loci having only MiMe alleles of the third MiMe component comprise OSD1. In some variations of the foregoing embodiments, the processed maize product is non-regenerable.

In some embodiments, provided herein is a processed maize product derived from a genetically modified maize plant, plant part, or plant cell having a partially-complemented MiMe genotype comprising: (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiment, the one or more MiMe loci of the component of progression through the first division of meiosis comprise PS1, JASON, or a combination thereof. In some variations of the foregoing embodiments, the processed maize product is non-regenerable.

In some embodiments, provided herein is a processed maize product derived from a genetically modified maize plant, plant part, or plant cell having a partially-complemented MiMe genotype comprising: (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiments, the one or more MiMe loci of the component of sister chromatid cohesion during the first division of meiosis comprise REC8, SWITCH1/DYAD, or a combination thereof. In yet additional variations of the foregoing embodiments, the one or more MiMe loci of the component of progression through the second division of meiosis comprise OSD1, CYCA1, TDM1, PC1, PC2, FC, or any combination thereof. In still additional variations of the foregoing embodiments, the one or more MiMe loci of the component of progression through the first division of meiosis comprise PS1, JASON, or a combination thereof. In some variations of the foregoing embodiments, the processed maize product is non-regenerable.

In some embodiments, provided herein is a genetically modified maize plant, plant part, or plant cell, or a processed maize product derived therefrom, having a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In certain embodiments, the genetically modified maize plant, plant part, or plant cell, or processed maize product derived therefrom, is triploid, tetraploid, pentaploid, hexaploid, heptaploid, or octoploid. In some variations, the one or more OSD1 loci comprise OSD1-1, OSD1-2, and/or OSD1-3, and/or the one or more PAIR1 loci comprise PAIR1-1 and/or PAIR1-2. In certain variations, the one or more OSD1 loci comprise OSD1-1 and OSD1-2. In some variations, the genetically modified maize plant, plant part, or plant cell comprises a) a rec8 allele comprising the polynucleotide sequence of SEQ ID NO: 110; and/or b) one or more osd1 alleles, each comprising a polynucleotide sequence selected from the group consisting of SEQ ID NOS: 108 and 109. Also provided herein is germplasm of the genetically modified maize plant, the germplasm comprising the complete MiMe genotype. Further provided herein is a genetically altered plant genome derived from the genetically modified maize plant, the genetically altered plant genome comprising the complete MiMe genotype.

In some embodiments, provided herein is a genetically modified maize plant, plant part, or plant cell, or a processed maize product derived therefrom, having a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In certain embodiments, the genetically modified maize plant, plant part, or plant cell, or processed maize product derived therefrom, is triploid, tetraploid, pentaploid, hexaploid, heptaploid, or octoploid. In some variations, the one or more OSD1 loci comprise OSD1-1, OSD1-2, and/or OSD1-3, and/or the one or more PAIR1 loci comprise PAIR1-1 and/or PAIR1-2. In certain variations, the one or more OSD1 loci comprise OSD1-1 and OSD1-2. In some variations, the genetically modified maize plant, plant part, or plant cell comprises a) a rec8 allele comprising the polynucleotide sequence of SEQ ID NO: 110; and/or b) one or more osd1 alleles, each comprising a polynucleotide sequence selected from the group consisting of SEQ ID NOS: 108 and 109. Also provided herein is germplasm of the genetically modified maize plant, the germplasm comprising the partial MiMe genotype. Further provided herein is a genetically altered plant genome derived from the genetically modified maize plant, the genetically altered plant genome comprising the partial MiMe genotype.

In some embodiments, provided herein is a genetically modified maize plant, plant part, or plant cell, or a processed maize product derived therefrom, having a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the genetically modified maize plant, plant part, or plant cell, or processed maize product derived therefrom, is triploid, tetraploid, pentaploid, hexaploid, heptaploid, or octoploid. In some variations, the one or more OSD1 loci comprise OSD1-1, OSD1-2, and/or OSD1-3. In certain variations, the one or more OSD1 loci comprise OSD1-1 and OSD1-2. In some variations, the genetically modified maize plant, plant part, or plant cell, optionally comprising a) a rec8 allele comprising the polynucleotide sequence of SEQ ID NO: 110; b) one or more osd1 alleles, each comprising a polynucleotide sequence selected from the group consisting of SEQ ID NOS: 108 and 109; and/or c) a spo11-1 allele comprising the polynucleotide sequence of SEQ ID NO: 111. Also provided herein is germplasm of the genetically modified maize plant, the germplasm comprising the complete MiMe genotype. Further provided herein is a genetically altered plant genome derived from the genetically modified maize plant, the genetically altered plant genome comprising the complete MiMe genotype.

In some embodiments, provided herein a genetically modified maize plant, plant part, or plant cell, or a processed maize product derived therefrom, having a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the genetically modified maize plant, plant part, or plant cell, or processed maize product derived therefrom, is triploid, tetraploid, pentaploid, hexaploid, heptaploid, or octoploid. In some variations, the one or more OSD1 loci comprise OSD1-1, OSD1-2, and/or OSD1-3. In certain variations, the one or more OSD1 loci comprise OSD1-1 and OSD1-2. In some variations, the genetically modified maize plant, plant part, or plant cell, optionally comprises a) a rec8 allele comprising the polynucleotide sequence of SEQ ID NO: 110; and/or b) one or more osd1 alleles, each comprising a polynucleotide sequence selected from the group consisting of SEQ ID NOS: 108 and 109; and/or c) a spo11-1 allele comprising the polynucleotide sequence of SEQ ID NO: 111. Also provided herein is germplasm of the genetically modified maize plant, the germplasm comprising the partial MiMe genotype. Further provided herein is a genetically altered plant genome derived from the genetically modified maize plant, the genetically altered plant genome comprising the partial MiMe genotype.

In some embodiments, provided herein is a genetically modified maize plant, plant part, or plant cell, or a processed maize product derived therefrom, having a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the genetically modified maize plant, plant part, or plant cell, or processed maize product derived therefrom, is triploid, tetraploid, pentaploid, hexaploid, heptaploid, or octoploid. In some variations, the genetically modified maize plant, plant part, or plant cell, optionally comprises a) a rec8 allele comprising the polynucleotide sequence of SEQ ID NO: 110; and/or b) a spo11-1 allele comprising the polynucleotide sequence of SEQ ID NO: 111. Also provided herein is germplasm of the genetically modified maize plant, the germplasm comprising the complete MiMe genotype. Further provided herein is a genetically altered plant genome derived from the genetically modified maize plant, the genetically altered plant genome comprising the complete MiMe genotype.

In some embodiments, provided herein is a genetically modified maize plant, plant part, or plant cell, or a processed maize product derived therefrom, having a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the genetically modified maize plant, plant part, or plant cell, or processed maize product derived therefrom, is triploid, tetraploid, pentaploid, hexaploid, heptaploid, or octoploid. In some variations, the genetically modified maize plant, plant part, or plant cell, optionally comprises a) a rec8 allele comprising the polynucleotide sequence of SEQ ID NO: 110; and/or b) a spo11-1 allele comprising the polynucleotide sequence of SEQ ID NO: 111. Also provided herein is germplasm of the genetically modified maize plant, the germplasm comprising the partial MiMe genotype. Further provided herein is a genetically altered plant genome derived from the genetically modified maize plant, the genetically altered plant genome comprising the partial MiMe genotype.

In some embodiments, provided herein a genetically modified maize plant, plant part, or plant cell, or a processed maize product derived therefrom, having a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In certain embodiments, the genetically modified maize plant, plant part, or plant cell, or processed maize product derived therefrom, is triploid, tetraploid, pentaploid, hexaploid, heptaploid, or octoploid. In some variations, the one or more PAIR1 loci comprise PAIR1-1 and/or PAIR1-2. In some variations, the genetically modified maize plant, plant part, or plant cell comprises a rec8 allele comprising the polynucleotide sequence of SEQ ID NO: 110. Also provided herein is germplasm of the genetically modified maize plant, the germplasm comprising the complete MiMe genotype. Further provided herein is a genetically altered plant genome derived from the genetically modified maize plant, the genetically altered plant genome comprising the complete MiMe genotype.

In some embodiments, provided herein a genetically modified maize plant, plant part, or plant cell, or a processed maize product derived therefrom, having a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In certain embodiments, the genetically modified maize plant, plant part, or plant cell, or processed maize product derived therefrom, is triploid, tetraploid, pentaploid, hexaploid, heptaploid, or octoploid. In some variations, the one or more PAIR1 loci comprise PAIR1-1 and/or PAIR1-2. In some variations, the genetically modified maize plant, plant part, or plant cell comprises a rec8 allele comprising the polynucleotide sequence of SEQ ID NO: 110. Also provided herein is germplasm of the genetically modified maize plant, the germplasm comprising the partial MiMe genotype. Further provided herein is a genetically altered plant genome derived from the genetically modified maize plant, the genetically altered plant genome comprising the partial MiMe genotype.

In some embodiments, provided herein is a genetically modified maize plant, plant part, or plant cell, or a processed maize product derived therefrom, having a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the genetically modified maize plant, plant part, or plant cell, or processed maize product derived therefrom, is triploid, tetraploid, pentaploid, hexaploid, heptaploid, or octoploid. In some variations, the genetically modified maize plant, plant part, or plant cell comprises a) a rec8 allele comprising the polynucleotide sequence of SEQ ID NO: 110; and/or b) a spo11-1 allele comprising the polynucleotide sequence of SEQ ID NO: 111. Also provided herein is germplasm of the genetically modified maize plant, the germplasm comprising the complete MiMe genotype. Further provided herein is a genetically altered plant genome derived from the genetically modified maize plant, the genetically altered plant genome comprising the complete MiMe genotype.

In some embodiments, provided herein is a genetically modified maize plant, plant part, or plant cell, or a processed maize product derived therefrom, having a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the genetically modified maize plant, plant part, or plant cell, or processed maize product derived therefrom, is triploid, tetraploid, pentaploid, hexaploid, heptaploid, or octoploid. In some variations, the genetically modified maize plant, plant part, or plant cell comprises a) a rec8 allele comprising the polynucleotide sequence of SEQ ID NO: 110; and/or b) a spo11-1 allele comprising the polynucleotide sequence of SEQ ID NO: 111. Also provided herein is germplasm of the genetically modified maize plant, the germplasm comprising the partial MiMe genotype. Further provided herein is a genetically altered plant genome derived from the genetically modified maize plant, the genetically altered plant genome comprising the partial MiMe genotype.

In some embodiments, provided herein is a genetically modified maize plant, plant part, or plant cell, or a processed maize product derived therefrom, having a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In certain embodiments, the genetically modified maize plant, plant part, or plant cell, or processed maize product derived therefrom, is triploid, tetraploid, pentaploid, hexaploid, heptaploid, or octoploid. In some variations, the one or more PAIR1 loci comprise PAIR1-1 and/or PAIR1-2. In some variations, the genetically modified maize plant, plant part, or plant cell, optionally comprising a rec8 allele comprises the polynucleotide sequence of SEQ ID NO: 110. Also provided herein is germplasm of the genetically modified maize plant, the germplasm comprising the complete MiMe genotype. Further provided herein is a genetically altered plant genome derived from the genetically modified maize plant, the genetically altered plant genome comprising the complete MiMe genotype.

In some embodiments, provided herein is a genetically modified maize plant, plant part, or plant cell, or a processed maize product derived therefrom, having a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In certain embodiments, the genetically modified maize plant, plant part, or plant cell, or processed maize product derived therefrom, is triploid, tetraploid, pentaploid, hexaploid, heptaploid, or octoploid. In some variations, the one or more PAIR1 loci comprise PAIR1-1 and/or PAIR1-2. In some variations, the genetically modified maize plant, plant part, or plant cell comprises a rec8 allele comprising the polynucleotide sequence of SEQ ID NO: 110. Also provided herein is germplasm of the genetically modified maize plant, the germplasm comprising the partial MiMe genotype. Further provided herein is a genetically altered plant genome derived from the genetically modified maize plant, the genetically altered plant genome comprising the partial MiMe genotype.

In some embodiments, provided herein is a genetically modified maize plant, plant part, or plant cell, or a processed maize product derived therefrom, having a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more only MiMe alleles at one or more SPO11-1 loci, wherein each of the MiMe alleles at the SPO11-1 locus comprise one or more genetic modifications resulting in decreased expression of SPO11-1. In certain embodiments, the genetically modified maize plant, plant part, or plant cell, or processed maize product derived therefrom, is triploid, tetraploid, pentaploid, hexaploid, heptaploid, or octoploid. In some variations, the one or more OSD1 loci comprise OSD1-1, OSD1-2, and/or OSD1-3, and/or the one or more PAIR1 loci comprise PAIR1-1 and/or PAIR1-2. In certain variations, the one or more OSD1 loci comprise OSD1-1 and OSD1-2. In some variations, the genetically modified maize plant, plant part, or plant cell comprises a) a rec8 allele comprising the polynucleotide sequence of SEQ ID NO: 110; b) one or more osd1 alleles, each comprising a polynucleotide sequence selected from the group consisting of SEQ ID NOs: 108 and 109; and/or c) a spo11-1 allele comprising the polynucleotide sequence of SEQ ID NO: 111. Also provided herein is germplasm of the genetically modified maize plant, the germplasm comprising the partially complemented MiMe genotype. Further provided herein is a genetically altered plant genome derived from the genetically modified maize plant, the genetically altered plant genome comprising the partially complemented MiMe genotype.

In some embodiments, provided herein is a genetically modified maize plant, plant part, or plant cell, or a processed maize product derived therefrom, having a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1. In certain embodiments, the genetically modified maize plant, plant part, or plant cell, or processed maize product derived therefrom, is triploid, tetraploid, pentaploid, hexaploid, heptaploid, or octoploid. In some variations, the one or more PAIR1 loci comprise PAIR1-1 and/or PAIR1-2. In some variations, the genetically modified maize plant, plant part, or plant cell comprises a) a rec8 allele comprising the polynucleotide sequence of SEQ ID NO: 110; and/or b) a spo11-1 allele comprising the polynucleotide sequence of SEQ ID NO: 111. Also provided herein is germplasm of the genetically modified maize plant, the germplasm comprising the partially complemented MiMe genotype. Further provided herein is a genetically altered plant genome derived from the genetically modified maize plant, the genetically altered plant genome comprising the partially complemented MiMe genotype.

In some embodiments, provided herein is a genetically modified maize plant, plant part, or plant cell, or a processed maize product derived therefrom, having a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1. In certain embodiments, the genetically modified maize plant, plant part, or plant cell, or processed maize product derived therefrom, is triploid, tetraploid, pentaploid, hexaploid, heptaploid, or octoploid. In some variations, the one or more PAIR1 loci comprise PAIR1-1 and/or PAIR1-2. In some variations, the genetically modified maize plant, plant part, or plant cell comprises a) a rec8 allele comprising the polynucleotide sequence of SEQ ID NO: 110; and/or b) a spo11-1 allele comprising the polynucleotide sequence of SEQ ID NO: 111. Also provided herein is germplasm of the genetically modified maize plant, the germplasm comprising the partially complemented MiMe genotype. Further provided herein is a genetically altered plant genome derived from the genetically modified maize plant, the genetically altered plant genome comprising the partially complemented MiMe genotype.

Sequences of MiMe Loci Gene Products and Alleles

Sequence Alignment 1: REC8 protein sequences from monocotyledonous plants.
Homologs identified by BLAST of Oryza sativa Os05g50410.1 from NSU.
Qsa1 Release 7 map to acnecot NCBI RefSeq, GenBank and UniProtXB protein databases

```
                                                       10        20        30        40        50        60        70        80        90       100
                                                ----:----|----:----|----:----|----:----|----:----|----:----|----:----|----:----|----:----|----:----|
Consensus                                       MFYSMQLLIARKAPLGQIWMAATLMXKINRKRLDKLDIIKICEEILNPSVPMALRLSGILMGGVVIVYERKVKLLVRDVSRLLIEINEAKXIXPVVEHTVL
Aegilops_tauschii_
 subsp._tauschii:
 (RefSeq: XP_020178692.1)                       ..................................................................................................
Brachypodium_distachyon:
 (RefSeq: XP_003567819.1)                       ...................A..............................................................K.R.A........
Hordeum_vulgare_subsp.
 vulgare: (XP_044984385.1)                      ........................I..FKS..R................................KX............VD........L.....
Musa_acuminata_
 subsp._malaccensis:
 (RefSeq: XP_018631669.1)                       ............................MRA.M..RK....................................T.F.V...A..KVKF.S.P...
Oryza_sativa_Japonica_Group:
 (RefSeq: XP_015638092.1)                       ..........................S...........................A.............A...............RVK..A.P...
Sorghum_bicolor:
 (RefSeq: XP_021302730.1)                       ..........................S............................................S........T.......R.K.AT.T.
Triticum_aestivum:
 (UniProt: A0A3852687)                          ..........................A..V.....................................................K.R.A.......
Zea_mays:
 (RefSeq: XP_008648328.1)                       ..........................S............................................T..............T.R.K.T.P..

110       120       130       140       150       160       170       180       190       200
                                                ----:----|----:----|----:----|----:----|----:----|----:----|----:----|----:----|----:----|----:----|
Consensus                                       PKGKAQAKYEAVTLPENDMEWEVEQPMLFSDIDGATARFRQXRLEOLDEQYVNVNLDEDSSRADXMHQAEAVNKTLVDMSESFLAEYDXSNRFERFDIA
Aegilops_tauschii_
 subsp._tauschii                                ............A........V.Y.......................I..R..........................................I.
Brachypodium_distachyon:
 (RefSeq: XP_003567819.1)                       ...........K............M...........N............S.D.G..F......EM..............................
Hordeum_vulgare_subsp.
 vulgare: (XP_044984385.1)                      ..............M.....L.K.V..TN.....................I..R..........................F...I.T........
Musa_acuminata_
 subsp._malaccensis:
 (RefSeq: XP_018631669.1)                       .RA.......F..........YV...P....M.P.ASI...A.QR...D..E.H.I.ID.R..L...GND......PE....FET.G..V....LY.H....VG
Oryza_sativa_Japonica_Group:
 (RefSeq: XP_015638092.1)                       ......T..............I..D.......EA....T..........D.I...................EN.....D.E....A..G...G...V.......T
Sorghum_bicolor:
 (RefSeq: XP_021302730.1)                       .................KSIN.V.....F..E..................F..G.......H..MR.................F...........
Triticum_aestivum:
 (UniProt: A0A3852687)                          ....................AV......VF.T..Y..T.............I..R........................................
Zea_mays:
 (RefSeq: XP_008648328.1)                       ......T............--IN.V......F..EP.........K..R.G..........Q...........H..DR...K............L..H........

210       220       230       240       250       260       270       280       290       300
                                                ----:----|----:----|----:----|----:----|----:----|----:----|----:----|----:----|----:----|----:----|
Consensus                                       DEKITIVNITPDXHPQAPSTLVPSPPRXEDPPQQEOXYAAPSPOEEPQQGDXLVKKEQEEQKMKEQQPXKKSSRKARGKGPQVIMDNNQIMIPGNIYQT
Aegilops_tauschii_                              ........H.L.G..E..........P.......C......IM.....S...............TY...T.RA..............V..S
```

```
                   Sequence Alignment 1: REC8 protein sequences from monocotyledonous plants.
                     Homologs identified by BLAST of Oryza sativa Os05g50410.1 from NSU.
            Qsal Release 7 map to acnecot NCBI RefSeq, GenBank and UniProtXB protein databases 310       320       330       340       350       360       370       380       390       400
                                                    |         |         |         |         |         |         |         |         |         |
subsp._tauschii:
(RefSeq: XP_020178692.1)        SEQ ID NO: 115  .........H........A....K........H......NQ......PS...O......R..NEP...........T.....T.....
Brachypodium_distachyon:
(RefSeq: XP_003567819.1)        SEQ ID NO: 116  ....IF........G..E.............P..F..Q.R......IR.......S...............T..K..T.RA........S
Hordeum_vulgare_subsp._
vulgare: (XP_044984385.1)       SEQ ID NO: 112  .E.KI..F..QEE.FEA...I..L.HEDEIRTFIMLHS.VENHQT.KEEQRA--.NDEDV.R....-V--....MR.PSMR...DR.L...
Musa_acuminata_
subsp._malaccensis:
(RefSeq: XP_018631669.1)        SEQ ID NO: 114  ...A.F.V...G..V.N........Q..S........NHH..S..LM..A...GAS.N..Q.........G...A.S.....K.R.DDE.M....D......V..
Oryza sativa Japonica Group:
(RefSeq: XP_015638092.1)        SEQ ID NO: 113  ...E........S..E..KV.........Q........E..V...FLVR......GP-----........K.TP.A.........REL............
Sorghum_bicolor:
(RefSeq: XP_021302730.1)        SEQ ID NO: 117  ...............H.L.G..E.............P.........C........IR........S...........TT....T.RA.........M......
Triticum_aestivum:
(UniProt: A0A3852687)           SEQ ID NO: 1    ..E...............EY.V....I......Q..I..E.PY......VHG......GP..ED........K..P.A.....I..-...V..S
Zea_mays:
(RefSeq: XP_008648328.1)                                                                                                                            NEV.R........N.........

Consensus                                       WLXDPSSLXSKRRXVKSLHKINPIKSIKIGDLMDLPPVALISXSKXSXLEDYYPKQLNQLXKECTEVKSPKXSSSXGDKSSSSSQEXQFRNSPPXXPPPQ
Aegilops_tauschii_
subsp._tauschii:                SEQ ID NO: 119  .........X....Q.R--......KA......E......S..M.C.DO.Q..I..Q........K..P..P...S...........K.....--....
(RefSeq: XP_020178692.1)        SEQ ID NO: 118
Brachypodium_distachyon:
(RefSeq: XP_003567819.1)        SEQ ID NO: 115  ....I..X.....R.S.-........QT..........H.......Y.EK.P..L.............S..PG....K.P.....Q.S.......
Hordeum_vulgare_subsp._
vulgare: (XP_044984385.1)       SEQ ID NO: 116  .......T...Q.R-.....QA..M.E......ST.MKC.DO.Q..I...Q.R......K.NP..P...S.V........T......
Musa_acuminata_
subsp._malaccensis:
(RefSeq: XP_018631669.1)        SEQ ID NO: 112  .Q.T.DIV..GRTQC..SV....T..SN.........GLEMFPAKVK..SP..E..RK...N---I.PS.....PPAQ.REVTETL.
Oryza sativa Japonica Group:
(RefSeq: XP_015638092.1)        SEQ ID NO: 114  ............IT..MRIN.--.V.L.........R.......L.S...SLEK.P..F.....E............AP..G...QQ.....P.Q.Q..L..QA..T
Sorghum_bicolor:
(RefSeq: XP_021302730.1)        SEQ ID NO: 113  ....A...V.....K.N.--NF.F..T..S......I..S...HDNS..S..L.....P.......D........T.V..GG......QR........Q......NE...
Triticum_aestivum:
(UniProt: A0A3852687)           SEQ ID NO: 117  .......T....Q.R.-.......KA........E......S..M.F.ND.Q..I..Q.............K..T.P...S...........K....P-----S...
Zea_mays:
(RefSeq: XP_008648328.1)        SEQ ID NO: 1    ....A...V....KLN.--NF.F..T..S....MI........HDNLFS..LC......P.........D......T.A..GG---QR........P..K...--...

410       420       430       440       450       460       470       480       490       500
                                                    |         |         |         |         |         |         |         |         |         |
Consensus                                       PQGXYQXEMGAQPMDFTPMDFTDGIEKLRANKSGLEXVXDXXHGDMSVTPGSPAGLSRRSASSSGGSGRGAFJPLDPEIQLPSSGRSKRXQHSSGRS
Aegilops_tauschii_
subsp._tauschii:                SEQ ID NO: 119  ...D-.N.........................M.......-F.G.F.GP...P........................G.L.....L.Q.....A..R.I......
(RefSeq: XP_020178692.1)        SEQ ID NO: 118
Brachypodium_distachyon:
(RefSeq: XP_003567819.1)        SEQ ID NO: 115  ...E..G...................................I.G........Y.R.D.AL..........................V........FY..G.......R........
```

Sequence Alignment 1: REC8 protein sequences from monocotyledonous plants.
Homologs identified by BLAST of Oryza sativa Os05g50410.1 from NSU.
Qsal Release 7 map to acnecot NCBI RefSeq, GenBank and UniProtXB protein databases

```
                                                                510        520        530        540        550        560        570        580        590    600
                                                              ----|----|----|----|----|----|----|----|----|----|----|----|----|----|----|----|----|----|----|
Hordeum_vulgare_subsp._                        SEQ ID NO: 116 ..D-.N........-....L..EM........-GS.G.F.GPL.A.................................G.L.G..P.QF.D..A..K.L....
vulgare: (XP_044984385.1)
Musa_acuminata_                                SEQ ID NO: 112 .LEEV.G.I.SN-----SL.VS-.......LEN.DFQGFD.AFSM..F......S...Q.SK.MP...H...N.E........-V....K......SK.
subsp._malaccensis:
(RefSeq: XP_018631669.1)
Oryza_sativa_Japonica_Group:                   SEQ ID NO: 114 ...VDNDR....FH-----V..A.D....G.T..-YGRDY.AF.S.....................G.TQ.....V........-..........K.
(RefSeq: XP_015638092.1)
Sorghum_bicolor:                               SEQ ID NO: 113 AG.E.EN.T.GL-.................M.A-.YDRAY.TL.S..................Q-..I...A.V........GR..A......
(RefSeq: XP_021302730.1)
Triticum_aestivum:                             SEQ ID NO: 117 ...D-.N.............M........................F.G.F.GP...P..........L........Q................A.R.L....
(UniProt: A0A3852687)
Zea_mays:                                      SEQ ID NO: 1   AG.E.EM.T.GL-.....L...........M.A.KYDRAYNTL.S................S-..TQ.......V..........G..A......
(RefSeq: XP_008648328.1)

Consensus                                      SEQ ID NO: 119 LGNLDPVEEFPLEQEVRDFKLRRLSDKGPRPDLELEETEPTQTPYXKQSXPAXDXITESIMSYLELHFDSPKAPQSESLSQLXMGMTTAXAARLFYQTC
Aegilops_tauschii_                             SEQ ID NO: 118 ...............M..G.E........IE....MV.......FT...S.-P.H..........E..D.P......TY..N..Q.........
subsp._tauschii:
(RefSeq: XP_020178692.1)
Brachypodium_distachyon:                       SEQ ID NO: 115 ..................S.........KG......I.....E....L.......M..PS.-T.QV........A.D..L........R.......
(RefSeq: XP_003567819.1)
Hordeum_vulgare_subsp._                        SEQ ID NO: 116 ..................I....M...G......V.EF......-M.........FS...S.-P.H..........E.AD..L......H.T..N..Q....
vulgare: (XP_044984385.1)
Musa_acuminata_                                SEQ ID NO: 112 FR.............L.Q.D..GS.I....ET......F......G......VTPP.N..V.NT..LL.RTM....T.G..........N..AF..YKHK..Q....
subsp._malaccensis:
(RefSeq: XP_018631669.1)
Oryza_sativa_Japonica_Group:                   SEQ ID NO: 114 F.............F..L...M.....V........-..I..............E.K.N.-I.QV.Q..........T.G.S........A.......K......
(RefSeq: XP_015638092.1)
Sorghum_bicolor:                               SEQ ID NO: 113 ......T...D...L..M.V.N....YA....-........ERR.N-N.KV..A.M.H.............G..........H.A......K.R......
(RefSeq: XP_021302730.1)
Triticum_aestivum:                             SEQ ID NO: 117 ....................M...E.E.......ME....-NV...........FM...S.-P.H.............E..D.P.......IY..N..Q....
(UniProt: A0A3852687)
Zea_mays:                                      SEQ ID NO: 1   ......T...D..........M......YV.....-.........ERR.N-M.K...T.Q.H.......T.GV.............H.A......K.R.....IA
(RefSeq: XP_008648328.1)
```

-continued

Sequence Alignment 1: REC8 protein sequences from monocotyledonous plants.
Homologs identified by BLAST of Oryza sativa Os05g50410.1 from NSU.
Qsal Release 7 map to acnecot NCBI RefSeq, GenBank and UniProtXB protein databases

```
                                                610       620       630
                                       ----:----|----:----|----:----|---
Consensus                      SEQ ID NO: 119 VLATXDXIKVRQXEPXGXELYGDILISRGXXM
Aegilops_tauschii_             SEQ ID NO: 118 .....L.R.....V.------.P.......AN.
  subsp._tauschii:
  (RefSeq: XP_020178692.1)
Brachypodium_distachyon:       SEQ ID NO: 115 .....L.R.....V.------.A.......LN.
  (RefSeq: XP_003567819.1)
Hordeum_vulgare_subsp._        SEQ ID NO: 116 .....R.H.....D.A------.P.H.K.AN.
  vulgare: (XP_044984385.1)
Musa_acuminata_                SEQ ID NO: 112 .V.C.F...Q.H.A------...S...PK.
  subsp._malaccensis:
  (RefSeq: XP_018631669.1)
Oryza_sativa_Japonica_Group:   SEQ ID NO: 114 .....H.F..N.L.-------...........PK.
  (RefSeq: XP_015638092.1)
Sorghum_bicolor:               SEQ ID NO: 113 .....F.Y.N...LK.H.E............SKI
  (RefSeq: XP_021302730.1)
Triticum_aestivum:             SEQ ID NO: 117 .....L.R.....V.------.P.......AN.
  (UniProt: A0A3852687)
Zea_mays:                      SEQ ID NO: 1   .....C.Y.....L.RK.D............LK.
  (RefSeq: XP_008648328.1)
```

TABLE 1

Percent identities of REC8 protein sequences from monocotyledonous plants.

| REC8 Monocot % ID | Musa acuminata subsp. malaccensis: (RefSeq: XP_018681669.1) | Zea mays: (RefSeq: XP_008648328.1) | Sorghum bicolor: (RefSeq: XP_021302730.1) | Oryza sativa Japonica Group: (RefSeq: XP_015638093.1) | Brachypodium distachyon: (RefSeq: XP_003567819.1) | Hordeum vulgare subsp. vulgare: (XP_044984305.1) | Triticum aestivum: (UniProt: A0A3B5Z6B7) |
|---|---|---|---|---|---|---|---|
| Zea mays: (RefSeq: XP_008648328.1) | 55.863 | | | | | | |
| Sorghum bicolor: (RefSeq: XP_021302730.1) | 53.71 | 86.721 | | | | | |
| Oryza sativa Japonica Group: (RefSeq: XP_015638093.1) | 52.674 | 67.585 | 68.182 | | | | |
| Brachypodium distachyon: (RefSeq: XP_003567819.1) | 55.628 | 72.386 | 72.683 | 70.425 | | | |
| Hordeum vulgare subsp. vulgare: (XP_044984305.1) | 51.545 | 64.542 | 65.579 | 63.725 | 75.413 | | |
| Triticum_aestivum: (UniProt: A0A3B5Z6B7) | 52.903 | 67.585 | 68.821 | 65.964 | 79.378 | 86.7 | |
| Aegilops tauschii subsp. tauschii: (RefSeq: XP_020178692.1) | 53.065 | 68.071 | 68.821 | 67.099 | 80.524 | 88.177 | 97.039 |

Sequence Alignment 2: SPO11-1 sequences from monocotyledonous plants.

SPO11-1 Monocots

Homologs identified by BLAST of Oryza sativa Os03g54091.1 from MSU -
Osa1 Release 7 map to monocot NCBI RefSeq, GenBank and UniProtKB protein databases

```
                                                  10        20        30        40        50        60        70        80        90       100
                                         ....|....|....|....|....|....|....|....|....|....|....|....|....|....|....|....|....|....|....|....|
Consensus                                MNAGRWIDIXXRRRATVLLAAFVPSFXDDERRGRRRLEEAALSDLLHXIKGIVXWVVAEVSAGRSPSXALMRYQNYCAXADSAAAAASPSTCACSYDAP
Aegilops tauschii:               SEQ ID NO: 128  ........-.-S----G................................K...G...I......L.....S.A...............
(RefSeq: XP_020158624.1)
Brachypodium distachyon:         SEQ ID NO: 124  ..-.-.S----G.-E.......-D.L......EQ......K......G.........G...V.N.........-----TS.....P.I.
(RefSeq: XP_003559449.1)
Hordeum vulgare subsp. vulgare:  SEQ ID NO: 125  -.E......-E.......-D.L......EQ......K......G.........G...V.N.........-----TS.....P.I.
(UniProt: A0A2875060)
Musa acuminata subsp.            SEQ ID NO: 127  .........-G.................................S......K......G.........L.........-----........
malaccensis: (XP_009380133.2)
Oryza sativa Japonica Group:     SEQ ID NO: 120  .V......DAQA.FIF........AQATT.MAGG.VSSSSP...QR...F.RSL.EDL.ND.P.V.D.R.....-----HDPSGN.P.GDNL.
(RefSeq: XP_001391702.1)
Sorghum bicolor:                 SEQ ID NO: 123  .......-E.....VAA.-------GE........Q...T-...R.R..R.......A......TV.........R.....-----S.S..AA.P......V.
(RefSeq: XP_002465440.1)
Triticum aestivum:               SEQ ID NO: 122  .......-D.......AP-------EG..QQL..Q........RR.......R..E.A.......R..........C....-----.......DS........P........
(UniProt: A0A3B5LTD1)
Zea mays: (RefSeq:               SEQ ID NO: 126  ..-.S...G.......-D.......AP-------EG..QQL..Q........RR.......R..E.A.......R..........C....-----.......DS........P........
XP_001347894.1)                  SEQ ID NO: 121  -.......-D.......AP-------EG..QQL..Q........RR.......R.I.E.A.......H...........IV.......-----.S.DS........P........Y.

110       120       130       140       150       160       170       180       190       200
                                         ....|....|....|....|....|....|....|....|....|....|....|....|....|....|....|....|....|....|....|....|
Consensus                                VGTDVLSLLRKEFHASRLMVLLRVLLVVQQLLQZMKHCSKRDIYYMYPSIFVBQAVVDRAINDICILFKCSRHNLNVVPVAKGLVMGWIRFVEGEKKVYC
Aegilops tauschii:               SEQ ID NO: 128  ............................................M..I.........................................
(RefSeq: XP_020158624.1)
Brachypodium distachyon:         SEQ ID NO: 124
(RefSeq: XP_003559449.1)
Hordeum vulgare subsp. vulgare:  SEQ ID NO: 125  ...I.C..........S......F.......E........I................................................
(UniProt: A0A2875060)
Musa acuminata subsp.            SEQ ID NO: 127  .....................................E.........M..I......................................
malaccensis: (XP_009380133.2)
Oryza sativa Japonica Group:     SEQ ID NO: 120  N.KEII.-VER.S..Y.L..F...II.......E..G.........H.AL.L........N..L.....QH.........GR......L.L.AGR..I..
(RefSeq: XP_001391702.1)
Sorghum bicolor:                 SEQ ID NO: 123  HRGS.............................Q...............................V...........L........E....
(RefSeq: XP_002465440.1)
Triticum aestivum:               SEQ ID NO: 122  HNDY.T...............K..Q...............................L.........V........................
(UniProt: A0A3B5LTD1)
Zea mays: (RefSeq:               SEQ ID NO: 126  .............................E...................M..I......V..............................
XP_001347894.1)                  SEQ ID NO: 121  .H.DV.T..........F.......Q......................V..........................M..............

210       220       230       240       250       260       270       280       290       300
                                         ....|....|....|....|....|....|....|....|....|....|....|....|....|....|....|....|....|....|....|....|
Consensus                                ITNVNAAFXIPVSIEAIKDVVSVAHYILVVEKETVFQRLANDKFCERNRCTVTTGRGYPDIPTRRFLRYLVEQLHLPAYCLVDSDPYGFDILATYKPGSM
Aegilops tauschii:               SEQ ID NO: 128  ......P............................A.........K.............................................
(RefSeq: XP_020158624.1)
Brachypodium distachyon:         SEQ ID NO: 125  .....S........T..I.........................................V......H........................
(RefSeq: XP_003559449.1)
```

-continued-

Sequence Alignment 2: SPO11-1 sequences from monocotyledonous plants.
SPO11-1 Monocots
Homologs identified by BLAST of Oryza sativa 0s03g54091.1 from MSU -
Osa1 Release 7 map to monocot NCBI RefSeq, GenBank and UniProtKB protein databases

```
                                              310       320       330       340       350       360       370       380       390       400
                                              |---------|---------|---------|---------|---------|---------|---------|---------|---------|
Hordeum_vulgare_subsp._vulgare:  SEQ ID NO: 127 ....T.P..........A........KK...............R...........................
(UniProt: A0A2B75060)
Musa_acuminata_subsp._           SEQ ID NO: 120 .NSPSTVYP...CL.EVV.T....RF.I....S........R......H........V......CL.QM..V....C.......MV.R..
malaccensis: (XP_009380133.2)
Oryza_sativa_Japonica_Group      SEQ ID NO: 123 V.................S.............D..I.........................V................V....A............L
(RefSeq: XP_001391702.1)
Sorghum_bicolor:                 SEQ ID NO: 122 ..........S...D.............................................................L
(RefSeq: XP_002465440.1)
Triticum_aestivum:               SEQ ID NO: 126 ....T.P...........A.........K...............................................
(UniProt: A0A3B5LTD1)
Zea_mays: (RefSeq:               SEQ ID NO: 121 .S.......S...D...................................L...........................L
XP_001347894.1)

Consensus                        SEQ ID NO: 128 QLAVDANLLRVPEIRWLGVFTSDFEEVCLPDCCLLXLSSEDRRKXEGILTRCYLHREAPEWRLELEAMLZKGVKFEIEALSASSISFLSQEYIPQKIKLG
Aegilops_tauschii:               SEQ ID NO: 124 ..........V......................Q.Q.......L.......K......K.....EM............................Q.R..
(RefSeq: XP_020158624.1)
Brachypodium_distachyon:         SEQ ID NO: 125 .................G...............V...D.....K.L............A................E..........................
(RefSeq: XP_003559449.1)
Hordeum_vulgare_subsp._vulgare:  SEQ ID NO: 127 .M........V......................Q.P.......T.L..................K..E..E..........S.............T.MD.
(UniProt: A0A2B75060)
Musa_acuminata_subsp._           SEQ ID NO: 120 .M...............S......H.LQK.H..R...E.Y.D.KK.A.AM.L....QK...K.M..V..QT......S..FN.L............T.MD.
malaccensis: (XP_009380133.2)
Oryza_sativa_Japonica_Group      SEQ ID NO: 123 ........M........D.......M..........A....S...........Q..............Q....C......E...K....Q.
(RefSeq: XP_001391702.1)
Sorghum_bicolor:                 SEQ ID NO: 122 .M.............D..................H.P...AR.A........V...S.......Q.........N....D.......Q.
(RefSeq: XP_002465440.1)
```

-continued

Sequence Alignment 2: SPO11-1 sequences from monocotyledonous plants.
SPO11-1 Monocots
Homologs identified by BLAST of Oryza sativa os03g54091.1 from MSU -
Osa1 Release 7 map to monocot NCBI RefSeq, GenBank and UniProtKB protein databases

```
Triticum_aestivum:              SEQ ID NO: 126 .......I.................Q.Q.........L.....K.....EM.........Q.R.
(UniProt: A0A3B5LTD1)
Zea_mays: (RefSeq:              SEQ ID NO: 121 ...H........D...............R.P...A...A.......S...Q...........N....H.......Q
XP_001347894.1)

- -
Consensus                       SEQ ID NO: 128 RXI
Aegilops_tauschii:              SEQ ID NO: 124 .Y.
(RefSeq: XP_020158624.1)
Brachypodium_distachyon:        SEQ ID NO: 125 .H.|
(RefSeq: XP_003559449.1)
Hordeum_vulgare_subsp._vulgare: SEQ ID NO: 127 .Y.
(UniProt: A0A2875060)
Musa_acuminata_subsp._          SEQ ID NO: 120 5YL
malaccensis: (XP_009380133.2)
Oryza_sativa_Japonica_Group:    SEQ ID NO: 123 .H.
(RefSeq: XP_001391702.1)
Sorghum_bicolor:                SEQ ID NO: 122 MHL
(RefSeq: XP_002465440.1)
Triticum_aestivum:              SEQ ID NO: 126 .Y.
(UniProt: A0A3B5LTD1)
Zea_mays: (RefSeq:              SEQ ID NO: 121 MHL
XP_001347894.1)
```

TABLE 2

Percent identities of SPO11-1 protein sequences from monocotyledonous plants.

| SPO11-1 Monocot % ID | Musa acuminata subsp. malaccensis: (XP_009380133.2) | Zea mays: (RefSeq: XP_008643458.1) | Sorghum bicolor: (RefSeq: XP_021304292.1) | Oryza sativa Japonic Group: (RefSeq: XP_015630525.1) | Aegilops tauschii: (UniProt: M8BE82) | Brachypodium distachyon: (RefSeq: XP_003559449.1) | Triticum aestivum: (UniProt: A0A3B6LTD1) |
|---|---|---|---|---|---|---|---|
| Zea mays: (RefSeq: XP_008643458.1) | 42.384 | | | | | | |
| Sorghum bicolor: (RefSeq: XP_021304292.1) | 48.25 | 80.867 | | | | | |
| Oryza sativa Japonic Group: (RefSeq: XP_015630525.1) | 50.877 | 56.522 | 65.274 | | | | |
| Aegilops tauschii: (UniProt: M8BE82) | 44.717 | 49.533 | 54.948 | 53.671 | | | |
| Brachypodium distachyon: (RefSeq: XP_003559449.1) | 57.895 | 62.557 | 71.354 | 73.958 | 66.076 | | |
| Triticum aestivum: (UniProt: A0A3B6LTD1) | 57.463 | 61.327 | 69.43 | 74.352 | 72.362 | 86.563 | |
| Hordeum vulgare subsp. vulgare: (UniProt: A0A287SD60) | 58 | 61.327 | 69.531 | 73.698 | 69.949 | 87.013 | 94.301 |

```
Sequence Alignment 3: PAIR1 sequences from monocotyledonous plants.
                                                  PAIR1 Monocots
          Homologs identified by BLAST of Oryza sativa Os03g01590.1 from MSU -
      Osa1 Release 7 map to monocot NCBI RefSeq, GenBank and UniProtKB protein databases 10         20         30         40         50         60         70         80         90        100
                                                  |          |          |          |          |          |          |          |          |          |
Consensus                                         MXGRVGEYNCPRQQRIQNRSASHSITPLLLGCSSGTGDHHCRRRLLAPARSREXXMKLKINKACDLXSISVLPPRRTGGSSGAGGXXXSXAAAVAAGSQ
Musa_acuminata_                       SEQ ID NO: 136 ......................................................R...G.......S..M.SG.B.LGR.Q.SQIHSQ.
  subsp._malaccensis:                 SEQ ID NO: 129
  (RefSeq: XP_018685297.1)
Triticum_aestivum:                    SEQ ID NO: 130 ........................................................A..............R....G...GGT.AP..AS.AQ.
  (UniProt: A0A3B6C7X9)
Hordeum_vulgare_subsp._vulgare:       SEQ ID NO: 131 ............................................T..................IA..............G---GRMS..AQQQQ.
  (RefSeq: XP_044983266.1)
Aegilops_tauschii:                    SEQ ID NO: 132 ...........................................................AMSG..SSIPQTDRL.------DWLS.WKL.II
  (UniProt: N1R2L9)
Brachypodium_distachyon:              SEQ ID NO: 133 ..................................................................................................
  (RefSeq: XP_014751501.1)
Sorghum_bicolor:                      SEQ ID NO: 134 ..........................................QA.................G.................G...E-AG.S...
  (UniProt: A0A1B86QR58)
Zea_mays: (RefSeq:                    SEQ ID NO: 3   ...............................................................G.................G...AG.S..P...
  XP_008660580.1)
Zea_mays: (GenBank:                   SEQ ID NO: 5   ...........................................AG.................S.................G---SSAA.....
  ONL92656.1)
Oryza_sativa_Japonica_Group:          SEQ ID NO: 135 ...............................................................IA................SA.GSV..VA..
  (RefSeq: XP_015632198.1)

110        120        130        140        150        160        170        180        190        200
                                                  |          |          |          |          |          |          |          |          |          |
Consensus                                         QRSQPMSQXSXSQQKGXXXSXXXXXXKGASFSQGMGSGGASFSQGRGASFSQSXSTGGAAAAFSQGGGGGGGASFSQGRGAFSQGSGXGAXXXSXGGG
Musa_acuminata_                       SEQ ID NO: 136 .S......................................................................................
  subsp._malaccensis:                 SEQ ID NO: 129
  (RefSeq: XP_018685297.1)
Triticum_aestivum:                    SEQ ID NO: 130 ....S...K.F...I.ASF.QGIGS.-------------------------------------------------G...AFSQ-G...
  (UniProt: A0A3B6C7X9)
Hordeum_vulgare_subsp._vulgare:       SEQ ID NO: 131 ....S...K.F..G.GVG.FSQSV.--------------------S-----------------------------T..VAAF.Q....
  (RefSeq: XP_044983266.1)
Aegilops_tauschii:                    SEQ ID NO: 132 V.ATYL---------------------------------------------------------------------
  (UniProt: N1R2L9)
Brachypodium_distachyon:              SEQ ID NO: 133 ......HSQQ-----------------------------------F-----------------------------
  (RefSeq: XP_014751501.1)
Sorghum_bicolor:                      SEQ ID NO: 134 ......H.---------------------------------------------------------------------
  (UniProt: A0A1B86QR58)
Zea_mays: (RefSeq:                    SEQ ID NO: 3   ......H.---------------------------------------------------------------------
  XP_008660580.1)
Zea_mays: (GenBank:                   SEQ ID NO: 5   ......L.Q-----------------------------------------------------------
  ONL92656.1)
```

Sequence Alignment 3: PAIR1 sequences from monocotyledonous plants.
PAIR1 Monocots
Homologs identified by BLAST of Oryza sativa Os03g01590.1 from MSU -
Osa1 Release 7 map to monocot NCBI RefSeq, GenBank and UniProtKB protein databases

```
                                                            210       220       230       240       250       260       270       280       290       300
                                                            |         |         |         |         |         |         |         |         |         |
Oryza_sativa_Japonica_Group:            SEQ ID NO: 135  .....L..SQQ.----------------------------------------------------------------------------------
(RefSeq: XP_015632198.1)

Consensus                                               XGSXGAXFSQGXKGGGGAAFSQGXXGGGSXFSQGGGXSSLLHSQSQLSQASLDENLLSLHLASPARDQRFGLHDKDSSKRMXSXPXSASSCVREESQLQL
Musa_acuminata_                         SEQ ID NO: 136
subsp._malaccensis:                     SEQ ID NO: 129  ...................I........................L....SFE.P.V..........N........SQE.N.L.KI.SLAPI..ET.
(RefSeq: XP_018685297.1)
Triticum_aestivum:                      SEQ ID NO: 130  G.AA--.........GG....A......SA....A............S......ESQA...............AMQE..P.....S.YLA........M.D.....
(UniProt: A0A3B6C7X9)
Hordeum_vulgare_subsp._vulgare:         SEQ ID NO: 131  A.G.D....R.....GG....A......SG....A............E.N....Q--.A............S.QE............TP.Y.A........D.....
(RefSeq: XP_044983266.1)
Aegilops_tauschii:                      SEQ ID NO: 132  .................................T.VPSPIVTSICM.---.VG..G...................................PPF.P...RAHE.PQ.Q.P
(UniProt: N1R2L9)
Brachypodium_distachyon:                SEQ ID NO: 133  ......P.............................................LE...GQT..QQ.PA..H..I....-NV.SQIP.F.PM.......Q....Q.
(RefSeq: XP_014751501.1)
Sorghum_bicolor:                        SEQ ID NO: 134  --.................VM.-S----...............T.....................................K.P.L.V............
(UniProt: A0A1B86QR58)
Zea_mays: (RefSeq:                      SEQ ID NO: 3    ------------------.VV------.S..A.........T..........................F....L..K.I.L.V.-----
XP_008660580.1)
Zea_mays: (GenBank:                     SEQ ID NO: 5    ------------------.AV--S---.A...............T.......................G.R..........K.T.L.VT.........
ONL92656.1)
Oryza_sativa_Japonica_Group:            SEQ ID NO: 135  ------------------.A................SA.........F.V..D..T..P.F............S.LA...........A.....
(RefSeq: XP_015632198.1)

310       320       330       340       350       360       370       380       390       400
                                                            |         |         |         |         |         |         |         |         |         |
Consensus                                               AKXPSNPXHRWNXPSLXDXRSFXELHSXLFECLTGSGLCGVXXNEDVERKFQHLASSVHKVGMVLDSVQNDVMQLNRAMKEASLDSGSIQQKXVVLXLSL
Musa_acuminata_                         SEQ ID NO: 136
subsp._malaccensis:                     SEQ ID NO: 129  TRAS..VM....AA.MS.N.-...........................QVS.EL.M.LR.IE..ENR..I......S.....V..A..L..EVEG.R..VS----
(RefSeq: XP_018685297.1)
Triticum_aestivum:                      SEQ ID NO: 130  ..I.T..I..S--.FL.S.C---------------------------------QV.............L.....Q.M..I...............G.........K.F...-L---
(UniProt: A0A3B6C7X9)
Hordeum_vulgare_subsp._vulgare:         SEQ ID NO: 131  TTT.T..I..S--.P.S----------------------------------QI.E................L..I.................S..........K.F........
(RefSeq: XP_044983266.1)
Aegilops_tauschii:                      SEQ ID NO: 132  VIV..STTL...PT.T.-C--------------------------------RV..A..R......SG............T..I.......T.D...K..VV...FD---
(UniProt: N1R2L9)
Brachypodium_distachyon:                SEQ ID NO: 133  .ISN.TI-P.RN.C.AES.--------------------------------QVA.A.HR..Q..N..CRIE..............I......S.............D...R.V.L.DN.
(RefSeq: XP_014751501.1)
Sorghum_bicolor:                        SEQ ID NO: 134  .T....V......P.G...-C-----------------------------.VPT...................N................................A.....M..I.....
(UniProt: A0A1B86QR58)
Zea_mays: (RefSeq:                      SEQ ID NO: 3    .TS...V.......P.G.----------------------------------.GPT...................M..........T.............T........I.L----
XP_008660580.1)
```

Sequence Alignment 3: PAIR1 sequences from monocotyledonous plants.
PAIR1 Monocots
Homologs identified by BLAST of Oryza sativa Os03g01590.1 from MSU -
Osa1 Release 7 map to monocot NCBI RefSeq, GenBank and UniProtKB protein databases

```
                                                      410       420       430       440       450       460       470       480       490       500
                                                        |         |         |         |         |         |         |         |         |         |
Zea mays: (GenBank:
ONL92656.1)                                SEQ ID NO: 5   ..TS...V.......P.S.YI...F..........T.VPA......M...................................A..........I....
Oryza_sativa_Japonica_Group:
(RefSeq: XP_015632198.1)                   SEQ ID NO: 135 ..L....V......IA.T.....-G-------QVT...................M.V....S.................R..IA.--------

Consensus                                  SEQ ID NO: 136 QKILMVKDLEAGSIQQNDSLLEXSLQQILKGQDDLKALXEKSTKSNXDQLXVLNSKXXKLBEISSXLSXLPKQXZKDLXQLXGDIFRIFTKXMEXIVRAI
Musa_acuminata_
subsp._malaccensis:
(RefSeq: XP_018685297.1)                   SEQ ID NO: 129 ----------------------------------.N.M.MV.NE..I.FIGG.LT IS..IKIS.-SG.VN..A.AVAI.QE.NFSR.AR.ECEVC.F.-SEK.VRESG.
Triticum_aestivum:
(UniProt: A0A3B6C7X9)                      SEQ ID NO: 130 ---------------------------------.D.K..........LKG.....P...GI--TR..D....I.V....VQTEFE.FK....F...E..GV...V
Hordeum_vulgare_subsp._vulgare:
(RefSeq: XP_044983266.1)                   SEQ ID NO: 131 ---------------------------------.D.K........L--.F.G.E..P...S......TR..D.MT.I.A..NHLQAEFG..K..TY.....E..G.A.G
Aegilops tauschii:
(UniProt: N1R2L9)                          SEQ ID NO: 132 -----------------------------.DT..K.I..N....V.A.N......L...N.I..RTS..N.M.LVV.VC...VQA..RE.H.....VL..D..GV..D
Brachypodium_distachyon:
(RefSeq: XP_014751501.1)                   SEQ ID NO: 133 .......Q.G........V..DN........G..E.L.GG.....P...S......TST.S....I..VWQEEIRA..R..H.........E.KGV......
Sorghum_bicolor:
(UniProt: A0A1B86QR58)                     SEQ ID NO: 134 ------L-----------.DT..KN..............V.SN...IS....T.....SN..D....T..I....IET..K.QMS........R.D..E....V
Zea_mays: (RefSeq:
XP_008660580.1)                            SEQ ID NO: 3   -----------------.DAE..KN..............V.SN...IS....T....YSN..D....T..I....IETN.K.QQS.T.......R.D..E....V
Zea_mays: (GenBank:
ONL92656.1)                                SEQ ID NO: 5   -----------------.DT.M.KN...G...V.V.SN..NIA......A......SN..V.....A..V.....IER..K.QQS......RNN..E.A..V
Oryza_sativa_Japonica_Group:
(RefSeq: XP_015632198.1)                   SEQ ID NO: 135 ----------.S----------------------FGS....H.P..TS......LGS..N....T.AT.QT.MQA-.R..Q..QTTVLNSNASK-SNE.

510       520       530       540       550       560       570       580       590       600
                                                        |         |         |         |         |         |         |         |         |         |
Consensus                                  SEQ ID NO: 136 RSLNXXEXAXXQMXXDQSCTTNGRPLMNQLPVDRNERPQVNQTPEVIRMSXTPVATMVXQTXVASLVNQTPVABGSPLMNQXPXANXXXXMNQTXVANGR
Musa_acuminata_
subsp._malaccensis:
(RefSeq: XP_018685297.1)                   SEQ ID NO: 129 K.S.NQHSVKF.SP.......................................................................................
Triticum_aestivum:
(UniProt: A0A3B6C7X9)                      SEQ ID NO: 130 ...DSRLPGVM..LA........AK....HTAAENE----S----------.....M..............P.M..Q..E.......G.V.DRRPQKKP.A....
Hordeum_vulgare_subsp._vulgare:
(RefSeq: XP_044983266.1)                   SEQ ID NO: 131 ..I.TRLD.-M..LAE......AKT..-----S--------------------------------------Q--------A..M.......T.V.VGSTL...GA..D.S
Aegilops tauschii:
(UniProt: N1R2L9)                          SEQ ID NO: 132 ...STK-P.VMP.LP.H........................---V------------------------------------------K.........KMSV..ERPT.....
Brachypodium_distachyon:
(RefSeq: XP_014751501.1)                   SEQ ID NO: 133 ...SR-P.AL..LE.R..YP.E.TWSS-----Q-------------------------------------V---------Q..D........I.L..ERLK.-------
Sorghum_bicolor:
(UniProt: A0A1B86QR58)                     SEQ ID NO: 134 ...SKID.-I..PT..H..T.....................................Q................N.s.................A.N.RH.VS.I.A..GKTLVS..S......
Zea_mays: (RefSeq:
XP_008660580.1)                            SEQ ID NO: 3   ...NKID.-I..PT..........................-----------------N---------------------------------ER.QVNQT.EVTRVSQTPVATMA..RP..K...
Zea_mays: (GenBank:
ONL92656.1)                                SEQ ID NO: 5   K...SKID.-I..PTE.R.......................................-----V--------------S..T.........A.A..N.RH..SKT..A..GKSV.R..PAE...
```

-continued

Sequence Alignment 3: PAIR1 sequences from monocotyledonous plants.
PAIR1 Monocots
Homologs identified by BLAST of Oryza sativa Os03g01590.1 from MSU
Osa1 Release 7 map to monocot NCBI RefSeq, GenBank and UniProtKB protein databases

```
                                                                                        700
                                                                                         |
Oryza_sativa_Japonica_Group:        SEQ ID NO: 135  S.TLATLQTQM.---------------------------------A-------------------DIRQ.RCDVFRVFTKEM----
(RefSeq: XP_015632198.1)

610       620       630       640       650       660       670       680       690
                                                     |         |         |         |         |         |         |         |         |
Consensus                           SEQ ID NO: 136  XLXSXQTPVAXGXPLXXNQXXXANGXXXXXQVPXXAANGXPXXNQTPVAXGRPXMXXQXXXXXGRSQMNQIPVAXGWPHTXKXXPAXXVKPAPLVXPXKX
Musa_acuminata_                     SEQ ID NO: 129  --------S.NYMDIKESLEG.IEEKK---------VSAA.LMSN--KQRS.PFKKEGKLESFK.KLTE------------------------------
subsp_malaccensis:
(RefSeq: XP_018685297.1)
Triticum_aestivum:                  SEQ ID NO: 130  PKRKN.A..N.R.QRK..AAG..WRPHRKKPTEI...SR.QRML.R..N...QV-K.TEAAD....T..K.E.N.----KALI.VTKPI.V.V.VHR.-
(UniProt: A0A3B6C7X9)
Hordeum_vulgare_subsp._vulgare:     SEQ ID NO: 131  P.MNH.G...D.R.Q-KR.RPA...RSQRKKQTPV.SGRAQRKR.R...N...QV-K.AQTAD......N...K.E.N.EALMKQVL..TQ.A.....YQR.-
(RefSeq: XP_044983266.1)
Aegilops tauschii:                  SEQ ID NO: 132  ------------K.S.-M.KMSV..ERPTMN.T.-V..R.LN......N.S.MTIN.ARVSN.....LK.T------T--------------------
(UniProt: N1R2L9)
Brachypodium_distachyon:            SEQ ID NO: 133  --------.SI.E.-M.LAVV..SPLIN.S.-V..RSQM.......N...Q.-DRTPVAN..PK.E.-........TNLF..RSSCSTK---------
(RefSeq: XP_014751501.1)
Sorghum_bicolor:                    SEQ ID NO: 134  S.M.-.V.T.N.K..-T..ASL..GSLMS.......K.LT..I.APK...M.-R.KTGER..P........S..T..N.I-..PE.H.....F.ASA
(UniProt: A0A1B86QR58)
Zea_mays: (RefSeq:                  SEQ ID NO: 3    H.V.-...A.N.K..-T..TSV..RSLMS.......K.LT..IA.PK...M.-R.KTAEG..P........D.....N.IHAPEVRH.V...C.----
XP_008660580.1)
Zea_mays: (GenBank:                 SEQ ID NO: 5    H.V.-...A.N.KT.-KR.TSVI..ISLMS.......K.VVI.I.APK...M.-R.KTAES..TE.E......S.R...N.I-.IAE.H......C.A.Q
ONL92656.1)
Oryza_sativa_Japonica_Group:        SEQ ID NO: 135  -----EGV.RAIRSVNSROAANQMMADQSY....-VS..WTQI......A..SP.-NRAPVAA....R...L.E--------T.VLS.ML.Y.KVT----
(RefSeq: XP_015632198.1)

710       720       730       740       750       760       770       780       790       800
                                                     |         |         |         |         |         |         |         |         |         |
Consensus                           SEQ ID NO: 136  KXAADPKPKVEQGKXKAXPGAQKLXGSXXXXRPVXPKQBEXAXXKVNXZXPAXKXEKVVXIIIDSDDDSDXEGGGSEXXASCVILXXXXGXEXGXXEX
Musa_acuminata_                     SEQ ID NO: 129  ------.HT.KHKHII----H-------------T.......F------------------RV.V.L.EE.-------I..L.VNKG--------TGKKS
subsp_malaccensis:
(RefSeq: XP_018685297.1)
Triticum_aestivum:                  SEQ ID NO: 130  --V.L..R...WMVP------..A.PSYS..AP..EQ.L.IQ...TEA.IN.MQATLG.L......G.V..AD.DWS......KLEAGCP.D.VVAE.A
(UniProt: A0A3B6C7X9)
Hordeum_vulgare_subsp._vulgare:     SEQ ID NO: 131  -KEGVQ..A...MS..GT......A..GDS..AS...EQ.L.IQ.D.AEA.IN.A--MLA.L...EEEEE-......GN....L.KSTEA.------GVAM
(RefSeq: XP_044983266.1)
Aegilops tauschii:                  SEQ ID NO: 132  ------AM.QRD---------------------LT.E----------------------NGRPQK.--------------------------------
(UniProt: N1R2L9)
Brachypodium_distachyon:            SEQ ID NO: 133  .......NI...DV..TT--P..F..SY..-LA...G.VLNR...QQE.TK.AP--.T.M......E---H------W...NTEPADLMK.ASRE.G
(RefSeq: XP_014751501.1)
Sorghum_bicolor:                    SEQ ID NO: 134  A.......A..DD..L.VL.---..T..RSR---T.....A.ST.F---SR.AAT....IF.E.-......-VHA---S.....RSSGS.A.AGA.ER.C
(UniProt: A0A1B86QR58)
Zea_mays: (RefSeq:                  SEQ ID NO: 3    ---.G.R....E..LR.V.---..T.CRSR-..T.....A.TNTKVVGR.AAT...IF.D.DS........AL........RPAPL.---S.AG.C
XP_008660580.1)
```

-continued

Sequence Alignment 3: PAIR1 sequences from monocotyledonous plants.
PAIR1 Monocots
Homologs identified by BLAST of Oryza sativa Os03g01590.1 from MSU
Osa1 Release 7 map to monocot NCBI RefSeq, GenBank and UniProtKB protein databases

```
                                                                    810        820        830        840        850        860        870
                                                                    |....:....|....:....|....:....|....:....|....:....|....:....|....:....|
Zea_mays: (GenBank:                                      SEQ ID NO: 5    -V.T.....DEE.L..L...TS.RSR--.A....A.NT..I--ST.AAT....IF.D.....N------VR......RPSGS.---SL.ER.C
ONL92656.1)
Oryza_sativa_Japonica_Group:                             SEQ ID NO: 135  -----L........V..A.-..PFA.SYY.-.A....V.IR...IQV..K.AP-.S....E......E------GR......NTE------T.SL.N
(RefSeq: XP_015632198.1)

Consensus                                                SEQ ID NO: 136  XXXXXGAEEXLEXLRRARXIDXTALPDVMXXKRRMGKAAPERREMQAXVXXXXPXKRTXXPNPKYDAZXXXX
Musa_acuminata_                                          SEQ ID NO: 129  SFMEEVQ.DT.R...K.-------------M.M.-------.Q.NSITVV-----
subsp._malaccensis:
(RefSeq: XP_018685297.1)
Triticum_aestivum:                                       SEQ ID NO: 130  --TSE.EG.A..........................AN.NANATVLV------------Q-DQR
(UniProt: A0A3B6C7X9)
Hordeum_vulgare_subsp._vulgare:                          SEQ ID NO: 131  AEEAM.EG.A..............-K-R.-------E.AN.V.LD-------H---
(RefSeq: XP_044983266.1)
Aegilops_tauschii:                                       SEQ ID NO: 132  ------------
(UniProt: N1R2L9)
Brachypodium_distachyon:                                 SEQ ID NO: 133  MQLLWS.RKRSRRK.ET.C..A.....RG.K........AQ.EE.VHVEAI.A...CR......EQWTA
(RefSeq: XP_014751501.1)
Sorghum_bicolor:                                         SEQ ID NO: 134  DLM.V....SQ..M.....-K-.................E------VGH
(UniProt: A0A1B86QR58)
Zea_mays: (RefSeq:                                       SEQ ID NO: 3    DLV.V....SQ...........................T.ACMP.-----E-------LGY
XP_008660580.1)
Zea_mays: (GenBank:                                      SEQ ID NO: 5    DLM.V....SQ..P....K-..................T.GVACM----P---L------LPA
ONL92656.1)
Oryza_sativa_Japonica_Group:                             SEQ ID NO: 135  KVT.Q.T..G............................SI.LAS-
(RefSeq: XP_015632198.1)
```

TABLE 3

Percent identities of PAIR1 protein sequences from monocotyledonous plants.

| PAIR1 Monocot % ID | Musa acuminata subsp. malaccensis: (RefSeq: XP_018685297.1) | Triticum aestivum: (UniProt: A0A3B6C7X9) | Hordeum vulgare subsp. vulgare: (RefSeq: XP_044983266.1) | Aegilops tauschii: (UniProt: N1R2L9) | Brachypodium distachyon: (RefSeq: XP_014751501.1) | Sorghum bicolor: (UniProt: A0A1B6QR58) | Zea mays: (RefSeq: XP_008660580.1) | Zea mays: (GenBank: ONL92656.1) |
|---|---|---|---|---|---|---|---|---|
| Triticum aestivum: (UniProt: A0A3B6C7X9) | 23.184 | | | | | | | |
| Hordeum vulgare subsp. vulgare: (RefSeq: XP_044983266.1) | 22.141 | 57.324 | | | | | | |
| Aegilops tauschii: (UniProt: N1R2L9) | 18.502 | 25.701 | 22.895 | | | | | |
| Brachypodium distachyon: (RefSeq: XP_014751501.1) | 17.04 | 30.976 | 28.61 | 29.61 | | | | |
| Sorghum bicolor: (UniProt: A0A1B6QR58) | 22.687 | 38.108 | 35.525 | 24.434 | 29.184 | | | |
| Zea mays: (RefSeq: XP_008660580.1) | 27.083 | 42.178 | 39.08 | 27.098 | 31.013 | 66.269 | | |
| Zea mays: (GenBank: ONL92656.1) | 24.598 | 38.937 | 36.156 | 24.959 | 29.602 | 69.4 | 67.903 | |
| Oryza sativa Japonica Group: (RefSeq: XP_015632198.1) | 29.354 | 38.735 | 36.75 | 27.006 | 32.721 | 39.493 | 44.658 | 42.165 |

```
Sequence Alignment 4: OSD1 protein sequences from monocotyledonous plants.
                                         OSD1 Monocots
         Homologs identified by BLAST of Oryza sativa 0s02g37850.1 from MSU -
    Osa1 Release 7 map to monocot NCBI RefSeq, Genbank and UniProtKB protein databases 10        20        30        40        50        60        70        80        90       100
                                       |         |         |         |         |         |         |         |         |         |
Consensus                        SEQ ID NO: 144 MSYTNFSXBKKMXEVRXASRXALADXSGGXXKGGGFFIRRRVASPGAVXXKGAVKPLARRVKSPSSNKENVPPXWAARAXPXKRRSPLPEWYPRTPLRDIT
Musa_acuminata_                  SEQ ID NO: 137 -----------A.T.QGVNRG-RETT.SATNL.W...-AAYLASRT.SRSTRVQS.VFATDD....T.SR..HKGRT.K....
subsp._malaccensis:
(RefSeq: XP_009415567.1)
Brachypodium distachyon:         SEQ ID NO: 138 ................-V......TV..T.V.ER.............E.......VE...A.R....PLT..........A..VATTQ-.....T..........S..........
(UniProt: I1IB35)
Hordeum vulgare subsp. vulgare:  SEQ ID NO: 139 ................A...I....T.A..R.........V...-V.......VD................L.P...........A...WTA.-.....F..................
(UniProt: F2EGV1)
Triticum aestivum:               SEQ ID NO: 140 ................A...I....T.V..R.........V.............VD.................P............A...WTA.-...................S...
(UniProt: A0A3B6PL33)
Aegilops tauschii:               SEQ ID NO: 141 ................A...M...A.V..R...........V.............VD.................P............A......W.A.-..................S...
(UniProt: M8CG24)
Sarghum bicolor:                 SEQ ID NO: 142 ---------------PQL.T....PV..RN----T..I....-...........-...........RTHF............VG........K.......................D......S...
(UniProt: C5XWE8)
Oryza sativa: (RefSeq:           SEQ ID NO: 143 ---------------P.M.DSK.T..GEL.........-...............LAAR.PG..........FTR..N.......V..VK.TAT........................D......
XP_015635088)
Zea mays: (UniProt: B4FG75)      SEQ ID NO: 4   ----------P.S.DGRSED....L....VG............................LAVR.VR........YI....H......LL.V..L.VT.-TK........G.........
Zea mays: (GenBank: AQK72186.1)  SEQ ID NO: 6   ------RNF.L..T.R.P.....I-----...M.T-.E....LVN......RP..QFL.............VG.F..T......T...........D..........
Zea mays: (GenBank: AQK72188.1)  SEQ ID NO: 7   .......QDV..PQL.T.-.P...SN-----A......................TSQA...A.......RT...............K.....................D....V....

110       120       130       140       150       160       170       180       190       200
                                       |         |         |         |         |         |         |         |         |         |
Consensus                        SEQ ID NO: 144 SIKXAXERHRSRLRXGGARQQBQWXEXSKSSEPXDXEYSSEPENPAQIDZXXHSKPDXSXXKTKETLGXXVKXXXXXXXVAKSATCLAEGXXXXXSKASD
Musa_acuminata_                  SEQ ID NO: 137 V.VN.L....N.V.A..TAR.RTSDPE---------------------AA---------VEKG.---LDSSSIPAAAGS.SVSAT.QPPQIC..SSNA
subsp._malaccensis:
(RefSeq: XP_009415567.1)
Brachypodium distachyon:         SEQ ID NO: 138 ..I..V..-KNL..D......L..T.D.....EN---------A.QDV.RRTPPTNGTLAAAVASDPAGSAQAVAST....V...TLKA----TG
(UniProt: I1IB35)
Hordeum vulgare subsp. vulgare:  SEQ ID NO: 139 ..I..V..-K...QD....M.L.DDEED....D.E..............EGI.---R.TAP.N...CV--GSAQVVETT.A.....G..KCATVVK...
(UniProt: F2EGV1)
Triticum aestivum:               SEQ ID NO: 140 VI..V..-K.....D.V....L..D.ED-....E..............E..............EGI.----G.TAP.N.....-GSAQVVETT.A......G..ESTTVVK...
(UniProt: A0A3B6PL33)
Aegilops tauschii:               SEQ ID NO: 141 VI..V..-K.....D.......L..D.ED-...E..............E..............EGI.----G.TAP.N......-GWAKVVETT.A......G..ESTTVVK...
(UniProt: M8CG24)
Sarghum bicolor:                 SEQ ID NO: 142 ..V..L.K-.N..EED.....HI..N.D.--PQ.V--------TT.VHAE..D..SQSTQ..Q.....V-.ASPGSTSA..NNV.SV..DKQEAS..SP.-
(UniProt: C5XWE8)
```

-continued

Sequence Alignment 4: OSD1 protein sequences from monocotyledonous plants.

OSD1 Monocots

Homologs identified by BLAST of Oryza sativa Os02g37850.1 from MSU Osa1 Release 7 map to monocot NCBI RefSeq, Genbank and UniProtKB protein databases

```
                                             210        220        230        240        250        260
                                         ....|....:....|....:....|....:....|....:....|....:....|....:
Oryza sativa: (RefSeq:                   SEQ ID NO: 143 A.A..IQ.-...:....I...Q.RS.TP.Q----NT--------------P------CTEVRDS.DV-EPGINSTQI..TP.SS..KDSLKIF.SP.-
XP_015635088)
Zea mays: (UniProt: B4FG75)              SEQ ID NO:   4 A.A..TQ.S...I-...Q.RS.RI.Q.SQ.VNVTT-----------.AEQDA.------IAEASHAVASG-SGSTEREA..NP..V..DDNLNVS.L.A-
Zea mays: (GenBank: AQK72186.1)          SEQ ID NO:   6 .V..I......QN...Q..I.T.DP..RSV.---------------.---------PI-------TPVQAEQ.S--PTTVDGQG.GSP...ED.KLKTS.VP.S
Zea mays: (GenBank: AQK72188.1)          SEQ ID NO:   7 .V..L.K-.N..EED....HI.SN.D.---Q.V.P----------------------TTAE.N.SQSTQ.Q..P.AVASGPSSTSA..NRV.SV...KQEAT----

Consensus                                SEQ ID NO: 144 DCSLQXPSXKPNDPSXXDKVEKKLSSSIEQIEKMVRRNLKRTPDPKAAQPSKXPAVQRRTLMSMR
Musa_acuminata_                          SEQ ID NO: 137 SSPRED.------.DQPTEY..N.ETY.GEM.RL.TE....S.M.P.KRA------K...I...
subsp._malaccensis:
(RefSeq: XP_009415567.1)
Brachypodium distachyon:                 SEQ ID NO: 138 .......T..RQG.H.ALS.LL..L.A.........CQ..TLG---------.TQ..........
(UniProt: I1lB35)
Hordeum vulgare subsp. vulgare:          SEQ ID NO: 139 .....S..R------.GE.D...Q.AN..HE......S........TRT..T..............
(UniProt: F2EGV1)
Triticum aestivum:                       SEQ ID NO: 140 .....S..R------.GE.D...Q.AN..QE..N..S.........TR...T..............
(UniProt: A0A3B6PL33)
Aegilops tauschii:                       SEQ ID NO: 141 .....ST.R------.GEVG...Q.A...DA......S........E.TR...T............
(UniProt: M8CG24)
Sorghum bicolor:                         SEQ ID NO: 142 .....MAPS......PA.-L...M..........HM.E.-------........L-V....I....
(UniProt: C5XWE8)
Oryza sativa: (RefSeq:                   SEQ ID NO: 143 ET..VT..K-.M..VLL.DM..........................KAA......R-.I......
XP_015635088)
Zea mays: (UniProt: B4FG75)              SEQ ID NO:   4 EG...NT.PK----.MDPALAD....G....KV..L..K......-SR...A.KK..T..N.....
Zea mays: (GenBank: AQK72186.1)          SEQ ID NO:   6 .....ATPS......ALA.L........................-S......R-TI...V.....
Zea mays: (GenBank: AQK72188.1)          SEQ ID NO:   7 .....VAPS......PA.L.........G..................HM.E.-H......V-V...I.....
```

TABLE 4A

Percent identities of OSD1 sequences from monocotyledonous plants.

| OSD1 Monocot % ID | *Musa acuminata* subsp. *malaccensis*: (RefSeq: XP_009415567.1) | Brachypodium distachyon: (UniProt: I1IB35) | *Hordeum vulgare* subsp. *vulgare*: (UniProt: F2EGV1) | Triticum aestivum: (UniProt: A0A3B6 PLJ3) | Aegilops tauschii: (UniProt: M8CG24) | Sorghum bicolor: (UniProt: C5XWE8) | Oryza sativa: (RefSeq: XP_015635088) | *Zea mays*: (UniProt: B4FG75) | *Zea mays*: (GenBank: AQK72186.1) |
|---|---|---|---|---|---|---|---|---|---|
| Brachypodium distachyon: (UniProt: I1IB35) | 26.033 | | | | | | | | |
| *Hordeum vulgare* subsp. *vulgare*: (UniProt: F2EGV1) | 29.098 | 55.645 | | | | | | | |
| Triticum aestivum: (UniProt: A0A3B6PLJ3) | 29.614 | 60.169 | 86.192 | | | | | | |
| Aegilops tauschii: (UniProt: M8CG24) | 28.755 | 59.322 | 82.427 | 93.805 | | | | | |
| Sorghum bicolor: (UniProt: C5XWE8) | 25.726 | 47.458 | 45.565 | 48.729 | 49.153 | | | | |
| Oryza sativa: (RefSeq: XP_015635088) | 29.596 | 47.28 | 44.262 | 46.154 | 46.154 | 48.101 | | | |
| *Zea mays*: (UniProt: B4FG75) | 27.778 | 41.975 | 41.736 | 42.553 | 42.979 | 40.664 | 55.508 | | |
| *Zea mays*: (GenBank: AQK72186.1) | 26.407 | 51.037 | 48.594 | 51.055 | 52.321 | 54.393 | 54.545 | 47.083 | |
| *Zea mays*: (GenBank: AQK72188.1) | 22.4 | 44.715 | 40.385 | 42.972 | 43.373 | 72.764 | 42.276 | 38.34 | 50 |

Sequence Alignment 5: CYCA1 protein sequences from monocotyledonous plants.

CYCA1 Monocots

Homologs identified by BLAST of Arabidopsis thaliana AT1G77390 from AGI - TAIR10 mapr to monocot NCBI RefSeq, GenBank and UniProtKB protein databases.

```
                                                          10        20        30        40        50        60        70        80        90       100
                                                 ....|....|....|....|....|....|....|....|....|....|....|....|....|....|....|....|....|....|....|....|
Consensus                                 SEQ ID NO: 157 MSSXAAXXRSSSSSXSTAASAKAKRPFAKKEGAGGAXXXAAXXAAAXQQQACKRVAKGNITTNVAAAXGRAAVGGGCGKVAPXTTGNAKLNSATSAAPVK
Zea_mays: (Refseq: MP_001188521.1)        SEQ ID NO: 10  ..TI.SR.....................T.....IAD.P..PK-AT.A-----............................RG...S..SL.N.MAP.SS-.....PT--.V.L
Zea_mays: (Refseq: MP_001105387.2)        SEQ ID NO: 13  ..TH.SR.......-V..............-...IA....TK.A-GPSPT..........T.V..........S......PGARV.---.AV.....PV-.....P..G..L
Oryza_sativa_Japonica_Group:              SEQ ID NO: 145 ..NL.AS.R...S.V..A.A........VG.G..GG-GK.AAG..A-----...........S-.S-....GGG-...........................GKA......L.A....
(RefSeq: XP_015630726.1)
Sorghum_bicolor:                          SEQ ID NO: 146 ..TI.SR.................A.....IS.....PK-V..A-Q-----.........................RG...V.....L.NA...P..S---.P----V.L
(RefSeq: XP_002455447.1)
Brachypodium distachyon:                  SEQ ID NO: 147 ...T..AS.RL...AA.---T.......MA.N.....K-P.GRM.-----....P...................L......G.V.T-...............VV.A....R.H...TV.
(RefSeq: KP_003566077.1)
Brachypodium distachyon:                  SEQ ID NO: 148 ...N..AS.RL.AT---T.T.......MA..S...K-LVDPV.V-----...............................G.V.T-...............VV.A....R.H...TV.
(RefSeq: KP_003566081.1)
Aegilops touschii subsp._strangu-         SEQ ID NO: 149 ..NS.AP.RF..AM..---ST........VP.....RA.A-GP.AAQQ--..........L.................A..............I.VV........R......
lata: (RefSeq: XP_020187359.1)
Oryza_sativa_Japonica_Group:              SEQ ID NO: 150 ..................................A....GK-A..GA.--...V......................................................
(RefSeq: XP_025879970.1)
Hordeum_vulgare_subsp._vulgare:           SEQ ID NO: 151 ..NP.AP.RF..AM..---T.........VP..A..RPA.GPA..P---................L......................G..............I.VV.A....R.S..A.
(XP_044975533.1)
Triticum_aestivum:                        SEQ ID NO: 152 ..NS.AP.RF..AM..---ST........VP.....RA.AGP..AQQ----..............L..............A..................I.VV........R......
(RefSeq: XP_044356181.1)
Oryza_sativa_Japonica_Group:              SEQ ID NO: 153 ...SL.SR.................A.......MA....KA.GTA.--...........A.....................V..PA....-..AL......PV-...V.L
(RefSeq: XP_002578069.1)
Sorghum_bicolor:                          SEQ ID NO: 154 ..TR.SR...............MA.....KA.GTA..-----Q---.........................R..F......W.
(RefSeq: XP_002454800.1)
Sorghum_bicolor:                          SEQ ID NO: 155 ..TF.SR......--AS........MD.N.A.GPRMTRPQ-----T---...............F.P..R.-...AV.....PA.TR....P....L.
(RefSeq: XP_021311446.1)
Musa_acuminata_subsp._malaccensis:        SEQ ID NO: 156 NRRPSISS.A.AAS----S.......AT.S.SKNPAAL.GQ---------.........A..S..QSKV.RNP.-...................R.LGANG.NI.-T..S.ST
(RefSeq: XP_018678008.1)

110       120       130       140       150       160       170       180       190       200
                                                 ....|....|....|....|....|....|....|....|....|....|....|....|....|....|....|....|....|....|....|....|
Consensus                                 SEQ ID NO: 157 KGSLATSARNVXXNIRGSAVKSASXKPAPXXSRHXSSXXQKSXVXPPKVPTXVPXAXXAPAXVPCSSPVSPGHSGDSVSXDSTMSTCDSMKSPDFEYID
Zea_mays: (Refseq: MP_001188521.1)        SEQ ID NO: 10  .P......S.SSS.....D.P.I....PVA..G.AT-.RHNNV......IADVPSR..L.S.TGL....R....S......V
Zea_mays: (Refseq: MP_001105387.2)        SEQ ID NO: 13  .P...-N..TI-...-..A.....I....PV..D..SE.HN.L---.....T.HVPSR..L.V......R.R...T.....
Oryza_sativa_Japonica_Group:              SEQ ID NO: 145 .....G...GT.-.A..........AT...E.AT...S.L...-.SI..T.AL.VT..........M......V.....
(RefSeq: XP_015630726.1)
Sorghum_bicolor:                          SEQ ID NO: 146 .P..........S.SSI-..Q........I......PV...G.AI....HN.P.-.....IADVPSH...L..TGL....R..F.I.D
(RefSeq: XP_002455447.1)
Brachypodium distachyon:                  SEQ ID NO: 147 .............IT.......V.TR.T.VT.CRG.TT--QKEIV....L.AAM.IV-.-..PI...........R..A..M..T.
(RefSeq: KP_003566077.1)
Brachypodium distachyon:                  SEQ ID NO: 148 .....VQ.ATA...SL........TR.T.-------KA.DIV........VM.I.AS.--I...C.A..Q..E.I.T.......
(RefSeq: KP_003566081.1)
Aegilops touschii subsp._strangu-         SEQ ID NO: 149 .....HASA.--.........FT.....VT....E..V...S.-...R....V..I.VP.---VI.F.............I.T.....L.
lata: (RefSeq: XP_020187359.1)
Oryza_sativa_Japonica_Group:              SEQ ID NO: 150 ..A.P-....................AE.....E.AP....S.I.---.....LSI..T.AP.VT.............S......
(RefSeq: XP_025879970.1)
```

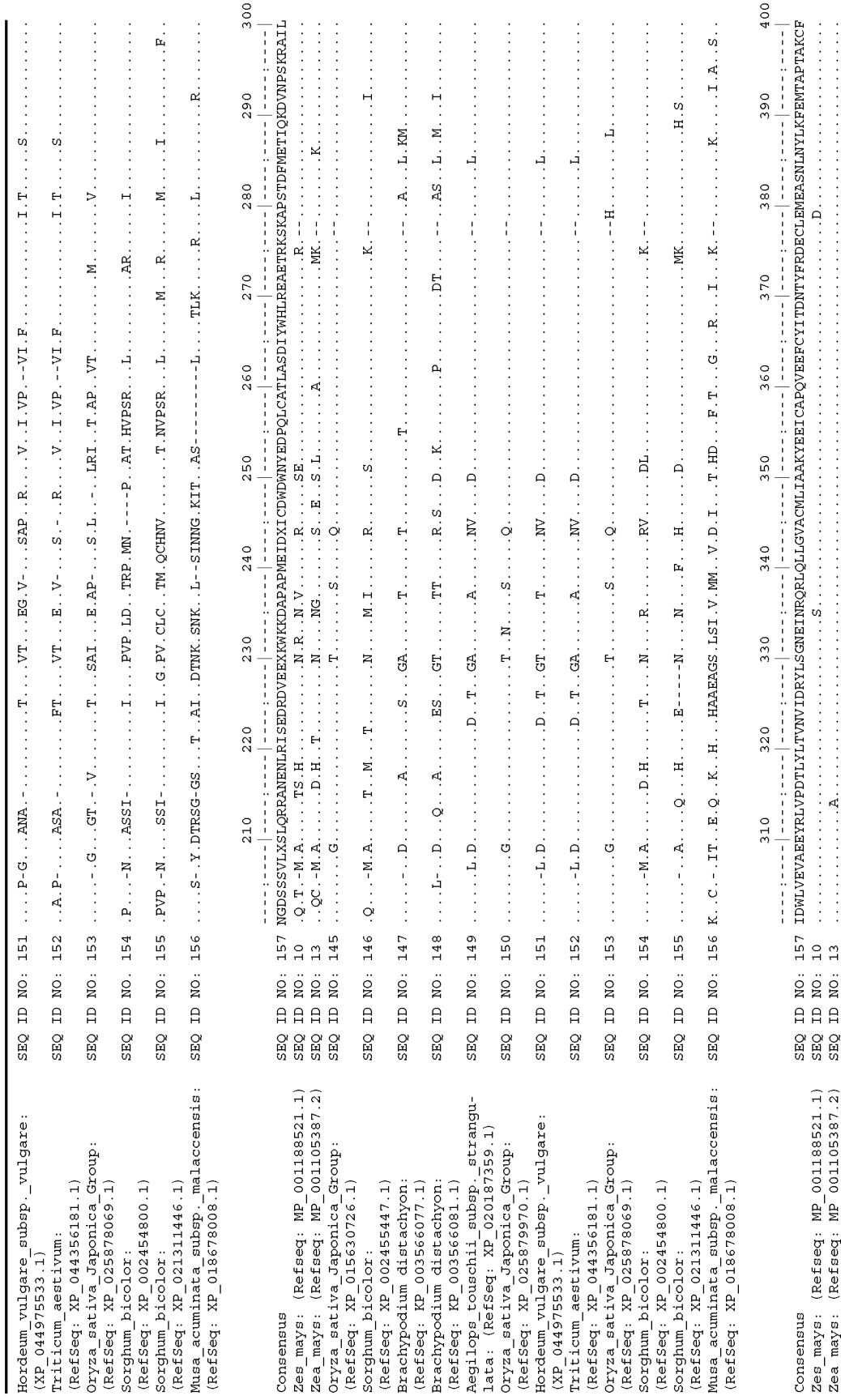

```
Sequence Alignment 5: CYCA1 protein sequences from monocotyledonous plants.
                                CYCA1 Monocots
Homologs identified by BLAST of Arabidopsis thaliana AT1G77390 from AGI -
TAIR10 mapr to monocot NCBI RefSeq, GenBank and UniProtKB protein databases.

410       420       430       440       450       460       470       480       490       500
                                                           ----+----|----+----|----+----|----+----|----+----|----+----|----+----|----+----|----+----|----+----|
Consensus                                      SEQ ID NO: 157  LRRFVHAAQVCDEDPALMLEFLANYVAELSLLEYSLLSYPPSLVAASAIFLAKFILQPTKXPMNSTLAMYIQYKPSELSDCVKALMRLFSVGPGSNLPAX
Zes_mays: (Refseq: MP_001188521.1)             SEQ ID NO: 10  ....A....A..........I.......I.......R...Y...........K.E....C..S
Zea_mays: (Refseq: MP_001105387.2)             SEQ ID NO: 13  ..A.S..A............I.......I.......R.V.Y...........E..T....S
Oryza_sativa_Japonica_Group:                   SEQ ID NO: 145 ....V..S............................................M..........
(RefSeq: XP_015630726.1)
Sorghum_bicolor:                               SEQ ID NO: 146 ....A....A..........I.......T.......R...Y...........C..S.T
(RefSeq: XP_002455447.1)
Brachypodium distachyon:                       SEQ ID NO: 147 ....V...............................V.S.............A..C
(RefSeq: KP_003566077.1)
Brachypodium distachyon:                       SEQ ID NO: 148 ..............P......N..............V...............S
(RefSeq: KP_003566081.1)
Aegilops_touschii_subsp._strangu-              SEQ ID NO: 149 .....................N..........A....L.S..............A..C......E.Q..C.A..K
lata: (RefSeq: XP_020187359.1)
Oryza_sativa_Japonica_Group:                   SEQ ID NO: 150 ..............P......................S..............A.H
(RefSeq: XP_025879970.1)
Hordeum_vulgare_subsp._vulgare:                SEQ ID NO: 151 .....................................S..............A.H....C
(XP_044975533.1)
Triticum_aestivum:                             SEQ ID NO: 152 .....................A...............S..............A.H....C
(RefSeq: XP_044356181.1)
Oryza_sativa_Japonica_Group:                   SEQ ID NO: 153 ..............P......N..............................
(RefSeq: XP_025878069.1)
```

-continued

Sequence Alignment 5: CYCA1 protein sequences from monocotyledonous plants.
CYCA1 Monocots
Homologs identified by BLAST of Arabidopsis thaliana AT1G77390 from AGI -
TAIR10 mapr to monocot NCBI RefSeq, GenBank and UniProtKB protein databases.

```
Sorghum_bicolor:                        SEQ ID NO: 154   ....A.S..A................S.I........N......I......H......Y......
(RefSeq: XP_002454800.1)
Sorghum_bicolor:                        SEQ ID NO: 155   ....A....A................I..........N......I..V..HVY......Y......
(RefSeq: XP_021311446.1)
Musa_acuminata_subsp._malaccensis:      SEQ ID NO: 156   ....I....GS.V...Q.......S..I......C.A..II........H......A.R..A..D..L.....D.........CTSS.N....
(RefSeq: XP_018678008.1)

510        520        530
                                                        ----|----|----|----|----|----|----|
Consensus                               SEQ ID NO: 157   REKYSQHKYKFVAKKQCPPSIPAEFFRDATC
Zea_mays: (Refseq: MP_001188521.1)      SEQ ID NO: 10    ...................Q..T......T.
Zea_mays: (Refseq: MP_001105387.2)      SEQ ID NO: 13    ...................Q..T......T.
Oryza_sativa Japonica_Group:            SEQ ID NO: 145   .....T.............P..T......A.
(RefSeq: XP_015630726.1)
Sorghum_bicolor:                        SEQ ID NO: 146   ......................Q..T......
(RefSeq: XP_002455447.1)
Brachypodium distachyon:                SEQ ID NO: 147   ..................LV.D.........
(RefSeq: KP_003566077.1)
Brachypodium distachyon:                SEQ ID NO: 148   ...........A.......MV.DY.C..A..
(RefSeq: KP_003566081.1)
Aegilops touschii_subsp._strangu-       SEQ ID NO: 149   ............G........T.V.......A.
lata: (RefSeq: XP_020187359.1)
Oryza_sativa Japonica_Group:            SEQ ID NO: 150   .....T...................H...V.S.........
(RefSeq: XP_025879970.1)
Hordeum vulgare_subsp._vulgare:         SEQ ID NO: 151   ............G........T.V...........A..
(XP_044975533.1)
Triticum_aestivum:                      SEQ ID NO: 152   ............G........T.V...........A..
(RefSeq: XP_044356181.1)
Oryza_sativa Japonica_Group:            SEQ ID NO: 153   .....T..............P........S.........
(RefSeq: XP_025878069.1)
Sorghum_bicolor:                        SEQ ID NO: 154   ......................Q..T......T.-
(RefSeq: XP_002454800.1)
Sorghum_bicolor:                        SEQ ID NO: 155   ..........................R.......T......V.W
(RefSeq: XP_021311446.1)
Musa_acuminata_subsp._malaccensis:      SEQ ID NO: 156   ..................V.A.....V.Q..RN
(RefSeq: XP_018678008.1)
```

TABLE 4B

Percent identities of CYCA1 sequences from monocotyledonous plants.

| TAM monocot % ID | Zea_mays: (RefSeq: NP_001288521.1) | Zea_mays: (RefSeq: NP_001105387.2) | Oryza_sativa_Japonica_Group: (RefSeq: XP_015630726.1) | Sorghum_bicolor: (RefSeq: XP_002455447.1) | Brachypodium_distachyon: (RefSeq: XP_003566077.1) | Brachypodium_distachyon: (RefSeq: XP_003566081.1) | Aegilops_tauschii_subsp._strangulata: (RefSeq: XP_020187359.1) |
|---|---|---|---|---|---|---|---|
| Zea_mays: (RefSeq: NP_001105387.2) | 80.271 | | | | | | |
| Oryza_sativa_Japonica_Group: (RefSeq: XP_015630726.1) | 74.618 | 75.483 | | | | | |
| Sorghum_bicolor: (RefSeq: XP_002455447.1) | 90.196 | 80.897 | 76.923 | | | | |
| Brachypodium_distachyon: (RefSeq: XP_003566077.1) | 72.692 | 72.763 | 77.457 | 73.359 | | | |
| Brachypodium_distachyon: (RefSeq: XP_003566081.1) | 66.667 | 67.446 | 71.869 | 67.636 | 81.518 | | |
| Aegilops_tauschii_subsp._strangulata: (RefSeq: XP_020187359.1) | 72.692 | 75.292 | 79.191 | 74.517 | 81.518 | 76.998 | |
| Oryza_sativa_Japonica_Group: (RefSeq: XP_025879970.1) | 72.394 | 73.529 | 88.78 | 75.049 | 76.07 | 70.76 | 77.626 |
| Hordeum_vulgare_subsp._vulgare: (XP_044975533.1) | 72.137 | 74.324 | 79.271 | 73.563 | 82.592 | 78.101 | 93.992 |
| Triticum_aestivum: (RefSeq: XP_044356181.1) | 72.692 | 74.757 | 78.846 | 74.71 | 81.942 | 77.043 | 98.826 |
| Oryza_sativa_Japonica_Group: (RefSeq: XP_025878069.1) | 74.419 | 75.342 | 89.784 | 76.953 | 76.311 | 71.401 | 79.029 |
| Sorghum_bicolor: (RefSeq: XP_002454880.1) | 82.364 | 86.22 | 77.264 | 84.932 | 74.806 | 68.544 | 76.311 |
| Sorghum_bicolor: (RefSeq: XP_021311446.1) | 77.649 | 79.183 | 73.18 | 78.876 | 72.78 | 66.538 | 71.622 |
| Musa_acuminata_subsp._malaccensis: (RefSeq: XP_018678008.1) | 61.315 | 62.109 | 63.938 | 62.451 | 61.644 | 59.687 | 62.695 |

TABLE 4B-continued

Percent identities of CYCA1 sequences from monocotyledonous plants.

| TAM monocot % ID | Oryza_sativa_Japonica_Group: (RefSeq: XP_025879970.1) | Hordeum_vulgare_subsp._vulgare: (XP_044975533.1) | Triticum_aestivum: (RefSeq: XP_044356181.1) | Oryza_sativa_Japonica_Group: (RefSeq: XP_025878069.1) | Sorghum_bicolor: (RefSeq: XP_002454880.1) | Sorghum_bicolor: (RefSeq: XP_021311446.1) |
|---|---|---|---|---|---|---|
| Zea_mays: (RefSeq: NP_001105387.2) | | | | | | |
| Oryza_sativa_Japonica_Group: (RefSeq: XP_015630726.1) | | | | | | |
| Sorghum_bicolor: (RefSeq: XP_002455447.1) | | | | | | |
| Brachypodium_distachyon: (RefSeq: XP_003566077.1) | | | | | | |
| Brachypodium_distachyon: (RefSeq: XP_003566081.1) | | | | | | |
| Aegilops_tauschii_subsp._strangulata: (RefSeq: XP_020187359.1) | | | | | | |
| Oryza_sativa_Japonica_Group: (RefSeq: XP_025879970.1) | | | | | | |
| Hordeum_vulgare_subsp._vulgare: (XP_044975533.1) | 77.799 | | | | | |
| Triticum_aestivum: (RefSeq: XP_044356181.1) | 77.67 | 94.186 | | | | |
| Oryza_sativa_Japonica_Group: (RefSeq: XP_025878069.1) | 91.498 | 77.992 | 79.377 | | | |
| Sorghum_bicolor: (RefSeq: XP_002454880.1) | 75.734 | 74.952 | 76.848 | 78.193 | | |
| Sorghum_bicolor: (RefSeq: XP_021311446.1) | 72.32 | 71.401 | 72.147 | 73.633 | 82.813 | |
| Musa_acuminata_subsp._malaccensis: (RefSeq: XP_018678008.1) | 63.636 | 62.33 | 63.014 | 64.484 | 63.796 | 61.719 |

TABLE 5

Table of SEQ ID NOs.

| SEQ ID NO. | Sequence | Plant Type | Sequence Source (Accession) |
|---|---|---|---|
| 1 | REC8 protein | monocot | Zea mays (RefSeq: XP_008648328.1) |
| 2 | SPO11-1 protein | monocot | Zea mays (RefSeq: NP_001347894.11) |
| 3 | PAIR1-1 protein | monocot | Zea mays (RefSeq: XP_008660580.1) |
| 4 | OSD1-1 protein | monocot | Zea mays (UniProt: B4FG75) |
| 5 | PAIR1-2 protein | monocot | Zea mays (GenBank: ONL92656.1) |
| 6 | OSD1-2 protein | monocot | Zea mays (GenBank: AQK72186.1) |
| 7 | OSD1-3 protein | monocot | Zea mays (GenBank: AQK72188.1) |
| 8 | JASON-1 protein | monocot | Zea mays (RefSeq: NP_001130670.1) |
| 9 | JASON-2 protein | monocot | Zea mays (RefSeq: NP_001130438.1) |
| 10 | CYCLIN-A1 protein | monocot | Zea mays (GenBank: NP_001288521.1) |
| 11 | TDM1 protein | monocot | Zea mays (RefSeq: NP_001141923.1) |
| 12 | PS1 protein | monocot | Zea mays (RefSeq: NP_001348386.1) |
| 13 | CYCLIN-A1 (CYCA1) protein | monocot | Zea mays (RefSeq: NP_001105387.2) |
| 14 | OSD1-1 target sequence | monocot | Zea mays |
| 15 | OSD1-1 target sequence | monocot | Zea mays |
| 16 | OSD1-1 target sequence | monocot | Zea mays |
| 17 | OSD1-1 target sequence | monocot | Zea mays |
| 18 | OSD1-1 target sequence | monocot | Zea mays |
| 19 | OSD1-1 target sequence | monocot | Zea mays |
| 20 | OSD1-1 target sequence | monocot | Zea mays |
| 21 | OSD1-1 target sequence | monocot | Zea mays |
| 22 | OSD1-1 target sequence | monocot | Zea mays |
| 23 | OSD1-1 target sequence | monocot | Zea mays |
| 24 | OSD1-2 target sequence | monocot | Zea mays |
| 25 | OSD1-2 target sequence | monocot | Zea mays |
| 26 | OSD1-2 target sequence | monocot | Zea mays |
| 27 | OSD1-2 target sequence | monocot | Zea mays |
| 28 | OSD1-2 target sequence | monocot | Zea mays |
| 29 | OSD1-2 target sequence | monocot | Zea mays |
| 30 | OSD1-2 target sequence | monocot | Zea mays |
| 31 | OSD1-2 target sequence | monocot | Zea mays |
| 32 | OSD1-2 target sequence | monocot | Zea mays |
| 33 | REC8 target sequence | monocot | Zea mays |
| 34 | REC8 target sequence | monocot | Zea mays |
| 35 | REC8 target sequence | monocot | Zea mays |
| 36 | REC8 target sequence | monocot | Zea mays |
| 37 | REC8 target sequence | monocot | Zea mays |
| 38 | REC8 target sequence | monocot | Zea mays |
| 39 | REC8 target sequence | monocot | Zea mays |
| 40 | REC8 target sequence | monocot | Zea mays |
| 41 | REC8 target sequence | monocot | Zea mays |
| 42 | SPO11-1 target sequence | monocot | Zea mays |
| 43 | SPO11-1 target sequence | monocot | Zea mays |
| 44 | SPO11-1 target sequence | monocot | Zea mays |
| 45 | SPO11-1 target sequence | monocot | Zea mays |
| 46 | SPO11-1 target sequence | monocot | Zea mays |
| 47 | SPO11-1 target sequence | monocot | Zea mays |
| 48 | SPO11-1 target sequence | monocot | Zea mays |
| 49 | SPO11-1 target sequence | monocot | Zea mays |
| 50 | SPO11-1 target sequence | monocot | Zea mays |
| 51 | SPO11-1 target sequence | monocot | Zea mays |
| 52 | SPO11-1 target sequence | monocot | Zea mays |
| 53 | SPO11-1 target sequence | monocot | Zea mays |
| 54 | SPO11-1 target sequence | monocot | Zea mays |
| 55 | SPO11-1 target sequence | monocot | Zea mays |
| 56 | SPO11-1 target sequence | monocot | Zea mays |
| 57 | SPO11-1 target sequence | monocot | Zea mays |
| 58 | SPO11-1 target sequence | monocot | Zea mays |
| 59 | SPO11-1 target sequence | monocot | Zea mays |
| 60 | SPO11-1 target sequence | monocot | Zea mays |
| 61 | OSD1-1-targeting region of gRNA | monocot | Zea mays |
| 62 | OSD1-1-targeting region of gRNA | monocot | Zea mays |
| 63 | OSD1-1-targeting region of gRNA | monocot | Zea mays |
| 64 | OSD1-1-targeting region of gRNA | monocot | Zea mays |
| 65 | OSD1-1-targeting region of gRNA | monocot | Zea mays |
| 66 | OSD1-1-targeting region of gRNA | monocot | Zea mays |
| 67 | OSD1-1-targeting region of gRNA | monocot | Zea mays |
| 68 | OSD1-1-targeting region of gRNA | monocot | Zea mays |
| 69 | OSD1-1-targeting region of gRNA | monocot | Zea mays |
| 70 | OSD1-1-targeting region of gRNA | monocot | Zea mays |
| 71 | OSD1-2-targeting region of gRNA | monocot | Zea mays |
| 72 | OSD1-2-targeting region of gRNA | monocot | Zea mays |
| 73 | OSD1-2-targeting region of gRNA | monocot | Zea mays |
| 74 | OSD1-2-targeting region of gRNA | monocot | Zea mays |
| 75 | OSD1-2-targeting region of gRNA | monocot | Zea mays |
| 76 | OSD1-2-targeting region of gRNA | monocot | Zea mays |
| 77 | OSD1-2-targeting region of gRNA | monocot | Zea mays |

TABLE 5-continued

Table of SEQ ID NOs.

| SEQ ID NO. | Sequence | Plant Type | Sequence Source (Accession) |
|---|---|---|---|
| 78 | OSD1-2-targeting region of gRNA | monocot | Zea mays |
| 79 | OSD1-2-targeting region of gRNA | monocot | Zea mays |
| 80 | REC8-targeting region of gRNA | monocot | Zea mays |
| 81 | REC8-targeting region of gRNA | monocot | Zea mays |
| 82 | REC8-targeting region of gRNA | monocot | Zea mays |
| 83 | REC8-targeting region of gRNA | monocot | Zea mays |
| 84 | REC8-targeting region of gRNA | monocot | Zea mays |
| 85 | REC8-targeting region of gRNA | monocot | Zea mays |
| 86 | REC8-targeting region of gRNA | monocot | Zea mays |
| 87 | REC8-targeting region of gRNA | monocot | Zea mays |
| 88 | REC8-targeting region of gRNA | monocot | Zea mays |
| 89 | SPO11-1-targeting region of gRNA | monocot | Zea mays |
| 90 | SPO11-1-targeting region of gRNA | monocot | Zea mays |
| 91 | SPO11-1-targeting region of gRNA | monocot | Zea mays |
| 92 | SPO11-1-targeting region of gRNA | monocot | Zea mays |
| 93 | SPO11-1-targeting region of gRNA | monocot | Zea mays |
| 94 | SPO11-1-targeting region of gRNA | monocot | Zea mays |
| 95 | SPO11-1-targeting region of gRNA | monocot | Zea mays |
| 96 | SPO11-1-targeting region of gRNA | monocot | Zea mays |
| 97 | SPO11-1-targeting region of gRNA | monocot | Zea mays |
| 98 | SPO11-1-targeting region of gRNA | monocot | Zea mays |
| 99 | SPO11-1-targeting region of gRNA | monocot | Zea mays |
| 100 | SPO11-1-targeting region of gRNA | monocot | Zea mays |
| 101 | SPO11-1-targeting region of gRNA | monocot | Zea mays |
| 102 | SPO11-1-targeting region of gRNA | monocot | Zea mays |
| 103 | SPO11-1-targeting region of gRNA | monocot | Zea mays |
| 104 | SPO11-1-targeting region of gRNA | monocot | Zea mays |
| 105 | SPO11-1-targeting region of gRNA | monocot | Zea mays |
| 106 | SPO11-1-targeting region of gRNA | monocot | Zea mays |
| 107 | SPO11-1-targeting region of gRNA | monocot | Zea mays |
| 108 | osd1-2 allele | monocot | Zea mays, PED-MN-MiMe |
| 109 | osd1-2 allele | monocot | Zea mays, PED-MN-MiMe |
| 110 | rec8 allele | monocot | Zea mays, PED-MN-MiMe |
| 111 | spo11 allele | monocot | Zea mays, PED-MN-MiMe |

TABLE 6

Exemplary combinations of in MiMe alleles of parent MiMe plants having a complete MiMe genotype.

| Genotype | Complete MiMe Genotype |
|---|---|
| 1 | rec8, spo11-1, cyca1 |
| 2 | rec8, pair1, cyca1 |
| 3 | rec8, pair1, spo11-1, cyca1 |
| 4 | rec8, spo11-1, TDM1* |
| 5 | rec8, pair1, TDM1* |
| 6 | rec8, pair1, spo11-1, TDM1* |
| 7 | rec8, spo11-1, TDM1*, cyca1 |
| 8 | rec8, pair1, TDM1*, cyca1 |
| 9 | rec8, pair1, spo11-1, TDM1*, cyca1 |
| 10 | spo11-1, ps1 |
| 10 | spo11-1, ps1, ps1-like |
| 11 | spo11-1, ps1-like |
| 12 | spo11-1, ps1-like, jason |
| 13 | spo11-1, jason |
| 14 | spo11-1, ps1, ps1-like, jason |
| 15 | pair1, ps1 |
| 16 | pair1, spo11-1, ps1 |
| 17 | spo11-1, ps1, ps1-like |
| 18 | pair1, spo11-1, ps1, ps1-like |
| 19 | pair1, ps1-like |
| 20 | pair1, spo11-1, ps1-like |
| 21 | pair1, ps1-like, jason |
| 22 | pair1, spo11-1, ps1-like, jason |
| 23 | pair1, jason |
| 24 | pair1, spo11-1, jason |
| 25 | pair1, ps1, ps1-like, jason |
| 26 | pair1, spo11-1, ps1, ps1-like, jason |
| 27 | rec8, spo11-1, osd1 |
| 28 | rec8, pair1, osd1 |
| 29 | rec8, pair1, spo11-1, osd1 |

*Dominant mutation

Enumerated Embodiments

The following enumerated embodiments are representative of some aspects of the invention.

1. A population of polyploid maize seed comprising a subpopulation of genetically uniform polyploid maize seed in an amount of at least 50% of the total number of seeds, the genetically uniform polyploid maize seed comprising three or more haplotypes of the same or related species of plant, wherein the population was obtained from a single plant or a set of F1 hybrids.
2. The population of embodiment 1, wherein the subpopulation of genetically uniform polyploid maize seed is triploid, tetraploid, pentaploid, hexaploid, heptaploid, or octaploid.
3. The population of embodiment 1 or 2, wherein the population of polyploid maize seed has an average pairwise genetic uniformity of at least 80%, at least 85%, at least 90%, at least 95%, at least 96%, at least 97%, at least 98%, at least 99%, or 100% as measured by the Jaccard similarity coefficient.
4. The population of any one of embodiments 1-3, wherein the population of polyploid maize seed comprises the subpopulation of genetically uniform polyploid maize seed in an amount of at least 70%, at least 90%, at least 95%, at least 96%, at least 97%, at least 98%, or at least 99% of the total number of seeds.
5. The population of embodiment 1-4, wherein each pair of seeds in the subpopulation of genetically uniform polyploid maize seed has a pairwise identity of at least 95%, at least 96%, at least 97%, at least 98%, at least 99%, or 100% as measured by the Jaccard similarity coefficient.

6. The population of any one of embodiments 1-5, wherein the subpopulation of genetically uniform polyploid maize seed has a complete MiMe genotype comprising:

(A)

MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components; or (B)

MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components.

7. The population of any one of embodiments 1-5, wherein the subpopulation of genetically uniform polyploid maize seed has a partial MiMe genotype comprising:

(A)

(a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components; or (B)

(a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components.

8. The population of any one of embodiments 1-5, wherein the subpopulation of genetically uniform polyploid maize seed has a partially-complemented MiMe genotype comprising:

(A)

(a) only MiMe alleles at one or more MiMe loci of a first MiMe component;

(b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;

(B)

(a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; or (C)

(a) only MiMe alleles at one or more MiMe loci of a first MiMe component, wherein the first MiMe component is a component of DNA double strand breakage during meiotic recombination;

(b) one or more MiMe alleles and one or more non-MiMe alleles at one or more MiMe loci of a second MiMe component;

(c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

9. The population of any one of embodiments 6-8f, wherein:
   (1) the one or more MiMe loci of the component of sister chromatid cohesion during the first division of meiosis comprise REC8, SWITCH1/DYAD, or a combination thereof;
   (2) the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof;
   (3) the one or more MiMe loci of the component of progression through the second division of meiosis comprise OSD1, CYCA1, TDM1, PC1, PC2, FC, or any combination thereof; and/or
   (4) the one or more MiMe loci of the component of progression through the first division of meiosis comprise PS1, JASON, or a combination thereof.

10. The population of any one of embodiments 1-9, wherein the subpopulation of genetically uniform polyploid maize seed comprises:
   (1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
   (2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;
   (3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1; (4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1, optionally wherein the population of polyploid maize seed is from a maize plant and the one or more OSD1 loci comprise OSD1-1 and OSD1-2;
   (5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
   (6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;
   (7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
   (8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1; (10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(14) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1; or

(15) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

11. The population of any one of embodiments 1-9, wherein the subpopulation of genetically uniform polyploid maize seed comprises one or more polynucleotide sequences selected from the group consisting of SEQ ID NOs: 108-111.

12. The population of any one of embodiments 1-11, wherein germination of a seed of the subpopulation of genetically uniform polyploid maize seed results in a sterile plant that produces inviable gametes, seedless fruit, or a combination thereof.

13. The population of any one of embodiments 1-12, wherein the population of polyploid maize seed comprises three or more haplotypes from the same species of maize.

14. A method of producing the population of polyploid maize seed of any one of embodiments 1-13, the method comprising:
   (a) generating a first parent MiMe plant and a second parent MiMe plant by introducing genetic modifications into one or more candidate lines to produce MiMe alleles in germplasm of a first parent MiMe plant, a second parent MiMe plant, and/or progenitors thereof, wherein the first parent MiMe plant and the second parent MiMe plant each comprise a complete MiMe genotype, and each of the progenitors comprises a partial MiMe genotype, wherein if progenitors are generated, the progenitors are further crossed to generate the first parent MiMe plant, the second parent MiMe plant, or both;
   (b) providing clonal gametes from the first parent MiMe plant and the second parent MiMe plant that together comprise the three or more haplotypes; and
   (c) crossing the clonal gametes to produce the population of polyploid maize seed;
   wherein the population of polyploid maize seed comprises a subpopulation of genetically uniform polyploid maize seed in an amount of at least 50% of the total number of seeds, the subpopulation of genetically uniform polyploid maize seed comprising the three or more haplotypes.

15. The method of embodiment 14, wherein the subpopulation of genetically uniform polyploid maize seed has a partially-complemented MiMe genotype, wherein:
   (A)
   (a) the first parent MiMe plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; and
   (b) the second parent MiMe plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component;
   wherein at least one of the MiMe loci having only MiMe alleles of the first MiMe component of the first parent MiMe plant is the same as at least one of the MiMe loci having only MiMe alleles of the first MiMe component of the second parent MiMe plant;
   wherein either (i) at least one of the MiMe loci having only MiMe alleles of the third MiMe component of the first parent MiMe plant is the same as at least one of the MiMe loci having only MiMe alleles of the third MiMe component of the second parent MiMe plant, or (ii) the one or more MiMe loci having only MiMe alleles of the third MiMe component of the first parent MiMe plant are distinct from the one or more MiMe loci having only MiMe alleles of the third MiMe component of the second parent MiMe plant; wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

(B)
   (a) the first parent MiMe plant has only MiMe alleles at one or more MiMe loci of a first MiMe component, only MiMe alleles at a first MiMe locus of a second MiMe component, and only non-MiMe alleles at a second MiMe locus of the second MiMe component; and
   (b) the second parent MiMe plant has only MiMe alleles at one or more MiMe loci of the first MiMe component, only non-MiMe alleles at the first MiMe locus of the second MiMe component, and only MiMe alleles at the second MiMe locus of the second MiMe component;
   wherein at least one of the MiMe loci having only MiMe alleles of the first MiMe component of the first parent MiMe plant is the same as at least one of the MiMe loci having only MiMe alleles of the first MiMe component of the second parent MiMe plant;
   wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; and (C)
   (a) the first parent MiMe plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination;
   (b) the second parent MiMe plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and wherein at least one of the MiMe loci having only MiMe alleles of the first MiMe component of the first parent MiMe plant is the same as at least one of the MiMe loci having only MiMe alleles of the first MiMe component of the second parent MiMe plant;
   wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

16. A method of producing the population of polyploid maize seed of any one of embodiments 1-13, the method comprising:
   (a) generating a first parent MiMe plant by introducing genetic modifications into one or more candidate lines to produce MiMe alleles in germplasm of the first parent MiMe plant or progenitors thereof, wherein the first parent MiMe plant comprises a complete MiMe genotype, and each of the progenitors comprises a partial MiMe genotype, wherein if progenitors are generated, the progenitors are further crossed to generate the first parent MiMe plant;
   (b) providing clonal gametes from the first parent MiMe plant;
   (c) providing haploid gametes from a homozygous parent non-MiMe plant; and
   (d) crossing the clonal gametes with the haploid gametes to produce the population of polyploid maize seed, wherein the clonal gametes and the haploid gametes together comprise three or more haplotypes, optionally wherein step (a) comprises generating the first parent MiMe plant, the second parent MiMe plant, or both.

17. A method of breeding a polyploid hybrid plant line, the method comprising:
   (a) obtaining a set of lines of a plant;
   (b) breeding the lines using traditional plant breeding methods to produce a set of candidate lines of the plant;
   (c) selecting two or more candidate lines together comprising three or more haplotypes;
   (d) generating a first parent MiMe plant and a second parent MiMe plant from the two or more candidate lines that together comprise the three or more haplotypes;
   (e) providing clonal gametes from each of the first and second parent MiMe plants;
   (f) crossing the clonal gametes to produce a hybrid polyploid maize seed comprising the three or more haplotypes;
   (g) growing the hybrid polyploid maize seed to produce a hybrid polyploid plant comprising three or more haplotypes; and
   (h) evaluating one or more characteristics of the hybrid polyploid plant;
   the method optionally further comprising
   (i) repeating steps (b)-(h) or steps (c)-(h) using the one or more characteristics of the hybrid polyploid plant evaluated in step (h) to guide the breeding of lines of step (b), the selecting of candidate lines of step (c), or both.

18. The method of embodiment 17, wherein:
   (A)
   (a) the first parent MiMe plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; and
   (b) the second parent MiMe plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component;
   wherein at least one of the MiMe loci having only MiMe alleles of the first MiMe component of the first parent MiMe plant is the same as at least one of the MiMe loci having only MiMe alleles of the first MiMe component of the second parent MiMe plant;
   wherein either (i) at least one of the MiMe loci having only MiMe alleles of the third MiMe component of the first parent MiMe plant is the same as at least one of the MiMe loci having only MiMe alleles of the third MiMe component of the second parent MiMe plant, or (ii) the one or more MiMe loci having only MiMe alleles of the third MiMe component of the first parent MiMe plant are distinct from the one or more MiMe loci having only MiMe alleles of the third MiMe component of the second parent MiMe plant; wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.
   (B)
   (a) the first parent MiMe plant has only MiMe alleles at one or more MiMe loci of a first MiMe component, only MiMe alleles at a first MiMe locus of a second MiMe component, and only non-MiMe alleles at a second MiMe locus of the second MiMe component; and
   (b) the second parent MiMe plant has only MiMe alleles at one or more MiMe loci of the first MiMe component, only non-MiMe alleles at the first MiMe locus of the second MiMe component, and only MiMe alleles at the second MiMe locus of the second MiMe component;
   wherein at least one of the MiMe loci having only MiMe alleles of the first MiMe component of the first parent MiMe plant is the same as at least one of the MiMe loci having only MiMe alleles of the first MiMe component of the second parent MiMe plant;
   wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; and
   (C)
   (a) the first parent MiMe plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination;
   (b) the second parent MiMe plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and wherein at least one of the MiMe loci having only MiMe alleles of the first MiMe component of the first parent MiMe plant is the same as at least one of the MiMe loci having only MiMe alleles of the first MiMe component of the second parent MiMe plant;

wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

19. A method of breeding a polyploid hybrid plant line, the method comprising:
   (a) obtaining a set of lines of a plant;
   (b) breeding the lines using traditional plant breeding methods to produce a set of candidate lines of the plant;
   (c) selecting two or more candidate lines together comprising three or more haplotypes;
   (d) generating a first parent MiMe plant from one of the two or more candidate lines;
   (e) providing clonal gametes from the first parent MiMe plant;
   (f) providing haploid gametes from a homozygous parent non-MiMe plant of one of the two or more candidate lines;
   (g) crossing the clonal gametes with the haploid gametes to produce a hybrid polyploid maize seed;
   (h) growing the hybrid polyploid maize seed to produce a hybrid polyploid plant; and
   (i) evaluating one or more characteristics of the hybrid polyploid plant, wherein the first parent MiMe plant and the homozygous parent non-MiMe plant together comprise three or more haplotypes, wherein the crossing of step (g) results in the hybrid polyploid maize seed comprising three or more haplotypes, and wherein the growing of step (h) results in the hybrid polyploid plant comprising three or more haplotypes;
   the method optionally further comprising
   (j) repeating steps (b)-(i) or steps (c)-(i) using the one or more characteristics of the hybrid polyploid plant evaluated in step (i) to guide the breeding of lines of step (b), the selecting of candidate lines of step (c), or both.

20. The method of any one of embodiments 14-19, wherein the first parent MiMe plant, the second parent MiMe plant, the parent non-MiMe plant, or any combination thereof are diploid, triploid, or tetraploid and the hybrid polyploid plant is tetraploid, pentaploid, hexaploid, heptaploid, or octaploid.

21. The method of any one of embodiments 14-20, wherein generating the first parent MiMe plant, the second parent MiMe plant, or both comprises:
   (1) introducing a complete MiMe genotype directly into two candidate lines to produce the first parent MiMe plant, the second parent MiMe plant, or both;
   (2) introducing a partial MiMe genotype into two candidate lines to produce two grandparent non-MiMe plants each having a partial MiMe genotype and crossing the grandparent non-MiMe plants each having a partial MiMe genotype to produce the first parent MiMe plant, optionally wherein generating the first parent MiMe plant, the second parent MiMe plant, or both further comprises introducing a complete MiMe genotype directly into a third candidate line to produce the second parent MiMe plant; or
   (3) introducing a partial MiMe genotype into four candidate lines to produce four grandparent non-MiMe plants each having a partial MiMe genotype, and crossing pairs of said grandparent non-MiMe plants each having a partial MiMe genotype to produce the first and second parent MiMe plants, optionally wherein generating the first parent MiMe plant, the second parent MiMe plant, or both further comprises propagating the first parent MiMe plant, the second parent MiMe plant, the grandparent non-MiMe plants, or any combination thereof to scale production of homogenous seed.

22. The method of any one of embodiments 14-21, wherein the first parent MiMe plant, the second parent MiMe plant, the hybrid polyploid plant, or any combination thereof has a complete MiMe genotype comprising:
   (A)
   MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components; or
   (B)
   MiMe alleles conferring decreased expression of one or more MiMe loci of each of a first and second MiMe component, wherein the first MiMe component and the second MiMe component are selected from the group consisting of (2) a component of DNA double strand breakage during meiotic recombination, and (4) a component of progression through the first division of meiosis, and each of the first MiMe component and the second MiMe component are different MiMe components.

23. The method of any one of embodiments 17-22, wherein each grandparent non-MiMe plant, the hybrid polyploid plant, or a combination thereof has a partial MiMe genotype comprising:
   (A)
   (a) one or more MiMe alleles conferring decreased expression of one or more MiMe loci of each of a first, second, and third MiMe component; and
   (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components; or (B)
(a) one or more MiMe alleles conferring decreased expression of one or more MiMe loci of each of the first and second MiMe component; and
(b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components.

24. The method of embodiment 18, 22, or 23, wherein:
(1) the one or more MiMe loci of the component of sister chromatid cohesion during the first division of meiosis comprise REC8, SWITCH1/DYAD, or a combination thereof;
(2) the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof;
(3) the one or more MiMe loci of the component of progression through the second division of meiosis comprise OSD1, CYCA1, TDM1, PC1, PC2, FC, or any combination thereof; and/or
(4) the one or more MiMe loci of the component of progression through the first division of meiosis comprise PS1, JASON, or a combination thereof.

25. The method of any one of embodiments 17-24, wherein the hybrid polyploid plant comprises:
(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;
(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1, optionally wherein the population of polyploid maize seed is from a maize plant and the one or more OSD1 loci comprise OSD1-1 and OSD1-2;
(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;
(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(14) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1; or

(15) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

26. The method of any one of embodiments 17-25, wherein one or more of the candidate lines of step (c) are inbred lines, hybrid lines, or a combination thereof.

27. The method of any one of embodiments 21-26, wherein the complete MiMe genotype, the partial MiMe genotype, or both are introduced by gene editing, transgenesis, or a combination thereof.

28. The method of embodiment 22-27, wherein the decreased expression of one or more of the MiMe loci is each independently achieved by gene disruption, gene knockout, gene knockdown, gene silencing, RNA interference, or induction of methylation.

29. The method of embodiment 22-28, wherein the decreased expression of one or more of the MiMe loci is each independently achieved by introducing into each candidate line or a progenitor thereof an insertion, a deletion, one or more nucleotide changes, or an inversion that results in decreased expression of the MiMe locus, optionally including a step of selection for decreased expression of the MiMe locus.

30. The method of embodiment 29, wherein the insertion, the deletion, the one or more nucleotide changes, or the inversion eliminates expression of the MiMe locus, optionally wherein the expression of the MiMe locus is eliminated by a premature stop codon present in the 70%, the first 60%, the first 50%, the first 40%, the first 30%, the first 20%, or the first 10% of the nucleotides of the coding sequence of the MiMe locus following the start codon in the 3' direction.

31. A method of producing a population of polyploid maize seed comprising:
   (a) providing clonal gametes from a pair of parent MiMe plants together comprising three or more haplotypes that were selected using the method of breeding of any one of embodiments 17, 18, and 20-30 based upon the polyploid plant comprising the three or more haplotypes having one or more desired characteristics; and
   (b) crossing the clonal gametes to produce the population of polyploid maize seed;
   wherein the population of polyploid maize seed comprises a subpopulation of genetically uniform polyploid maize seed in an amount of at least 50% of the total number of seeds, the subpopulation of genetically uniform polyploid maize seed comprising the three or more haplotypes.

32. A method of producing a population of polyploid maize seed comprising:
   (a) selecting three or more haplotypes using the method of breeding of any one of embodiments 19-30 based upon the polyploid plant comprising said three or more haplotypes having one or more desired characteristics;
   (b) providing clonal gametes from a parent MiMe plant;
   (c) providing haploid gametes from a homozygous parent non-MiMe plant;
   (d) crossing the clonal gametes with the haploid gametes to produce the population of polyploid maize seed;
   wherein the parent MiMe plant and the homozygous parent non-MiMe plant together comprise the three or more haplotypes selected in step (a), wherein the crossing of step (d) results in a population of polyploid maize seed comprising a subpopulation of genetically uniform polyploid maize seed in an amount of at least 50% of the total number of seeds, the subpopulation of genetically uniform polyploid maize seed comprising the three or more haplotypes.

33. The method of embodiment 31 or 32, wherein the population of polyploid maize seed has an average pairwise genetic uniformity of at least 80%, at least 85%, at least 90%, at least 95%, at least 96%, at least 97%, at least 98%, at least 99%, or 100% as measured by the Jaccard similarity coefficient.

34. The method of any one of embodiments 31-33, wherein the population of polyploid maize seed comprises the subpopulation of genetically uniform polyploid maize seed in an amount of at least 70%, at least 90%, at least 95%, at least 96%, at least 97%, at least 98%, or at least 99% of the total number of seeds.

35. The method of any one of embodiments 31-34, wherein each pair of seeds in the subpopulation of genetically uniform polyploid maize seed has a pairwise identity of at least 95%, at least 96%, at least 97%, at least 98%, at least 99%, or 100% as measured by the Jaccard similarity coefficient.

36. A genetically modified plant, plant part, or plant cell comprising:
   (A) three or more haplotypes; and
   (B)
      (i) a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;
      ii) a partial MiMe genotype comprising:
         (a) one or more MiMe alleles conferring decreased expression of one or more MiMe loci of each of a first, second, and third MiMe component; and
         (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;
      iii) a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components;

iv) a partial MiMe genotype comprising:
  (a) one or more MiMe alleles conferring decreased expression of one or more MiMe loci of each of the first and second MiMe component; and
  (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components;

v) a partially complemented MiMe genotype comprising:
  (a) only MiMe alleles at one or more MiMe loci of a first MiMe component;
  (b) one or more MiMe alleles and one or more non-MiMe alleles at a first MiMe locus of a second MiMe component, and one or more MiMe alleles and one or more non-MiMe alleles at a second MiMe locus of the second MiMe component; and
  (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component,
  wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;

vi) a partially complemented MiMe genotype comprising:
  (a) only MiMe alleles at one or more MiMe loci of a first MiMe component; and
  (b) one or more MiMe alleles and one or more non-MiMe alleles at a first MiMe locus of a second MiMe component, and one or more MiMe alleles and one or more non-MiMe alleles at a second MiMe locus of the second MiMe component,
  wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; or vii) a partially complemented MiMe genotype comprising:
  (a) only MiMe alleles at one or more MiMe loci of a first MiMe component, wherein the first MiMe component is a component of DNA double strand breakage during meiotic recombination;
  (b) one or more MiMe alleles and one or more non-MiMe alleles at one or more MiMe loci of a second MiMe component;
  (c) one or more MiMe alleles and one or more non-MiMe alleles at one or more MiMe loci of a third MiMe component; and
  (d) one or more MiMe alleles and one or more non-MiMe alleles at one or more MiMe loci of a fourth MiMe component,
  wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

37. The genetically modified plant, plant part, or plant cell of embodiment 36, wherein:
  (1) the one or more MiMe loci of the component of sister chromatid cohesion during the first division of meiosis comprise REC8, SWITCH1/DYAD, or a combination thereof;
  (2) the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof;
  (3) the one or more MiMe loci of the component of progression through the second division of meiosis comprise OSD1, CYCA1, TDM1, PC1, PC2, FC, or any combination thereof; and/or
  (4) the one or more MiMe loci of the component of progression through the first division of meiosis comprise PS1, JASON, or a combination thereof.

38. The genetically modified plant, plant part, or plant cell of embodiment 36 or 37, comprising:
  (1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
  (2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1, optionally wherein the one or more OSD1 loci comprise OSD1-1 and OSD1-2;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(14) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1; or

(15) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

39. The genetically modified plant, plant part, or plant cell of any one of embodiments 36-38, comprising one or more polynucleotide sequences selected from the group consisting of SEQ ID NOs: 108-111.

40. The genetically modified plant, plant part, or plant cell of any one of embodiments 36-39, wherein:
   (i) the genetically modified plant part is a non-regenerable plant part; or
   (ii) the genetically modified plant cell is a non-regenerable plant cell.

41. The genetically modified plant, plant part, or plant cell of any one of embodiments 36-40, wherein the plant part is a flower, a pistil, a leaf, a stem, a petiole, a cutting, a tissue, a seed coat, an ovule, pollen, a root, a rootstock, a scion, a fruit, a cotyledon, a hypocotyl, a protoplast, an embryo, an anther, or a portion thereof.

42. A processed plant product derived from the genetically modified plant, plant part, or plant cell of any one of embodiments 36-41 wherein the processed plant product comprises a detectable amount of the one or more MiMe alleles of the genetically modified plant, plant part, or plant cell.

43. The processed plant product of embodiment 42, wherein the processed plant product:
   (i) is selected from the group consisting of plant biomass, oil, meal, food starch, syrup, animal feed, flour, flakes, bran, lint, hulls, and processed seed; and/or
   (ii) is non-regenerable.

44. Germplasm of the population of polyploid maize seeds of any one of embodiments 1-13.

45. A population of polyploid maize seed comprising a subpopulation of genetically uniform polyploid maize seed in an amount of at least 50% of the total number of seeds, the genetically uniform polyploid maize seed comprising three or more haplotypes of the same or related species of plant, wherein the population was obtained from a single plant or a set of F1 hybrids, wherein the subpopulation of genetically uniform polyploid maize seed comprise (A) (1) a germplasm genetic modification means for inhibiting sister chromatid cohesion during the first division of meiosis, (2) a germplasm genetic modification means for inhibiting DNA double strand breakage during meiotic recombination, and (3) a germplasm genetic modification means for inhibiting progression through the second division of meiosis; or (B) (2) a germplasm genetic modification means for preventing DNA double strand breakage during meiotic recombination, and (4) a germplasm genetic modification means for preventing progression through the first division of meiosis;
   wherein each of the germplasm genetic modifications are (i) a complete set that achieves the inhibition, (ii) a partial set that does not achieve inhibition, or (iii)

partially complemented at one or more of the genetic modification means and achieve sterility.

46. The population of embodiment 45, wherein the subpopulation of genetically uniform polyploid maize seed is triploid, tetraploid, pentaploid, hexaploid, heptaploid, or octaploid.

47. The population of embodiment 45 or 46, wherein the population of polyploid maize seed has an average pairwise genetic uniformity of at least 80%, at least 85%, at least 90%, at least 95%, at least 96%, at least 97%, at least 98%, at least 99%, or 100% as measured by the Jaccard similarity coefficient.

48. The population of any one of embodiments 45-47, wherein the population of polyploid maize seed comprises the subpopulation of genetically uniform polyploid maize seed in an amount of at least 70%, at least 90%, at least 95%, at least 96%, at least 97%, at least 98%, or at least 99% of the total number of seeds.

49. The population of embodiment 45-48, wherein each pair of seeds in the subpopulation of genetically uniform polyploid maize seed has a pairwise identity of at least 95%, at least 96%, at least 97%, at least 98%, at least 99%, or 100% as measured by the Jaccard similarity coefficient.

50. The population of any one of embodiments 45-49, wherein the subpopulation of genetically uniform polyploid maize seed has a complete MiMe genotype comprising the complete set of germplasm genetic modification means as follows:
    (A)
    (1) the germplasm genetic modification means for inhibiting sister chromatid cohesion during the first division of meiosis comprise only MiMe alleles at one or more MiMe loci of a component of sister chromatid cohesion during the first division of meiosis, (2) the germplasm genetic modification means for inhibiting DNA double strand breakage during meiotic recombination comprise only MiMe alleles at one or more MiMe loci of a component of DNA double strand breakage during meiotic recombination, and (3) the germplasm genetic modification means for inhibiting progression through the second division of meiosis comprise only MiMe alleles at one or more Mime loci of progression through the second division of meiosis; or
    (B)
    (2) the germplasm genetic modification means for inhibiting DNA double strand breakage during meiotic recombination comprise only MiMe alleles at one or more MiMe loci of a component of DNA double strand breakage during meiotic recombination, and (4) the germplasm genetic modification means for inhibiting progression through the first division of meiosis comprise only MiMe alleles at one or more MiMe loci of a component of progression through the first division of meiosis.

51. The population of any one of embodiments 45-49, wherein the subpopulation of genetically uniform polyploid maize seed has a partial MiMe genotype comprising the partial set of germplasm genetic modification means as follows:
    (A)
    (1) the germplasm genetic modification means for inhibiting sister chromatid cohesion during the first division of meiosis comprise at least one MiMe allele and at least one non-MiMe allele at one or more MiMe loci for a component of sister chromatid cohesion during the first division of meiosis comprise, (2) the germplasm genetic modification means for inhibiting DNA double strand breakage during meiotic recombination comprise at least one MiMe allele and at least one non-MiMe allele at one or more MiMe loci for a component of DNA double strand breakage during meiotic recombination, and (3) the germplasm genetic modification means for inhibiting progression through the second division of meiosis comprise at least one MiMe allele and at least one non-MiMe allele at one or more MiMe loci for a component of progression through the second division of meiosis; or
    (B)
    (2) the germplasm genetic modification means for inhibiting DNA double strand breakage during meiotic recombination comprise at least one MiMe allele and at least one non-MiMe allele at one or more MiMe loci for a component of DNA double strand breakage during meiotic recombination, and (4) the germplasm genetic modification means for inhibiting progression through the first division of meiosis comprise at least one MiMe allele and at least one non-MiMe allele at one or more MiMe loci for a component of progression through the first division of meiosis.

52. The population of any one of embodiments 45-49, wherein the subpopulation of genetically uniform polyploid maize seed has a partially-complemented MiMe genotype comprising the partially complemented set of germplasm genetic modification means as follows:
    (A)
    (1) the germplasm genetic modification means for inhibiting sister chromatid cohesion during the first division of meiosis comprises at least one MiMe allele at at least a first MiMe locus of a component of sister chromatid cohesion during the first division of meiosis, (2) the germplasm genetic modification means for inhibiting DNA double strand breakage during meiotic recombination comprises at least one MiMe allele at at least a first MiMe locus of a component of DNA double strand breakage during meiotic recombination, and (3) the germplasm genetic modification means for inhibiting progression through the second division of meiosis comprises at least one MiMe allele at at least a first MiMe locus of a component of progression through the second division of meiosis, wherein at least one of (1), (2), and (3) comprise one or more MiMe alleles and one or more non-MiMe alleles at the first MiMe locus of the component, and one or more MiMe alleles and one or more non-MiMe alleles at a second MiMe locus of the component, and wherein one or both of the others of (1), (2), and (3) comprise only MiMe alleles at at least the first MiMe locus of the component; or
    (B)
    (2) the germplasm genetic modification means for inhibiting DNA double strand breakage during meiotic recombination comprises at least one MiMe allele at at least a first MiMe locus of a component of DNA double strand breakage during meiotic recombination, and (4) the germplasm genetic modification means for preventing progression through the first division of meiosis comprises at least one MiMe allele at at least a first MiMe locus of a component of progression through the first division of meiosis, wherein one of (2) and (4) comprises one or more MiMe alleles and one or more non-MiMe alleles at the first MiMe locus of the component, and one or more MiMe alleles and one or more non-MiMe alleles at a second MiMe locus of the component, and the other of (2) and (4) comprises only MiMe alleles at at least the first MiMe locus of the component; or (C)
- (2) the germplasm genetic modification means for inhibiting DNA double strand breakage during meiotic recombination comprise at least one MiMe allele at at least a first MiMe locus of a component of DNA double strand breakage during meiotic recombination;
- (1) the germplasm genetic modification means for inhibiting sister chromatid cohesion during the first division of meiosis comprises at least one MiMe allele and at least one non-MiMe allele at one or more MiMe loci for a component of sister chromatid cohesion during the first division of meiosis;
  - (3) the germplasm genetic modification means for inhibiting progression through the second division of meiosis comprises at least one MiMe allele and at least one non-MiMe allele at one or more MiMe loci for a component of progression through the second division of meiosis; and
  - (4) the germplasm genetic modification means for inhibiting progression through the first division of meiosis comprise at least one MiMe allele and at least one non-MiMe allele at one or more MiMe loci for a component of progression through the first division of meiosis.

53. The population of any one of embodiments 50-52, wherein:
- (1) the one or more MiMe loci of the component of sister chromatid cohesion during the first division of meiosis comprise REC8, SWITCH1/DYAD, or a combination thereof;
- (2) the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof;
- (3) the one or more MiMe loci of the component of progression through the second division of meiosis comprise OSD1, CYCA1, TDM1, PC1, PC2, FC, or any combination thereof; and/or
- (4) the one or more MiMe loci of the component of progression through the first division of meiosis comprise PS1, JASON, or a combination thereof.

54. The population of any one of embodiments 45-53, wherein the subpopulation of genetically uniform polyploid maize seed comprises:
- (1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
- (2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;
- (3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
- (4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1, optionally wherein the population of polyploid maize seed is from a maize plant and the one or more OSD1 loci comprise OSD1-1 and OSD1-2;
- (5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
- (6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(14) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1; or

(15) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

55. The population of any one of embodiments 45-54, wherein the subpopulation of genetically uniform polyploid maize seed comprises one or more polynucleotide sequences selected from the group consisting of SEQ ID NOs: 108-111.

56. The population of any one of embodiments 45-55, wherein germination of a seed of the subpopulation of genetically uniform polyploid maize seed results in a sterile plant that produces inviable gametes, seedless fruit, or a combination thereof.

57. The population of any one of embodiments 45-56, wherein the population of polyploid maize seed comprises three or more haplotypes from the same species of maize.

58. A method of producing the population of polyploid maize seed of any one of embodiments 45-57, the method comprising:
  (0) generating a first parent MiMe plant and a second parent MiMe plant by introducing genetic modifications into germplasms of one or more candidate lines of a plant to generate the first parent MiMe plant, the second parent MiMe plant, and/or progenitors thereof, wherein the first parent MiMe plant and the second parent MiMe plant together comprise three or more haplotypes, and wherein each of the first parent MiMe plant, the second parent MiMe plant, and/or the progenitors thereof comprises:
    (A) (1) a germplasm genetic modification means for inhibiting sister chromatid cohesion during the first division of meiosis, (2) a germplasm genetic modification means for inhibiting DNA double strand breakage during meiotic recombination, and (3) a germplasm genetic modification means for inhibiting progression through the second division of meiosis; or
    (B) (2) a germplasm genetic modification means for preventing DNA double strand breakage during meiotic recombination, and (4) a germplasm genetic modification means for preventing progression through the first division of meiosis;
  wherein each of the germplasm genetic modifications are (i) a complete set that achieves the inhibition, or (ii) a partial set that does not achieve inhibition;
  wherein if progenitors are generated, the progenitors are further crossed to generate the first parent MiMe plant, the second parent MiMe plant, or both, and wherein the generating the first parent MiMe plant, the second parent MiMe plant, and/or the progenitors thereof comprises selecting for plants comprising the germplasm genetic modification means after introducing the germplasm genetic modification means;
  (a) providing clonal gametes from the first parent MiMe plant and the second parent MiMe plant that together comprise the three or more haplotypes; and
  (b) crossing the clonal gametes to produce the population of polyploid maize seed;
  wherein the population of polyploid maize seed comprises a subpopulation of genetically uniform polyploid maize seed in an amount of at least 50% of the total number of seeds, the subpopulation of genetically uniform polyploid maize seed comprising the three or more haplotypes.

59. The method of embodiment 58, wherein the subpopulation of genetically uniform polyploid maize seed has a partially-complemented MiMe genotype, wherein:
  (A)
  (a) the first parent MiMe plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; and
  (b) the second parent MiMe plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component;
  wherein at least one of the MiMe loci having only MiMe alleles of the first MiMe component of the first parent MiMe plant is the same as at least one of the MiMe loci having only MiMe alleles of the first MiMe component of the second parent MiMe plant;
  wherein either (i) at least one of the MiMe loci having only MiMe alleles of the third MiMe component of the first parent MiMe plant is the same as at least one of the MiMe loci having only MiMe alleles of the third MiMe component of the second parent MiMe plant, or (ii) the one or more MiMe loci having only MiMe alleles of the third MiMe component of the first parent MiMe plant are distinct from the one or more MiMe loci having only MiMe alleles of the third MiMe component of the second parent MiMe plant; wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.
  (B)
  (a) the first parent MiMe plant has only MiMe alleles at one or more MiMe loci of a first MiMe component, only MiMe alleles at a first MiMe locus of a second MiMe component, and only non-MiMe alleles at a second MiMe locus of the second MiMe component; and (b) the second parent MiMe plant has only MiMe alleles at one or more MiMe loci of the first MiMe component, only non-MiMe alleles at the first MiMe locus of the second MiMe component, and only MiMe alleles at the second MiMe locus of the second MiMe component;

wherein at least one of the MiMe loci having only MiMe alleles of the first MiMe component of the first parent MiMe plant is the same as at least one of the MiMe loci having only MiMe alleles of the first MiMe component of the second parent MiMe plant;

wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; and (C)
(a) the first parent MiMe plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination;

(b) the second parent MiMe plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and wherein at least one of the MiMe loci having only MiMe alleles of the first MiMe component of the first parent MiMe plant is the same as at least one of the MiMe loci having only MiMe alleles of the first MiMe component of the second parent MiMe plant;

wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

60. A method of producing the population of polyploid maize seed of any one of embodiments 45-57, the method comprising:

(0) generating a first parent MiMe plant by introducing genetic modifications into germplasms of one or more candidate lines of a plant to generate the first parent MiMe plant or progenitors thereof, and wherein each of the first parent MiMe plant or the progenitors thereof comprises:

(A) (1) a germplasm genetic modification means for inhibiting sister chromatid cohesion during the first division of meiosis, (2) a germplasm genetic modification means for inhibiting DNA double strand breakage during meiotic recombination, and (3) a germplasm genetic modification means for inhibiting progression through the second division of meiosis; or (B) (2) a germplasm genetic modification means for preventing DNA double strand breakage during meiotic recombination, and (4) a germplasm genetic modification means for preventing progression through the first division of meiosis;

wherein each of the germplasm genetic modifications are (i) a complete set that achieves the inhibition, (ii) a partial set that does not achieve inhibition, or (iii) partially complemented at one or more of the genetic modification means and achieve sterility;

wherein if progenitors are generated, the progenitors are further crossed to generate the first parent MiMe plant, and wherein the generating the first parent MiMe plant and/or the progenitors thereof comprises selecting for plants comprising the germplasm genetic modification means after introducing the germplasm genetic modification means;

(a) providing clonal gametes from the first parent MiMe plant;

(b) providing haploid gametes from a homozygous parent non-MiMe plant; and (c) crossing the clonal gametes with the haploid gametes to produce the population of polyploid maize seed, wherein the clonal gametes and the haploid gametes together comprise three or more haplotypes, optionally wherein step (a) comprises generating the first parent MiMe plant, the second parent MiMe plant, or both.

61. A method of breeding a polyploid hybrid plant line, the method comprising:

(a) obtaining a set of lines of a plant;

(b) breeding the lines using traditional plant breeding methods to produce a set of candidate lines of the plant;

(c) selecting two or more candidate lines together comprising three or more haplotypes;

(d) generating a first parent MiMe plant and a second parent MiMe plant from the two or more candidate lines that together comprise the three or more haplotypes;

(e) providing clonal gametes from each of the first and second parent MiMe plants;

(f) crossing the clonal gametes to produce a hybrid polyploid maize seed comprising the three or more haplotypes;

(g) growing the hybrid polyploid maize seed to produce a hybrid polyploid plant comprising three or more haplotypes; and (h) evaluating one or more characteristics of the hybrid polyploid plant;

the method optionally further comprising (i) repeating steps (b)-(h) or steps (c)-(h) using the one or more characteristics of the hybrid polyploid plant evaluated in step (h) to guide the breeding of lines of step (b), the selecting of candidate lines of step (c), or both.

62. The method of embodiment 61, wherein:

(A)
(a) the first parent MiMe plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; and
(b) the second parent MiMe plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component;
wherein at least one of the MiMe loci having only MiMe alleles of the first MiMe component of the first parent MiMe plant is the same as at least one of the MiMe loci having only MiMe alleles of the first MiMe component of the second parent MiMe plant;
wherein either (i) at least one of the MiMe loci having only MiMe alleles of the third MiMe component of the first parent MiMe plant is the same as at least one of the MiMe loci having only MiMe alleles of the third MiMe component of the second parent MiMe plant, or (ii) the one or more MiMe loci having only MiMe alleles of the third MiMe component of the first parent MiMe plant are distinct from the one or more MiMe loci having only MiMe alleles of the third MiMe component of the second parent MiMe plant;
wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

(B)
(a) the first parent MiMe plant has only MiMe alleles at one or more MiMe loci of a first MiMe component, only MiMe alleles at a first MiMe locus of a second MiMe component, and only non-MiMe alleles at a second MiMe locus of the second MiMe component; and
(b) the second parent MiMe plant has only MiMe alleles at one or more MiMe loci of the first MiMe component, only non-MiMe alleles at the first MiMe locus of the second MiMe component, and only MiMe alleles at the second MiMe locus of the second MiMe component;
wherein at least one of the MiMe loci having only MiMe alleles of the first MiMe component of the first parent MiMe plant is the same as at least one of the MiMe loci having only MiMe alleles of the first MiMe component of the second parent MiMe plant;
wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; and (C)
(a) the first parent MiMe plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination;
(b) the second parent MiMe plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and
wherein at least one of the MiMe loci having only MiMe alleles of the first MiMe component of the first parent MiMe plant is the same as at least one of the MiMe loci having only MiMe alleles of the first MiMe component of the second parent MiMe plant;
wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

63. A method of breeding a polyploid hybrid plant line, the method comprising:
(a) obtaining a set of lines of a plant;
(b) breeding the lines using traditional plant breeding methods to produce a set of candidate lines of the plant;
(c) selecting two or more candidate lines together comprising three or more haplotypes;
(d) generating a first parent MiMe plant from one of the two or more candidate lines;
(e) providing clonal gametes from the first parent MiMe plant;
(f) providing haploid gametes from a homozygous parent non-MiMe plant of one of the two or more candidate lines;
(g) crossing the clonal gametes with the haploid gametes to produce a hybrid polyploid maize seed;
(h) growing the hybrid polyploid maize seed to produce a hybrid polyploid plant; and (i) evaluating one or more characteristics of the hybrid polyploid plant,
wherein the first parent MiMe plant and the homozygous parent non-MiMe plant together comprise three or more haplotypes, wherein the crossing of step (g) results in the hybrid polyploid maize seed comprising three or more haplotypes, and wherein the growing of step (h) results in the hybrid polyploid plant comprising three or more haplotypes;
the method optionally further comprising
(j) repeating steps (b)-(i) or steps (c)-(i) using the one or more characteristics of the hybrid polyploid plant evaluated in step (i) to guide the breeding of lines of step (b), the selecting of candidate lines of step (c), or both.

64. The method of any one of embodiments 58-64, wherein the first parent MiMe plant, the second parent MiMe plant, the parent non-MiMe plant, or any combination thereof are diploid, triploid, or tetraploid and the hybrid polyploid plant is tetraploid, pentaploid, hexaploid, heptaploid, or octaploid.

65. The method of any one of embodiments 58-64, wherein generating the first parent MiMe plant, the second parent MiMe plant, or both comprises:
(1) introducing a complete MiMe genotype directly into two candidate lines to produce the first parent MiMe plant, the second parent MiMe plant, or both;
(2) introducing a partial MiMe genotype into two candidate lines to produce two grandparent non-MiMe plants each having a partial MiMe genotype and crossing the grandparent non-MiMe plants each having a partial MiMe genotype to produce the first parent MiMe plant, optionally wherein generating the first parent MiMe plant, the second parent MiMe plant, or both further comprises introducing a complete MiMe genotype directly into a third candidate line to produce the second parent MiMe plant; or
(3) introducing a partial MiMe genotype into four candidate lines to produce four grandparent non-MiMe plants each having a partial MiMe genotype, and crossing pairs of said grandparent non-MiMe plants each having a partial MiMe genotype to produce the first and second parent MiMe plants,
optionally wherein generating the first parent MiMe plant, the second parent MiMe plant, or both further comprises propagating the first parent MiMe plant, the second parent MiMe plant, the grandparent non-MiMe plants, or any combination thereof to scale production of homogenous seed.

66. The method of any one of embodiments 58-65, wherein the first parent MiMe plant, the second parent MiMe plant, the hybrid polyploid plant, or any combination thereof has a complete MiMe genotype comprising:
(A)
MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components; or
(B)
MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components.

67. The method of any one of embodiments 61-66, wherein each grandparent non-MiMe plant, the hybrid polyploid plant, or a combination thereof has a partial MiMe genotype comprising:
(A)
(a) one or more MiMe alleles conferring decreased expression of one or more MiMe loci of each of a first, second, and third MiMe component; and
(b) one or more non-MiMe alleles at the one or more MiMe loci of each of the first, second, and third MiMe component,
wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components; or
(B)
(a) one or more MiMe alleles conferring decreased expression of one or more MiMe loci of each of the first and second MiMe component; and
(b) one or more non-MiMe alleles at the one or more MiMe loci of each of the first and second MiMe component,
wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components.

68. The method of embodiment 18, 66, or 67, wherein:
(1) the one or more MiMe loci of the component of sister chromatid cohesion during the first division of meiosis comprise REC8, SWITCH1/DYAD, or a combination thereof;
(2) the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof;
(3) the one or more MiMe loci of the component of progression through the second division of meiosis comprise OSD1, CYCA1, TDM1, PC1, PC2, FC, or any combination thereof; and/or (4) the one or more MiMe loci of the component of progression through the first division of meiosis comprise PS1, JASON, or a combination thereof.

69. The method of any one of embodiments 61-68, wherein the hybrid polyploid plant comprises:
(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;
(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1, optionally wherein the population of polyploid maize seed is from a maize plant and the one or more OSD1 loci comprise OSD1-1 and OSD1-2;
(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;
(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;
(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;
(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;
(13) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;
(14) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1; or
(15) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

70. The method of any one of embodiments 61-69, wherein one or more of the candidate lines of step (c) are inbred lines, hybrid lines, or a combination thereof.

71. The method of any one of embodiments 65-70, wherein the complete MiMe genotype, the partial MiMe genotype, or both are introduced by gene editing, transgenesis, or a combination thereof.

72. The method of embodiment 66-71, wherein the decreased expression of one or more of the MiMe loci is each independently achieved by gene disruption, gene knockout, gene knockdown, gene silencing, RNA interference, or induction of methylation.

73. The method of embodiment 66-71, wherein the decreased expression of one or more of the MiMe loci is each independently achieved by introducing into each candidate line an insertion, a deletion, one or more nucleotide changes, or an inversion that results in decreased expression of the MiMe locus, optionally including a step of selection for decreased expression of the MiMe locus.

74. The method of embodiment 73, wherein the insertion, the deletion, the one or more nucleotide changes, or the inversion eliminates expression of the MiMe locus, optionally wherein the expression of the MiMe locus is eliminated by a premature stop codon present in the 70%, the first 60%, the first 50%, the first 40%, the first 30%, the first 20%, or the first 10% of the nucleotides of the coding sequence of the MiMe locus following the start codon in the 3' direction.

75. A method of producing a population of polyploid maize seed comprising:
   (a) providing clonal gametes from a pair of parent MiMe plants together comprising three or more haplotypes that were selected using the method of breeding of any one of embodiments 61, 62, and 64-74 based upon the polyploid plant comprising the three or more haplotypes having one or more desired characteristics; and
   (b) crossing the clonal gametes to produce the population of polyploid maize seed;
   wherein the population of polyploid maize seed comprises a subpopulation of genetically uniform polyploid maize seed in an amount of at least 50% of the total number of seeds, the subpopulation of genetically uniform polyploid maize seed comprising the three or more haplotypes.

76. A method of producing a population of polyploid maize seed comprising:
   (a) selecting three or more haplotypes using the method of breeding of any one of embodiments 63-74 based upon the polyploid plant comprising said three or more haplotypes having one or more desired characteristics;
   (b) providing clonal gametes from a parent MiMe plant;
   (c) providing haploid gametes from a homozygous parent non-MiMe plant;
   (d) crossing the clonal gametes with the haploid gametes to produce the population of polyploid maize seed;
   wherein the parent MiMe plant and the homozygous parent non-MiMe plant together comprise the three or more haplotypes selected in step (a), wherein the crossing of step (d) results in a population of polyploid maize seed comprising a subpopulation of genetically uniform polyploid maize seed in an amount of at least 50% of the total number of seeds, the subpopulation of genetically uniform polyploid maize seed comprising the three or more haplotypes.

77. The method of embodiment 75 or 76, wherein the population of polyploid maize seed has an average pairwise genetic uniformity of at least 80%, at least 85%, at least 90%, at least 95%, at least 96%, at least 97%, at least 98%, at least 99%, or 100% as measured by the Jaccard similarity coefficient.

78. The method of any one of embodiments 75-77, wherein the population of polyploid maize seed comprises the subpopulation of genetically uniform polyploid maize seed in an amount of at least 70%, at least 90%, at least 95%, at least 96%, at least 97%, at least 98%, or at least 99% of the total number of seeds.

79. The method of any one of embodiments 75-78, wherein each pair of seeds in the subpopulation of genetically uniform polyploid maize seed has a pairwise identity of at least 95%, at least 96%, at least 97%, at least 98%, at least 99%, or 100% as measured by the Jaccard similarity coefficient.

80. A genetically modified plant, plant part, or plant cell comprising:
   (A) three or more haplotypes; and
   (B)
      (i) a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;
      ii) a partial MiMe genotype comprising:
         (a) one or more MiMe alleles conferring decreased expression of one or more MiMe loci of each of a first, second, and third MiMe component; and
         (b) one or more non-MiMe alleles at the one or more MiMe loci of each of the first, second, and third MiMe component,
         wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;
      iii) a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components;
      iv) a partial MiMe genotype comprising:
         (a) one or more MiMe alleles conferring decreased expression of one or more MiMe loci of each of the first and second MiMe component; and
         (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components;
      v) a partially complemented MiMe genotype comprising:
         (a) only MiMe alleles at one or more MiMe loci of a first MiMe component;
         (b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;

vi) a partially complemented MiMe genotype comprising:
  (a) only MiMe alleles at one or more MiMe loci of a first MiMe component; and
  (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; or vii) a partially complemented MiMe genotype comprising:
  (a) only MiMe alleles at one or more MiMe loci of a first MiMe component, wherein the first MiMe component is a component of DNA double strand breakage during meiotic recombination;
  (b) one or more MiMe alleles and one or more non-MiMe alleles at one or more MiMe loci of a second MiMe component;
  (c) one or more MiMe alleles and one or more non-MiMe alleles at one or more MiMe loci of a third MiMe component; and
  (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

81. The genetically modified plant, plant part, or plant cell of embodiment 80, wherein:
  (1) the one or more MiMe loci of the component of sister chromatid cohesion during the first division of meiosis comprise REC8, SWITCH1/DYAD, or a combination thereof;
  (2) the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof;
  (3) the one or more MiMe loci of the component of progression through the second division of meiosis comprise OSD1, CYCA1, TDM1, PC1, PC2, FC, or any combination thereof; and/or
  (4) the one or more MiMe loci of the component of progression through the first division of meiosis comprise PS1, JASON, or a combination thereof.

82. The genetically modified plant, plant part, or plant cell of embodiment 80 or 81, comprising:
  (1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
  (2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;
  (3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
  (4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1, optionally wherein the one or more OSD1 loci comprise OSD1-1 and OSD1-2;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(14) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1; or

(15) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

83. The genetically modified plant, plant part, or plant cell of any one of embodiments 80-82, comprising one or more polynucleotide sequences selected from the group consisting of SEQ ID NOs: 108-111.

84. The genetically modified plant, plant part, or plant cell of any one of embodiments 80-83, wherein:
  (i) the genetically modified plant part is a non-regenerable plant part; or
  (ii) the genetically modified plant cell is a non-regenerable plant cell.

85. The genetically modified plant, plant part, or plant cell of any one of embodiments 80-84, wherein the plant part is a flower, a pistil, a leaf, a stem, a petiole, a cutting, a tissue, a seed coat, an ovule, pollen, a root, a rootstock, a scion, a fruit, a cotyledon, a hypocotyl, a protoplast, an embryo, an anther, or a portion thereof.

86. A processed plant product derived from the genetically modified plant, plant part, or plant cell of any one of embodiments 80-85 wherein the processed plant product comprises a detectable amount of the one or more MiMe alleles of the genetically modified plant, plant part, or plant cell.

87. The processed plant product of embodiment 86, wherein the processed plant product:
  (i) is selected from the group consisting of plant biomass, oil, meal, food starch, syrup, animal feed, flour, flakes, bran, lint, hulls, and processed seed; and/or
  (ii) is non-regenerable.

88. Germplasm of the population of polyploid maize seeds of any one of embodiments 45-59.

89. A population of polyploid maize seed comprising a subpopulation of genetically uniform polyploid maize seed in an amount of at least 50% of the total number of seeds, the genetically uniform polyploid maize seed comprising three or more haplotypes of the same or related species of plant, wherein the population was obtained from a single plant or a set of F1 hybrids, wherein the subpopulation of genetically uniform polyploid maize seed comprise
  (A) (1) one or more MiMe alleles at each of one or more MiMe loci of a component of sister chromatid cohesion during the first division of meiosis comprising REC8, SWITCH1/DYAD, or a combination thereof, (2) one or more MiMe alleles at each of one or more MiMe loci of a component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (3) one or more MiMe alleles at each of one or more MiMe loci of the component of progression through the second division of meiosis comprising OSD1, CYCA1, TDM1, PC1, PC2, FC, or any combination thereof; or
  (B) (2) one or more MiMe alleles at each of one or more MiMe loci of the component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (4) one or more MiMe alleles at each of one or more MiMe loci of the component of progression through the first division of meiosis comprise PS1, JASON, or a combination thereof;
  wherein each of the of the MiMe alleles comprises a germplasm genetic modification,
  wherein at least one seed, or a plant grown therefrom, of the population of polyploid maize seed has been selected for lack of expression of each of the one or more MiMe loci, and
  wherein the subpopulation of genetically uniform polyploid maize seeds comprises (i) a complete MiMe genotype comprising only MiMe alleles at each of the one or more MiMe loci, (ii) a partial MiMe genotype comprising at least one MiMe allele and at least one non-MiMe allele at each of the one or more MiMe loci, or (iii) a partially complemented MiMe genotype comprising only MiMe alleles at a first MiMe locus of the one or more MiMe loci and at least one MiMe allele and at least one non-MiMe allele at a second MiMe locus of the one or more MiMe loci.

90. The population of embodiment 89, wherein the subpopulation of genetically uniform polyploid maize seed is triploid, tetraploid, pentaploid, hexaploid, heptaploid, or octaploid.

91. The population of embodiment 89 or 90, wherein the population of polyploid maize seed has an average pairwise genetic uniformity of at least 80%, at least 85%, at least 90%, at least 95%, at least 96%, at least 97%, at least 98%, at least 99%, or 100% as measured by the Jaccard similarity coefficient.

92. The population of any one of embodiments 89-91, wherein the population of polyploid maize seed comprises the subpopulation of genetically uniform polyploid maize seed in an amount of at least 70%, at least 90%, at least 95%, at least 96%, at least 97%, at least 98%, or at least 99% of the total number of seeds.

93. The population of embodiment 89-92, wherein each pair of seeds in the subpopulation of genetically uniform polyploid maize seed has a pairwise identity of at least 95%, at least 96%, at least 97%, at least 98%, at least 99%, or 100% as measured by the Jaccard similarity coefficient.

94. The population of any one of embodiments 89-93, wherein the subpopulation of genetically uniform polyploid maize seed has a partially-complemented MiMe genotype comprising:
(A)
  (a) only MiMe alleles at one or more MiMe loci of a first MiMe component;
  (b) one or more MiMe alleles and one or more non-MiMe alleles at a first MiMe locus of a second MiMe component, and one or more MiMe alleles and one or more non-MiMe alleles at a second MiMe locus of the second MiMe component; and
  (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component,
  wherein the first MiMe component, the second MiMe component, and the third MiMe component are selected from the group consisting of (1) the component of sister chromatid cohesion during the first division of meiosis, (2) the component of DNA double strand breakage during meiotic recombination, and (3) the component of progression through the second division of meiosis, and each of the first MiMe component, the second MiMe component, and the third MiMe component are different MiMe components;
(B)
  (a) only MiMe alleles at one or more MiMe loci of a first MiMe component; and
  (b) one or more MiMe alleles and one or more non-MiMe alleles at a first MiMe locus of a second MiMe component, and one or more MiMe alleles and one or more non-MiMe alleles at a second MiMe locus of the second MiMe component,
  wherein the first MiMe component and the second MiMe component are selected from the group consisting of (2) the component of DNA double strand breakage during meiotic recombination and (4) the component of progression through the first division of meiosis and each of the first MiMe component and the second MiMe component are different MiMe components; or
(C)
  (a) only MiMe alleles at one or more MiMe loci of a first MiMe component, wherein the first MiMe component is the component of DNA double strand breakage during meiotic recombination;
  (b) one or more MiMe alleles and one or more non-MiMe alleles at one or more MiMe loci of a second MiMe component;
  (c) one or more MiMe alleles and one or more non-MiMe alleles at one or more MiMe loci of a third MiMe component; and
  (d) one or more MiMe alleles and one or more non-MiMe alleles at one or more MiMe loci of a fourth MiMe component,
  wherein the second MiMe component, the third MiMe component, and the fourth MiMe component are selected from the group consisting of (1) the component of sister chromatid cohesion during the first division of meiosis, (3) the component of progression through the second division of meiosis, and (4) the component of progression through the first division of meiosis, and each of the second MiMe component, the third MiMe component, and the fourth MiMe component are different MiMe components.

95. The population of any one of embodiments 89-94, wherein the subpopulation of genetically uniform polyploid maize seed comprises:
  (1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
  (2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;
  (3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1, optionally wherein the population of polyploid maize seed is from a maize plant and the one or more OSD1 loci comprise OSD1-1 and OSD1-2;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(14) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1; or

(15) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

96. The population of any one of embodiments 89-95, wherein the subpopulation of genetically uniform polyploid maize seed comprises one or more polynucleotide sequences selected from the group consisting of SEQ ID NOs: 108-111.

97. The population of any one of embodiments 89-96, wherein germination of a seed of the subpopulation of genetically uniform polyploid maize seed results in a sterile plant that produces inviable gametes, seedless fruit, or a combination thereof.

98. The population of any one of embodiments 89-97, wherein the population of polyploid maize seed comprises three or more haplotypes from the same species of maize.

99. A method of producing the population of polyploid maize seed of any one of embodiments 89-98, the method comprising:
   (a) generating a first parent MiMe plant and a second parent MiMe plant by introducing genetic modifications into one or more candidate lines to produce MiMe alleles in germplasm of a first parent MiMe plant, a second parent MiMe plant, and/or progenitors thereof, wherein the first parent MiMe plant and the second parent MiMe plant each comprise a complete MiMe genotype, and each of the progenitors comprises a partial MiMe genotype, wherein if progenitors are generated, the progenitors are further crossed to generate the first parent MiMe plant, the second parent MiMe plant, or both;
   (b) providing clonal gametes from the first parent MiMe plant and the second parent MiMe plant that together comprise the three or more haplotypes; and
   (c) crossing the clonal gametes to produce the population of polyploid maize seed;
wherein the population of polyploid maize seed comprises a subpopulation of genetically uniform polyploid maize seed in an amount of at least 50% of the total number of seeds, the subpopulation of genetically uniform polyploid maize seed comprising the three or more haplotypes.

100. The method of embodiment 99, wherein the subpopulation of genetically uniform polyploid maize seed has a partially-complemented MiMe genotype, wherein:
   (A)
   (a) the first parent MiMe plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; and
   (b) the second parent MiMe plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component;
   wherein at least one of the MiMe loci having only MiMe alleles of the first MiMe component of the first parent MiMe plant is the same as at least one of the MiMe loci having only MiMe alleles of the first MiMe component of the second parent MiMe plant;
   wherein either (i) at least one of the MiMe loci having only MiMe alleles of the third MiMe component of the first parent MiMe plant is the same as at least one of the MiMe loci having only MiMe alleles of the third MiMe component of the second parent MiMe plant, or (ii) the one or more MiMe loci having only MiMe alleles of the third MiMe component of the first parent MiMe plant are distinct from the one or more MiMe loci having only MiMe alleles of the third MiMe component of the second parent MiMe plant;

wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

(B)
(a) the first parent MiMe plant has only MiMe alleles at one or more MiMe loci of a first MiMe component, only MiMe alleles at a first MiMe locus of a second MiMe component, and only non-MiMe alleles at a second MiMe locus of the second MiMe component; and (b) the second parent MiMe plant has only MiMe alleles at one or more MiMe loci of the first MiMe component, only non-MiMe alleles at the first MiMe locus of the second MiMe component, and only MiMe alleles at the second MiMe locus of the second MiMe component;

wherein at least one of the MiMe loci having only MiMe alleles of the first MiMe component of the first parent MiMe plant is the same as at least one of the MiMe loci having only MiMe alleles of the first MiMe component of the second parent MiMe plant;

wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; and (C)
(a) the first parent MiMe plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination;

(b) the second parent MiMe plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and wherein at least one of the MiMe loci having only MiMe alleles of the first MiMe component of the first parent MiMe plant is the same as at least one of the MiMe loci having only MiMe alleles of the first MiMe component of the second parent MiMe plant;

wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

101. A method of producing the population of polyploid maize seed of any one of embodiments 1-98, the method comprising:
(a) generating a first parent MiMe plant by introducing genetic modifications into one or more candidate lines to produce MiMe alleles in germplasm of the first parent MiMe plant or progenitors thereof, wherein the first parent MiMe plant comprises a complete MiMe genotype, and each of the progenitors comprises a partial MiMe genotype, wherein if progenitors are generated, the progenitors are further crossed to generate the first parent MiMe plant;
(b) providing clonal gametes from the parent MiMe plant;
(c) providing haploid gametes from a homozygous parent non-MiMe plant; and
(d) crossing the clonal gametes with the haploid gametes to produce the population of polyploid maize seed,
wherein the clonal gametes and the haploid gametes together comprise three or more haplotypes, optionally wherein step (a) comprises generating the first parent MiMe plant, the second parent MiMe plant, or both.

102. A method of breeding a polyploid hybrid plant line, the method comprising:
(a) obtaining a set of lines of a plant;
(b) breeding the lines using traditional plant breeding methods to produce a set of candidate lines of the plant;
(c) selecting two or more candidate lines together comprising three or more haplotypes;
(d) generating a first parent MiMe plant and a second parent MiMe plant from the two or more candidate lines that together comprise the three or more haplotypes;
(e) providing clonal gametes from each of the first and second parent MiMe plants;
(f) crossing the clonal gametes to produce a hybrid polyploid maize seed comprising the three or more haplotypes;
(g) growing the hybrid polyploid maize seed to produce a hybrid polyploid plant comprising three or more haplotypes; and
(h) evaluating one or more characteristics of the hybrid polyploid plant, wherein the first parent MiMe plant, the second parent MiMe plant, and the hybrid polyploid plant each independently comprise:
(A) (1) one or more MiMe alleles at each of one or more MiMe loci of a component of sister chromatid cohesion during the first division of meiosis comprising REC8, SWITCH1/DYAD, or a combination thereof, (2) one or more MiMe alleles at each of one or more MiMe loci of a component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (3) one or more MiMe alleles at each of one or more MiMe loci of the component of progression through the second division of meiosis comprising OSD1, CYCA1, TDM1, PC1, PC2, FC, or any combination thereof; or (B) (2) one or more MiMe alleles at each of one or more MiMe loci of the component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (4) one or more MiMe alleles at each of one or more MiMe loci of the component of progression through the first division of meiosis comprise PS1, JASON, or a combination thereof;

wherein each of the of the MiMe alleles comprises a germplasm genetic modification, wherein the method comprises selecting the first parent MiMe plant, the second parent MiMe plant, the hybrid polyploid plant, or any combination thereof for lack of expression of the one or more MiMe loci, and wherein the first parent MiMe plant and the second parent MiMe plant each independently comprise a complete MiMe genotype comprising only MiMe alleles at each of the one or more MiMe loci, and wherein the hybrid polyploid plant comprises (i) a complete MiMe genotype comprising only MiMe alleles at each of the one or more MiMe loci, or (ii) a partially complemented MiMe genotype comprising only MiMe alleles at a first MiMe locus of the one or more MiMe loci and at least one MiMe allele and at least one non-MiMe allele at a second MiMe locus of the one or more MiMe loci;

the method optionally further comprising
(i) repeating steps (b)-(h) or steps (c)-(h) using the one or more characteristics of the hybrid polyploid plant evaluated in step (h) to guide the breeding of lines of step (b), the selecting of candidate lines of step (c), or both.

103. The method of embodiment 102, wherein:
(A)
(a) the first parent MiMe plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; and
(b) the second parent MiMe plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component;
wherein at least one of the MiMe loci having only MiMe alleles of the first MiMe component of the first parent MiMe plant is the same as at least one of the MiMe loci having only MiMe alleles of the first MiMe component of the second parent MiMe plant;

wherein either (i) at least one of the MiMe loci having only MiMe alleles of the third MiMe component of the first parent MiMe plant is the same as at least one of the MiMe loci having only MiMe alleles of the third MiMe component of the second parent MiMe plant, or (ii) the one or more MiMe loci having only MiMe alleles of the third MiMe component of the first parent MiMe plant are distinct from the one or more MiMe loci having only MiMe alleles of the third MiMe component of the second parent MiMe plant;

wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

(B)
(a) the first parent MiMe plant has only MiMe alleles at one or more MiMe loci of a first MiMe component, only MiMe alleles at a first MiMe locus of a second MiMe component, and only non-MiMe alleles at a second MiMe locus of the second MiMe component; and
(b) the second parent MiMe plant has only MiMe alleles at one or more MiMe loci of the first MiMe component, only non-MiMe alleles at the first MiMe locus of the second MiMe component, and only MiMe alleles at the second MiMe locus of the second MiMe component;
wherein at least one of the MiMe loci having only MiMe alleles of the first MiMe component of the first parent MiMe plant is the same as at least one of the MiMe loci having only MiMe alleles of the first MiMe component of the second parent MiMe plant;
wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; and (C)
(a) the first parent MiMe plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination;
(b) the second parent MiMe plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and wherein at least one of the MiMe loci having only MiMe alleles of the first MiMe component of the first parent MiMe plant is the same as at least one of the MiMe loci having only MiMe alleles of the first MiMe component of the second parent MiMe plant;

wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

104. A method of breeding a polyploid hybrid plant line, the method comprising:
(a) obtaining a set of lines of a plant;
(b) breeding the lines using traditional plant breeding methods to produce a set of candidate lines of the plant;
(c) selecting two or more candidate lines together comprising three or more haplotypes;
(d) generating a first parent MiMe plant from one of the two or more candidate lines;
(e) providing clonal gametes from the first parent MiMe plant;
(f) providing haploid gametes from a homozygous parent non-MiMe plant of one of the two or more candidate lines;
(g) crossing the clonal gametes with the haploid gametes to produce a hybrid polyploid maize seed;
(h) growing the hybrid polyploid maize seed to produce a hybrid polyploid plant; and
(i) evaluating one or more characteristics of the hybrid polyploid plant, wherein the first parent MiMe plant and the homozygous parent non-MiMe plant together comprise three or more haplotypes, wherein the crossing of step (g) results in the hybrid polyploid maize seed comprising three or more haplotypes, and wherein the growing of step (h) results in the hybrid polyploid plant comprising three or more haplotypes;

wherein the first parent MiMe plant and the hybrid polyploid plant each independently comprise:

(A) (1) one or more MiMe alleles at each of one or more MiMe loci of a component of sister chromatid cohesion during the first division of meiosis comprising REC8, SWITCH1/DYAD, or a combination thereof, (2) one or more MiMe alleles at each of one or more MiMe loci of a component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (3) one or more MiMe alleles at each of one or more MiMe loci of the component of progression through the second division of meiosis comprising OSD1, CYCA1, TDM1, PC1, PC2, FC, or any combination thereof; or (B) (2) one or more MiMe alleles at each of one or more MiMe loci of the component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (4) one or more MiMe alleles at each of one or more MiMe loci of the component of progression through the first division of meiosis comprise PS1, JASON, or a combination thereof;

wherein each of the of the MiMe alleles comprises a germplasm genetic modification, wherein the method comprises screening the first parent MiMe plant, the hybrid polyploid plant, or any combination thereof for lack of expression of the one or more MiMe loci, and wherein the first parent MiMe comprises a complete MiMe genotype comprising only MiMe alleles at each of the one or more MiMe loci, the parent non-MiMe plant comprises only non-MiMe alleles at each of the one or more MiMe loci, and the hybrid polyploid plant comprises a partial MiMe genotype comprising at least one MiMe allele and at least one non-MiMe allele at each of the one or more MiMe loci, the method optionally further comprising (j) repeating steps (b)-(i) or steps (c)-(i) using the one or more characteristics of the hybrid polyploid plant evaluated in step (i) to guide the breeding of lines of step (b), the selecting of candidate lines of step (c), or both.

105. The method of any one of embodiments 101-104, wherein the first parent MiMe plant, the second parent MiMe plant, the parent non-MiMe plant, or any combination thereof are diploid, triploid, or tetraploid and the hybrid polyploid plant is tetraploid, pentaploid, hexaploid, heptaploid, or octaploid.

106. The method of any one of embodiments 101-105, wherein generating the first parent MiMe plant, the second parent MiMe plant, or both comprises:
(1) introducing a complete MiMe genotype directly into two candidate lines to produce the first parent MiMe plant, the second parent MiMe plant, or both;
(2) introducing a partial MiMe genotype into two candidate lines to produce two grandparent non-MiMe plants each having a partial MiMe genotype and crossing the grandparent non-MiMe plants each having a partial MiMe genotype to produce the first parent MiMe plant, optionally wherein generating the first parent MiMe plant, the second parent MiMe plant, or both further comprises introducing a complete MiMe genotype directly into a third candidate line to produce the second parent MiMe plant; or
(3) introducing a partial MiMe genotype into four candidate lines to produce four grandparent non-MiMe plants each having a partial MiMe genotype, and crossing pairs of said grandparent non-MiMe plants each having a partial MiMe genotype to produce the first and second parent MiMe plants, optionally wherein generating the first parent MiMe plant, the second parent MiMe plant, or both further comprises propagating the first parent MiMe plant, the second parent MiMe plant, the grandparent non-MiMe plants, or any combination thereof to scale production of homogenous seed.

107. The method of any one of embodiments 102-106, wherein the hybrid polyploid plant comprises:
(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1, optionally wherein the population of polyploid maize seed is from a maize plant and the one or more OSD1 loci comprise OSD1-1 and OSD1-2;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(14) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1; or

(15) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

108. The method of any one of embodiments 102-107, wherein one or more of the candidate lines of step (c) are inbred lines, hybrid lines, or a combination thereof.

109. The method of any one of embodiments 102-108, wherein the complete MiMe genotype, the partial MiMe genotype, or both are introduced by gene editing, transgenesis, or a combination thereof.

110. The method of embodiment 102-109, wherein the decreased expression of one or more of the MiMe loci is each independently achieved by gene disruption, gene knockout, gene knockdown, gene silencing, RNA interference, or induction of methylation.

111. The method of embodiment 102-110, wherein the decreased expression of one or more of the MiMe loci is each independently achieved by introducing into each candidate line or a progenitor thereof an insertion, a deletion, one or more nucleotide changes, or an inversion that results in decreased expression of the MiMe locus, optionally including a step of selection for decreased expression of the MiMe locus.

112. The method of embodiment 111, wherein the insertion, the deletion, the one or more nucleotide changes, or the inversion eliminates expression of the MiMe locus, optionally wherein the expression of the MiMe locus is eliminated by a premature stop codon present in the 70%, the first 60%, the first 50%, the first 40%, the first 30%, the first 20%, or the first 10% of the nucleotides of the coding sequence of the MiMe locus following the start codon in the 3' direction.

113. A method of producing a population of polyploid maize seed comprising:
(a) providing clonal gametes from a pair of parent MiMe plants together comprising three or more haplotypes that were selected using the method of breeding of any one of embodiments 102, 103, and 105-112 based upon the polyploid plant comprising the three or more haplotypes having one or more desired characteristics; and (b) crossing the clonal gametes to produce the population of polyploid maize seed;

wherein the population of polyploid maize seed comprises a subpopulation of genetically uniform polyploid maize seed in an amount of at least 50% of the total number of seeds, the subpopulation of genetically uniform polyploid maize seed comprising the three or more haplotypes.

114. A method of producing a population of polyploid maize seed comprising:
   (a) selecting three or more haplotypes using the method of breeding of any one of embodiments 104-112 based upon the polyploid plant comprising said three or more haplotypes having one or more desired characteristics;
   (b) providing clonal gametes from a parent MiMe plant;
   (c) providing haploid gametes from a homozygous parent non-MiMe plant;
   (d) crossing the clonal gametes with the haploid gametes to produce the population of polyploid maize seed;
   wherein the parent MiMe plant and the homozygous parent non-MiMe plant together comprise the three or more haplotypes selected in step (a), wherein the crossing of step (d) results in a population of polyploid maize seed comprising a subpopulation of genetically uniform polyploid maize seed in an amount of at least 50% of the total number of seeds, the subpopulation of genetically uniform polyploid maize seed comprising the three or more haplotypes.

115. The method of embodiment 113 or 114, wherein the population of polyploid maize seed has an average pairwise genetic uniformity of at least 80%, at least 85%, at least 90%, at least 95%, at least 96%, at least 97%, at least 98%, at least 99%, or 100% as measured by the Jaccard similarity coefficient.

116. The method of any one of embodiments 113-115, wherein the population of polyploid maize seed comprises the subpopulation of genetically uniform polyploid maize seed in an amount of at least 70%, at least 90%, at least 95%, at least 96%, at least 97%, at least 98%, or at least 99% of the total number of seeds.

117. The method of any one of embodiments 113-116, wherein each pair of seeds in the subpopulation of genetically uniform polyploid maize seed has a pairwise identity of at least 95%, at least 96%, at least 97%, at least 98%, at least 99%, or 100% as measured by the Jaccard similarity coefficient.

118. A genetically modified plant, plant part, or plant cell comprising:
   (A) three or more haplotypes; and
   (B)
      (a) (1) one or more MiMe alleles at each of one or more MiMe loci of a component of sister chromatid cohesion during the first division of meiosis comprising REC8, SWITCH1/DYAD, or a combination thereof, (2) one or more MiMe alleles at each of one or more MiMe loci of a component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (3) one or more MiMe alleles at each of one or more MiMe loci of the component of progression through the second division of meiosis comprising OSD1, CYCA1, TDM1, PC1, PC2, FC, or any combination thereof; or
      (b) (2) one or more MiMe alleles at each of one or more MiMe loci of the component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (4) one or more MiMe alleles at each of one or more MiMe loci of the component of progression through the first division of meiosis comprise PS1, JASON, or a combination thereof;
   wherein each of the of the MiMe alleles comprises a germplasm genetic modification comprising introduction of a premature in-frame stop codon present in the first 30% of the nucleotides of the coding sequence of the MiMe locus following the start codon in the 3' direction, thereby generating a MiMe allele, and wherein the subpopulation of genetically uniform polyploid maize seeds comprises (i) a complete MiMe genotype comprising only MiMe alleles at each of the one or more MiMe loci, (ii) a partial MiMe genotype comprising at least one MiMe allele and at least one non-MiMe allele at each of the one or more MiMe loci, or (iii) a partially complemented MiMe genotype comprising only MiMe alleles at a first MiMe locus of the one or more MiMe loci and at least one MiMe allele and at least one non-MiMe allele at a second MiMe locus of the one or more MiMe loci
   wherein the partially-complemented MiMe genotype comprises:
   (i)
      (a) only MiMe alleles at one or more MiMe loci of a first MiMe component;
      (b) one or more MiMe alleles and one or more non-MiMe alleles at a first MiMe locus of a second MiMe component, and one or more MiMe alleles and one or more non-MiMe alleles at a second MiMe locus of the second MiMe component; and
      (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component,
      wherein the first MiMe component, the second MiMe component, and the third MiMe component are selected from the group consisting of (1) the component of sister chromatid cohesion during the first division of meiosis, (2) the component of DNA double strand breakage during meiotic recombination, and (3) the component of progression through the second division of meiosis, and each of the first MiMe component, the second MiMe component, and the third MiMe component are different MiMe components;
   (ii)
      (a) only MiMe alleles at one or more MiMe loci of a first MiMe component; and
      (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) the component of DNA double strand breakage during meiotic recombination and (4) the component of progression through the first division of meiosis and each of the first MiMe component and the second MiMe component are different MiMe components; or (iii)
(a) only MiMe alleles at one or more MiMe loci of a first MiMe component, wherein the first MiMe component is the component of DNA double strand breakage during meiotic recombination;
(b) one or more MiMe alleles and one or more non-MiMe alleles at one or more MiMe loci of a second MiMe component;
(c) one or more MiMe alleles and one or more non-MiMe alleles at one or more MiMe loci of a third MiMe component; and
(d) one or more MiMe alleles and one or more non-MiMe alleles at one or more MiMe loci of a fourth MiMe component,
wherein the second MiMe component, the third MiMe component, and the fourth MiMe component are selected from the group consisting of (1) the component of sister chromatid cohesion during the first division of meiosis, (3) the component of progression through the second division of meiosis, and (4) the component of progression through the first division of meiosis, and each of the second MiMe component, the third MiMe component, and the fourth MiMe component are different MiMe components.

119. The genetically modified plant, plant part, or plant cell of embodiment 118, comprising:
(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;
(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1, optionally wherein the population of polyploid maize seed is from a maize plant and the one or more OSD1 loci comprise OSD1-1 and OSD1-2;
(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;
(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(14) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1; or

(15) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

120. The genetically modified plant, plant part, or plant cell of embodiment 118 or 119, comprising one or more polynucleotide sequences selected from the group consisting of SEQ ID NOs: 108-111.

121. The genetically modified plant, plant part, or plant cell of any one of embodiments 118-120, wherein:
  (i) the genetically modified plant part is a non-regenerable plant part; or
  (ii) the genetically modified plant cell is a non-regenerable plant cell.

122. The genetically modified plant, plant part, or plant cell of any one of embodiments 118-121, wherein the plant part is a flower, a pistil, a leaf, a stem, a petiole, a cutting, a tissue, a seed coat, an ovule, pollen, a root, a rootstock, a scion, a fruit, a cotyledon, a hypocotyl, a protoplast, an embryo, an anther, or a portion thereof.

123. A processed plant product derived from the genetically modified plant, plant part, or plant cell of any one of embodiments 118-122 wherein the processed plant product comprises a detectable amount of the one or more MiMe alleles of the genetically modified plant, plant part, or plant cell.

124. The processed plant product of embodiment 123, wherein the processed plant product:
  (i) is selected from the group consisting of plant biomass, oil, meal, food starch, syrup, animal feed, flour, flakes, bran, lint, hulls, and processed seed; and/or
  (ii) is non-regenerable.

125. Germplasm of the population of polyploid maize seeds of any one of embodiments 89-98.

126. A method of producing comprising a subpopulation of genetically uniform polyploid seed in an amount of at least 50% of the total number of seeds, the genetically uniform polyploid seed comprising three or more haplotypes of the same or related species of plant, wherein the population was obtained from a single plant or a set of F1 hybrids, the method comprising:
  (1)
    (a) generating a first parent MiMe plant and a second parent MiMe plant;
    (b) providing clonal gametes from the first parent MiMe plant and the second parent MiMe plant that together comprise the three or more haplotypes; and
    (c) crossing the clonal gametes to produce the population of polyploid seed, or
  (2)
    (a) generating a first parent MiMe plant;
    (b) providing clonal gametes from the parent MiMe plant;
    (c) providing haploid gametes from a homozygous parent non-MiMe plant; and
    (d) crossing the clonal gametes with the haploid gametes to produce the population of polyploid seed,
  wherein the generating in step (a) comprises introducing the following MiMe alleles (A) or (B) at the following MiMe loci by (i) introducing genetic modifications in the MiMe loci and selecting for lack of expression at the MiMe loci, (ii) introducing an expression construct for a silencing RNA targeting the MiMe loci, or (iii) introducing a natural MiMe allele or selecting a first parent MiMe plant, a second parent MiMe plant or a progenitor with the natural allele for use in combination with (i) and/or (ii) for other MiMe alleles; wherein genetic modifications and/or expression constructs are introduced into one or more candidate lines to produce MiMe alleles in germplasm of a first parent MiMe plant, a second parent MiMe plant, and/or progenitors thereof, wherein the first parent MiMe plant and the second parent MiMe plant each comprise a complete MiMe genotype, and each of the progenitors comprises a partial MiMe genotype, wherein if progenitors are generated, the progenitors are further crossed to generate the first parent MiMe plant, the second parent MiMe plant, or both:
  (A) (1) one or more MiMe alleles at one or more MiMe loci of a component of sister chromatid cohesion during the first division of meiosis comprising REC8 (i.e., a gene encoding a protein having at least 60% sequence identity to one of NP 001105829.1, XP 008648327.1, XP 008648329.1, and XP 008648328.1 or to XP 006347252.1), SWITCH1/DYAD (i.e., a gene encoding a protein having at least 60% sequence identity to one of NP_001139538.1, XP 008662288.1 and C0RWW9 or to M1BMI9), or a combination thereof, (2) one or more MiMe alleles at one or more MiMe loci of a component of DNA double strand breakage during meiotic recombination comprising PAIR1 (i.e., a gene encoding a protein having at least 60% sequence identity to one of XP 008660580.1, AOA1D6JK92, AOA1D6JK93, AOA1D6JK94, and A0A1D6PM18 or to one of XP 006339791.2 and MOZGU5), SPO11-1 (i.e., a gene encoding a protein having at least 60% sequence identity to one of NP 001347894.1, XP 008643457.1, XP 008643458.1, XP 008643459.1, XP 020408860.1, and XP 008643458.1 or to one of XP 006346146.1, M1COB8, and M1CP72), SPO11-2 (i.e., a gene encoding a protein having at least 60% sequence identity to one of XP 020406911.1, NP_001298099.1 and NP_001141583.1 or to one of XP 006344018.1, XP 006367265.1 and M1CP72), PRD1 (i.e., a gene encoding a protein having at least 60% sequence identity to one of XP 020399554.1, XP 020399553.1 and A0A1D6P5Q4 or to one of XP 015163123.1 and M1CA99), PRD2 (i.e., a gene encoding a protein having at least 60% sequence identity to one of NP_001130070.1, XP 035822500.1 and A0A3L6F902 or to one of XP 015162530.1 and M1AS84), DFO (i.e., a gene encoding a protein having at least 60% sequence identity to one of XP 020397706.1, AOA1D6QG87 and AOA3L6EXP8 or to one of XP 006350870.1 and M1CZR2), MTOPVIB (i.e., a gene encoding a protein having at least 60% sequence identity to one of XP 008645058.1, AOA3L6EMU7 and AOA1D6GVU9 or to one of XP 015166906.1, XP 015166907.1 and M1CGP5), DSY1, SY1, SY2, SY3, SY4, or any combination thereof, and (3) one or more MiMe alleles at one or more MiMe loci of the component of progression through the second division of meiosis comprising OSD1 (i.e., a gene encoding a protein having at least 60% sequence identity to one of AOA1D6HBV9, AOA1D6HBW0, B4FCP3, B4FG75, and B6T7U1 or to one of XP 006351336.1), CYCA1 (i.e., a gene encoding a protein having at least 60% sequence identity to one of NP_001105387.2, NP_001288521.1 and XP 008656316.2 or to one of XP 006351137.1, XP 006351136.1 and XP 006351138.1), TDM1 (i.e., a gene encoding a protein having at least 60% sequence identity to one of NP_001170740.1, NP_001141607.1 and XP 008651103.1 or to one of XP 006350746.1, XP 006340757.1 and XP 006360343.1), PC1, PC2, FC, or any combination thereof; or (B) (2) one or more MiMe alleles at one or more MiMe loci of the component of DNA double strand breakage during meiotic recombination comprising PAIR1 (i.e., a gene encoding a protein having at least 60% sequence identity to one of), SPO11-1 (i.e., a gene encoding a protein having at least 60% sequence identity to one of), SPO11-2, PRD1, PRD2, DFO, MTOPVIB, DSY1, SY1, SY2, SY3, SY4, or any combination thereof, and (4) one or more MiMe alleles at one or more MiMe loci of the component of progression through the first division of meiosis comprise PS1 (i.e., a gene encoding a protein having at least 60% sequence identity to one of NP_001348386.1, XP 035820777.1 and XP 008668271.1 or to one of XP 006351164.1, XP 006353632.1 and M1AJ10), JASON (i.e., a gene encoding a protein having at least 60% sequence identity to one of NP_001132267.1, XP 008647301.1 and NP_001130670.1 or to one of XP 006352001.1, XP 015160469.1 and M1CT79), or a combination thereof;

wherein the subpopulation of genetically uniform polyploid seeds comprises (i) a complete MiMe genotype comprising only MiMe alleles at each of the one or more MiMe loci, (ii) a partial MiMe genotype comprising at least one MiMe allele and at least one non-MiMe allele at each of the one or more MiMe loci, or (iii) a partially complemented MiMe genotype comprising only MiMe alleles at a first MiMe locus of the one or more MiMe loci and at least one MiMe allele and at least one non-MiMe allele at a second MiMe locus of the one or more MiMe loci.

127. The method of embodiment 126, wherein the subpopulation of genetically uniform polyploid seed is triploid, tetraploid, pentaploid, hexaploid, heptaploid, or octaploid.

128. The method of embodiment 126 or 127, wherein the population of polyploid seed has an average pairwise genetic uniformity of at least 80%, at least 85%, at least 90%, at least 95%, at least 96%, at least 97%, at least 98%, at least 99%, or 100% as measured by the Jaccard similarity coefficient.

129. The population of any one of embodiments 126-128, wherein the population of polyploid seed comprises the subpopulation of genetically uniform polyploid seed in an amount of at least 70%, at least 90%, at least 95%, at least 96%, at least 97%, at least 98%, or at least 99% of the total number of seeds.

130. The population of embodiment 126-129, wherein each pair of seeds in the subpopulation of genetically uniform polyploid seed has a pairwise identity of at least 95%, at least 96%, at least 97%, at least 98%, at least 99%, or 100% as measured by the Jaccard similarity coefficient.

131. The population of any one of embodiments 126-130, wherein the subpopulation of genetically uniform polyploid seed has a partially-complemented MiMe genotype comprising:

(A)
 (a) only MiMe alleles at one or more MiMe loci of a first MiMe component;
 (b) one or more MiMe alleles and one or more non-MiMe alleles at a first MiMe locus of a second MiMe component, and one or more MiMe alleles and one or more non-MiMe alleles at a second MiMe locus of the second MiMe component; and
 (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component,
 wherein the first MiMe component, the second MiMe component, and the third MiMe component are selected from the group consisting of (1) the component of sister chromatid cohesion during the first division of meiosis, (2) the component of DNA double strand breakage during meiotic recombination, and (3) the component of progression through the second division of meiosis, and each of the first MiMe component, the second MiMe component, and the third MiMe component are different MiMe components;

(B)
 (a) only MiMe alleles at one or more MiMe loci of a first MiMe component; and
 (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) the component of DNA double strand breakage during meiotic recombination and (4) the component of progression through the first division of meiosis and each of the first MiMe component and the second MiMe component are different MiMe components; or (C)
 (a) only MiMe alleles at one or more MiMe loci of a first MiMe component, wherein the first MiMe component is the component of DNA double strand breakage during meiotic recombination;
 (b) one or more MiMe alleles and one or more non-MiMe alleles at one or more MiMe loci of a second MiMe component;
 (c) one or more MiMe alleles and one or more non-MiMe alleles at one or more MiMe loci of a third MiMe component; and
 (d) one or more MiMe alleles and one or more non-MiMe alleles at one or more MiMe loci of a fourth MiMe component,
 wherein the second MiMe component, the third MiMe component, and the fourth MiMe component are selected from the group consisting of (1) the component of sister chromatid cohesion during the first division of meiosis, (3) the component of progression through the second division of meiosis, and (4) the component of progression through the first division of meiosis, and each of the second MiMe component, the third MiMe component, and the fourth MiMe component are different MiMe components.

132. The method of any one of embodiments 126-131, wherein the subpopulation of genetically uniform polyploid seed comprises:
    (1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
    (2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;
    (3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
    (4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1, optionally wherein the population of polyploid seed is from a maize plant and the one or more OSD1 loci comprise OSD1-1 and OSD1-2
    (5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
    (6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;
    (7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
    (8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;
    (9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(14) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1; or

(15) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

133. The population of any one of embodiments 126-132, wherein the subpopulation of genetically uniform polyploid seed comprises one or more polynucleotide sequences selected from the group consisting of SEQ ID NOs: 108-111.

EXAMPLES

The presently disclosed subject matter will be better understood by reference to the following Examples, which are provided as exemplary of the inventions, and not by way of limitation.

Example 1: General Methods

GM: Methods
GM1: Identifying Homologs of Genes Underlying MiMe-Like Phenotype Across Plant Species Core genes involved in the conversion of meiosis to mitosis (mitosis instead of meiosis or MiMe) were identified through alignment with any of the canonical reference sequences for REC8, OSD1 (e.g., OSD1-1, OSD1-2, and/or OSD1-3 from maize), PAIR1 (e.g., PAIR1-1 and/or PAIR1-2 from maize), SPO11-1. JASON (e.g., .JASON-1 and JASON-2 from maize), CYCA1 (also known as CYCLIN-A1 or as TARDY ASYNCHRONOUS MEIOSIS (TAM), TDM1, and/or PS1 as shown in Table 5 (SEQ IDs 1-12). Amino acid sequences of the protein isoforms predicted from open reading frames of these genes were aligned to the NCBI RefSeq (O'Leary et al. (2016) Reference sequence (RefSeq) database at NCBI: current status, taxonomic expansion, and functional annotation. Nucleic Acids Res. 44 (D1): D733-D745), UniProtKB Swiss-Prot and TrEMBL (The UniProt Consortium (2019) UniProt: a worldwide hub of protein knowledge, Nucleic Acids Res. 47 (D1): D506-D515. https://doi.org/10.1093/nar/gky 1049) protein databases. These alignments were performed using default parameters (gap opening penalty=11, gap extension penalty=1, E-value=10, word size=3, max score=25, query filter=SEG, substitution matrix=BLOSUM 62) in Protein-Protein BLAST 2.11.0+(O'Leary et al. (2016)). For example, core MiMe genes in a plant's genome may be identified through alignment with the REC8, OSD1, PAIR1, and SPO11-1 sequences from *Oryza sativa*.

Candidate orthologs were further validated through alignments between the identified orthologs and canonical protein sequences in Table 5 using Clustal Omega—1.2.4 with default parameters (substitution matrix=GONNET) for protein-protein alignments. The canonical protein sequences used were those from *Arabidopsis thaliana* for dicots, and those from *Oryza sativa* for monocots. In some cases, the canonical protein sequences available were from *Arabidopsis thaliana*. Results were filtered for relevant species and were further manually curated to remove spurious alignments. Orthologs with an amino acid consensus greater than 50% when aligning maize queries against potential maize sequences were considered as candidate orthologs with a preference for the highest conservation of amino acid sequence and exon structure relative to the canonical set (SEQ ID NOs: 1-12, Table 5).

GM1.1: Identification of Target DNA Sequences for crRNA Design

The protein Blast results were aligned to a genomic database using BLAST's "tblastn" search, specifically the Protein Query-Translated Subject BLAST 2.11.0+ with default parameters (gap opening penalty=11, gap extension penalty=1, E-value=10, word size=3, max score=25, query filter=SEG, query genetic code=universal, substitution matrix=BLOSUM 62). The corresponding nucleotide sequences of identified orthologs and any putative paralogs were extracted from this search, including 5 kb upstream of each gene, using custom shell scripts. These sequences were then aligned to each other using Clustal Omega—1.2.4 with default parameters (substitution matrix=GONNET). Most likely candidate sequences, with the highest identity to the canonical sequences and with the most conserved exon structure were used to design CRISPR RNA (crRNA) for an appropriate CRISPR-associated (Cas) nuclease.

GM1.2: Design of crRNA for DNA Editing with a Cas Nuclease

For each species of interest, the most probable candidate sequences identified from the protein BLAST, tblastn, and Clustal Omega workflows were targeted for crRNA design in Geneious Prime 2020.0.3, with protospacer adjacent motif (PAM) sites near each candidate identified for an appropriate Cas nuclease. crRNA with high specificity targeting the first or second exons or promoter sequences were generally preferred, but high-scoring crRNA targeting later exons were also selected. Resulting sequences were exported and scaffolds for an appropriate Cas nuclease were added. Functional crRNAs were synthesized by IDT (Integrated DNA Technologies, Newark, NJ, USA) using standard RNA synthesis. The process was repeated for each target gene, including REC8, OSD1 (e.g., OSD1-1, OSD1-2, and/or OSD1-3 from maize), PAIR1 (e.g., PAIR1-1 and/or PAIR1-2 from maize), SPO11-1, JASON (e.g., JASON-1 and JASON-2 from maize), CYCA1 (e.g., CYCA1-1 and CYCA1-2 from maize), TDM1, and/or PS1 crRNA were screened for editing efficiency in protoplasts.

In monocots, editing was achieved by stable integration of two distinct DNA cassettes, one of which contained an appropriate codon-optimized Cas nuclease (i.e., the nuclease construct) and the other of which contained an array of crRNAs targeting MiMe alleles (i.e., the guide RNA construct). The DNA sequences corresponding to the crRNAs were inserted into a standard crRNA guide array between repeats, which were recognized and cleaved by either an appropriate ribonuclease or a ribozyme. The cassettes were each driven by their own plant ubiquitin promoter; however, plant U6 promoters or other suitable promoters with sufficient expression to achieve editing in the target plant were also tested and achieved similar results.

GM2: Ribonucleoprotein Preparation

To prepare ribonucleoproteins (RNPs), 2 μL of New England Biolabs buffer (NEBuffer™) 2.1 (10× stock) was placed into a 1.5 mL microcentrifuge tube with 10-600 pmol of crRNA and with an equal amount of the selected Cas nuclease protein. The final volume was adjusted to 20 μL using nuclease-free water. The solution was prepared fresh and used after a 15-minute incubation at room temperature.

GM3: Sequence-Based Edit Confirmation

Primers were designed to amplify each gene, and protoplasts were generated. Further details on plant selection, plant growth, protoplast generation, and protoplast transfection, are provided in the species-specific protocols in the Examples below.

Some transfected protoplasts were incubated at room temperature for 24 to 48 hours, then lysed and one or more long-range direct polymerase chain reactions (PCRs) were performed on the crude lysates. Other transfected protoplasts were regenerated, and DNA was then extracted from these protoplasts' regenerated callus, leaf, or other plant tissue. PCR products were pooled by transfection sample and a seqWell™ (Beverly, MA, USA) library preparation was performed to generate an Illumina (Illumina, San Diego, CA, USA) library. Samples were loaded onto an Illumina iSeq (Illumina, San Diego, CA, USA) and sequenced with a paired-end 150 nt sequencing kit. Sequences were analyzed by aligning FASTQ files to reference sequences and mutations adjacent to target sites for each gene were tabulated relative to a control. Editing efficiency was calculated based on the frequency of observed mutations in the reads obtained for a given sample, and this information was used to calculate how many plants should be screened to identify the multi-gene knockouts required to induce the clonal gamete production.

PCR amplicons were used to prepare Illumina sequencing libraries using plexWell 96 kits (seqWell™ Beverly, MA, USA) and libraries were sequenced on an Illumina iSeq (Illumina, San Diego, CA, USA). FASTQ data sets were aligned to the corresponding reference genomes using the BWA-MEM algorithm (Li, H. (2013) Aligning sequence reads, clone sequences and assembly contigs with BWA-MEM. arXiv preprint arXiv:1303.3997) and variants were visualized and quantified using custom scripts. Editing efficiency was calculated as the fraction of reads in an edited sample with on-target mutations relative to an unedited control. Editing efficiency was determined for each guide and used to estimate the minimum number of plants needed to recover the required multi-gene knockout.

GM4: Flow Cytometry

Flow cytometry was performed on parent plants and on the progeny using the methods of Galbraith et al. 1983 (Rapid flow cytometric analysis of the cell cycle in intact plant tissues. *Science*. 220(4601): 1049-1051). Further details on parent plant selection and methods of crossing are provided in the species-specific protocols in the Examples below. Briefly, intact nuclei were extracted, filtered, and stained with propidium iodide as per instructions of the CyStain® PI Absolute P kit (Sysmex America, Lincolnshire, IL, USA). DNA content of nuclei was determined by applying the samples to a BD Accuri C6 Flow Cytometer. Gating was performed and genomic DNA content was calculated by comparing the peak area for the sample to the known position of a control with known ploidy. The ploidy of the unknown samples was determined based on relative comparison to each control.

GM5: Analysis of Genetic Uniformity Using the Jaccard Similarity Coefficient

The Jaccard similarity coefficient was used to measure genetic uniformity of populations of seeds. The Jaccard index, Jaccard similarity index, or Jaccard similarity coefficient (Jaccard, P. (1908) Nouvelles Recherches sur la Distribution Florale. Bulletin de la Société Vaudoise des Sciences Naturelles. Vol. 44) is a metric used to compare the similarity of two sets. In the context of molecular plant genetics, the Jaccard index, Jaccard similarity index, or Jaccard similarity coefficient, is commonly applied to quantify the pairwise genetic similarity or uniformity of plants based on the presence or absence of shared alleles at loci spread throughout the genome (Paz and Veilleux (1997). Genetic diversity based on randomly amplified polymorphic DNA (RAPD) and its relationship with the performance of diploid potato hybrids. Journal of the American Society for Horticultural Sci. 122(6): 740-747; Vosman et al. (2004). The establishment of 'essential derivation' among rose varieties, using AFLP. Theoretical and Applied Genetics. 109: 1718-1725; Noli et al. (2013). Criteria for the definition of similarity thresholds for identifying essentially derived varieties. Plant Breeding. 132(6): 525-531; Vijayakumar et al. (2021) High temperature induced changes in quality and yield parameters of tomato (Solanum lycopersicum L.) and similarity coefficients among genotypes using SSR markers. Heliyon. 7(2); Dalamu et al. (2023). Genetic Diversity and Population Structure Analyses Using Simple Sequence Repeat Markers and Phenotypic Traits in Native Potato Collection in India. Potato Research: 1-25).

The Jaccard similarity coefficient is defined as the ratio of the number of shared items to the total number of distinct items in the two sets. In the context of molecular plant genetics, it can be used to quantify the proportion of shared alleles between two plants.

The formula for calculating the Jaccard similarity coefficient is:

$$J(A,B) = |A \cap B|/|A \cup B|$$

Where A represents the set of unique alleles without duplicates in one plant, B the set of unique alleles without duplicates in the other plant, $|A \cap B|$ represents the number of shared alleles (the cardinality of the intersection) between the plants, and $|A \cup B|$ represents the number of distinct alleles (the cardinality of the union) between the plants.

This formula computes the cardinality of the intersection (common elements) of two sets (the shared alleles) divided by the cardinality of the union (all alleles) of the two sets (all distinct alleles present). The resulting value of the Jaccard similarity coefficient ranges from 0 to 1, where 0 indicates no shared alleles, and 1 indicates complete uniformity.

The average pairwise genetic uniformity of the populations of seed was calculated as the average Jaccard similarity coefficient of all possible pairs of plants within the population. We note that in the context of genetic pairwise similarity estimations, the size of A should be the same as, or very close to, the size of B to avoid misinterpretation.

Genotyping results found in the Examples below (such as in Example 2's section ZR4) were encoded so that each allele at each locus represents a unique member of the set of total alleles. The number of shared alleles between each pair of progeny were divided by the total number of distinct alleles present in the two plants, and the results are the Jaccard index, Jaccard similarity index, or Jaccard similarity coefficient.

GM6: Population Genotyping

All relevant parent and progeny plants were sequenced via whole genome shotgun (WGS) sequencing. DNA samples were sequenced by Novogene. Libraries were prepared using the NEBNext® Ultra™ II for DNA Library Prep kit, and paired-end 2×150 reads were sequenced on an Illumina NovaSeq 6000 or NovaSeq X plus. Germline SNPs and small indels were called in all relevant parents using a standard whole genome variant calling pipeline. WGS data was aligned to a reference genome with BWA-MEM (Li, H. (2013) Aligning sequence reads, clone sequences and assembly contigs with BWA-MEM. arXiv preprint arXiv: 1303.3997). PCR duplicates were removed and SNPs and small indels were called and jointly genotyped with GATK (McKenna, A et al. (2010) The Genome Analysis Toolkit: a MapReduce framework for analyzing next-generation DNA sequencing data. Genome research, 20(9), pp. 1297-1303). Tri-allelic and tetra-allelic markers were established to genotype populations.

Tri-allelic (containing three alleles) markers were used when one parent was expected to contribute one distinct haplotype while the other parent was expected to contribute two distinct haplotypes. Pairs of SNPs that were close enough to be directly phased by 150 bp Illumina reads were used. Each SNP was unique/exclusive to one of the parents. One SNP/parent was homozygous while the other was heterozygous (REF/ALT or ALT1/ALT2). To genotype progeny, we looked for the presence of both ALT alleles (one from each parent) as well as the presence of the reference allele or second alternate allele of the heterozygous SNPs. If all alleles were observed and phasing was consistent with parental haplotypes, then the locus was genotyped as tri-allelic.

Tetra-allelic (containing four alleles) markers were used when both parents were expected to contribute two distinct haplotypes. Trios of SNPs that were close enough to be directly phased by 150 bp Illumina reads were used. One SNP was unique/exclusive to one parent and the two other SNPs were unique/exclusive to the other parent. All SNPs were heterozygous. The ALT alleles of the two SNPs exclusive to the same parent were on opposing haplotypes. To genotype progeny, we looked for the presence of all three ALT alleles (one from one parent and two from the other) as well as the presence of the reference allele or second alternate allele of the solo heterozygous SNPs. If all alleles were observed and phasing was consistent with parental haplotypes, then the locus was genotyped as tetra-allelic.

After establishing markers, markers were filtered, genotyped, and checked for quality across all progenies (via WGS data) using a combination of manual and custom automated techniques.

Example 2: Generating Genetically Uniform Tetraploid Hybrid Maize

ZM: Methods
ZM1: Plant Materials for crRNA Guide Screening

For crRNA guide screening, seeds of *Zea mays* B73, Hi-II, or Fast-Flowering Mini-Maize ("FFMM-AT6") (McCaw et al. (2020) Development of a Transformable Fast-Flowering Mini-Maize as a Tool for Maize Gene Editing. Frontiers in Genome Editing. doi: 10.3389/fgeed.2020.622227) were planted in a plug tray filled with PRO-MIX HP, covered with a humidome, and underlain with a seedling heating mat that maintained a soil temperature of about 30° C. After 4 days, when seedlings germinated enough to reach light, they were covered by a box to block light. When the second leaf was about 10 cm longer than the first leaf, it was removed and used for protoplast isolation.

ZM2: Protoplast Isolation

Approximately thirty minutes before digestion of the cell wall, 1-2 g of leaves were sliced into thin sections of about 0.5 mm in width and placed in a petri dish with 20 ml of digest solution (0.6 M Mannitol, 10 mM MES (pH5.7), 1 mM $CaCl_2$, 5 mM β-mercaptoethanol, 0.1% Bovine Serum Albumin, 1.5% Cellulase R10 and 0.3% Macerozyme R10). Leaf sections were then vacuum infiltrated for 30 minutes at room temperature, then incubated in the dark while shaking at 40 RPM for two hours. After two hours protoplasts were liberated by shaking at 80 RPM for 5 minutes. Protoplasts were then filtered through a 75 μM mesh and transferred to two round bottom tubes. The protoplasts were pelleted at 100×g for 5 minutes, then were washed twice by resuspending in a cool wash solution (0.6 M mannitol, 20mMKCl, 4 mM MES (pH5.7)) and pelleting. Finally, protoplasts were resuspended in 10 ml of wash solution and incubated on ice for one hour. Cells were quantified using a Bürker hemocytometer and stored on ice in the dark until transfection. A sample was also reserved to test cell viability using FDA staining as described by Larkin (1976. Purification and viability determinations of plant protoplasts. Planta 128(3): 213-216).

ZM3: Transfection

Immediately before transfection, a fresh polyethylene glycol (PEG) solution was prepared according to Cao et al. (2014. PEG-mediated transient gene expression and silencing system in maize mesophyll protoplasts: a valuable tool for signal transduction study in maize. Acta Physiologiae Plantarum. 36(5): 1271-1281). Protoplasts were centrifuged at 100×g for 5 minutes and resuspended in a volume of MMG transformation buffer (4 mM MES, pH 5.7, 0.4 M mannitol and 15 mM $MgCl_2$) as described by Cao et al. (2014) to achieve a cell density of 1-2×10⁶ protoplasts/mL. 15 μL of RNP was freshly prepared as described in Example 1's section GM2 and added to wells of a 48-well plate. Alternatively, 20 μg of plasmid DNA total in 15 μL of sterile deionized water was added to a 48-well plate. Next, 200 μL of protoplast suspension was mixed with the RNP solution (or plasmid DNA) by pipetting with wide bore tips, after which the approximately 215 μL of PEG solution was added and gently mixed by pipetting up and down with a wide bore tip until Schlieren lines were no longer visible. After a 20-minute incubation at room temperature, 800 μl of incubation solution (0.6 M mannitol, 4 mM KCl, 4 mM MES) was added to the approximately 215 μL of PEG solution and mixed again by pipetting. The protoplasts were then pelleted from the resulting solution at 100×g for 2 minutes, after which the plates were rotated and centrifuged again at 100× g for 2 minutes. The supernatant was then removed, and 2 mL of incubation solution (0.6 M mannitol, 4 mM KCl, 4 mM MES) was added to the wells. Protoplasts were resuspended according to Cao et al. 2014 and then incubated in the dark for 2 days at 27° C. After this incubation, 30 ul of cells were collected from the bottom of the wells and pipetted into a PCR plate where they were lysed, and DNA was extracted using the Platinum Direct Polymerase kit (#A44647100 ThermoFisher Scientific). A sample from each well was also evaluated for cell viability using FDA staining as described by Larkin (1976. Purification and viability determinations of plant protoplasts. Planta 128(3): 213-216).

ZM4: Plasmids for Biolistic Transformation

Figure 5:
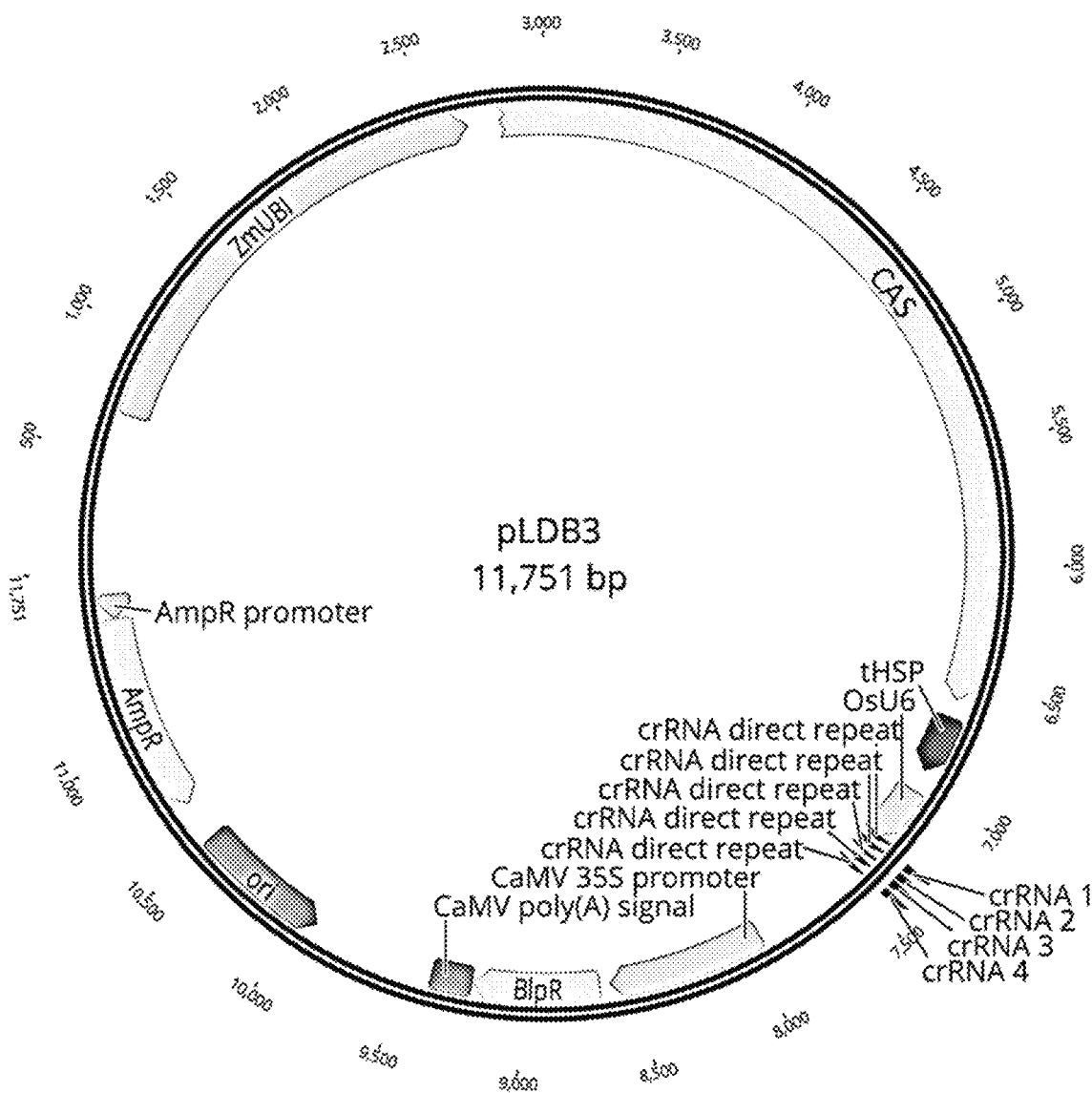
FIG. 5 depicts a plasmid map of pLDB3, used to introduce MiMe gene edits in Zea mays.
Figure 6:
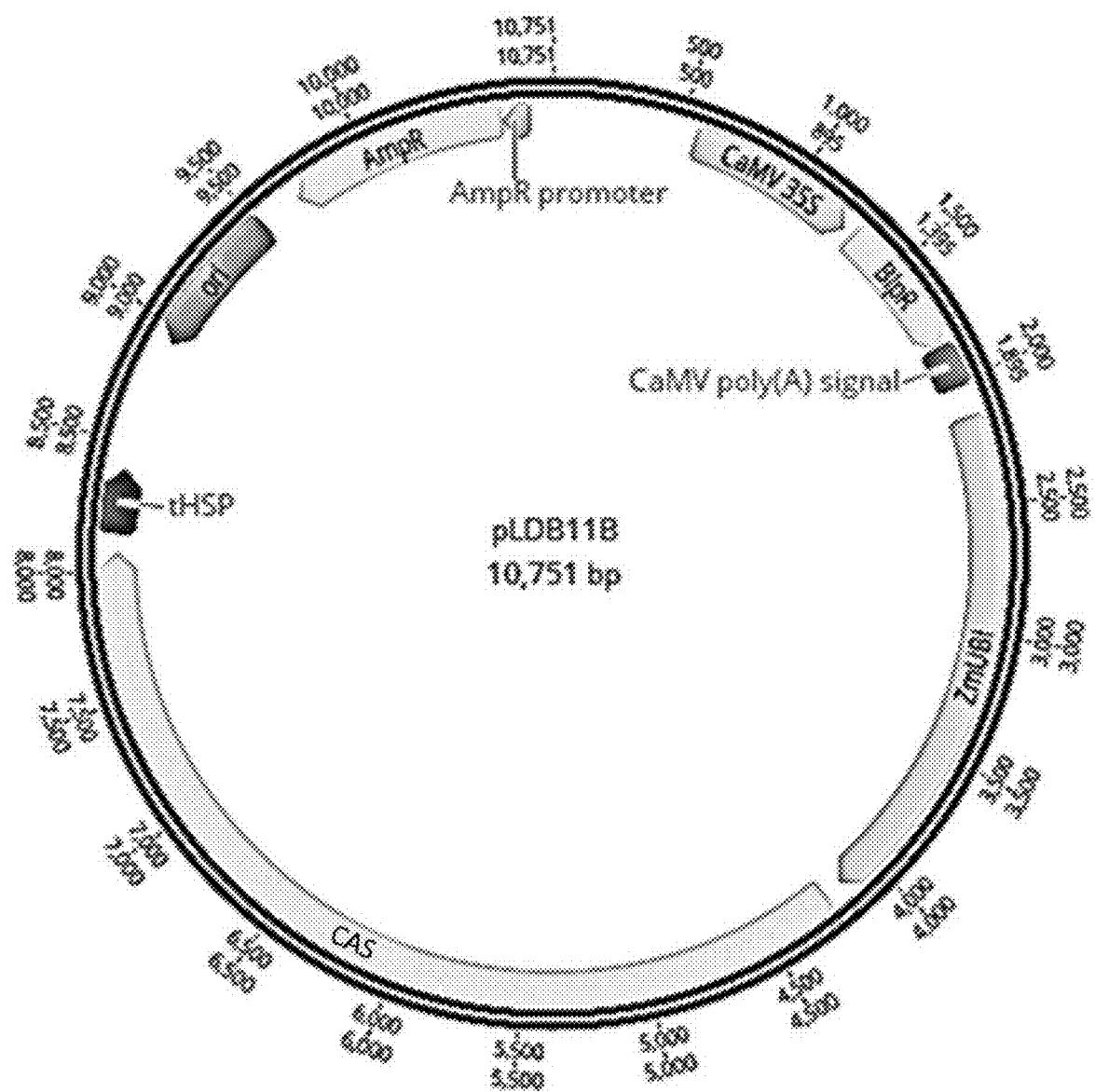
FIG. 6 depicts a plasmid map of pLDB111B, used to introduce MiMe gene edits in Zea mays.
Figure 7:
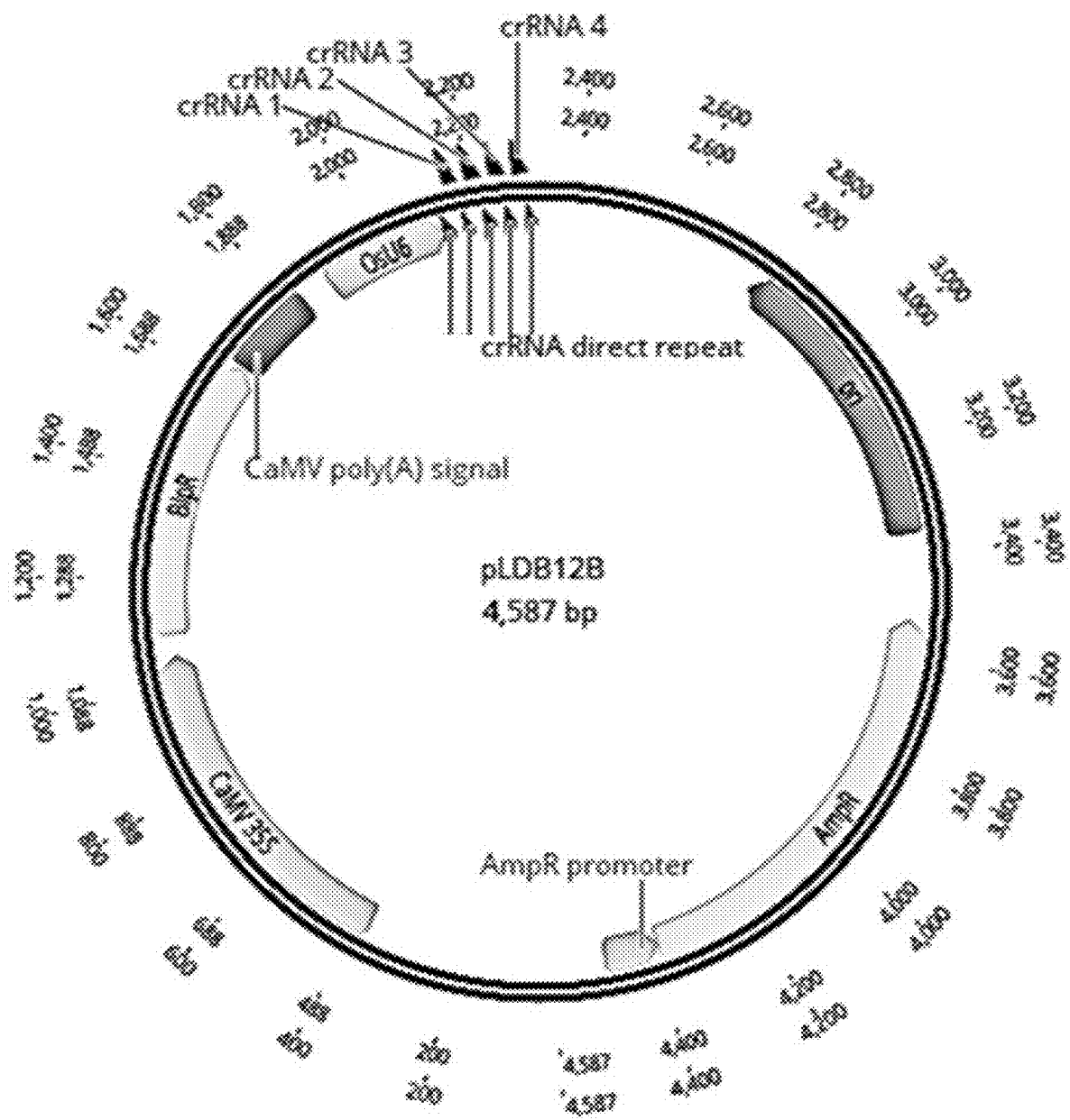
FIG. 7 depicts a plasmid map of pLDB12B, used to introduce MiMe gene edits in Zea mays.
Figure 8:
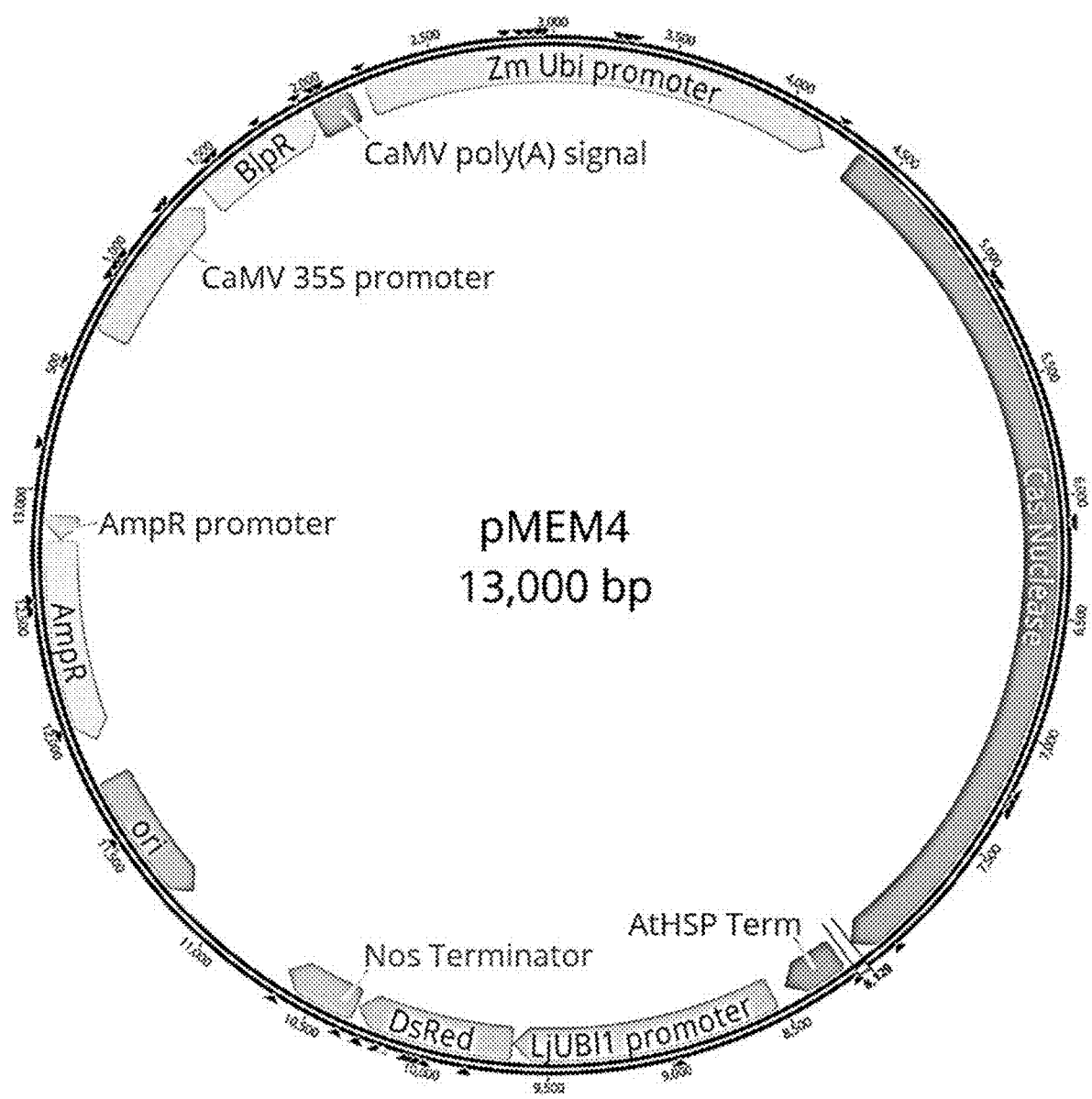
FIG. 8 depicts a plasmid map of pMEM4, used to introduce MiMe gene edits in Zea mays.
Figure 10:
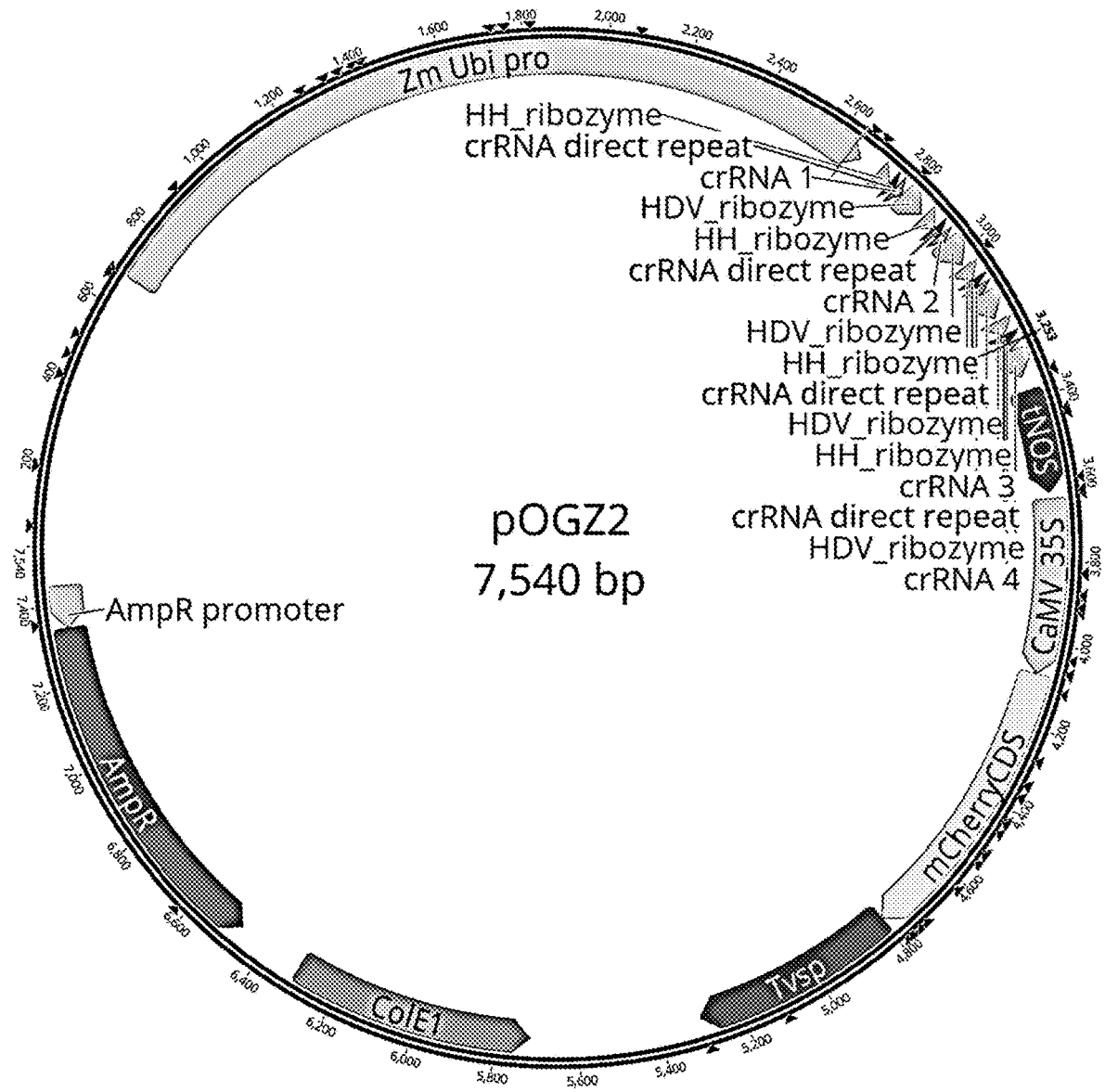
FIG. 10 depicts a plasmid map of pOGZ2, used to introduce MiMe gene edits in Zea mays.
Figure 11:
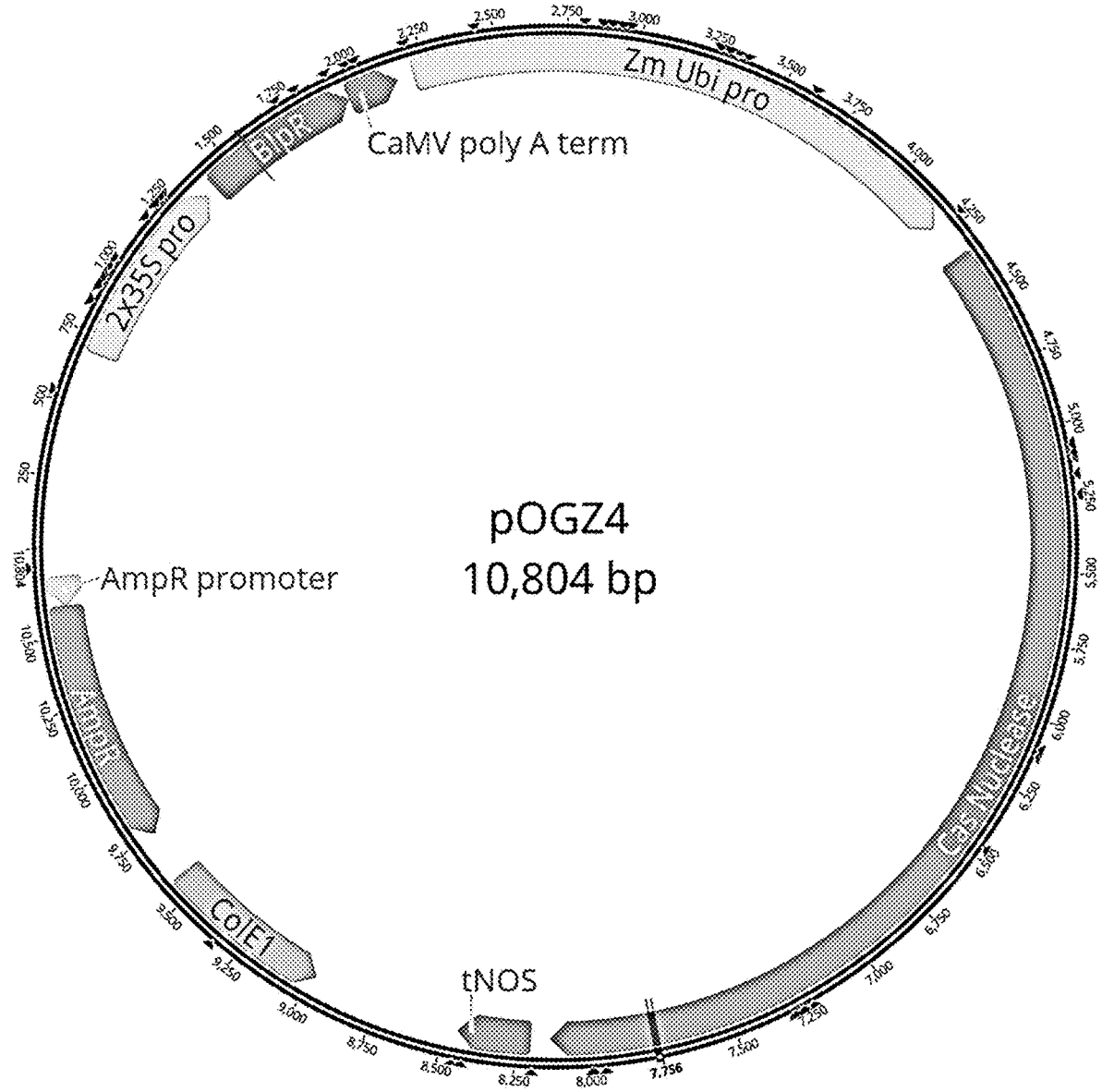
FIG. 11 depicts a plasmid map of pOGZ4, used to introduce MiMe gene edits in Zea mays.
Figure 21:
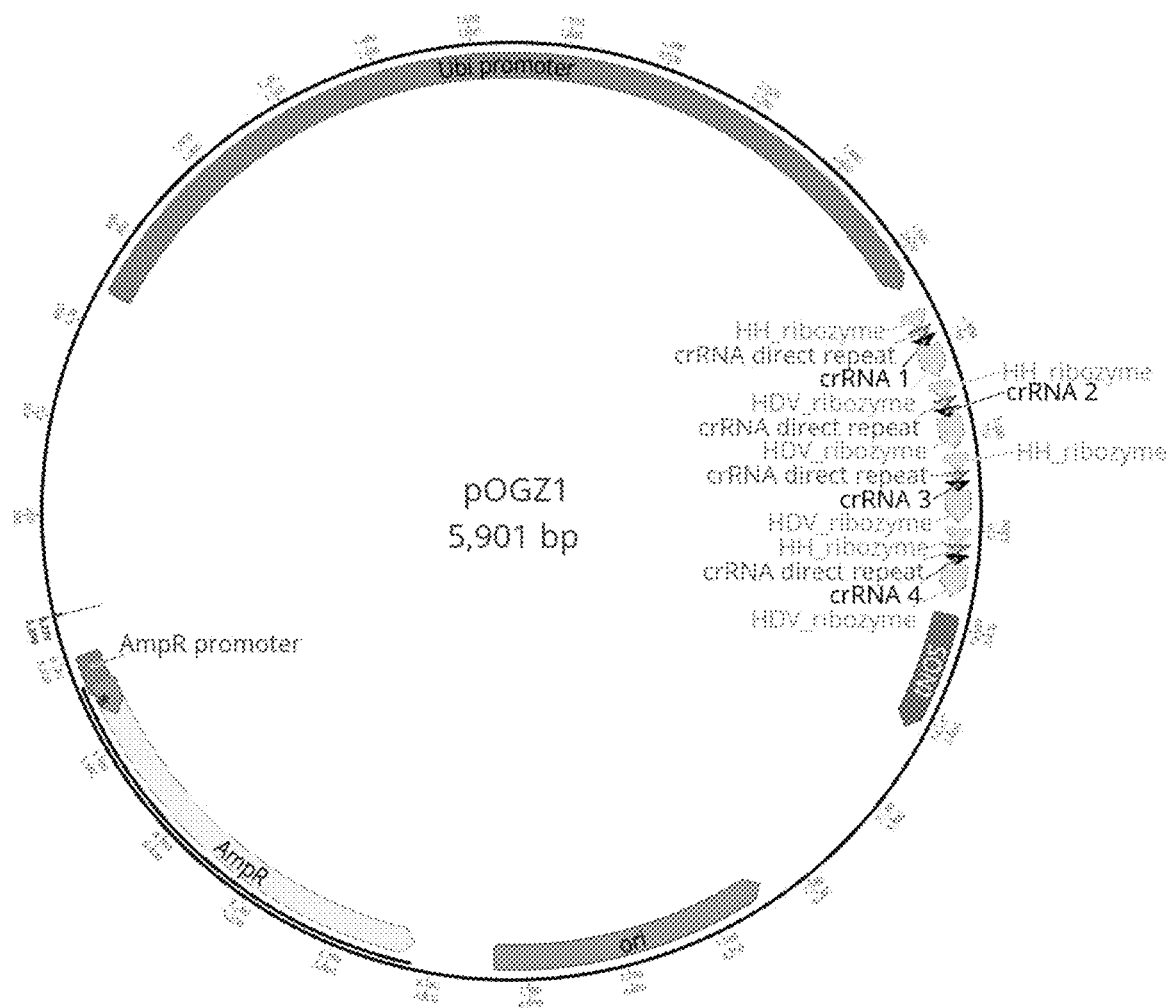
FIG. 21 depicts a plasmid map of pOGZ1, used to introduce MiMe gene edits in Zea mays.

Plasmids were constructed for use in biolistic transformations of *Zea mays*. The most efficient crRNA guides were determined during guide screening in protoplasts, then guide constructs were designed placing those gRNAs between crRNA direct repeats or crRNA direct repeats and self-cleaving ribozyme sequences. These sequences were then synthesized and cloned into standard vectors. Plasmids encoding crRNA guides ("guide constructs") included pOGZ2 (FIG. 10), pMEM6b (FIG. 9) and pOGZ1 (FIG. 21). Plasmids encoding a Cas nuclease ("nuclease construct") were also synthesized including plasmids pLDB3 (FIG. 5), pLDB11B (FIG. 6), pLDB12B (FIG. 7), pMEM4 (FIG. 8) and pOGZ4 (FIG. 11). The components for each of these plasmids are listed in Table 7. For example, when transforming the combination of the guide construct pOGZ1 (FIG. 21) and nuclease encoding plasmid pMEM4 (FIG. 8), the MiMe loci which were targeted for editing were OSD1 (OSD1-1 and OSD1-2), SPO11, and REC8. Additional plasmids were constructed to target OSD1-1, OSD1-2, OSD1-3, and combinations thereof.

Using this approach, the guide constructs shown in Table 7 can be readily modified to target any combination of MiMe loci that can result in a partial or complete MiMe genotype including, for example, REC8, OSD1-1, OSD1-2, OSD1-3, PAIR1-1, PAIR1-2, SPO11-1, JASON-1, JASON-2, CYCA1-1, CYCA1-2, TDM1, and/or PS1. Additionally, the separated guide construct and nuclease construct can be transformed into separate lines to achieve parent MiMe plants with various crossing schemes as described further below in section ZM9, or the guide construct and nuclease construct can be co-transformed into the same line to directly achieve a MiMe genotype (the "TO approach").

TABLE 7

Components of the plasmids used in biolistic experiments.

| Plasmid | For plant expression | Vector backbone components for multiplication in *E. coli* |
|---|---|---|
| pLDB3 (FIG. 5) | ZmUBI: Maize Ubiquitin promoter<br>CAS: coding sequence of the selected Cas nuclease<br>tHSP: terminator sequence from *Arabidopsis thaliana* Heat shock protein 18.2 | ori: origin of replication<br>AmpR promoter: Ampicillin resistance promoter<br>AmpR: Ampicillin resistance |

TABLE 7-continued

Components of the plasmids used in biolistic experiments.

| Plasmid | For plant expression | Vector backbone components for multiplication in E. coli |
|---|---|---|
| | OsU6: RNA polymerase III promoter from *Oryza sativa* crRNA multiplex cassette containing 4 crRNAs targeting REC8, OSD1-1, OSD1-2, and SPO11 with poly-T termination signal CaMV 35S promoter: constitutive promoter derived from the Cauliflower mosaic virus BlpR: Bialaphos resistance gene CaMV poly(A) signal: terminator from Cauliflower mosaic virus | |
| pLDB11B (FIG. 6) | ZmUBI: Maize Ubiquitin promoter CAS: coding sequence of the selected Cas nuclease tHSP: terminator sequence from *Arabidopsis thaliana* Heat shock protein 18.2 CaMV 35S: constitutive promoter derived from the Cauliflower mosaic virus BlpR: Bialaphos resistance gene CaMV poly(A) signal: terminator from Cauliflower mosaic virus | ori: origin of replication AmpR promoter: Ampicillin resistance promoter AmpR: Ampicillin resistance |
| pLDB12B (FIG. 7) | OsU6: RNA polymerase III promoter from *Oryza sativa* crRNA multiplex cassette containing 4 or more crRNAs targeting REC8, OSD1-1, OSD1-2, and SPO11 with poly-T termination signal tHSP: terminator sequence from *Arabidopsis thaliana* Heat shock protein 18.2 CaMV 35S: constitutive promoter derived from the Cauliflower mosaic virus BlpR: Bialaphos resistance gene CaMV poly(A) signal: terminator from the Cauliflower mosaic virus | ori: origin of replication AmpR promoter: Ampicillin resistance promoter AmpR: Ampicillin resistance |
| pMEM4 (FIG. 8) | Zm Ubi promoter: Maize Ubiquitin promoter Cas Nuclease: coding sequence of the selected Cas nuclease AtHSP Term: terminator sequence from *Arabidopsis thaliana* Heat shock protein 18.2 LjUBI1 promoter: *Lotus japonicus* polyubiquitin promoter DsRed: red fluorescent protein reporter gene Nos Terminator: Nopaline synthase terminator from *Agrobacterium tumefaciens* CaMV 35S promoter: constitutive promoter derived from the Cauliflower mosaic virus BlpR: Bialaphos resistance gene CaMV poly(A) signal: terminator from Cauliflower mosaic virus | ori: origin of replication AmpR promoter: Ampicillin resistance promoter AmpR: Ampicillin resistance |
| pMEM6b (FIG. 9) | OsU6 Pro: RNA polymerase III promoter from *Oryza sativa* crRNA multiplex cassette containing 4 crRNAs targeting REC8, OSD1-1, OSD1-2, and SPO11 with poly-T termination signal LjUBI1 pro: *Lotus japonicus* polyubiquitin promoter GFP: green fluorescent protein reporter gene CaMV 35S Pro: constitutive promoter derived from the Cauliflower mosaic virus BlpR: Bialaphos resistance gene CaMV poly A term: terminator from Cauliflower mosaic virus | ColE1: origin of replication AmpR promoter: Ampicillin resistance promoter AmpR: Ampicillin resistance |

TABLE 7-continued

Components of the plasmids used in biolistic experiments.

| Plasmid | For plant expression | Vector backbone components for multiplication in E. coli |
|---|---|---|
| pOGZ1 (FIG. 21) | Ubi promoter: Maize Ubiquitin promoter | ori: origin of replication |
| | crRNA multiplex cassette containing 4 or more crRNAs targeting REC8, OSD1-1, OSD1-2, and SPO11 | AmpR promoter: Ampicillin resistance promoter |
| | HH_ribozyme and HDV_ribozyme: non-coding RNA sequences that are capable of self-cleavage | AmpR: Ampicillin resistance |
| | tNOS: Nopaline synthase terminator from *Agrobacterium tumefaciens* | |
| pOGZ2 (FIG. 10) | Zm Ubi pro: Maize Ubiquitin promoter | ColE1: origin of replication |
| | crRNA multiplex cassette containing 4 or more crRNAs targeting REC8, OSD1-1, OSD1-2, and SPO11 | AmpR promoter: Ampicillin resistance promoter |
| | HH_ribozyme and HDV_ribozyme: non-coding RNA sequences that are capable of self-cleavage | AmpR: Ampicillin resistance |
| | tNOS: Nopaline synthase terminator from *Agrobacterium tumefaciens* | |
| | CaMV_35S: constitutive promoter derived from the Cauliflower mosaic virus | |
| | mCherryCDS: red fluorescent protein reporter gene | |
| | Tvsp: Vegetative storage protein terminator from *Glycine max* | |
| pOGZ4 (FIG. 11) | 2 × 35S pro: 35S promoter with duplicated enhancer region from Cauliflower Mosaic Virus | ColE1: origin of replication |
| | BlpR: Bialaphos resistance gene | AmpR promoter: Ampicillin resistance promoter |
| | CaMV poly A term: terminator from the Cauliflower mosaic virus | AmpR: Ampicillin resistance |
| | Zm Ubi pro: Maize Ubiquitin promoter | |
| | Cas Nuclease: the chosen Cas nuclease | |
| | tNOS: Nopaline synthase terminator from *Agrobacterium tumefaciens* | |

ZM5: Plant Materials for Biolistic Transformation

Transformable diploid FFMM-AT6 and Hi-II were planted and grown with 16-hour/28° C. day and 8-hour/25° C. night cycles to produce ears containing immature embryos. Ears were harvested about 9 to 12 days after pollination and were surface sterilized using commercial bleach prior to performing embryo extraction as described by Wang et al. 2020 (Biolistic DNA delivery in maize immature embryos. Biolistic DNA Delivery in Plants: Methods and Protocols. pp. 177-195). Embryos were extracted and placed on either N6 Medium according to Wang and Frame 2009 (Wang, K. and Frame, B. (2009) Biolistic gun-mediated maize genetic transformation. Transgenic maize: methods and protocols. pp. 29-45) or 605T medium according to, for example, Jones et al. 2019 (Maize transformation using the morphogenic genes Baby Boom and Wuschel2. In *Transgenic Plants*. pp. 81-93. Humana Press, New York, NY) or, for example, Masters et al. 2020 (*Agrobacterium* Mediated Immature Embryo Transformation of Recalcitrant Maize Inbred Lines Using Morphogenic Genes. J. Vis. Exp. (156): e60782, doi:10.3791/60782). After that, embryos were incubated at 28° C. for 3 days. In some experiments, the incubation step described in the previous sentence was skipped and embryos were placed directly on N6 Osmotic Medium according to Wang et al. 2020.

ZM6: Biolistic Mediated Transformation

Biolistic mediated transformation was performed according to Wang et al. 2020 with the modifications noted below. Bombardment was performed on the day of embryo extraction. Embryos were extracted to N6 osmotic medium (Wang et al. 2020) and incubated at 27° C. for 4 hours prior to bombardment. For bombardment, 125 ng plasmid DNA per shot was loaded onto 0.1 mg gold particles using 0.1 μL of a transfection reagent, TransIT®-2020, scaled to the number of shots. Gold particles were first mixed by pipetting with plasmid DNA in 50 μl sterile deionized water, then TransIT®-2020 was added and mixed by pipetting again. This mixture was incubated on ice for 10 minutes with gentle vortexing every 1 minute. Gold particles were centrifuged for 1 minute at 100×g and the supernatant was removed. Gold particles were washed with 50 ul of 100% ethanol, then resuspended in 7 μl of 100% ethanol per shot and loaded onto macrocarriers. Embryos were bombarded at 450 psi using a Bio-Rad Biolistic® PDS-1000 biolistic device.

ZM7: Selection and Regeneration of Plants

For Hi-II callus, selection was performed according to Wang et al. 2020 with the modifications noted below. After bombardment, embryos were plated on N6 Selection I medium (1.5 mg/L bialaphos) and incubated at 27° C. in the dark for 2 weeks. After the 2-week incubation, callus was transferred to N6 Selection II (N6 SII) (3 mg/L bialaphos) and callus was further incubated for 2 weeks at 27° C. in the dark. Callus was transferred to fresh N6 SII medium every 2 weeks and checked for continual editing. Once sufficient editing was achieved, callus was moved directly to Regeneration II medium (Wang et al. 2020). Callus on Regeneration II medium was then incubated for 1 additional week at 27° C. in the dark, before being moved to a 16-hour day/8-hour night cycle in a lighted growth chamber with dim light and maintained at about 27° C. After 5 days of acclimation to the dim light, the light intensity was increased to about 100 ppfd light.

Once leafy shoots appeared, they were transferred to MS medium with 2 mg/L bialaphos as described in Wang et al. 2020. Once roots grew to a total length of >5 cm, the plantlets were transferred to soil. Leaf material was extracted and Illumina sequencing was performed to identify loss-of-function edits. Single plants were screened using the same technique as described in Example 1's section GM3 to identify individual events containing bi-allelic or mono-allelic conformations of each target gene including, for example, REC8, OSD1-1, OSD1-2, OSD1-3, PAIR1-1, PAIR1-2, SPO11-1, JASON-1, JASON-2, CYCA1, TDM1, PS1, or any combination thereof.

ZM8: Plant Growth and Crossing Conditions

Regenerated plants with confirmed edits in target MiMe alleles were transplanted from tissue culture into PRO-MIX HP substrate and acclimatized in a growth chamber with 16-hour, 25° C. day, and 8-hour, 20° C. night with 60% relative humidity and 16-hour day length. After two to three weeks, plants were transplanted to soil and grown under greenhouse conditions with a continued 16-hour daylength. Once plants produced flowers, they were outcrossed as male or female to desired lines to introgress the transgene or edited alleles.

ZM9: Crossing

Crossing Scheme 1. In some experiments, the cross begins with a single rooted plant transformed with the nuclease construct (designated PED-MRN11) and a single rooted plant transformed with guide construct (designated PED-MRG12). PED-MRN11 can be backcrossed to inbred lines designated PED-MR-A and PED-MR-C, respectively. Hybrid plants containing the nuclease construct pLDB11 can be selected, further backcrossed, and then designated PED-A-MRN11 and PED-C-MRN11, respectively. Separately, PED-MRG11 can be backcrossed to inbred lines designated PED-MR-B and PED-MR-D, respectively. Hybrid plants containing the guide construct pLDB12 are selected, further backcrossed, and then designated PED-B-MRG12 and PED-D-MRG12, respectively. PED-A-MRN11 can then be crossed to PED-B-MRG12 and plants containing both the nuclease construct and the guide construct and a complete MiMe genotype comprising bi-allelic edits in the target MiMe loci selected and designated PED-AB-MiMe1. Similarly, PED-C-MRN11 can be crossed to PED-D-MRG12, and progeny plants containing both the nuclease construct and the guide construct and a complete MiMe genotype comprising homozygous or bi-allelic edits in the target MiMe loci selected and designated PED-CD-MiMe2. PED-AB-MiMe1 can then be crossed to PED-CD-MiMe2, resulting in a genetically uniform hybrid population of tetraploid maize with four haplotypes designated PED-ABCD-Tet1.

Crossing Scheme 2. In some experiments, the cross begins with two rooted plants, each bearing mono-allelic mutations in MiMe alleles and generated as discussed in Crossing Scheme 1, but by selecting for mono-allelic mutations in MiMe alleles (sometimes referred to here as a "HetMiMe" plant) instead of bi-allelic mutations. These plants are designated PED-MR2A or PED-MR2B respectively, grown to maturity, and then crossed to each of the inbred lines PED-MR-E, PED-MR-F, PED-MR-G, and PED-MR-H. Seeds from the resulting hybrids are screened for mono-allelic nonfunctional mutations (HetMiMe plants) as described in Example 1's section GM3, and plants are again grown to maturity. Plants with the mono-allelic edits can be identified and backcrossed to produce lines with the respective mono-allelic mutations in each respective inbred background designated as PED-E-HetMiMe, PED-F-HetMiMe, PED-G-HetMiMe, and PED-H-HetMiMe. From the plants in each of these HetMiMe populations, heterozygous knockout plants and lines are then screened and intercrossed to make PED-E-HetMiMe×PED-F-HetMiMe hybrids and PED-G-HetMiMe×PED-H-HetMiMe hybrids. These hybrids are then screened, and two individual plants bearing a complete MiMe genotype (comprising bi-allelic mutations in the MiMe alleles) are identified and designated PED-EF-MiMe1 and PED-GH-MiMe2. PED-EF-MiMe1 can then be crossed to PED-GH-MiMe2, resulting in a genetically uniform hybrid population of tetraploid maize with four haplotypes designated PED-EFGH-Tet1.

Crossing Scheme 3. In some experiments, the cross began with one rooted F1 hybrid designated PED-MR3A-JK, bearing mono-allelic mutations in some MiMe alleles and bi-allelic mutations in other MiMe alleles and generated as discussed in Crossing Scheme 1, but by selecting for this configuration of mutations in MiMe alleles (instead of selecting for bi-allelic mutations). PED-MR3A-JK was then grown to maturity, selfed, and the resulting progeny were screened for plants with full bi-allelic mutations in the MiMe alleles. Separately, an inbred diploid designated PED-MR3B-LL was doubled in ploidy by using colchicine in tissue culture. PED-MR3A-JK was then crossed to PED-MR3B-LL, resulting in a genetically uniform hybrid population of tetraploid maize with three haplotypes designated PED-JKLL-Tet1.

ZM10: Genotyping

High-quality genomic DNA was extracted from maize plants using Qiagen Dneasy Plant Mini kits (QIAGEN, Germantown, MD, USA). Purity was determined using a spectrophotometer, Nanodrop™ One-C (Thermo Fisher), and quantified with a fluorometer, Qubit™ Flex Fluorometer (Thermo Fisher). Samples were adjusted to a final concentration of 20 ng/µL. Markers were established and populations were genotyped as described in Example 1's section GM6. Alternatively, maize plants may be genotyped using targeted Genotyping By Sequencing (tGBS) (Ott et al. (2017) tGBS® genotyping-by-sequencing enables reliable genotyping of heterozygous loci. Nucleic acids research 45(21): e178-e178)."

ZR: Results

ZR1: Guide Screening

Figure 22A:
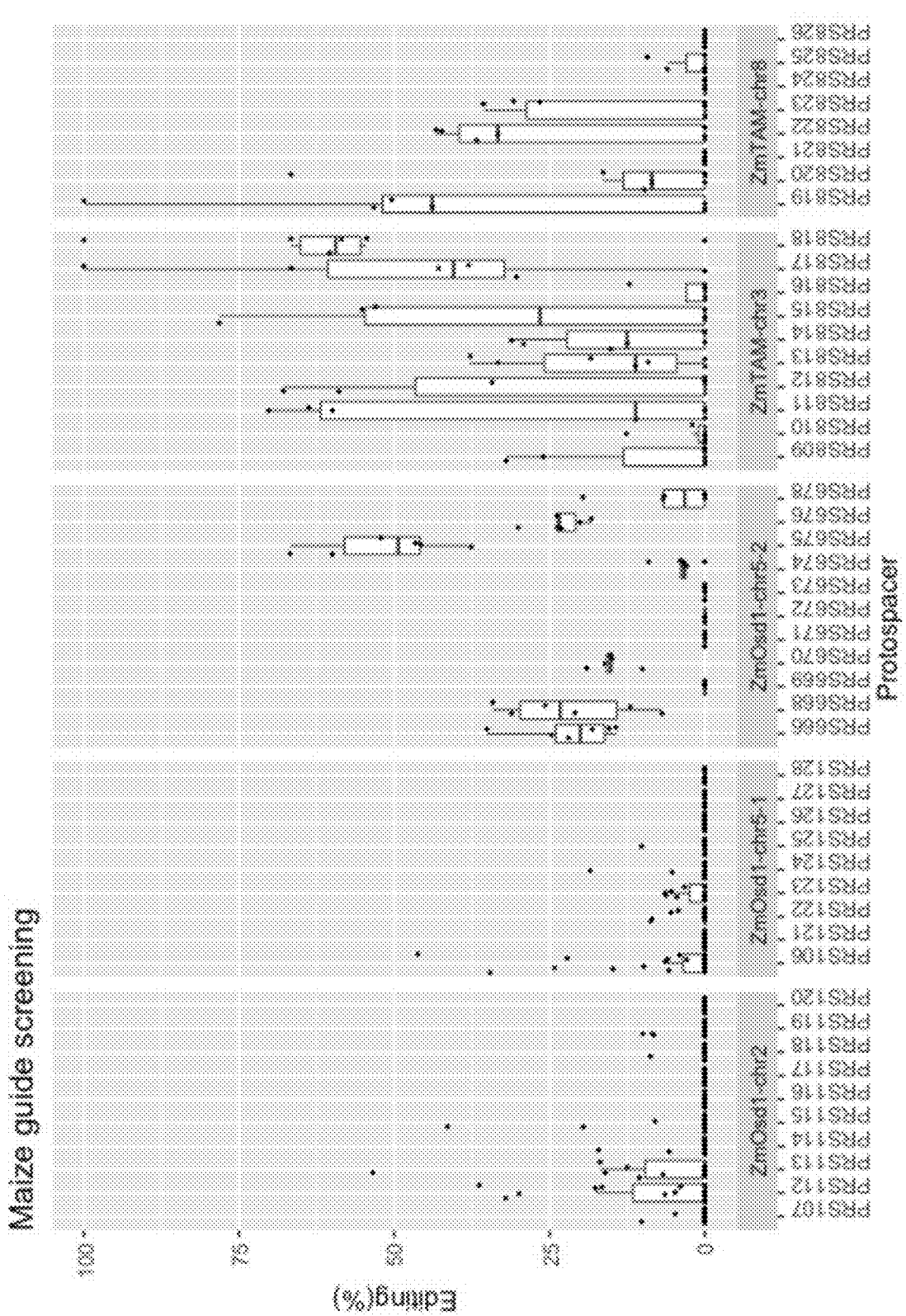
FIGS. 22A-22B show the screening results for guide RNA screening for edits in maize.
Figure 22B:
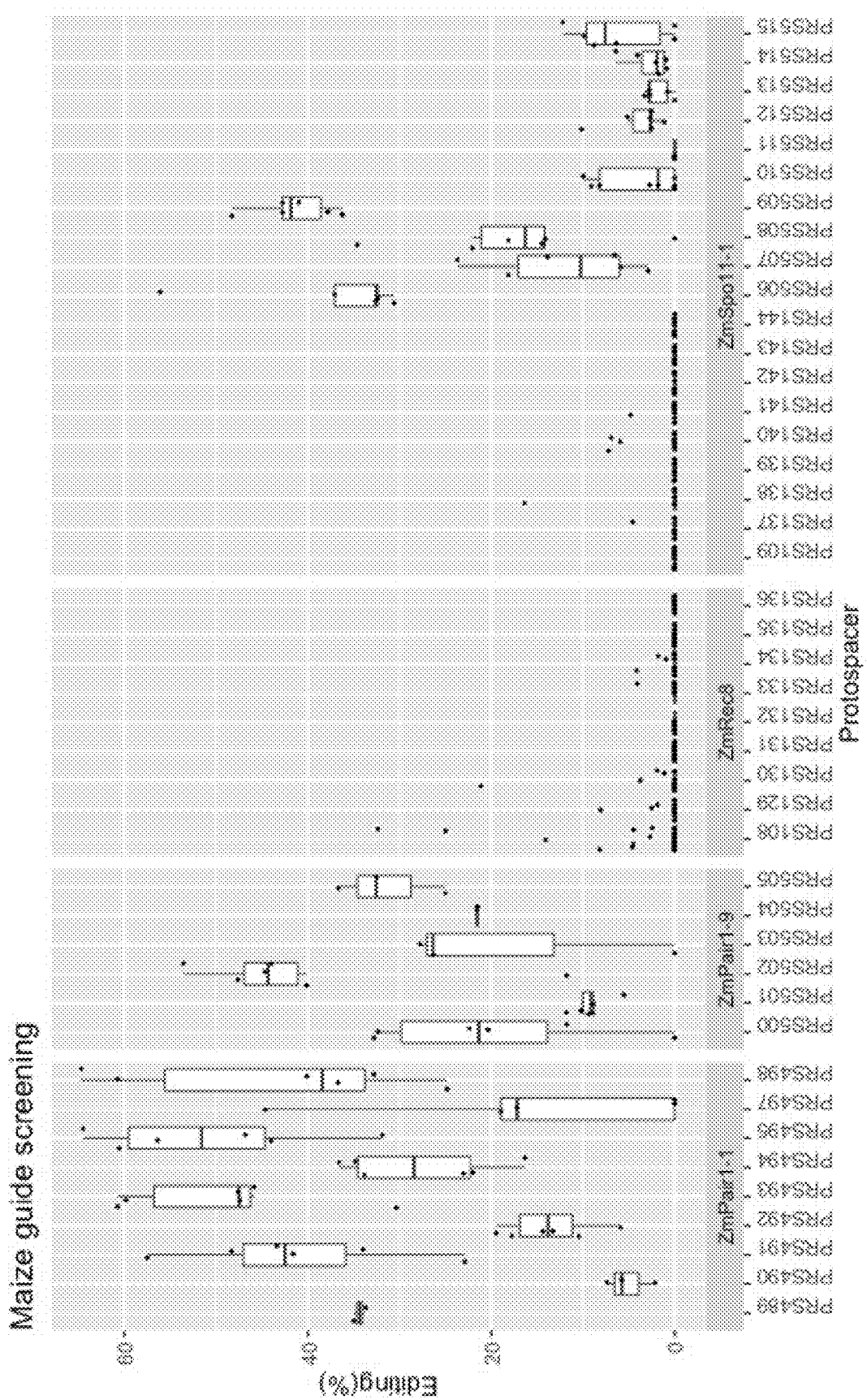

Guide RNAs were screened by RNP transfection or plasmid transfection as described in section ZM3. For maize protoplasts, a total of 10 guide RNAs were screened that targeted conserved regions of OSD1-1 (Table 8, SEQ ID NOs: 107-120). A total of 9 guide RNAs were screened that targeted conserved regions of OSD1-2 (Table 8, SEQ ID NOs: 24-32). A total of 9 guide RNAs were screened that targeted conserved regions of REC8 (Table 8, SEQ ID NOs: 33-41). A total of 19 guide RNAs were screened that targeted conserved regions of SPO11-1 (Table 8, SEQ ID NOs: 42-60). Editing efficiency was calculated by sequencing as described in Example 1's section GM3, and the resulting data presented in FIG. 22A and FIG. 22B. Based on this data, candidate guide RNAs were produced, as illustrated in Table 9. Guide RNA SEQ ID NO: 62 was chosen for editing OSD1-1; guide RNA SEQ ID NO: 71 was chosen for editing OSD1-2; guide RNA SEQ ID NO: 82 was chosen for editing REC8; guide RNA SEQ ID NO: 98 was chosen for editing SPO11-1.

TABLE 8

Sequences for conserved regions of MiMe genes targeted in maize.

| SEQ ID NO. | PRSG# | Target DNA sequence |
|---|---|---|
| 14 | PRS107 | TGGTGGTGTTGGTGGTGGAG |
| 15 | PRS112 | TCAGGAGGGTGGCCTCGCCG |
| 16 | PRS113 | GGCGTTGAGGGTCACACCGA |
| 17 | PRS114 | TCGGTGTGACCCTCAACGCC |
| 18 | PRS115 | CAATGGCCGTAATATCACGG |
| 19 | PRS116 | ATCAGGAGGGTGGCCTCGCC |
| 20 | PRS117 | GTCGGTGTGACCCTCAACGC |
| 21 | PRS118 | CTGCAGAGCCCCGAGATGCC |
| 22 | PRS119 | CTGGATGGTACCCCAGGACG |
| 23 | PRS120 | GCAATGGCCGTAATATCACG |
| 24 | PRS106 | GAGGATGGCAAGCTGAAGAC |
| 25 | PRS121 | ACGATTGATGTGATGTCACG |
| 26 | PRS122 | CCTGACTGGTACCCGAGGAC |
| 27 | PRS123 | AAGATGCTTGAAGTGAGGAC |
| 28 | PRS124 | ACAGCACCATTCACCAGCAC |
| 29 | PRS125 | CCATCCTCCAAACAGGTTGC |
| 30 | PRS126 | AGCTTGCCATCCTCCAAACA |
| 31 | PRS127 | CCGATCTGTGGATCCAATAA |
| 32 | PRS128 | TCCTCCTCTCAATTGCCTGC |
| 33 | PRS108 | CGGTTGATCTTCGAGTGGAG |
| 34 | PRS129 | ATGATGTCGAGCTTGTCGAG |
| 35 | PRS130 | GAACCCCTCGGTGCCCATGG |
| 36 | PRS131 | TCGAGCCGTTTGCGGTTGAT |
| 37 | PRS132 | CTCTCGTACACGATCACCAC |
| 38 | PRS133 | ACCTTCCTCTCGTACACGAT |
| 39 | PRS134 | CTGTAGAGAAGCTTCACCTT |
| 40 | PRS135 | GAGTGGAGCGTCGCCGCCAT |
| 41 | PRS136 | TCGCGCGGAAGGCGCCGCTC |
| 42 | PRS109 | ATCCTGCGGAGGAGGAGCGC |
| 43 | PRS137 | TTCTGCTGCAGGAGCTGCTG |
| 44 | PRS138 | CTCCAGCCTCCGCCGCAACT |
| 45 | PRS139 | GATCCTGCGGAGGAGGAGCG |
| 46 | PRS140 | GCTCCCTGCAGAAGTAGCAG |
| 47 | PRS141 | AAGTGCAGCCGGCACAATCT |

TABLE 8-continued

Sequences for conserved regions of MiMe genes targeted in maize.

| SEQ ID NO. | PRSG# | Target DNA sequence |
|---|---|---|
| 48 | PRS142 | GAGCGGCGCCGCTCGTCGCC |
| 49 | PRS143 | AAGAGTATGCAGATATCGTT |
| 50 | PRS144 | GAGCAGTGCTTGTTCTGCTG |
| 51 | PRS506 | GATGTATTCGTACTGAGGCG |
| 52 | PRS507 | ATTGCCTCAATGTCAACAGG |
| 53 | PRS508 | CACATATCTTGGCTCCCTGC |
| 54 | PRS509 | GTGATGGGCTGGATAAGATT |
| 55 | PRS510 | TGGAGGGCGAAAAGAAAGTG |
| 56 | PRS511 | CCTTCTGTATATTCAGGCTT |
| 57 | PRS512 | TCCATTCCTGTTGACATTGA |
| 58 | PRS513 | TTCTCTTGCAGATGTTGTTA |
| 59 | PRS514 | CAGTGTTCCAGCGTTTGGCC |
| 60 | PRS515 | ACAGAACTTGTCATTGGCCA |

TABLE 9

Sequences for guide RNAs targeting MiMe genes in maize.

| SEQ ID NO. | PRSG# | Guide RNA sequence |
|---|---|---|
| 61 | PRS107G | UGGUGGUGUUGGUGGUGGAG |
| 62 | PRS112G | UCAGGAGGGUGGCCUCGCCG |
| 63 | PRS113G | GGCGUUGAGGGUCACACCGA |
| 64 | PRS114G | UCGGUGUGACCCUCAACGCC |
| 65 | PRS115G | CAAUGGCCGUAAUAUCACGG |
| 66 | PRS116G | AUCAGGAGGGUGGCCUCGCC |
| 67 | PRS117G | GUCGGUGUGACCCUCAACGC |
| 68 | PRS118G | CUGCAGAGCCCCGAGAUGCC |
| 69 | PRS119G | CUGGAUGGUACCCCAGGACG |
| 70 | PRS120G | GCAAUGGCCGUAAUAUCACG |
| 71 | PRS106G | GAGGAUGGCAAGCUGAAGAC |
| 72 | PRS121G | ACGAUUGAUGUGAUGUCACG |
| 73 | PRS122G | CCUGACUGGUACCCGAGGAC |
| 74 | PRS123G | AAGAUGCUUGAAGUGAGGAC |
| 75 | PRS124G | ACAGCACCAUUCACCAGCAC |
| 76 | PRS125G | CCAUCCUCCAAACAGGUUGC |
| 77 | PRS126G | AGCUUGCCAUCCUCCAAACA |
| 78 | PRS127G | CCGAUCUGUGGAUCCAAUAA |

TABLE 9-continued

Sequences for guide RNAs targeting MiMe genes in maize.

| SEQ ID NO. | PRSG# | Guide RNA sequence |
|---|---|---|
| 79 | PRS128G | UCCUCCUCUCAAUUGCCUGC |
| 80 | PRS108G | CGGUUGAUCUUCGAGUGGAG |
| 81 | PRS129G | AUGAUGUCGAGCUUGUCGAG |
| 82 | PRS130G | GAACCCCUCGGUGCCCAUGG |
| 83 | PRS131G | UCGAGCCGUUUGCGGUUGAU |
| 84 | PRS132G | CUCUCGUACACGAUCACCAC |
| 85 | PRS133G | ACCUUCCUCUCGUACACGAU |
| 86 | PRS134G | CUGUAGAGAAGCUUCACCUU |
| 87 | PRS135G | GAGUGGAGCGUCGCCGCCAU |
| 88 | PRS136G | UCGCGCGGAAGGCGCCGCUC |
| 89 | PRS109G | AUCCUGCGGAGGAGGAGCGC |
| 90 | PRS137G | UUCUGCUGCAGGAGCUGCUG |
| 91 | PRS138G | CUCCAGCCUCCGCCGCAACU |
| 92 | PRS139G | GAUCCUGCGGAGGAGGAGCG |
| 93 | PRS140G | GCUCCCUGCAGAAGUAGCAG |
| 94 | PRS141G | AAGUGCAGCCGGCACAAUCU |
| 95 | PRS142G | GAGCGGCGCCGCUCGUCGCC |
| 96 | PRS143G | AAGAGUAUGCAGAUAUCGUU |
| 97 | PRS144G | GAGCAGUGCUUGUUCUGCUG |
| 98 | PRS506G | GAUGUAUUCGUACUGAGGCG |
| 99 | PRS507G | AUUGCCUCAAUGUCAACAGG |
| 100 | PRS508G | CACAUAUCUUGGCUCCCUGC |
| 101 | PRS509G | GUGAUGGGCUGGAUAAGAUU |
| 102 | PRS510G | UGGAGGGCGAAAAGAAAGUG |
| 103 | PRS511G | CCUUCUGUAUAUUCAGGCUU |
| 104 | PRS512G | UCCAUUCCUGUUGACAUUGA |
| 105 | PRS513G | UUCUCUUGCAGAUGUUGUUA |
| 106 | PRS514G | CAGUGUUCCAGCGUUUGGCC |
| 107 | PRS515G | ACAGAACUUGUCAUUGGCCA |

ZR2: Transformation and Selection of Regenerated Plants

To produce the first parent MiMe plant, a 2n Hi-II AxB Hybrid mother plant was crossed by pollen from a 2n Fast-Flowering Mini-Maize AT6 (FFMM-AT6) father. 14 days after pollination, the ear was harvested and placed at 4° C. overnight. The next morning, embryos were extracted, plated, and bombarded according to section ZM6 using the Bio-Rad Biolistic® PDS-1000 and 0.6 µm gold particles coated with the guide construct pOGZ1 and the nuclease construct pMEM4 loaded in a 3:1 molar ratio, respectively. Plasmid and gold were mixed in 50 µL sterile water, then a transfection reagent, TransIT®-2020, was added to bind the plasmid to the gold. Each gene gun shot was prepared with 125 ng DNA, 0.1 mg 0.6 µm gold particles, and 0.1 µL TransIT®-2020, and the gold particles were resuspended in 7 µL 100% ethanol and loaded onto macrocarriers, allowed to dry, then fired into the immature zygotic embryos at 450 psi. Gene gun settings were set according to Wang 2020. Plant PED-MN-HetMiMe was selected with a mono-allelic 10 bp frameshift-inducing mutation in osd1-1, bi-allelic frameshift-inducing 13 bp and 17 bp mutations in osd1-2, a 12 bp mutation in rec8 that disrupted a highly conserved coding region, and a mono-allelic 7 bp frameshift-inducing mutation in spo11. The plant was regenerated from tissue culture, grown in the greenhouse, then self-pollinated to produce T1 F2 seed population PED-MN-SPP. This seed was germinated, and a parent MiMe plant PED-MN-MiMe having bi-allelic loss-of-function mutations at osd1-2 and homozygous loss-of-function mutations at rec8 and spo11 was selected. PED-MN-MiMe showed fertility restoration and shed viable pollen. No edits of osd1-1 could be recovered from PED-MN-SPP.

Figure 23E:
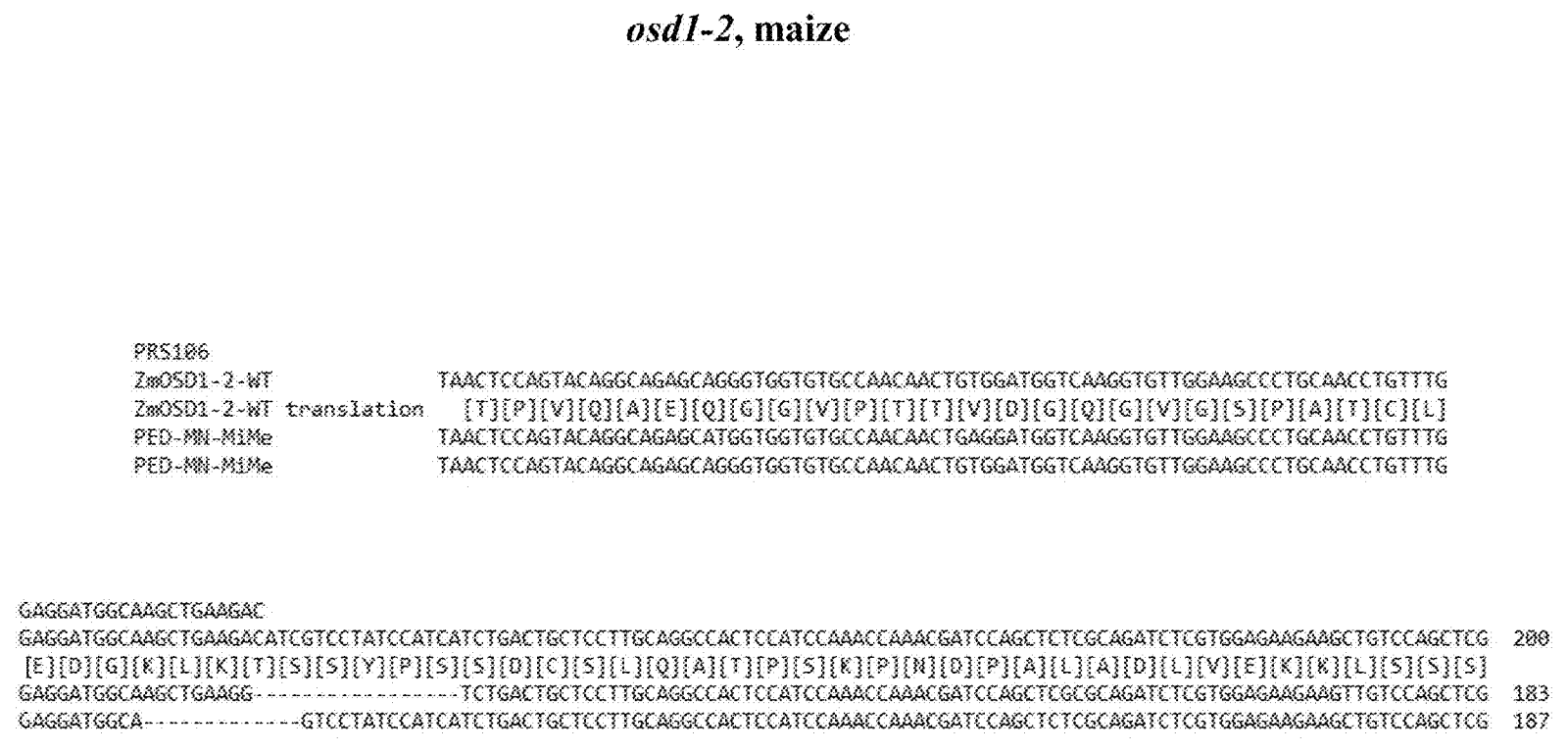

As an example, edits to the parent MiMe plant PED-MN-MiMe (rec8/osd1-2/spo11-1) are illustrated in FIGS. 23A-23C. In that figure, the predicted protein sequences are illustrated with respect to the unedited wildtype protein sequence and a consensus sequence, wherein an "X" in the consensus sequence indicates that there is no consensus for that amino acid position; wherein a dot ("•") in the parent MiMe plant sequence indicates that the respective amino acid matches the consensus sequence; and wherein a dash ("-") in the parent MiMe plant sequence indicates that the respective amino acid is present in the consensus sequence but is absent in the parent MiMe plant sample sequence. The deletion in REC8 disrupts a conserved protein sequence motif (FIGS. 23A and 23D). Frameshift inducing deletions in both alleles of osd1-2 (FIGS. 23B and 23E) and spo11-1 (FIGS. 23C and 23F) result in premature stop codons. Premature stop codons are denoted by an asterisk ("*") in FIGS. 23B-23C.

ZR3: Crossing and Seed Extraction

Pollen from PED-MN-MiMe (osd1-2/rec8/spo11) was collected and crossed to female PED-OO-4n plants, where PED-OO-4n was an inbred 4n tetraploid LH244, resulting in the Boosted Maize Population ("BMP"). Ears were harvested approximately 21-22 days after pollination, and BMP embryos were rescued to a non-selective MS rooting medium to germinate in the dark at 27° C. Once germinated, the plants were moved to rooting medium in a lighted incubator. Once rooted, the plants were moved to pots with PRO-MIX HP and covered with a humidity dome to acclimate before being transplanted to soil in the greenhouse.

ZR4: Genotypic Evaluation

DNA samples were sequenced by Novogene. Libraries were prepared using the NEBNext® Ultra™ 11 for DNA Library Prep kit and paired-end 2×150 reads were sequenced on an Illumina NovaSeq 6000 or a NovaSeqxPlus. Markers were established and populations were genotyped as described in GM6.

For the parent MiMe plant PED-MN-MiMe and parent non-MiMe PED-OO-4n, DNA samples were sequenced to a depth of 120,987,086,400 bp, and 104,384,408,100 bp, respectively. For the BMP progeny plants, DNA samples were sequenced to an average depth of 96,945,478,675 bp.

Figure 24:
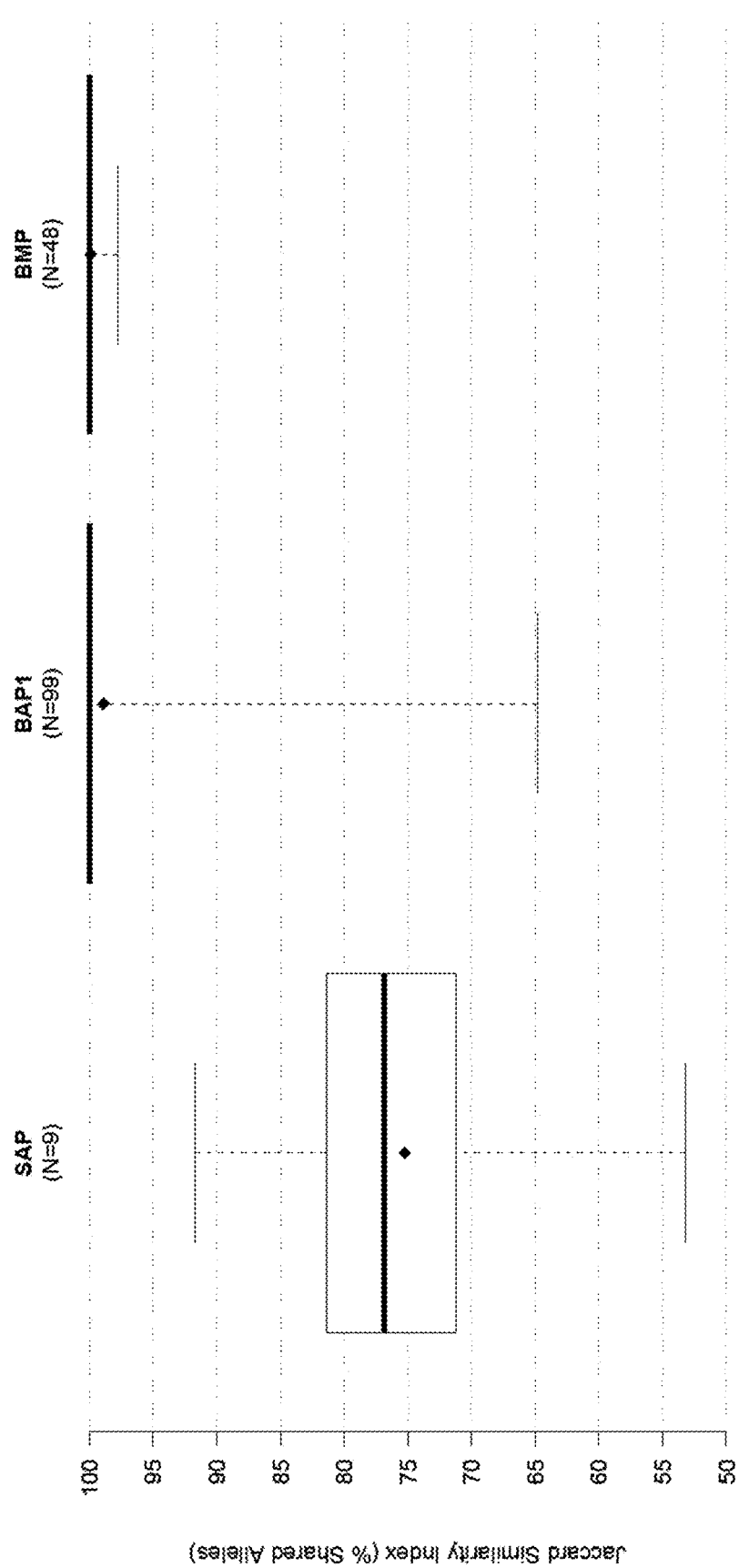
FIG. 24 illustrates the expected pairwise identity (or percentage of shared alleles as estimated by the Jaccard Similarity among genotypes) of randomly selected individuals within each population (SAP—Standard Arabidopsis Population, BAP1-Boosted Arabidopsis Population 1. BMP—Boosted Maize Population). The diamonds denote the expected or mean pairwise identity between genotyped plants in each population. The black bars are the median or second quartile. The boxes each represent the interquartile range from the first to the third quartile, and the dashed whiskers display the minimum and maximum pairwise identity between genotyped individuals in each population.
Figure 25A:
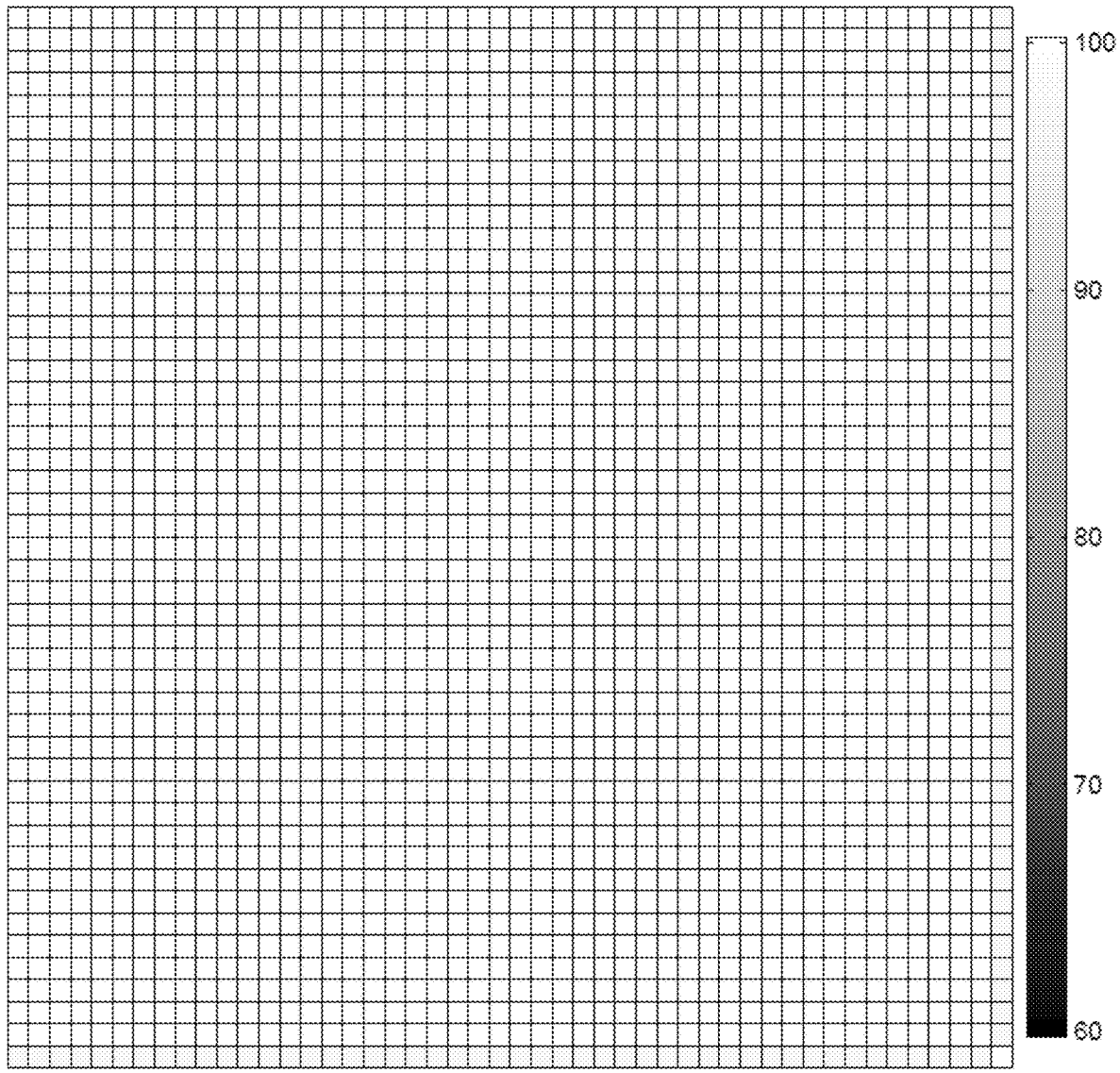
FIG. 25A shows a matrix for pairwise identity as estimated by the Jaccard similarity coefficient of 44 molecular markers genotyped between 48 tetraploid maize plants in Boosted Maize Population (BMP).
Figure 25B:
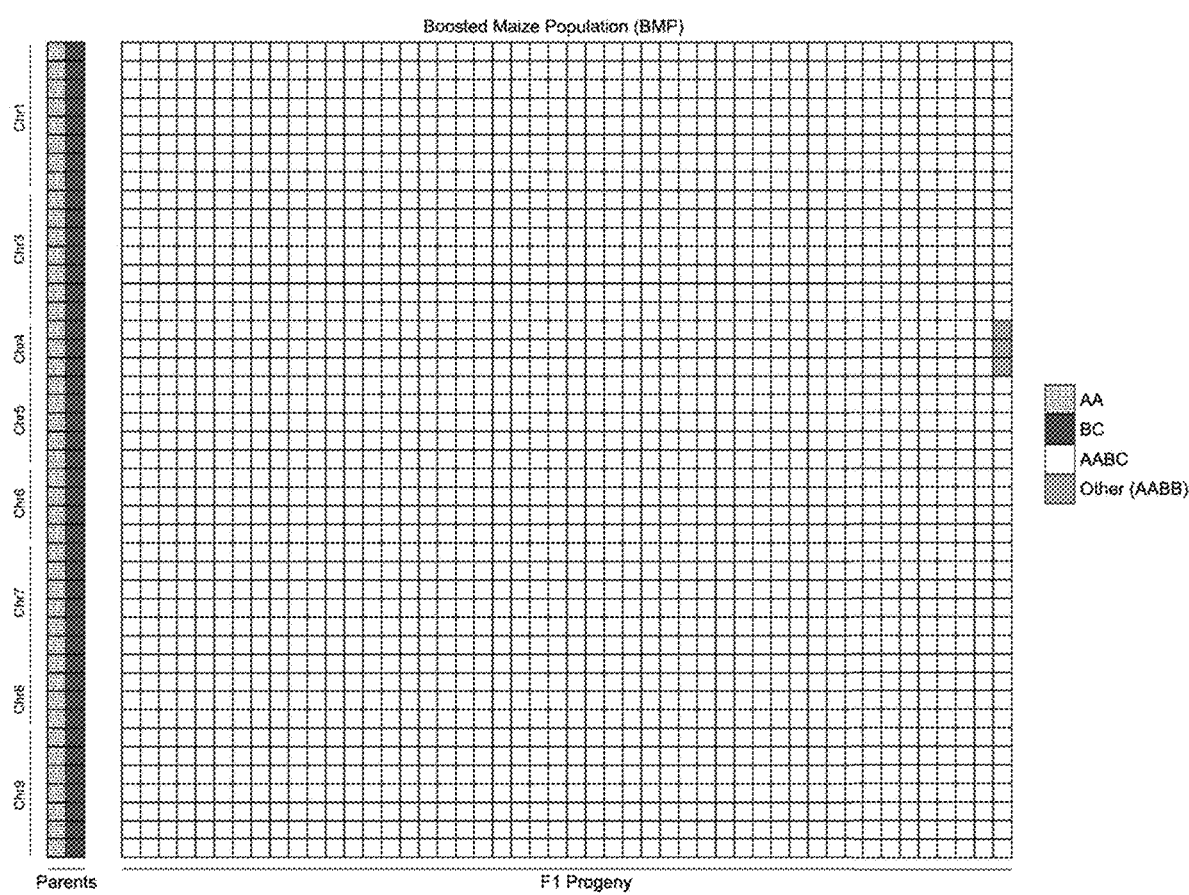
FIG. 25B shows a summary of the genotyping results at 44 triallelic markers across 48 progeny comprising the Boosted Maize Population (BMP). The horizontal axis corresponds to individual tetraploid progeny as well as the two diploid parent plants for reference. The vertical axis corresponds to individual triallelic markers distributed across 8 separate chromosomes. The coloration of each cell denotes the specific configuration of haplotypes observed at that marker (where A=LH244, B=A188, and C=FFMM-AT6). Samples with markers that are "AABC" have three haplotypes. Marker design was limited to regions of the genome where heterozygous parental SNPs were present. No usable markers were found on chromosome 2 or chromosome 10. The parent genotypes are displayed along the left-most rows.

After filtering for high quality markers, a genotype matrix was assembled for BMP (FIG. 25B). Across the BMP population, the average pairwise genetic uniformity as measured by the Jaccard similarity coefficient was 99.9% (visualized as a pairwise matrix in FIG. 25A). This data is illustrated by the population uniformity graph in FIG. 24.

ZR5: Phenotypic Evaluation of MiMe Progeny

Figure 26A:
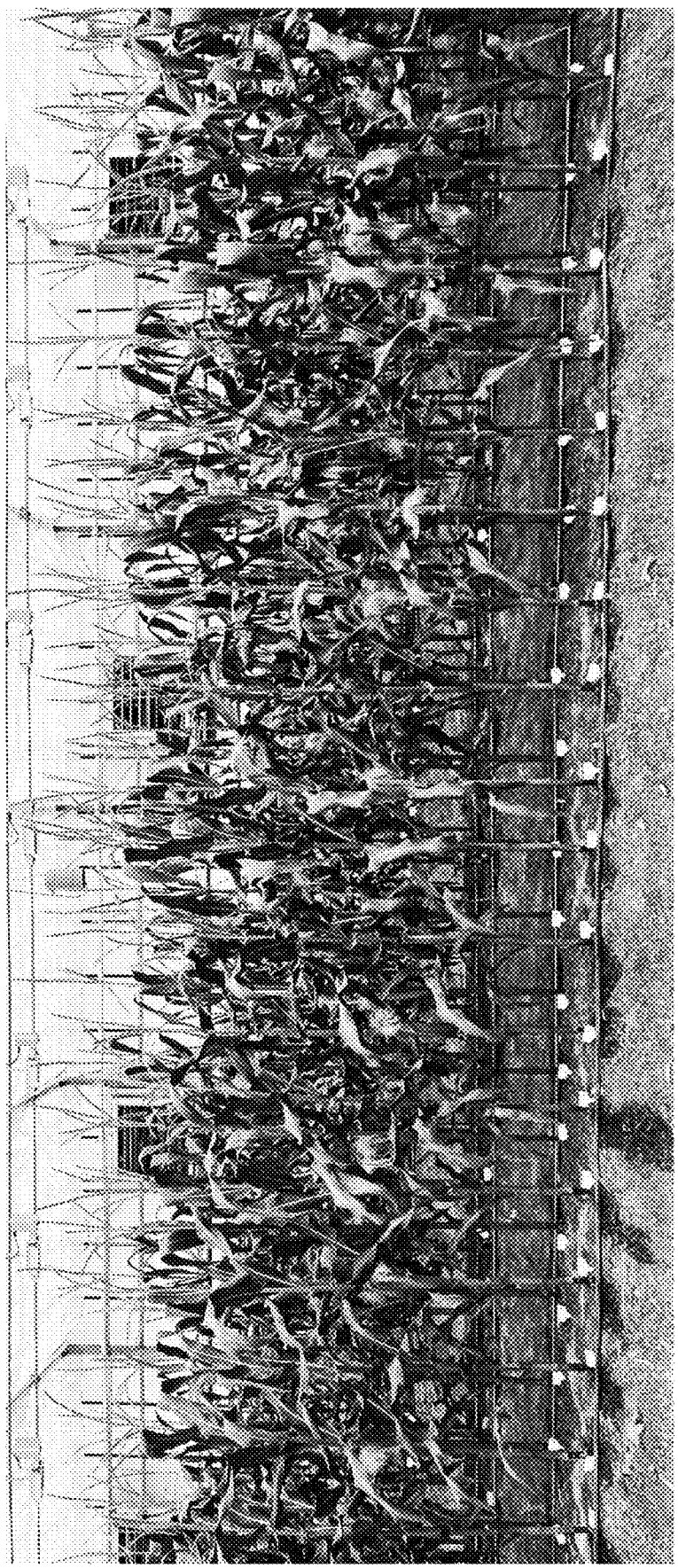
FIGS. 26A-26D show examples of BMP individuals.
Figure 26B:
Figure 26C:
Figure 26D:

The BMP plants demonstrated a phenotypically uniform size, growth, and appearance, whereas typically the progeny of an F1 hybrid of non-inbred lines would show segregational variance. Maize plants from BMP are shown in FIG. 26A. All plants are 68 days post-embryo rescue and 57 days post-transplant from tissue culture to soil. A close-up of the right-hand side of FIG. 26A is shown in FIG. 26B, showing a close-up view of three BMP plants. FIG. 26C shows healthy BMP plants readily producing fruit, which are further displayed as a close-up view of the ears in FIG. 26D.

Example 3: Generating Genetically Uniform Tetraploid Hybrid *Arabidopsis* with Three or Four Haplotypes AM: Methods
AM1: Plant Materials and Protoplast Isolation Plants from *Arabidopsis* accessions that were selected and tested included Landsberg, Shahdara, HR-10, Ws-2, Col-0 (CS851557-S1), CS851294, Columbia ("Col-0"), Col-0×Shahdara F1, Landsberg×Shahdara F1, Col-0×Shahdara F2, Landsberg×Shahdara F2, Col-0 (CS851557-S1)×HR-10 F2, Col-0×HR-10 F2, and Shahdara×Ws-2 F2.

Before germinating, seeds were surface sterilized using 70% ethanol solution for 5 min. Then, seeds were rinsed with sterile, distilled water five times. Seeds were stratified at 4° C. and then germinated on hormone-free AGM (*Arabidopsis* Germination Medium) containing half strength Murashige and Skoog basal salts, 10 g/L sucrose, 0.5 g/L MES and 8 g/L Agar (pH 5.8) and grown under 18-hour light/6-hour dark photoperiod (40-60 µmol photons m-2 s-1) at 23° C. Approximately 1 gram of leaves from each batch of 10-day old seedlings was removed under aseptic conditions for protoplast extraction.

For protoplast isolation, leaves were sliced into thin sections approximately 1 mm in width and incubated in an enzyme solution composed of 0.5% (weight/volume) Cellulase RS (Duchefa Biochemie, The Netherlands) and 0.5% (weight/volume) Macerozyme R10 (Duchefa Biochemie, The Netherlands) in MMC solution (10 mM MES, 0.47 M Mannitol, 10 mM Calcium Chloride) for a final volume of 10 mL. Sliced leaves in the digest solution were then incubated for around 15 hours at 24° C. in darkness. The protoplasts were then liberated from the leaf tissue with 15-minute shaking at 40 RPM at room temperature.

Protoplasts were then diluted with equal volume of At-W5 buffer (154 mM NaCl, 125 mM $CaCl_2$, 5 mM KCl, 2 mM MES, pH 5.7) and harvested through 40 µm sterile cell filters into sterile 50 mL conical tubes, then centrifuged at 150×g for 5 minutes. Supernatant was removed and cells were resuspended in 2 mL At-W5 buffer by gently rocking, then slowly layered onto 6 mL of 0.6 M sucrose solution as described in Jeong et al. 2021 (Optimization of protoplast regeneration in the model plant *Arabidopsis thaliana*. Plant methods 17(1): 1-16) in a new tube. Tubes were centrifuged at 150×g for 8 minutes. After centrifugation a thick dark band of protoplasts appeared at the interface of the two solutions. This band was harvested in one continuous motion using a sterile serological pipette and combined with 30 mL of At-W5 buffer. The samples were centrifuged at 150×g for 5 minutes and resuspended in 10 mL of At-W5 buffer. Cells were quantified using a Bürker hemocytometer and stored at 4° C. in the dark until transfection. A sample was reserved from each isolation to test cell viability using FDA staining as described by Larkin 1976 (Purification and viability determinations of plant protoplasts. *Planta*. 128(3): 213-216).

AM2: Transfection

Protoplast transfection proceeded in a similar fashion to Yoo et al. 2007 (*Arabidopsis* mesophyll protoplasts: a versatile cell system for transient gene expression analysis. Nature protocols. 2(7): 1565-1572). Protoplasts were centrifuged at 150×g for 5 minutes and resuspended in a volume of transformation MMG buffer (4 mM MES, pH 5.7, 0.4 M mannitol and 15 mM $MgCl_2$) sufficient to achieve a cell density of $2×10^6$ protoplasts/mL. For each transfection reaction, 20 µL of freshly prepared RNP solution as described in Example 1's section GM2 was added to the bottom of a 15 mL round bottom tube, and then 100 µL of protoplasts suspended in transformation MMG buffer was added and mixed with the RNP solution. Next, 120 µL of freshly prepared PEG solution (40% PEG4000, 0.2 M mannitol and 100 mM $CaCl_2$) was added and gently mixed by rotating the tubes. After a 15-minute incubation at room temperature, the transfection mixture was diluted with 5 mL of At-W5 solution and gently mixed to stop the transfection process. The transfected cells were then washed twice following centrifugation at 150×g for 5 minutes using a 0.5 M mannitol solution. Cells with the same transfection reactions were combined to achieve a final protoplast density of $2×10^6$ protoplasts/mL in 0.5 M mannitol solution for alginate encapsulation.

AM3: Encapsulation and Regeneration of Plants

An equal volume of transfected cells was combined with a 2.8% sodium alginate solution and then gently mixed together. The protoplast-alginate mixture was then poured onto a $CaCl_2$ agar plate and incubated at room temperature for 30 minutes, after which 2 mL of $CaCl_2$ solution was added to further solidify the hydrogel. The protoplast-alginate gel was then cut into 4 pieces and a quarter of the gel was placed in a Petri dish with Protoplast Induction Medium (PIM), as described in Jeong et al. 2021.

Plant regeneration protocols were based on Jeong et al. 2021 with some modifications summarized as follows. Following encapsulation in thin alginate layers, the protoplasts were incubated in darkness for 4 weeks, and fresh PIM was added weekly. Cell division started after about one week, and when microcalli reached a size of about 500 µm, the PIM was replaced with Callus Induction Medium (CIM). Calli were allowed to grow to about 1-2 mm size in CIM, after which they were plated on solid Shoot Induction Medium (SIM). After 3 weeks, or when the shoots reached a size of approximately 5-10 mm, they were excised from the calli and transferred to Rooting Medium (RM).

Plants were then propagated in vitro and genotyped using the same sequencing methods described in Example 1's section GM3. Plants containing bi-allelic mutations in target MiMe genes were further multiplied and prepared for planting.

AM4: Plant Growth and Crossing Conditions

Once plants had completely regenerated in vitro from protoplasts, rooted plantlets were transferred to 3.5-inch pots filled with wetted PROMIX HP Growing Medium (Premier Tech Horticulture, Quakertown, PA, USA). 18 pots were placed in each tray, and trays were covered with plastic domes for 3 days. Afterwards, lids were slowly removed by opening them more every day over the course of 3 days. Plants were grown under 18-hour light/6-hour dark photoperiod (40-70 µmol photons m-2 s-1) at 21-22° C. Plants were watered with distilled water and fertilized with 1×

Miracle Grow, indoor concentration (The Scotts Company LLC, Marysville, OH, USA) dissolved in distilled water.

Regenerated plants with confirmed edits in each target gene including REC8, OSD1, and PAIR1 and/or SPO11 were transplanted from tissue culture into substrate and then acclimatized under cool white lights at 24° C. with approximately 60% relative humidity and 16-hour daylength. When plants produced flowers, pollen was collected, and cross pollination was performed under the same environmental conditions. About 21 days after pollination, siliques were removed and seeds were extracted, dried, and prepared for planting.

AM5: Seed Germination and Genotyping

Following seed extraction, seeds were surface sterilized using 1 mL of 70% ethanol solution for 5 min. Then, seeds were rinsed with 1 mL of sterile, distilled water five times. Sterilized seeds were sown on hormone-free AGM (*Arabidopsis* Germination Medium) in Petri dishes. After one week, seedlings exhibiting germination were transplanted to soil, where they were allowed to grow for 2 months before leaves were removed for DNA extraction. High quality genomic DNA was extracted from leaves of randomly selected plants from each population used for genotyping using Qiagen Dneasy Plant Mini kits (Cat. No. 69104) (QIAGEN, Germantown, MD, USA). Purity was determined using a spectrophotometer and DNA was quantified with a fluorometer as described in Example 2's section PM5. Samples were adjusted to a final concentration of 20 ng/μL. Markers were established and populations were genotyped as described in GM6.

AM6: Fertility and Parthenocarpy Testing

Fertility was determined by counting the number of seeds per fruit (silique) for 20 unopened, mature fruits per plant. Parthenocarpic fruit development was induced by application of gibberellic acid. Pistils were treated with a 0.1 μmol/μL gibberellic acid solution ("GA3 treated") or with a buffered control ("mock-treated") solution as described in Vivian-Smith et al. 1999 (Genetic analysis of growth-regulator-induced parthenocarpy in *Arabidopsis*. Plant Physiology. 121(2): 437-452) Flowers were not emasculated prior to treatment. Some flowers were left to develop normally ("untreated"). On 8 days post-application, fruit length was measured, and on 12 days post-application, some fruits were removed for clearing according to the protocol outlined in Sprunck et al. 2012 (Egg cell-secreted EC1 triggers sperm cell activation during double fertilization. *Science*. 338 (6110): 1093-1097). Cleared fruits were imaged the following day.

AR: Results

AR1: Guide RNA Screening

Figure 27:
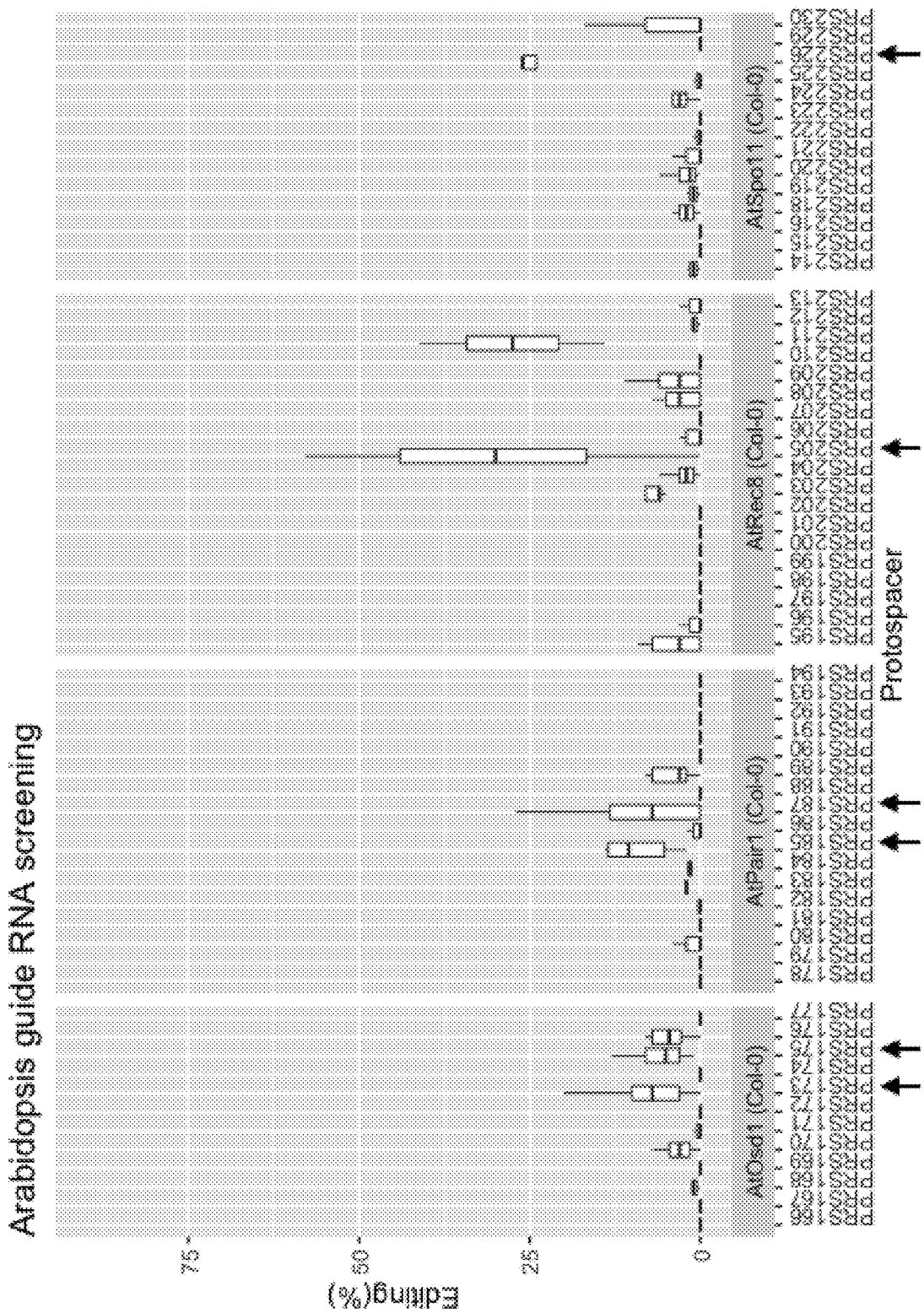
FIG. 27 shows the results for guide RNA screening for edits in A. thaliana. Editing efficiency is displayed as the proportion of sequence reads edited compared to wild-type (vertical axis, in percentage) across a range of selected protospacers (horizontal axis) across four different genes (horizontal axis, grey boxes). From left to right, the A. thaliana orthologs are listed for OSD1 ("AtOsd1 (Col-0)"), PAIR1 ("AtPair1 (Col-0)"), REC8 ("AtRec8 (Col-0)"), and SPO11-1 ("AtSpo11-1 (Col-0)"). The black arrows indicate which sites were explored further, based on the guide RNA screening results.

A total of 62 guide RNAs targeting the conserved regions of the OSD1, SPO11-1, REC8 or PAIR1 genes were transfected in triplicate in protoplasts from multiple plants from the *Arabidopsis* accessions described in section AM1. Editing efficiency was calculated by sequencing as described in Example 1's section GM3, and the resulting data presented in FIG. 27. Based on this data, the guide RNAs indicated with black arrows in FIG. 27 were chosen for editing the OSD1 gene, the PAIR1 gene, the REC8 gene, and the SPO11-1 gene.

AR2: Generation of Parent MiMe Plants

Regenerated plants were screened using the sequencing methods described in Example 1's section GM3. About 1% of the regenerated plants screened (1,903 total plants) had mutations predicted to result in either nonfunctional or non-expressed MiMe alleles, resulting in a MiMe genotype. Such plants were chosen for the crosses described below, which had mutations predicted to result in either nonfunctional or non-expressed rec8, osd1, and pair1 alleles, or nonfunctional or non-expressed rec8, osd1, and spo11-1 alleles.

Two unique plants designated PED-AR-BC and PED-AR-AA were chosen to move forward as parent MiMe plants for partial complementation crosses, within which each parent which had bi-allelic edits resulting in two distinctive complete MiMe genotypes for rec8, osd1, pair1, and rec8, osd1, spo11-1, respectively. Microscopic analysis of microsporogenesis showed these parent MiMe plants also produced dyads instead of tetrads, and also produced viable pollen. The parent MiMe plant PED-AR-BC (rec8/osd1/pair1) was derived from F2 individuals which themselves were derived from a selfed F1 hybrid between Col-0 (CS851557-S1) and diploid inbred HR-10. The parent MiMe plant PED-AR-AA (rec8/osd1/spo11-1) was derived from an inbred individual of Shahdara.

Two unique plants designated PED-AR-BC and PED-AR-DE were chosen to move forward as parent MiMe plants for crossing, each of which had bi-allelic edits resulting in a complete MiMe genotype for rec8, osd1 and pair1. Microscopic analysis of microsporogenesis showed that all three parent MiMe plants produced dyads instead of tetrads and produced viable pollen. The parent MiMe plant PED-AR-DE (rec8/osd1/pair1) was derived from an F2 plant which itself derived from a selfed F1 hybrid between diploid inbred Col-0 and diploid inbred HR-10.

As an example, edits for the parent MiMe plant PED-AR-AA (rec8/osd1/spo11-1) are illustrated in FIGS. 39A-39C. In that figure, the predicted protein sequences are illustrated with respect to the unedited wildtype protein sequence and a consensus sequence, wherein an "X" in the consensus sequence indicates that there is no consensus for that amino acid position; wherein a dot (" ") in the parent MiMe plant sequence indicates that the respective amino acid matches the consensus sequence; and wherein a dash ("-") in the parent MiMe plant sequence indicates that the respective amino acid is present in the consensus sequence but is absent in the parent MiMe plant sample sequence. Frameshift inducing deletions in alleles of osd1 (FIGS. 28A, 28D, and 28E), spo11-1 (FIGS. 28B and 28F), one allele of rec8 (FIGS. 28C and 28G), and pair1 (FIG. 28H) result in premature stop codons. Premature stop codons are denoted by an asterisk ("*") in FIGS. 28A-28C. Another allele of rec8 has a 9 bp deletion resulting in the loss of three (3) amino acid residues in a highly conserved domain of the protein which is expected to disrupt its function (FIGS. 28C and 28G).

AR3: Generation of Genetically Uniform Tetraploid *Arabidopsis* Seed

Parent MiMe plants were crossed using hand pollination. Seeds resulting from crosses were germinated following the procedures described in section AM1. In total, two genetically uniform populations of tetraploid *Arabidopsis* seed with either three or four haplotypes were created, from the parent MiMe plants described in section AR2.

The first genetically uniform population of tetraploid *Arabidopsis* seed referred to herein as Boosted *Arabidopsis* Population 1 ("BAP1") consisted tetraploid individuals with three haplotypes, derived from a cross between a female parent MiMe plant PED-AR-BC (rec8/osd1/pair1) and a male parent MiMe plant PED-AR-AA (rec8/osd1/spo11-1).

The second genetically uniform population of tetraploid *Arabidopsis* seed referred to herein as Boosted *Arabidopsis* Population 2 ("BAP2") consisted of tetraploid individuals with four haplotypes derived from a cross between a female parent MiMe plant PED-AR-BC (rec8/osd1/pair1) and a male parent MiMe plant PED-AR-DE (rec8/osd1/pair1).

For each individual, young leaf tissue or inflorescences were chosen for flow cytometry. All MiMe parent plants used for crosses were shown to be diploid having mean peak fluorescences consistent with diploid control plants. All individuals from BAP1 and BAP2 (except 1 individual from BAP1) were shown to be tetraploid with mean peak fluorescence values double that of diploid control plants. One individual from BAP1 had an intermediate mean peak between the tetraploid and diploid peaks, indicative of triploidy.

AR5: Genotypic Evaluation of BAP1, BAP2, and MiMe Parent Plants

Reads for wild type HR-10 were obtained from the Sequence Read Archive SRA (SRR492282). DNA samples were sequenced by Novogene. Libraries were prepared using the NEBNext® Ultra™ II for DNA Library Prep kit, and paired-end 2×150 reads were sequenced on an Illumina NovaSeq 6000 or NovaSeq X plus.

For the parent MiMe plants PED-AR-BC and PED-AR-AA, DNA samples were sequenced to a depth of 6,261,903,000 bp, and 6,856,028,700 bp, respectively. For the BAP1 progeny plants, DNA samples were sequenced to an average depth of 3,735,085,029 bp. For the parent MiMe plant PED-AR-DE, DNA samples were sequenced to a depth of 4,690,109,700 bp. For the BAP2 progeny plants, DNA samples were sequenced to an average depth of 3,938,238,717 bp. Reads were aligned to the TAIR10 reference genome with BWA-MEM (v0.7.17-r1188) (Li, H. 2013) and alignments were sorted and indexed with samtools (v1.15.1).

For BAP1 variants were called and jointly genotyped for parents (PED-AR-AA and PED-AR-BC), wild type HR-10, and all 100 progeny plants with GATK (v4.3.0.0) (McKenna, A et al. (2010) The Genome Analysis Toolkit: a MapReduce framework for analyzing next-generation DNA sequencing data. Genome research, 20(9), pp. 1297-1303). To identify heterozygous blocks in the F2 parent, only SNPs with the following characteristics are considered for analysis: (i) the SNP is either bi-allelic or tri-allelic amongst the three parental haplotypes; (ii) the SNP is homozygous ALT/ALT in HR-10 and not missing in PED-AR-BC; (iii) the SNP has a Mapping Quality (MQ) score of 60 and it is covered by at least 20 reads in PED-AR-BC; and (iv) the SNP is not within 200 bp of any indel. Using these SNPs, larger genotype blocks were defined by binning SNPs into non-overlapping 100 kbp windows. Each bin was assigned the modal genotype of its constituent SNPs. This method partitioned the PED-AR-BC genome into blocks of either homozygous REF/REF (0/0), homozygous ALT/ALT (1/1) or heterozygous REF/ALT (0/1) states. In total, six heterozygous blocks were identified spanning 61,735,056 bp (51.81% of the TAIR10 reference genome). A similar method was used to identify heterozygous blocks in PED-AR-DE. After establishing heterozygous blocks in the hybrid parents, markers were established and populations were genotyped as described in GM6.

Figure 29A:
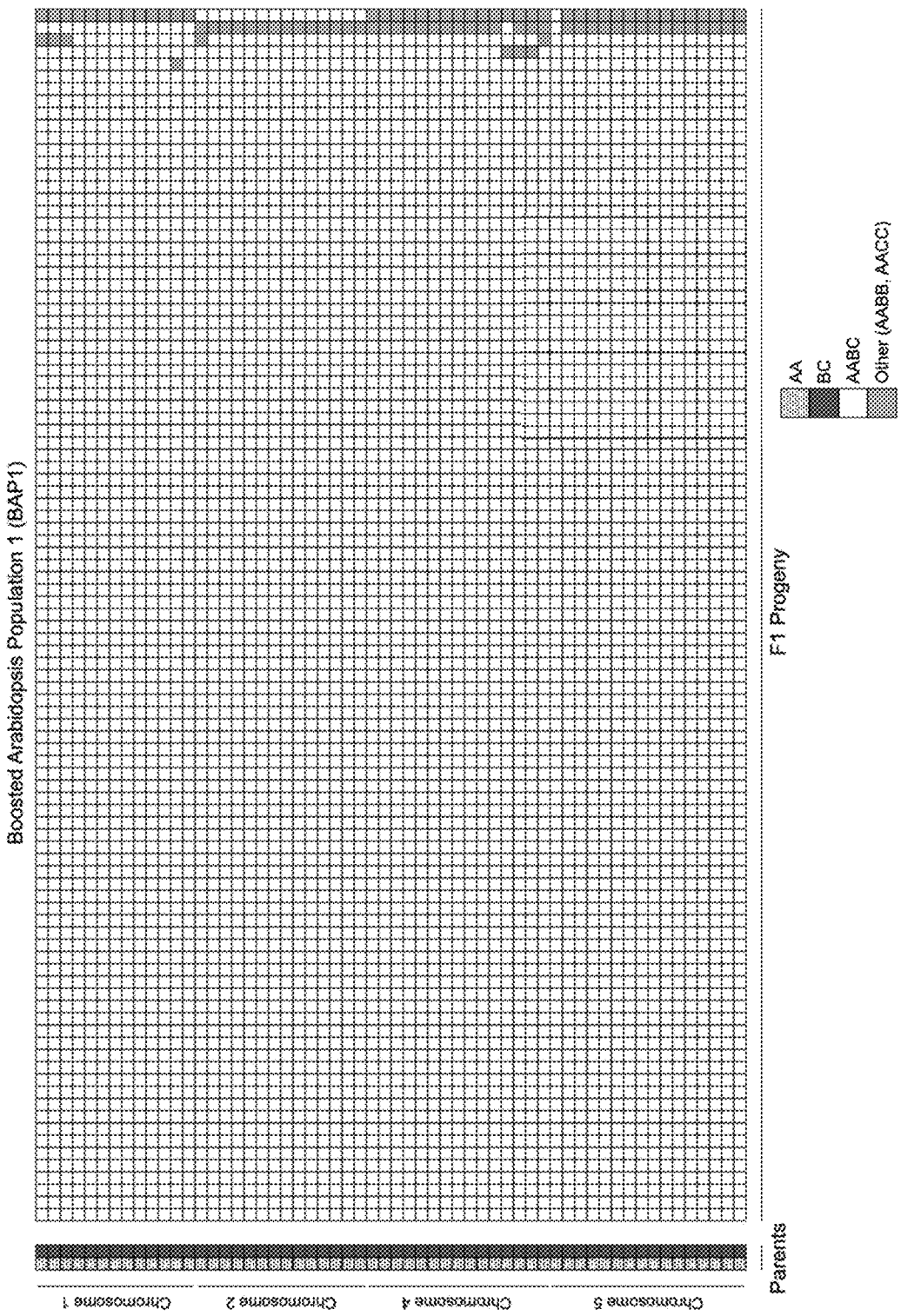
FIGS. 29A-29D show heatmaps comparing genotype distributions and measures of uniformity in MiMe and control populations of A. thaliana.

After filtering for high quality markers and excluding the one triploid plant, a genotype matrix was assembled for BAP1 (FIG. 29A). Across the BAP1 population, the average pairwise genetic uniformity as measured by the Jaccard similarity coefficient was 98.9% (visualized as a pairwise similarity matrix in FIG. 29D). These data are illustrated by the population uniformity graph in FIG. 24. The genetic uniformity was similar for the BAP2 population.

AR6: Genotypic Evaluation of Non-MiMe Progeny (SAP)

The extent of genotypic uniformity of a standard population of non-MiMe×non-MiMe tetraploid *Arabidopsis* seed was also determined. The population of non-MiMe tetraploid *Arabidopsis* seed referred to herein as the Standard *Arabidopsis* Population ("SAP") consisted of nine tetraploid individuals derived from a cross between a female parent non-MiMe tetraploid plant Col-0 (CS851557-S1)×HR-10 (doubled F2 hybrid obtained through protoplast regeneration) and a male parent non-MiMe tetraploid plant Shahdara (doubled inbred obtained through protoplast regeneration).

Reads for wild type HR-10 were obtained from the Sequence Read Archive SRA (SRR492282). DNA samples were sequenced by Novogene. Libraries were prepared using the NEBNext® Ultra™ II for DNA Library Prep kit, and paired-end 2×150 reads were sequenced on an Illumina NovaSeq 6000. For the female parent non-MiMe plant (Col-0 (CS851557-S1)×HR-10 F2), DNA samples were sequenced to a depth of 5,956,964,100 bp. For SAP plants, DNA samples were sequenced to an average depth of 3,998,928,200 bp. Markers were established and populations were genotyped as described in GM6.

Figure 29B:
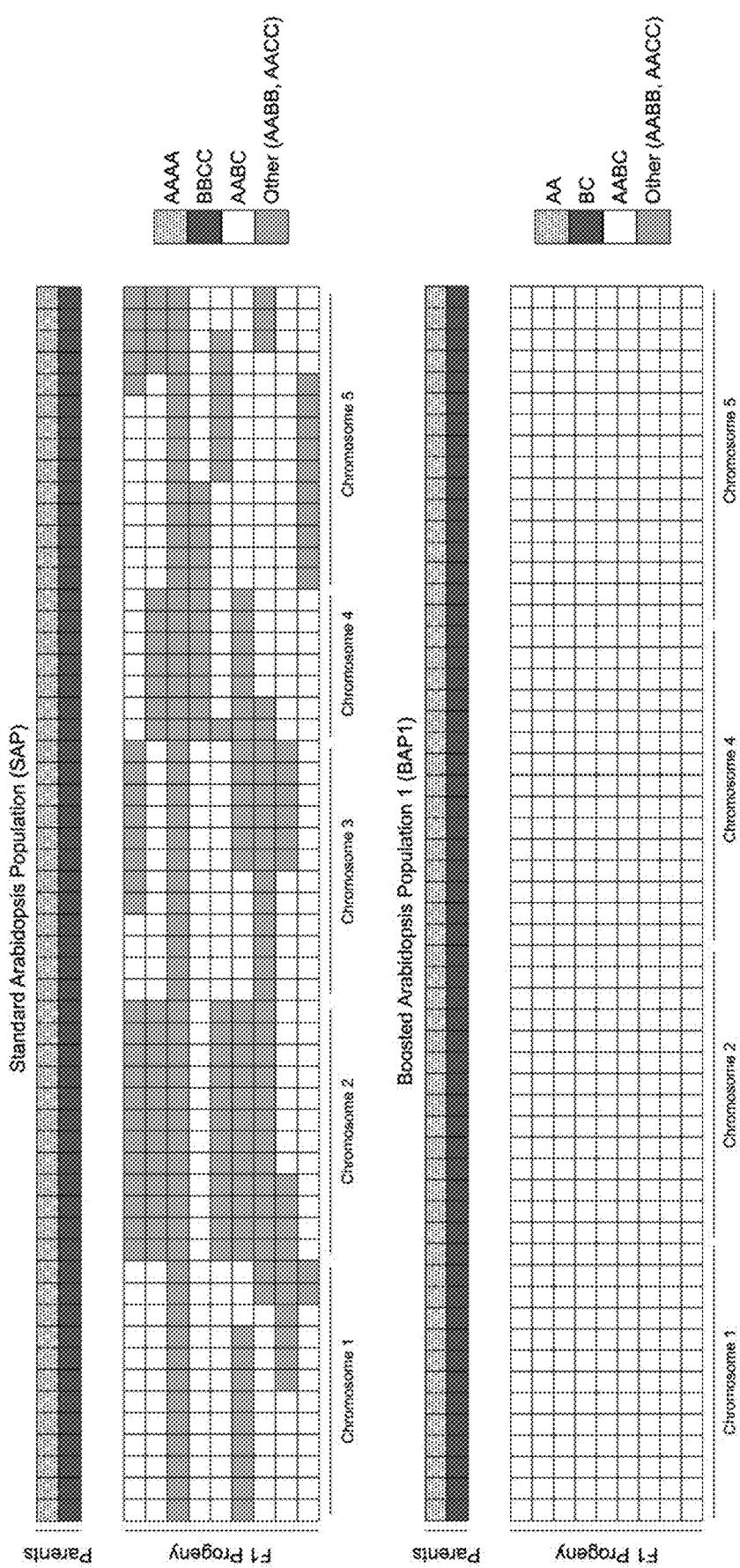
Figure 29C:
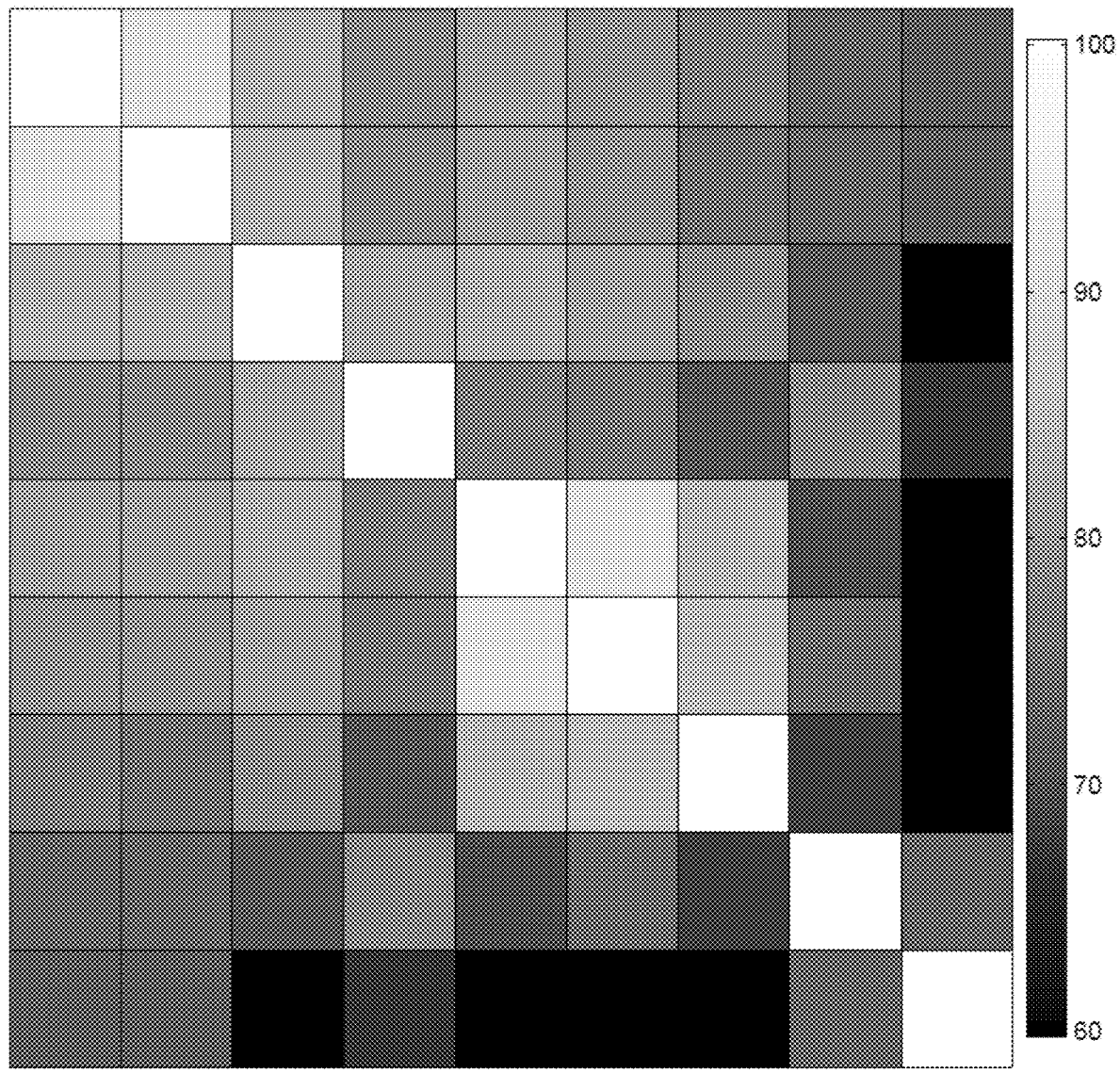
Figure 29D:
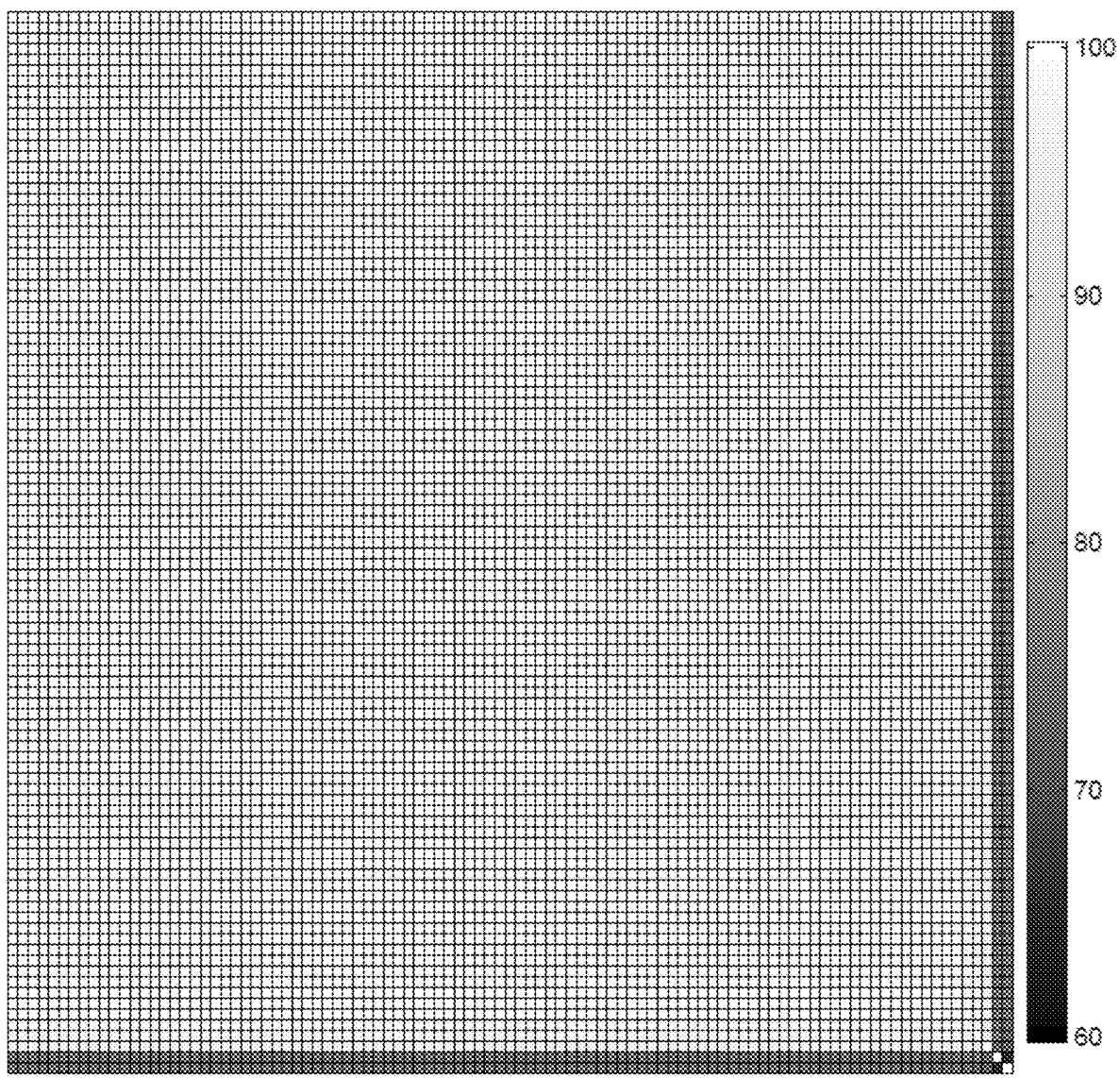

After filtering for high quality markers, a genotype matrix was assembled for SAP (FIG. 29B, top). Across the SAP population, the average pairwise genetic uniformity as measured by the Jaccard similarity coefficient was 75.2% (visualized as a pairwise similarity matrix in FIG. 29C). These data are further illustrated by the population uniformity graph in FIG. 24.

AR7: Phenotypic Evaluation, Parthenocarpy, and Enlarged Seedless Fruit

Figure 30A:
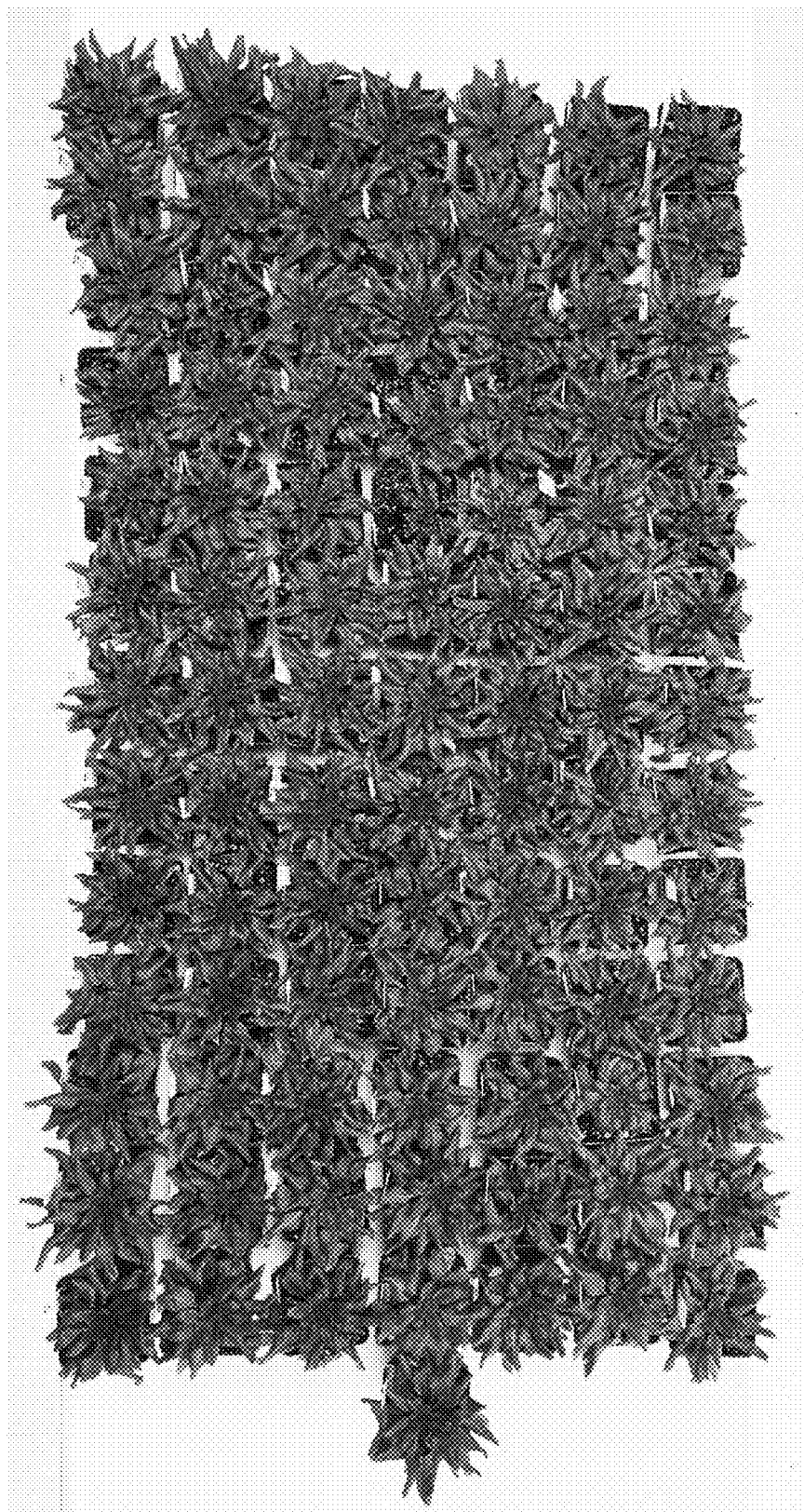
FIGS. 30A-30B show BAP1 plants.
Figure 30B:
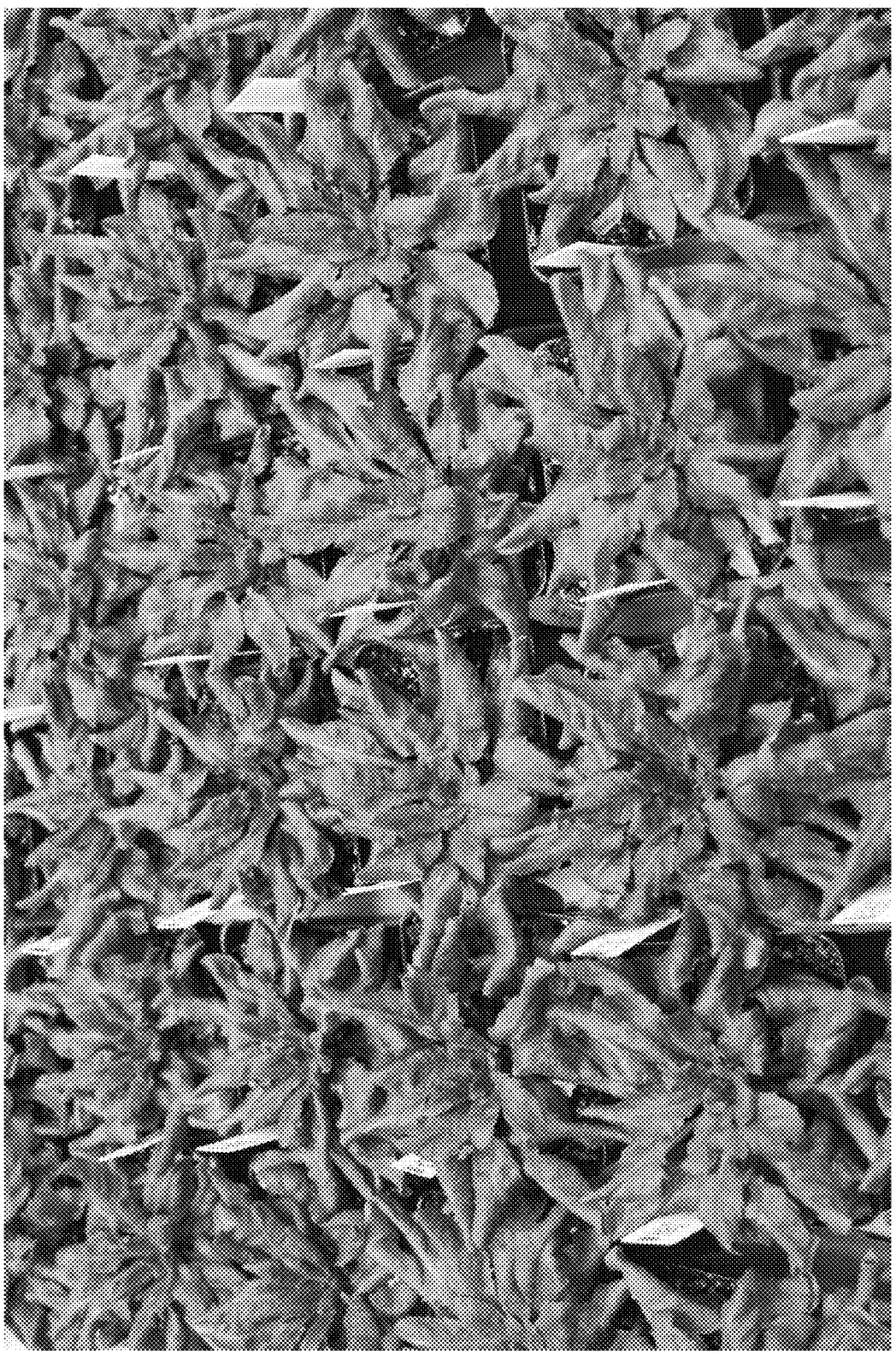

The plants from BAP1 and BAP2 were uniform in size, growth and appearance for their respective population. For example, plants from BAP1 are shown in FIG. 30A at 48 days after planting. A subset of the same plants from BAP1 are shown from a closer distance in FIG. 30B, also at 48 days after planting.

Plants from BAP1 had a partially-complemented spo11-1/pair1 MiMe genotype (rec8/rec8, osd1/osd1, spo11-1/pair1) which did not exhibit a wild-type meiosis phenotype because the MiMe loci of the first MiMe component and the MiMe loci of the third MiMe component of both the first and second parent MiMe plants were rec8 and osd1 respectively at both loci, but which also did not exhibit a MiMe phenotype either due to the complementation of a first MiMe locus (pair1) of the second MiMe component with a second MiMe locus (spo11-1) of the second MiMe component. Instead, plants from BAP1 produced parthenocarpic seedless fruit (siliques)

Figure 31A:
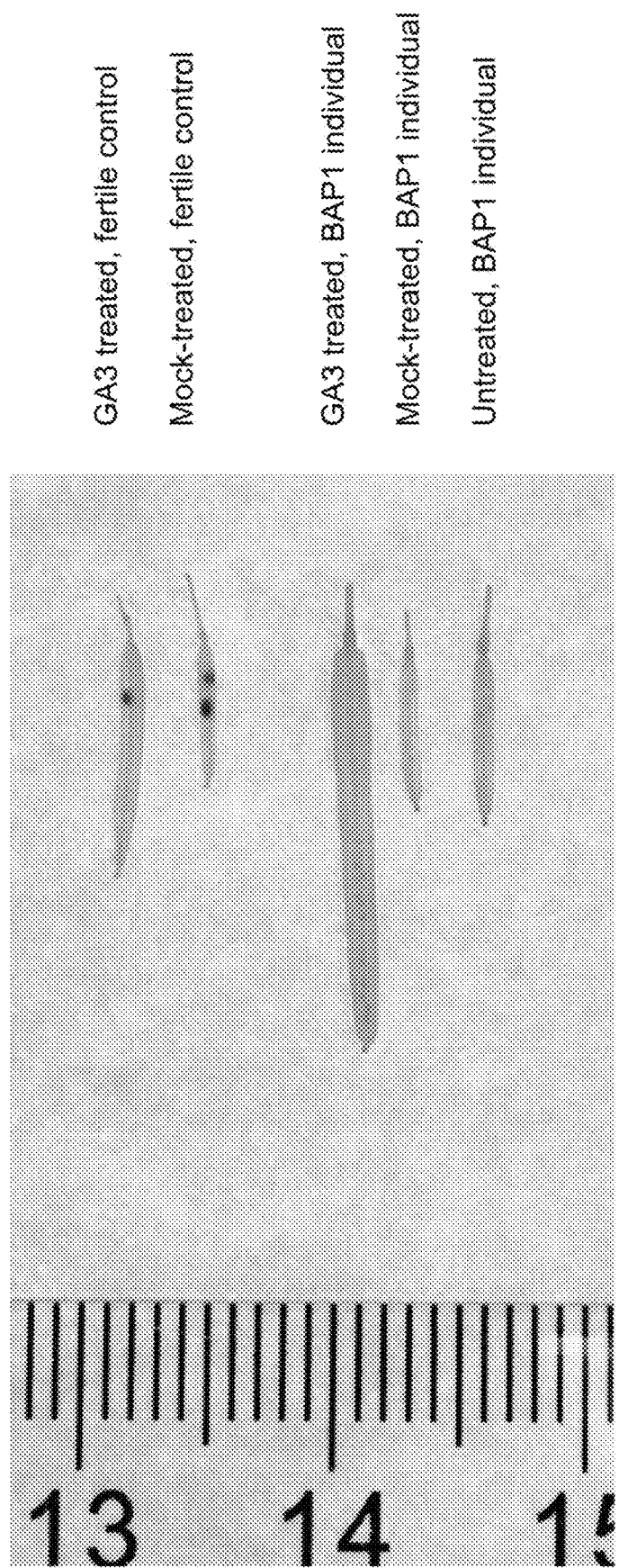
FIGS. 31A-31D show formation of parthenocarpic (seedless) fruits across MiMe *Arabidopsis* plants and controls.
Figure 31B:
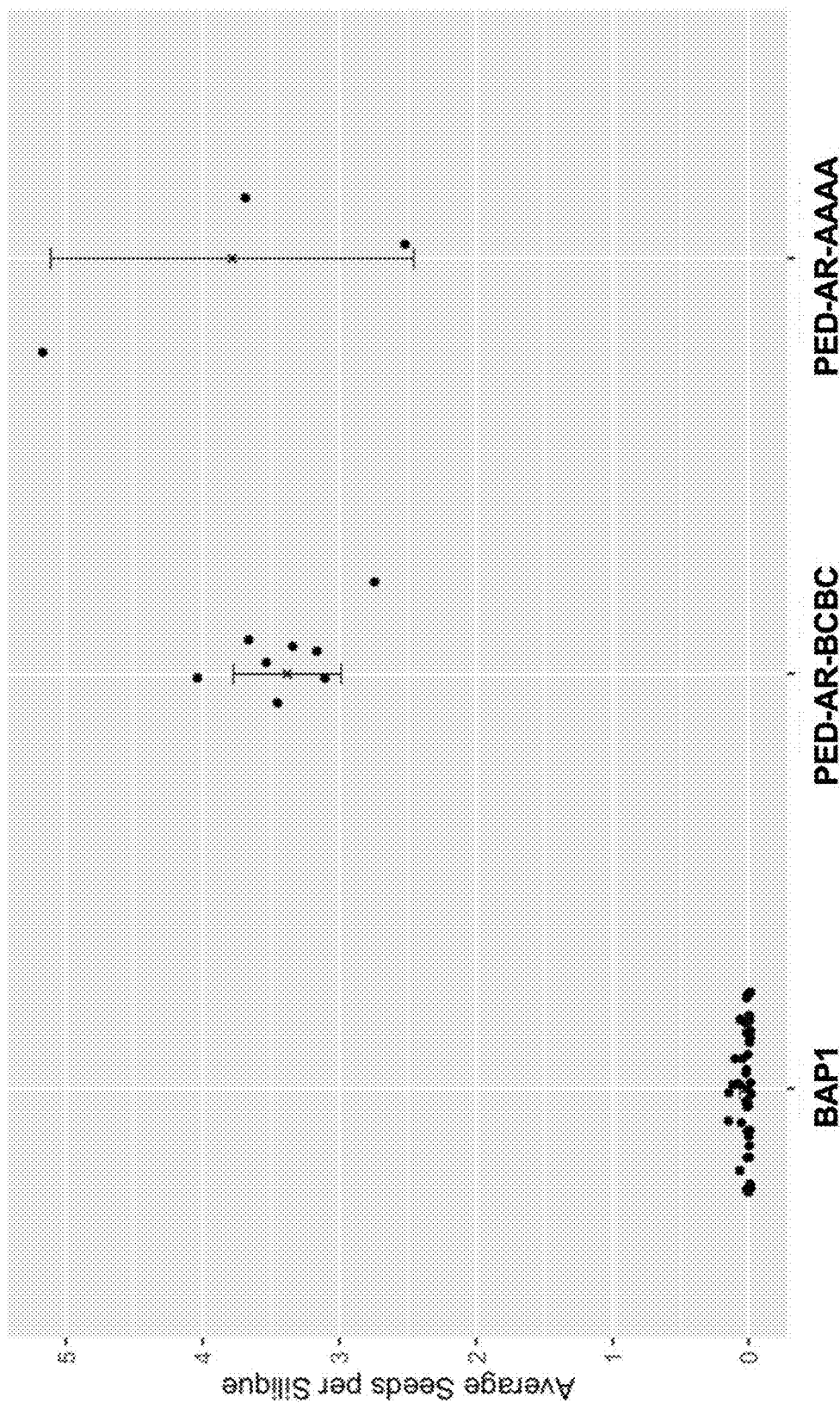

For example, FIG. 31A shows seedless fruit from BAP1 plants treated, untreated or mock-treated with gibberellic acid (GA3) to induce fruit development, compared to fruit from treated or mock-treated fertile *Arabidopsis* control plants as described in section AM6. When 42 plants from BAP1 were randomly selected and 20 fruits were randomly observed from each selected plant, it was determined that 31 of the 42 BAP1 plants produced no seeds, and the average amount was 0.15 seeds/fruit when considering all 42 plants. The seeds that were collected from the BAP1 plants failed to germinate under standard conditions, and demonstrating that all 42 plants from BAP1 failed to produce viable seed, and can therefore be considered seedless. In contrast, the fertile *Arabidopsis* control plants produced about 3 to 4 seeds/fruit. (FIG. 31B). The control plants were doubled versions of the BAP1 parent MiMe plants designated as PED-AR-AAAA (doubled version of PED-AR-AA) and PED-AR-BCBC (doubled version of PED-AR-BC).

Figure 31C:
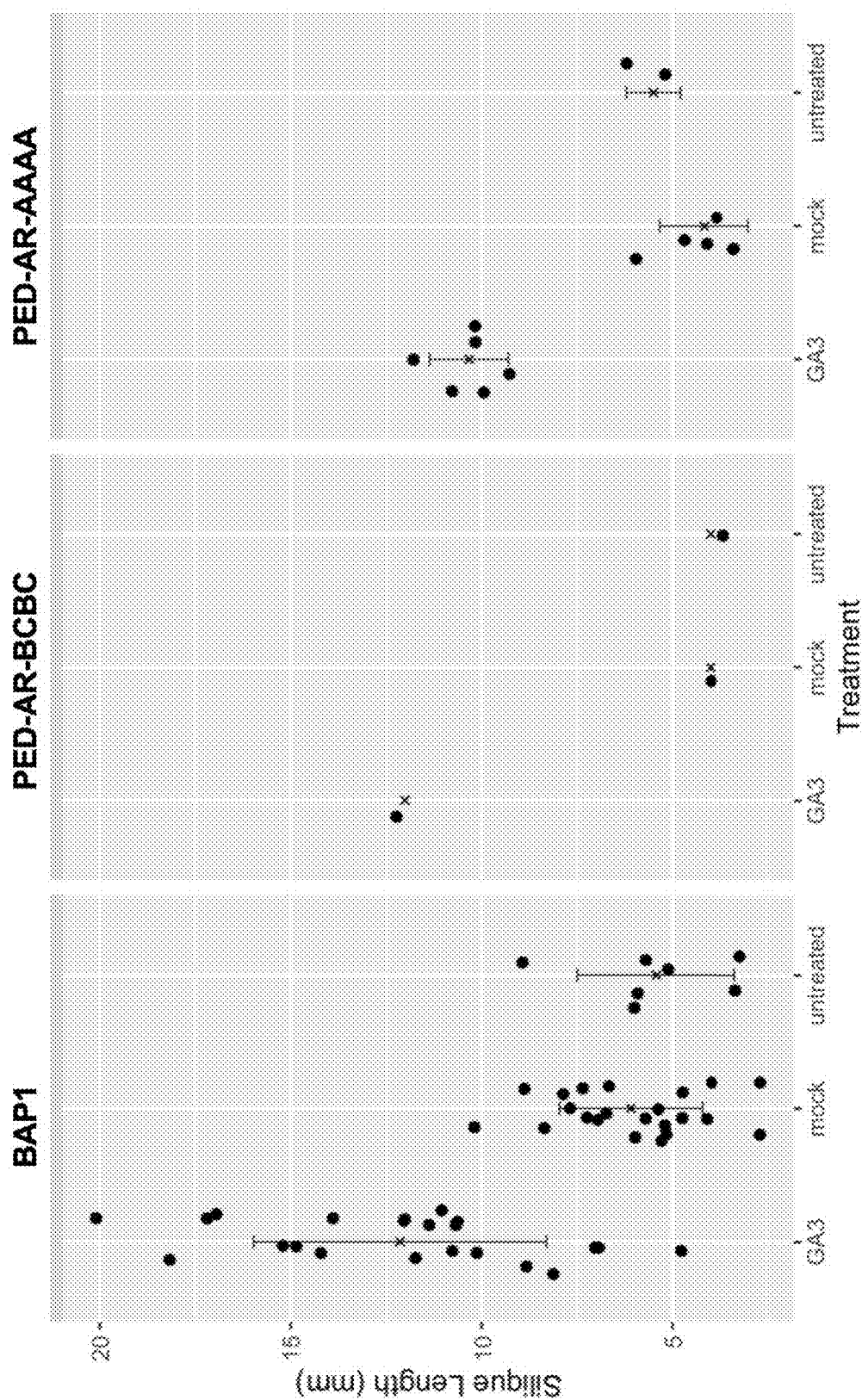

As illustrated in FIG. 31A, the size of the fruit from GA3-treated BAP1 plants was often enlarged compared to fruit from control plants. The increase in fruit length (mm) was quantified for GA3-treated BAP1 compared to those from controls and illustrated in the graph provided by FIG. 31C. As illustrated in the photograph in FIG. 42A, the thickness and overall size of BAP1 fruit was also enlarged compared to that from a control plant.

Figure 31D:
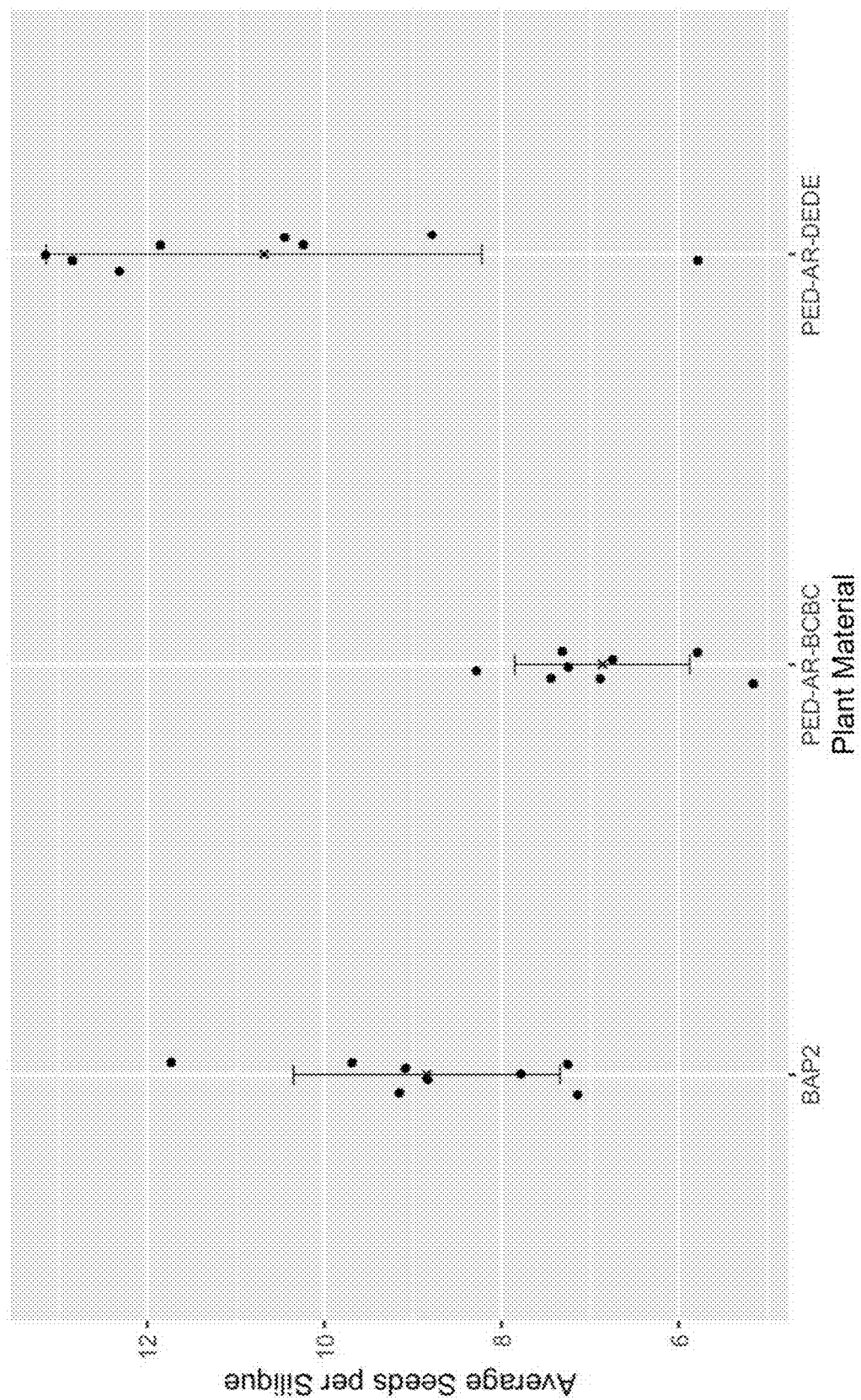

On the other hand, plants from BAP2 were fertile with an average of 8.84 seeds/fruit as illustrated in FIG. 31D. The control plants were doubled versions of the BAP2 parent MiMe plants designated as PED-AR-BCBC (doubled version of PED-AR-BC) and PED-AR-DEDE (doubled version of PED-AR-DE). PED-AR-BCBC plants had an average of 6.86 seeds/fruit, whereas PED-AR-DEDE plants had an average of 10.68 seeds/fruit.

Without being held to any one particular theory, we interpret these results to indicate that functional copies of SPO11-1 and PAIR1 complement their respective knockouts and restore the cellular function of DNA double strand breakage, thus having essentially the same phenotype as a rec8 mutant and producing fragmented chromosomes at the end of the first meiotic division. The skipping of a second division becomes irrelevant because the fragmented chromosomes will not produce viable gametes. Because viable gametes are not produced, egg cells cannot be produced to lead to seeds. Similarly, complementing cyca1 and osd1 will result in similar phenotype due to progression through the second division of meiosis causing random or non-assortment of chromosomes.

Example 4: Breeding to Combine Edited and/or Natural MiMe Alleles in Grandparent Non-MiMe Plants to Produce Parent MiMe Plants This Example describes a method of producing a population of polyploid seed by first generating four grandparent non-MiMe plants having partial MiMe genotypes comprising edited and/or natural MiMe alleles, then crossing the grandparent non-MiMe plants to produce two parent MiMe plants having complete MiMe genotypes, and finally crossing the two parent MiMe plants to produce the population of polyploid seeds. Exemplary variations of this method are depicted in FIGS. 14 and 15. This method may be used to produce polyploid hybrid seeds having three or more haplotypes, e.g., if the grandparent non-MiMe plants together comprise three or more haplotypes. The methods are described below for maize, but may be modified to be applied to any polyploid plant for which suitable transformation and gene editing methods are known to one of skill in the art.

Figure 9:
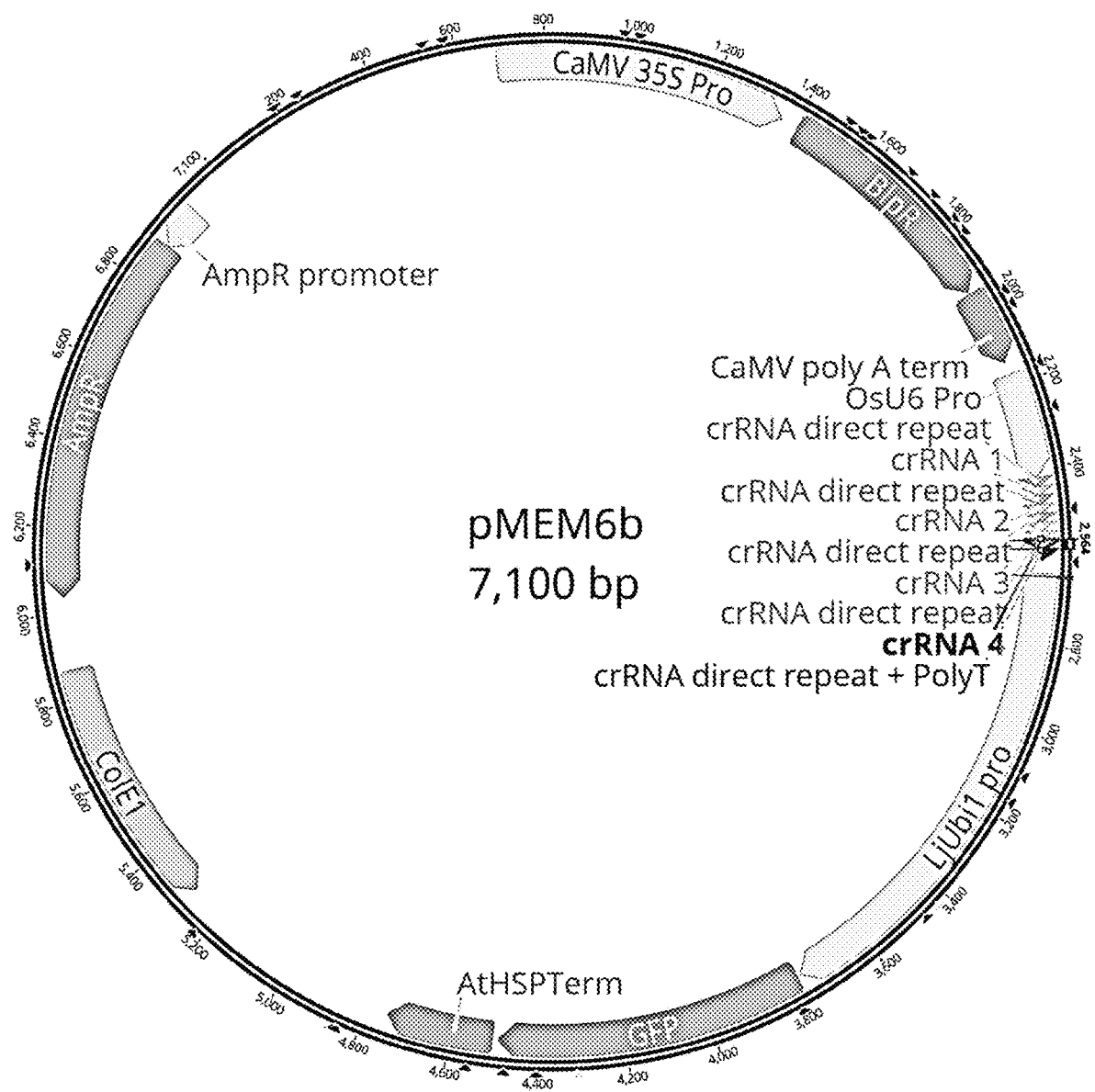
FIG. 9 depicts a plasmid map of pMEM6b, used to introduce MiMe gene edits in Zea mays.

A construct for expressing a nuclease (e.g., pMEM4 shown in FIG. 8, or a similar construct) is bombarded into maize line PED495, and events are selected as described in Wang and Frame (2009. Biolistic gun-mediated maize genetic transformation. *Transgenic maize: methods and protocols*, pp. 29-45). Separately, a construct for expressing a gRNA targeting a MiMe locus (e.g., pMEM6b as shown in FIG. 9 or a similar construct) is bombarded into maize line PED495, and events are selected as described in Wang and Frame 2009. $T_0$ plants containing the nuclease construct are crossed with $T_0$ plants containing the gRNA construct to produce $T_1F_1$ hybrid plants containing both transgenes. The $T_1F_1$ hybrid plants are screened for editing of the MiMe locus targeted by the gRNA, and any plants with editing are self-pollinated or outcrossed to produce plants heterozygous for knock-out edits of individual MiMe loci. Plants that are heterozygous for edits of single or multiple MiMe loci are crossed together or crossed to natural knockout alleles to produce four plants, each heterozygous for the targeted MiMe genotype, e.g., osd1/- (e.g., osd1-1/-, osd1-2/-, osd1-3/-, or any combination thereof), spo11/-, and spo8/- (i.e., each having a partial MiMe genotype). These plants are called $A_{HetMiMe}$, $B_{HetMiMe}$, $C_{HetMiMe}$, and $D_{HetMiMe}$ and are considered grandparent non-MiMe plants each having a partial MiMe genotype. These plants are crossed in an A×B and C×D fashion to and screened for plants with a homozygous knockout genotype at all 4 MiMe alleles. These plants are called $AB_{MiMe}$ and $CD_{MiMe}$. These are considered parent MiMe plants and are recovered at a rate of approximately 1/256. These $AB_{MiMe}$ and $CD_{MiMe}$ parent MiMe plants can then be crossed together to produce a population tetraploid ABCD seed which can be grown into a tetraploid ABCD plant.

Example 5: Editing of Hybrid Maize Lines to Directly Produce Parent MiMe Plants

This Example describes an additional method to produce parent MiMe plants by directly editing two hybrid maize lines and screening for plants with a complete MiMe genotype. Exemplary methods of breeding and producing hybrid polyploid seed comprising directly editing two hybrid plant lines to produce parent MiMe plants are depicted in FIGS. 12, 13, and 19. This method may be used to produce polyploid hybrid seeds having three or more haplotypes, e.g., if two hybrid lines together comprising three or more haplotypes are directly edited to produce the parent MiMe plants.

PED071 and hybrid PED495 are crossed together to make hybrid embryos that are co-bombarded with gRNA construct pOGZ2 (FIG. 10), and one of pMEM4 (FIG. 8), or pOGZ4 (FIG. 11) as a nuclease construct as well as a selectable marker for bialaphos resistance as described in Wang and Frame 2009 with modifications (using described bombardment with TransIT-2020). Additionally a hybrid of PED071 and PED195 is transformed with an identical co-bombardment and transgenic plants can be selected per McCaw et al. (2020. Development of a Transformable Fast-Flowering Mini-Maize as a Tool for Maize Gene Editing. Frontiers in Genome Editing. doi: 10.3389/fgeed.2020.622227), with modifications of using bombardment as described (using described bombardment with TransIT-2020) rather than transformation with *Agrobacterium*. The hybrid transformants are screened for two or more independent events with complete knockout MiMe genotype to act as parent MiMe plants. These parent MiMe plants are crossed to produce a uniform population of tetraploid seed having 3 or more haplotypes, which may be grown into a plant having 3 or more haplotypes. These 3 or more haplotypes may be a combination of PED071, PED195, and an F2 segregant of PED495. They may also be a combination of PED071 and two distinct genotypes that are the result of F2 segregation of PED495.

What is claimed is:

1. A population of polyploid maize seed comprising genetically uniform polyploid maize seed in an amount of at least 70% of the total number of seeds, the genetically uniform polyploid maize seed comprising three or four haplotypes of the same or related species of maize, wherein the population is all of the seeds obtained from a single maize plant or two or more F1 hybrid maize plants, wherein the genetically uniform polyploid maize seed is tetraploid and comprises MiMe alleles, the MiMe alleles comprising:
   (1) a genetic modification at a REC8 locus or an RNA interference construct that targets an mRNA from a REC8 locus, wherein the REC8 locus comprises a nucleotide sequence encoding a REC8 protein having at least 95% sequence identity to the amino acid sequence set forth in SEQ ID NO: 1, wherein the genetic modification at the REC8 locus or the RNA interference construct targeting the mRNA from the REC8 locus reduces or eliminates the function of the REC8 protein;
   (2) a genetic modification at a SPO11-1 locus or an RNA interference construct that targets an mRNA from a SPO11-1 locus, wherein the SPO11-1 locus comprises a nucleotide sequence encoding a SPO11-1 protein having at least 95% sequence identity to the amino acid sequence set forth in SEQ ID NO: 2, wherein the genetic modification at the SPO11-1 locus or the RNA interference construct targeting the mRNA from the SPO11-1 locus reduces or eliminates the function of the SPO11-1 protein; and
   (3) a genetic modification at an OSD1-2 locus or an RNA interference construct that targets an mRNA from an OSD1-2 locus, wherein the OSD1-2 locus comprises a nucleotide sequence encoding an OSD1-2 protein having at least 95% sequence identity to the amino acid sequence set forth in SEQ ID NO: 6, wherein the genetic modification at the OSD1-2 locus or the RNA interference construct targeting the mRNA from the OSD1-2 locus reduces or eliminates the function of the OSD1-2 protein, wherein the MiMe alleles do not comprise a MiMe allele at an OSD1-1 locus or a MiMe allele at an OSD1-3 locus, wherein the genetically uniform polyploid maize seed has:
   (i) a complete MiMe genotype comprising the MiMe alleles, or
   (ii) a partial MiMe genotype comprising the MiMe alleles.

2. The population of claim 1, wherein the population of polyploid maize seed comprises the genetically uniform polyploid maize seed in an amount of at least 90%, at least 95%, at least 96%, at least 97%, at least 98%, or at least 99% of the total number of seeds.

3. The population of claim 1, wherein the genetically uniform polyploid maize seed has a complete MiMe genotype comprising the MiMe alleles, wherein the complete MiMe genotype comprises:
   (1) only MiMe alleles at the REC8 locus, wherein each of the MiMe alleles at the REC8 locus comprises the genetic modification at the REC8 locus, wherein the genetic modification at the REC8 locus comprises a deletion or one or more nucleotide changes positioned in the first 500 nucleotides of the nucleotide sequence encoding the REC8 protein;
   (2) only MiMe alleles at the SPO11-1 locus, wherein each of the MiMe alleles at the SPO11-1 locus comprises the genetic modification at the SPO11-1 locus, wherein the genetic modification at the SPO11-1 locus comprises a deletion or one or more nucleotide changes positioned in the first 500 nucleotides of the nucleotide sequence encoding the SPO11-1 protein; and
   (3) only MiMe alleles at the OSD1-2 locus, wherein each of the MiMe alleles at the OSD1-2 locus comprises the genetic modification at the OSD1-2 locus, wherein the genetic modification at the OSD1-2 locus comprises a deletion or one or more nucleotide changes positioned in the first 500 nucleotides of the nucleotide sequence encoding the OSD1-2 protein.

4. The population of claim 1, wherein the genetically uniform polyploid maize seed has a partial MiMe genotype comprising the MiMe alleles, wherein the partial MiMe genotype comprises:
   (1) at least one MiMe allele and at least one non-MiMe allele at the REC8 locus, wherein each of the MiMe alleles at the REC8 locus comprises the genetic modification at the REC8 locus, wherein the genetic modification at the REC8 locus comprises a deletion or one or more nucleotide changes positioned in the first 500 nucleotides of the nucleotide sequence encoding the REC8 protein;
   (2) at least one MiMe allele and at least one non-MiMe allele at the SPO11-1 locus, wherein each of the MiMe alleles at the SPO11-1 locus comprises the genetic modification at the SPO11-1 locus, wherein the genetic modification at the SPO11-1 locus comprises a deletion or one or more nucleotide changes positioned in the first 500 nucleotides of the nucleotide sequence encoding the SPO11-1 protein; and
   (3) at least one MiMe allele and at least one non-MiMe allele at the OSD1-2 locus, wherein each of the MiMe alleles at the OSD1-2 locus comprises the genetic modification at the OSD1-2 locus, wherein the genetic modification at the OSD1-2 locus comprises a deletion or one or more nucleotide changes positioned in the first 500 nucleotides of the nucleotide sequence encoding the OSD1-2 protein.

5. The population of claim 4, wherein the partial MiMe genotype comprises:
   (i) a first and second MiMe allele and two non-MiMe alleles at the OSD1-2 locus, wherein the first MiMe allele at the OSD1-2 locus comprises the polynucleotide sequence of SEQ ID NO: 108 and the second MiMe allele at the OSD1-2 locus comprises the polynucleotide sequence of SEQ ID NO: 109;
   (ii) two MiMe alleles and two non-MiMe alleles at the REC8 locus, wherein each of the MiMe alleles at the REC8 locus comprises the polynucleotide sequence of SEQ ID NO: 110; and
   (iii) two MiMe alleles and two non-MiMe alleles at the SPO11-1 locus, wherein each of the MiMe alleles at the SPO11-1 locus comprise the polynucleotide sequence of SEQ ID NO: 111.

6. The population of claim 1, wherein the genetically uniform polyploid maize seed has three haplotypes.

* * * * *

SEQUENCE LISTING

```
Sequence total quantity: 157
SEQ ID NO: 1           moltype = AA  length = 603
FEATURE                Location/Qualifiers
```

```
                        -continued source               1..603
                     mol_type = protein
                     organism = Zea mays
SEQUENCE: 1
MFYSHQLLAR KAPLGQIWMA ATLHSKINRK RLDKLDIIKI CEEILNPSVP MALRLSGILM   60
GGVVIVYERK VKLLYTDVSR LLTEINEAWR IKPVTDPTVL PKGKTQAKYE AVTLPEINMV  120
VEQPMFFSEP DGAKFRRMGL EDLDEQYVQV NLDDDDFSHA DDRHQAKAVN ITLVDNFESG  180
LAETDLFNHF ERFDIADDET TVNITPDEYP QVPSTLIPSP PRQEDIPQQE EPYYAAPSPV  240
HGEPQQGGPE DQEEQKMKQP PKASKRKARW EVPRVIMDNN QMMIPGNIYQ TWLKDASSLV  300
SKRRKLNSNF NFIRSTKISD LMHIPPVALI SHDNLFSELC YPKPLMQLWK DCTEVKSTKA  360
SSGGGQRSSSQ EPQPKNSPPQ AGGEYEMETG GLPMDLTDGI EKLRANMSAK YDRAYNILHS  420
DHSVTPGSPA GLSRRSASSS GGSGAFIQL DPEVQLPSGS GRSKRGQHSS ARSLGNLDTV  480
EEDFPLEQEV RDFKMRRLSD YVPTPDLLEE TEPTQTPYER RSNPMDKITE TIQSHLKLHF  540
DTPGVPQSES LSHLAHGMTK ARAARLFYQI AVLATCDYIK VTQLERKGDE LYGDILISRG  600
LKM                                                               603

SEQ ID NO: 2         moltype = AA  length = 383
FEATURE              Location/Qualifiers
source               1..383
                     mol_type = protein
                     organism = Zea mays
SEQUENCE: 2
MAGRDKRRRA APLEGDEQQL RRRLEEAALL LRRIKGLVRW IVEEVAAGRS PSIVLHRYRN   60
YCSSADSASP SPCACSYDIP VGTDVLSLLH KDYHTSRLNV LLRVLFVVQQ LLQQNKHCSK  120
RDIYYMYPSI FVEVAVVDRA INDICILFKC SRHNLNVVPV VKGLVMGWIR FMEGEKKVYC  180
ITSVNAAFSI PVDIEAIKDV VSVAHYILVV EKETVFQRLA NDKFCERNRC IVITGRGYPD  240
IPTRRFLRYL VELLHLPAYC LVDSDPYGFD ILATYKFGSL QLAHDANLLR VPDIRWLGVF  300
TSDFEEYCLP DCCLLRLSPE DRRKAEGILA RCYLHREAPE WRSELEAMLQ KGVKFEIEAL  360
SANSISFLSH EYIPQKIKQG MHL                                          383

SEQ ID NO: 3         moltype = AA  length = 562
FEATURE              Location/Qualifiers
source               1..562
                     mol_type = protein
                     organism = Zea mays
SEQUENCE: 3
MKLKINKACD LGSISVLPPR RTGGSGGAGG AGSSAAPVAA GSQQRSQPMS QHSFSQGVVG   60
SGGASSLLHS QSQLSQASLD ENLLTLHLAS PARDQRFGFH DDLSKKMTSL PVSSASCVRE  120
ESQLQLAKTS SNPVHRWNPS LPDGRSVGPT EDVERKFQHM ASSVHKVGMV LDSVQTDVMQ  180
LNRAMKEATL DSGSIQQKIV LLDDALLQKNL KGQDDLKALV ESNTKSISDQ LTVLNSYSNK  240
LDEISSTLSI LPKQIETNLK QQQSDTFRIF RKDMEEIVRA VRSLNNKIDA IQMPTDQSCT  300
TNGRPLMNQL PVDRNERPQV NQTPEVTRVS QTPVATMANQ RPVAKGRHLV SQTPAANGKP  360
LTNQTSVANG RSLMSQVPAA NGKPLTNQIA VPKGRPMMRQ KTAEGGRPQM NQIPVADGWP  420
HTNKIHAPEV RHPVPLVCPA AGPRPKVEEG KLRAVPQKLT GCRSRVTPKQ EEAATNTKVV  480
VGRAAATEKV VIFIDDDSDD GGSEALASCV ILRPAPLGSG AGECDLVKVG AEESQEILRR  540
ARKRRRREMQ AIVACMPPEL GY                                          562

SEQ ID NO: 4         moltype = AA  length = 227
FEATURE              Location/Qualifiers
source               1..227
                     mol_type = protein
                     organism = Zea mays
SEQUENCE: 4
MPESRDGRSE DLADLSGGVG GGGFFIRRVA SPGALAVRGV RKPLARRYIS PSRNKENLLP   60
VWALRVTPTK RSPLPGWYPR TPLRDITAIA KAIQRSRSRI AAAQQRSQRI EQSQSVNVT  120
TPAQAEQDAH IAEASHAVAS GSGSTEREAV ANPATVLADD NLNVSSLAAE GSLNTPPKPM  180
DPALADKKLS GSIEKVEKLV RKNLKRTSRA AQASRRATQR RNLMSMR               227

SEQ ID NO: 5         moltype = AA  length = 609
FEATURE              Location/Qualifiers
source               1..609
                     mol_type = protein
                     organism = Zea mays
SEQUENCE: 5
MTGAGMKLKI NKACDLSSIS VLPPRRTGGS GGAGSSAAAA AVAAGSQQRS QPLSQQSFSQ   60
GAVGSGGASS LLHSQSQLSQ ASLDENLLTL HLASPARDQG FRLHDDSSKK MTSLPVTSAS  120
CVREESQLQL AKTSSNPVHR WNPSLPDSRY FIELHSFLFE CLTGSGLTGV VPAEDVERKF  180
QHMASSVHKV GMVLDSVQND TMQLNRAMKE AALDSGSIQQ KIVVLDTSMQ KNLKGQGDLK  240
VLVESNTKNI ADQLAVLNSH SNKLVEISSA LSVLPKQIER DLKQQQSDIF RIFRNNMEEI  300
ARAVKSLNSK IDAIQMPTEQ RCTTNGRPLM NQLPVDRNER PQVNQTPEVT RVSQTTVASL  360
VNQAPAANGR HLMSKTPAAN GKSVMRQTPA ENGRHLVSQT PAANGKTLKR QTSVTNGISL  420
MSQVPAANGK PVVIQIPAPK GRPMMRQKTA ESGRTEMNEI PVASGRPHTN KIPIAEVHPA  480
PLVCPAKQVA TDPKPKVDEE KLKALPQKLT SSRSRVAPKQ EEAANTKVIS RAAATEKVVI  540
FIDDSDDDND VRASCVILRP SGSGSLGERE CDLMKVGAEE SQEIPRRARK RRRREMQATV  600
GVACMPLPA                                                          609

SEQ ID NO: 6         moltype = AA  length = 224
FEATURE              Location/Qualifiers
source               1..224
```

```
                          mol_type = protein
                          organism = Zea mays
SEQUENCE: 6
MRNFKMLEVR TARRPALADI SGGGFFMRTV ESPGAVLVNG AVKRPARQFL SPSSNKENVP     60
PVGAFRATPK RRTPLPDWYP RTPLRDITSI VKAIERRRSR LQNAAAQQQI QWTEDPSRSV    120
DPITPVQAEQ GGVPTTVDGQ GVGSPATCLE DGKLKTSSYP SSDCSLQAQTP SKPNDPALAD  180
LVEKKLSSSI EQIEKMVRRN LKRTSKAAQP SKRTIQRRVL MSMR                     224

SEQ ID NO: 7              moltype = AA   length = 226
FEATURE                   Location/Qualifiers
source                    1..226
                          mol_type = protein
                          organism = Zea mays
SEQUENCE: 7
MSYTNFSQDY KMPQLRTASR PALASNSAGG FFIRRRVASP GTSQAKGAAK PLARRVRTPA     60
ARAKPKRRSP LPDWYPRVPL RDITSIVKAL EKRNRLEEDA ARQHIQSNED SSQPVDPTTA    120
EHSNPDSQST QTQETPGAVA SGPSSTSAVA NRVTSVAEGK QEATDCSLQV APSKPNDPSP    180
ADLVKKLSGS IEQIEKMVRR HMKETHPKAA QPSKVVVQRR ILMSMR                   226

SEQ ID NO: 8              moltype = AA   length = 453
FEATURE                   Location/Qualifiers
source                    1..453
                          mol_type = protein
                          organism = Zea mays
SEQUENCE: 8
MRRCAEAIAR AVVEFLDAVI LAFIRSCFGA RPRRGSGLRV RPTPAPPRSP SLSAHLAAVS     60
WSSSFQDALV RGDRAAEVIW DEEGLVRDGR FHEDLADGCG IDEELRREAS YLKLCGTISE    120
TPAELRNEQS YENNLETTNE CDSKLTYGPP ANCKLLFEAN SSQGQRNPRC EERHSLRSIL    180
NSEDAGRHHG AEYVPRSASS EKRLFQNMQH KPLDSGGSPF PTPLVLRDDM QTPGTAYASH    240
RGTSISGKRV RTRKQFIYPV LRSIENRLQQ IELTEDSSPL ASSDPLKERD LGADSTKDPT    300
QASSTSVVKS GLSETPSYSA PDPNASYGVE ESLSKSNSDE KNAALSLSRW LKSSSADAEN    360
QDDEDCSFLT EKPVFMVAPD LNLDTSNPTP RLPKAWDGNG IPNTTTRYRE DQRVSWHTTP    420
FEQRLLKVLS DEDRCPPRKV VRGKLFHLEE TAE                                 453

SEQ ID NO: 9              moltype = AA   length = 432
FEATURE                   Location/Qualifiers
source                    1..432
                          mol_type = protein
                          organism = Zea mays
SEQUENCE: 9
MMGCLFGCFR ASGDGGDAKG AGDRNTSLAP ATTTIQQDG TGRRIRPPSR NALSAVFQRE      60
DEGSRAAQAA SSWAEQTGES KRMDQELEPQ TIIQKNCGAL LQTTNNIQSV LRDADSVHQK    120
ETHSGCLPVM SDDVHFMEAP KVENCETPPR SHQSSTVPDA TSSSKTNDEL RTSATSLKNN    180
VEESTNENDT EACVQGEEQQ QALDLAEDFE ECGVSKEDFF PPEKLEDPKC AKNDHVVSME    240
ISISDECSLF QSSEGSVSPS NKIRGSMNTT STEKSPKTEA TIHATRKKLL KSNTSELELP    300
SLAQWLKPPN PKKAFRDEAV TGDRSHSAKS SDEDRPIIGM VAAHWKDKEP ANFTSKWWDG    360
NGIPNSTNKY KEDQKVSWHA TPFEERLEKA LSEEKSLSER NCSSGKTSQF LGVEGEESDT    420
AGSNRLYATA YA                                                        432

SEQ ID NO: 10             moltype = AA   length = 509
FEATURE                   Location/Qualifiers
source                    1..509
                          mol_type = protein
                          organism = Zea mays
SEQUENCE: 10
MSTIAASRRS SSSSSSATAK RPAIADGPGG PKATAAQAKK RVALGNITNV AARGGRASVG     60
GSLGNVMAPT SSAKLNPTVP LKKPSLATSA RSVSSSIRGS ADKPASIKPA PPVARHGSAT    120
QRHNNVPPPK VPTIADVPSR APALVSCTGL VSPGRSGDSV SSDETMSTCD SMKSPDFEYV    180
DNQDTSMLAS LQRRTSEHLR ISEDRDVEEN KRKKNAVAPM EIDRICDVDS EYEDPQLCAT    240
LASDIYMHLR EAETKKRPST DFMETIQKDV NPSMRAILID WLVEVAEEYR LVPDTLYLTV    300
NYIDRYLSGN EISRQRLQLL GVACMLIAAK YEEICAPQVE EFCYITDNTY FRDEVLDMEA    360
SVLNYLKFEM TAPTAKCFLR RFARAAQACD EDPALHLEFL ANYIAELSLL EYSLLSYPPS    420
LIAASAIFLA RFILQPTKYP WNSTLAHYTQ YKPSKLSECV KALHRLCSVG SGSNLPAIRE    480
KYSQHKYKFV AKKQCPPQIP TEFFRDTTC                                      509

SEQ ID NO: 11             moltype = AA   length = 298
FEATURE                   Location/Qualifiers
source                    1..298
                          mol_type = protein
                          organism = Zea mays
SEQUENCE: 11
MASSKRRFGA AGGADKKDLF HVVHKVPAGD SPYVVAKHLQ LVEKQPDVAI VWFWKAINSG     60
DRVDSALKDM AMVMKQQDRS EEAIEAIRSF RHLCSKQAQE SLDNLLIDLY KKCGKVEEQI    120
ELLKQKLKSI YLGEAFNGKA TKKARSHGKK FQVSIQQETS RILGNLGWAY MQQNNFEAAE    180
LVYRKAQAIE PDANRACNLG LCLIKQGRHD EARQALEDVR LRRIYGSEDG KVVARAEQLL    240
RELNPLQCVS SPFQVGLSVH EGIMGKPDLV VMNEWTPFRS RRLPVFEEIA TFRDQMAC     298

SEQ ID NO: 12             moltype = AA   length = 1096
FEATURE                   Location/Qualifiers
```

```
source                  1..1096
                        mol_type = protein
                        organism = Zea mays
SEQUENCE: 12
MAAADGDALI AAFAVSKGGI VLKHIFLNAP PPEAMCGSGG REVESDEEDP PVMVGRHPDC    60
HVLVDHPSVS RFHLELRCRR RQSLITVTDL HSVHGTWVSG RRIPPNTPVD LATGDTLRLG   120
ASKREYKLLW LSLREAFEMD DLMYMPSLPE EDKEEPYVKE PSSKLLPGHR DSVNMETHQD   180
TSEQIVSEDI AFPAKVAPSA PPLSEFLQPF FVEEHSLSQF HEKRNGVTEE KLVDKNQISE   240
SFGSLIIQEM PGTLTNAGKS IQSGEQEDAS NKVSKRSKLK SVKSLRVDTG RSSERSSTLS   300
HSFQKGDQND IVVCSQSCGT ECAVCIALFG ISEIEKAEEK EELIAEDNVD MNPPASMIME   360
GNMNERKPDN YIPQDPIGAK LQKKLGLLDS ALPLHFKDDV FADKEIPQWN VASVHTESEL   420
LSEYLIIPEV KHDDLNHLNL EEGLSKSENI NPNKITEGPG NCQLEGTIRG NLFDNLDTDG   480
IEEGEEICPL DKDEITPNGS GNIIMERSNI VLKPTISQQL MDSISPLNLD HGDFSENENS   540
MLNTGDQMKL NEPVSENLNP LIPTDEKYLK SQTEECMPIS YLEFKDDILL DRENSVLAPR   600
KYEAMSPVRQ ENLFSDKENV TPASKVKTVV RGVLGTRMDN SVSAANASNK NKVLGSRVDN   660
SVSTENSSNK KQCELSSKSK KVHTVDFDVF YSDKENLTPI SSGGMKARKC FPKDLSVDLD   720
QDQEAFCSDK ENLTPLSSAA RKTRDMSGNL TRVESAVTKK RVVGRLPFQT LVSNSPLRPA   780
SSHDCTCAVA RPAGVAAGDL AIKLEDKLND LSCNGHESGS AGEGMKTWTM VANTDSLLDD   840
ESRKAIMLLK GLKGTRLFIP RIVIRELDSM KQREGLFRRS TKATSILQWI EECMARESWW   900
IHVQSSADMF PVAPTPPATP SAQRIDEEIE ISSGSFNPMM ALFGPRSSAA LADMISPRPE   960
DRVLDCALLV SRVRSNEKVV VLSNSVTLKI KAMAEGLPCE GAKEFRESLV DPSSRRFMWA  1020
ASAPRGSAWS CLDASALAEN YYNSRHHAMK RRVLVAARPS ESEAAKGLKL ILRHNSLYAQ  1080
ATDAVNKTPL VSLAAV                                                 1096

SEQ ID NO: 13           moltype = AA  length = 502
FEATURE                 Location/Qualifiers
source                  1..502
                        mol_type = protein
                        organism = Zea mays
SEQUENCE: 13
MSTHAASRRS SSSSAVAKRP AIAEGATKAA GPGPTAAQAK KRTALVNITN VAAPGARVAA    60
VGKVAPPVTG AKLNPATSGA PLKKPSLANA RTIRGSAAKS ASIKPAPPVS RHDSSSEQKH   120
NVLVPTTVHV PSRAPALVPY SSFVSPGRSR DSVSTDETMS TCDSMKSPDF EYIDNGGCSM   180
LASLQRRADE HLRTSEDRDV EENKWKKNGP APMEIDSICE VDSNLEDPQL CAALASDIYM   240
HLREAEMKKR PSTDFMKTIQ KDVNPSMRAI LIDWLVEVAE EYRLAPDTLY LTVNYIDRYL   300
SGNEINRQRL QLLGVACMLI AAKYEEICAP QVEEFCYITD NTYFRDEVLE MEASVLNYLK   360
FEMTAPTAKC FLRRFARSAQ ACDEDPAHLL EFLANYIAEL SLLEYSLLSY PPSLIAASAI   420
FLARFVLQPT KYPWNSTLAH YTQYKPSELS ECVKTLHRLS SVGPGSNLPA IREKYSQHKY   480
KFVAKKQCPP QIPAEFFRDA AC                                           502

SEQ ID NO: 14           moltype = DNA  length = 20
FEATURE                 Location/Qualifiers
source                  1..20
                        mol_type = unassigned DNA
                        organism = Zea mays
SEQUENCE: 14
tggtggtgtt ggtggtggag                                               20

SEQ ID NO: 15           moltype = DNA  length = 20
FEATURE                 Location/Qualifiers
source                  1..20
                        mol_type = unassigned DNA
                        organism = Zea mays
SEQUENCE: 15
tcaggagggt ggcctcgccg                                               20

SEQ ID NO: 16           moltype = DNA  length = 20
FEATURE                 Location/Qualifiers
source                  1..20
                        mol_type = unassigned DNA
                        organism = Zea mays
SEQUENCE: 16
ggcgttgagg gtcacaccga                                               20

SEQ ID NO: 17           moltype = DNA  length = 20
FEATURE                 Location/Qualifiers
source                  1..20
                        mol_type = unassigned DNA
                        organism = Zea mays
SEQUENCE: 17
tcggtgtgac cctcaacgcc                                               20

SEQ ID NO: 18           moltype = DNA  length = 20
FEATURE                 Location/Qualifiers
source                  1..20
                        mol_type = unassigned DNA
                        organism = Zea mays
SEQUENCE: 18
caatggccgt aatatcacgg                                               20
```

```
SEQ ID NO: 19              moltype = DNA   length = 20
FEATURE                    Location/Qualifiers
source                     1..20
                           mol_type = unassigned DNA
                           organism = Zea mays
SEQUENCE: 19
atcaggaggg tggcctcgcc                                                    20

SEQ ID NO: 20              moltype = DNA   length = 20
FEATURE                    Location/Qualifiers
source                     1..20
                           mol_type = unassigned DNA
                           organism = Zea mays
SEQUENCE: 20
gtcggtgtga ccctcaacgc                                                    20

SEQ ID NO: 21              moltype = DNA   length = 20
FEATURE                    Location/Qualifiers
source                     1..20
                           mol_type = unassigned DNA
                           organism = Zea mays
SEQUENCE: 21
ctgcagagcc ccgagatgcc                                                    20

SEQ ID NO: 22              moltype = DNA   length = 20
FEATURE                    Location/Qualifiers
source                     1..20
                           mol_type = unassigned DNA
                           organism = Zea mays
SEQUENCE: 22
ctggatggta ccccaggacg                                                    20

SEQ ID NO: 23              moltype = DNA   length = 20
FEATURE                    Location/Qualifiers
source                     1..20
                           mol_type = unassigned DNA
                           organism = Zea mays
SEQUENCE: 23
gcaatggccg taatatcacg                                                    20

SEQ ID NO: 24              moltype = DNA   length = 20
FEATURE                    Location/Qualifiers
source                     1..20
                           mol_type = unassigned DNA
                           organism = Zea mays
SEQUENCE: 24
gaggatggca agctgaagac                                                    20

SEQ ID NO: 25              moltype = DNA   length = 20
FEATURE                    Location/Qualifiers
source                     1..20
                           mol_type = unassigned DNA
                           organism = Zea mays
SEQUENCE: 25
acgattgatg tgatgtcacg                                                    20

SEQ ID NO: 26              moltype = DNA   length = 20
FEATURE                    Location/Qualifiers
source                     1..20
                           mol_type = unassigned DNA
                           organism = Zea mays
SEQUENCE: 26
cctgactggt acccgaggac                                                    20

SEQ ID NO: 27              moltype = DNA   length = 20
FEATURE                    Location/Qualifiers
source                     1..20
                           mol_type = unassigned DNA
                           organism = Zea mays
SEQUENCE: 27
aagatgcttg aagtgaggac                                                    20

SEQ ID NO: 28              moltype = DNA   length = 20
FEATURE                    Location/Qualifiers
source                     1..20
                           mol_type = unassigned DNA
                           organism = Zea mays
SEQUENCE: 28
```

```
acagcaccat tcaccagcac                                                   20

SEQ ID NO: 29           moltype = DNA   length = 20
FEATURE                 Location/Qualifiers
source                  1..20
                        mol_type = unassigned DNA
                        organism = Zea mays
SEQUENCE: 29
ccatcctcca aacaggttgc                                                   20

SEQ ID NO: 30           moltype = DNA   length = 20
FEATURE                 Location/Qualifiers
source                  1..20
                        mol_type = unassigned DNA
                        organism = Zea mays
SEQUENCE: 30
agcttgccat cctccaaaca                                                   20

SEQ ID NO: 31           moltype = DNA   length = 20
FEATURE                 Location/Qualifiers
source                  1..20
                        mol_type = unassigned DNA
                        organism = Zea mays
SEQUENCE: 31
ccgatctgtg gatccaataa                                                   20

SEQ ID NO: 32           moltype = DNA   length = 20
FEATURE                 Location/Qualifiers
source                  1..20
                        mol_type = unassigned DNA
                        organism = Zea mays
SEQUENCE: 32
tcctcctctc aattgcctgc                                                   20

SEQ ID NO: 33           moltype = DNA   length = 20
FEATURE                 Location/Qualifiers
source                  1..20
                        mol_type = unassigned DNA
                        organism = Zea mays
SEQUENCE: 33
cggttgatct tcgagtggag                                                   20

SEQ ID NO: 34           moltype = DNA   length = 20
FEATURE                 Location/Qualifiers
source                  1..20
                        mol_type = unassigned DNA
                        organism = Zea mays
SEQUENCE: 34
atgatgtcga gcttgtcgag                                                   20

SEQ ID NO: 35           moltype = DNA   length = 20
FEATURE                 Location/Qualifiers
source                  1..20
                        mol_type = unassigned DNA
                        organism = Zea mays
SEQUENCE: 35
gaacccctcg gtgcccatgg                                                   20

SEQ ID NO: 36           moltype = DNA   length = 20
FEATURE                 Location/Qualifiers
source                  1..20
                        mol_type = unassigned DNA
                        organism = Zea mays
SEQUENCE: 36
tcgagccgtt tgcggttgat                                                   20

SEQ ID NO: 37           moltype = DNA   length = 20
FEATURE                 Location/Qualifiers
source                  1..20
                        mol_type = unassigned DNA
                        organism = Zea mays
SEQUENCE: 37
ctctcgtaca cgatcaccac                                                   20

SEQ ID NO: 38           moltype = DNA   length = 20
FEATURE                 Location/Qualifiers
source                  1..20
                        mol_type = unassigned DNA
                        organism = Zea mays
```

```
SEQUENCE: 38
accttcctct cgtacacgat                                               20

SEQ ID NO: 39          moltype = DNA  length = 20
FEATURE                Location/Qualifiers
source                 1..20
                       mol_type = unassigned DNA
                       organism = Zea mays
SEQUENCE: 39
ctgtagagaa gcttcaccTT                                               20

SEQ ID NO: 40          moltype = DNA  length = 20
FEATURE                Location/Qualifiers
source                 1..20
                       mol_type = unassigned DNA
                       organism = Zea mays
SEQUENCE: 40
gagtggagcg tcgccgccat                                               20

SEQ ID NO: 41          moltype = DNA  length = 20
FEATURE                Location/Qualifiers
source                 1..20
                       mol_type = unassigned DNA
                       organism = Zea mays
SEQUENCE: 41
tcgcgcggaa ggcgccgctc                                               20

SEQ ID NO: 42          moltype = DNA  length = 20
FEATURE                Location/Qualifiers
source                 1..20
                       mol_type = unassigned DNA
                       organism = Zea mays
SEQUENCE: 42
atcctgcgga ggaggagcgc                                               20

SEQ ID NO: 43          moltype = DNA  length = 20
FEATURE                Location/Qualifiers
source                 1..20
                       mol_type = unassigned DNA
                       organism = Zea mays
SEQUENCE: 43
ttctgctgca ggagctgctg                                               20

SEQ ID NO: 44          moltype = DNA  length = 20
FEATURE                Location/Qualifiers
source                 1..20
                       mol_type = unassigned DNA
                       organism = Zea mays
SEQUENCE: 44
ctccagcctc cgccgcaact                                               20

SEQ ID NO: 45          moltype = DNA  length = 20
FEATURE                Location/Qualifiers
source                 1..20
                       mol_type = unassigned DNA
                       organism = Zea mays
SEQUENCE: 45
gatcctgcgg aggaggagcg                                               20

SEQ ID NO: 46          moltype = DNA  length = 20
FEATURE                Location/Qualifiers
source                 1..20
                       mol_type = unassigned DNA
                       organism = Zea mays
SEQUENCE: 46
gctccctgca gaagtagcag                                               20

SEQ ID NO: 47          moltype = DNA  length = 20
FEATURE                Location/Qualifiers
source                 1..20
                       mol_type = unassigned DNA
                       organism = Zea mays
SEQUENCE: 47
aagtgcagcc ggcacaatct                                               20

SEQ ID NO: 48          moltype = DNA  length = 20
FEATURE                Location/Qualifiers
source                 1..20
                       mol_type = unassigned DNA
```

```
                                 organism = Zea mays
SEQUENCE: 48
gagcggcgcc gctcgtcgcc                                                  20

SEQ ID NO: 49           moltype = DNA  length = 20
FEATURE                 Location/Qualifiers
source                  1..20
                        mol_type = unassigned DNA
                        organism = Zea mays
SEQUENCE: 49
aagagtatgc agatatcgtt                                                  20

SEQ ID NO: 50           moltype = DNA  length = 20
FEATURE                 Location/Qualifiers
source                  1..20
                        mol_type = unassigned DNA
                        organism = Zea mays
SEQUENCE: 50
gagcagtgct tgttctgctg                                                  20

SEQ ID NO: 51           moltype = DNA  length = 20
FEATURE                 Location/Qualifiers
source                  1..20
                        mol_type = unassigned DNA
                        organism = Zea mays
SEQUENCE: 51
gatgtattcg tactgaggcg                                                  20

SEQ ID NO: 52           moltype = DNA  length = 20
FEATURE                 Location/Qualifiers
source                  1..20
                        mol_type = unassigned DNA
                        organism = Zea mays
SEQUENCE: 52
attgcctcaa tgtcaacagg                                                  20

SEQ ID NO: 53           moltype = DNA  length = 20
FEATURE                 Location/Qualifiers
source                  1..20
                        mol_type = unassigned DNA
                        organism = Zea mays
SEQUENCE: 53
cacatatctt ggctccctgc                                                  20

SEQ ID NO: 54           moltype = DNA  length = 20
FEATURE                 Location/Qualifiers
source                  1..20
                        mol_type = unassigned DNA
                        organism = Zea mays
SEQUENCE: 54
gtgatgggct ggataagatt                                                  20

SEQ ID NO: 55           moltype = DNA  length = 20
FEATURE                 Location/Qualifiers
source                  1..20
                        mol_type = unassigned DNA
                        organism = Zea mays
SEQUENCE: 55
tggagggcga aaagaaagtg                                                  20

SEQ ID NO: 56           moltype = DNA  length = 20
FEATURE                 Location/Qualifiers
source                  1..20
                        mol_type = unassigned DNA
                        organism = Zea mays
SEQUENCE: 56
ccttctgtat attcaggctt                                                  20

SEQ ID NO: 57           moltype = DNA  length = 20
FEATURE                 Location/Qualifiers
source                  1..20
                        mol_type = unassigned DNA
                        organism = Zea mays
SEQUENCE: 57
tccattcctg ttgacattga                                                  20

SEQ ID NO: 58           moltype = DNA  length = 20
FEATURE                 Location/Qualifiers
source                  1..20
```

```
                            mol_type = unassigned DNA
                            organism = Zea mays
SEQUENCE: 58
ttctcttgca gatgttgtta                                               20

SEQ ID NO: 59               moltype = DNA  length = 20
FEATURE                     Location/Qualifiers
source                      1..20
                            mol_type = unassigned DNA
                            organism = Zea mays
SEQUENCE: 59
cagtgttcca gcgtttggcc                                               20

SEQ ID NO: 60               moltype = DNA  length = 20
FEATURE                     Location/Qualifiers
source                      1..20
                            mol_type = unassigned DNA
                            organism = Zea mays
SEQUENCE: 60
acagaacttg tcattggcca                                               20

SEQ ID NO: 61               moltype = RNA  length = 20
FEATURE                     Location/Qualifiers
source                      1..20
                            mol_type = unassigned RNA
                            organism = Zea mays
SEQUENCE: 61
tggtggtgtt ggtggtggag                                               20

SEQ ID NO: 62               moltype = RNA  length = 20
FEATURE                     Location/Qualifiers
source                      1..20
                            mol_type = unassigned RNA
                            organism = Zea mays
SEQUENCE: 62
tcaggagggt ggcctcgccg                                               20

SEQ ID NO: 63               moltype = RNA  length = 20
FEATURE                     Location/Qualifiers
source                      1..20
                            mol_type = unassigned RNA
                            organism = Zea mays
SEQUENCE: 63
ggcgttgagg gtcacaccga                                               20

SEQ ID NO: 64               moltype = RNA  length = 20
FEATURE                     Location/Qualifiers
source                      1..20
                            mol_type = unassigned RNA
                            organism = Zea mays
SEQUENCE: 64
tcggtgtgac cctcaacgcc                                               20

SEQ ID NO: 65               moltype = RNA  length = 20
FEATURE                     Location/Qualifiers
source                      1..20
                            mol_type = unassigned RNA
                            organism = Zea mays
SEQUENCE: 65
caatggccgt aatatcacgg                                               20

SEQ ID NO: 66               moltype = RNA  length = 20
FEATURE                     Location/Qualifiers
source                      1..20
                            mol_type = unassigned RNA
                            organism = Zea mays
SEQUENCE: 66
atcaggaggg tggcctcgcc                                               20

SEQ ID NO: 67               moltype = RNA  length = 20
FEATURE                     Location/Qualifiers
source                      1..20
                            mol_type = unassigned RNA
                            organism = Zea mays
SEQUENCE: 67
gtcggtgtga ccctcaacgc                                               20

SEQ ID NO: 68               moltype = RNA  length = 20
FEATURE                     Location/Qualifiers
```

```
source                  1..20
                        mol_type = unassigned RNA
                        organism = Zea mays
SEQUENCE: 68
ctgcagagcc ccgagatgcc                                                    20

SEQ ID NO: 69           moltype = RNA   length = 20
FEATURE                 Location/Qualifiers
source                  1..20
                        mol_type = unassigned RNA
                        organism = Zea mays
SEQUENCE: 69
ctggatggta ccccaggacg                                                    20

SEQ ID NO: 70           moltype = RNA   length = 20
FEATURE                 Location/Qualifiers
source                  1..20
                        mol_type = unassigned RNA
                        organism = Zea mays
SEQUENCE: 70
gcaatggccg taatatcacg                                                    20

SEQ ID NO: 71           moltype = RNA   length = 20
FEATURE                 Location/Qualifiers
source                  1..20
                        mol_type = unassigned RNA
                        organism = Zea mays
SEQUENCE: 71
gaggatggca agctgaagac                                                    20

SEQ ID NO: 72           moltype = RNA   length = 20
FEATURE                 Location/Qualifiers
source                  1..20
                        mol_type = unassigned RNA
                        organism = Zea mays
SEQUENCE: 72
acgattgatg tgatgtcacg                                                    20

SEQ ID NO: 73           moltype = RNA   length = 20
FEATURE                 Location/Qualifiers
source                  1..20
                        mol_type = unassigned RNA
                        organism = Zea mays
SEQUENCE: 73
cctgactggt acccgaggac                                                    20

SEQ ID NO: 74           moltype = RNA   length = 20
FEATURE                 Location/Qualifiers
source                  1..20
                        mol_type = unassigned RNA
                        organism = Zea mays
SEQUENCE: 74
aagatgcttg aagtgaggac                                                    20

SEQ ID NO: 75           moltype = RNA   length = 20
FEATURE                 Location/Qualifiers
source                  1..20
                        mol_type = unassigned RNA
                        organism = Zea mays
SEQUENCE: 75
acagcaccat tcaccagcac                                                    20

SEQ ID NO: 76           moltype = RNA   length = 20
FEATURE                 Location/Qualifiers
source                  1..20
                        mol_type = unassigned RNA
                        organism = Zea mays
SEQUENCE: 76
ccatcctcca aacaggttgc                                                    20

SEQ ID NO: 77           moltype = RNA   length = 20
FEATURE                 Location/Qualifiers
source                  1..20
                        mol_type = unassigned RNA
                        organism = Zea mays
SEQUENCE: 77
agcttgccat cctccaaaca                                                    20

SEQ ID NO: 78           moltype = RNA   length = 20
```

```
FEATURE                 Location/Qualifiers
source                  1..20
                        mol_type = unassigned RNA
                        organism = Zea mays
SEQUENCE: 78
ccgatctgtg gatccaataa                                                    20

SEQ ID NO: 79           moltype = RNA   length = 20
FEATURE                 Location/Qualifiers
source                  1..20
                        mol_type = unassigned RNA
                        organism = Zea mays
SEQUENCE: 79
tcctcctctc aattgcctgc                                                    20

SEQ ID NO: 80           moltype = RNA   length = 20
FEATURE                 Location/Qualifiers
source                  1..20
                        mol_type = unassigned RNA
                        organism = Zea mays
SEQUENCE: 80
cggttgatct tcgagtggag                                                    20

SEQ ID NO: 81           moltype = RNA   length = 20
FEATURE                 Location/Qualifiers
source                  1..20
                        mol_type = unassigned RNA
                        organism = Zea mays
SEQUENCE: 81
atgatgtcga gcttgtcgag                                                    20

SEQ ID NO: 82           moltype = RNA   length = 20
FEATURE                 Location/Qualifiers
source                  1..20
                        mol_type = unassigned RNA
                        organism = Zea mays
SEQUENCE: 82
gaacccctcg gtgcccatgg                                                    20

SEQ ID NO: 83           moltype = RNA   length = 20
FEATURE                 Location/Qualifiers
source                  1..20
                        mol_type = unassigned RNA
                        organism = Zea mays
SEQUENCE: 83
tcgagccgtt tgcggttgat                                                    20

SEQ ID NO: 84           moltype = RNA   length = 20
FEATURE                 Location/Qualifiers
source                  1..20
                        mol_type = unassigned RNA
                        organism = Zea mays
SEQUENCE: 84
ctctcgtaca cgatcaccac                                                    20

SEQ ID NO: 85           moltype = RNA   length = 20
FEATURE                 Location/Qualifiers
source                  1..20
                        mol_type = unassigned RNA
                        organism = Zea mays
SEQUENCE: 85
accttcctct cgtacacgat                                                    20

SEQ ID NO: 86           moltype = RNA   length = 20
FEATURE                 Location/Qualifiers
source                  1..20
                        mol_type = unassigned RNA
                        organism = Zea mays
SEQUENCE: 86
ctgtagagaa gcttcacctt                                                    20

SEQ ID NO: 87           moltype = RNA   length = 20
FEATURE                 Location/Qualifiers
source                  1..20
                        mol_type = unassigned RNA
                        organism = Zea mays
SEQUENCE: 87
gagtggagcg tcgccgccat                                                    20
```

| | | |
|---|---|---|
| SEQ ID NO: 88<br>FEATURE<br>source | moltype = RNA   length = 20<br>Location/Qualifiers<br>1..20<br>mol_type = unassigned RNA<br>organism = Zea mays | |
| SEQUENCE: 88<br>tcgcgcggaa ggcgccgctc | | 20 |
| SEQ ID NO: 89<br>FEATURE<br>source | moltype = RNA   length = 20<br>Location/Qualifiers<br>1..20<br>mol_type = unassigned RNA<br>organism = Zea mays | |
| SEQUENCE: 89<br>atcctgcgga ggaggagcgc | | 20 |
| SEQ ID NO: 90<br>FEATURE<br>source | moltype = RNA   length = 20<br>Location/Qualifiers<br>1..20<br>mol_type = unassigned RNA<br>organism = Zea mays | |
| SEQUENCE: 90<br>ttctgctgca ggagctgctg | | 20 |
| SEQ ID NO: 91<br>FEATURE<br>source | moltype = RNA   length = 20<br>Location/Qualifiers<br>1..20<br>mol_type = unassigned RNA<br>organism = Zea mays | |
| SEQUENCE: 91<br>ctccagcctc cgccgcaact | | 20 |
| SEQ ID NO: 92<br>FEATURE<br>source | moltype = RNA   length = 20<br>Location/Qualifiers<br>1..20<br>mol_type = unassigned RNA<br>organism = Zea mays | |
| SEQUENCE: 92<br>gatcctgcgg aggaggagcg | | 20 |
| SEQ ID NO: 93<br>FEATURE<br>source | moltype = RNA   length = 20<br>Location/Qualifiers<br>1..20<br>mol_type = unassigned RNA<br>organism = Zea mays | |
| SEQUENCE: 93<br>gctccctgca gaagtagcag | | 20 |
| SEQ ID NO: 94<br>FEATURE<br>source | moltype = RNA   length = 20<br>Location/Qualifiers<br>1..20<br>mol_type = unassigned RNA<br>organism = Zea mays | |
| SEQUENCE: 94<br>aagtgcagcc ggcacaatct | | 20 |
| SEQ ID NO: 95<br>FEATURE<br>source | moltype = RNA   length = 20<br>Location/Qualifiers<br>1..20<br>mol_type = unassigned RNA<br>organism = Zea mays | |
| SEQUENCE: 95<br>gagcggcgcc gctcgtcgcc | | 20 |
| SEQ ID NO: 96<br>FEATURE<br>source | moltype = RNA   length = 20<br>Location/Qualifiers<br>1..20<br>mol_type = unassigned RNA<br>organism = Zea mays | |
| SEQUENCE: 96<br>aagagtatgc agatatcgtt | | 20 |
| SEQ ID NO: 97<br>FEATURE<br>source | moltype = RNA   length = 20<br>Location/Qualifiers<br>1..20<br>mol_type = unassigned RNA<br>organism = Zea mays | |
| SEQUENCE: 97<br>gagcagtgct tgttctgctg | | 20 |

-continued

```
SEQ ID NO: 98              moltype = RNA  length = 20
FEATURE                    Location/Qualifiers
source                     1..20
                           mol_type = unassigned RNA
                           organism = Zea mays
SEQUENCE: 98
gatgtattcg tactgaggcg                                                  20

SEQ ID NO: 99              moltype = RNA  length = 20
FEATURE                    Location/Qualifiers
source                     1..20
                           mol_type = unassigned RNA
                           organism = Zea mays
SEQUENCE: 99
attgcctcaa tgtcaacagg                                                  20

SEQ ID NO: 100             moltype = RNA  length = 20
FEATURE                    Location/Qualifiers
source                     1..20
                           mol_type = unassigned RNA
                           organism = Zea mays
SEQUENCE: 100
cacatatctt ggctccctgc                                                  20

SEQ ID NO: 101             moltype = RNA  length = 20
FEATURE                    Location/Qualifiers
source                     1..20
                           mol_type = unassigned RNA
                           organism = Zea mays
SEQUENCE: 101
gtgatgggct ggataagatt                                                  20

SEQ ID NO: 102             moltype = RNA  length = 20
FEATURE                    Location/Qualifiers
source                     1..20
                           mol_type = unassigned RNA
                           organism = Zea mays
SEQUENCE: 102
tggagggcga aaagaaagtg                                                  20

SEQ ID NO: 103             moltype = RNA  length = 20
FEATURE                    Location/Qualifiers
source                     1..20
                           mol_type = unassigned RNA
                           organism = Zea mays
SEQUENCE: 103
ccttctgtat attcaggctt                                                  20

SEQ ID NO: 104             moltype = RNA  length = 20
FEATURE                    Location/Qualifiers
source                     1..20
                           mol_type = unassigned RNA
                           organism = Zea mays
SEQUENCE: 104
tccattcctg ttgacattga                                                  20

SEQ ID NO: 105             moltype = RNA  length = 20
FEATURE                    Location/Qualifiers
source                     1..20
                           mol_type = unassigned RNA
                           organism = Zea mays
SEQUENCE: 105
ttctcttgca gatgttgtta                                                  20

SEQ ID NO: 106             moltype = RNA  length = 20
FEATURE                    Location/Qualifiers
source                     1..20
                           mol_type = unassigned RNA
                           organism = Zea mays
SEQUENCE: 106
cagtgttcca gcgtttggcc                                                  20

SEQ ID NO: 107             moltype = RNA  length = 20
FEATURE                    Location/Qualifiers
source                     1..20
                           mol_type = unassigned RNA
                           organism = Zea mays
SEQUENCE: 107
```

```
acagaacttg tcattggcca                                                    20

SEQ ID NO: 108           moltype = DNA   length = 412
FEATURE                  Location/Qualifiers
source                   1..412
                         mol_type = unassigned DNA
                         organism = Zea mays
SEQUENCE: 108
tactaactgc tagctgcagg caattgagag gaggagaagt cgtctgcaga atgctgcagc         60
tcagcagcag atccagtgga cagaagaccc ttcccgatct gtggatccaa taactccagt        120
acaggcagag cagggtggtg tgccaacaac tgtggatggt caaggtgttg gaagccctgc        180
aacctgtttg gaggatggca gtcctatcca tcatctgact gctccttgca ggccactcca        240
tccaaaccaa acgatccagc tctcgcagat tcgtggaga agaagctgtc cagctcgata         300
gagcagatcg agaagatggt gcggcgaaac ctgaagagaa cttcgaaggc cgctcagcct        360
tccaagagga ccatccagag gcgcgtcctg atgtccatgc gatgagctga ga               412

SEQ ID NO: 109           moltype = DNA   length = 444
FEATURE                  Location/Qualifiers
source                   1..444
                         mol_type = unassigned DNA
                         organism = Zea mays
SEQUENCE: 109
ctggaaattt gctgatgtac taactgctag ttgcaggcaa ttgagaggag gagaagtcgt         60
ctgcagaatg ctgcagctca gcagcagatc ctgtggacaa agacccttc ccgatctgtg        120
gatccaataa ctccagtaca ggcagagcat ggtggtgtgc caacaactga ggatggtcaa       180
ggtgttggaa gccctgcaac ctgtttggag gatggcaagt cctatgctg actgctcctt       240
gcaggccact ccatccaaac caaacgatcc agctcgcgca gatctcgtgg agaagaagtt       300
gtccagctcg atagagcaga tcgagaagat ggtgcggcga aacctgaaga gaacttcgaa       360
ggccgctcag ccttccaaga ggaccatcca gaggcgcgtc ctgatgtcca tgcgatgagc       420
tgagaaaagct atctgctctg ccat                                              444

SEQ ID NO: 110           moltype = DNA   length = 400
FEATURE                  Location/Qualifiers
source                   1..400
                         mol_type = unassigned DNA
                         organism = Zea mays
SEQUENCE: 110
tggcggcgac gctccactcg aagatcaacc gcaaacggct cgacaagctc gacatcatca         60
aaatctggtg gggaaactgg tcccagggat tcgagttccg cacggttttg actgctatt        120
ttgtgttttt tttatttgtt tttgctgact tttgtttgtg tgtttcactt ttagtgagga       180
aattttgaac ccctcggtgc ggctctctgg aatcctcatg ggtgagttcg attttgcttg       240
cgccaccca aactgttcct cccatttttt ggatagtttt ttttacgtt ccaatttcca        300
tggtcgaaaa ttcgaaaatgc gtgagcaggt ggcgtggtga tcgtgtacga gaggaaggtg       360
aagcttctct acagtaagtt tcttcctccc tacatcctac                              400

SEQ ID NO: 111           moltype = DNA   length = 400
FEATURE                  Location/Qualifiers
source                   1..400
                         mol_type = unassigned DNA
                         organism = Zea mays
SEQUENCE: 111
aacattgcac ctactgagca cagacctacg aagatggagg ggtacatgta gtagatgtcc         60
ctcttggagc agtgcttgtt ctgctgcagg agctgctgca ccacgaacag cacccctcagg       120
agcacatcta cgcatgaaca acgcatcaga agtaattag tgtgatcaca taaatgcaaa        180
gatttagatg tattcgtact gaggtgtggt agtccttgtg gagcagagag aggacgtccg        240
tgccgacggg gatgtcgtag ctgcaggcac tgcaatcacg cacgagcgcg cgcccagggt       300
ctacggatgt cacacatttg ggtgaaaatt gttcgaggga tgtgacggtg aattggtcgg       360
gaaggagatg atcccgggag cgggcgcgga agctaaacca                              400

SEQ ID NO: 112           moltype = AA    length = 591
FEATURE                  Location/Qualifiers
source                   1..591
                         mol_type = protein
                         organism = Musa acuminata
SEQUENCE: 112
MFYSHQLLAR KAPLGQIWMA ATMRAKMNRR KLDKLDIIKI CEEILNPSVP MALRLSGILM         60
GGVVIVYERK VKLLYDDVTR FLVEINAAWK VKTVSDPTVL PRAKAQAKFE AVTLPEYVDM        120
EPEQPMMFPD ASIATAAFQR MRLDDLEEHY INIDLRDDDL AGNDHQAEPE NITLFETFGS        180
GVAETDLYNH FERFDVGDDE THINFTPQEE PQFEATLIPS LPHEDEIRTF THLHSAVENH        240
QTEEKEEQRA NDEDVQRQQP VKRKAHRKPS HRIMDDRQLM IPGNIYQLWL QDTSDIVSKR        300
GRTQCLRSVN PIRSTKISNL MDLPPVALIS GLEMFPAKVH YPSPLMELWR KCTEVNISPS        360
GDKSPPAQQR EVTETLLEEV QGEIGSNSLD VSIEKLRANL ENLDFQGFDD AFSMDHFVTP        420
GSSAGQSSKS MPSSGSGHAF MPLEPEIQLP SVRSKRKQHS SSKSFRNLDP VEEELPLQQD        480
VRGSKIRRLS ETGPTPDFEL EETGPTQTPV TPPSNPAVDN TTLLIRTHLK LHFDTPGAPQ        540
SESLNQLAFG MYKRKAAQLF YQTCVLVTCD FIKVQQHEAY GDISISRGPK M                 591

SEQ ID NO: 113           moltype = AA    length = 605
FEATURE                  Location/Qualifiers
source                   1..605
```

```
                        mol_type = protein
                        organism = Sorghum bicolor
SEQUENCE: 113
MFYSHQLLAR KQPLGQIWMA ATLHSKINRK RLDKLDIIKI CEEILNPSVP MALRLSGILM    60
GGVVIVYERK VKLLYSDVSR LLTEINEAWR IKPATDTTVL PKGKAQAKYE AVTLPEKSIN   120
MVVEQPMFFS ETDGARFRGM RLEDLDEQYF NVNLGDDDFS HADHRHQAEA VNITLVDNFE   180
SGFAETDVFN RFERFDIADD ETTVNISPDE HPKVPSTLVP SPPRQEDPPQ QEEQYAAPFL   240
VREEPQQGGP EEQKMKQTPK ASKRKARREL PQVIMDNNQM MIPGNIYQTW LKDASSLVSK   300
RRKVNSNFNF IRSTKISDLM DIPPVSLISH DNSSSELYYP KPLMQLWKDC TEVKSTKVSS   360
GGQRSSSQEQ QPRNSPPHEF PPQAGGEYEM ETGGLPMDFT DGIEKLRANM SAEYDRAYDT   420
LHSDHSVTPG SPGLSRRSAS SSGGSGQAFI PLDAEVQLPS GSGRSKRGRH SSARSLGNLD   480
TVEEDFPLEL EVMDVKMRRL SDYAPTPDLL EETEPTQTPY ERRSNPMDKV TEAIMSHLKL   540
HFDSPGAPQS ESLSHLAHGM TKARAARLFY QTTVLATFDY INVTQLKPHG EELYGDILIS   600
RGSKI                                                               605

SEQ ID NO: 114          moltype = AA  length = 608
FEATURE                 Location/Qualifiers
source                  1..608
                        mol_type = protein
                        organism = Oryza sativa
SEQUENCE: 114
MFYSHQLLAR KAPLGQIWMA ATLHSKINRK RLDKLDIIKI CEEILNPSVP MALRLSGILM    60
GGVAIVYERK VKALYDDVSR FLIEINEAWR VKPVADPTVL PKGKTQAKYE AVTLPENIMD   120
MDVEQPMLFS EADTTRFRGM RLEDDDDQYI NVNLDDDDFS RAENHHQADA ENITLADNFG   180
SGLGETDVFN RFERFDITDD DATFNVTPDG HPQVPSNLVP SPPRQEDSPQ QQENHHAASS   240
PLHEEAQGGG ASVKNEQEQQ KMKGQQPAKS SKRKKRRKDE EVMMDNDQIM IPGNVYQTWL   300
KDPSSLITKR HRINSKVNLI RSIKIRDLMD LPLVSLISSL EKSPLEFYYP KELMQLWKEC   360
TEVKSPKAPS SGGQQSSSPE QQQRNLPPQA FPTQPQVDND REMGFHPVDF ADDIEKLRGN   420
TSGEYGRDYD AFHSDHSVTP GSPGLSRRSA SSSGGSGRGF TQLDPEVQLP SGRSKRQHSS   480
GKSFGNLDPV EEEFPPEQEL RDFKMRRLSD VGPTPDLLEE IEPTQTPYEK KSNPIDQVTQ   540
SIHSYLKLHF DTPGASQSES LSQLAHGMTT AKAARLFYQA CVLATHDFIK VNQLEPYGDI   600
LISRGPKM                                                            608

SEQ ID NO: 115          moltype = AA  length = 603
FEATURE                 Location/Qualifiers
source                  1..603
                        mol_type = protein
                        organism = Brachypodium distachyon
SEQUENCE: 115
MFYSHQLLAR KAPLGQIWMA ATLHAKINRK RLDKLDIIKI CEEILNPSVP MALRLSGILM    60
GGVVIVYERK VKLLYDDVSR LLVDINEAWR IRPVVDHTVL PKGKAQAKYK AVTLPENMMD   120
MEVEQPMLFS DTNTARFRGM SLDDLGEQYF NVNLDDDDFS RAEHHHQAEA VNITLVDNFE   180
SGLAETDVFN RFERFDIADD DTTVNITPDE HPQAPSTLAP SPPKEDPPQQ QEQHYAAPSP   240
NQEEPQQGDP SKDQEEQKMK ERQPNRPSKR KARGKGPQVT MDNQTMIPGN IYQTWLKDPL   300
SLISKRRRVS SKINPIQTIK IGDLMELPPV ALISYSEKSP LELYYPKQLM QLWKECTEVK   360
SPKSSSPGGK SPSSQEQQSR NSPPQPQGEY QGEMGAQPMD FTDGIEKIRG NKSGEYERVD   420
DALHGDHSVT PGSPGLSRRS ASSSGGSGRG AFVPLDPEIQ FYSGGGRSKR RQHSSGRSLG   480
NLDPVEEESP LEQEVKGFKL RRLSDIGPTP ELLEETELTQ TPYHKQPSPT DQVTESIHSY   540
LKLHFDAPDA PLSESLSQLT YGMTTARAAR LFYQTCVLAT LDRIKVTQVE PYGAILISRG   600
LNM                                                                 603

SEQ ID NO: 116          moltype = AA  length = 603
FEATURE                 Location/Qualifiers
source                  1..603
                        mol_type = protein
                        organism = Hordeum vulgare
SEQUENCE: 116
MFYSHQLLAR KAPLGQIWIA ATFKSKINRR RLDKLDIIKI CEEILNPSVP MALRLSGILM    60
GGVVIVYKKK VKLLYDDVSR LLIELNEAWK IRPVVDHTVL PKGKAQAKYE AVTLPENMMD   120
MELERPVLFT NTDTARFRGM RLEDLDEQYV NVNLDDDDIS RADRHHQAEA VNITLVDNFE   180
SGFAETDIFT RFERFDIADD DTIFNITPDG HPEAPSTLVP SPPRPEDPFQ QQQQRAAPSP   240
IREEPQQGDS LKEQEEQKTK EKQPTKRAKR KARGKGPQVI MDNQIMIPGN IYQSWLKDPS   300
SLTSKRRQVR SKINPIQAIK MGELMDLPPS TLMCCSDDSQ EIYYPQQLRQ LWKECTKVNP   360
PKPSSSSGVK SSSSSQETQP RNSSPQPQGD QNEMGAQPMD FTDLIEEMRA NKSGGFEGVF   420
DGPLGAHSVT PGSPGLSRRS ASSSGGSGRG GFLPLGPEIP LQFGDGRAKR KQLSSGRSLG   480
NLDPIEEEFP MEQEGRDFKL RRVSEFGPTP DLMEETEPTQ TPFSKQSSPP DHITESIHSY   540
LKLHFESADA PLSESLSHLT HGMNTAQAAR LFYQTCVLAT RDHIKVTQDE AYGPIHISKG   600
ANM                                                                 603

SEQ ID NO: 117          moltype = AA  length = 608
FEATURE                 Location/Qualifiers
source                  1..608
                        mol_type = protein
                        organism = Triticum aestivum
SEQUENCE: 117
MFYSHQLLAR KAPLGQIWMA ATLHAKINRK RLVKLDIIKI CEEILNPSVP MALRLSGILM    60
GGVVIVYERK VKLLYDDVSR LLIEINEAWK IRPAVDHTVL PKGKAQAKYE AVTLPENAVD   120
MEVEQPVFFT DTYTTRFRGM RLEDLDEQYV NVNLDDDDIS RADRHHQAEA VNITLVDNFE   180
SGLAETDIFN RFERFDIADD DTTVHITLDG HPEAPSTLVP SPPRPEDPPQ QQEQCAAPSP   240
```

```
IREEPQQGDS LKEQEEQKTT EQQPTKRAKR KARGKGPQVI IDNQIMIPGN VYQSWLKDPS    300
SLTSKRRQVR SKINPIKAIK IGELMDLPPS ALMSFSNDSQ EIYYPQQLMQ LWKECTKVKT    360
PKPSSSSGDK SSSSSQEKQP RNPSPQPQGD QNEMGAQPMD FTPMDFTDGI EKMRANKSGE    420
FEGVFDGPHG DPSVTPGSPG LSRRSASSSG GSGRGAFLPL DPEIQLQSGS GRAKRRQLSS    480
GRSLGNLDPV EEEFPMEQEE REFKLRRLSD MEPTPDLMVE TEPTQTPFMK QSSPPDHITE    540
SIHSYLKLHF ESPDAPPSES LSQLTYGMNT AQAARLFYQT CVLATLDRIK VTQVEPYGPI    600
LISRGANM                                                             608

SEQ ID NO: 118          moltype = AA  length = 608
FEATURE                 Location/Qualifiers
source                  1..608
                        mol_type = protein
                        organism = Aegilops tauschii
SEQUENCE: 118
MFYSHQLLAR KAPLGQIWMA ATLHAKINRK RLDKLDIIKI CEEILNPSVP MALRLSGILM    60
GGVVIVYERK VKLLYDDVSR LLIEINEAWK IRPAVDHTVL PKGKAQAKYE AVTLPENAMD    120
MEVEQPVLFT DTDTARFRGM RLEDLDEQYV NVNLDDDDIS RADRHHQAEA VNITLVDNFE    180
SGLAETDIFN RFERFDIADD DTTVHITLDG HPEAPSTLVP SPPRPEDPPQ QQEQCAAPSP    240
IHEEPQQGDS LKEQEEQKTT EQQPTKRAKR KARGKGPQVI MDNQIMIPGN VYQSWLKDPS    300
SLISKRRQVR SKINPIKAIK IGELMDLPPS ALMCSDDSQ EIYYPQQLMQ LWKECTKVKP    360
PKPSSSSGDK SSSSSQEKQP RNSPPQPQGD QNEMGAQPMD FTPMDFTDGI EKMRANKSGE    420
FEGVFDGPHG DPSVTPGSPG LSRRSASSSG GSGRGGFLPL DPEILLQSGS GRAKRRQLSS    480
GRSLGNLDPV EEEFPMEQEG REFKLRRLSD IEPTPDLMVE TEPTQTPFTK QSSPPDHITE    540
SIHSYLKLHF ESPDAPPSES LSQLTYGMNT AQAARLFYQT CVLATLDRIK VTQVEPYGPI    600
LISRGANM                                                             608

SEQ ID NO: 119          moltype = AA  length = 630
FEATURE                 Location/Qualifiers
source                  1..630
                        mol_type = protein
                        organism = synthetic construct
VARIANT                 351
                        note = Xaa = L or I
VARIANT                 473
                        note = Xaa = L or I
VARIANT                 1..630
                        note = Xaa = Any Amino Acid, or no amino acid (except at
                         positions 351 and 473)
SEQUENCE: 119
MFYSHQLLAR KAPLGQIWMA ATLHXKINRK RLDKLDIIKI CEEILNPSVP MALRLSGILM    60
GGVVIVYERK VKLLYDDVSR LLIEINEAWX IXPVVDHTVL PKGKAQAKYE AVTLPENXMD    120
MEVEQPMLFS DTDIATARFR GMRLEDLDEQ YVNVLDDDDD FSRADXHHQA EAVNITLVDN    180
FESGLAETDX FNRFERFDIA DDDTTVNITP DXHPQAPSTL VPSPPPRXEDP EPQQQEQHXAA   240
PSPXXEEPQQ GDXLVKKEQE EQKMKEQQPX KXSKRKARGK GPQVIMDNNQ IMIPGNIYQT    300
WLKDPSSLXS KRRXVXCLSK INPIRSIKIG DLMDLPPVAL ISXSXXSXLE XYYPKQLMQL    360
WKECTEVKSP KXSSSSGXKS SSXEQQXQNX PPRNSPPQPQ GXYQXEMGAQ PMDFTPMDFT    420
DGIEKLRANK SGLEXEXVXD XXHGDHSVTP GSPAGLSRRS ASSSGGSGRG AFXPLDPEIQ    480
LPSGSGRSKR XQHSSGRSLG NLDPVEEEFP LEQEVRDFKL RRLSDXGPTP DLELEETEPT    540
QTPYXKQSXP AXDXITESIH SYLKLHFDSP XAPGESLSQ LXHGMTTAXA ARLFYQTCVL    600
ATXDXIKVTQ XEPXGXELYG XILISRGXNM                                     630

SEQ ID NO: 120          moltype = AA  length = 393
FEATURE                 Location/Qualifiers
source                  1..393
                        mol_type = protein
                        organism = Musa acuminata
SEQUENCE: 120
MNVGRWIDID AQARPIFLLA AFVPSFAQAT TRMAGGRVSS SSPSDLLQRI KGFVRSLVED    60
LSNDRPPSVA LDRYRNYCHD PSGNCTCGDN LPNGKEIISV EESHAYRLL VLFRVLLIIQ    120
QLLQENKHGS KRDIYYMHPA LFLEQAVVDR AINNICILLK CSRQHLNVVP VGRGLVMGWL    180
RFLEAGRKIY CINSPSTVYP IPVCLEEVVD IVSVARFIIV VEKESVFQRL ANDRFCERNH    240
CIVITGRGYP DVPTRRFLCL LVQHLHLPVY CLVDCDPYGF DILMVYRFGS MQMAYDANLL    300
RVPEISWLGV FHSDLQKYHL PDRCLLELTS DDKKKAEAML LRCYLQKEAP KWRMELEVML    360
QTGVKFEIES LSFNSLSFLS EYIPTKIHDG SYL                                  393

SEQ ID NO: 121          moltype = AA  length = 383
FEATURE                 Location/Qualifiers
source                  1..383
                        mol_type = protein
                        organism = Zea mays
SEQUENCE: 121
MAGRDKRRRA APLEGDEQQL RRLEEAALL LRRIKGLVRW IVEEVAAGRS PSIVLHRYRN    60
YCSSADSASP SPCACSYDIP VGTDVLSLLH KDYHTSRLNV LLRVLFVVQQ LLQQNKHCSK    120
RDIYYMYPSI FVEVAVVDRA INDICILFKC SRHNLNVVPV VKGLVMGWIR FMEGEKKVYC    180
ITSVNAAFSI PVDIEAIKDV VSVAHYILVV EKETVFQRLA NDKFCERNRC IVITGRGYPD    240
IPTRRFLRYL VELLHLPAYC LVDSDPYGFD ILATYKFGSL QLAHDANLLR VPDIRWLGVF    300
TSDFEEYCLP DCCLLRLSPE DRRKAEGILA RCYLHREAPE WRSELEAMLQ KGVKFEIEAL    360
SANSISFLSH EYIPQKIKQG MHL                                            383
```

```
SEQ ID NO: 122            moltype = AA   length = 383
FEATURE                   Location/Qualifiers
source                    1..383
                          mol_type = protein
                          organism = Sorghum bicolor
SEQUENCE: 122
MAGRDKRRRA APLEGDEQQL RRRQEEAALL LRRIKGLVRW VVEEVAAGRS PSIVLHRYRN   60
YCSAADSASP SPCACSYDVP VGTDVLSLLH NDYHTSRLNV LLRVLLVVQK LLQQNKHCSK  120
RDIYYMYPSI FVEVAVVDRA INDICILLKC SRHNLNVVPV VKGLVMGWIR FVEGEKKVYC  180
ITNVNAAFSI PVDIEAIKDV VSVAHYILVV EKETVFQRLA NDKFCERNRC IVITGRGYPD  240
IPTRRFLRYL VEQLHLPAYC LVDSDPYGFD ILATYKFGSL QLAHDANLLR VPDIRWLGVF  300
TSDFEEYCLP DCCLLHLSPE DRRKAERILA RCYLHREVPE WRSELEAMLQ KGVKFEIEAL  360
SANSISFLSD EYIPQKIKQG MHL                                         383

SEQ ID NO: 123            moltype = AA   length = 381
FEATURE                   Location/Qualifiers
source                    1..381
                          mol_type = protein
                          organism = Oryza sativa
SEQUENCE: 123
MAGREKRRRV AALDGEERRR RQEEAATLLH RIRGLVRWVV AEVAAGRSPT VALHRYQNYC   60
SSASAAAASP CACSYDPVG TDVLSLLHRG SHASRLNVLL RVLLVVQQLL QQNKHCSKRD  120
IYYMYPSIFQ EQAVVDRAIN DICVLFKCSR HNLNVVPVAK GLVMGWIRFL EGEKEVYCVT  180
NVNAAFSIPV SIEAIKDVVS VADYILIVEK ETVFQRLAND KFCERNRCIV ITGRGYPDIP  240
TRRFLRYLVE QLHLPVYCLV DADPYGFDIL ATYKFGSLQL AYDANFLRVP DIRWLGVFTS  300
DFEDYRLPDC CLLHLSSEDR RKAEGILSRC YLHREAPQWR LELEAMLQKG VKFEIEALSA  360
CSISFLSEEY IPKKIKQGRH I                                           381

SEQ ID NO: 124            moltype = AA   length = 387
FEATURE                   Location/Qualifiers
source                    1..387
                          mol_type = protein
                          organism = Aegilops tauschii
SEQUENCE: 124
MAGSGKRRRA TVLDDDERRG RRRLEEAALL LHKIKGLVGW VVAEISAGRS PSLALHRYQN   60
YCASADAAAA AASPSTCACS YDAPVGTDVL SLLRKEFHAS RLNVLLRVLL VVQQLLQENK  120
HCSKRDIYYM YPSMFVEQAI VDRAINDICI LFKCSRHNLN VVPVAKGLVM GWIRFVEGEK  180
KVYCITNVNA AFPIPVSIEA IKDVVSAHY ILVVEKEAVF QRLANDKFCE KNRCIVITGR  240
GYPDIPTRRF LRYLVEQLHL PAYCLVDSDP YGFDILATYK FGSMQLAYDA NVLRVPEIRW  300
LGVFTSDFEE YCLPDCCQLQ LSSEDRRKLE GILTRCYLHK EAPEWRLKLE AMLEMGVKFE  360
IEALSASSIS FLSQEYIPQQ IRLGRYI                                     387

SEQ ID NO: 125            moltype = AA   length = 383
FEATURE                   Location/Qualifiers
source                    1..383
                          mol_type = protein
                          organism = Brachypodium distachyon
SEQUENCE: 125
MEGREKRRRA TVLDDDDELR GRRREQEAAL LLHKIKGLVG WVVAEVGAGR SPSVALNRYQ   60
NYCTSAAASP PTCACSYDAP VGTDILCLLR KEFHASRLSV LLRVLVVQQ LLQQNKHCSK  120
RDIYYMYPSI FIEQAVVDRA INDICILFKC SRHNLNVVPV AKGLVMGWIR FVEGEKKVYC  180
ITNVNAAFSI PVSIETIKDI VSVAHYILVV EKETVFQRLA NDKFCERNRC IVITGRGYPD  240
VPTRRFLRHL VEQLHLPAYC LVDSDPYGFD ILATYKFGSM QLAYDANLLR VPGIRWLGVF  300
TSDFEEYCLP DYCLLDLSSE DRKKLEGILT RCYLHREAPE WRAELEAMLE KGVKFEIEAL  360
SASSISFLSQ EYIPQKIKLG RHI                                         383

SEQ ID NO: 126            moltype = AA   length = 386
FEATURE                   Location/Qualifiers
source                    1..386
                          mol_type = protein
                          organism = Triticum aestivum
SEQUENCE: 126
MAGSGKRRRA TVLDDDERRG RRRLEEAALL LHKIKGLVGW VVAEIAGRS PSLALHRYQN   60
YCACASAAAA ASPSTCACSY DAPVGTDVLS LLRKEFHASR LNVLLRVLLV VQQLLQENKH  120
CSKRDIYYMY PSMFVEQAIV DRAINDICIL FKCSRHNLNV VPVAKGLVMG WIRFVEGEKK  180
VYCITNVNTA FPIPVSIEAI KDVVSAHYI LVVEKEAVFQ RLANDKFCEK NRCIVITGRG  240
YPDIPTRRFL RYLVEQLHLP AYCLVDSDPY GFDILATYKF GSMQLAYDAN ILRVPEIRWL  300
GVFTSDFEEY CLPDCCQLQL SSEDRRKLEG ILTRCYLHKE APEWRLKLEA MLEMGVKFEI  360
EALSASSISF LSQEYIPQQI RLGRYI                                      386

SEQ ID NO: 127            moltype = AA   length = 384
FEATURE                   Location/Qualifiers
source                    1..384
                          mol_type = protein
                          organism = Hordeum vulgare
SEQUENCE: 127
MAGRGKRRRA TVLDDDERRG RRRLEESALL LHKIKGLVGW VVAELSAGRS PSLALHRYQN   60
YCASAAAAS PSTCACSYDA PVGTDVLSLL RKEFHASRLN VLLRVLLVVQ QLLQENKHCS  120
KRDIYYMYPS MFVEQAIVDR AINDICILFK CSRHNLNVVP VAKGLVMGWI RFVEGEKKVY  180
```

```
CITNVNTAFP IPVSIEAIKD VVSVAHYILV VEKEAVFQRL ANDKFCKKNR CIVITGRGYP  240
DIPTRRFLRY LVEQLRLPAY CLVDSDPYGF DILATYKFGS MQMAYDANVL RVPEIRWLGV  300
FTSDFEEYCL PDCCQLPLSS EDTRKLEGIL TRCYLHREAP EWRLKLEEML EKGVKFEIEA  360
LSSSSISFLS QEYIPQKIKL GRYI                                       384

SEQ ID NO: 128         moltype = AA   length = 454
FEATURE                Location/Qualifiers
source                 1..454
                       mol_type = protein
                       organism = synthetic construct
VARIANT                454
                       note = Xaa = L or I
VARIANT                173
                       note = Xaa = Q or E
VARIANT                450
                       note = Xaa = Q or E
VARIANT                1..454
                       note = Xaa = Any Amino Acid, or no amino acid (except at
                         positions 454, 173 and 450)
SEQUENCE: 128
MNAGRWIDIX KRRRATVLLA AXVPSFADDD ERRGRRRLEE AALSDLLHXI KGLVRWVVAE   60
VXAGRSPSXA LHRYQNYCXS AXAAXXSPWF SFRARSRDHL LPDQFTVTSL EQFXPKCVTS  120
VDPGRALVRX XCACSYDXPV GTDVLSLLXK EXHASRLNVL LRVLLVVQQL LQXNKHCSKR  180
DIYYMYPSIF VEQAVVDRAI NDICILFKCS RHNLNVVPVA KGLVMGWIRF VEGEKKVYCI  240
TNVNAAFXIP VSIEAIKDVV SVAHYILVVE KETVFQRLAN DKFCERNRCI VITGRGYPDI  300
PTRRFLRYLV EQLHLPAYCL VDSDPYGFDI LATYKFGSMQ LAYDANLLRV PEIRWLGVFT  360
SDFEEYCLPD CCLLXLSSED RRKXEGILTR CYLHREAPEW RXELEAMLEK GVKFEIEALS  420
ASSISFLSQE YIPQKIKLGR XXXXXXXXXX XATX                             454

SEQ ID NO: 129         moltype = AA   length = 397
FEATURE                Location/Qualifiers
source                 1..397
                       mol_type = protein
                       organism = Musa acuminata
SEQUENCE: 129
MKLRINKACD LGSISVLPPR RSGGMSSGGD GLGRSQASQI RSQSQQSFSQ GISLSQLSQS   60
SFEEPLVNDQ RFGSQEKDNS LRKISSLAPI ALTREESQLQ LTRASSNVMH RWNAASMSDN  120
RFQVSEELEH KLRHIESSIN RVGMILDSVQ SDVMQVNRAA KLSLEVEGI RQKVSLLENS  180
MQQMVKWEDD IKAFIGGSLT SISDQLIKIS SSGKVNEIAS AVATLQEQMF SRLARLECEV  240
CRFFSEKEVR ESGIKSSNNQ HSVKFQSPMS GNYMDIKESL EGNIEEKKVS AAPLMSNKQR  300
SPPFKKEGKL ESFKSKLTEP KHTVKHKHII PHTKQEEFVR VIVDLDEESD GGISCLIVNK  360
GTGKKSSFME EVQEDTLRIL RKARMKKRRQ MNSITVV                          397

SEQ ID NO: 130         moltype = AA   length = 634
FEATURE                Location/Qualifiers
source                 1..634
                       mol_type = protein
                       organism = Triticum aestivum
SEQUENCE: 130
MKLKINKACD LASISVLPPR RTRGSSGGGG GGGTSAPAAA SAAQQQRSQS MSQKSFSQGI   60
GASFSQGIGS GGASFSQGSG GGGAAFSQGG GGGGAAFSQ GGGGGAAFSQ GGGGGASFS  120
QGGGSASLLH AQSQLSQASL DESLLSLLSQ APARDQRFAM QEDPSKRMSS YLASSASSCM  180
RDESQLQLAK IPTNPIHRWS PSFLDSRCQV NEDVERKFLH LASSVQKMGM ILDSVQNDVM  240
QLNRGMKEAS LDSGSIQKKF VLLEDSLKQI LKGDDLKAL LKGSTKSNPD QLGILTRKLD  300
EISSILSVLP KQVQTEFEQF KGDIFRFFTK EMEGVVRAVR SDSRLPGVM QMLADQSCTT  360
NAKPLMNHTA AENESPLMNQ TQVAEGSPLM NQGPVADRRP QKKPTAVANG RPKRKNQTAV  420
ANGRPQRKNQ AAGANWRPHR KKPTEIAANS RPQRHLTRVA NGRPQVKQTE AADGRSQTNQ  480
KPEANGKALI PVTKPIPVPV VYHRKAVDLK PRVEQWMVPK LAGPSYSRPA PPKEQELAIQ  540
KVNTEAPINK MQATLGILID SDDDGDYEGA DSDWSASCVI LKLEAGCPGD EVVAEEATSE  600
GEGEALEILR RARKRRREA NANANATVLV QDQR                             634

SEQ ID NO: 131         moltype = AA   length = 670
FEATURE                Location/Qualifiers
source                 1..670
                       mol_type = protein
                       organism = Hordeum vulgare
SEQUENCE: 131
MKLTINKACD IASISVLPPR RTGGSSGGGG RMSAAAAQQQ QQQRSQSMSQ KSFSQGGGGV   60
GSFSQSVGAS FSQGMGSGGA SFSQGRGASF SQSSSTGGAA AAFSQGGGGG GGASFSQGR  120
GASFSQGSGT GGAVAAFSQG GGAGSGGADF SQGRGGGGAA FSQGGGGGGA SFSQGGGSGS  180
LLHAQSQLSE ASLNENLLSQ APARDQRFSL QEDSSKRTPS YPASSASCVR EDSQLQLTTI  240
PTNPIHRWSP SLPDSRCQIN EEVERKFQHL ASSVHKLGMI LDSVQNDVMQ LNRSMKEASL  300
DSGSIQKKFV LLEDSLKQIL KGQDDIKALF EGSTESNPDQ LSVLNSHTRK LDEMTSILSA  360
LPNHLQAEFG QLKGDTYRIF TKEMEGIARG IRSINTRLDA MQMLAEQSCT TNAKTLMNQT  420
AVAHGSPLMN QTPVAVGSTL MNQGAVADGS PLMNHQGPVA DGRPQKRQRP AANGRSQRKK  480
QTPVASGRAQ RKRQRPVANG RPQVKQAQTA DGRSQMNQKP EANGEALMKQ VLPATQVAPA  540
PLVYQRKKEG VQPKAEQGMS KAGTGAQKLA GSGDSRPASP KEQELAIQKD NAEAPINKAM  600
LAILIDSDEE EEEGGGSEGN ASCVLLKSTE AGGGVAMAEE AMGEGEALEI LRRARKRRRR  660
EEAMAVVLDH                                                       670
```

```
SEQ ID NO: 132          moltype = AA  length = 362
FEATURE                 Location/Qualifiers
source                  1..362
                        mol_type = protein
                        organism = Aegilops tauschii
SEQUENCE: 132
MAMSGINSSI PQTDRLVDWL SAWKLGIIVR ATYLSTLVPS PIVTSICHLV GDQGFGLHDD    60
SSKRMPPFPP SSASRAHEEP QQQQPVIVPS STTLRWNPSP TDTRCRVNED AERRFQHLSG   120
SVHKVGMVLD SVQTDVIQLN RTMKDASLKS GVVQQKFDLL EDTLQKIIKG QNDLKVLAEN   180
STKSNLDQLN VINSRTSKLN EMSLVVSVCP KQVQADLREL HGDIFRVLTK DMEGVVRDIR   240
SLSTKPAVMP MLPDHVVAKG SPLMNKMSVA NERPTMNQTP VAKGSPLMNK MSVANERPTM   300
NQTPVANGRP LMNQTPVANG SPMIINQARV GNGRSQLKQT PVTDAMPQRD LTPEINGRPQ   360
KD                                                                 362

SEQ ID NO: 133          moltype = AA  length = 522
FEATURE                 Location/Qualifiers
source                  1..522
                        mol_type = protein
                        organism = Brachypodium distachyon
SEQUENCE: 133
MPSQSQLLEA SLGQTLLSQQ LPAPAHDQIF GLHNVSSQIP SFPPNSASCV QEESQQQLAK    60
ISNNTIPWRN PCLAESRCQV ANEDAEHRFQ QLANSVCRIE MVLDSVQNDV IQLNRSMKEA   120
SLDSDSIQRK VVLLDNSLQK ILMVQDGEAG SIQQNDVLLD NSLQQILKGQ DGLKELLEGG   180
TKSNPDQLSV LNSHTSTLSE ISSILSVWQE EIRADLRQLH GDIFRIFTKE MKGVVRAIRS   240
LNSRPAALQM LEDRSCYPNE RTWSSQVQVA DGSPLMNQIP LANERLKMNQ TPVSIGEPLM   300
NLAVVANGSP LINQSPVANG RSQMNQTPVA NGRPQMDRTP VANGRPHMEQ ITTNLFPARS   360
SCSTKAADPK PNIEQGDVKA TTPKLFGSSY MLAPKQGEVL NRKVNQQEPT KKAPVTIMID   420
SDDDSEGHAS WVILNTEPAD LMKEASREEG MQLLWSARKR SRRKRETRCI DATALPDVMR   480
GKKRMGKAAP EAQEEEAVHV EAIPAKRTCR PNPKYDAEQW TA                     522

SEQ ID NO: 134          moltype = AA  length = 656
FEATURE                 Location/Qualifiers
source                  1..656
                        mol_type = protein
                        organism = Sorghum bicolor
SEQUENCE: 134
MAGRVGEYNC PRQQRIQNRS ASHSITPLLL GCSSGTGDHH CRRRLLAPAR SREQAMKLKI    60
NKACDLGSIS VLPPRRTGGS GGAGEAGSSA AAVAAGSQQR SQPMSHSQQS FSQGVMGSGG   120
ASSLLHSQSQ LSQASLDENL LSLHLASPTR DQRFGLHDDS SKKMPSLPVS SASCVREESQ   180
LQLAKTPSNP VHRWNPSLPD GRCVVPTEDV ERKFQHMASS VHKVGMVLDS VQNDVMQLNR   240
AMKEAALDSG SMQQKIVVLD TSLQKNLKGQ DDLKALVESN TKSISDQLTV LNSHSNKLDE   300
ISSTLSILPK QIETDLKQQH SDIFRIFRKD MEEIVRAVRS LNSKIDAIQM PTDQRCTING   360
RPLMNQLPVD RNERPQVNQT PEVTRMSQTP VATMVNQTSV ASLVNQTPAA NGRHLVSQIP   420
AANGKTLVSQ TSVANGRSLM SQVPTANGKP LTNQASLANG GSLMSQVPAA NGKPLTNQIP   480
APKGRPMMRQ KTGERGRPQM NQIPVASGWT HTNKIPAPEV HPAPLVFPAS AKAAADPKAK   540
VDDGKLKVLP QKLTGSRSRV TPKQEEAAST KFSRAAATEK VVIFIEDSDD DSDVRASSCV   600
ILRSSGSGAG AGAGERECDL MKVGAEESQE IMRRARKRRR REMQATVASM PPEVGH       656

SEQ ID NO: 135          moltype = AA  length = 492
FEATURE                 Location/Qualifiers
source                  1..492
                        mol_type = protein
                        organism = Oryza sativa
SEQUENCE: 135
MKLKMNKACD IASISVLPPR RTGGSSGASA SGSVAVAVAS QPRSQPLSQS QQSFSQGASA    60
SLLHSQSQFS QVSLDDNLLT LLPSPTRDQR FGLHDDSSKR MSSLPASSAS CAREESQLQL   120
AKLPSNPVHR WNPSIADTRS GQVTNEDVER KFQHLASSVH KMGMVVDSVQ SDVMQLNRAM   180
KEASLDSGSI RQKIAVLESS LQQILKGQDD LKALFGSSTK HNPDQTSVLN SLGSKLNEIS   240
STLATLQTQM QARQLQGDQT TVLNSNASKS NEISSTLATL QTQMQADIRQ LRCDVFRVFT   300
KEMEGVVRAI RSVNSRPAAM QMMADQSYQV PVSNGWTQIN QTPVAAGRSP MNRAPVAAGR   360
SRMNQLPETK VLSSAHLVYPA KVTDLKPKVE QGKVKAAPQK PFASSYYRVA PKQEEVAIRK   420
VNIQVPAKKA PVSIIIESDD DSEGRASCVI LKTETGSKEW KVTKQGTEEG LEILRRARKR   480
RRREMQSIVL AS                                                      492

SEQ ID NO: 136          moltype = AA  length = 872
FEATURE                 Location/Qualifiers
source                  1..872
                        mol_type = protein
                        organism = synthetic construct
VARIANT                 507
                        note = Xaa = L or I
VARIANT                 475
                        note = Xaa = Q or E
VARIANT                 748
                        note = Xaa = Q or E
VARIANT                 868
                        note = Xaa = Q or E
VARIANT                 461
```

```
                        note = Xaa = N or D
VARIANT                 574
                        note = Xaa = N or D
VARIANT                 1..872
                        note = Xaa = Any Amino Acid, or no amino acid (except at
                          positions 507, 475, 748, 868, 461 and 574)
SEQUENCE: 136
MXGRVGEYNC PRQQRIQNRS ASHSITPLLL GCSSGTGDHH CRRRLLAPAR SREXXMKLKI    60
NKACDLXSIS VLPPRRTGGS SGAGGGXXXS XAAAVAAGSQ QRSQPMSQXS XSQGXGXXXS   120
XXXXXGASFS QGMGSGGASF SQGRGASFSQ SXSTGGAAAA FSQGGGGGGG GASFSQGRGA   180
SFSQGSGXGG AXXXXSXGGG XGSXGAXFSQ GXGGGGAAFS QGXGGGXGSF SQGGGXSSLL   240
HSQSQLSQAS LDENLLSLHL ASPARDQRFG LHDKDSSKRM XSXPXSSASS CVREESQLQL   300
AKXPSNPXHR WNXPSLXDXR SFXELHSXLF ECLTGSGLCG VXXNEDVERK FQHLASSVHK   360
VGMVLDSVQN DVMQLNRAMK EASLDSGSIQ QKXVVLXLSL QKILMVXDLE AGSIQQNDXL   420
LEXSLQQILK GQDDLKALXE XSTKSNXDQL XVLNSHXXKL XEISSXLSXL PKQXXXDLXQ   480
LXGDIFRIFT KXMEXIVRAI RSLNXXXXAX XQMXXDQSCT TNGRPLMNQL PVDRNERPQV   540
NQTPEVTRMS XTPVATMVXQ TXVASLVNQT PVAXGSPLMN QXPXANXXXX MNQTXVANGR   600
XLXSXQTPVA XGXPLXXNQX XXANGXXXXX QVPXXAANGX PXXNQTPVAX GRPXMXXQXX   660
XXXGRSQMNQ IPVAXGWPHT XKXXPAXXVX PAPLVXPXKX KXAADPKPKV EQGKXXAXPG   720
AQKLXGSXXX RPVXPKQEEX AXXKVNXXXP AXKKEKVVXI IIDSDDDSDX EGGGSEXXAS   780
CVILXXXXXG XGXEXGXXEX XXXKXGAEEX LEILRRARXI DXTALPDVMX XKRRMGKAAP   840
ERREMQAXVX XXXPXKRTXX PNPKYDAXXX XX                                 872

SEQ ID NO: 137          moltype = AA  length = 202
FEATURE                 Location/Qualifiers
source                  1..202
                        mol_type = protein
                        organism = Musa acuminata
SEQUENCE: 137
MAETRQGVNR GRETTGSATN LGFWIRRAAY LASRTGSRST RVQSVVFATD DKENVTPSRA    60
ARRRGRTRKS PLPEWYPRTP LRDITVIVNA LERRRMRVRA AATARQRTSD PEPAAVEKGL   120
LDSSSIPAAA GSSSVSATEQ PPQICSSSNA SSPREDPPDQ PTEYEKNLEI YIGEMERLVT   180
ENLKRSPMPP AKRAKRTLIS MR                                           202

SEQ ID NO: 138          moltype = AA  length = 232
FEATURE                 Location/Qualifiers
source                  1..232
                        mol_type = protein
                        organism = Brachypodium distachyon
SEQUENCE: 138
MVEVRTVSRT AVAERSGGGF FIRRVESPGA VVEKGAAKRL ARRPLTPSSN KENVPPAWAV    60
ATTQKRRSTL PEWYPRSPLR DITSIIKAVE RKNLLRDAAA RQQLQWTEDS SEPENPAQAD   120
QDVHRRTPPT NGTLAAAAVA SDPAGSAQAV ASTSATCVAE GTLKAATGDC SLQTPSRQGN   180
HPALSDLLEK LLASSIEQIE KMVCQNLTLG DPKAAQPSKT QAVQRRTLMS MR           232

SEQ ID NO: 139          moltype = AA  length = 238
FEATURE                 Location/Qualifiers
source                  1..238
                        mol_type = protein
                        organism = Hordeum vulgare
SEQUENCE: 139
MAEVRIASRT AAADRSGGGG GFFVRRVVSP GAVVDKGAVK PLARLVPSPS SNKENVPPAW    60
AAWTAPKRRS FLPEWYPRTP LRDITSIIKA VERKSRLQDA AARHQLQWDD EEDSSEPDDE   120
EYSSEPENPA QTDEGIHRST APTNETLCVG SAQVVETTAA SATCLGEGKC ATVVKASDDC   180
SLQSPSRPSG EDDVEKQLAN SIHEIEKMVS RNLKRTDPKA TRTSKTPAVQ RRTLMSMR    238

SEQ ID NO: 140          moltype = AA  length = 226
FEATURE                 Location/Qualifiers
source                  1..226
                        mol_type = protein
                        organism = Triticum aestivum
SEQUENCE: 140
MAEVRIASRT AVADRSGGGF FVRRVASPGA VVDKGAVKPL ARRVPSPSSN KENVPPAWAA    60
WTAPKRRSSL PEWYPRTPLR DITSVIKAVE RKSRLRDAVA RQQLQWDEED SSEPEDPAQT   120
DEGIHGSTAP TNETLGVGSA QVVETTAASA TCLGEGESTT VVKASDDCSL QSPSRPSGED   180
DVEKQLANSI QEIENMVSRN LKRTDPKATR PSKTPAVQRR TLMSMR                 226

SEQ ID NO: 141          moltype = AA  length = 226
FEATURE                 Location/Qualifiers
source                  1..226
                        mol_type = protein
                        organism = Aegilops tauschii
SEQUENCE: 141
MAEVRMASRA AVADRSGGGF FVRRVASPGA VVDKGAVKPL ARRVPSPSSN KENVPPAWAA    60
WAAPKRRSSL PEWYPRTPLR DITSVIKAVE RKSRLRDAAA RQQLQWDEED SSEPEDPAQT   120
DEGIHGSTAP TNETLGVGWA KVVETTAASA TCLGEGESTT VVKASDDCSL QSTSRPSGEV   180
GVEKQLASSI DAIEKMVSRN LKRTDPEATR PSKTPAVQRR TLMSMR                 226

SEQ ID NO: 142          moltype = AA  length = 225
```

```
FEATURE                 Location/Qualifiers
source                  1..225
                        mol_type = protein
                        organism = Sorghum bicolor
SEQUENCE: 142
MPQLRTASRP VLARNSTGGI FIRRRVASPG GAVKPLARRV RTHFSNKENV PPVGAARAKP   60
KRRSPLPDWY PRSPLRDITS IVKALEKRNR LEEDAARQHI QWNEDSPQPV DPTTTVHAEH  120
SDPDSQSTQT QETLGVVASP GSTSAVANNV TSVAEDKQEA SSSPSDCLQM APSKPNDPSP  180
ADLEKKMSSS IEQIEKMVRR HMKETPKAAQ PSKLVVQRRI LMSMR                 225

SEQ ID NO: 143          moltype = AA  length = 216
FEATURE                 Location/Qualifiers
source                  1..216
                        mol_type = protein
                        organism = Oryza sativa
SEQUENCE: 143
MPEMRDSKRT ALGELSGGGG FFIRRVASPG ALAARGPGKP LARRFIRPSN NKENVPPVWA   60
VKATATKRRS PLPDWYPRTP LRDITAIAKA IQRSRLRIAA AQQRSQTPEQ NTPHCTEVRD  120
SLDVEPGINS TQIVATPASS LAKDSLKIFS SPSETSLVTP SKPMDPVLLD DMEKKLSSSI  180
EQIEKMVRRN LKRTPKAAAA QPSKRAIQRR TLMSMR                           216

SEQ ID NO: 144          moltype = AA  length = 265
FEATURE                 Location/Qualifiers
source                  1..265
                        mol_type = protein
                        organism = synthetic construct
VARIANT                 9
                        note = Xaa = N or D
VARIANT                 122
                        note = Xaa = L or I
VARIANT                 150
                        note = Xaa = Q or E
VARIANT                 1..265
                        note = Xaa = Any Amino Acid, or no amino acid (except at
                          positions 9, 122 and 150)
SEQUENCE: 144
MSYTNFSXXX KMXEVRXASR XALADXSGGX XGGGFFIRRR VASPGAVXXK GAVKPLARRV   60
XSPSSNKENV PPXWAARAXP XKRRSPLPEW YPRTPLRDIT SIXKAXERRR SRLRXAAARQ  120
QXQWXEXSXS SEPXDXEYSS EPENPAQTDX XXHSXPDXSX XXTXETLGXX VXXXXXXXXV  180
AXSATCLAEG XXXXXSXASD DCSLQXPSXK PNDPSXXDXV EKKLSSSIEQ IEKMVRRNLK  240
RTPDPKAAQP SKXPAVQRRT LMSMR                                       265

SEQ ID NO: 145          moltype = AA  length = 508
FEATURE                 Location/Qualifiers
source                  1..508
                        mol_type = protein
                        organism = Oryza sativa
SEQUENCE: 145
MSSNLAASRR SSSSSSVAAA AAAKRPAVGE GGGGGGGKAA AGAAAAKKRV ALSNISNVAA   60
GGGAPGKAGN AKLNLAASAA PVKKGSLASG RNVGTNRASA VKSASAKPAP AISRHESATQ  120
KESVLPPKVP SIVPTAALAP VTVPCSSFVS PMHSGDSVSV DETMSTCDSM KSPEFEYIDN  180
GDSSSVLGSL QRRANENLRI SEDRDVEETK WKKDAPSPME IDQICDVDNN YEDPQLCATL  240
ASDIYMHLRE AETRKRPSTD FMETIQKDVN PSMRAILIDW LVEVAEEYRL VPDTLYLTVN  300
YIDRYLSGNE INRQRLQLLG VACMLIAAKY EEICAPQVEE FCYITDNTYF RDEVLEMEAS  360
VLNYLKFEVT APTAKCFLRR FVRVAQVSDE DPALHLEFLA NYVAELSLLE YNLLSYPPSL  420
VAASAIFLAK FILQPTKHPW NSTLAHYTQY KSSELSDCVK ALHRLFSVGP GSNLPAIREK  480
YTQHKYKFVA KKPCPPSIPT EFFRDATC                                    508

SEQ ID NO: 146          moltype = AA  length = 505
FEATURE                 Location/Qualifiers
source                  1..505
                        mol_type = protein
                        organism = Sorghum bicolor
SEQUENCE: 146
MSTIAASRRS SSSSAAAKR PAISEGAGGP KVAAAQAKKR VALGNITNVA ARGGRAVVGG    60
GLGNAAPPTT SAKLNPAVPL KKPSLASARS VSSIRGQAVK SASIKPAPPV SRHGSAIQKH  120
NVPPPKVPTI ADVPSHAPAL VPCTGLVSPG RSGDFVSIDD TMSTCDSMKS PDFEYIDNQD  180
SSMLASLQRR TNEHLRITED RDVEENKWKK NAIAPMEIDR ICDVDNEYED PQLCATLASD  240
IYMHLREAET KKRPSTDFME TIQKDINPSM RAILIDWLVE VSEEYRLVPD TLYLTVNYID  300
RYLSGNEINR QRLQLLGVAC MLIAAKYEEI CAPQVEEFCY ITDNTYFRDE VLDMETSVLK  360
YLKFEMTAPT AKCFLRRFAR AAQACDEDPA LHLEFLANYI AELSLLEYNL LSYPPSLIAA  420
SAIFLARFIL QPTKYPWNST LAHYTQYKPS ELSDCVKALH RLCSVGSGTN LPAIREKYSQ  480
HKYKFVAKKQ CPPQIPTEFF RDATC                                       505

SEQ ID NO: 147          moltype = AA  length = 510
FEATURE                 Location/Qualifiers
source                  1..510
                        mol_type = protein
                        organism = Brachypodium distachyon
```

```
SEQUENCE: 147
MSSTAAASRR LSSSAATATA KRPAMAENAG GAKPAGRMAA QQPKKRVALG NLTNVAAGAV     60
GRTGCGKVAV VTAGNARLHS ATSTVPVKKG SLASARNVIT NRGSAVKSVS TRPTPVTSCR    120
GSTTQKEIVP PPKLPAAMPI VAPPIVPCSS FVSPRHSADS MSTDETMSTC DSMKSPDFEY    180
IDNGDSSVLD SLQRRANANL RISEDSDVEG AKWKKDATAP MEIDTICDVD NNYEDTQLCA    240
TLASDIYMHL REAETRKRPA TDFLEKMQKD VNPSMRAILI DWLVEVAEEY RLVPDTLYLT    300
VNYIDRYLSG NEINRQRLQL LGVACMLIAA KYEEICAPQV EEFCYITDNT YFKDEVLDME    360
ASVLNYLKFE MTAPTPKCFL RRFVRVAQVC DEDPALHLEF LANYVAELSL LEYSLLAYPP    420
SLVAASAVFL SKFILQPTKC PWNSTLAHYT QYKASELCDC VKALHRLFSV GPGSNLPAIR    480
EKYSQHKYKF VAKKQCPPLV PADFFRDATC                                    510

SEQ ID NO: 148           moltype = AA  length = 501
FEATURE                  Location/Qualifiers
source                   1..501
                         mol_type = protein
                         organism = Brachypodium distachyon
SEQUENCE: 148
MSSNAAASRR LSSATTATAK RPAMAESAGG AKLVDPVAVQ QAKKRVALGN ITNIAAGAMG     60
RTGCGKVAVA TPGNARLHST TSAAPVKKGS LASVQNAIAN RSLAVKSAST RPTPKAEDIV    120
PPPKVPTVMP IAASAIVPCC SFASPQHSED SISTDETMST SDSMKSPDLE YIDNGDSLVL    180
DSLQQRANAN LRISEESDVE GTKWKKDATT PMEIDNISDV DDNYKDPQLC ATLPSDIYMH    240
LRDTETRKRP ASDFLETMQK DINPSMRAIL IDWLVEVSEE YRLVPDTLYL TVNYIDRYLS    300
GNEINRQRLQ LLGVACMLIA AKHEEICAPQ VEEFCYITDN TYFKDEVLEM EASVINYLKF    360
EMTAPTAKCF LRRFVRAAQV CDEDPALHLE SLACYVTELS LLEYSLLVYP PSLVAASALF    420
LSKFILQPTK SPWNSTLAHY TQYKASELCD CVKELQRLFC VAPGSKLPAI REKYSQHKYK    480
FAAKKQCPPM VPADYFCDAA C                                             501

SEQ ID NO: 149           moltype = AA  length = 510
FEATURE                  Location/Qualifiers
source                   1..510
                         mol_type = protein
                         organism = Aegilops tauschii
SEQUENCE: 149
MSSNSAAPRR FSSAMSTSTA KRPAVPEGAR AAAGPAAAQQ QAKKRVALGN LTTNVAAAAA     60
GRAGCGKIAV VTTGNARLNS ATSAAPVKKG ALPSARHASA NRGSAVKSAF TKPAPVTSRH    120
ESSVQKESVP PRKVPTVVPI AVPAVIPFSS FVSPGHSGDS ISTDETMSSC DSMKSPDFEY    180
IDNGDSSLLD SLQRRANENL RISDDRTVEG AKWKKDAAAP MEIDNVCDVD DNYEDPQLCA    240
TLASDIYMHL REAETRKRPS TDFLETIQKD VNPSMRAILI DWLVEVAEEY RLVPDTLYLT    300
VNYIDRYLSG NEINRQRLQL LGVACMLIAA KYEEICAPQV EEFCYITDNT YFKDEVLDME    360
ASVLNYLKFE MTAPTAKCFL RRFVRAAQVC DEDPPLHLEF LANYVAELSL LEYSLLAYPP    420
SLVAASAIFL SKFILQPAKH PWNSTLAHYT QYKPSELCDC VKALHRLFSV GPGSNLPAIR    480
EKYSQHKYKF VGKKQCPTSV PAEFFRDAAC                                    510

SEQ ID NO: 150           moltype = AA  length = 478
FEATURE                  Location/Qualifiers
source                   1..478
                         mol_type = protein
                         organism = Oryza sativa
SEQUENCE: 150
MAAKRPAAGE GGGKAAAGAA AAKKRVALVN ITNVAAAANN AKFNSATWAA PVKKGSLASG     60
RNVCTNRVSA VKSASAKPAP AISRHESAPQ KESVIPPKVL SIVPTAAPAP VTVPCSSFVS    120
PMHSGDSVSV DETMSMCDSM KSPDFEYIDN GDSSSVLGSL QRRANENLRI SEDRDVEETK    180
WNKDAPSPME IDQICDVDNN YEDPQLCATL ASDIYMHLRE AETRKRPSTD FMETIQKDVN    240
PSMRAILIDW LVEVAEEYRL VPDTLYLTVN YIDRYLSGNE INRQRLQLLG VACMLIAAKY    300
EEICAPQVEE FCYITDNTYF RDEVLEMEAS VLNYLKFEAP TAKCFLRRFV RAQVCDEDPP    360
DPALHLEFLA NYVAELSLLE YNLLSYPPSL VAASAIFLAK FILQPTKHPW NSTLAHYTQY    420
KSSELSDCVK ALHRLFSVGP GSNLPAIREK YTQHKYKFVA KKHCPPSVPS EFFRDATC     478

SEQ ID NO: 151           moltype = AA  length = 515
FEATURE                  Location/Qualifiers
source                   1..515
                         mol_type = protein
                         organism = Hordeum vulgare
SEQUENCE: 151
MSSNPAAPRR FSSAMSTATA KRPAVPEGAA GARPAAGPAA AAPQQQAKKR VALGNLTNVA     60
AAAGGRAGCG KIAVVTAGNA RLSSATAAAP VKKGSLPGAR NANANRGSAV KSASTKPAPV    120
TSRHEGSVQK ESAPPPRKVP TVVPIAVPAV IPFSSFVSPG HSGDSISTDE TMSSCDSMKS    180
PDFEYIDNGD SSLLDSLQRR ANENLRISDD RTVEGTKWKK DATAPMEIDN VCDVDDNYED    240
PQLCATLASD IYMHLREAET RKRPSTDFLE TIQKDVNPSM RAILIDWLVE VAEEYRLVPD    300
TLYLTVNYID RYLSGNEINR QRLQLLGVAC MLIAAKYEEI CAPQVEEFCY ITDNTYFKDE    360
VLDMEASVLN YLKFEMTAPT AKCFLRRFVR AAQVCDEDPP LHLEFLANYV AELSLLEYSL    420
LAYPPSLVAA SAIFLSKFIL QPAKHPWNST LAHYTQYKPS ELCDCVKALH RLFSVGPGSN    480
LPAIREKYSQ HKYKFVGKKQ CPTSVPAEFF RDAAC                               515

SEQ ID NO: 152           moltype = AA  length = 510
FEATURE                  Location/Qualifiers
source                   1..510
                         mol_type = protein
                         organism = Triticum aestivum
```

```
SEQUENCE: 152
MSSNSAAPRR FSSAMSTSTA KRPAVPEGAR AAAGPAAAQQ QAKKRVALGN LTTNVAAAAA      60
GRAGCGKIAV VTTGNARLNS ATSAAPVKKG ALPSARNASA NRGSAVKSAF TKPAPVTSRH     120
ESSVQKESVP PRKVPTVVPI AVPAVIPFSS FVSPGHSGDS ISTDETMSSC DSMKSPDFEY     180
IDNGDSSLLD SLQRRANENL RISDDRTVEG AKWKKDAAAP MEIDNVCDVD DNYEDPQLCA     240
TLASDIYMHL REAETRKRPS TDFLETIQKD VNPSMRAILI DWLVEVAEEY RLVPDTLYLT     300
VNYIDRYLSG NEINRQRLQL LGVACMLIAA KYEEICAPQV EEFCYITDNT YFKDEVLDME     360
ASVLNYLKFE MTAPTAKCFL RRFVRAAQVC DEDPPLHLEF LANYVAELSL LEYSLLAYPP     420
SLVAASAIFL SKFILQPAKH PWNSTLAHYT QYKPSELCDC VKALHRLFSV GPGSNLPAIR     480
EKYSQHKYKF VGKKQCPTSV PAEFFRDAAC                                      510

SEQ ID NO: 153          moltype = AA  length = 491
FEATURE                 Location/Qualifiers
source                  1..491
                        mol_type = protein
                        organism = Oryza sativa
SEQUENCE: 153
MSSSLASRRS SSSSAAKRPA AGEGGGKAAA GAAAAKKRVA LGNITNVAAA ANNAKFNSAT      60
WAAPVKKGSL ASGRNVGTNR VSAVKSASTK PASAISRHES APQKESVLPP KVLRIVPTAA     120
PAPVTVPCSS FVSPMHSGDS VSVDETMSTC DSMKSPDFEY IDNGDSSSVL GSLQRRANEN     180
LRISEDRDVE ETKWKKDAPS PMEIDQICDV DNNYEDPQLC ATLASDIYMH LREAETRKHP     240
STDFMETLQK DVNPSMRAIL IDWLVEVAEE YRLVPDTLYL TVNYIDRYLS GNEINRQRLQ     300
LLGVACMLIA AKYKEICAPQ VEEFCYITDN TYFRDEVLEM EASVLNYLKF EMTAPTAKCF     360
LRRFVRVAQV SDEDPALHLE FLANYVAELS LLEYNLLSYP PSLVAASAIF LAKFILQPAK     420
HPWNSTLAHY TQYKSSELSD CVKALHRLFC VGPGSNLPAI REKYTQHKYK FVAKKPCPPS     480
IPTEFFRDST C                                                          491

SEQ ID NO: 154          moltype = AA  length = 502
FEATURE                 Location/Qualifiers
source                  1..502
                        mol_type = protein
                        organism = Sorghum bicolor
SEQUENCE: 154
MSTRAASRRS SSSSAAAKRP AMAEGAKAAG TAAAQAKKRA ALGNITNVVA APAGRAAALG      60
KVAPPVTGAK LNSATSAVPL KKPSLANARN ASSIRGSAVK SASIKPAPPV PRLDSSTRPK     120
HNVPVPATVH VPSRAPALVP CSSFVSPARS GDSVSIDETM STCDSMKSPD FEYIDNGDSS     180
MLASLQRRAD EHLRISEDTD VEENKWKKNA PAPMEIDRVC DVDNDLEDPQ LCATLASDIY     240
MHLREAETKK RPSTDFMETI QKDVNPSMRA ILIDWLVEVA EEYRLVPDTL YLTVNYIDRY     300
LSGNEINRQR LQLLGVACML IAAKYEEICA PQVEEFCYIT DNTYFRDEVL EMEASVLNYL     360
KFEMTAPTAK CFLRRFARSA QACDEDPALH LEFLASYIAE LSLLEYNLLS YPPSLIAASA     420
IFLARFILQP TKYPWNSTLS HYTQYKPSEL SDCVKALHRL FSVGPGSNLP AIREKYSQHK     480
YKFVAKKQCP PQIPTEFFRD TT                                              502

SEQ ID NO: 155          moltype = AA  length = 505
FEATURE                 Location/Qualifiers
source                  1..505
                        mol_type = protein
                        organism = Sorghum bicolor
SEQUENCE: 155
MSTFAASRRS SSSAASKRPA MDENAAGGPR WTRPQATKRV ALGNITNVAA PAPGRRAAVG      60
KVAPPATTRA KLNPATSAAP LKKPYPANAR NVSSIRGSAV KSASIKPGPP VSCLCSSTMQ     120
QKHNVPPPKV PTTVNVPSRA PALVPCSSFM SPGRSGDSVS MDETMSICDS MKSPDFEFID     180
NGDSSVLASL QRQANEHLRI SEENKWKKNA PAPFEIDHIC DVDNDYEDPQ LCATLASDIY     240
MHLREAEMKK SKRPSTDFME TIHKSVNPSM RAILIDWLVE VAEEYRLVPD TLYLTVNYID     300
RYLSGNEIDR QRLQLLGVTC MLIAAKYEEI CAPQVEEFCY ITDSTYFRDD VLEMEASVLN     360
YLKFEMAAPT PKCFLRRFAR AAQACDEDPA LHLEFLANYI AELSLLEYNL LSYPPSLIAA     420
SAVFLARYVL QPTKYPWNST LAHYTQYKPS ELSDCVKALH RLFSVGPGSN LPAIREKYSQ     480
HKYKFVARKQ CPPSIPTEFF RDVTW                                           505

SEQ ID NO: 156          moltype = AA  length = 492
FEATURE                 Location/Qualifiers
source                  1..492
                        mol_type = protein
                        organism = Musa acuminata
SEQUENCE: 156
MNRRPSISSS ASAASASAKR PAATESASKM PAALAGQAKK RVALANISNQ SKVARNPARP      60
LGAKGANINT TSSASTKKGS LSSYRDTRSG GSSAVTSAAI KPDTNKSSNK SSLSINNGPK     120
ITVPACLVPC STLKSPGHSR DSVSLDETMS TCDSMRSPDF EYIDKGDCSV ITSLERQANK     180
NLHISEHAAE AGSKLSIDVP MMMEVDDIID VDTNHDDPQF CTTLAGDIYR HLRIAETKKR     240
PSTDFMEKIQ KDINASMRSI LIDWLVEVAE EYRLVPDTLY LTVNYIDRYL SGNEINRQRL     300
QLLGVSCMLI AAKYEEICAP QVEEFCYITD NTYFKDEVFQ MEADVLKYLK YEMTAPTVKC     360
FLRRFIRAAQ GSDEVPALQL EFLASYVAEI SLLEYSLLCY APSLIAASAI FLARFILQPA     420
KRPWNATLDH YTLYKPSDLS DCVKALHRLF CTSSGNNLPA IREKYSQHKY KFVAKKYCPA     480
SIPAEYFQDA RN                                                         492

SEQ ID NO: 157          moltype = AA  length = 531
FEATURE                 Location/Qualifiers
source                  1..531
                        mol_type = protein
```

-continued

| | organism = synthetic construct |
|---|---|
| VARIANT | 1..531 |
| | note = Any Amino Acid, or no amino acid |

SEQUENCE: 157

```
MSSXAAXXRS  SSSSXSTAAS  AXAKRPAXXE  GAGGAXXXAA  XXAAAXQQQA  KKRVALGNIT   60
TNVAAAAXGR  AAVGGGCGKV  APXTTGNAKL  NSATSAAPVK  KGSLATSARN  VXXNIRGSAV  120
KSASXKPAPX  XSRHXSSXXQ  KEXVXPPPKV  PTXVPXAXXA  PAXVPCSSFV  SPGHSGDSVS  180
XDETMSTCDS  MKSPDFEYID  NGDSSSVLXS  LQRRANENLR  ISEDRDVEEX  KWKKDAPAPM  240
EIDXICDVDN  NYEDPQLCAT  LASDIYMHLR  EAETRKSKRP  STDFMETIQK  DVNPSMRAIL  300
IDWLVEVAEE  YRLVPDTLYL  TVNYIDRYLS  GNEINRQRLQ  LLGVACMLIA  AKYEEICAPQ  360
VEEFCYITDN  TYFRDEVLEM  EASVLNYLKF  EMTAPTAKCF  LRRFVRAAQV  CDEDPALHLE  420
FLANYVAELS  LLEYSLLSYP  PSLVAASAIF  LAKFILQPTK  XPWNSTLAHY  TQYKPSELSD  480
CVKALHRLFS  VGPGSNLPAI  REKYSQHKYK  FVAKKQCPPS  IPAEFFRDAT  C           531
```